US012767669B2

(12) United States Patent
Xue et al.

(10) Patent No.: US 12,767,669 B2
(45) Date of Patent: Oct. 20, 2026

(54) GALLIUM-SALOPHEN ANTIMICROBIAL COMPOUNDS AND METHODS OF USE THEREOF

(71) Applicant: UNIVERSITY OF MARYLAND, BALTIMORE, Baltimore, MD (US)

(72) Inventors: Fengtian Xue, Potomac, MD (US); Angela Wilks, Baltimore, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 811 days.

(21) Appl. No.: 18/000,802

(22) PCT Filed: Jun. 4, 2021

(86) PCT No.: PCT/US2021/035892
§ 371 (c)(1),
(2) Date: Dec. 5, 2022

(87) PCT Pub. No.: WO2021/247992
PCT Pub. Date: Dec. 9, 2021

(65) Prior Publication Data

US 2023/0227476 A1 Jul. 20, 2023

Related U.S. Application Data

(60) Provisional application No. 63/035,603, filed on Jun. 5, 2020.

(51) Int. Cl.
*C07F 5/00* (2006.01)
*A61P 31/04* (2006.01)

(52) U.S. Cl.
CPC .............. *C07F 5/003* (2013.01); *A61P 31/04* (2018.01)

(58) Field of Classification Search
None
See application file for complete search history.

(56) References Cited

U.S. PATENT DOCUMENTS 9,539,367 B2 1/2017 Britigan et al.
2017/0283763 A1 10/2017 Newman et al.

FOREIGN PATENT DOCUMENTS

WO 2019214691 A1 11/2019

OTHER PUBLICATIONS

Mitchell-Koch. Electroanalysis, 2005, 17, Nos. 15-16, 1347-1353 (Year: 2005).*

Shen. Journal of Organometallic Chemistry, 1999, 590, 242-247 (Year: 1999).*

Gonawala. Chemical Communications,2016, 52, 8440-8443, supporting information pp. 1-10 (Year: 2016).*

Hill. European Journal of Inorganic Chemistry, 1998, 67-72 (Year: 1998).*

Beiraghi et al. "Selective Separation and Preconcentration of trace Amounts of Gallium in Water and Rice Samples using Cloud Point Extraction and Determination by Inductively Coupled Plasma-Atomic Emission Spectrometry" International Journal of New Chemistry. Mar. 2018. vol 5, p. 124-139; p. 124, abstract, p. 126, Fig.1, p. 137, para 1.

He et al. "Symmetrical bis-salophen probe serves as a selectively and sensitively fluorescent switch of gallium ions in living cells and zebrafish" Talanta. Jul. 4, 2019 (Jul. 4, 2019) vol. 205, p. 1-9; p. 3, Figure 1a.

Centola et al. "Gallium(III)-Salophen as a Dual Inhibitor of Pseudomonas aeruginosa Heme Sensing and Iron Acquisition" ACS Infectious Diseases.—Jun. 17, 2020 (Jun. 17, 2020) vol. 6, p. 2073-2085; entire document.

International Search Report and Written Opinion Dated Oct. 28, 2021 for International Patent Application No. PCT/US2021/035892, 10 pages.

European Extended Search Report for corresponding European Application No. 21818664.1, dated May 31, 2024, 17 pages.

Truscott James C et al: "Synthesis, structure and DFT study of novel Ga(III) complexes containing a tetradentate ligand", Journal of Molecular Structure, Elsevier Amsterdam, NL, vol. 1203, Nov. 4, 2019, 9 pages.

* cited by examiner

*Primary Examiner* — Noble E Jarrell

(74) *Attorney, Agent, or Firm* — Morgan, Lewis & Bockius LLP

(57) ABSTRACT

Gallium-salophen compounds, and methods of using the same for the treatment of disease are disclosed.

19 Claims, 39 Drawing Sheets

A

B

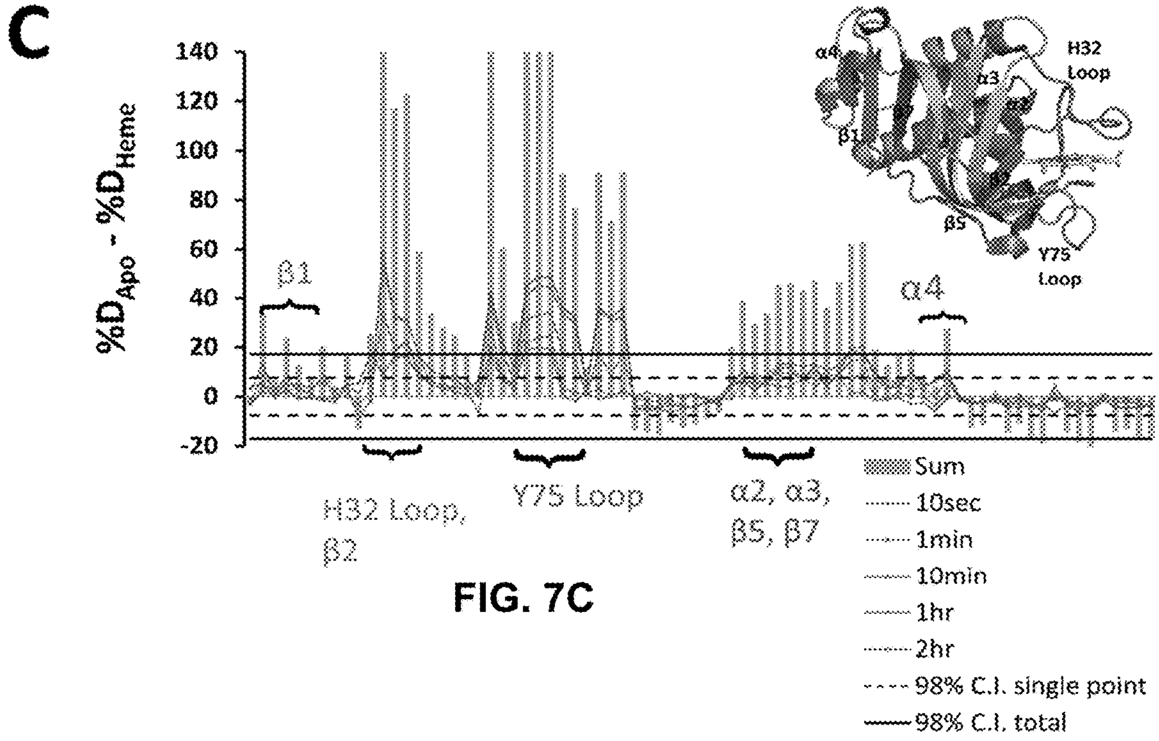
FIG. 7C
FIG. 7D
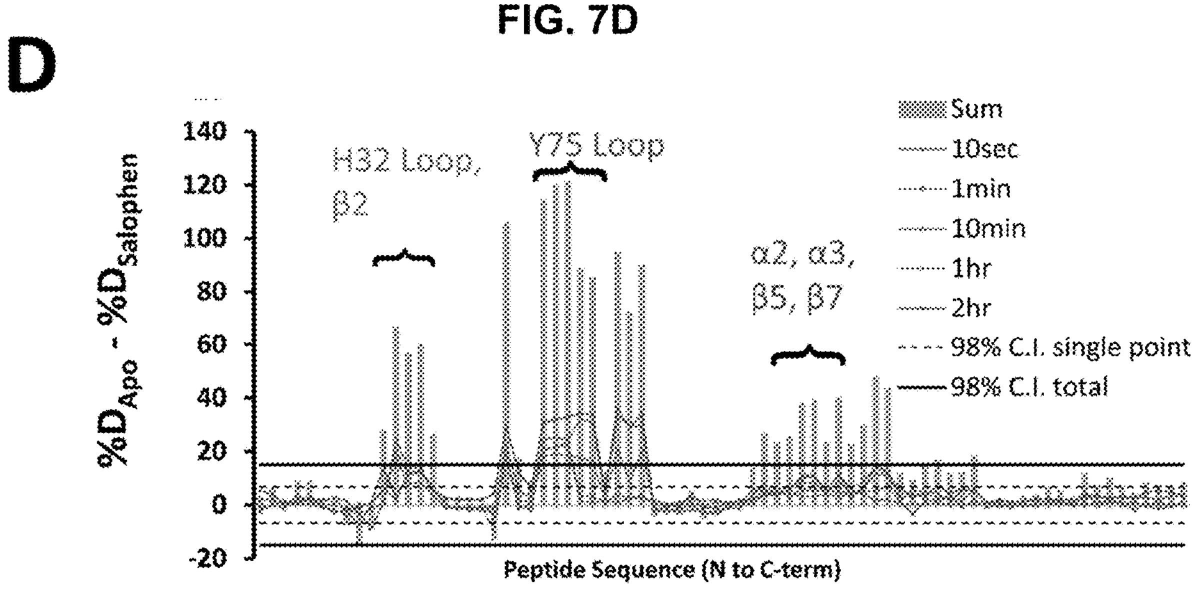

| Cmpd | $K_D$,nM |
|---|---|
| Heme | 350 ± 50 |
| GaPPIX | 280 ± 30 |
| FeSal | 1050 ± 100 |
| GaSal | 1110 ± 220 |

| Ligand | $K_D$ (nM) |
|---|---|
| Apo-HasAp | 230 ± 80 |
| Holo-HasAp | 120 ± 20 |
| GaSal-HasAp | 140 ± 30 |

C

| | R'1 | R'2 | R'3 | R'4 | R'5 | R'6 |
|---|---|---|---|---|---|---|
| R1 | -0.19 | -0.21 | -0.18 | -0.17 | -0.17 | -0.11 |
| R2 | -0.17 | -0.23 | -0.22 | -0.18 | -0.14 | -0.10 |
| R3 | -0.16 | -0.16 | -0.25 | -0.23 | -0.15 | -0.14 |
| R4 | -0.16 | -0.15 | -0.15 | -0.14 | -0.13 | -0.10 |
| R5 | -0.16 | -0.17 | -0.17 | -0.20 | -0.15 | -0.13 |
| R6 | -0.15 | -0.16 | -0.14 | -0.11 | -0.15 | -0.13 |

Polymyxin

Colistin (1952)

Aminoglycoside

Gentamicin (1964)

Penicillin

Piperacillin (1981)

Cephalosporin

Ceftazidime (1984)

Monobactam

Aztreonam (1986)

Tobramycin (1974)

Ticarcillin (1983)

Cefepime (1994)

Ciprofloxacin (1987)

Fluoroquinolone

Cefiderocol
(MIC 0.06-0.5 μg/ml)

A catechol-mimic
siderophore

| Cmpd | $K_D$,nM |
|---|---|
| Heme | 350 ± 50 |
| GaPPIX | 290 ± 30 |
| FeSal | 1100 ± 100 |
| GaSal | 1000 ± 220 |

I

II 2,4-dihydroxybenzaldehyde

2a

2b

2c

Compound 2

GaSal-1

GaSal-2

GaSal-3

GaSal-4

GaSal-2

GaSal-3

GaSal-4

GALLIUM-SALOPHEN ANTIMICROBIAL COMPOUNDS AND METHODS OF USE THEREOF

CROSS-REFERENCE TO RELATED APPLICATIONS

The present application is a U.S. National Phase Application under 35 U.S.C. § 371 of International Application PCT/US2021/035892, filed Jun. 4, 2021, which claims priority to U.S. Provisional Patent Application No. 63/035,603, filed Jun. 5, 2020, each of which is incorporated by reference herein in its entirety.

STATEMENT AS TO FEDERALLY SPONSORED RESEARCH

This invention was made with government support under Grant Number AI134886 awarded by the National Institutes of Health. The government has certain rights in the invention

FIELD

The disclosure relates generally to gallium-salophen compounds and methods of treating or preventing conditions associated with inhibition of HasAp protein activity and/or the *P. aeruginosa* siderophore iron uptake system.

BACKGROUND

*Pseudomonas aeruginosa* is an opportunistic bacterium that causes life-threatening infections in immunocompromised patients. Multidrug-resistant *P. aeruginosa* has been classified by the CDC as a "serious threat" to public health owing to its ability to overcome many current treatment strategies. It frequently causes infection in immunocompromised patients and is a leading cause of nosocomial infections. *P. aeruginosa* is the second leading cause of ventilator-associated pneumonias in intensive care facilities, and the primary cause of respiratory infection in cystic fibrosis (CF) patients where it persists for decades. It is particularly problematic for cystic fibrosis (CF) patients, who suffer from life-threatening chronic infection where even direct delivery of the antibiotic tobramycin to the lung is becoming ineffective. While new antibiotics are entering the pipeline, many candidates in Phase I-III trials have minimal activity against *P. aeruginosa* and new developments are typically improved versions of existing inhibitors rather than new classes of antibiotics. These targets typically include essential cellular pathways such as peptidoglycan or protein synthesis, which often see resistance emerge within a few years of introduction.

SUMMARY

The disclosure provides in one aspect a compound of formula (I), or a pharmaceutically acceptable salt, solvate, hydrate, cocrystal, or prodrug thereof:

formula (I)

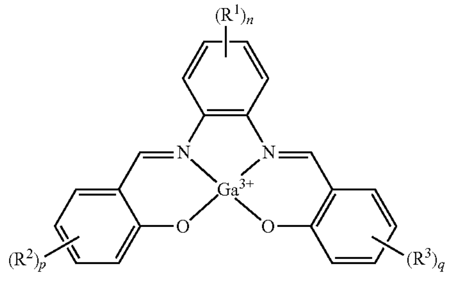

wherein in formula (I):

each $R^1$ is a substituent independently selected at each occurrence from halogen, optionally substituted alkyl, optionally substituted alkylaryl, optionally substituted alkylheteroaryl, optionally substituted alkenyl, optionally substituted alkynyl, optionally substituted cycloalkyl, optionally substituted aryl, optionally substituted aralkyl, optionally substituted haloalkyl, optionally substituted alkoxy, and optionally substituted heteroaryl;

each $R^2$ and $R^3$ is a substituent independently selected at each occurrence from halogen, optionally substituted alkyl, optionally substituted alkylaryl, optionally substituted alkylheteroaryl, optionally substituted alkenyl, optionally substituted alkynyl, optionally substituted cycloalkyl, optionally substituted aryl, optionally substituted aralkyl, optionally substituted haloalkyl, optionally substituted alkoxy, and optionally substituted heteroaryl;

wherein one $R^1$ and one $R^2$, one $R^1$ and one $R^3$, or one $R^2$ and one $R^3$ may optionally be joined together;

n is an integer from 0 to 4;

p is an integer from 0 to 4; and q is an integer from 0 to 4.

In some embodiments, each $R^1$ is independently —$OR^a$, wherein each $R^a$ is independently selected at each occurrence from the group consisting of optionally substituted alkyl, optionally substituted alkylaryl, optionally substituted alkylcycloalkyl, and optionally substituted alkylheteroaryl. In some embodiments, each $R^2$ and $R^3$ is independently —$OR^b$ or —$(CH_2)OR^b$, wherein each $R^b$ is independently selected at each occurrence from the group consisting of optionally substituted alkyl, optionally substituted alkylaryl, optionally substituted alkylcycloalkyl, optionally substituted alkylheteroaryl, and optionally substituted heterocyclyl. In some embodiments, one $R^2$ and one $R^3$ join together to form —$O(CH_2)_rO$—, wherein r is an integer from 4 to 7. In some embodiments, each $R^1$ is independently selected at each occurrence from the group consisting of —OMe, —OEt, —OPr, —OiPr,

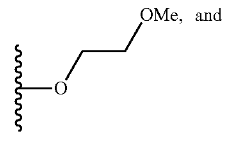

and

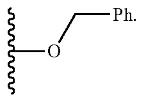

In some embodiments, each $R^2$ is independently selected at each occurrence from the group consisting of

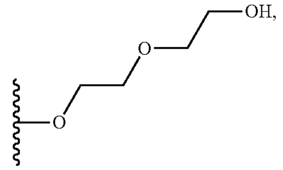
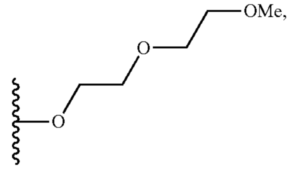
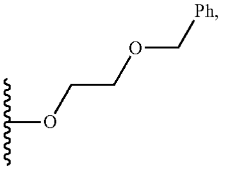
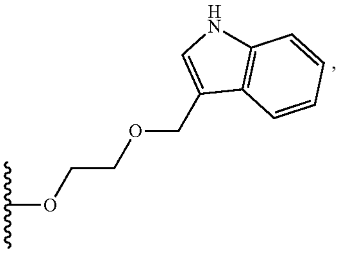
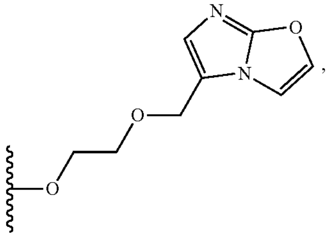
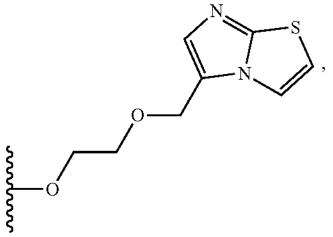
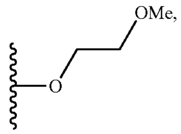
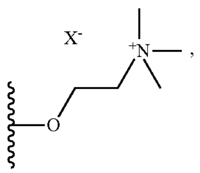
-continued
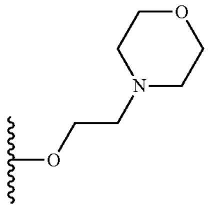
, and
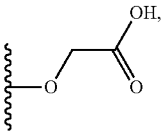
wherein $X^-$ is independently at each occurrence selected from $Br^-$, $Cl^-$, and $I^-$. In some embodiments, each $R^2$ is independently selected at each occurrence from the group consisting of
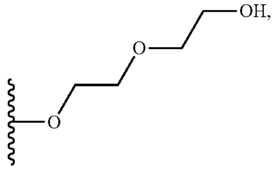
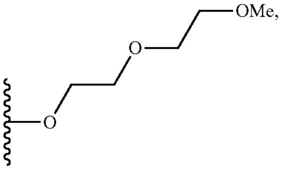
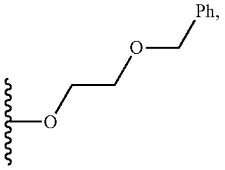
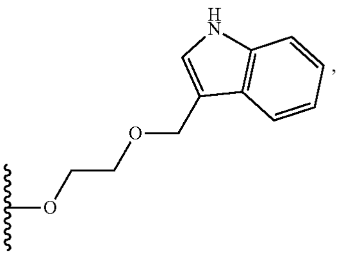
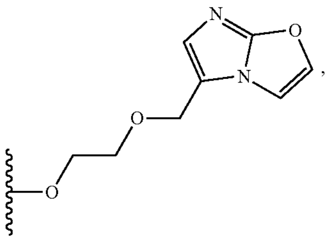

-continued

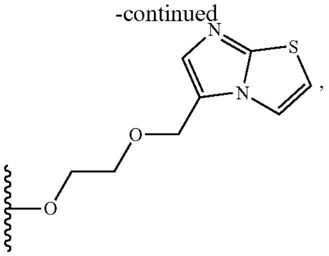

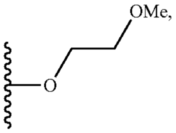

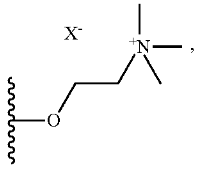

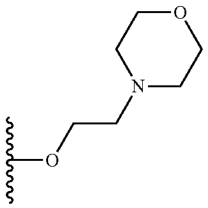

and

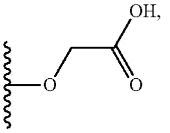

wherein $X^-$ is independently at each occurrence selected from $Br^-$, $Cl^-$, and $I^-$. In some embodiments, n is 1 or 2. In some embodiments, p is 1 or 2. In some embodiments, q is 1 or 2.

The disclosure provides in one aspect a compound of formula (II), or a pharmaceutically acceptable salt, solvate, hydrate, cocrystal, or prodrug thereof:

formula (II)

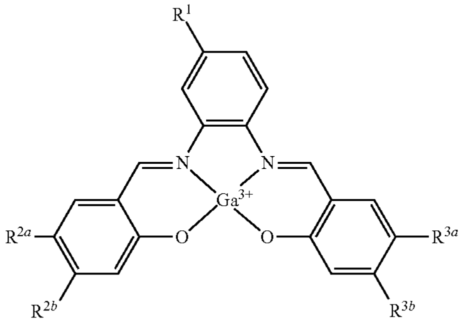

wherein in formula (II):

$R^1$ is selected from the group consisting of H, halogen, optionally substituted alkyl, optionally substituted alkylaryl, optionally substituted alkylhetaryl, optionally substituted alkenyl, optionally substituted alkynyl, optionally substituted cycloalkyl, optionally substituted aryl, optionally substituted aralkyl, optionally substituted haloalkyl, optionally substituted alkoxy, and optionally substituted heteroaryl; and $R^{2a}$, $R^{2b}$, $R^{3a}$ and $R^{3b}$ is each independently selected from the group consisting of H, halogen, optionally substituted alkyl, optionally substituted alkylaryl, optionally substituted alkylhetaryl, optionally substituted alkenyl, optionally substituted alkynyl, optionally substituted cycloalkyl, optionally substituted aryl, optionally substituted aralkyl, optionally substituted haloalkyl, optionally substituted alkoxy, and optionally substituted heteroaryl.

In some embodiments, $R^1$ is selected from the group consisting of —OMe, —OEt, —OPr, —OiPr,

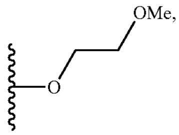

and

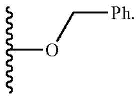

In some embodiments, each $R^{2a}$ and $R^{2b}$ is independently selected at each occurrence from the group consisting of

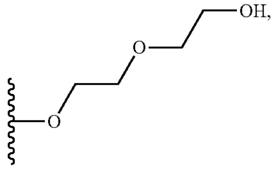

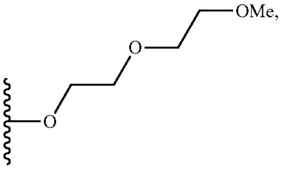

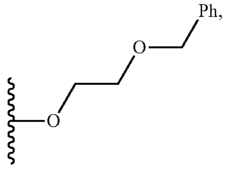

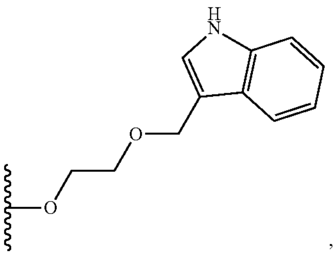

,

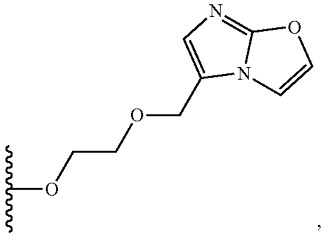

,

-continued
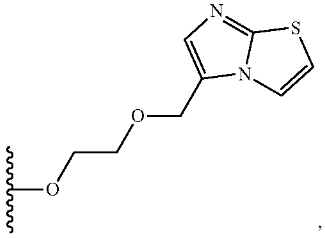
,
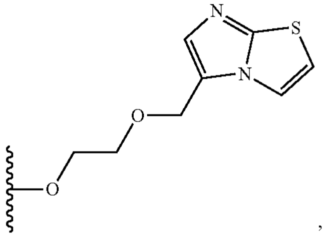
,
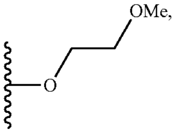
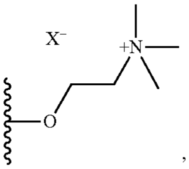
,
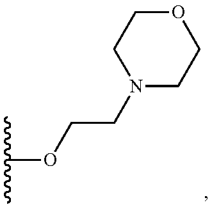
, and
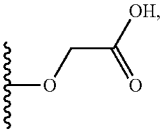
wherein $X^-$ is independently at each occurrence selected from $Br^-$, $Cl^-$, and $I^-$. In some embodiments, each $R^{3a}$ and $R^{3b}$ is independently selected at each occurrence from the group consisting of
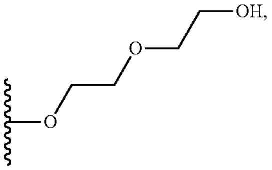
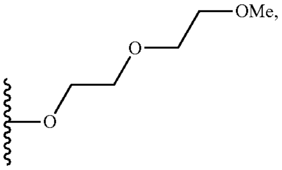
-continued
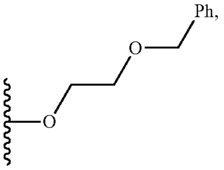
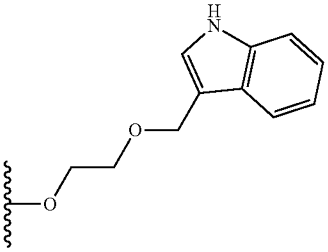
,
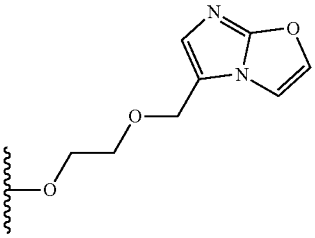
,
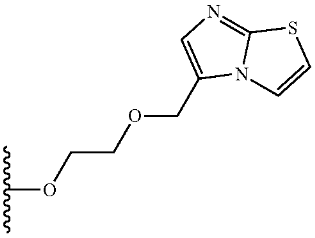
,
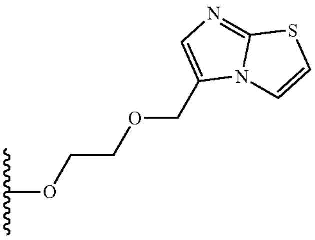
,
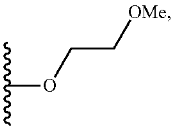
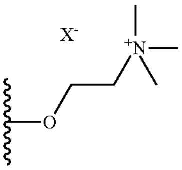
,
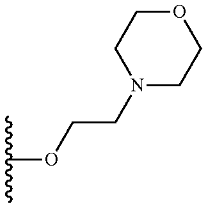
, and -continued

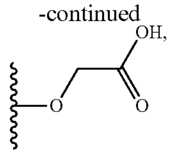

wherein $X^-$ is independently at each occurrence selected from $Br^-$, $Cl^-$, and $I^-$.

The disclosure provides in one aspect a compound of any one of formula (III), formula (IV), formula (V), formula (VI), formula (VII), formula (VIII), formula (IX), or formula (X), or a pharmaceutically acceptable salt, solvate, hydrate, cocrystal, or prodrug thereof:

formula (III)

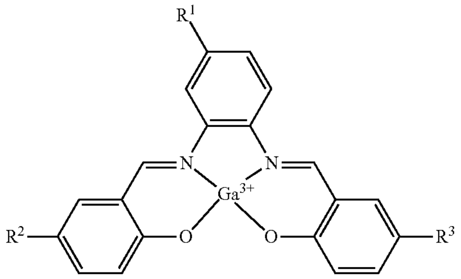

formula (IV)

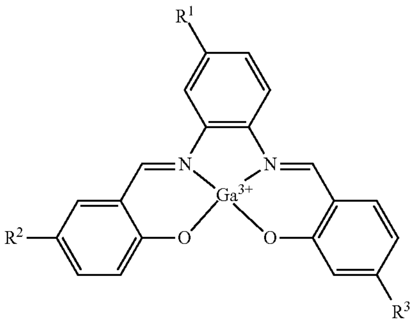

formula (V)

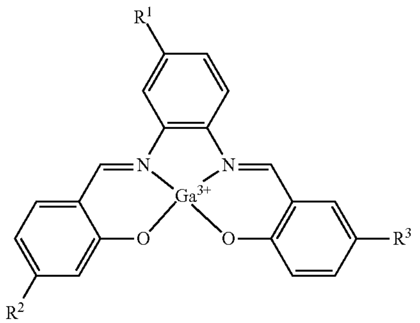

-continued formula (VI)

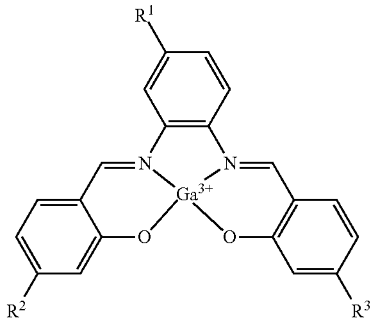

formula (VII)

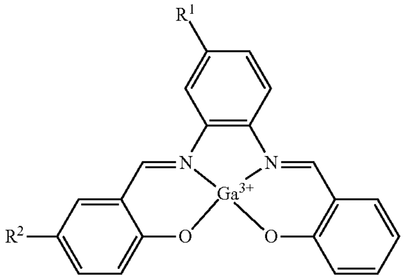

formula (VIII)

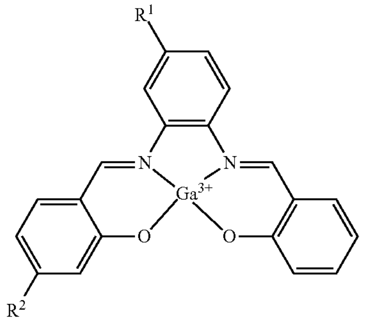

formula (IX)

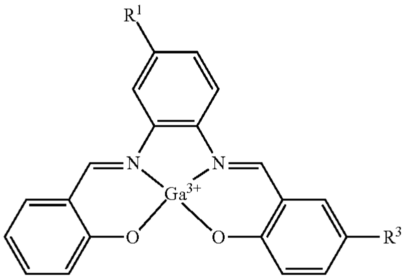

formula (X)

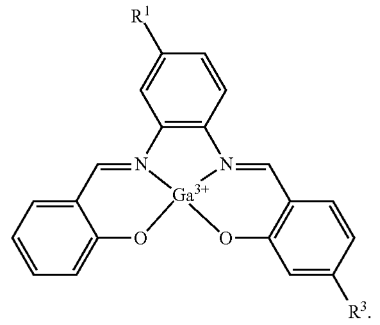

In some embodiments, $R^1$ is independently selected at each occurrence from the group consisting of —OMe, —OEt, —OPr, —OiPr,
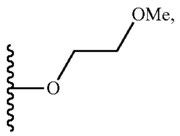
and
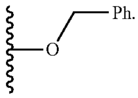
In some embodiments, $R^2$ is selected from the group consisting of
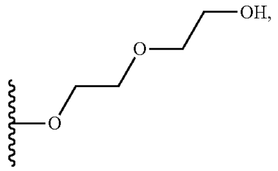
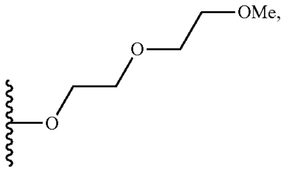
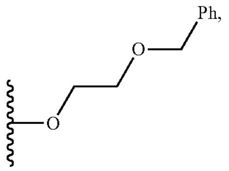
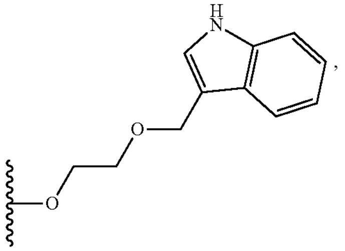
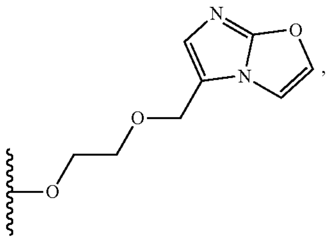
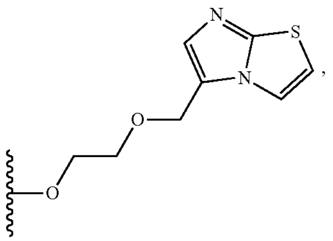
-continued
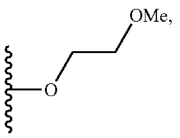
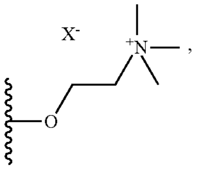
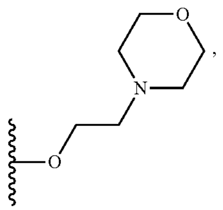
and
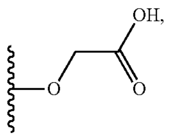
wherein $X^-$ is independently at each occurrence selected from $Br^-$, $Cl^-$, and $I^-$. In some embodiments, $R^3$ is selected from the group consisting of
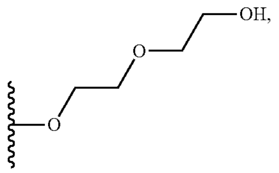
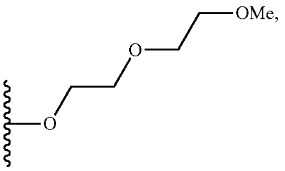
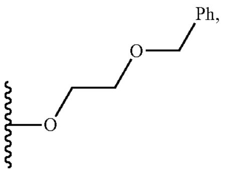
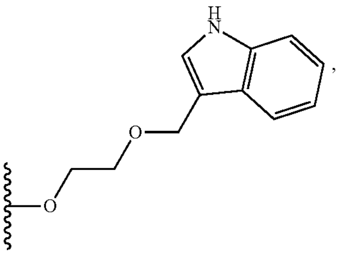

-continued

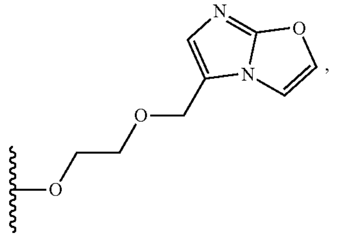

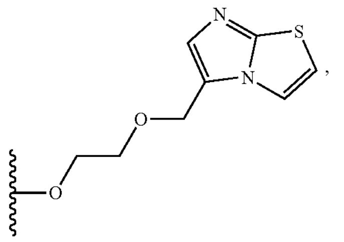

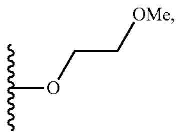

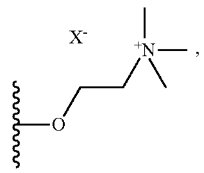

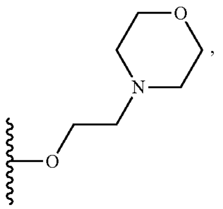

and

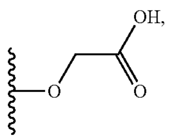

wherein selected from $Br^-$, $Cl^-$, and $I^-$.

The disclosure provides in one aspect a compound of formulas 1001 to 1567, or a pharmaceutically acceptable salt, solvate, hydrate, cocrystal, or prodrug thereof.

The disclosure provides in one aspect a compound of formula (XI), or a pharmaceutically acceptable salt, solvate, hydrate, cocrystal, or prodrug thereof formula (XI)

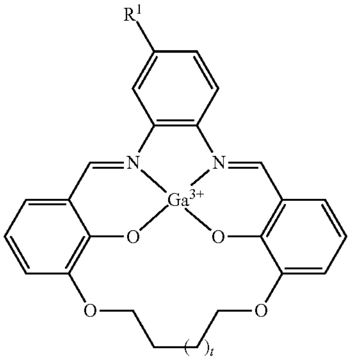

wherein in formula (XI):

$R^1$ is selected from the group consisting of H, halogen, optionally substituted alkyl, optionally substituted alkylaryl, optionally substituted alkylhetaryl, optionally substituted alkenyl, optionally substituted alkynyl, optionally substituted cycloalkyl, optionally substituted aryl, optionally substituted aralkyl, optionally substituted haloalkyl, optionally substituted alkoxy, and optionally substituted heteroaryl; and t is an integer from 1 to 4.

In some embodiments, $R^1$ is selected from the group consisting of —OMe, —OEt, —OPr, —OiPr,

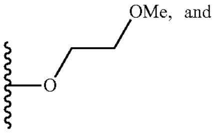

and

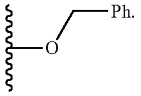

The disclosure provides in one aspect a compound of any one of formulas 2001 to 2028.

In some embodiments, the compound is selected from:

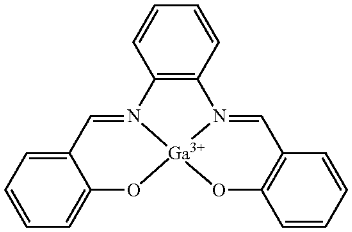

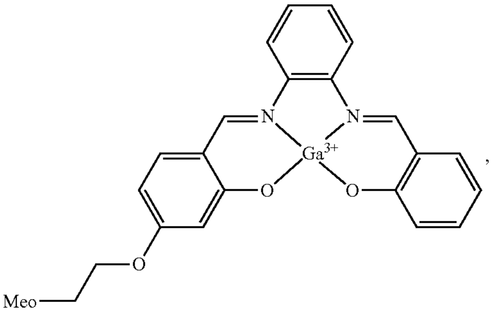

-continued

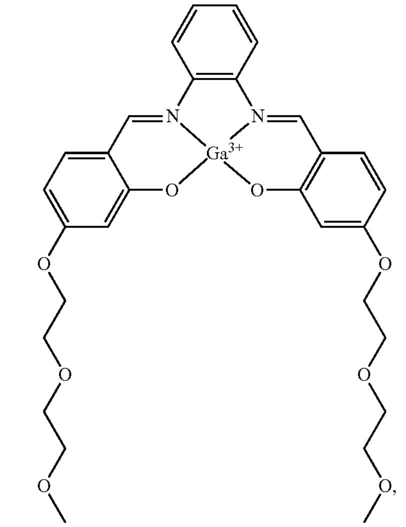

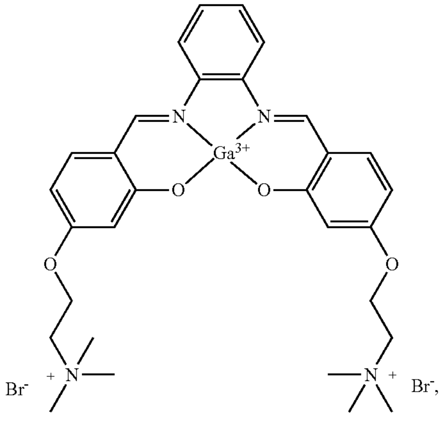

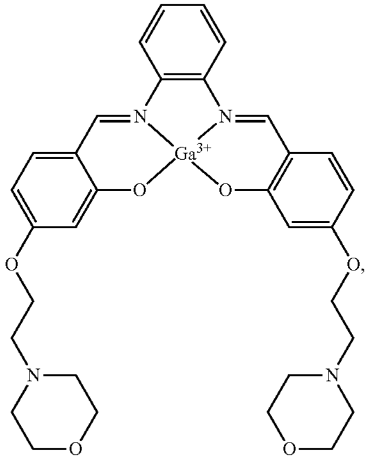

and

-continued

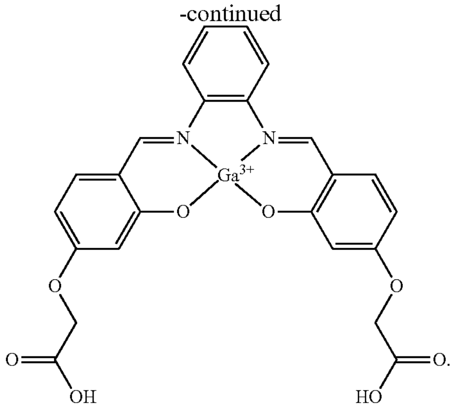

In some embodiments, the compound inhibits HasAp protein activity. In some embodiments, the compound inhibits the *P. aeruginosa* siderophore iron uptake system. In some embodiments, the compound inhibits both HasAp protein activity and the *P. aeruginosa* siderophore iron uptake system.

In one aspect, the disclosure provides a pharmaceutical composition for treating a condition alleviated by inhibiting HasAp protein activity, the pharmaceutical composition comprising one or more compounds of the disclosure, or a pharmaceutically acceptable salt, solvate, hydrate, cocrystal, or prodrug thereof, and a pharmaceutically acceptable carrier.

In one aspect, the disclosure provides a pharmaceutical composition for treating a condition alleviated by inhibiting the *P. aeruginosa* siderophore iron uptake system, the pharmaceutical composition comprising one or more compounds of the disclosure, or a pharmaceutically acceptable salt, solvate, hydrate, cocrystal, or prodrug thereof, and a pharmaceutically acceptable carrier.

In one aspect, the disclosure provides a pharmaceutical composition for treating a condition alleviated by dual inhibition of HasAp protein activity and the *P. aeruginosa* siderophore iron uptake system, the pharmaceutical composition comprising one or more compounds of the disclosure, or a pharmaceutically acceptable salt, solvate, hydrate, cocrystal, or prodrug thereof, and a pharmaceutically acceptable carrier.

In some embodiments, the condition is selected from sepsis, meningitis, endocarditis, osteomyelitis, otitis media, sinusitis, pneumonia, chronic respiratory tract infection, catheter infection, postoperative peritonitis, postoperative biliary tract, tricuspid valve endocarditis, ecthyma gangrenosum, eyelid abscess, lacrimal cystitis, conjunctivitis, corneal ulcer, corneal abscess, panophthalmitis, orbital infection, urinary tract infection, complicated urinary tract infection, catheter infection, perianal abscess, severe burns, airway burns, pressure ulcer infections, cystic fibrosis, and a bacterial infection.

In one aspect, the disclosure provides a pharmaceutical composition for treating or preventing a bacterial infection, the pharmaceutical composition comprising one or more compounds of the disclosure, or a pharmaceutically acceptable salt, solvate, hydrate, cocrystal, or prodrug thereof, and a pharmaceutically acceptable carrier.

In some embodiments, the bacterial infection is caused by a bacterium selected from *P. aeruginosa, Serratia marcescens, Bordetella pertussis, Bordetella bronchiseptica, Bordetella avium, Yersinia pestis, Yersinia pseudotuberculosis*, and *Acinetobacter baumannii.*

In one aspect, the disclosure provides a method of treating a condition by inhibiting HasAp protein activity in a patient in need of said treatment, the method comprising administering to the patient a therapeutically effective amount of a compound of the disclosure or a pharmaceutically acceptable salt, solvate, hydrate, cocrystal, or prodrug thereof.

In one aspect, the disclosure provides a method of treating a condition by inhibiting the *P. aeruginosa* siderophore iron uptake system in a patient in need of said treatment, the method comprising administering to the patient a therapeutically effective amount of a compound of the disclosure or a pharmaceutically acceptable salt, solvate, hydrate, cocrystal, or prodrug thereof.

In one aspect, the disclosure provides a method of treating a condition by dual inhibition of the HasAp protein activity and the *P. aeruginosa* siderophore iron uptake system in a patient in need of said treatment, the method comprising administering to the patient a therapeutically effective amount of a compound of the disclosure or a pharmaceutically acceptable salt, solvate, hydrate, cocrystal, or prodrug thereof.

In some embodiments, the condition is selected from sepsis, meningitis, endocarditis, osteomyelitis, otitis media, sinusitis, pneumonia, chronic respiratory tract infection, catheter infection, postoperative peritonitis, postoperative biliary tract, tricuspid valve endocarditis, ecthyma gangrenosum, eyelid abscess, lacrimal cystitis, conjunctivitis, corneal ulcer, corneal abscess, panophthalmitis, orbital infection, urinary tract infection, complicated urinary tract infection, catheter infection, perianal abscess, severe burns, airway burns, pressure ulcer infections, cystic fibrosis, and a bacterial infection.

In one aspect, the disclosure provides a method for treating or preventing a bacterial infection in a patient in need of said treatment, the method comprising administering to the patient a therapeutically effective amount of a compound of the disclosure or a pharmaceutically acceptable salt, solvate, hydrate, cocrystal, or prodrug thereof.

In some embodiments, the bacterial infection is caused by a bacterium selected from *P. aeruginosa, Serratia marcescens, Bordetella pertussis, Bordetella bronchiseptica, Bordetella avium, Yersinia pestis, Yersinia pseudotuberculosis*, and *Acinetobacter baumannii*.

BRIEF DESCRIPTION OF THE FIGURES

FIG. 7 illustrates the conformational changes of HasAp upon ligand binding. FIG. 7C illustrates the relative deuteration of HasAp bound to heme. FIG. 7D illustrates the relative deuteration of HasAp bound to GaSal. Individual peptides are plotted from N to C-terminus based on first residue number. For each peptide, differences in percent deuteration at each time point are color coded according to the legend with the sum of all differences integrated over time are represented in gray bars. 98% confidence intervals are represented as dashed (for individual time points) and solid (for total sums) lines. Peptides exceeding both confidence intervals were considered to display a statistically significant difference in deuterium uptake between the apo and ligand bound form and were mapped on to the crystal structure of holo-HasAp (FIG. 7C, inset; PDB 3ELL). Positive values indicate protection from deuteration upon ligand binding and negative values indicate increased deuteration of a region upon ligand binding. Significant regions are highlighted and color coded on the HasAp structure (FIG. 7C, inset).

8C illustrates the heme binding site with heme (blue) and salophen (red) overlaid. Potential contacts between the H32 loop and heme are drawn in red dashed lines.

Figure 9A:
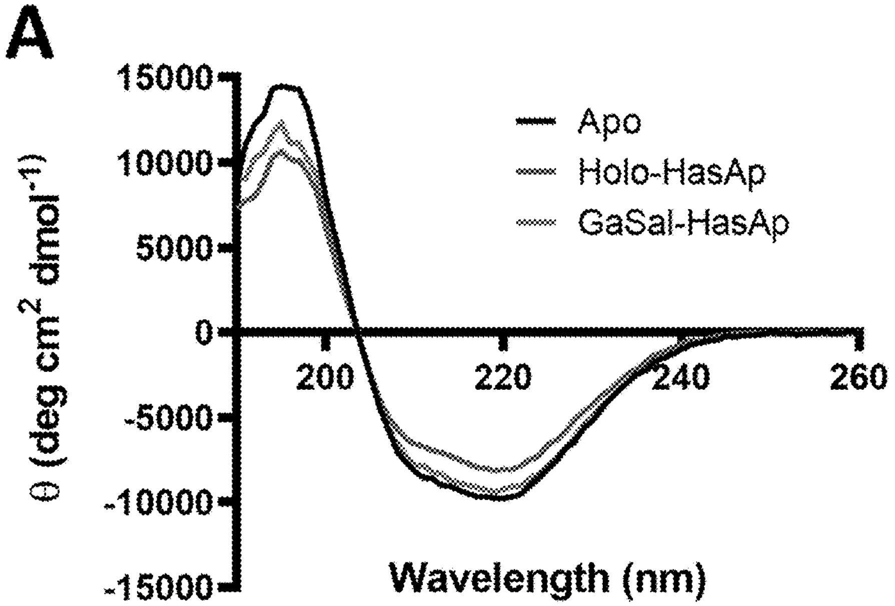
Figure 9B:
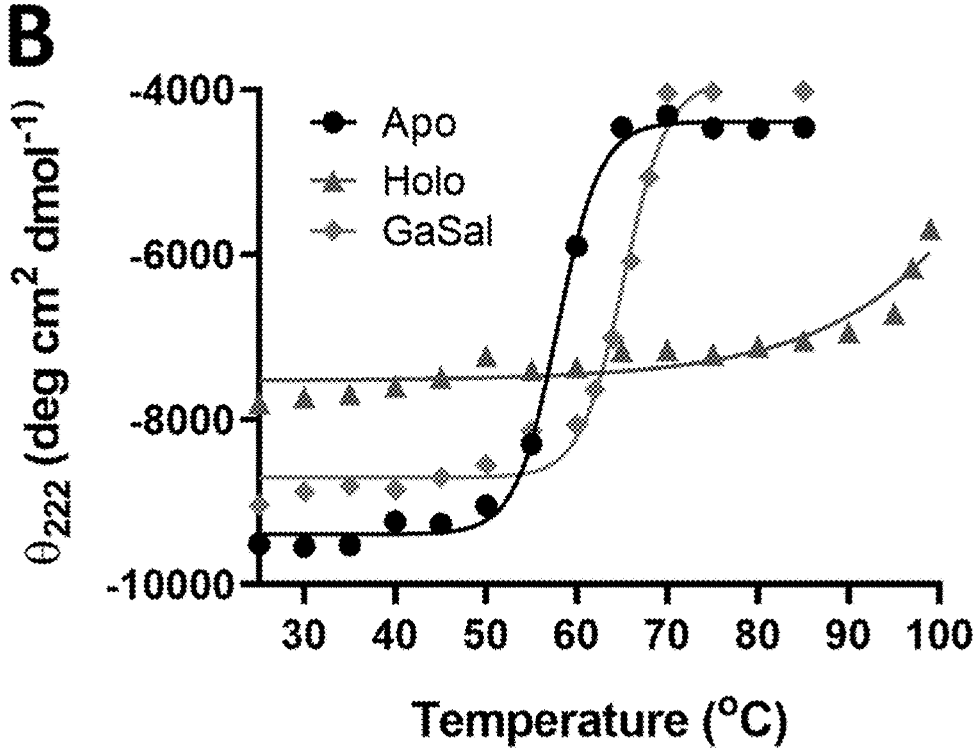

FIG. 9 illustrates the thermal denaturation of HasAp bound to Heme or GaSal. FIG. 9A illustrates the comparison of three ligand states at 25° C. FIG. 9B illustrates the thermal denaturation profiles at 222 nm fit to a sigmoidal distribution. CD spectra were recorded.

Figures 10A, 10B:
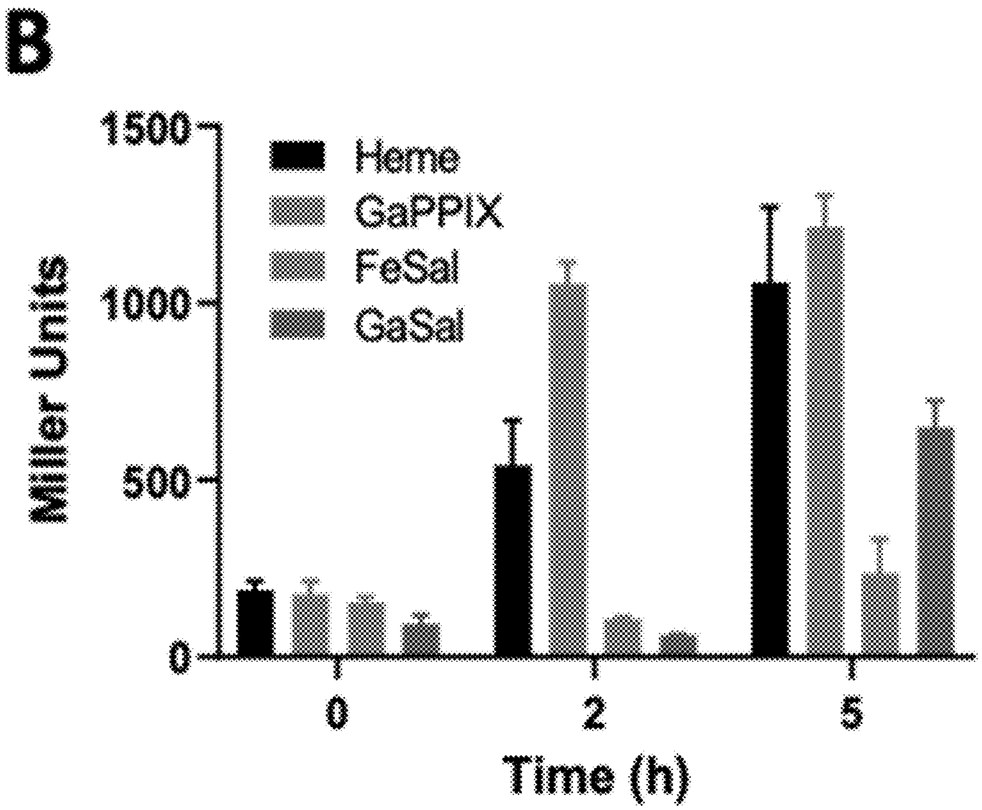
Figure 10C:
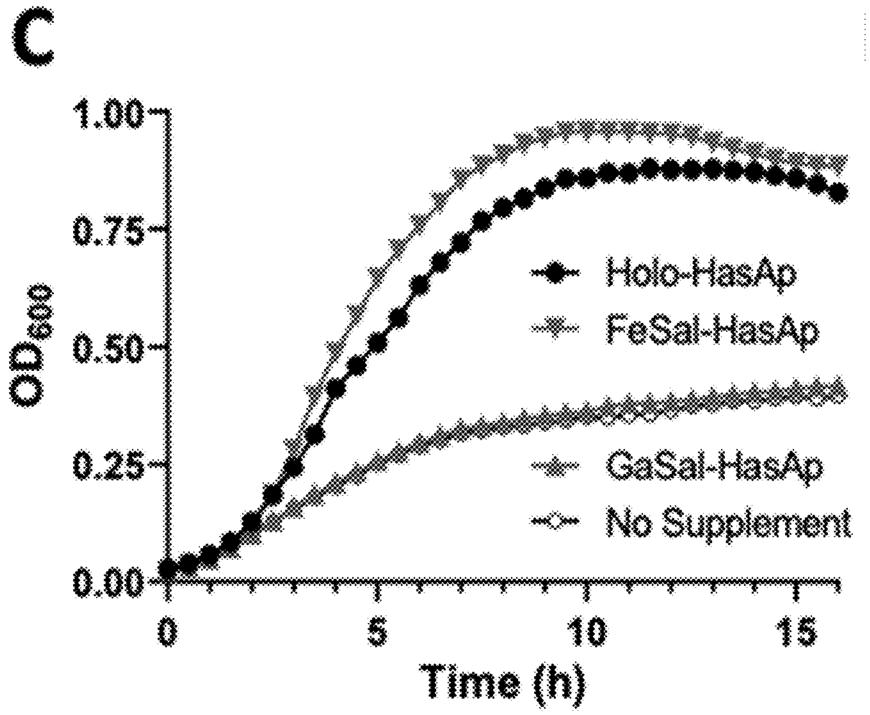
Figure 10D:
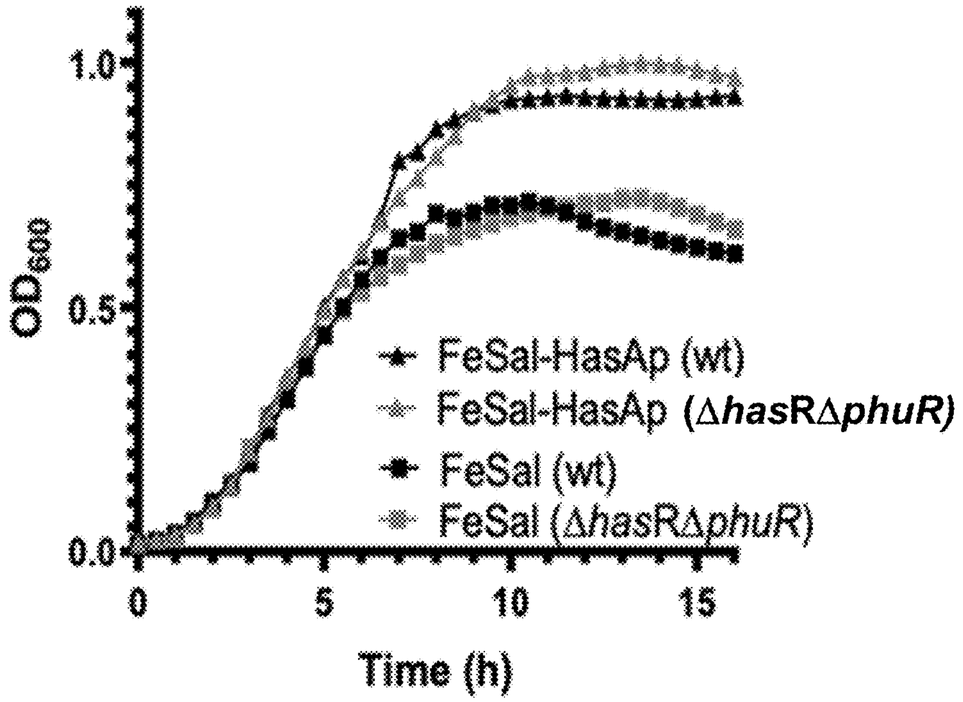
Figure 10E:
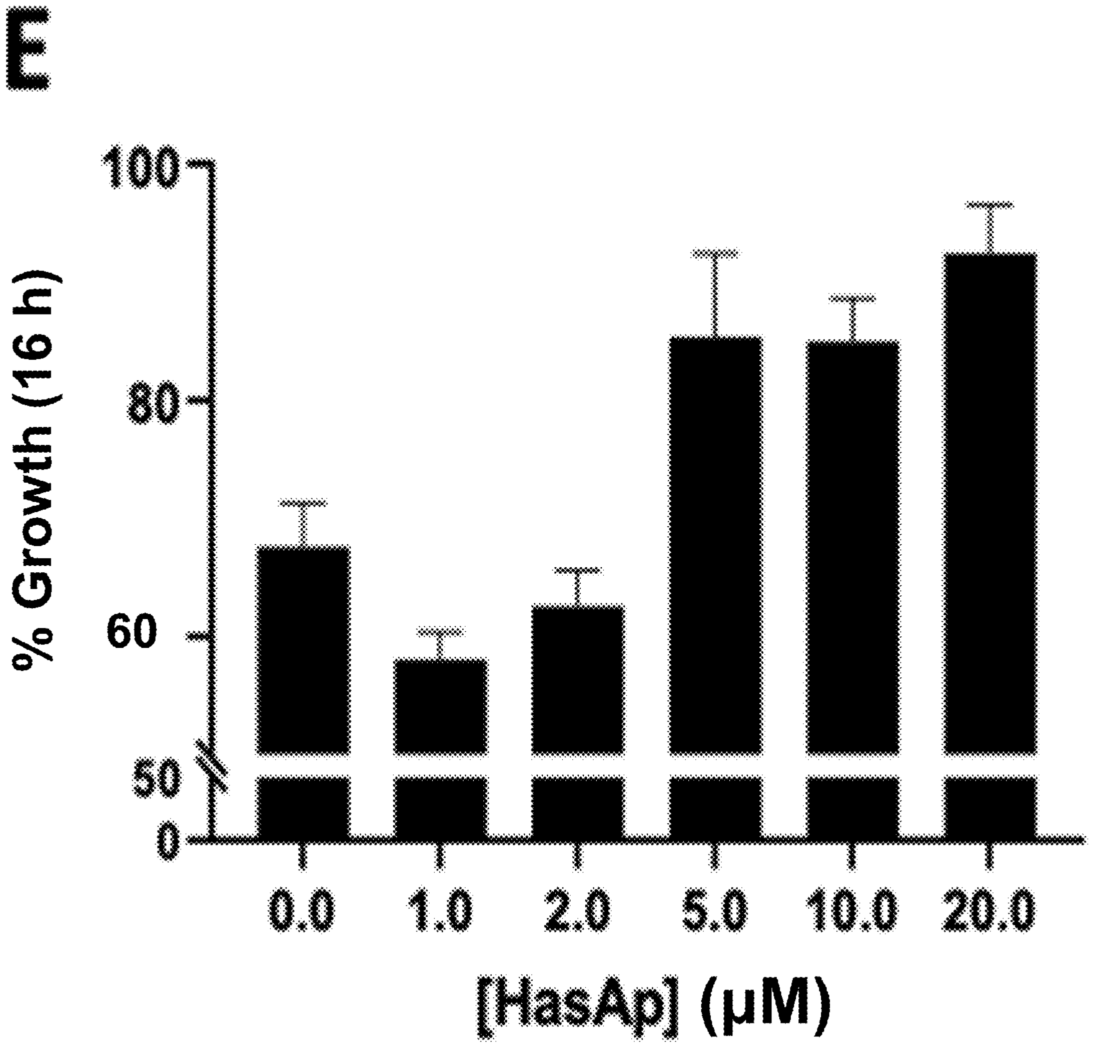

FIG. 10A illustrates binding affinity determination by FQ. FIG. 10B illustrates transcriptional reporter assays. β-Galactosidase activity corrected for $OD_{600}$ from 0-5 h. The PAO1 hasR-lacZ reporter strain supplemented with 1 μM holo-HasAp, GaPPIX-HasAp, FeSal-HasAp or CaSal-HasAp. FIG. 10C illustrates GaSal activity in the PAO1 ΔhasRΔphuR strain. Cultures were grown in M9 minimal media with iron-limited supplements $FeCl_3$ (400 nM) and GaSal (2.8 μg/mL). Data represent the average of three wells in a 96-well plate with blanks subtracted. FIG. 10D illustrates PAO1 WT and ΔhasRΔphuR strains in the presence of Fe-Sal-HasAp. Cultures were supplemented with FeSal or FeSal-HasAp (1 μM) ligands and grown for 16 h in a 96-well microplate. Data represents the average of three growth wells with blank (cell-free) wells subtracted. FIG. 10E illustrates HasAp titration alleviates GaSal toxicity in PAO1 ΔhasAp. Wells were prepared in M9 minimal media with $FeCl_3$ (400 nM) and GaSal (7 μM), with HasAp supplemented at increasing concentrations.

Figures 11A, 11B:
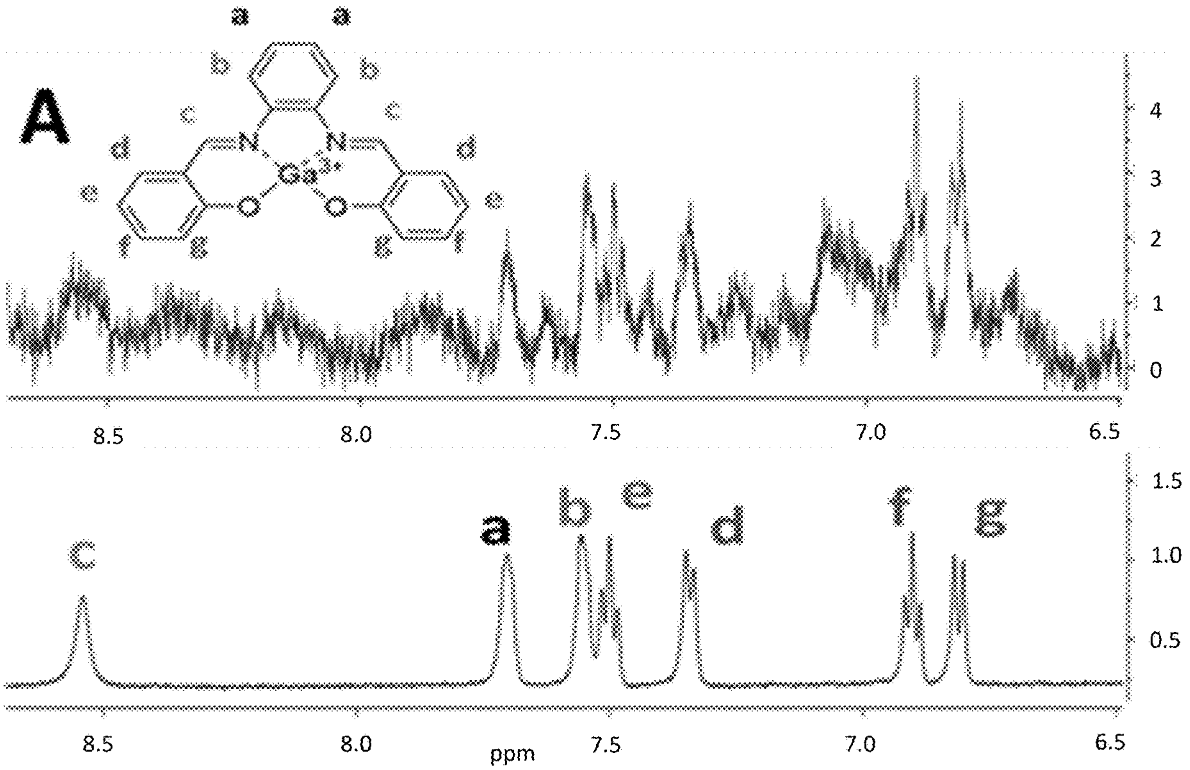

FIG. 11A illustrates the STD spectrum (top) and $^1$H NMR (bottom) of GaSal (1 mM) and HasAp (10 μM) in PAO1 supernatant, in M9 Minimal Media. FIG. 11B illustrates binding affinities of HasAp complexes to HasR determined by SPR.

Figure 12A:
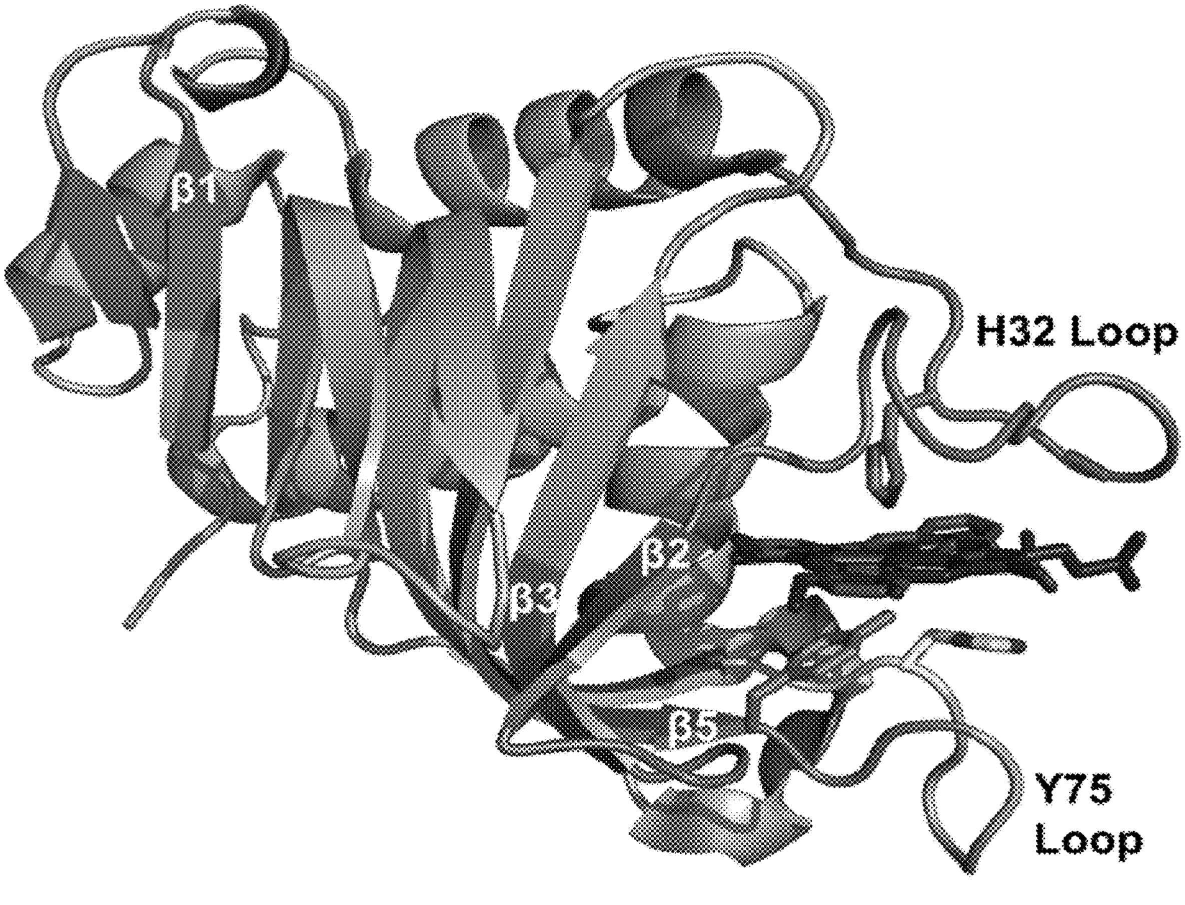
Figure 12B:
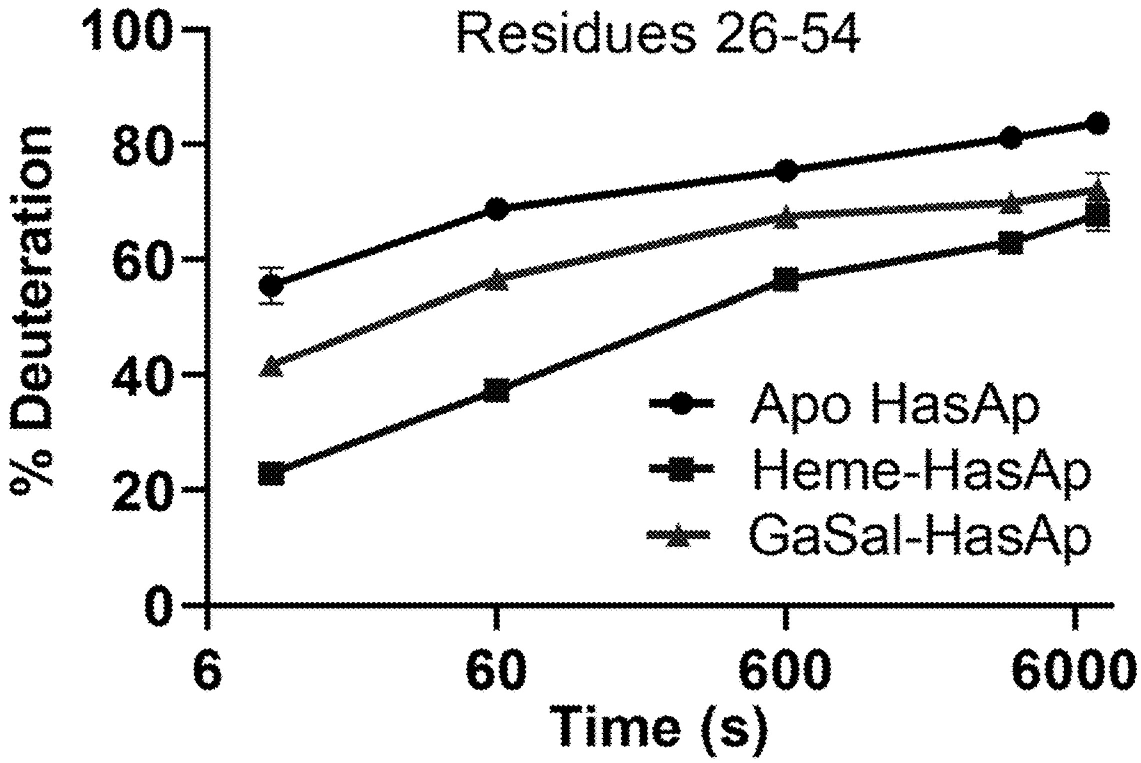
Figure 12C:
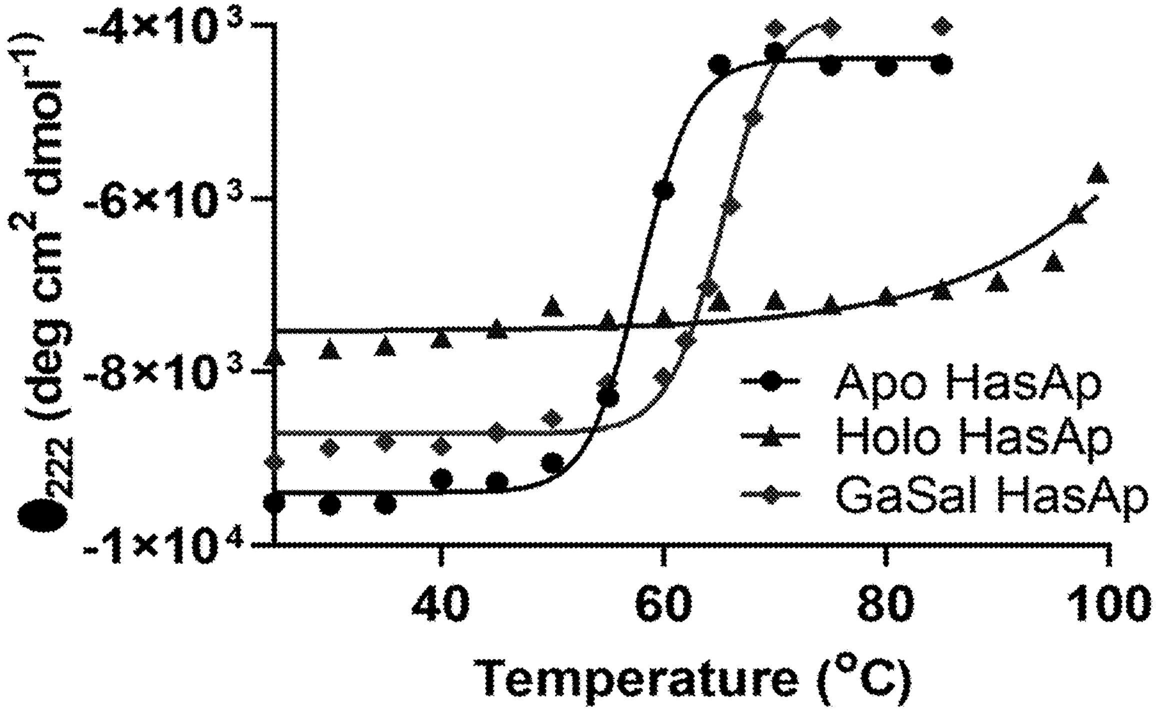

FIG. 12A illustrates regions showing the most significant changes in deutierium uptake labeled (purple) and mapped onto the structure of holo-HasAp. Heme was shown in blue and GaSal was shown in red. FIG. 12B illustrates deuteration of a peptide of residues 26-54. FIG. 12C illustrates thermal denaturation profiles of apo-, holo-, and GaSal-HasAp.

Figure 13:
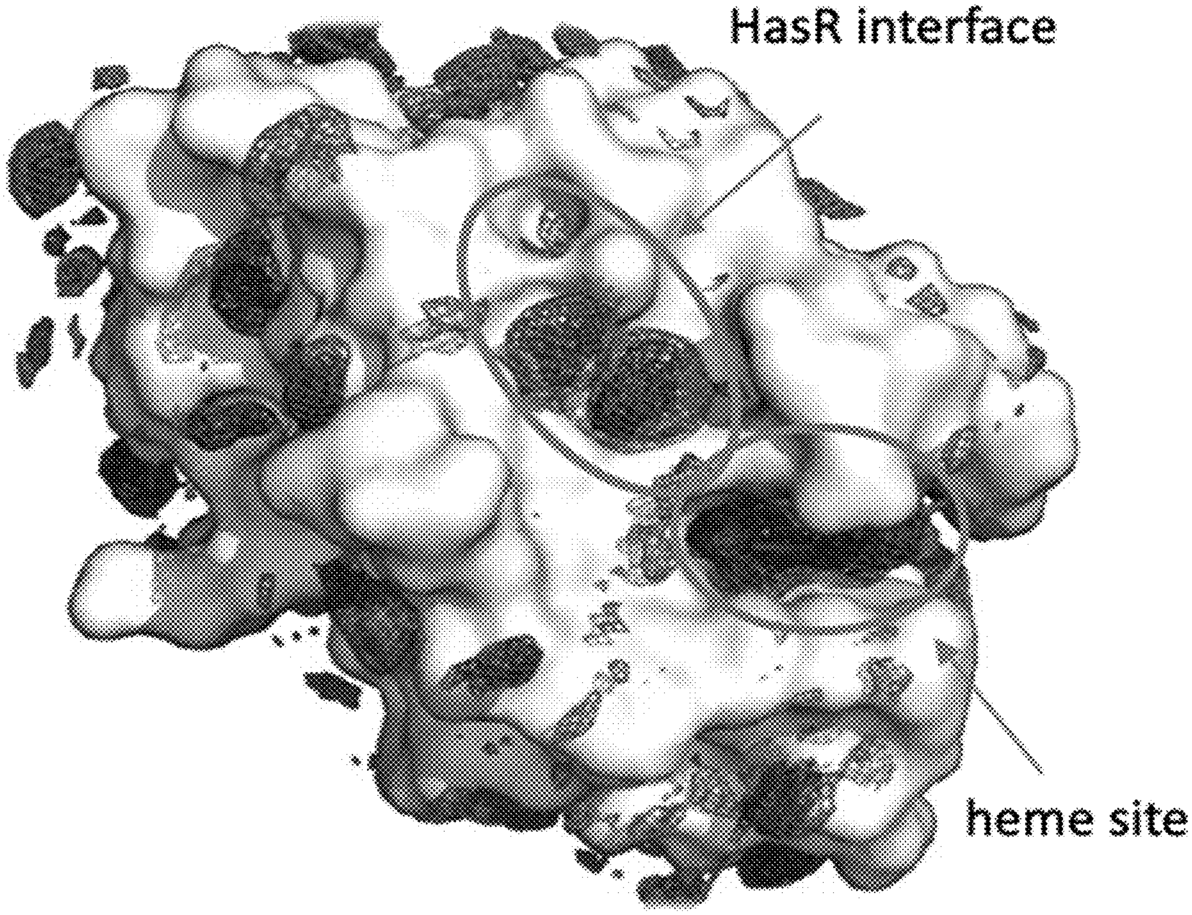

FIG. 13 illustrates the binding mode of GaSal in HasAp (PDB ID: 3w8m) overlaid with the SILCS apolar (green), H-bond-donor (blue), H-bond-acceptor (red), negative (orange), and positive (cyan) FragMaps. FragMaps are shown at contour levels of −1.0 kcal/mol or the generic apolar Hbond-donor and Hbond-acceptor maps and at −1.5 kcal/mol for the generic apolar, negative, and positive maps.

Figure 14:
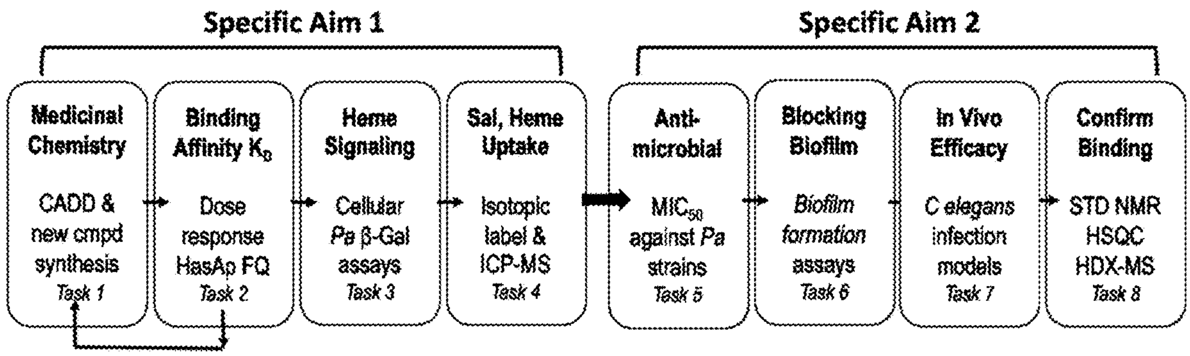

FIG. 14 illustrates an exemplary strategy for the development of new compounds.

Figures 15A, 15B:
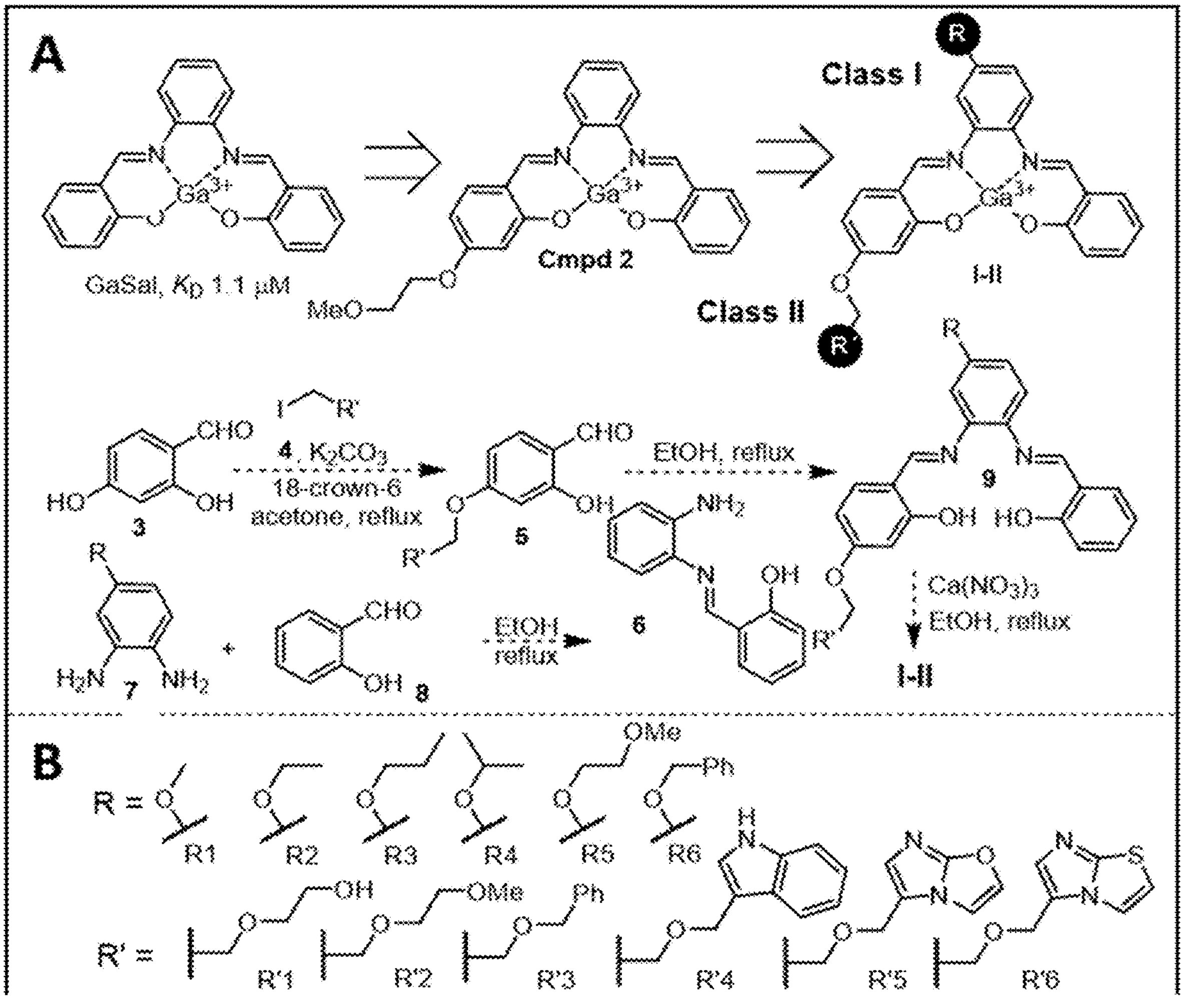

FIG. 15A illustrates the design of new metal-salophen complexes, including the synthesis of metal-salophen complexes I-II and exemplary functional groups for R and R'. FIG. 15B illustrates SILCS based LGFE energy differences (kcal/mol) compared to compound 2.

Figure 16:
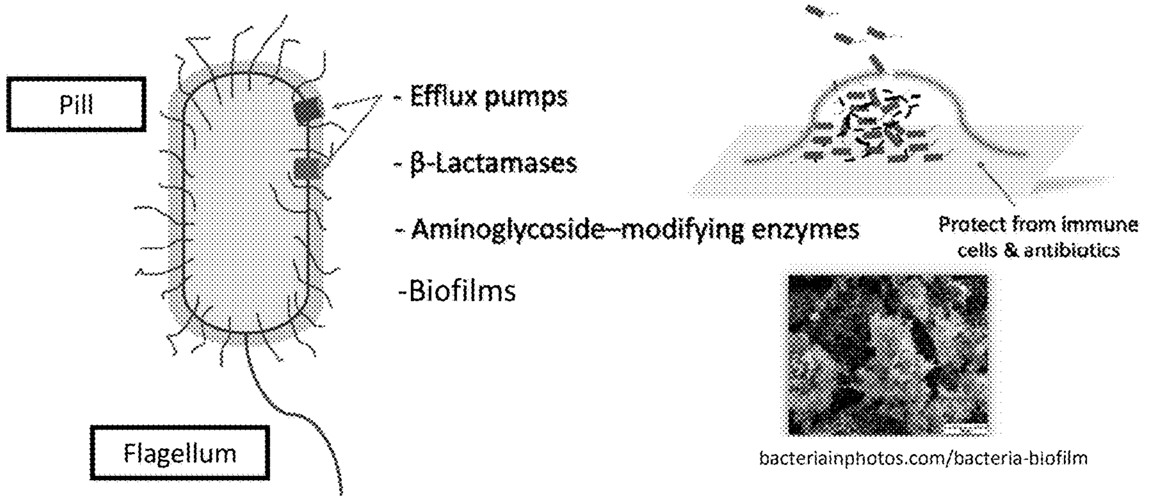

FIG. 16 illustrates an image of *P. aeruginosa* and its respective mechanisms for protection from immune cells and antibiotics.

Figure 17:
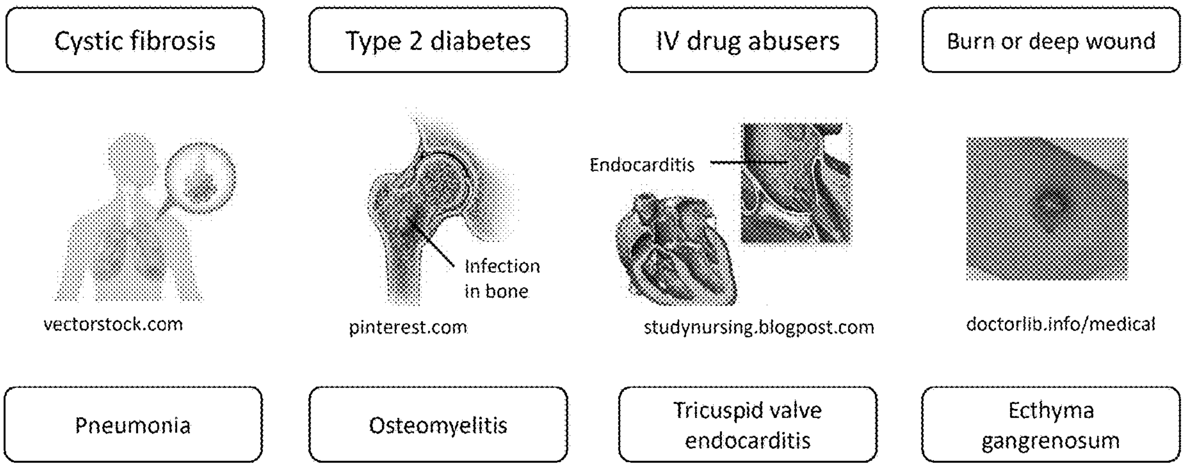

FIG. 17 illustrates examples of opportunistic but life-threatening infections caused by *P. aeruginosa* in immunocompromised subjects.

Figure 18:
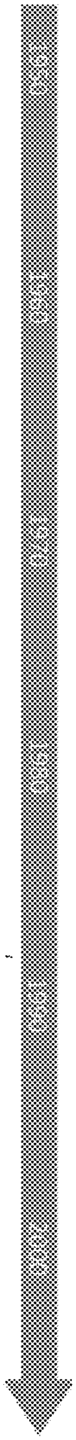
Figure 18:
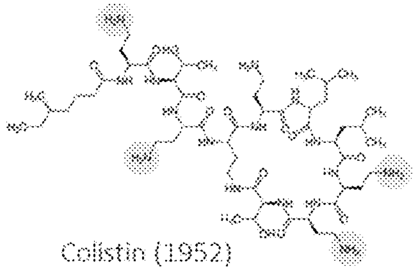
Figure 18:
Figure 18:
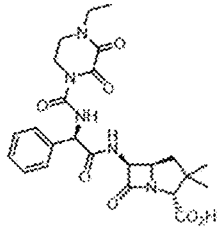
Figure 18:
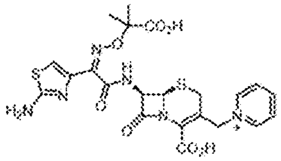
Figure 18:
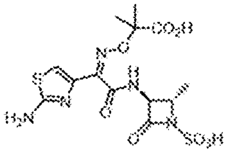
Figure 18:
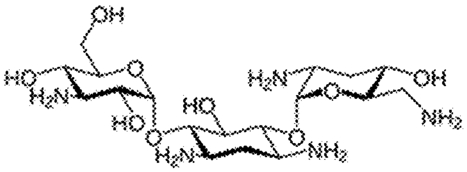
Figure 18:
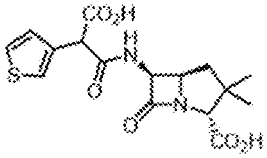
Figure 18:
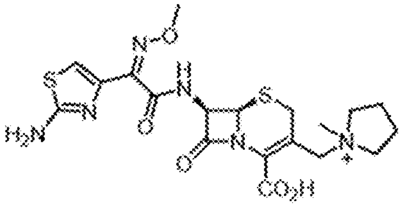
Figure 18:
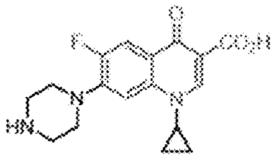

FIG. 18 illustrates compounds currently available for treating *P. aeruginosa* infections.

Figure 19:
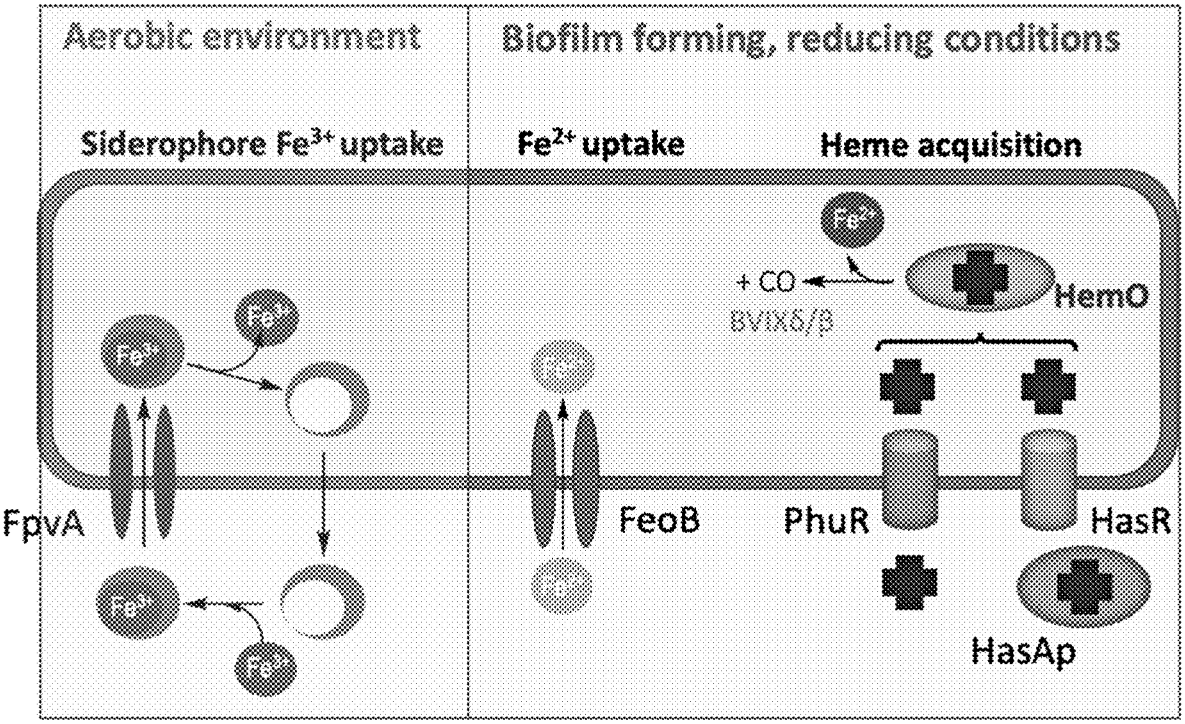

FIG. 19 illustrates the *P. aeruginosa* iron acquisition systems, including the heme acquisition system and the siderophore iron uptake system.

Figure 20:
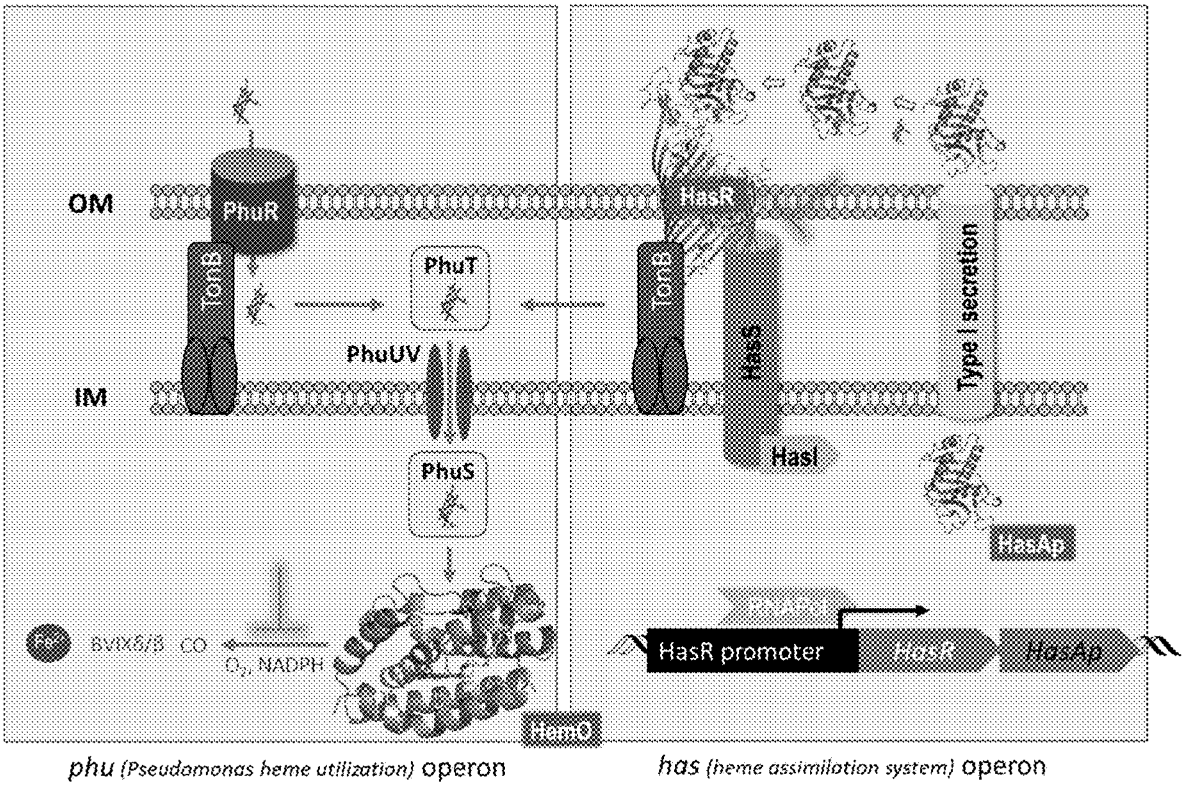

FIG. 20 illustrates the *P. aeruginosa* heme acquisition system.

Figure 21:
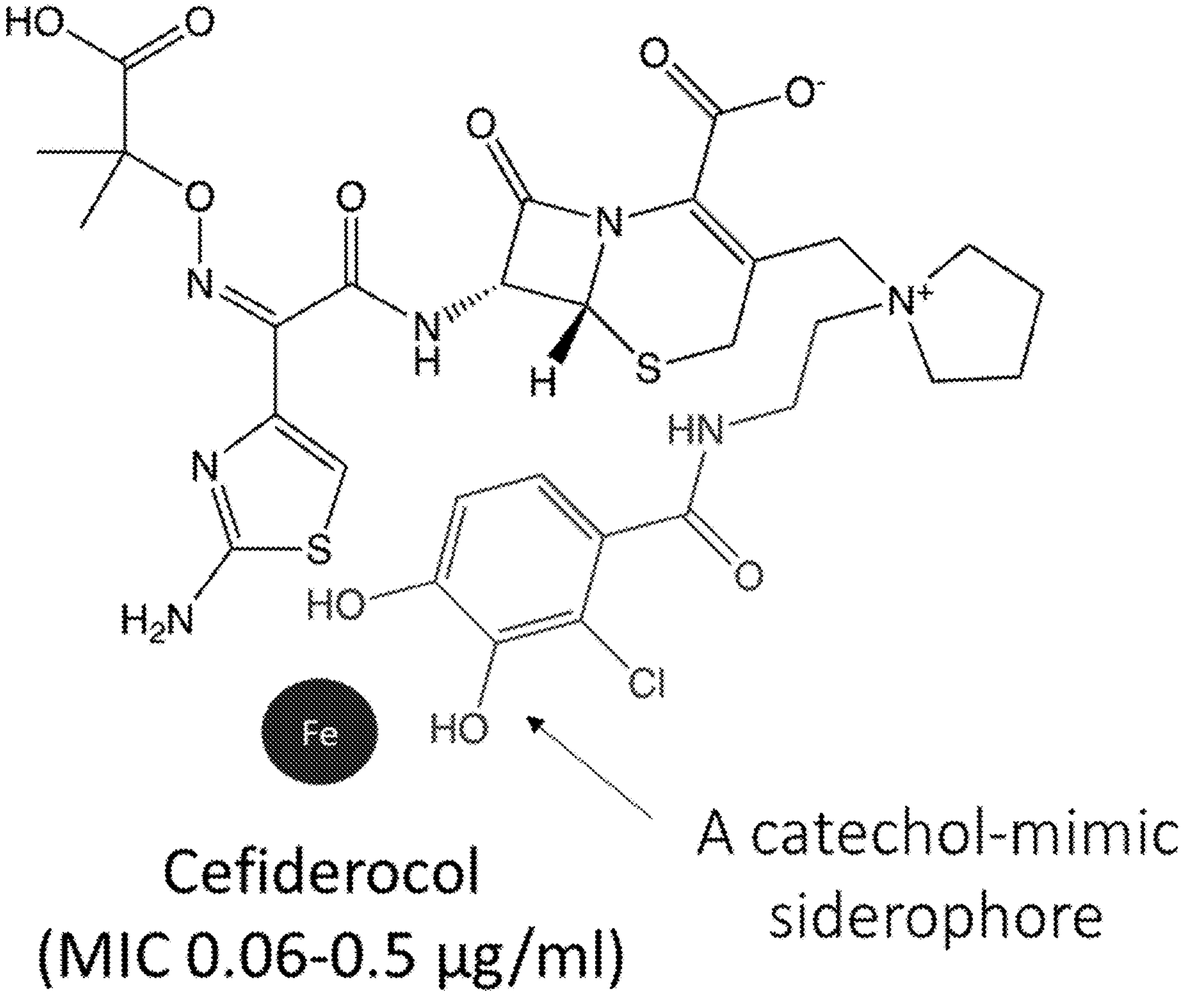

FIG. 21 illustrates the structure of an antibiotic (Cefiderocol) that can also act as a siderophore.

Figure 22:
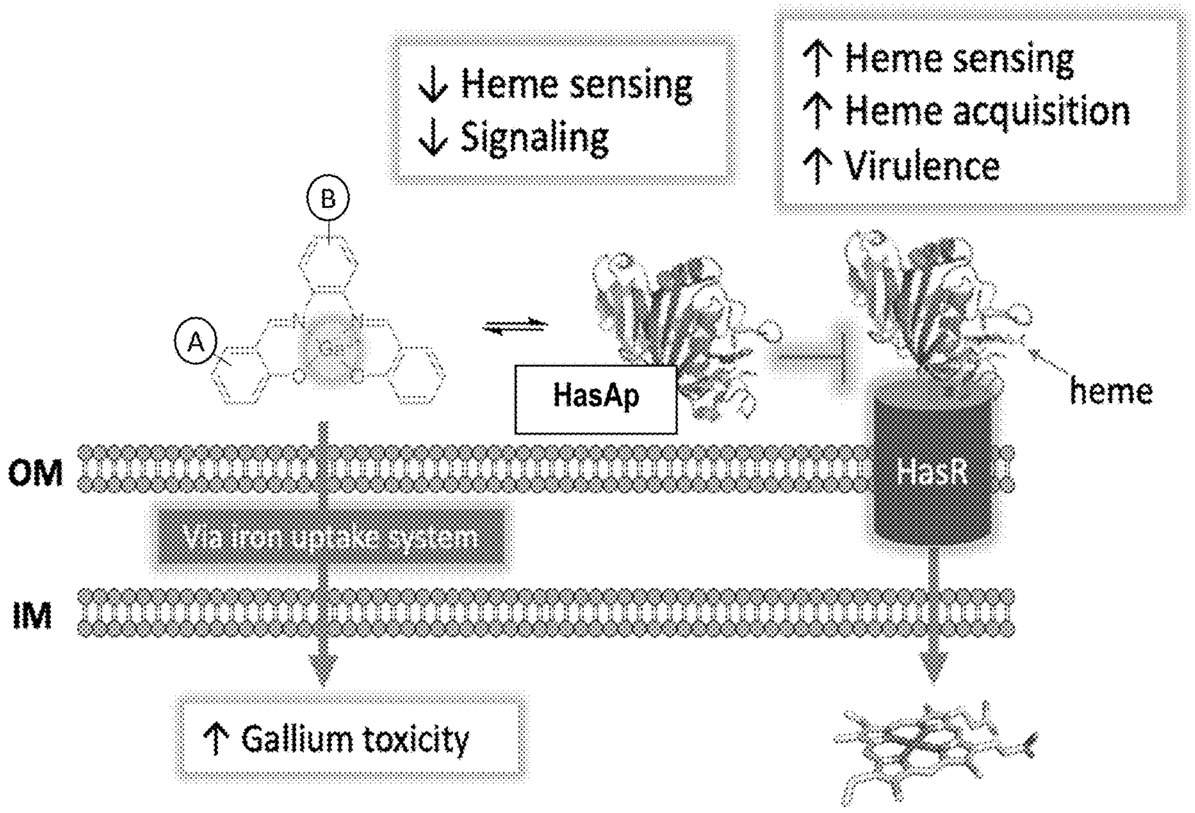

FIG. 22 illustrates an exemplary design strategy of compounds that simultaneously target both the heme signaling and utilization and the iron acquisition system.

Figure 23:
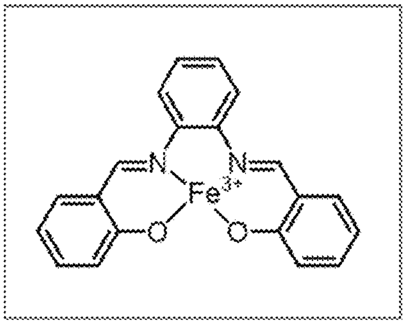
Figure 23:
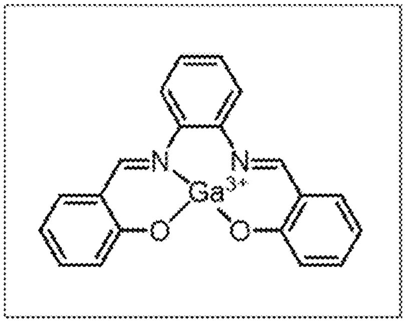
Figure 23:
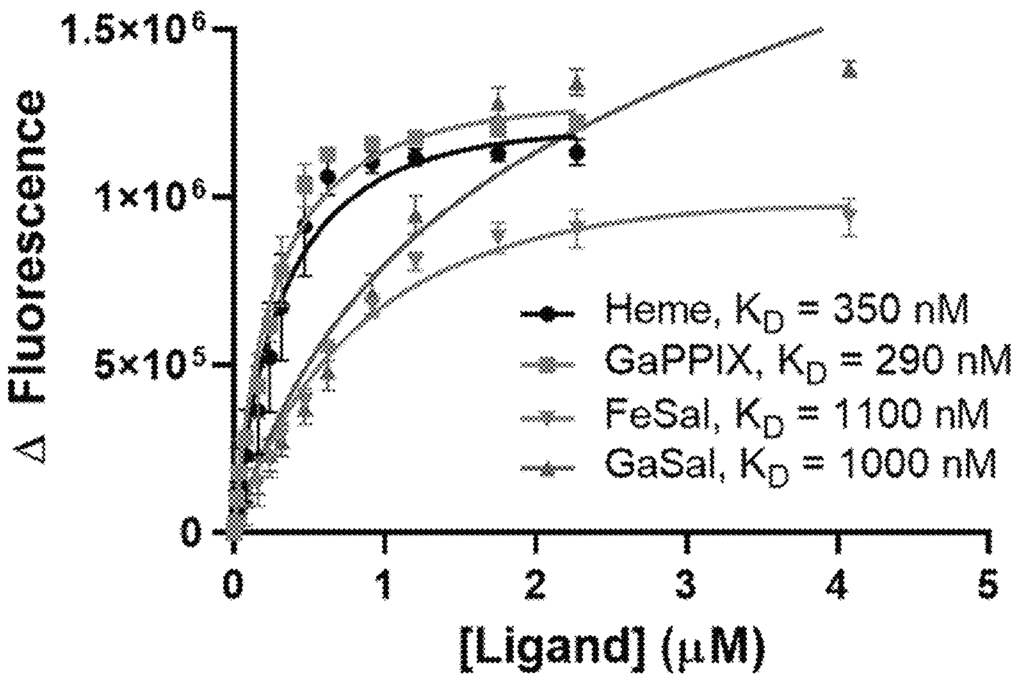

FIG. 23 illustrates the binding affinity of metallosalophens (GaSal and FeSal) to HasAp.

Figure 24:
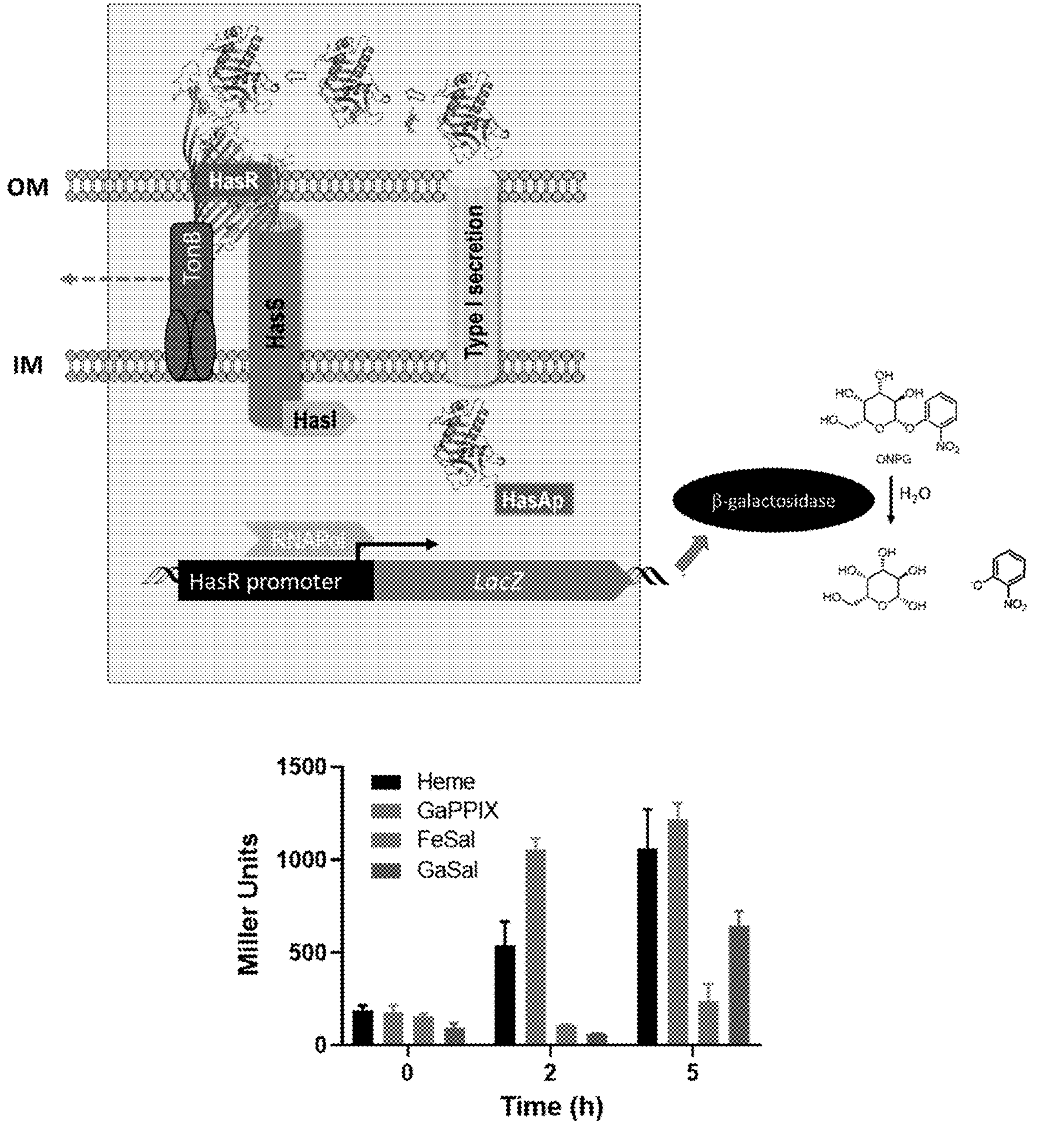

FIG. 24 illustrates that GaSal inhibits heme signaling and utilization based on the measured production of β-galactosidase.

Figure 25A:
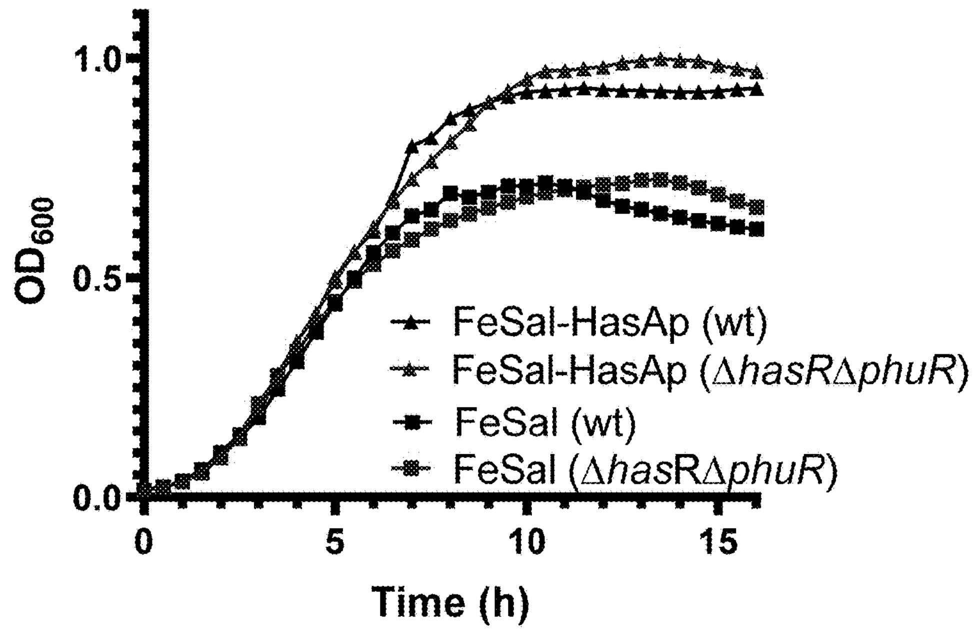
Figure 25B:
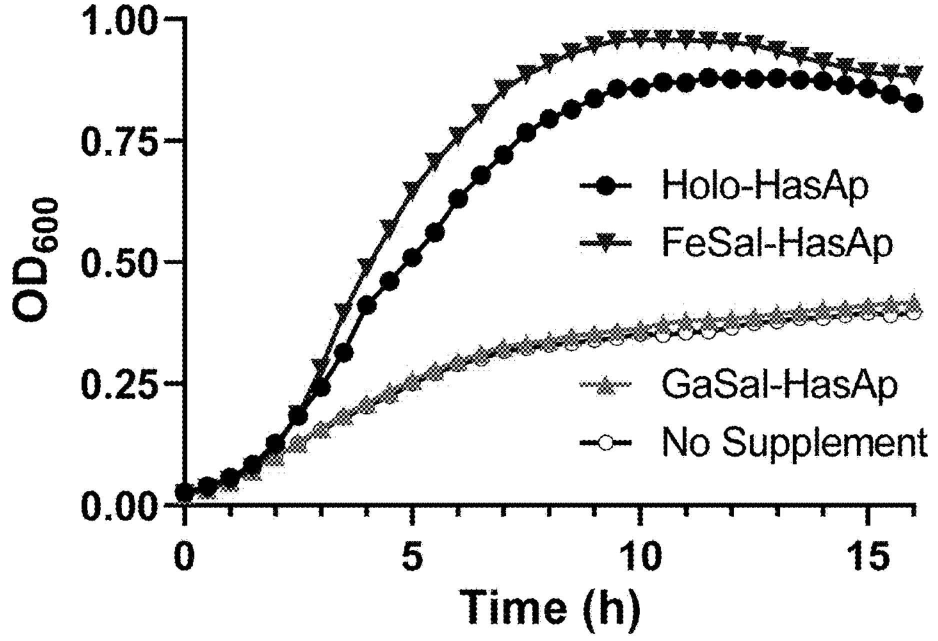

FIGS. 25A-25B illustrate that GaSal kills *P. aeruginosa* via gallium toxicity. FIG. 25A illustrates that FeSal-HasAp supports growth of *P. aeruginosa*. FIG. 25B illustrates that GaSal-HasAp exhibited antibacterial activity ($MIC_{50}$ of ~2.8 μg/mL).

Figure 26:
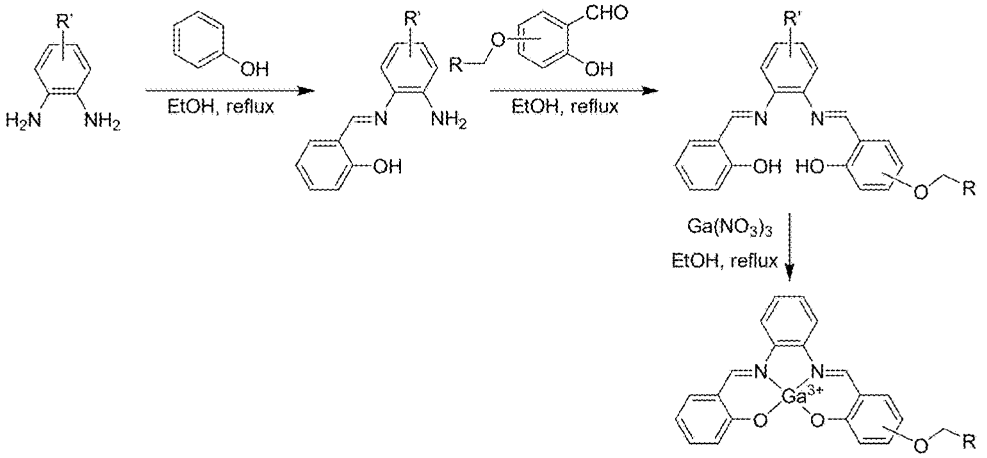
Figure 26:
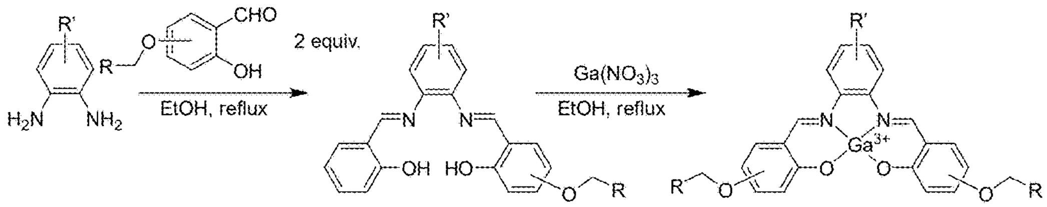
Figure 26:
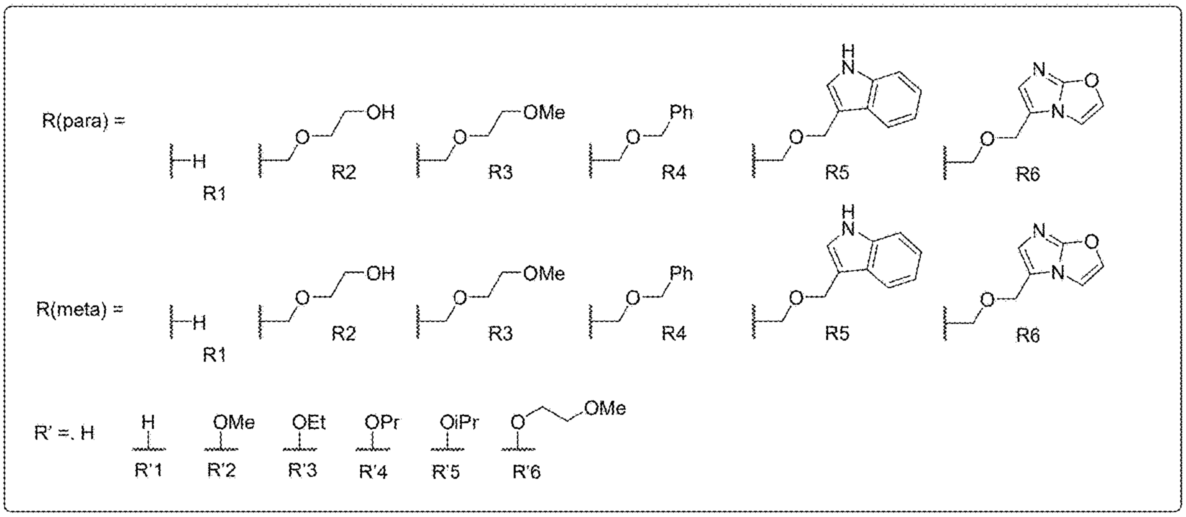

FIG. 26 illustrates compounds and an exemplary synthesis of gallium salophen complexes I and II.

Figure 27:
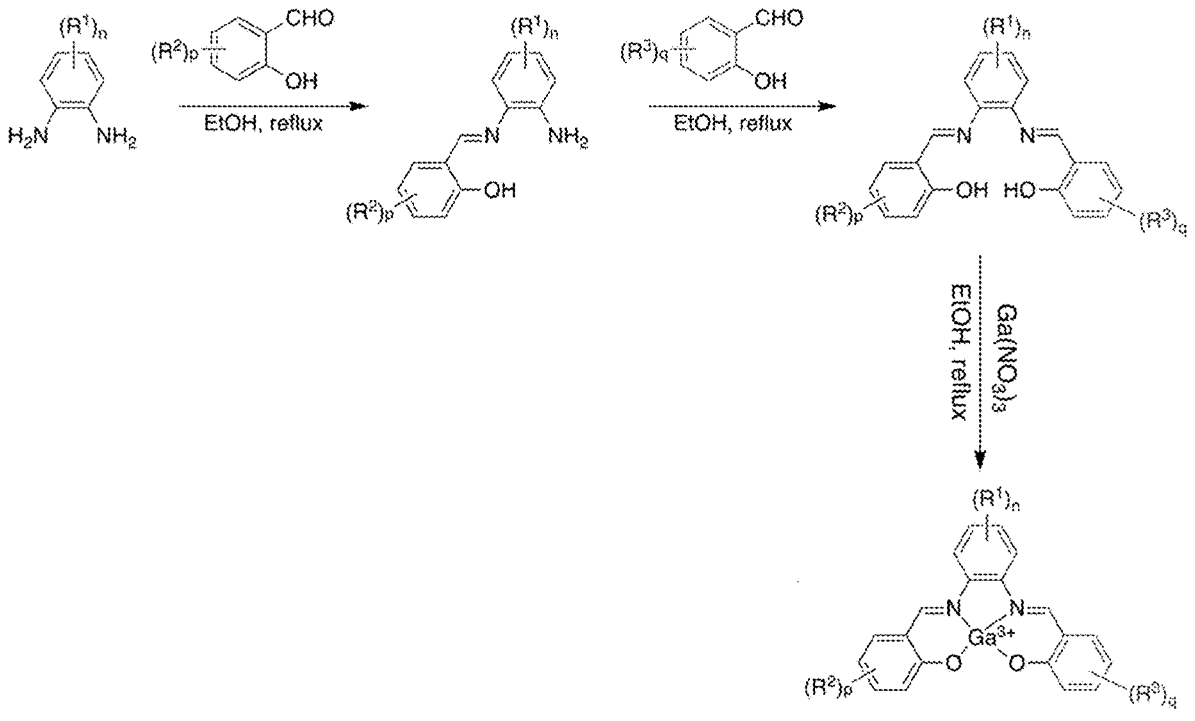

FIG. 27 illustrates an exemplary synthesis of examples of gallium salophen complexes.

Figure 28:
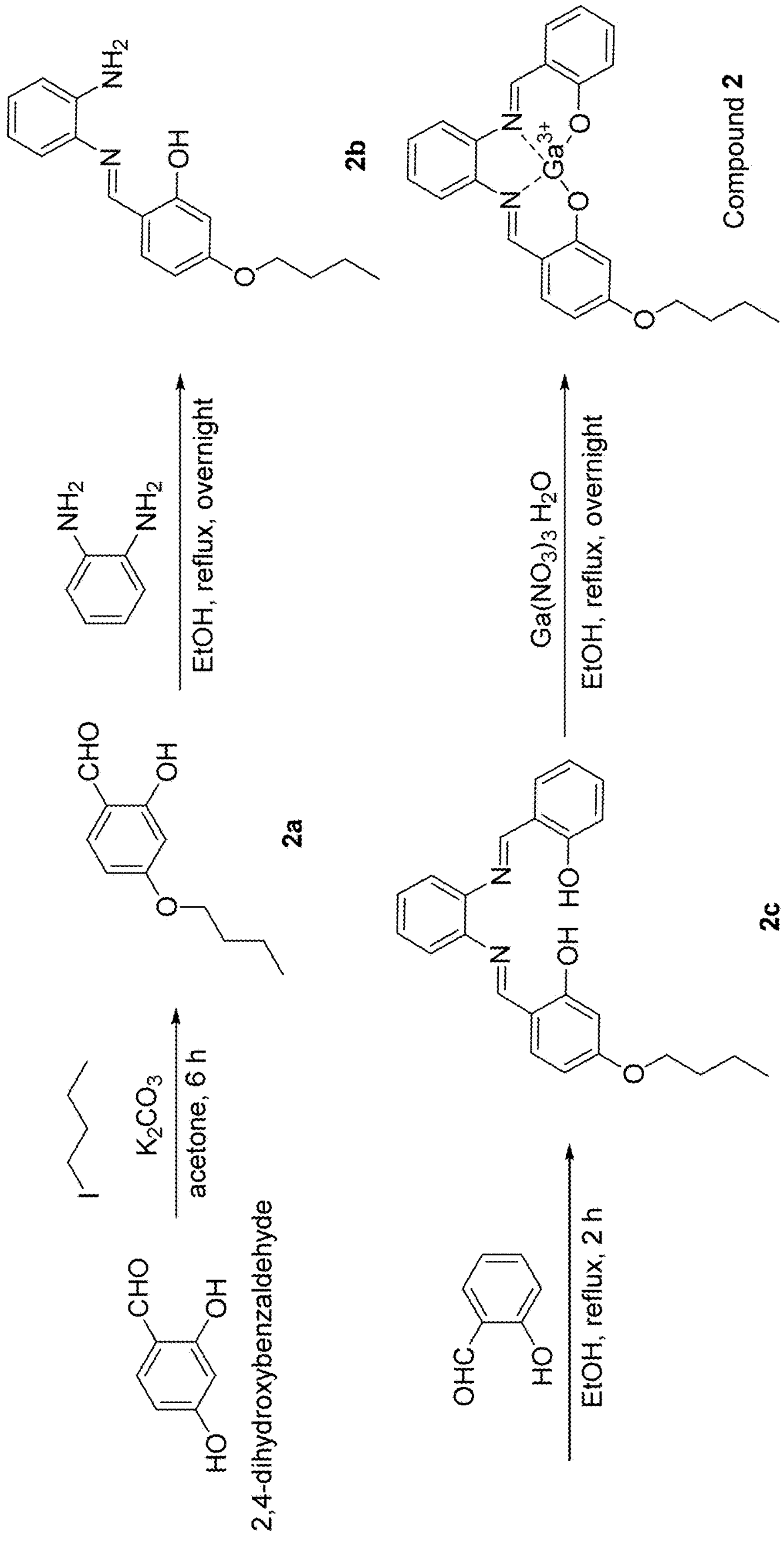

FIG. 28 illustrates an exemplary synthesis of compound 2.

Figure 29:
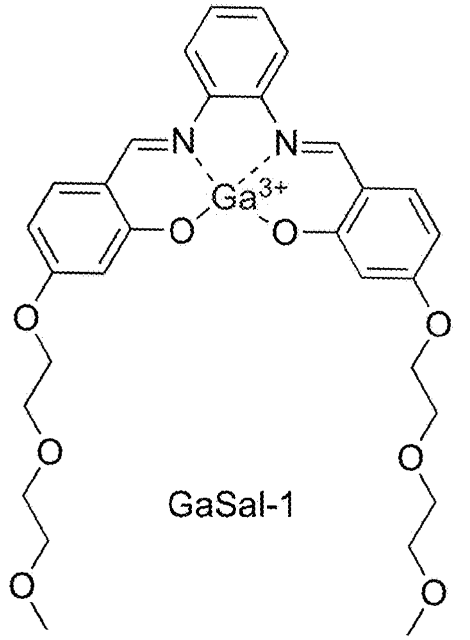
Figure 29:
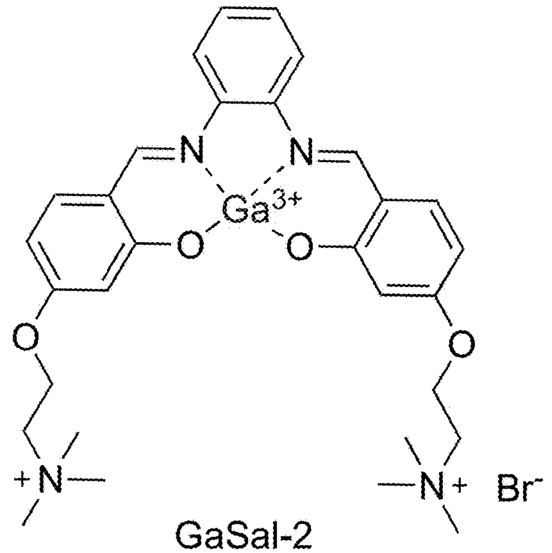
Figure 29:
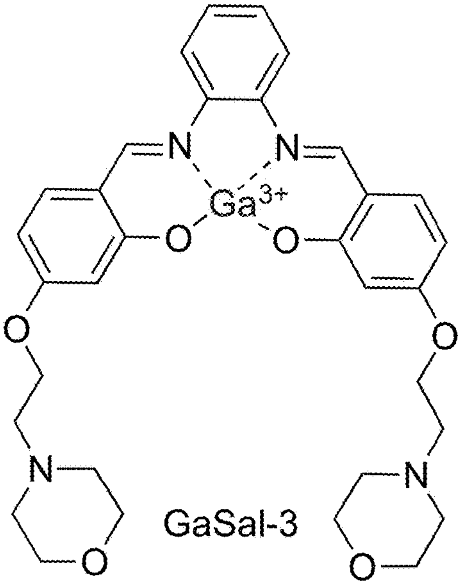
Figure 29:
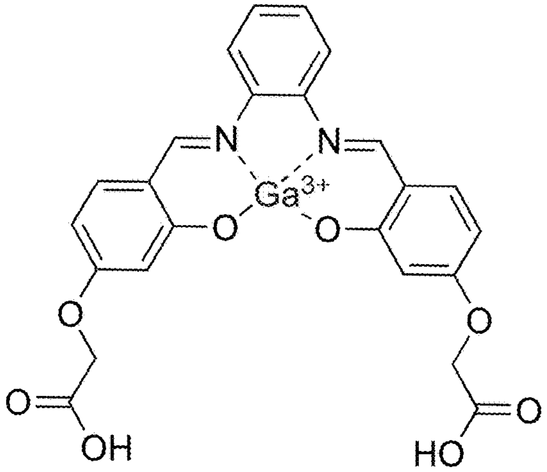

FIG. 29 illustrates the structures of compounds GaSal-1, GaSal-2, GaSal-3, and GaSal-4.

Figure 30:
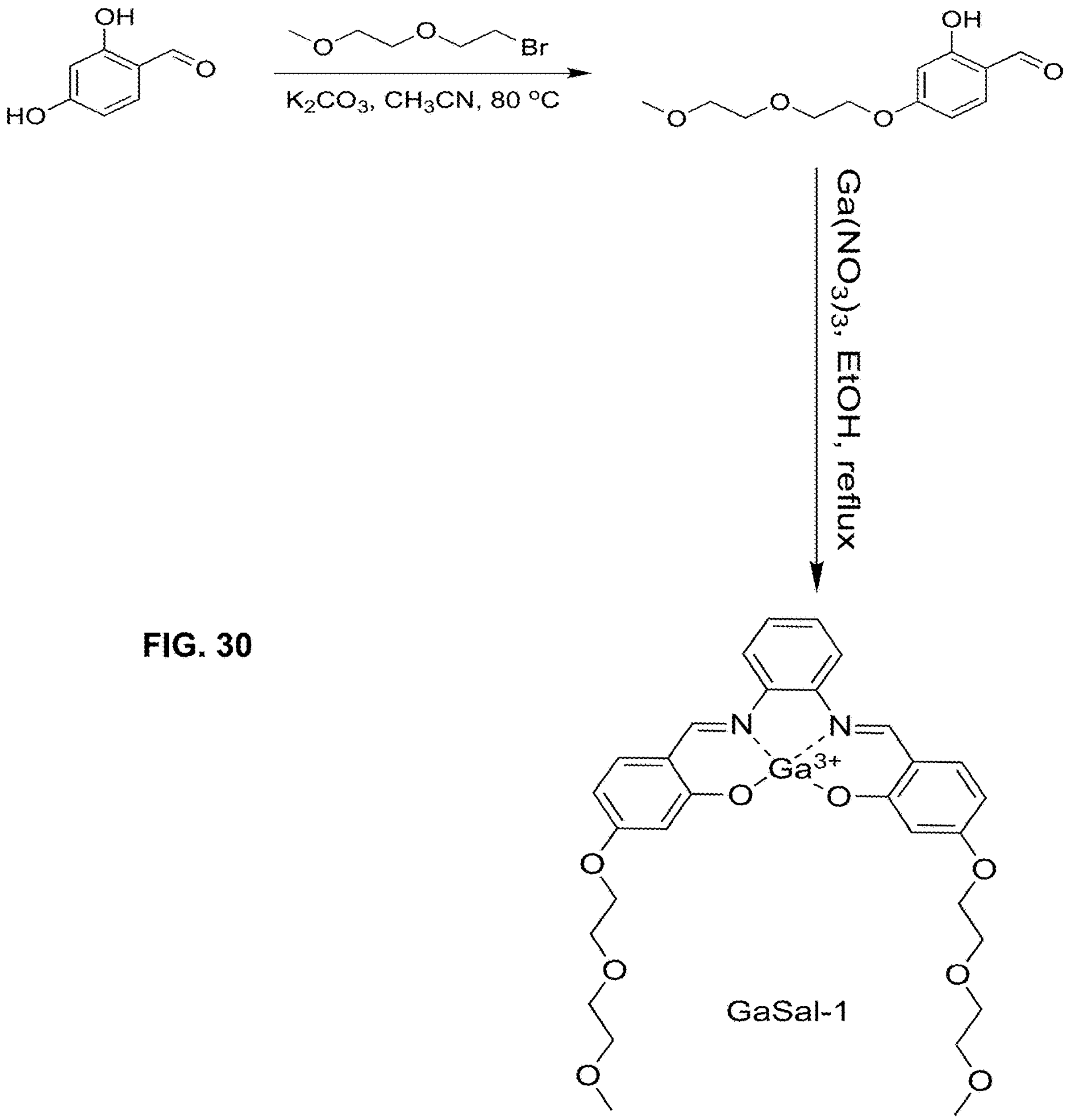

FIG. 30 illustrates an exemplary synthesis of GaSal-1.

Figure 31:
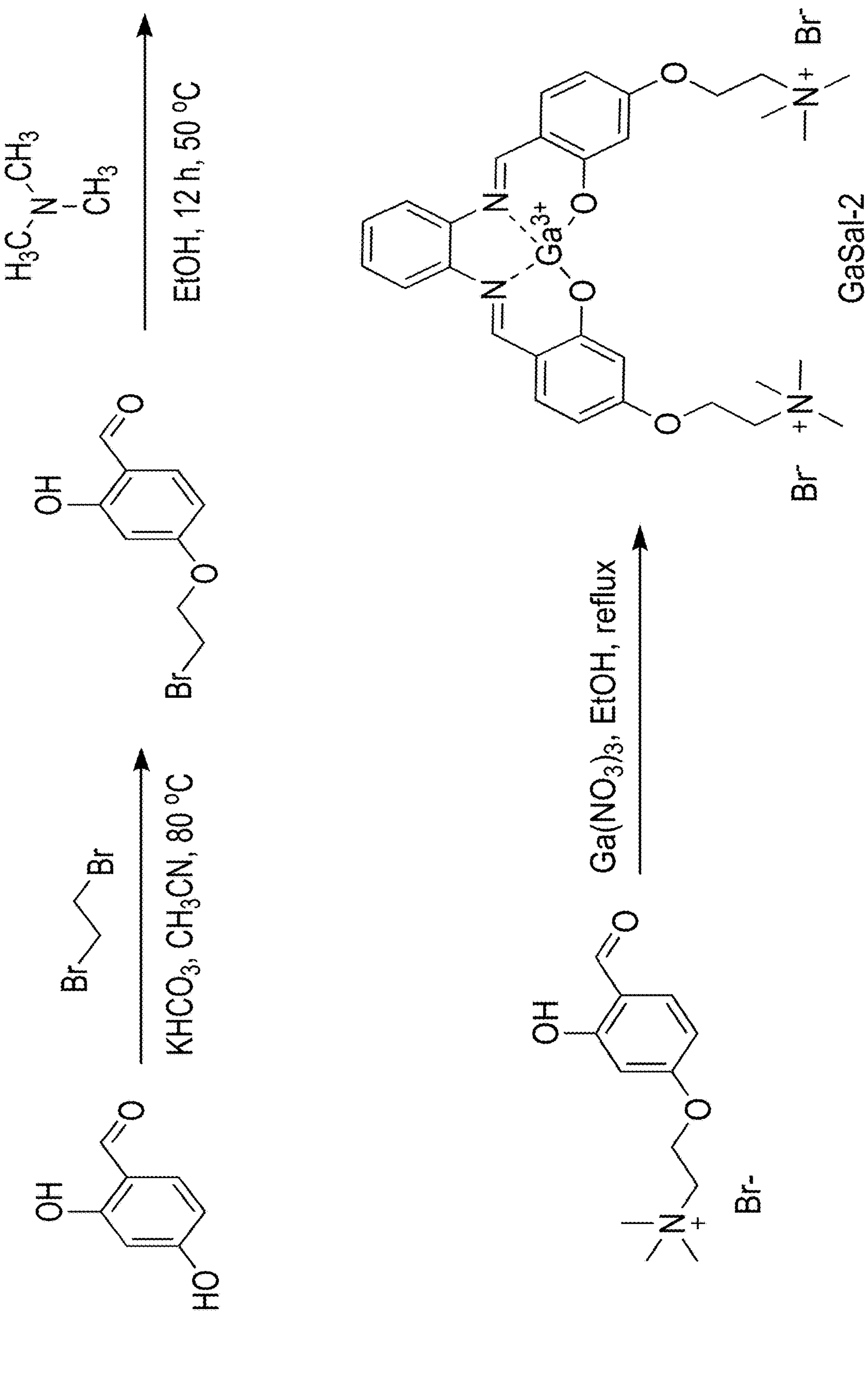

FIG. 31 illustrates an exemplary synthesis of GaSal-2.

Figure 32:
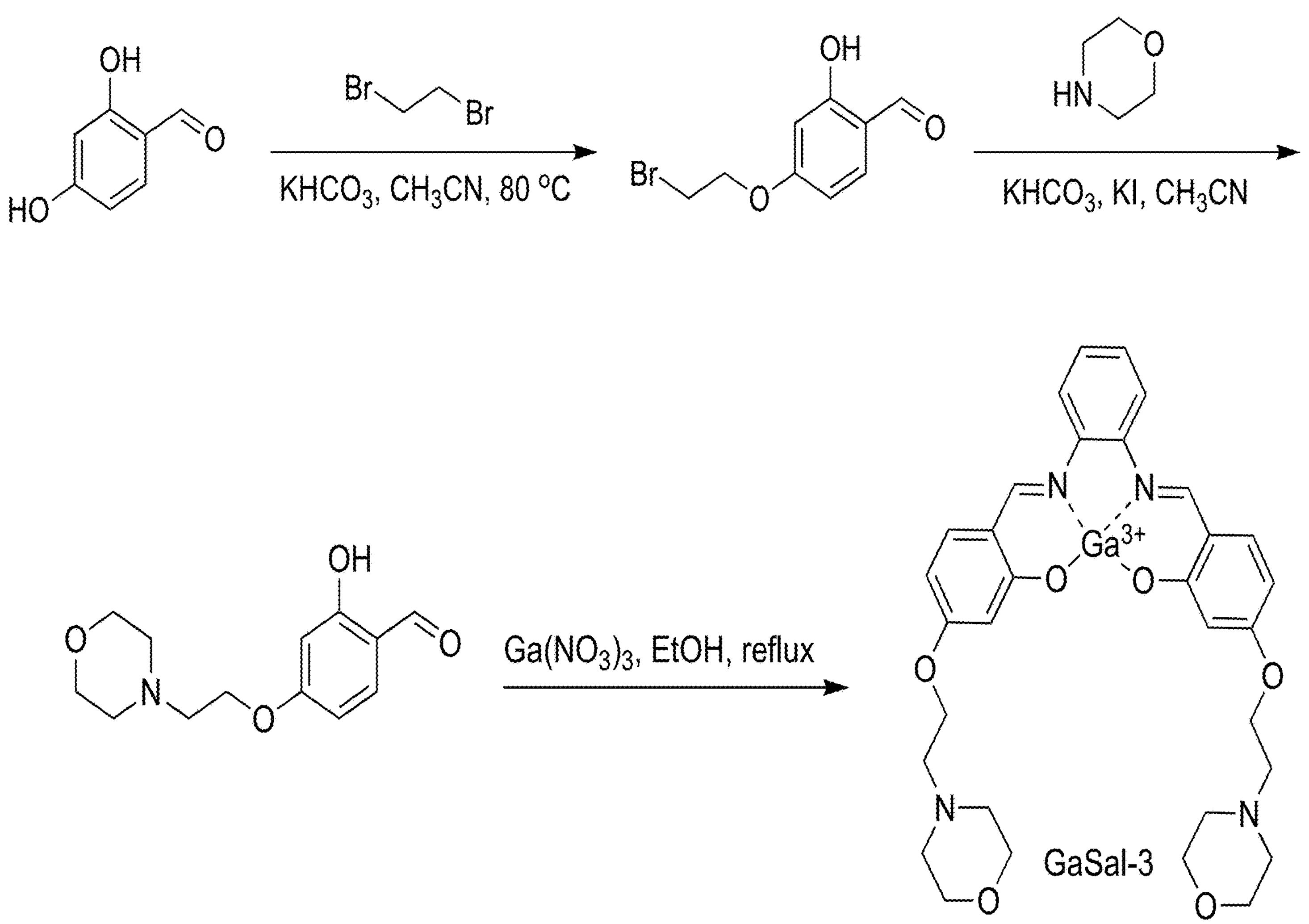

FIG. 32 illustrates an exemplary synthesis of GaSal-3.

Figure 33:
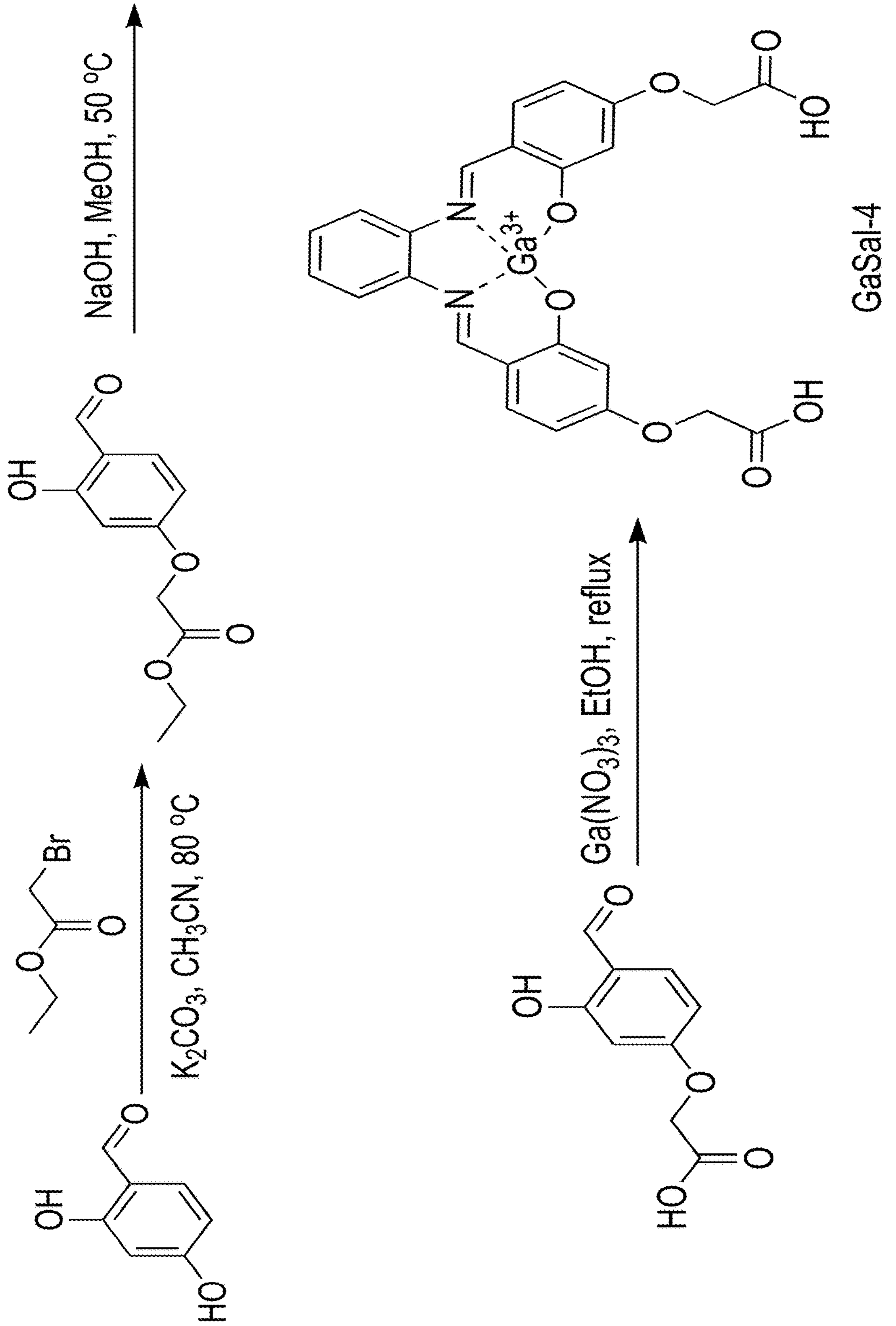

FIG. 33 illustrates an exemplary synthesis of GaSal-1.

DETAILED DESCRIPTION

Unless defined otherwise, all technical and scientific terms used herein have the same meaning as is commonly understood by one of skill in the art to which this disclosure belongs. All patents and publications referred to herein are incorporated by reference in their entireties.

Definitions

As used herein, the terms "administer," "administration" or "administering" refer to (1) providing, giving, dosing, and/or prescribing by either a health practitioner or his authorized agent or under his or her direction according to the disclosure; and/or (2) putting into, taking or consuming by the mammal, according to the disclosure.

The terms "co-administration," "co-administering," "administered in combination with," "administering in combination with," "simultaneous," and "concurrent," as used herein, encompass administration of two or more active pharmaceutical ingredients to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

The terms "active pharmaceutical ingredient" and "drug" include, but are not limited to, the compounds described herein and, more specifically: compounds of formula (I), formula (II), formula (III), formula (IV), formula (V), formula (VI), or formula (VII), formula (VIII), formula (IX), formula (X), formula (XI), and their features and limitations as described herein; compounds of formulas 1001-1567 and 2001-2028, and their features and limitations as described herein; compounds GaSal, compound 2, compound I, compound II, complex I, complex II, macrocyclic ligand III, GaSal-1, GaSal-2, GaSal-3, GaSal-4, and their features and limitations as described herein. The terms "active pharmaceutical ingredient" and "drug" may also include those compounds described herein that bind HasAp and/or the *P. aeruginosa* siderophore iron uptake system, and thereby modulate HasAp protein activity and/or *P. aeruginosa* siderophore iron uptake system activity, selectively bind HasAp, selectively bind the *P. aeruginosa* siderophore iron uptake system, or dually bind HasAp and *P. aeruginosa* siderophore iron uptake system.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., increased sensitivity to apoptosis). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit. A prophylactic effect includes delaying or eliminating the appearance of a disease or condition, delaying or eliminating the onset of symptoms of a disease or condition, slowing, halting, or reversing the progression of a disease or condition, or any combination thereof.

The terms "QD," "qd," or "q.d." mean quaque die, once a day, or once daily. The terms "BID," "bid," or "b.i.d." mean bis in die, twice a day, or twice daily. The terms "TID," "tid," or "t.i.d." mean ter in die, three times a day, or three times daily. The terms "QID," "qid," or "q.i.d." mean quater in die, four times a day, or four times daily.

The term "pharmaceutically acceptable salt" refers to salts derived from a variety of organic and inorganic counter ions known in the art. Pharmaceutically acceptable acid addition salts can be formed with inorganic acids and organic acids. Preferred inorganic acids from which salts can be derived include, for example, hydrochloric acid, hydrobromic acid, sulfuric acid, nitric acid and phosphoric acid. Preferred organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts. The term "cocrystal" refers to a molecular complex derived from a number of cocrystal formers known in the art. Unlike a salt, a cocrystal typically does not involve hydrogen transfer between the cocrystal and the drug, and instead involves intermolecular interactions, such as hydrogen bonding, aromatic ring stacking, or dispersive forces, between the cocrystal former and the drug in the crystal structure.

"Pharmaceutically acceptable carrier" or "pharmaceutically acceptable excipient" is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the disclosure is contemplated. Additional active pharmaceutical ingredients, such as other drugs disclosed herein, can also be incorporated into the described compositions and methods.

As used herein, the terms "treat," "treatment," and/or "treating" may refer to the management of a disease, disorder, or pathological condition, or symptom thereof with the intent to cure, ameliorate, stabilize, and/or control the disease, disorder, pathological condition or symptom thereof. Regarding control of the disease, disorder, or pathological condition more specifically, "control" may include the absence of condition progression, as assessed by the response to the methods recited herein, where such response may be complete (e.g., placing the disease in remission) or partial (e.g., lessening or ameliorating any symptoms associated with the condition).

As used herein, the terms "modulate" and "modulation" refer to a change in biological activity for a biological molecule (e.g., a protein, gene, peptide, antibody, and the like), where such change may relate to an increase in biological activity (e.g., increased activity, agonism, activation, expression, upregulation, and/or increased expression) or decrease in biological activity (e.g., decreased activity, antagonism, suppression, deactivation, downregulation, and/or decreased expression) for the biological molecule. In some embodiments, the biological molecules modulated by the methods and compounds of the disclosure to effect treatment may include the HasAp protein and protein of the *P. aeruginosa* siderophore iron uptake system.

As used herein, the term "prodrug" refers to a derivative of a compound described herein, the pharmacologic action of which results from the conversion by chemical or metabolic processes in vivo to the active compound. Prodrugs include compounds wherein an amino acid residue, or a polypeptide chain of two or more (e.g., two, three or four) amino acid residues is covalently joined through an amide or ester bond to a free amino, hydroxyl or carboxylic acid group of a compound of formula (I), formula (II), formula (III), formula (IV), formula (V), formula (VI), or formula (VII), formula (VIII), formula (IX), formula (X), formula (XI), a compound of any of formulas 1001-1567 and 2001-2028, or any of compounds GaSal, compound 2, compound I, compound II, complex I, complex II, macrocyclic ligand III, GaSal-1, GaSal-2, GaSal-3, and GaSal-4. The amino acid residues include but are not limited to the 20 naturally occurring amino acids commonly designated by one or three letter symbols but also include, for example, 4-hydroxyproline, hydroxylysine, desmosine, isodesmosine, 3-methylhistidine, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters (e.g., methyl esters and acetoxy methyl esters). Prodrug esters as employed herein includes esters and carbonates formed by reacting one or more hydroxyls of compounds of the method of the disclosure with alkyl, alkoxy, or aryl substituted acylating agents employing procedures known to those skilled in the art to generate acetates, pivalates, methylcarbonates, benzoates and the like. As further examples, free hydroxyl groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxyl and amino groups are also included, as are carbonate prodrugs, sulfonate prodrugs, sulfonate esters and sulfate esters of hydroxyl groups. Free amines can also be derivatized to amides, sulfonamides or phosphonamides. All of the stated prodrug moieties may incorporate groups including but not limited to ether, amine and carboxylic acid functionalities. Moreover, any compound that can be converted in vivo to provide the bioactive agent (e.g., a compound of formula (I), formula (II), formula (III), formula (IV), formula (V), formula (VI), or formula (VII), formula (VIII), formula (IX), formula (X), formula (XI), a compound of any of formulas 1001-1567 and 2001-2028, or any of compounds GaSal, compound 2, compound I, compound II, complex I, complex II, macrocyclic ligand III, GaSal-1, GaSal-2, GaSal-3, and GaSal-4) is a prodrug within the scope of the disclosure. Various forms of prodrugs are well known in the art. A comprehensive description of pro drugs and prodrug derivatives are described in: (a) The Practice of Medicinal Chemistry, Camille G. Wermuth et al., (Academic Press, 1996); (b) Design of Prodrugs, edited by H. Bundgaard, (Elsevier, 1985); (c) A Textbook of Drug Design and Development, P. Krogsgaard-Larson and H. Bundgaard, eds., (Harwood Academic Publishers, 1991). In general, prodrugs may be designed to improve the penetration of a drug across biological membranes in order to obtain improved drug absorption, to prolong duration of action of a drug (slow release of the parent drug from a prodrug, decreased first-pass metabolism of the drug), to target the drug action (e.g. organ or tumor-targeting, lymphocyte targeting), to modify or improve aqueous solubility of a drug (e.g., i.v. preparations and eyedrops), to improve topical drug delivery (e.g. dermal and ocular drug delivery), to improve the chemical/enzymatic stability of a drug, or to decrease off-target drug effects, and more generally in order to improve the therapeutic efficacy of the compounds utilized in the disclosure.

Unless otherwise stated, the chemical structures depicted herein are intended to include compounds which differ only in the presence of one or more isotopically enriched atoms. For example, compounds where one or more hydrogen atoms is replaced by deuterium or tritium, or wherein one or more carbon atoms is replaced by $^{13}C$- or $^{14}C$-enriched carbons, are within the scope of this disclosure.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, preferably from 0% to 10%, more preferably from 0% to 5% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

"Alkyl" refers to a straight or branched hydrocarbon chain radical consisting solely of carbon and hydrogen atoms, containing no unsaturation, having from one to ten carbon atoms (e.g., $(C_{1-10})$alkyl or $C_{1-10}$ alkyl). Whenever it appears herein, a numerical range such as "1 to 10" refers to each integer in the given range—e.g., "1 to 10 carbon atoms" means that the alkyl group may consist of 1 carbon atom, 2 carbon atoms, 3 carbon atoms, etc., up to and including 10 carbon atoms, although the definition is also intended to cover the occurrence of the term "alkyl" where no numerical range is specifically designated. Typical alkyl groups include, but are in no way limited to, methyl, ethyl, propyl, isopropyl, n-butyl, isobutyl, sec-butyl isobutyl, tertiary butyl, pentyl, isopentyl, neopentyl, hexyl, septyl, octyl, nonyl and decyl. The alkyl moiety may be attached to the rest of the molecule by a single bond, such as for example, methyl (Me), ethyl (Et), n-propyl (Pr), 1-methylethyl (isopropyl), n-butyl, n-pentyl, 1,1-dimethylethyl (t-butyl) and 3-methylhexyl. Unless stated otherwise specifically in the specification, an alkyl group is optionally substituted by one or more of substituents which are independently heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, $—OR^a$, $—SR^a$, $—OC(O)—R^a$, $—N(R^a)_2$, $—C(O)R^a$, $—C(O)OR^a$, $—OC(O)N(R^a)_2$, $—C(O)N(R^a)_2$, $—N(R^a)C(O)OR^a$, $—N(R^a)C(O)R^a$, $—N(R^a)C(O)N(R^a)_2$, $N(R^a)C(NR^a)N(R^a)_2$, $—N(R^a)S(O)_tR^a$ (where t is 1 or 2), $—S(O)_tR^a$ (where t is 1 or 2), $—S(O)_tOR^a$ (where t is 1 or 2), $—S(O)_tN(R^a)_2$ (where t is 1 or 2), or $PO_3(R^a)_2$ where each $R^a$ is independently hydrogen, fluoroalkyl, carbocyclyl, carbocyclylalkyl, aryl, aralkyl, heterocycloalkyl, heterocycloalkylalkyl, heteroaryl or heteroarylalkyl.

"Alkylaryl" refers to an -(alkyl)aryl radical where aryl and alkyl are as disclosed herein and which are optionally substituted by one or more of the substituents described as suitable substituents for aryl and alkyl respectively.

"Alkylhetaryl" refers to an -(alkyl)hetaryl radical where hetaryl and alkyl are as disclosed herein and which are optionally substituted by one or more of the substituents described as suitable substituents for aryl and alkyl respectively.

"Alkylheterocycloalkyl" refers to an -(alkyl) heterocyclyl radical where alkyl and heterocycloalkyl are as disclosed herein and which are optionally substituted by one or more of the substituents described as suitable substituents for heterocycloalkyl and alkyl respectively.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (i.e., $(C_{2-10})$alkenyl or $C_{2-10}$ alkenyl). Whenever it appears herein, a numerical range such as "2 to 10" refers to each integer in the given range—e.g., "2 to 10 carbon atoms" means that the alkenyl group may consist of 2 carbon atoms, 3 carbon atoms, etc., up to and including 10 carbon atoms. The alkenyl moiety may be attached to the rest of the molecule by a single bond, such as for example, ethenyl (i.e., vinyl), prop-1-enyl (i.e., allyl), but-1-enyl, pent-1-enyl and penta-1,4-dienyl. Unless stated otherwise specifically in the specification, an alkenyl group is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, $—OR^a$, $—SR^a$, $—OC(O)—R^a$, $—N(R^a)_2$, $—C(O)R^a$, $—C(O)OR^a$, $—OC(O)N(R^a)_2$, $—C(O)N(R^a)_2$, $—N(R^a)C(O)OR^a$, $—N(R^a)C(O)R^a$, $—N(R^a)C(O)N(R^a)_2$, $N(R^a)C(NR^a)N(R^a)_2$, $—N(R^a)S(O)_tR^a$ (where t is 1 or 2), $—S(O)_tR^a$ (where t is 1 or 2), $—S(O)_tOR^a$ (where t is 1 or 2), $—S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to an -(alkenyl)cycloalkyl radical where alkenyl and cycloalkyl are as disclosed herein and which are optionally substituted by one or more of the substituents described as suitable substituents for alkenyl and cycloalkyl respectively.

"Alkynyl" refers to a straight or branched hydrocarbon chain radical group consisting solely of carbon and hydrogen atoms, containing at least one triple bond, having from two to ten carbon atoms (i.e., $(C_{2-10})$alkynyl or $C_{2-10}$ alkynyl). Whenever it appears herein, a numerical range such as "2 to 10" refers to each integer in the given range—e.g., "2 to 10 carbon atoms" means that the alkynyl group may consist of 2 carbon atoms, 3 carbon atoms, etc., up to and including 10 carbon atoms. The alkynyl may be attached to the rest of the molecule by a single bond, for example, ethynyl, propynyl, butynyl, pentynyl and hexynyl. Unless stated otherwise specifically in the specification, an alkynyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, $—OR^a$, $—SR^a$, $—OC(O)—R^a$, $—N(R^a)_2$, $—C(O)R^a$, $—C(O)OR^a$, $—OC(O)N(R^a)_2$, $—C(O)N(R^a)_2$, $—N(R^a)C(O)OR^a$, $—N(R^a)C(O)R^a$, $—N(R^a)C(O)N(R^a)_2$, $N(R^a)C(NR^a)N(R^a)_2$, $—N(R^a)S(O)_tR^a$ (where t is 1 or 2), $—S(O)_tR^a$ (where t is 1 or 2), $—S(O)_tOR^a$ (where t is 1 or 2), $—S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkynyl-cycloalkyl" refers to an -(alkynyl)cycloalkyl radical where alkynyl and cycloalkyl are as disclosed herein and which are optionally substituted by one or more of the substituents described as suitable substituents for alkynyl and cycloalkyl respectively.

"Carboxaldehyde" refers to a —(C═O)H radical.

"Carboxyl" refers to a —(C═O)OH radical.

"Cyano" refers to a —CN radical.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e. $(C_{3-10})$cycloalkyl or $C_{3-10}$ cycloalkyl). Whenever it appears herein, a numerical range such as "3 to 10" refers to each integer in the given range—e.g., "3 to 10 carbon atoms" means that the cycloalkyl group may consist of 3 carbon atoms, etc., up to and including 10 carbon atoms. Illustrative examples of cycloalkyl groups include, but are not limited to the following moieties: cyclopropyl, cyclobutyl, cyclopentyl, cyclopentenyl, cyclohexyl, cyclohexenyl, cycloheptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, $—OR^a$, $—SR^a$, $—OC(O)—R^a$, $—N(R^a)_2$, $—C(O)R^a$, $—C(O)OR^a$, $—OC(O)N(R^a)_2$, $—C(O)N(R^a)_2$, $—N(R^a)C(O)OR^a$, $—N(R^a)C(O)R^a$, $—N(R^a)C(O)N(R^a)_2$, $N(R^a)C(NR^a)N(R^a)_2$, $—N(R^a)S(O)_tR^a$ (where t is 1 or 2), $—S(O)_tR^a$ (where t is 1 or 2), $—S(O)_tOR^a$ (where t is 1 or 2), $—S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl-alkenyl" refers to a -(cycloalkyl)alkenyl radical where cycloalkyl and alkenyl are as disclosed herein and which are optionally substituted by one or more of the substituents described as suitable substituents for cycloalkyl and alkenyl, respectively.

"Cycloalkyl-heterocycloalkyl" refers to a -(cycloalkyl)heterocycloalkyl radical where cycloalkyl and heterocycloalkyl are as disclosed herein and which are optionally substituted by one or more of the substituents described as suitable substituents for cycloalkyl and heterocycloalkyl, respectively.

"Cycloalkyl-heteroaryl" refers to a -(cycloalkyl)heteroaryl radical where cycloalkyl and heteroaryl are as disclosed herein and which are optionally substituted by one or more of the substituents described as suitable substituents for cycloalkyl and heteroaryl, respectively.

The term "alkoxy" refers to the group —O-alkyl, including from 1 to 8 carbon atoms of a straight, branched, cyclic configuration and combinations thereof attached to the parent structure through an oxygen. Examples include, but are not limited to, methoxy, ethoxy, propoxy, isopropoxy, cyclopropyloxy and cyclohexyloxy. "Lower alkoxy" refers to alkoxy groups containing one to six carbons.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, $—OR^a$, $—SR^a$, $—OC(O)—R^a$, $—N(R^a)_2$, $—C(O)R^a$, $—C(O)OR^a$, $—OC(O)N(R^a)_2$, $—C(O)N(R^a)_2$, $—N(R^a)C(O)OR^a$, $—N(R^a)C(O)R^a$, $—N(R^a)C(O)N(R^a)_2$, $N(R^a)C(NR^a)N(R^a)_2$, $—N(R^a)S(O)_tR^a$ (where t is 1 or 2), $—S(O)_tR^a$ (where t is 1 or 2), $—S(O)_tOR^a$ (where t is 1 or 2), $—S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxycarbonyl" refers to a group of the formula (alkoxy)(C═O)— attached through the carbonyl carbon wherein the alkoxy group has the indicated number of carbon atoms. Thus a $(C_{1-6})$alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group.

The term "substituted alkoxycarbonyl" refers to the group (substituted alkyl)-O—C(O)— wherein the group is attached to the parent structure through the carbonyl functionality. Unless stated otherwise specifically in the specification, the alkyl moiety of an alkoxycarbonyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N$(R^a)_2$, —C(O)N$(R^a)_2$, —N$(R^a)$C(O)O$R^a$, —N$(R^a)$C(O)$R^a$, —N$(R^a)$C(O)N$(R^a)_2$, N$(R^a)$C(N$R^a$)N$(R^a)_2$, —N$(R^a)$S(O)$_t$$R^a$ (where t is 1 or 2), —S(O)$_t$$R^a$ (where t is 1 or 2), —S(O)$_t$O$R^a$ (where t is 1 or 2), —S(O)$_t$N$(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyl" refers to the groups (alkyl)-C(O)—, (aryl)-C(O)—, (heteroaryl)-C(O)—, (heteroalkyl)-C(O)— and (heterocycloalkyl)-C(O)—, wherein the group is attached to the parent structure through the carbonyl functionality. If the R radical is heteroaryl or heterocycloalkyl, the hetero ring or chain atoms contribute to the total number of chain or ring atoms. Unless stated otherwise specifically in the specification, the alkyl, aryl or heteroaryl moiety of the acyl group is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N$(R^a)_2$, —C(O)N$(R^a)_2$, —N$(R^a)$C(O)O$R^a$, —N$(R^a)$C(O)$R^a$, —N$(R^a)$C(O)N$(R^a)_2$, N$(R^a)$C(N$R^a$)N$(R^a)_2$, —N$(R^a)$S(O)$_t$$R^a$ (where t is 1 or 2), —S(O)$_t$$R^a$ (where t is 1 or 2), —S(O)$_t$O$R^a$ (where t is 1 or 2), —S(O)$_t$N$(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyloxy" refers to a R(C═O)O— radical wherein R is alkyl, aryl, heteroaryl, heteroalkyl or heterocycloalkyl, which are as described herein. If the R radical is heteroaryl or heterocycloalkyl, the hetero ring or chain atoms contribute to the total number of chain or ring atoms. Unless stated otherwise specifically in the specification, the R of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N$(R^a)_2$, —C(O)N$(R^a)_2$, —N$(R^a)$C(O)O$R^a$, —N$(R^a)$C(O)$R^a$, —N$(R^a)$C(O)N$(R^a)_2$, N$(R^a)$C(N$R^a$)N$(R^a)_2$, —N$(R^a)$S(O)$_t$$R^a$ (where t is 1 or 2), —S(O)$_t$$R^a$ (where t is 1 or 2), —S(O)$_t$O$R^a$ (where t is 1 or 2), —S(O)$_t$N$(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acylsulfonamide" refers a —$S(O)_2$—N$(R^a)$—C(═O)— radical, where $R^a$ is hydrogen, alkyl, fluoroalkyl, carbocyclyl, carbocyclylalkyl, aryl, aralkyl, heterocycloalkyl, heterocycloalkylalkyl, heteroaryl or heteroarylalkyl. Unless stated otherwise specifically in the specification, an acylsulfonamide group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N$(R^a)_2$, —C(O)N$(R^a)_2$, —N$(R^a)$C(O)O$R^a$, —N$(R^a)$C(O)$R^a$, —N$(R^a)$C(O)N$(R^a)_2$, N$(R^a)$C(N$R^a$)N$(R^a)_2$, —N$(R^a)$S(O)$_t$$R^a$ (where t is 1 or 2), —S(O)$_t$$R^a$ (where t is 1 or 2), —S(O)$_t$O$R^a$ (where t is 1 or 2), —S(O)$_t$N$(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl "Amino" or "amine" refers to a —$N(R^a)_2$ radical group, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —$N(R^a)_2$ group has two $R^a$ substituents other than hydrogen, they can be combined with the nitrogen atom to form a 4-, 5-, 6- or 7-membered ring. For example, —$N(R^a)_2$ is intended to include, but is not limited to, 1-pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N$(R^a)_2$, —C(O)N$(R^a)_2$, —N$(R^a)$C(O)O$R^a$, —N$(R^a)$C(O)$R^a$, —N$(R^a)$C(O)N$(R^a)_2$, N$(R^a)$C(N$R^a$)N$(R^a)_2$, —N$(R^a)$S(O)$_t$$R^a$ (where t is 1 or 2), —S(O)$_t$$R^a$ (where t is 1 or 2), —S(O)$_t$O$R^a$ (where t is 1 or 2), —S(O)$_t$N$(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "substituted amino" also refers to N-oxides of the groups —NH$R^a$, and N$R^a$$R^a$ each as described above. N-oxides can be prepared by treatment of the corresponding amino group with, for example, hydrogen peroxide or m-chloroperoxybenzoic acid.

"Amide" or "amido" refers to a chemical moiety with formula —C(O)N$(R)_2$ or —NHC(O)R, where R is selected from the group consisting of hydrogen, alkyl, cycloalkyl, aryl, heteroaryl (bonded through a ring carbon) and heteroalicyclic (bonded through a ring carbon), each of which moiety may itself be optionally substituted. The $R^2$ of —$N(R)_2$ of the amide may optionally be taken together with the nitrogen to which it is attached to form a 4-, 5-, 6- or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound disclosed herein, thereby forming a prodrug. The procedures and specific groups to make such amides are known to those of skill in the art and can readily be found in seminal sources such as Greene and Wuts, Protective Groups in Organic Synthesis, $3^{rd}$ Ed., John Wiley & Sons, New York, N.Y., 1999, which is incorporated herein by reference in its entirety.

"Aromatic" or "aryl" or "Ar" refers to an aromatic radical with six to ten ring atoms (e.g., $C_6$-$C_{10}$ aromatic or $C_6$-$C_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "aryloxy" refers to the group —O-aryl.

The term "substituted aryloxy" refers to aryloxy wherein the aryl substituent is substituted (i.e., —O-(substituted aryl)). Unless stated otherwise specifically in the specification, the aryl moiety of an aryloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). The procedures and specific groups to make esters are known to those of skill in the art and can readily be found in seminal sources such as Greene and Wuts, Protective Groups in Organic Synthesis, $3^{rd}$ Ed., John Wiley & Sons, New York, N.Y., 1999, which is incorporated herein by reference in its entirety. Unless stated otherwise specifically in the specification, an ester group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Halo," "halide," or, alternatively, "halogen" is intended to mean fluoro, chloro, bromo or iodo. The terms "haloalkyl," "haloalkenyl," "haloalkynyl," and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl," "heteroalkenyl," and "heteroalkynyl" refer to optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given—e.g., $C_1$-$C_4$ heteroalkyl which refers to the chain length in total, which in this example is 4 atoms long. A heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroalkylaryl" refers to an -(heteroalkyl)aryl radical where heteroalkyl and aryl are as disclosed herein and which are optionally substituted by one or more of the substituents described as suitable substituents for heteroalkyl and aryl, respectively.

"Heteroalkylheteroaryl" refers to an -(heteroalkyl)heteroaryl radical where heteroalkyl and heteroaryl are as disclosed herein and which are optionally substituted by one or more of the substituents described as suitable substituents for heteroalkyl and heteroaryl, respectively.

"Heteroalkylheterocycloalkyl" refers to an -(heteroalkyl) heterocycloalkyl radical where heteroalkyl and heterocycloalkyl are as disclosed herein and which are optionally substituted by one or more of the substituents described as suitable substituents for heteroalkyl and heterocycloalkyl, respectively.

"Heteroalkylcycloalkyl" refers to an -(heteroalkyl)cycloalkyl radical where heteroalkyl and cycloalkyl are as disclosed herein and which are optionally substituted by one or more of the substituents described as suitable substituents for heteroalkyl and cycloalkyl, respectively.

"Heteroaryl" or "heteroaromatic" or "HetAr" or "Het" refers to a 5- to 18-membered aromatic radical (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range—e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical—e.g., a pyridyl group with two points of attachment is a pyridylidene. A N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical are optionally oxidized. One or more nitrogen atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e., thienyl). Unless stated otherwise specifically in the specification, a heteroaryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

Substituted heteroaryl also includes ring systems substituted with one or more oxide (—O—) substituents, such as, for example, pyridinyl N-oxides.

"Heteroarylalkyl" refers to a moiety having an aryl moiety, as described herein, connected to an alkylene moiety, as described herein, wherein the connection to the remainder of the molecule is through the alkylene group.

"Heterocycloalkyl" or "heterocyclyl" refer to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range—e.g., "3 to 18 ring atoms" means that the heterocycloalkyl group may consist of 3 ring atoms, 4 ring atoms, etc., up to and including 18 ring atoms. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

"Nitro" refers to the $-NO_2$ radical.

"Oxa" refers to the —O— radical.

"Oxo" refers to the =O radical.

"Isomers" are different compounds that have the same molecular formula. "Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon can be specified by either (R) or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R) or (S). The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Enantiomeric purity" as used herein refers to the relative amounts, expressed as a percentage, of the presence of a specific enantiomer relative to the other enantiomer. For example, if a compound, which may potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (S)-isomer and 20% (R)-isomer, the enantiomeric purity of the compound with respect to the (S)-isomeric form is 80%. The enantiomeric purity of a compound can be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or Pirkle's reagents, or derivatization of a compounds using a chiral compound such as Mosher's acid followed by chromatography or nuclear magnetic resonance spectroscopy.

In some embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., Enantiomers, Racemates and Resolutions, Wiley Interscience, New York (1981); E. L. Eliel, Stereochemistry of Carbon Compounds, McGraw-Hill, New York (1962); and E. L. Eliel and S. H. Wilen, Stereochemistry of Organic Compounds, Wiley-Interscience, New York (1994).

The terms "enantiomerically enriched" and "non-racemic," as used herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, or such as at least 80% by weight. In some embodiments, the enrichment can be significantly greater than 80% by weight, providing a "substantially enantiomerically enriched" or a "substantially non-racemic" preparation, which refers to preparations of compositions which have at least 85% by weight of one enantiomer relative to other enantiomer, such as at least 90% by weight, or such as at least 95% by weight. The terms "enantiomerically pure" or "substantially enantiomerically pure" refers to a composition that comprises at least 98% of a single enantiomer and less than 2% of the opposite enantiomer.

"Moiety" refers to a specific segment or functional group of a molecule. Chemical moieties are often recognized chemical entities embedded in or appended to a molecule.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

A "leaving group or atom" is any group or atom that will, under selected reaction conditions, cleave from the starting material, thus promoting reaction at a specified site. Examples of such groups, unless otherwise specified, include halogen atoms and mesyloxy, p-nitrobenzensulphonyloxy and tosyloxy groups.

"Protecting group" is intended to mean a group that selectively blocks one or more reactive sites in a multifunctional compound such that a chemical reaction can be carried out selectively on another unprotected reactive site and the group can then be readily removed or deprotected after the selective reaction is complete. A variety of protecting groups are disclosed, for example, in T. H. Greene and P. G. M. Wuts, Protective Groups in Organic Synthesis, Third Edition, John Wiley & Sons, New York (1999).

"Solvate" refers to a compound in physical association with one or more molecules of a pharmaceutically acceptable solvent.

"Substituted" means that the referenced group may have attached one or more additional groups, radicals or moieties individually and independently selected from, for example, acyl, alkyl, alkylaryl, cycloalkyl, aralkyl, aryl, carbohydrate, carbonate, heteroaryl, heterocycloalkyl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and protected derivatives thereof. The substituents themselves may be substituted, for example, a cycloalkyl substituent may itself have a halide substituent at one or more of its ring carbons. The term "optionally substituted" means optional substitution with the specified groups, radicals or moieties.

"Sulfanyl" refers to groups that include —S-(optionally substituted alkyl), —S-(optionally substituted aryl), —S-(optionally substituted heteroaryl) and —S-(optionally substituted heterocycloalkyl).

"Sulfinyl" refers to groups that include —S(O)—H, —S(O)-(optionally substituted alkyl), —S(O)-(optionally substituted amino), —S(O)-(optionally substituted aryl), —S(O)— (optionally substituted heteroaryl) and —S(O)-(optionally substituted heterocycloalkyl).

"Sulfonyl" refers to groups that include —$S(O_2)$—H, —$S(O_2)$-(optionally substituted alkyl), —$S(O_2)$-(optionally substituted amino), —$S(O_2)$-(optionally substituted aryl), —$S(O_2)$-(optionally substituted heteroaryl), and —$S(O_2)$-(optionally substituted heterocycloalkyl).

"Sulfonamidyl" or "sulfonamido" refers to a —S(═O)$_2$—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —S(═O)$_2$—NRR radical may be taken together with the nitrogen to which it is attached to form a 4-, 5-, 6- or 7-membered ring. A sulfonamido group is optionally substituted by one or more of the substituents described for alkyl, cycloalkyl, aryl, heteroaryl, respectively.

"Sulfoxyl" refers to a —S(═O)$_2$OH radical.

"Sulfonate" refers to a —S(═O)$_2$—OR radical, where R is selected from the group consisting of alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, heteroaryl, respectively.

Compounds of the disclosure also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

For the avoidance of doubt, it is intended herein that particular features (for example integers, characteristics, values, uses, diseases, formulae, compounds or groups) described in conjunction with a particular aspect, embodiment or example of the disclosure are to be understood as applicable to any other aspect, embodiment or example described herein unless incompatible therewith. Thus such features may be used where appropriate in conjunction with any of the definition, claims or embodiments defined herein. All of the features disclosed in this specification (including any accompanying claims, abstract and drawings), and/or all of the steps of any method or process so disclosed, may be combined in any combination, except combinations where at least some of the features and/or steps are mutually exclusive. The disclosure is not restricted to any details of any disclosed embodiments. The disclosure extends to any novel one, or novel combination, of the features disclosed in this specification (including any accompanying claims, abstract and drawings), or to any novel one, or any novel combination, of the steps of any method or process so disclosed.

Moreover, as used herein, the term "about" means that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed disclosure. All embodiments of the disclosure can, in the alternative, be more specifically defined by any of the transitional terms "comprising," "consisting essentially of," and "consisting of."

Inhibitors of Heme Assimilation System (has) and/or the *P. aeruginosa* Siderophore Iron Uptake System Recently, the development of antivirulence agents that reduce the ability of bacteria to colonize or spread has gained traction with the hope that such strategies will slow resistance development by exerting less selective evolutionary pressure. The regulation of many virulence factors is dependent on iron acquisition from the host, which also serves as a necessary nutrient for survival. In response to bacterial competition, host iron levels are kept tightly regulated reducing circulating iron in the form of transferrin and increasing expression of ferritin, minimizing the availability of labile iron for bacterial consumption. This innate immune response often referred to as "nutritional immunity" aims to keep the availability of essential nutrients at concentrations below what would permit colonization and growth.

Though *P. aeruginosa* and many other gram-negative pathogens secrete iron-chelating siderophores, the low abundance of labile iron shifts the preference to heme-bound iron, which is more abundant in a host. Furthermore, chronic infections in CF patients show evolution towards heme as a preferred iron source along with a decrease in production of pyoverdine, a high-affinity siderophore. The non-redundant heme uptake systems in *P. aeruginosa*, which involve a primary heme transporter Phu (*Pseudomonas* heme uptake)

system and the heme sensing Has (Heme assimilation system) system, has been previously characterized. While the Phu system is the predominant uptake transporter, the Has system relies on the secretion of an extracellular hemophore, HasAp, to deliver exogenous heme through the outer-membrane receptor HasR. The release of heme to HasR in turn activates the ECF σ-factor HasI that binds to the has promoter recruiting RNA polymerase and upregulating the has operon. These recent studies have further shown that the heme metabolite biliverdin IXβ (BVIX β) positively regulates HasAp translation providing a positive feedback loop that is highly tunable and rapidly responsive to fluctuating extracellular heme levels.

The complex transcriptional and post-transcriptional regulation over the has system is consistent with its significance in infection where it has been shown to be highly upregulated in transcriptomic analysis of an acute mouse lung infection (~300-fold for hasAp, ~70-fold for hasR). Furthermore, it was shown that deletion of hasR significantly reduces bacterial load, highlighting the importance of heme sensing and adaptation in infection and suggesting that HasAp is an attractive therapeutic target. Targeting the Has system combines the advantages of disrupting heme acquisition while inhibiting the ability to sense the extracellular environment. Indirectly, the reduction in heme uptake caused by inhibition of the heme signaling cascade will lead to lower levels of BVIXβ and further repress the heme signaling ability. Moreover, HasAp is an extracellular target that circumvents typical roadblocks of penetrating gram-negative membranes and multi-drug efflux pumps that typically enhance antibiotic resistance.

Though structural work has extensively characterized HasAp, the HasAp/HasR interaction is still under investigation which complicates the development of molecules targeting the protein-protein interaction. Alternatively, recent reports have demonstrated that synthetic iron complexes bind in the heme site and are coordinated by the same heme-binding residues, opening the door to heme mimicry as a targeting strategy. Of note is the N,N'-disalicylal-1,2-phenylenediamine ("salophen") complex, which is synthetically modular and more soluble than many of the larger macrocycles. The use of metallosalophen complexes has also been investigated for potential anticancer applications, establishing their bioactivity as metallotherapeutics.

The design of antimicrobials that inhibit heme sensing and iron uptake have a significant advantage over traditional strategies targeting solely iron uptake. Presently, strategies aimed at targeting iron uptake have shown gallium to be an effective iron mimic due to its similar size to iron and redox-inactivity. Currently, formulations of gallium including the FDA-approved Ganite ($Ga(NO_3)_3$) are in clinical trials for efficacy as antibiotics, though reports of gallium inducing virulence factor production have also emerged. Since the binding of the metallosalophens to HasAp has been confirmed, the salophen-HasAp complex and its effect on the Has system in *P. aeruginosa* was sought for further characterization, and it was found that both $Fe^{3+}$-salophen (FeSal) and $Ga^{3+}$-salophen (GaSal) complexes inhibited transcriptional activation of the has operon. The use of GaSal also inhibited growth as a result of uptake as a xenosiderophore through a currently unidentified receptor. Therefore, GaSal inhibits heme sensing while simultaneously causing toxicity following active uptake through the siderophore receptors. This dual mechanism of action has several advantages not the least of which is the reduced propensity to develop resistance.

Figure 1A:
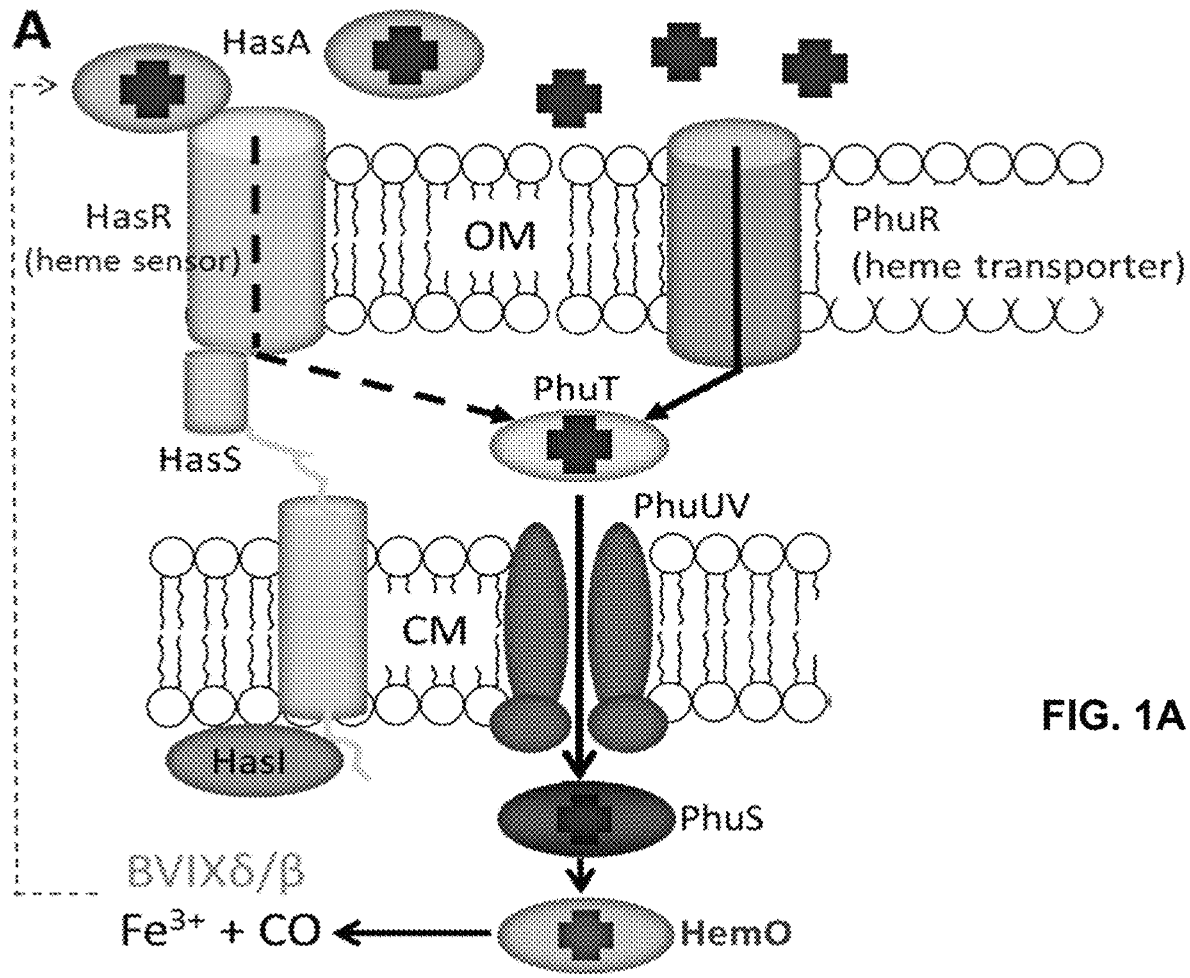
FIG. 1A illustrates Heme utilization in *P. aeruginosa*. Heme is taken up via PhuR or HasR, and internalized by the PhuT/UV. Heme is transferred from PhuS to HemO. HemO derived BVIXδ/β isomers are excreted. The secreted hemophore HasAp is post-transcriptionally regulated by BVIXβ. The σ-factor HasI is activated through holo-HasA-HasR interaction and release of the anti-σ factor HasI.
Figure 1B:
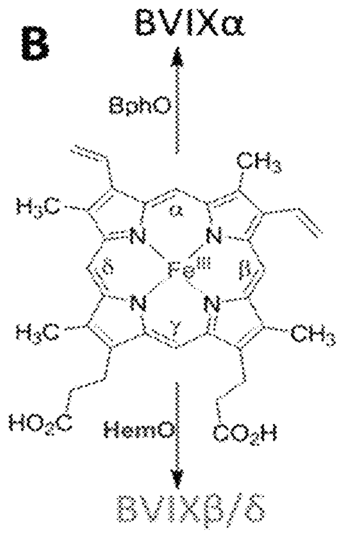
FIG. 1B illustrates BVIX isomers on cleavage by HemO or the phytochrome associated BphO.

Iron regulates several virulence factors in *P. aeruginosa* including exotoxins, proteases and biofilm formation. Iron is scarce within the host, with the majority being sequestered in iron-binding proteins such as transferrin and ferritin, or in the form of heme. On infection, the innate immune response further limits iron by upregulating iron-storage systems and producing iron-binding proteins such as siderocalins. *P. aeruginosa* overcomes this iron-limitation by a number of mechanisms including the secretion of siderophores (pyoverdine, pyochelin), $Fe^{2+}$ uptake (Feo), and heme acquisition systems. The phu (*Pseudomonas* heme utilization) operon encodes the major heme transporter (PhuR, FIG. 1A), periplasmic heme binding protein (PhuT), an ATP-binding transporter PhuUV, and the cytoplasmic heme binding protein (PhuS). The has operon encodes a hemophore HasAp and a Type I secretion system. Holo-HasAp mediates an extra cytoplasmic signal through HasR, activating the σ-factor HasI that recruits RNA polymerase and activates transcription of the has operon. This cell surface signaling system (CSS) allows *P. aeruginosa* to regulate and fine tune heme uptake in response to external heme levels. The flux of heme into the cell is driven by the concerted action of the cytoplasmic heme binding protein PhuS and heme oxygenase (HemO), yielding BVIXβ, BVIXδ and CO while releasing iron (FIG. 1B).

Figure 2A:
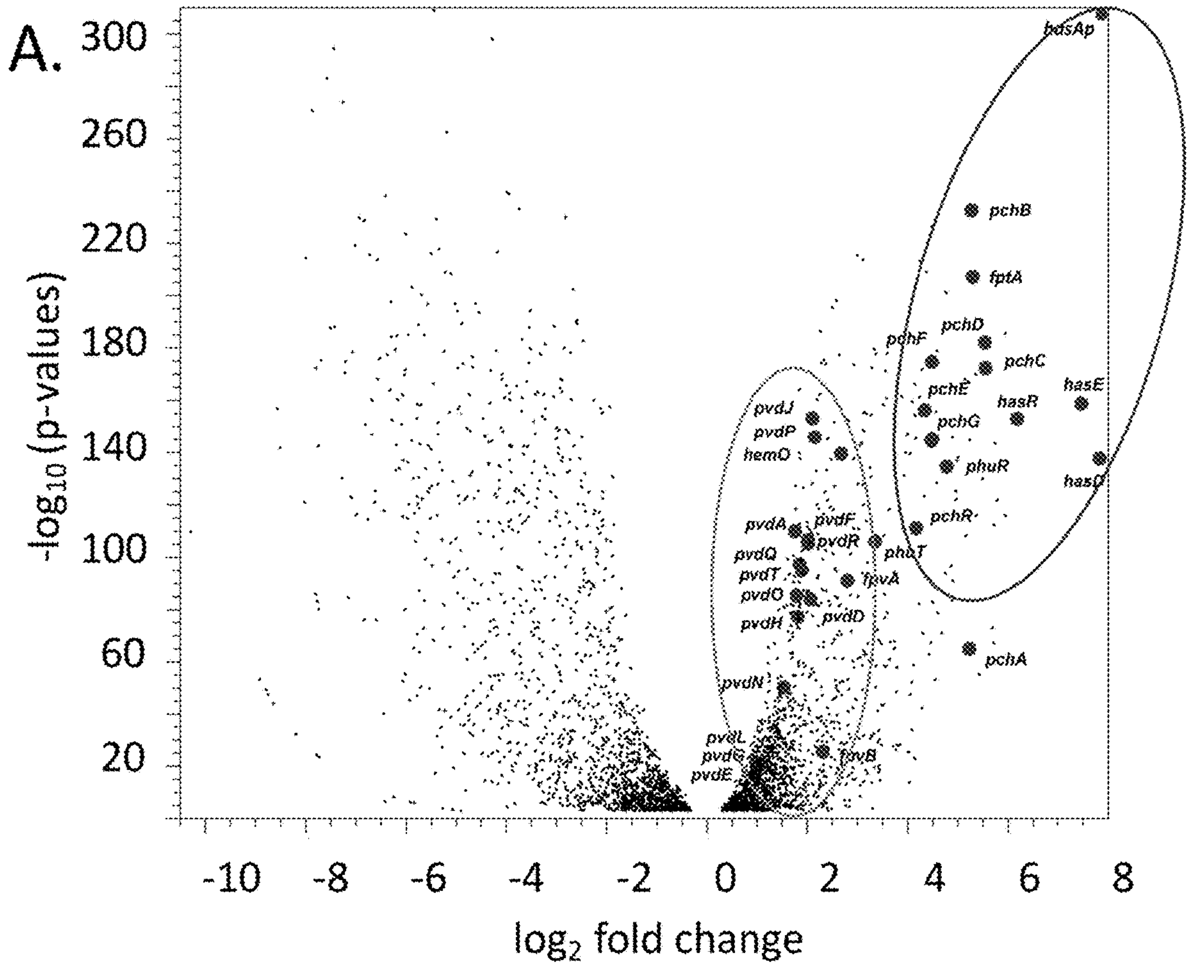
FIG. 2A illustrates dual RNA-seq transcriptomics in a volcano plot of differentially expressed genes in acute murine *pneumoniae* versus growth on PIA. All iron/heme uptake genes (●). Circled in red heme uptake and pch biosynthesis genes and in green pvd biosynthesis genes.

It has been shown that *P. aeruginosa* within the CF lung adapts to utilize heme and $Fe^{2+}$ while decreasing its dependence on the major siderophore pyoverdine. Within the host, *P. aeruginosa* adapts to utilize heme through positive selection for mutations within the phuR promoter, leading to increased expression of heme transporter PhuR. Mutations in the phu promoter are concomitant with the loss of the pyoverdine biosynthesis genes. It was also confirmed that overtime, this adaption in longitudinal clinical isolates becomes more efficient at metabolizing heme, while decreasing pyoverdine production. Interestingly, studies have shown heme levels are unusually high in the lungs of CF patients because of spontaneous bleeding as a result of chronic airway inflammation. Lungs removed from CF patients who underwent transplantation contain large quantities of iron and heme, suggesting that bleeding events occur over the lifetime of the patient. Such micro-bleeds coupled with periodic pulmonary exacerbations promote *P. aeruginosa* infection. The ability to adapt and utilize heme as the primary iron source requires the ability to sense the extracellular environment via the has system. Indeed, the need to sense heme during in infection is supported in a murine acute lung infection model where dual RNA-seq showed upregulation of hasAp (~300-fold), hasR (~70-fold), and phuR (~30-fold) compared to *P. aeruginosa* in vitro (FIG. 2A). Deletion of the signaling receptor HasR (ΔhasR) showed significantly lower bacterial load in the murine acute lung infection compared to PAO1.

In one aspect of the disclosure, the compounds disclosed herein exhibit the dual activity of inhibiting the heme dependent CSS cascade while acting as a substrate for siderophore receptor uptake. In some embodiments, the compounds described herein target HasAp and block the ability of *P. aeruginosa* to sense its environment while also limiting iron availability. In some embodiments, compounds described herein are actively taken up as a xenosiderophore, and therefore the ability of *P. aeruginosa* to switch from heme to iron-uptake increases the potential for toxicity and dysregulation of iron homeostasis. The heme sensing and uptake systems represent virulence mechanisms that can be targeted within the host, but are not essential for survival outside of the host, and therefore bacteria face less selective pressure to develop resistance. In another aspect of the disclosure, the compounds disclosed herein represent a novel formulation strategy for gallium, which was found to be an effective an iron-mimicking element.

In some embodiments, the compounds described herein inhibit heme sensing and intracellular iron homeostasis, resulting in dysregulation of related metabolic and virulence pathways. In some embodiments, the compounds described herein target the extracellular hemophore HasAp and xenosiderophore receptor uptake. In some embodiments, the compounds described herein inhibit the extracellular hemophore HasAp and act as a substrate for the siderophore receptor uptake. In some embodiments, the compounds described herein inhibit both heme sensing/transport and iron uptake. In some embodiments, the compounds described herein inhibit the interaction between HasAp and HasR.

In some embodiments, the compounds described herein inhibit HasAp protein activity. In some embodiments, the compounds described herein inhibit the *P. aeruginosa* siderophore iron uptake system. In some embodiments, the compounds described herein inhibit both HasAp protein activity and the *P. aeruginosa* siderophore iron uptake system The disclosure provides in one aspect a compound of formula (I), or a pharmaceutically acceptable salt, solvate, hydrate, cocrystal, or prodrug thereof:

formula (I)

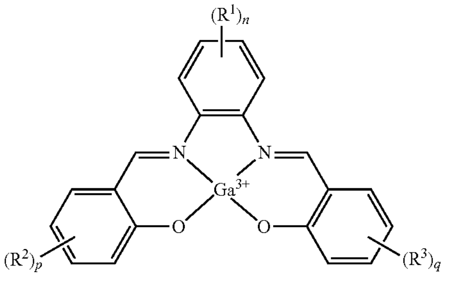

wherein in formula (I):

each $R^1$ is a substituent independently selected at each occurrence from halogen, optionally substituted alkyl, optionally substituted alkylaryl, optionally substituted alkylheteroaryl, optionally substituted alkenyl, optionally substituted alkynyl, optionally substituted cycloalkyl, optionally substituted aryl, optionally substituted aralkyl, optionally substituted haloalkyl, optionally substituted alkoxy, and optionally substituted heteroaryl;

each $R^2$ and $R^3$ is a substituent independently selected at each occurrence from halogen, optionally substituted alkyl, optionally substituted alkylaryl, optionally substituted alkylheteroaryl, optionally substituted alkenyl, optionally substituted alkynyl, optionally substituted cycloalkyl, optionally substituted aryl, optionally substituted aralkyl, optionally substituted haloalkyl, optionally substituted alkoxy, and optionally substituted heteroaryl;

wherein one $R^1$ and one $R^2$, one $R^1$ and one $R^3$, or one $R^2$ and one $R^3$ may optionally be joined together;

n is an integer from 0 to 4;

p is an integer from 0 to 4; and q is an integer from 0 to 4.

In some embodiments, each $R^1$ is independently —$OR^a$; wherein each $R^a$ is independently selected at each occurrence from the group consisting of optionally substituted alkyl, optionally substituted alkylaryl, optionally substituted alkylcycloalkyl, and optionally substituted alkylheteroaryl. In some embodiments, each $R^1$ is independently selected at each occurrence from the group consisting of —OMe, —OEt, —OPr, —OiPr,

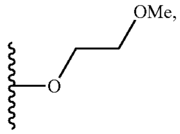 and 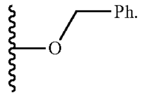

In some embodiments, each $R^2$ and $R^3$ is independently —$OR^b$ or —$(CH_2)OR^b$, wherein each $R^b$ is independently selected at each occurrence from the group consisting of optionally substituted alkyl, optionally substituted alkylaryl, optionally substituted alkylcycloalkyl, and optionally substituted alkylheteroaryl. In some embodiments, the alkyl is substituted with one or more substituents selected from alkoxy, —OH, phenyl, heterocyclyl, optionally substituted amino, and —$C(O)OR^c$, wherein each $R^c$ is independently at each occurrence H or alkyl. In some embodiments, each $R^2$ and $R^3$ is independently at each occurrence selected from —$O(CH_2)_nO(CH_2)_nOR^c$, —$O(CH_2)_nOCH_2$phenyl, —$O(CH_2)_nOCH_2$heterocyclyl, —$O(CH_2)_nN(R^c)_2$, —$O(CH_2)_nN(R^c)_3{}^+X^-$, —$O(CH_2)_nC(O)OR^c$, —$O(CH_2)_n$heterocyclyl, wherein each $R^c$ is independently at each occurrence H or alkyl, each X– is independently at each occurrence selected from $Br^-$, $Cl^-$, and $I^-$, and each n is independently at each occurrence an integer from 1 to 4. In some embodiments, n is 2. In some embodiments, the heterocyclyl is selected from indole, imidazo[2,1-b]oxazole, imidazo[2,1-b]thiazole, and morpholinyl.

In some embodiments, each $R^2$ is independently selected at each occurrence from the group consisting of

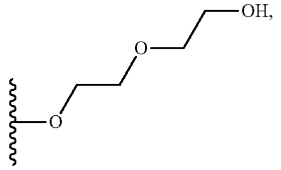

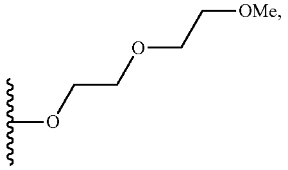

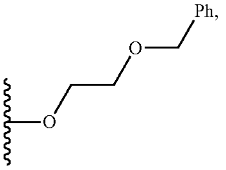

-continued
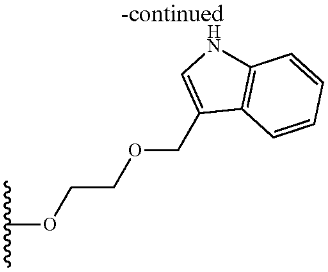
,
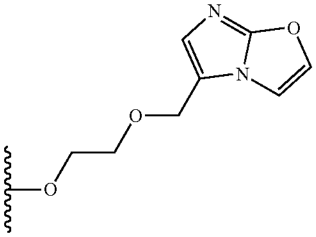
,
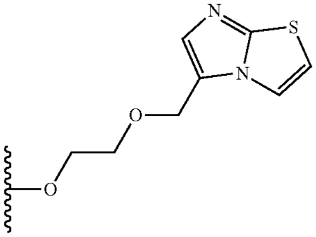
,
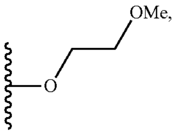
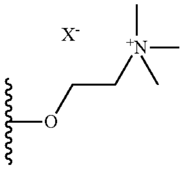
,
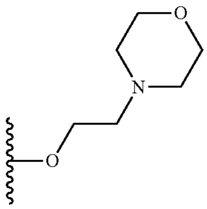
, and
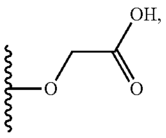
wherein $X^-$ is independently at each occurrence selected from $Br^-$, $Cl^-$, and $I^-$.
In some embodiments, each $R^2$ is independently selected at each occurrence from the group consisting of
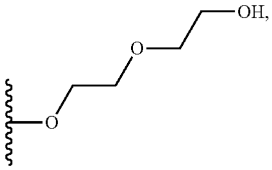
-continued
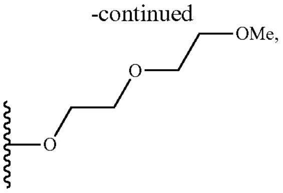
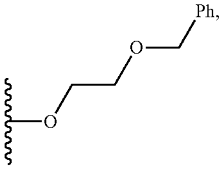
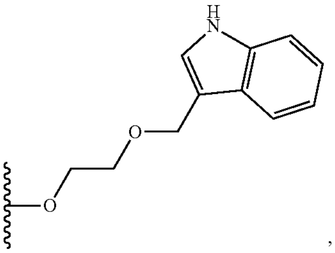
,
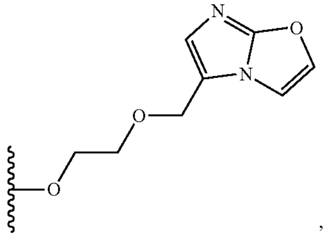
,
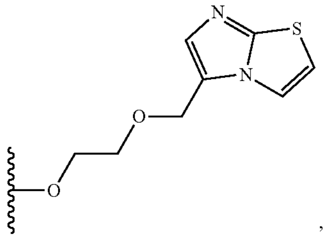
,
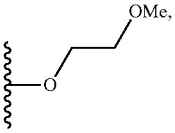
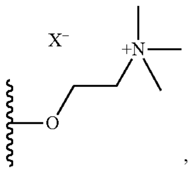
,
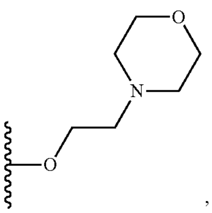
, and
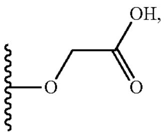

wherein $X^-$ is independently at each occurrence selected from $Br^-$, $Cl^-$, and $I^-$.

In some embodiments, one $R^2$ and one $R^3$ join together to form —$O(CH_2)_rO$—, wherein r is an integer from 4 to 7.

In some embodiments, each $R^2$ is the same as each $R^3$. In some embodiments, each $R^2$ is different from each $R^3$.

In some embodiments, n is 1 or 2. In some embodiments, p is 1 or 2. In some embodiments, q is 1 or 2.

The disclosure provides in another aspect a compound of formula (II), or a pharmaceutically acceptable salt, solvate, hydrate, cocrystal, or prodrug thereof:

formula (II)

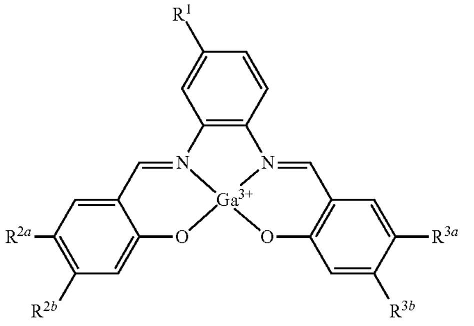

wherein in formula (II):

$R^1$ is selected from the group consisting of H, halogen, optionally substituted alkyl, optionally substituted alkylaryl, optionally substituted alkylhetaryl, optionally substituted alkenyl, optionally substituted alkynyl, optionally substituted cycloalkyl, optionally substituted aryl, optionally substituted aralkyl, optionally substituted haloalkyl, optionally substituted alkoxy, and optionally substituted heteroaryl; and $R^{2a}$, $R^{2b}$, $R^{3a}$ and $R^{3b}$ is each independently selected from the group consisting of H, halogen, optionally substituted alkyl, optionally substituted alkylaryl, optionally substituted alkylhetaryl, optionally substituted alkenyl, optionally substituted alkynyl, optionally substituted cycloalkyl, optionally substituted aryl, optionally substituted aralkyl, optionally substituted haloalkyl, optionally substituted alkoxy, and optionally substituted heteroaryl.

In some embodiments, each $R^1$ is independently —$OR^a$; wherein each $R^a$ is independently selected at each occurrence from the group consisting of optionally substituted alkyl, optionally substituted alkylaryl, optionally substituted alkylcycloalkyl, and optionally substituted alkylheteroaryl. In some embodiments, $R^1$ is selected from the group consisting of —OMe, —OEt, —OPr, —OiPr,

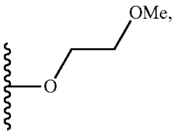, and 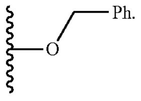.

In some embodiments, $R^{2a}$ and $R^{2b}$ are each independently selected from —$OR^b$ or —$(CH_2)OR^b$, wherein each $R^b$ is independently selected at each occurrence from the group consisting of optionally substituted alkyl, optionally substituted alkylaryl, optionally substituted alkylcycloalkyl, and optionally substituted alkylheteroaryl. In some embodiments, the optionally substituted alkyl is selected from —$(CH_2)_nN(R^c)_2$, —$(CH_2)_nN(R^c)_3{}^+X^-$, —$(CH_2)_nC(O)OR^c$, —$(CH_2)_n$heterocyclyl, wherein each $R^c$ is independently at each occurrence H or alkyl, $X^-$ is independently at each occurrence selected from $Br^-$, $Cl^-$, $I^-$, and n is an integer from 1 to 4. In some embodiments, n is 2. In some embodiments, the heterocyclyl is a morpholinyl.

In some embodiments, $R^{2a}$ and $R^{2b}$ are each independently selected from the group consisting of

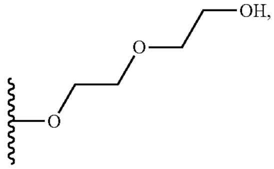,

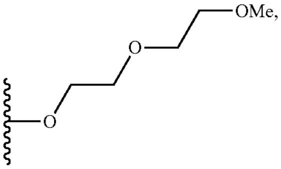,

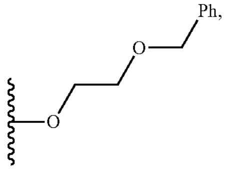,

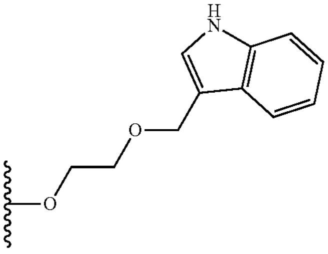,

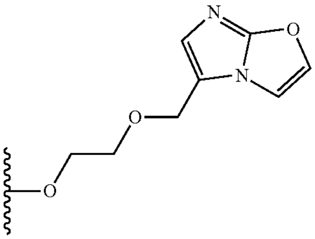,

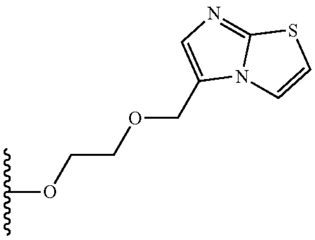,

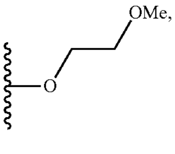,

-continued

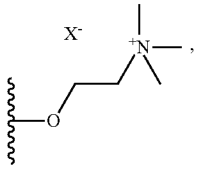

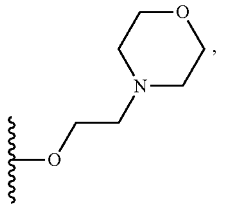

and

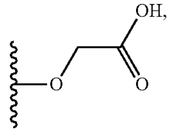

wherein $X^-$ is independently at each occurrence selected from $Br^-$, $Cl^-$, and $I^-$.

In some embodiments, $R^{3a}$ and $R^{3b}$ are each independently selected from $—OR^b$ or $—(CH_2)OR^b$, wherein each $R^b$ is independently selected at each occurrence from the group consisting of optionally substituted alkyl, optionally substituted alkylaryl, optionally substituted alkylcycloalkyl, and optionally substituted alkylheteroaryl. In some embodiments, the optionally substituted alkyl is selected from $—(CH_2)_nN(R^c)_2$, $—(CH_2)_nN(R^c)_3X^-$, $—(CH_2)_nC(O)OR^c$, $—(CH_2)_n$heterocyclyl, wherein each $R^c$ is independently at each occurrence H or alkyl, $X^-$ is independently at each occurrence selected from $Br^-$, $Cl^-$, $I^-$, and n is an integer from 1 to 4. In some embodiments, n is 2. In some embodiments, the heterocyclyl is a morpholinyl.

In some embodiments, $R^{3a}$ and $R^{3b}$ are each independently selected from the group consisting of

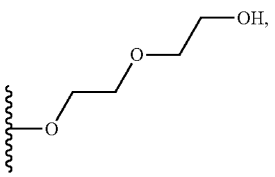

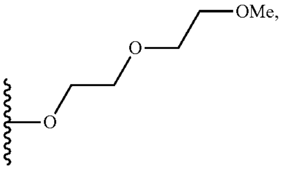

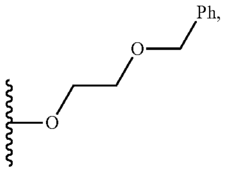

-continued

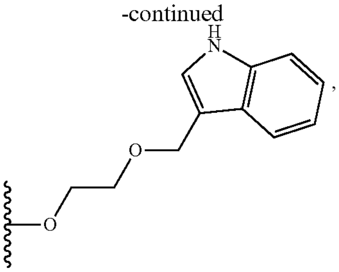

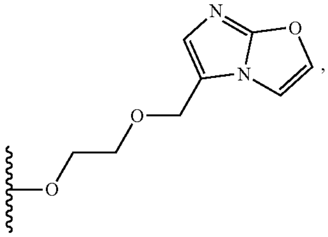

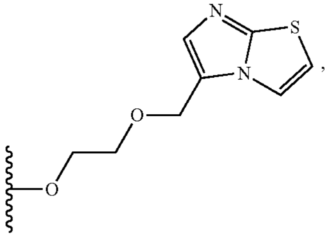

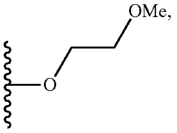

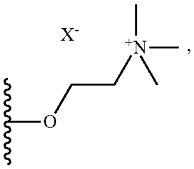

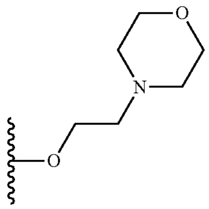

and

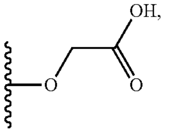

wherein $X^-$ is independently at each occurrence selected from $Br^-$, $Cl^-$, and $I^-$.

In some embodiments, $R^{2a}$ is the same as $R^{3a}$. In some embodiments, $R^{2a}$ is different from $R^{3a}$. In some embodiments, $R^{2a}$ is the same as $R^{3b}$. In some embodiments, $R^{2a}$ is different from $R^{3b}$. In some embodiments, $R^{2b}$ is the same as $R^{3a}$. In some embodiments, $R^{2b}$ is different from $R^{3a}$. In some embodiments, $R^{2b}$ is the same as $R^{3b}$. In some embodiments, $R^{2b}$ is different from $R^{3b}$.

In some embodiments, the compound of formula (II) is selected from Table 1, wherein $X^-$ is independently at each occurrence selected from $Br^-$, $Cl^-$, and $I^-$:

TABLE 1
formula (II)
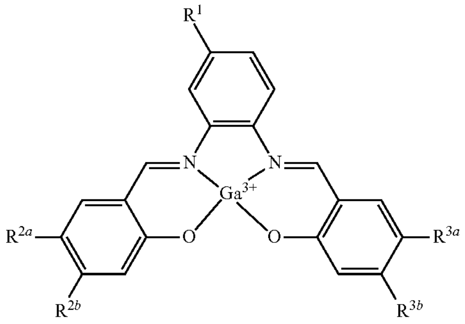
| Compound # | $R^1$ | $R^{2a}$ | $R^{2b}$ | $R^{3a}$ | $R^{3b}$ |
|---|---|---|---|---|---|
| 1001 | H | H | H | H | H |
| 1002 | —OMe | H | H | H | H |
| 1003 | —OEt | H | H | H | H |
| 1004 | —OPr | H | H | H | H |
| 1005 | —OiPr | H | H | H | H |
| 1006 | 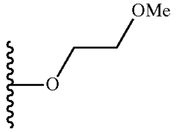 [SMILES: *OCCOC] | H | H | H | H |
| 1007 | 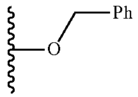 | H | H | H | H |
| 1008 | H | 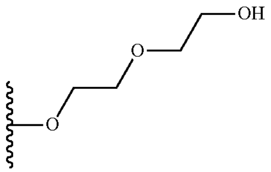 | H | H | H |

TABLE 1-continued
formula (II)
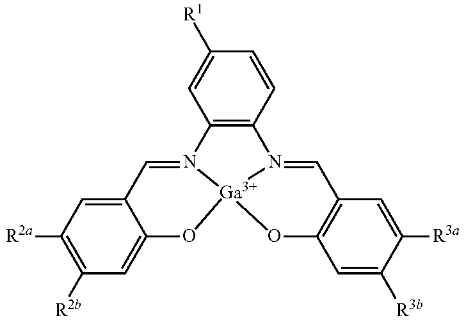
| Compound # | $R^1$ | $R^{2a}$ | $R^{2b}$ | $R^{3a}$ | $R^{3b}$ |
| --- | --- | --- | --- | --- | --- |
| 1009 | —OMe | 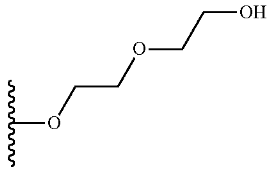 | H | H | H |
| 1010 | —OEt | 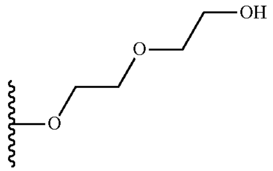 [SMILES: *OCCOCCO] | H | H | H |
| 1011 | —OPr | 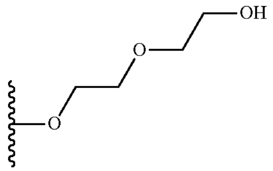 | H | H | H |
| 1012 | —OiPr | 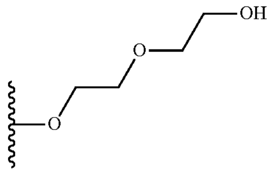 | H | H | H |

TABLE 1-continued
formula (II)
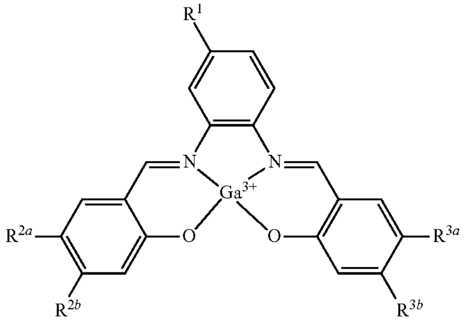
| Compound # | R1 | R2a | R2b | R3a | R3b |
|---|---|---|---|---|---|
| 1013 | 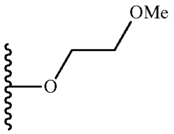 | 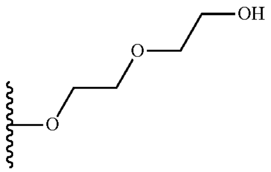 [SMILES: *OCCOCCO] | H | H | H |
| 1014 | 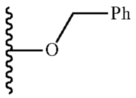 [SMILES: *OCc1ccccc1] | 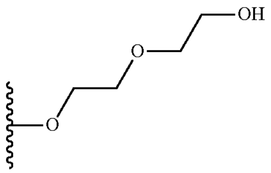 [SMILES: *OCCOCCO] | H | H | H |
| 1015 | H | 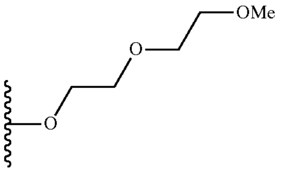 [SMILES: *OCCOCCOC] | H | H | H |

TABLE 1-continued
formula (II)
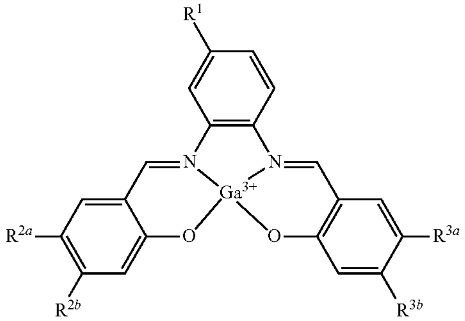
| Compound # | $R^1$ | $R^{2a}$ | $R^{2b}$ | $R^{3a}$ | $R^{3b}$ |
|---|---|---|---|---|---|
| 1016 | —OMe | 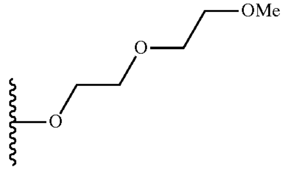 [SMILES: *OCCOCCOC] | H | H | H |
| 1017 | —OEt | 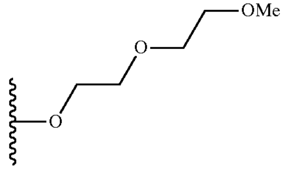 [SMILES: *OCCOCCOC] | H | H | H |
| 1018 | —OPr | 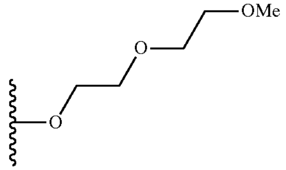 | H | H | H |
| 1019 | —OiPr | 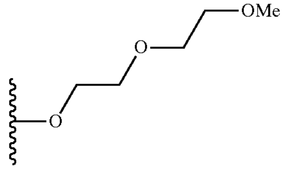 | H | H | H |

TABLE 1-continued
formula (II)
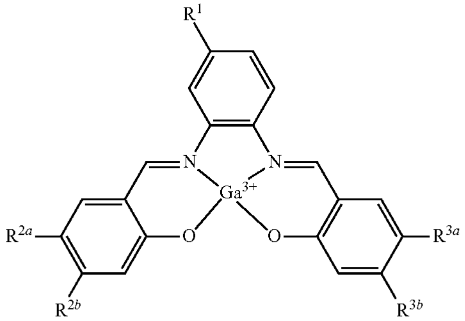
| Compound # | $R^1$ | $R^{2a}$ | $R^{2b}$ | $R^{3a}$ | $R^{3b}$ |
|---|---|---|---|---|---|
| 1020 | 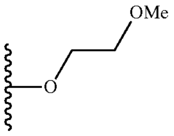 | 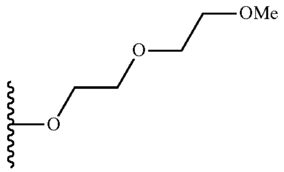 | H | H | H |
| 1021 | 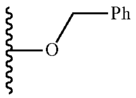 [SMILES: *OCc1ccccc1] | 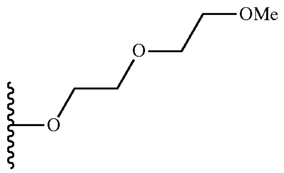 [SMILES: *OCCOCCOC] | H | H | H |
| 1022 | H | 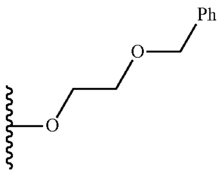 [SMILES: *OCCOCc1ccccc1] | H | H | H |

TABLE 1-continued
formula (II)
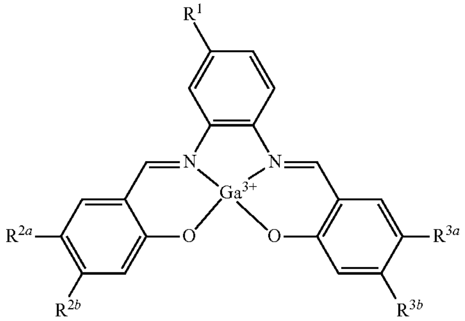
| Compound # | $R^1$ | $R^{2a}$ | $R^{2b}$ | $R^{3a}$ | $R^{3b}$ |
|---|---|---|---|---|---|
| 1023 | —OMe | 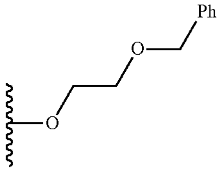 [SMILES: *OCCOCc1ccccc1] | H | H | H |
| 1024 | —OEt | 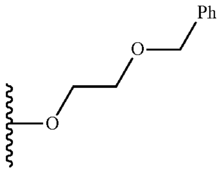 [SMILES: *OCCOCc1ccccc1] | H | H | H |
| 1025 | —OPr | 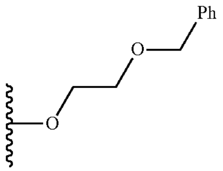 [SMILES: *OCCOCc1ccccc1] | H | H | H |
| 1026 | —OiPr | 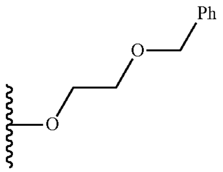 [SMILES: *OCCOCc1ccccc1] | H | H | H |

TABLE 1-continued
formula (II)
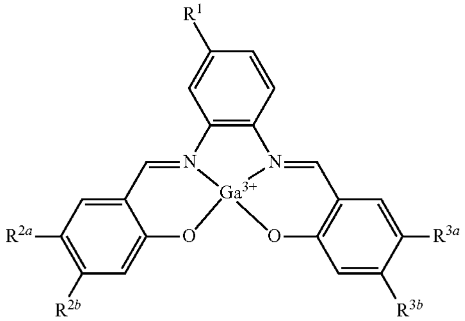
| Compound # | $R^1$ | $R^{2a}$ | $R^{2b}$ | $R^{3a}$ | $R^{3b}$ |
|---|---|---|---|---|---|
| 1027 | 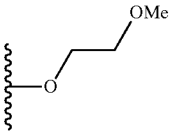 | 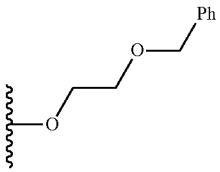 [SMILES: *OCCOCc1ccccc1] | H | H | H |
| 1028 | 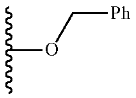 [SMILES: *OCc1ccccc1] | 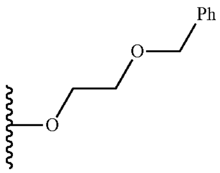 [SMILES: *OCCOCc1ccccc1] | H | H | H |
| 1029 | H | 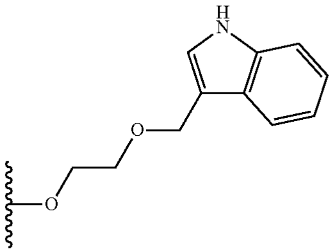 [SMILES: *OCCOCc1c[nH]c2ccccc12] | H | H | H |

TABLE 1-continued
formula (II)
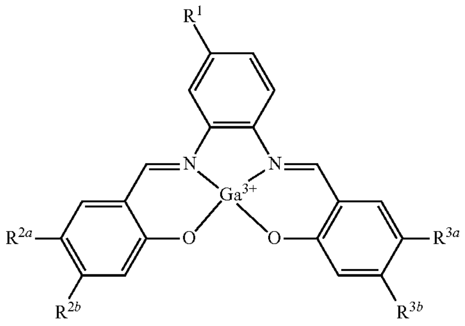
| Compound # | $R^1$ | $R^{2a}$ | $R^{2b}$ | $R^{3a}$ | $R^{3b}$ |
|---|---|---|---|---|---|
| 1030 | —OMe | 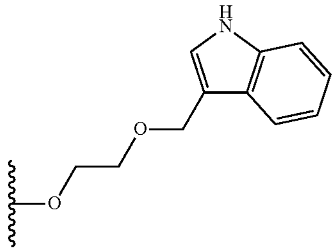 [SMILES: *OCCOCc1c[nH]c2ccccc12] | H | H | H |
| 1031 | —OEt | 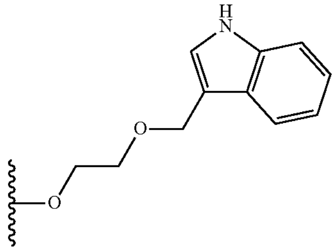 [SMILES: *OCCOCc1c[nH]c2ccccc12] | H | H | H |

TABLE 1-continued
formula (II)
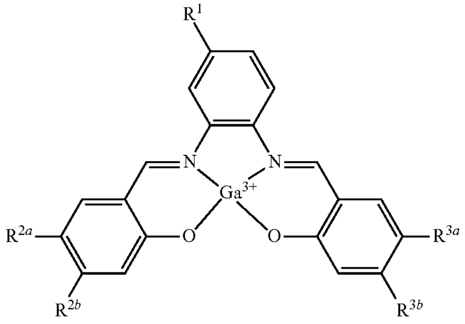
| Compound # | $R^1$ | $R^{2a}$ | $R^{2b}$ | $R^{3a}$ | $R^{3b}$ |
|---|---|---|---|---|---|
| 1032 | —OPr | 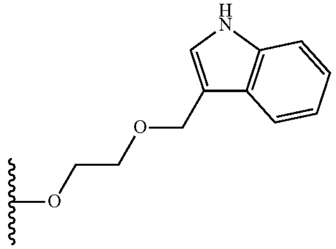 [SMILES: *OCCOCc1c[nH]c2ccccc12] | H | H | H |
| 1033 | —OiPr | 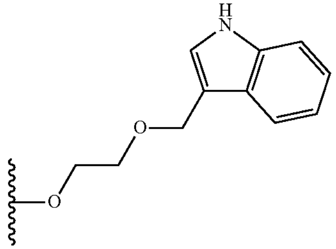 [SMILES: *OCCOCc1c[nH]c2ccccc12] | H | H | H |

TABLE 1-continued
formula (II)
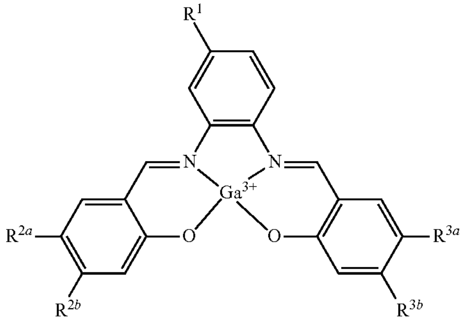
| Compound # | $R^1$ | $R^{2a}$ | $R^{2b}$ | $R^{3a}$ | $R^{3b}$ |
|---|---|---|---|---|---|
| 1034 | 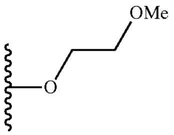 | 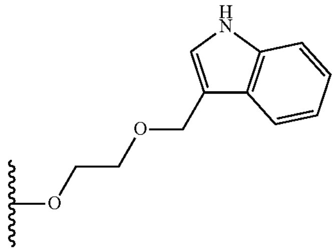 [SMILES: *OCCOCc1c[nH]c2ccccc12] | H | H | H |
| 1035 | 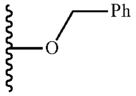 [SMILES: *OCc1ccccc1] | 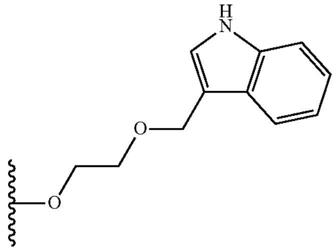 [SMILES: *OCCOCc1c[nH]c2ccccc12] | H | H | H |

TABLE 1-continued
formula (II)
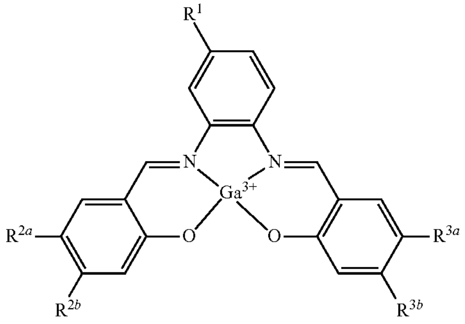
| Compound # | $R^1$ | $R^{2a}$ | $R^{2b}$ | $R^{3a}$ | $R^{3b}$ |
|---|---|---|---|---|---|
| 1036 | H | 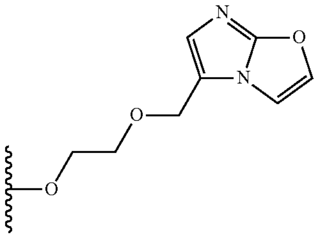 [SMILES: *OCCOCc1cnc2occn12] | H | H | H |
| 1037 | —OMe | 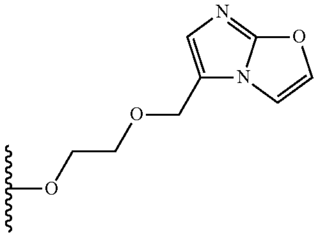 [SMILES: *OCCOCc1cnc2occn12] | H | H | H |
| 1038 | —OEt | 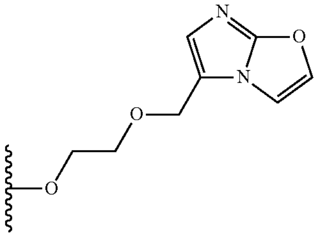 [SMILES: *OCCOCc1cnc2occn12] | H | H | H |

TABLE 1-continued
formula (II)
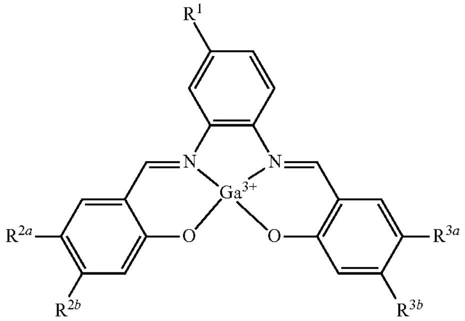
| Compound # | $R^1$ | $R^{2a}$ | $R^{2b}$ | $R^{3a}$ | $R^{3b}$ |
|---|---|---|---|---|---|
| 1039 | —OPr | 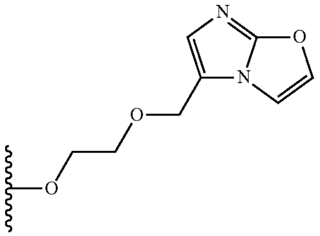 [SMILES: *OCCOCc1cnc2occn12] | H | H | H |
| 1040 | —OiPr | 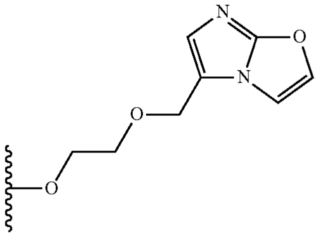 [SMILES: *OCCOCc1cnc2occn12] | H | H | H |

TABLE 1-continued
formula (II)
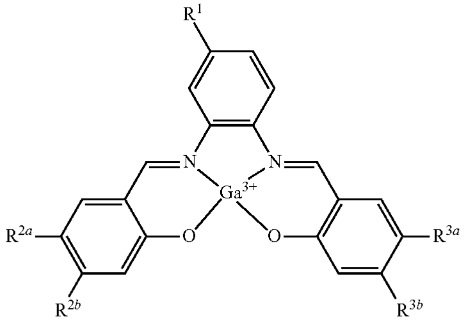
| Compound # | $R^1$ | $R^{2a}$ | $R^{2b}$ | $R^{3a}$ | $R^{3b}$ |
|---|---|---|---|---|---|
| 1041 | 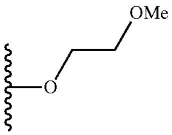 | 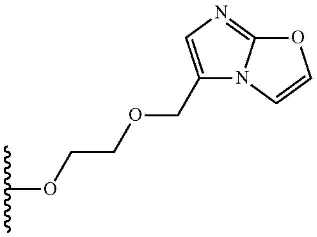 [SMILES: *OCCOCc1cnc2occn12] | H | H | H |
| 1042 | 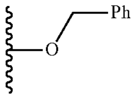 [SMILES: *OCc1ccccc1] | 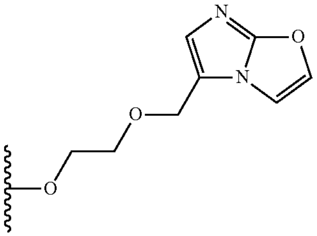 [SMILES: *OCCOCc1cnc2occn12] | H | H | H |

TABLE 1-continued
formula (II)
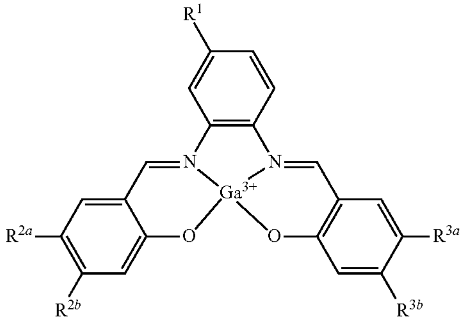
| Compound # | $R^1$ | $R^{2a}$ | $R^{2b}$ | $R^{3a}$ | $R^{3b}$ |
|---|---|---|---|---|---|
| 1043 | H | 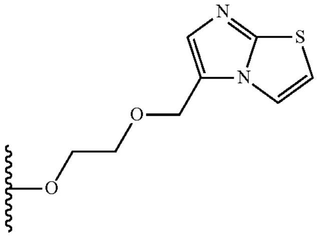 [SMILES: *OCCOCc1cnc2sccn12] | H | H | H |
| 1044 | —OMe | 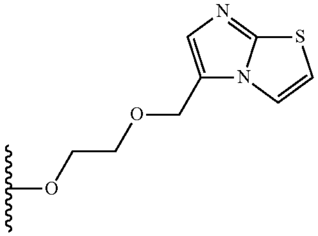 [SMILES: *OCCOCc1cnc2sccn12] | H | H | H |

TABLE 1-continued
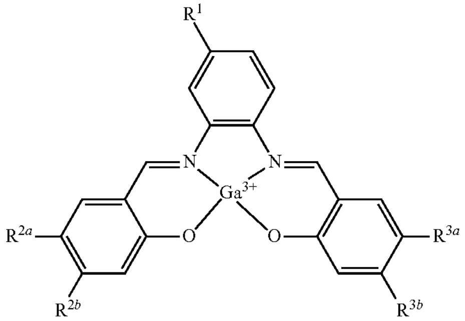
formula (II)
| Compound # | $R^1$ | $R^{2a}$ | $R^{2b}$ | $R^{3a}$ | $R^{3b}$ |
|---|---|---|---|---|---|
| 1045 | —OEt | 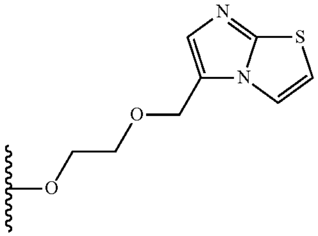 [SMILES: *OCCOCc1cnc2sccn12] | H | H | H |
| 1046 | —OPr | 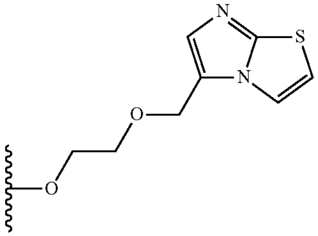 [SMILES: *OCCOCc1cnc2sccn12] | H | H | H |

TABLE 1-continued
formula (II)
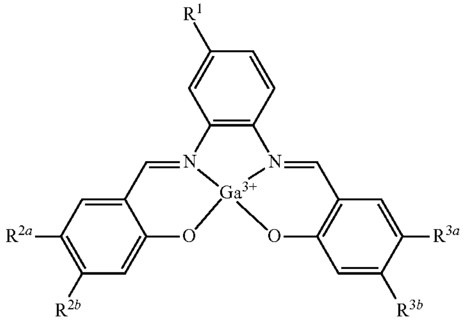
| Compound # | $R^1$ | $R^{2a}$ | $R^{2b}$ | $R^{3a}$ | $R^{3b}$ |
|---|---|---|---|---|---|
| 1047 | —OiPr | 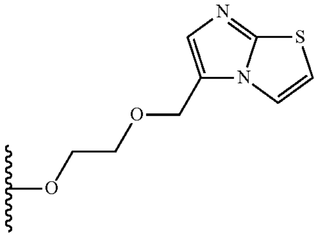 [SMILES: *OCCOCc1cnc2sccn12] | H | H | H |
| 1048 | 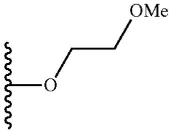 | 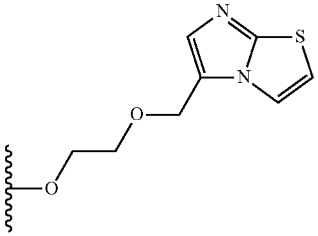 [SMILES: *OCCOCc1cnc2sccn12] | H | H | H |

TABLE 1-continued
formula (II)
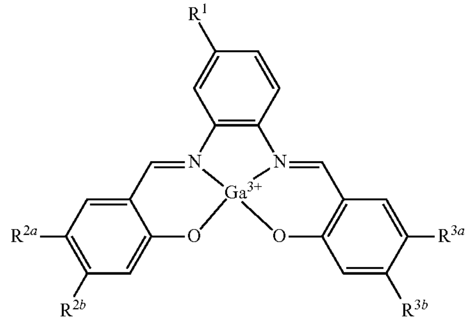
| Compound # | $R^1$ | $R^{2a}$ | $R^{2b}$ | $R^{3a}$ | $R^{3b}$ |
|---|---|---|---|---|---|
| 1049 | 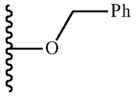 [SMILES: *OCc1ccccc1] | 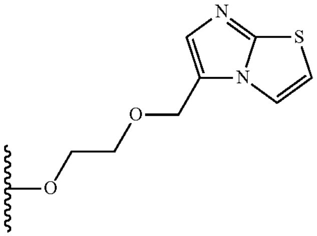 [SMILES: *OCCOCc1cnc2sccn12] | H | H | H |
| 1050 | H | H | 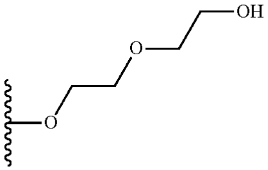 [SMILES: *OCCOCCO] | H | H |
| 1051 | —OMe | H | 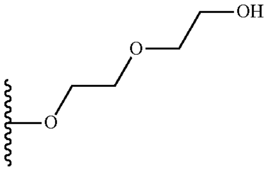 | H | H |

TABLE 1-continued
formula (II)
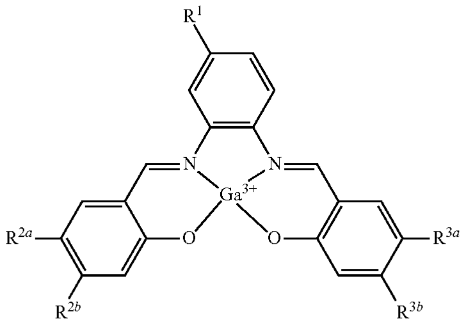
| Compound # | $R^1$ | $R^{2a}$ | $R^{2b}$ | $R^{3a}$ | $R^{3b}$ |
|---|---|---|---|---|---|
| 1052 | —OEt | H | 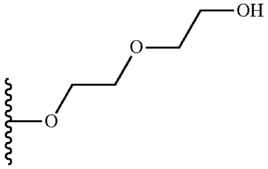 | H | H |
| 1053 | —OPr | H | 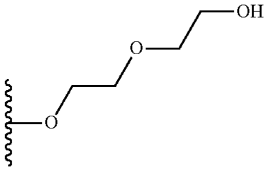 [SMILES: *OCCOCCO] | H | H |
| 1054 | —OiPr | H | 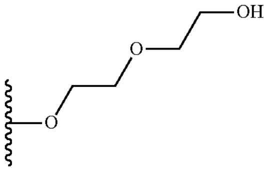 | H | H |
| 1055 | 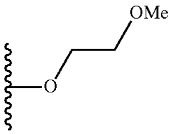 [SMILES: *OCCOC] | H | 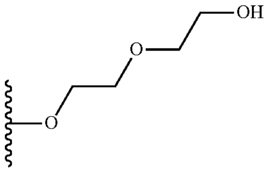 | H | H |

TABLE 1-continued
formula (II)
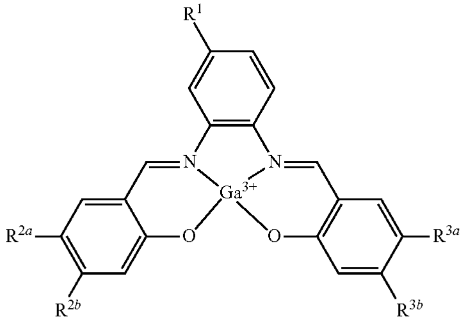
| Compound # | $R^1$ | $R^{2a}$ | $R^{2b}$ | $R^{3a}$ | $R^{3b}$ |
|---|---|---|---|---|---|
| 1056 | 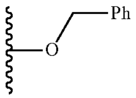 [SMILES: *OCc1ccccc1] | H | 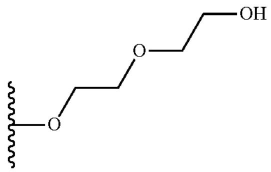 [SMILES: *OCCOCCO] | H | H |
| 1057 | H | H | 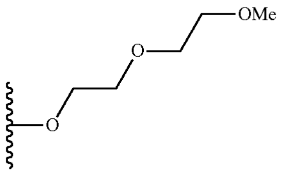 [SMILES: *OCCOCCOC] | H | H |
| 1058 | —OMe | H | 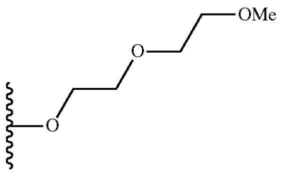 [SMILES: *OCCOCCOC] | H | H |
| 1059 | —OEt | H | 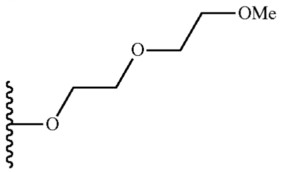 [SMILES: *OCCOCCOC] | H | H |

TABLE 1-continued
formula (II)
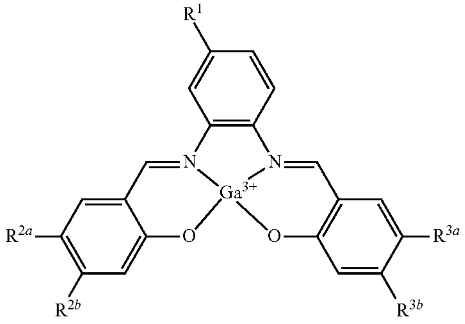
| Compound # | $R^1$ | $R^{2a}$ | $R^{2b}$ | $R^{3a}$ | $R^{3b}$ |
| --- | --- | --- | --- | --- | --- |
| 1060 | —OPr | H | 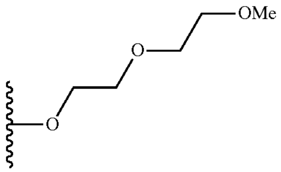 [SMILES: *OCCOCCOC] | H | H |
| 1061 | —OiPr | H | 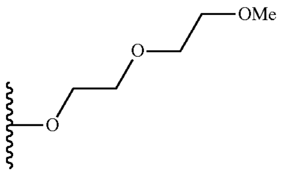 [SMILES: *OCCOCCOC] | H | H |
| 1062 | 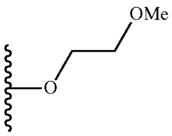 | H | 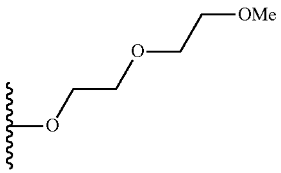 [SMILES: *OCCOCCOC] | H | H |

TABLE 1-continued
formula (II)
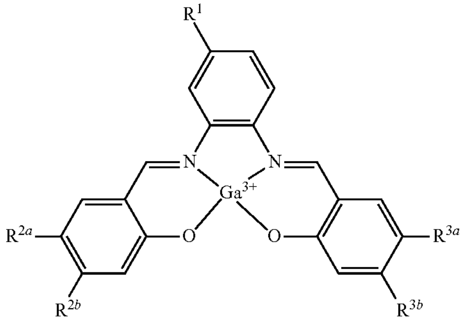
| Compound # | $R^1$ | $R^{2a}$ | $R^{2b}$ | $R^{3a}$ | $R^{3b}$ |
|---|---|---|---|---|---|
| 1063 | 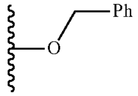 [SMILES: *OCc1ccccc1] | H | 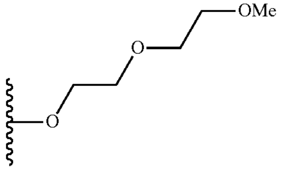 [SMILES: *OCCOCCOC] | H | H |
| 1064 | H | H | 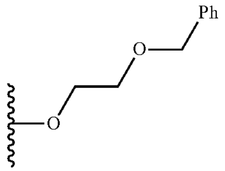 [SMILES: *OCCOCc1ccccc1] | H | H |
| 1065 | —OMe | H | 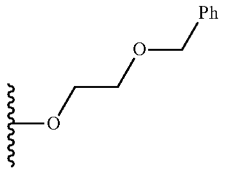 | H | H |
| 1066 | —OEt | H | 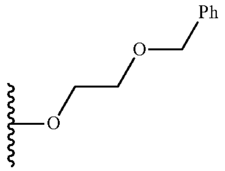 | H | H |

TABLE 1-continued
formula (II)
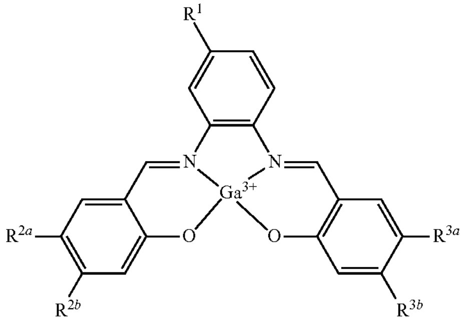
| Compound # | $R^1$ | $R^{2a}$ | $R^{2b}$ | $R^{3a}$ | $R^{3b}$ |
|---|---|---|---|---|---|
| 1067 | —OPr | H | 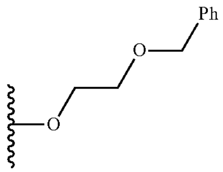 | H | H |
| 1068 | —OiPr | H | 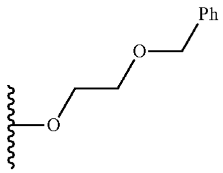 | H | H |
| 1069 | 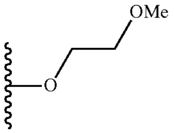 | H | 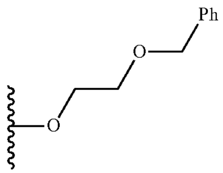 | H | H |

TABLE 1-continued
formula (II)
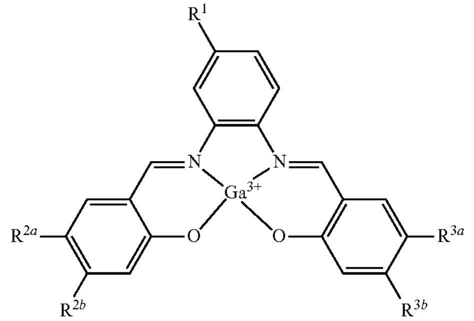
| Compound # | $R^1$ | $R^{2a}$ | $R^{2b}$ | $R^{3a}$ | $R^{3b}$ |
|---|---|---|---|---|---|
| 1070 | 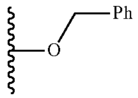 [SMILES: *OCc1ccccc1] | H | 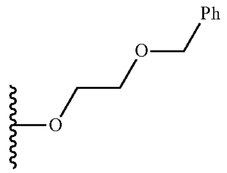 | H | H |
| 1071 | H | H | 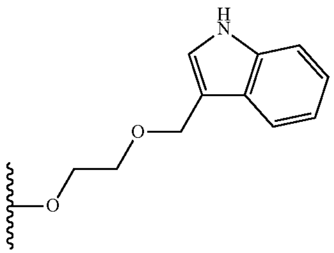 [SMILES: *OCCOCc1c[nH]c2ccccc12] | H | H |
| 1072 | —OMe | H | 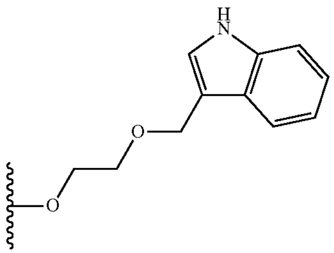 [SMILES: *OCCOCc1c[nH]c2ccccc12] | H | H |

TABLE 1-continued
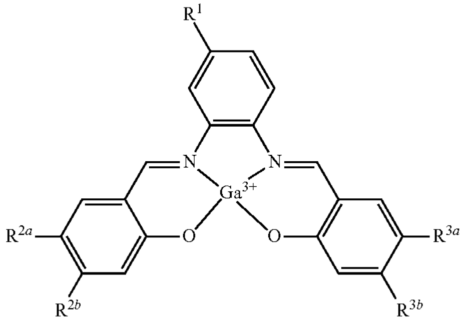
formula (II)
| Compound # | $R^1$ | $R^{2a}$ | $R^{2b}$ | $R^{3a}$ | $R^{3b}$ |
|---|---|---|---|---|---|
| 1073 | —OEt | H | 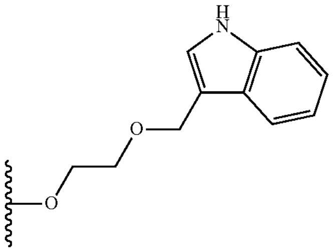 [SMILES: *OCCOCc1c[nH]c2ccccc12] | H | H |
| 1074 | —OPr | H | 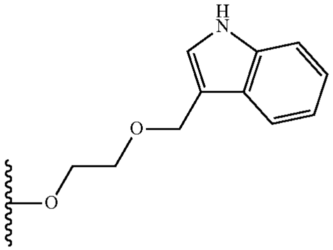 [SMILES: *OCCOCc1c[nH]c2ccccc12] | H | H |

TABLE 1-continued
formula (II)
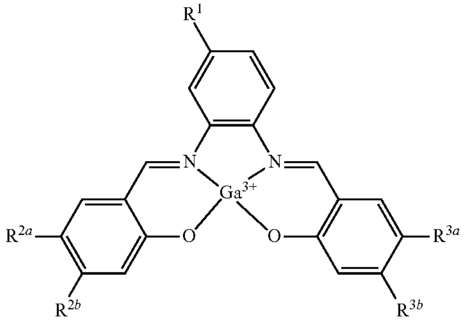
| Compound # | $R^1$ | $R^{2a}$ | $R^{2b}$ | $R^{3a}$ | $R^{3b}$ |
|---|---|---|---|---|---|
| 1075 | —OiPr | H | 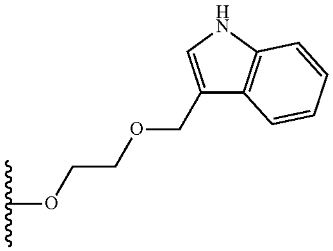 [SMILES: *OCCOCc1c[nH]c2ccccc12] | H | H |
| 1076 | 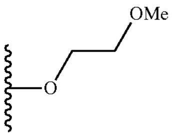 [SMILES: *OCCOC] | H | 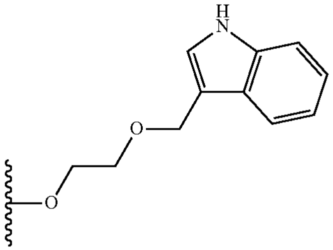 [SMILES: *OCCOCc1c[nH]c2ccccc12] | H | H |

TABLE 1-continued
formula (II)
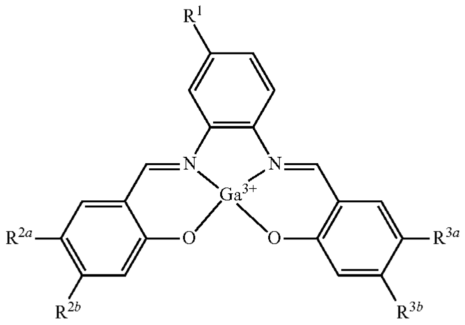
| Compound # | $R^1$ | $R^{2a}$ | $R^{2b}$ | $R^{3a}$ | $R^{3b}$ |
|---|---|---|---|---|---|
| 1077 | 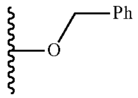 [SMILES: *OCc1ccccc1] | H | 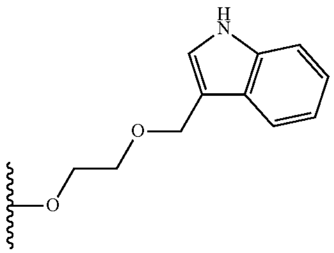 [SMILES: *OCCOCc1c[nH]c2ccccc12] | H | H |
| 1078 | H | H | 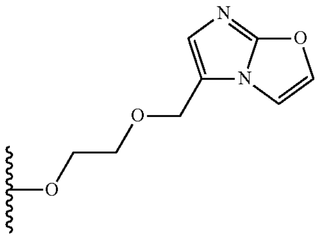 [SMILES: *OCCOCc1cnc2occn12] | H | H |

TABLE 1-continued
formula (II)
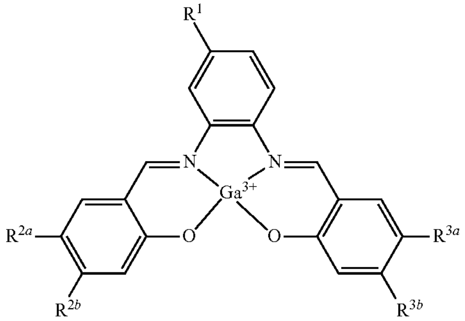
| Compound # | $R^1$ | $R^{2a}$ | $R^{2b}$ | $R^{3a}$ | $R^{3b}$ |
|---|---|---|---|---|---|
| 1079 | —OMe | H | 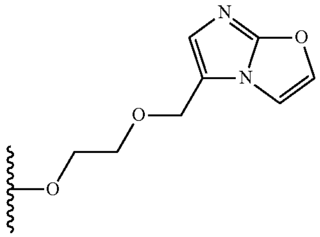 [SMILES: *OCCOCc1cnc2occn12] | H | H |
| 1080 | —OEt | H | 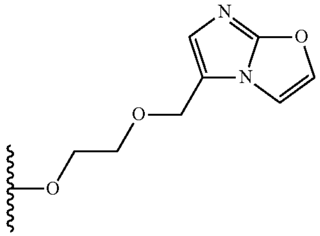 [SMILES: *OCCOCc1cnc2occn12] | H | H |
| 1081 | —OPr | H | 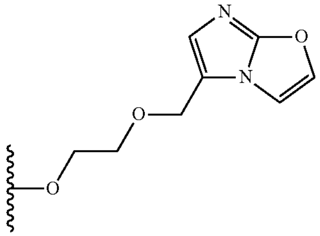 [SMILES: *OCCOCc1cnc2occn12] | H | H |

TABLE 1-continued
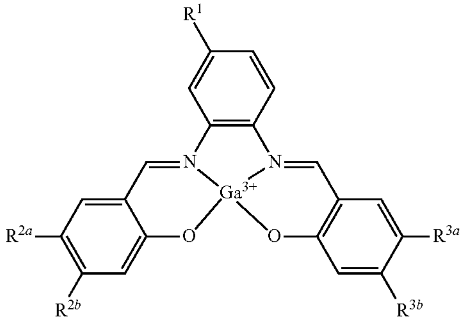
formula (II)
| Compound # | $R^1$ | $R^{2a}$ | $R^{2b}$ | $R^{3a}$ | $R^{3b}$ |
|---|---|---|---|---|---|
| 1082 | —OiPr | H | 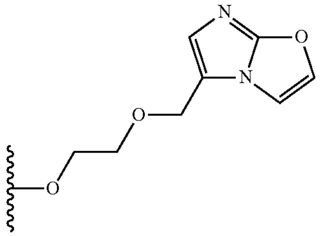 [SMILES: *OCCOCc1cnc2occn12] | H | H |
| 1083 | 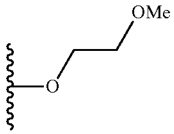 | H | 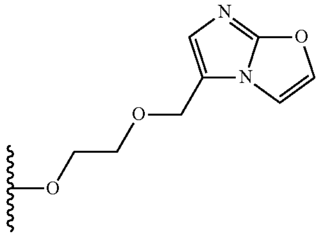 [SMILES: *OCCOCc1cnc2occn12] | H | H |

TABLE 1-continued
formula (II)
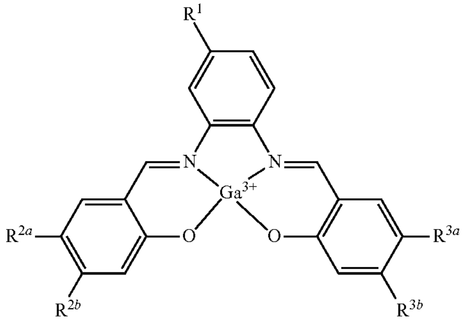
| Compound # | $R^1$ | $R^{2a}$ | $R^{2b}$ | $R^{3a}$ | $R^{3b}$ |
|---|---|---|---|---|---|
| 1084 | 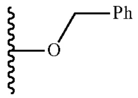 [SMILES: *OCc1ccccc1] | H | 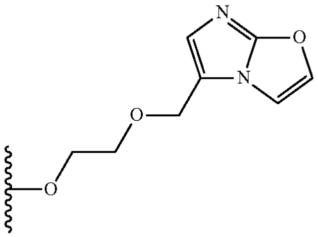 [SMILES: *OCCOCc1cnc2occn12] | H | H |
| 1085 | H | H | 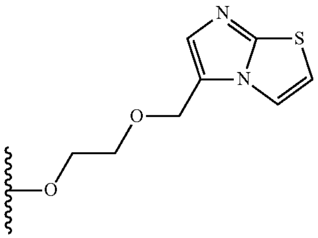 [SMILES: *OCCOCc1cnc2sccn12] | H | H |

TABLE 1-continued
formula (II)
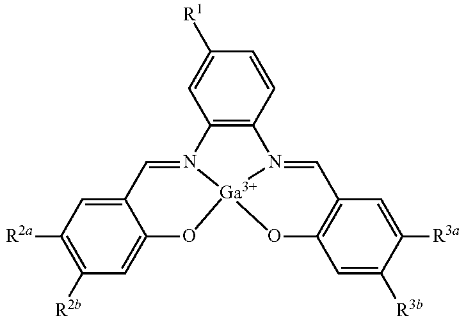
| Compound # | $R^1$ | $R^{2a}$ | $R^{2b}$ | $R^{3a}$ | $R^{3b}$ |
| --- | --- | --- | --- | --- | --- |
| 1086 | —OMe | H | 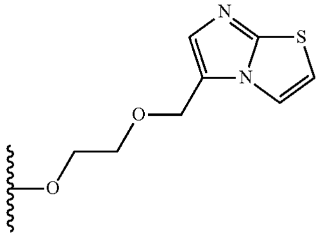 [SMILES: *OCCOCc1cnc2sccn12] | H | H |
| 1087 | —OEt | H | 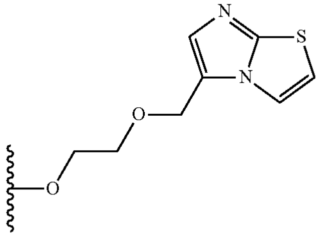 [SMILES: *OCCOCc1cnc2sccn12] | H | H |

TABLE 1-continued
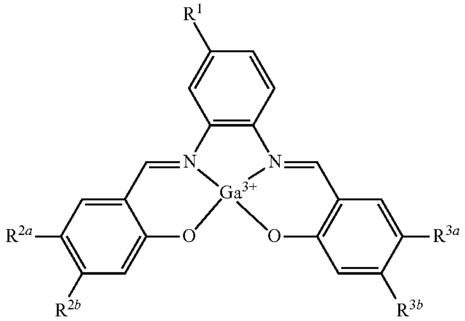
formula (II)
| Compound # | $R^1$ | $R^{2a}$ | $R^{2b}$ | $R^{3a}$ | $R^{3b}$ |
|---|---|---|---|---|---|
| 1088 | —OPr | H | 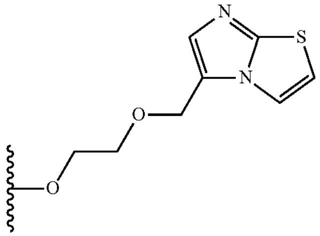 [SMILES: *OCCOCc1cnc2sccn12] | H | H |
| 1089 | —OiPr | H | 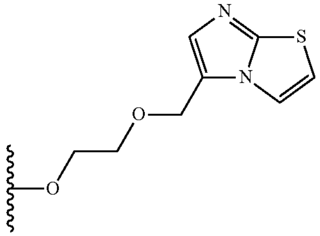 [SMILES: *OCCOCc1cnc2sccn12] | H | H |

TABLE 1-continued
formula (II)
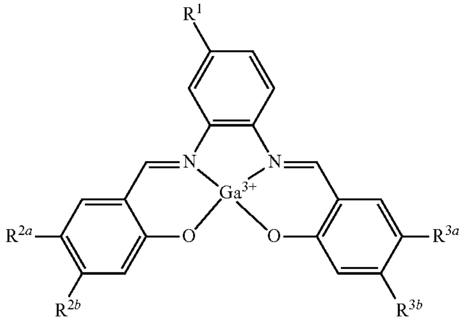
| Compound # | $R^1$ | $R^{2a}$ | $R^{2b}$ | $R^{3a}$ | $R^{3b}$ |
|---|---|---|---|---|---|
| 1090 | 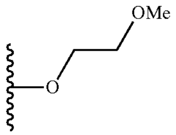 | H | 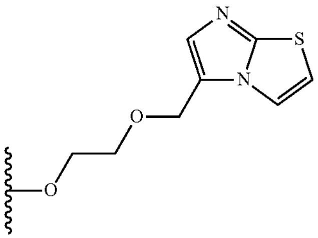 [SMILES: *OCCOCc1cnc2sccn12] | H | H |
| 1091 | 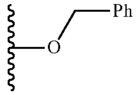 [SMILES: *OCc1ccccc1] | H | 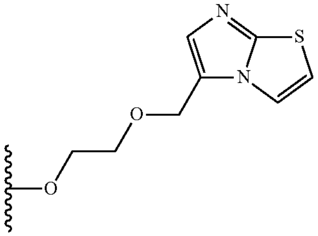 [SMILES: *OCCOCc1cnc2sccn12] | H | H |
| 1092 | H | H | H | 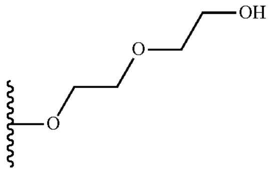 [SMILES: *OCCOCCO] | H |

TABLE 1-continued
formula (II)
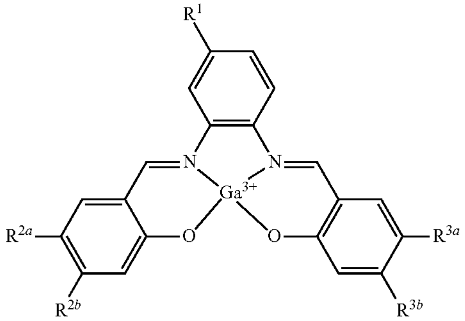
| Compound # | $R^1$ | $R^{2a}$ | $R^{2b}$ | $R^{3a}$ | $R^{3b}$ |
|---|---|---|---|---|---|
| 1093 | —OMe | H | H | 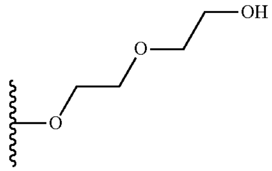 | H |
| 1094 | —OEt | H | H | 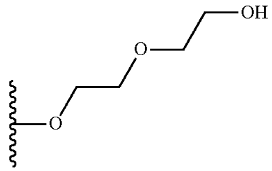 | H |
| 1095 | —OPr | H | H | 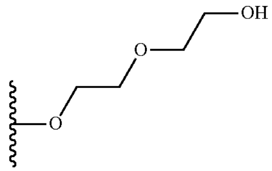 | H |
| 1096 | —OiPr | H | H | 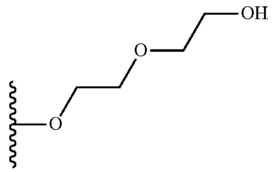 | H |

TABLE 1-continued
formula (II)
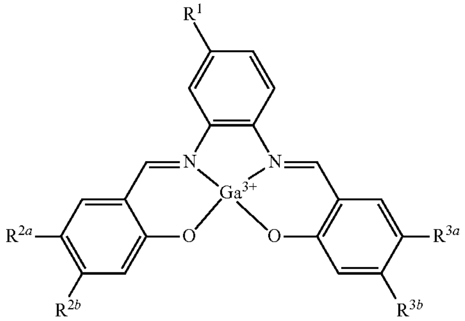
| Compound # | $R^1$ | $R^{2a}$ | $R^{2b}$ | $R^{3a}$ | $R^{3b}$ |
|---|---|---|---|---|---|
| 1097 | 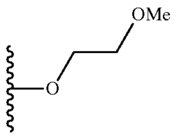 | H | H | 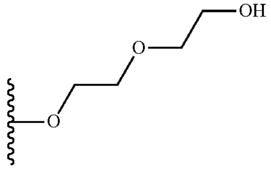 [SMILES: *OCCOCCO] | H |
| 1098 | 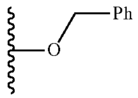 [SMILES: *OCc1ccccc1] | H | H | 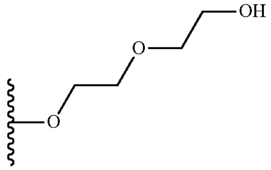 | H |
| 1099 | H | H | H | 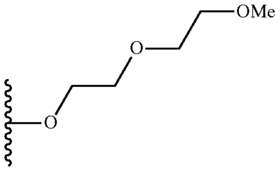 [SMILES: *OCCOCCOC] | H |

TABLE 1-continued
formula (II)
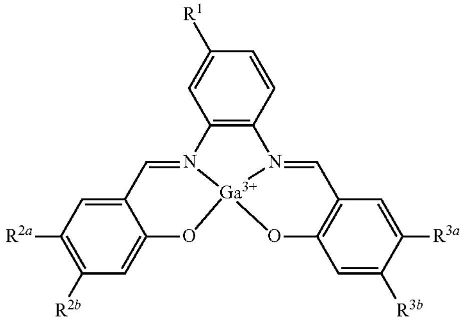
| Compound # | $R^1$ | $R^{2a}$ | $R^{2b}$ | $R^{3a}$ | $R^{3b}$ |
|---|---|---|---|---|---|
| 1100 | —OMe | H | H | 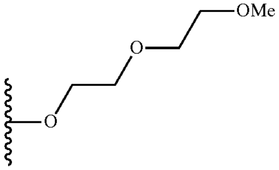 | H |
| 1101 | —OEt | H | H | 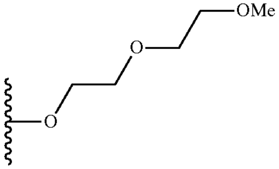 | H |
| 1102 | —OPr | H | H | 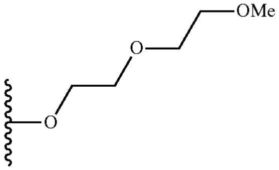 | H |
| 1103 | —OiPr | H | H | 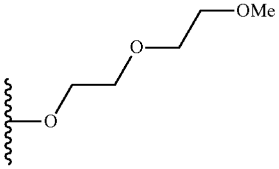 | H |

TABLE 1-continued
formula (II)
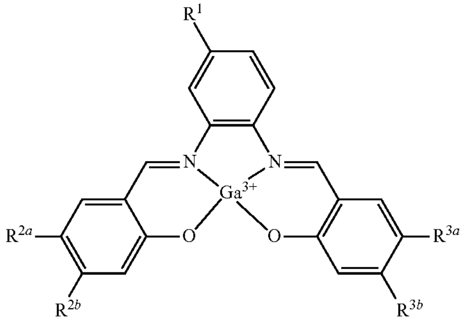
| Compound # | R1 | $R^{2a}$ | $R^{2b}$ | $R^{3a}$ | $R^{3b}$ |
|---|---|---|---|---|---|
| 1104 | 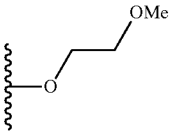 | H | H | 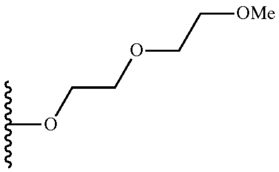 | H |
| 1105 | 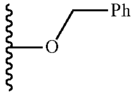 [SMILES: *OCc1ccccc1] | H | H | 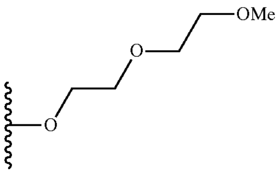 [SMILES: *OCCOCCOC] | H |
| 1106 | H | H | H | 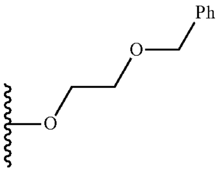 [SMILES: *OCCOCc1ccccc1] | H |

TABLE 1-continued
formula (II)
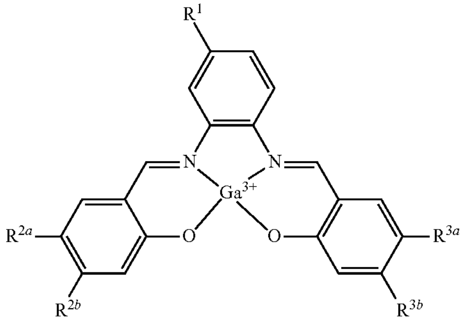
| Compound # | $R^1$ | $R^{2a}$ | $R^{2b}$ | $R^{3a}$ | $R^{3b}$ |
|---|---|---|---|---|---|
| 1107 | —OMe | H | H | 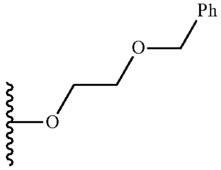 [SMILES: *OCCOCc1ccccc1] | H |
| 1108 | —OEt | H | H | 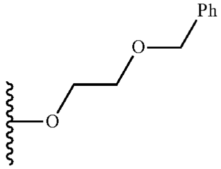 [SMILES: *OCCOCc1ccccc1] | H |
| 1109 | —OPr | H | H | 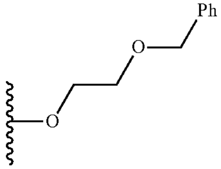 [SMILES: *OCCOCc1ccccc1] | H |
| 1110 | —OiPr | H | H | 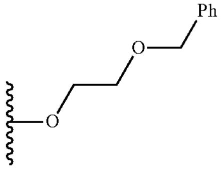 | H |

TABLE 1-continued
formula (II)
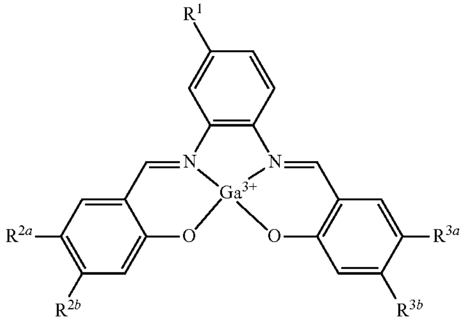
| Compound # | $R^1$ | $R^{2a}$ | $R^{2b}$ | $R^{3a}$ | $R^{3b}$ |
|---|---|---|---|---|---|
| 1111 | 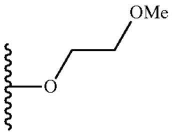 | H | H | 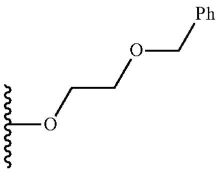 | H |
| 1112 | 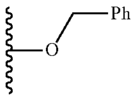 [SMILES: *OCc1ccccc1] | H | H | 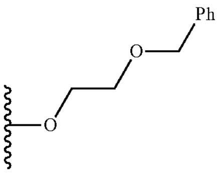 [SMILES: *OCCOCc1ccccc1] | H |
| 1113 | H | H | H | 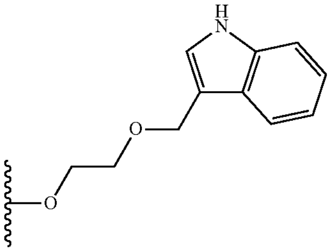 [SMILES: *OCCOCc1c[nH]c2ccccc12] | H |

TABLE 1-continued
formula (II)
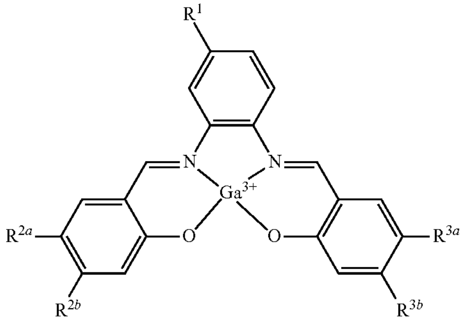
| Compound # | $R^1$ | $R^{2a}$ | $R^{2b}$ | $R^{3a}$ | $R^{3b}$ |
|---|---|---|---|---|---|
| 1114 | —OMe | H | H | 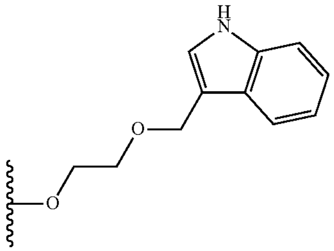 [SMILES: *OCCOCc1c[nH]c2ccccc12] | H |
| 1115 | —OEt | H | H | 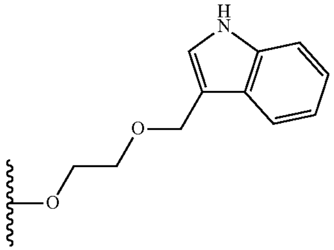 [SMILES: *OCCOCc1c[nH]c2ccccc12] | H |

TABLE 1-continued
formula (II)
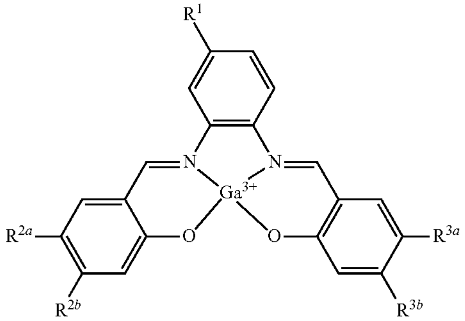
| Compound # | $R^1$ | $R^{2a}$ | $R^{2b}$ | $R^{3a}$ | $R^{3b}$ |
|---|---|---|---|---|---|
| 1116 | —OPr | H | H | 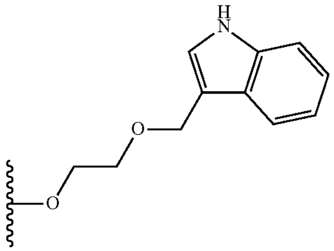 [SMILES: *OCCOCc1c[nH]c2ccccc12] | H |
| 1117 | —OiPr | H | H | 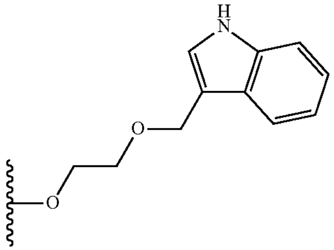 [SMILES: *OCCOCc1c[nH]c2ccccc12] | H |

TABLE 1-continued
formula (II)
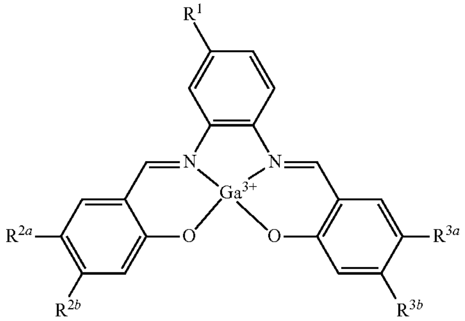
| Compound # | $R^1$ | $R^{2a}$ | $R^{2b}$ | $R^{3a}$ | $R^{3b}$ |
|---|---|---|---|---|---|
| 1118 | 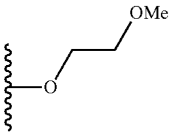 | H | H | 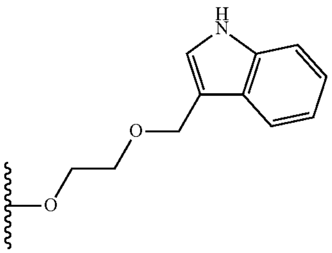 [SMILES: *OCCOCc1c[nH]c2ccccc12] | H |
| 1119 | 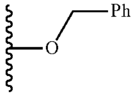 [SMILES: *OCc1ccccc1] | H | H | 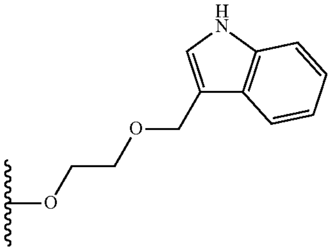 [SMILES: *OCCOCc1c[nH]c2ccccc12] | H |

TABLE 1-continued
formula (II)
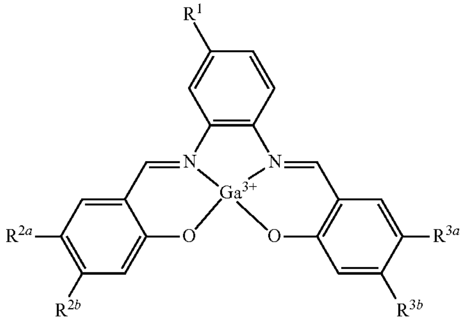
| Compound # | $R^1$ | $R^{2a}$ | $R^{2b}$ | $R^{3a}$ | $R^{3b}$ |
|---|---|---|---|---|---|
| 1120 | H | H | H | 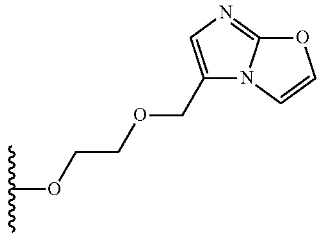 [SMILES: *OCCOCc1cnc2occn12] | H |
| 1121 | —OMe | H | H | 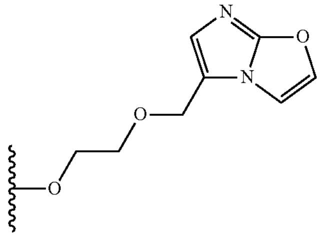 [SMILES: *OCCOCc1cnc2occn12] | H |
| 1122 | —OEt | H | H | 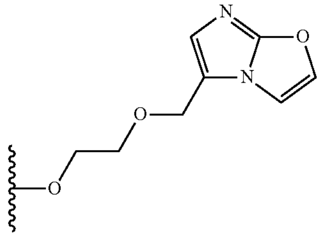 [SMILES: *OCCOCc1cnc2occn12] | H |

TABLE 1-continued
formula (II)
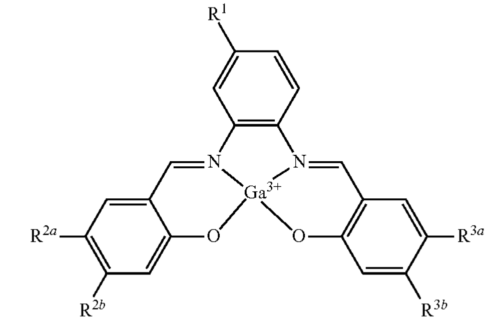
| Compound # | $R^1$ | $R^{2a}$ | $R^{2b}$ | $R^{3a}$ | $R^{3b}$ |
|---|---|---|---|---|---|
| 1123 | —OPr | H | H | 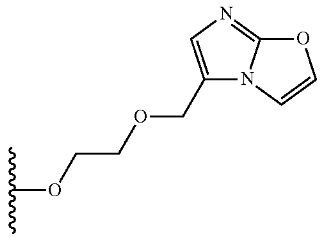 [SMILES: *OCCOCc1cnc2occn12] | H |
| 1124 | —OiPr | H | H | 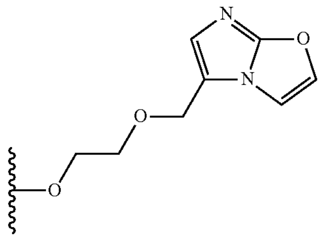 [SMILES: *OCCOCc1cnc2occn12] | H |

TABLE 1-continued
formula (II)
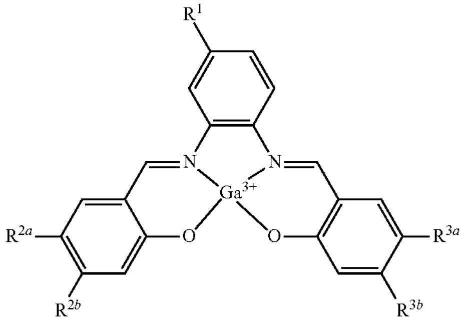
| Compound # | $R^1$ | $R^{2a}$ | $R^{2b}$ | $R^{3a}$ | $R^{3b}$ |
|---|---|---|---|---|---|
| 1125 | 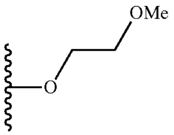 | H | H | 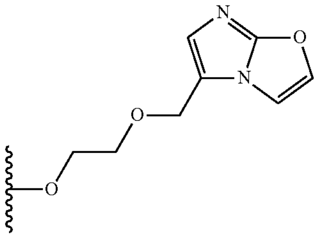 [SMILES: *OCCOCc1cnc2occn12] | H |
| 1126 | 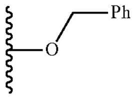 [SMILES: *OCc1ccccc1] | H | H | 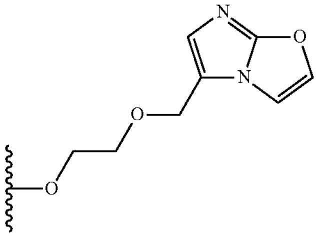 [SMILES: *OCCOCc1cnc2occn12] | H |

TABLE 1-continued
formula (II)
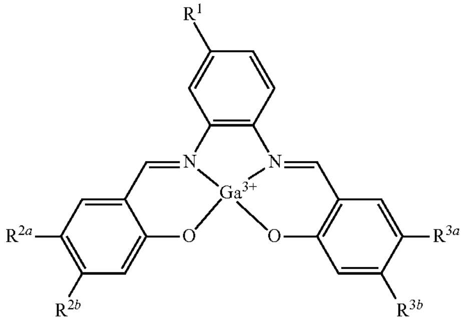
| Compound # | $R^1$ | $R^{2a}$ | $R^{2b}$ | $R^{3a}$ | $R^{3b}$ |
|---|---|---|---|---|---|
| 1127 | H | H | H | 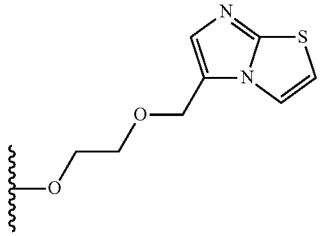 [SMILES: *OCCOCc1cnc2sccn12] | H |
| 1128 | —OMe | H | H | 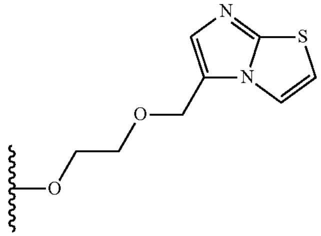 [SMILES: *OCCOCc1cnc2sccn12] | H |

TABLE 1-continued
formula (II)
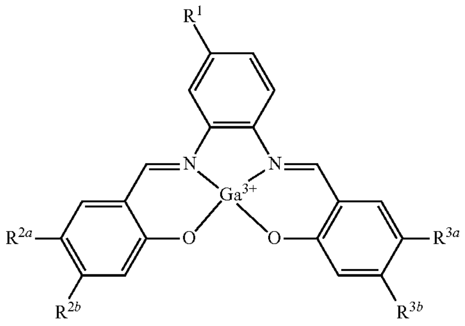
| Compound # | $R^1$ | $R^{2a}$ | $R^{2b}$ | $R^{3a}$ | $R^{3b}$ |
|---|---|---|---|---|---|
| 1129 | —OEt | H | H | 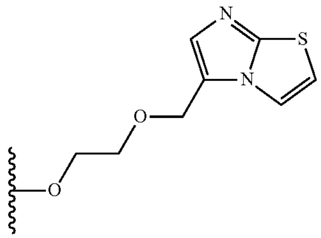 [SMILES: *OCCOCc1cnc2sccn12] | H |
| 1130 | —OPr | H | H | 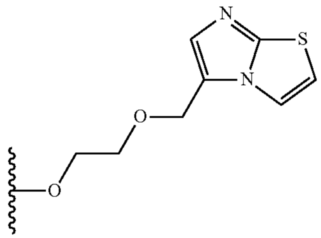 [SMILES: *OCCOCc1cnc2sccn12] | H |

TABLE 1-continued
formula (II)
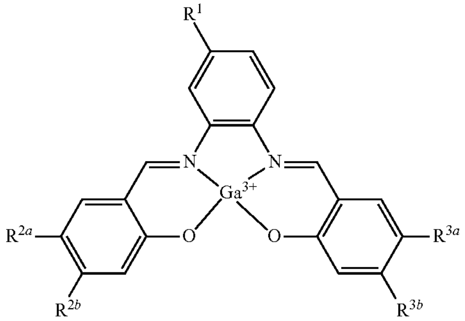
| Compound # | $R^1$ | $R^{2a}$ | $R^{2b}$ | $R^{3a}$ | $R^{3b}$ |
|---|---|---|---|---|---|
| 1131 | —OiPr | H | H | 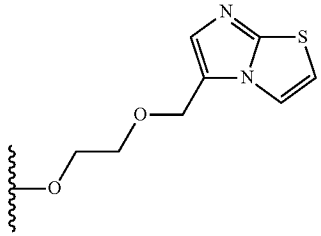 [SMILES: *OCCOCc1cnc2sccn12] | H |
| 1132 | 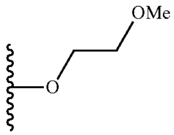 | H | H | 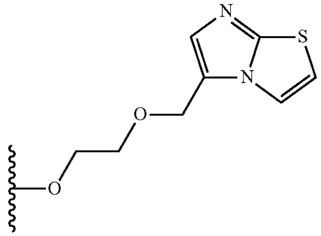 [SMILES: *OCCOCc1cnc2sccn12] | H |

TABLE 1-continued
formula (II)
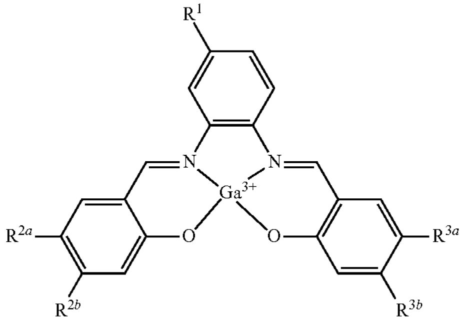
| Compound # | $R^1$ | $R^{2a}$ | $R^{2b}$ | $R^{3a}$ | $R^{3b}$ |
|---|---|---|---|---|---|
| 1133 | 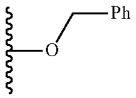 [SMILES: *OCc1ccccc1] | H | H | 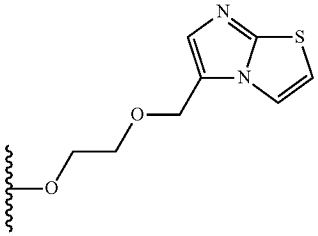 [SMILES: *OCCOCc1cnc2sccn12] | H |
| 1134 | H | H | H | H | 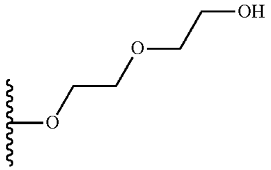 |
| 1135 | —OMe | H | H | H | 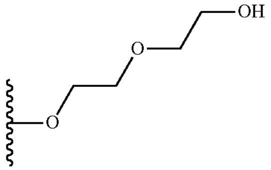 |

TABLE 1-continued
formula (II)
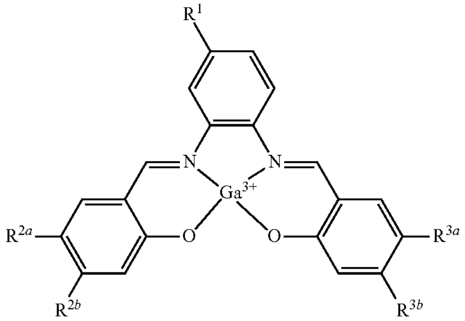
| Compound # | $R^1$ | $R^{2a}$ | $R^{2b}$ | $R^{3a}$ | $R^{3b}$ |
|---|---|---|---|---|---|
| 1136 | —OEt | H | H | H | 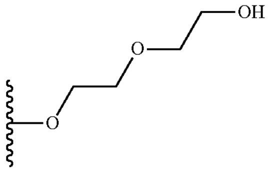 |
| 1137 | —OPr | H | H | H | 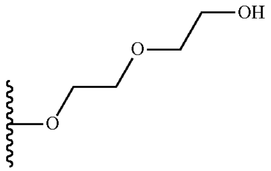 [SMILES: *OCCOCCO] |
| 1138 | —OiPr | H | H | H | 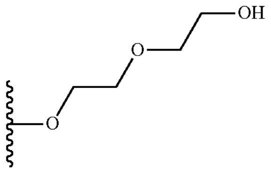 |
| 1139 | 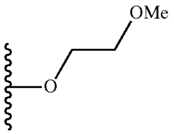 [SMILES: *OCCOC] | H | H | H | 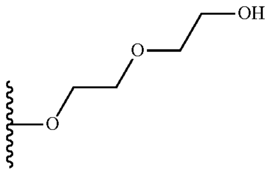 |

TABLE 1-continued
formula (II)
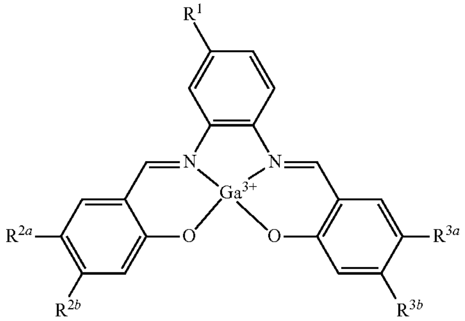
| Compound # | R1 | R2a | R2b | R3a | R3b |
|---|---|---|---|---|---|
| 1140 | 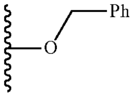 [SMILES: *OCc1ccccc1] | H | H | H | 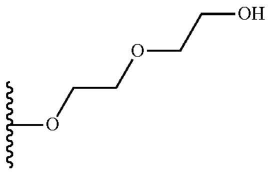 [SMILES: *OCCOCCO] |
| 1141 | H | H | H | H | 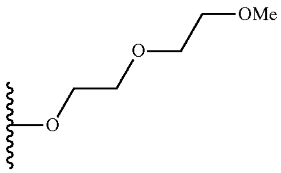 [SMILES: *OCCOCCOC] |
| 1142 | —OMe | H | H | H | 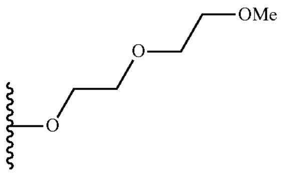 [SMILES: *OCCOCCOC] |

TABLE 1-continued
formula (II)
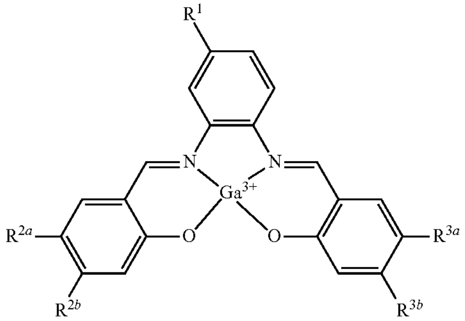
| Compound # | $R^1$ | $R^{2a}$ | $R^{2b}$ | $R^{3a}$ | $R^{3b}$ |
|---|---|---|---|---|---|
| 1143 | —OEt | H | H | H | 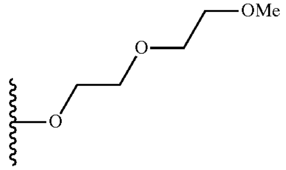 [SMILES: *OCCOCCOC] |
| 1144 | —OPr | H | H | H | 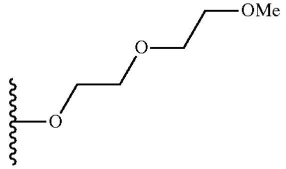 [SMILES: *OCCOCCOC] |
| 1145 | —OiPr | H | H | H | 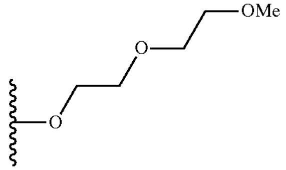 |
| 1146 | 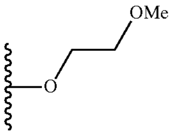 [SMILES: *OCCOC] | H | H | H | 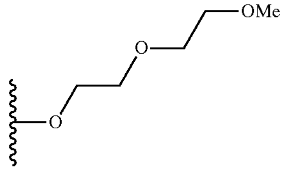 [SMILES: *OCCOCCOC] |

TABLE 1-continued
formula (II)
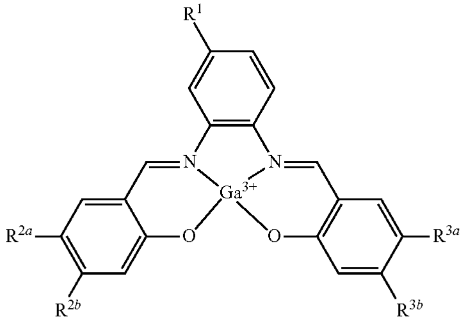
| Compound # | $R^1$ | $R^{2a}$ | $R^{2b}$ | $R^{3a}$ | $R^{3b}$ |
|---|---|---|---|---|---|
| 1147 | 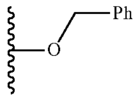 [SMILES: *OCc1ccccc1] | H | H | H | 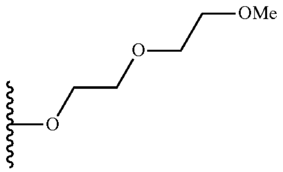 |
| 1148 | H | H | H | H | 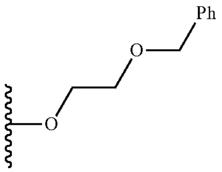 [SMILES: *OCCOCc1ccccc1] |
| 1149 | —OMe | H | H | H | 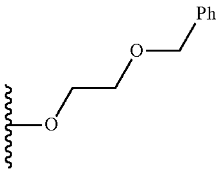 [SMILES: *OCCOCc1ccccc1] |

TABLE 1-continued
formula (II)
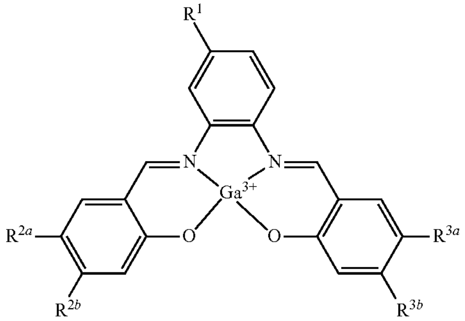
| Compound # | $R^1$ | $R^{2a}$ | $R^{2b}$ | $R^{3a}$ | $R^{3b}$ |
|---|---|---|---|---|---|
| 1150 | —OEt | H | H | H | 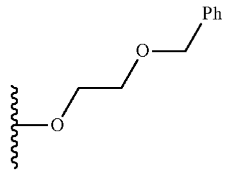 [SMILES: *OCCOCc1ccccc1] |
| 1151 | —OPr | H | H | H | 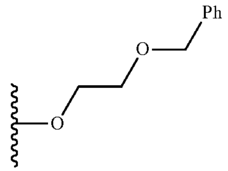 [SMILES: *OCCOCc1ccccc1] |
| 1152 | —OiPr | H | H | H | 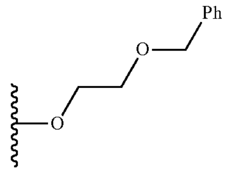 [SMILES: *OCCOCc1ccccc1] |
| 1153 | 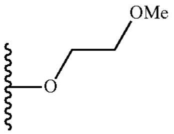 [SMILES: *OCCOC] | H | H | H | 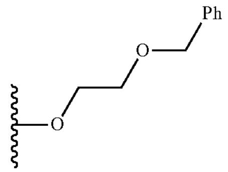 |

TABLE 1-continued
formula (II)
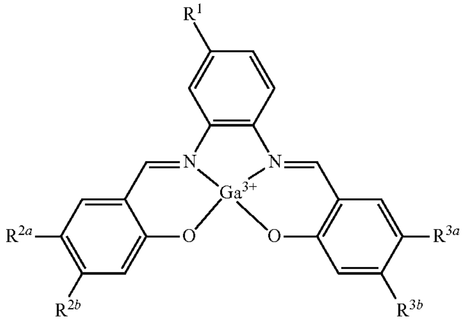
| Compound # | $R^1$ | $R^{2a}$ | $R^{2b}$ | $R^{3a}$ | $R^{3b}$ |
|---|---|---|---|---|---|
| 1154 | 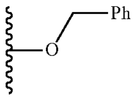 [SMILES: *OCc1ccccc1] | H | H | H | 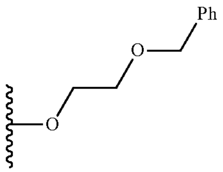 |
| 1155 | H | H | H | H | 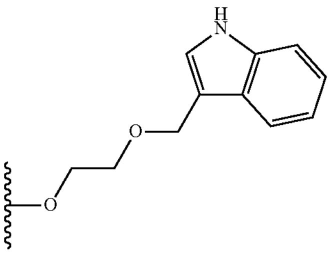 [SMILES: *OCCOCc1c[nH]c2ccccc12] |
| 1156 | —OMe | H | H | H | 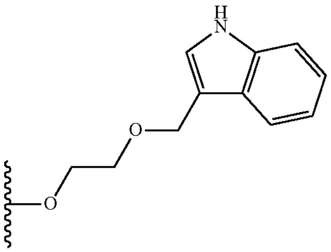 [SMILES: *OCCOCc1c[nH]c2ccccc12] |

TABLE 1-continued
formula (II)
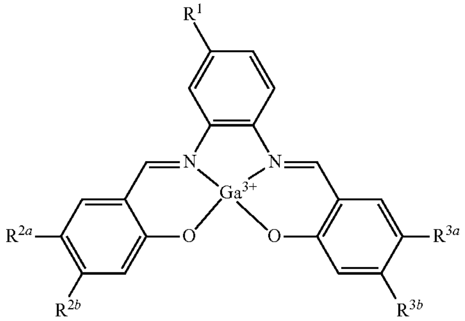
| Compound # | $R^1$ | $R^{2a}$ | $R^{2b}$ | $R^{3a}$ | $R^{3b}$ |
|---|---|---|---|---|---|
| 1157 | —OEt | H | H | H | 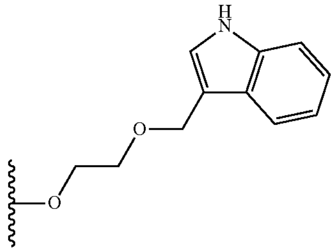 [SMILES: *OCCOCc1c[nH]c2ccccc12] |
| 1158 | —OPr | H | H | H | 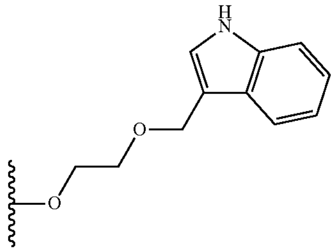 [SMILES: *OCCOCc1c[nH]c2ccccc12] |

TABLE 1-continued
formula (II)
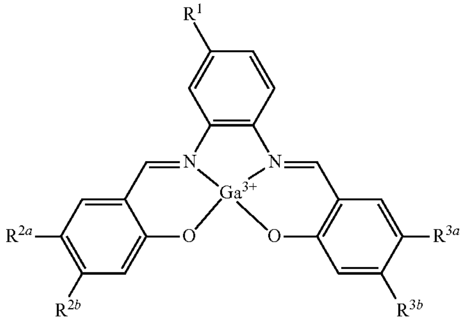
| Compound # | $R^1$ | $R^{2a}$ | $R^{2b}$ | $R^{3a}$ | $R^{3b}$ |
| --- | --- | --- | --- | --- | --- |
| 1159 | —OiPr | H | H | H | 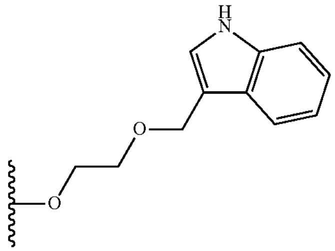 [SMILES: *OCCOCc1c[nH]c2ccccc12] |
| 1160 | 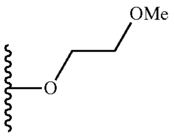 [SMILES: *OCCOC] | H | H | H | 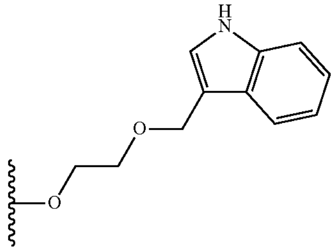 [SMILES: *OCCOCc1c[nH]c2ccccc12] |

TABLE 1-continued
formula (II)
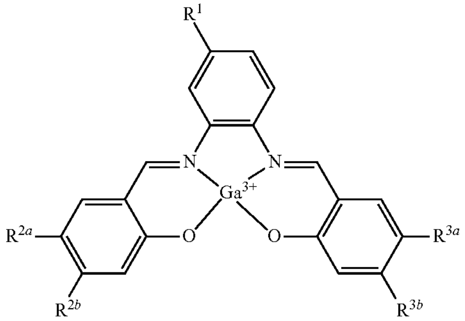
| Compound # | $R^1$ | $R^{2a}$ | $R^{2b}$ | $R^{3a}$ | $R^{3b}$ |
|---|---|---|---|---|---|
| 1161 | 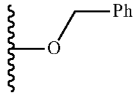 [SMILES: *OCc1ccccc1] | H | H | H | 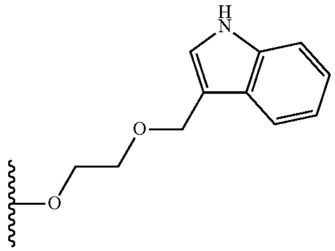 [SMILES: *OCCOCc1c[nH]c2ccccc12] |
| 1162 | H | H | H | H | 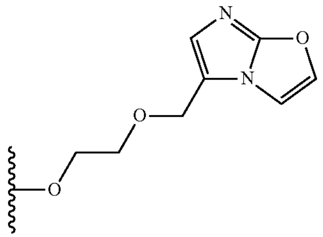 [SMILES: *OCCOCc1cnc2occn12] |

TABLE 1-continued
formula (II)
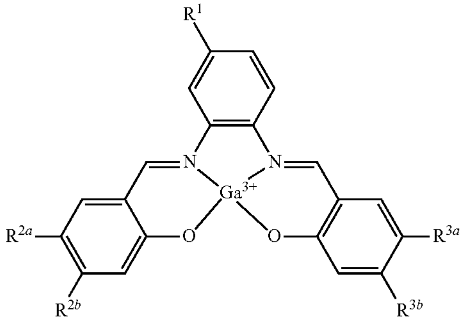
| Compound # | $R^1$ | $R^{2a}$ | $R^{2b}$ | $R^{3a}$ | $R^{3b}$ |
|---|---|---|---|---|---|
| 1163 | —OMe | H | H | H | 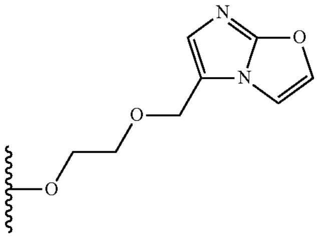 [SMILES: *OCCOCc1cnc2occn12] |
| 1164 | —OEt | H | H | H | 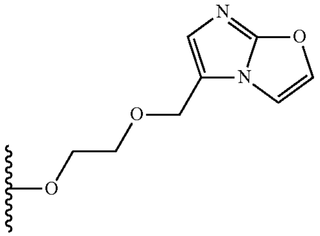 [SMILES: *OCCOCc1cnc2occn12] |
| 1165 | —OPr | H | H | H | 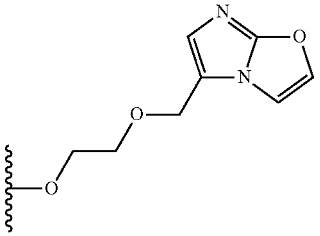 [SMILES: *OCCOCc1cnc2occn12] |

TABLE 1-continued
formula (II)
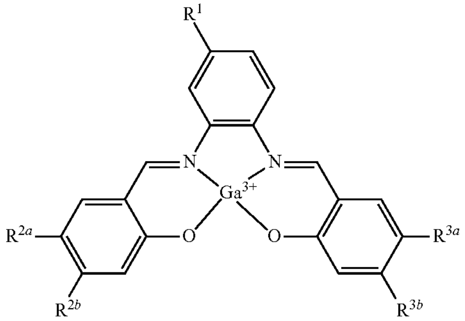
| Compound # | $R^1$ | $R^{2a}$ | $R^{2b}$ | $R^{3a}$ | $R^{3b}$ |
|---|---|---|---|---|---|
| 1166 | —OiPr | H | H | H | 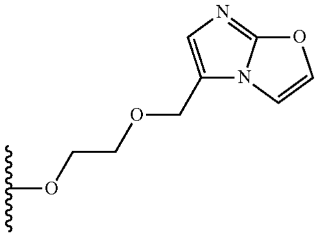 [SMILES: *OCCOCc1cnc2occn12] |
| 1167 | 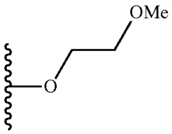 | H | H | H | 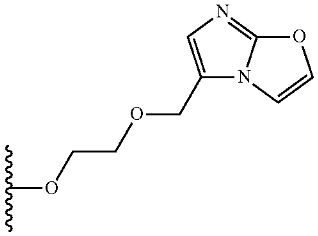 [SMILES: *OCCOCc1cnc2occn12] |

TABLE 1-continued
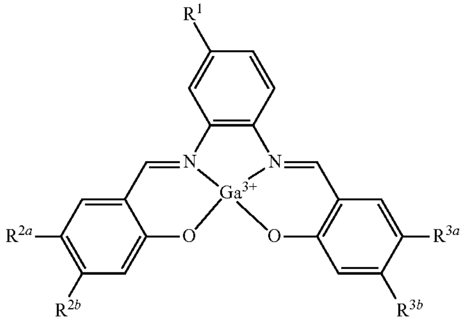
formula (II)
| Compound # | $R^1$ | $R^{2a}$ | $R^{2b}$ | $R^{3a}$ | $R^{3b}$ |
|---|---|---|---|---|---|
| 1168 | 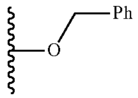 [SMILES: *OCc1ccccc1] | H | H | H | 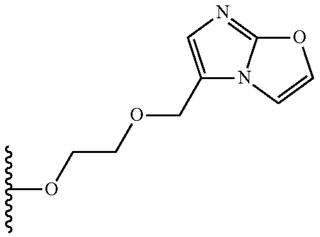 [SMILES: *OCCOCc1cnc2occn12] |
| 1169 | H | H | H | H | 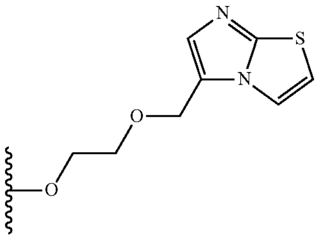 [SMILES: *OCCOCc1cnc2sccn12] |

TABLE 1-continued
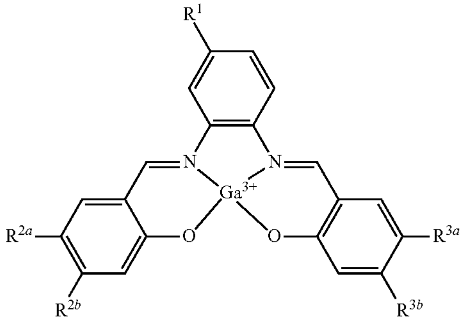
formula (II)
| Compound # | $R^1$ | $R^{2a}$ | $R^{2b}$ | $R^{3a}$ | $R^{3b}$ |
|---|---|---|---|---|---|
| 1170 | —OMe | H | H | H | 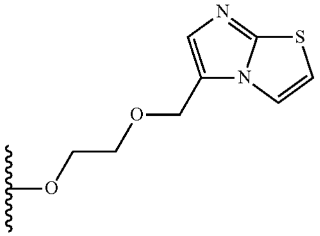 [SMILES: *OCCOCc1cnc2sccn12] |
| 1171 | —OEt | H | H | H | 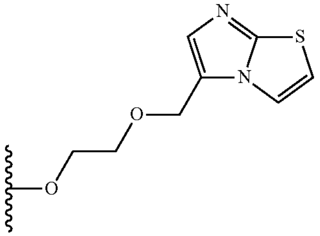 [SMILES: *OCCOCc1cnc2sccn12] |

TABLE 1-continued
formula (II)
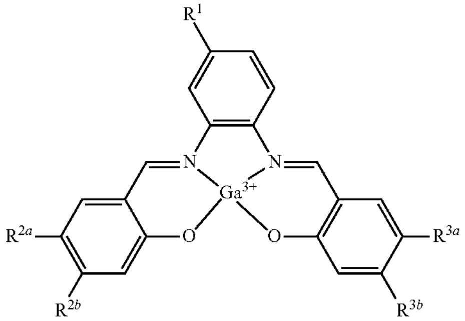
| Compound # | $R^1$ | $R^{2a}$ | $R^{2b}$ | $R^{3a}$ | $R^{3b}$ |
|---|---|---|---|---|---|
| 1172 | —OPr | H | H | H | 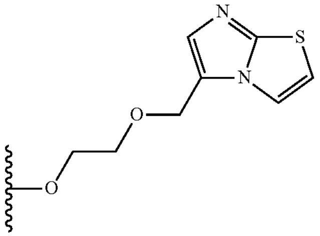 [SMILES: *OCCOCc1cnc2sccn12] |
| 1173 | —OiPr | H | H | H | 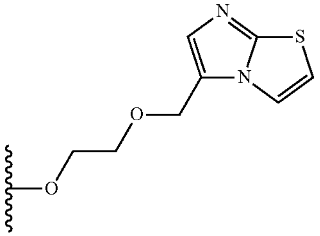 [SMILES: *OCCOCc1cnc2sccn12] |

TABLE 1-continued
formula (II)
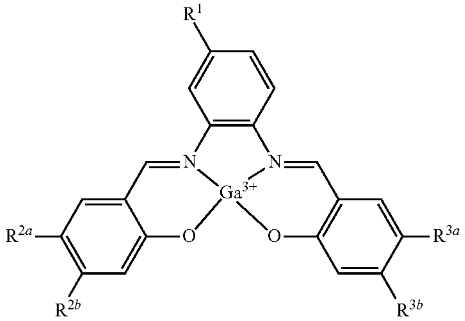
| Compound # | $R^1$ | $R^{2a}$ | $R^{2b}$ | $R^{3a}$ | $R^{3b}$ |
|---|---|---|---|---|---|
| 1174 | 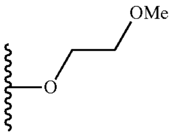 | H | H | H | 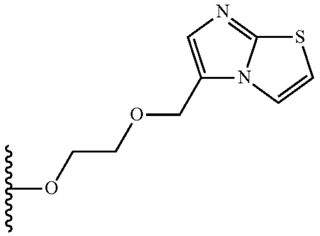 [SMILES: *OCCOCc1cnc2sccn12] |
| 1175 | 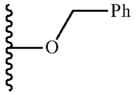 [SMILES: *OCc1ccccc1] | H | H | H | 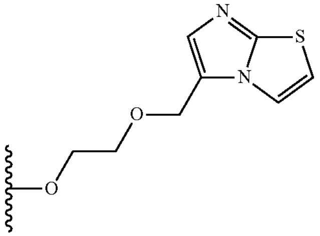 [SMILES: *OCCOCc1cnc2sccn12] |
| 1176 | H | 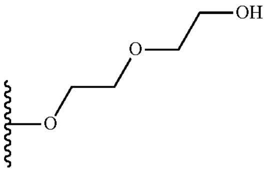 [SMILES: *OCCOCCO] | H | 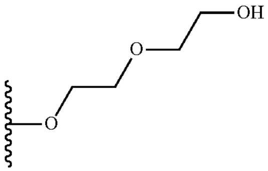 [SMILES: *OCCOCCO] | H |

TABLE 1-continued
formula (II)
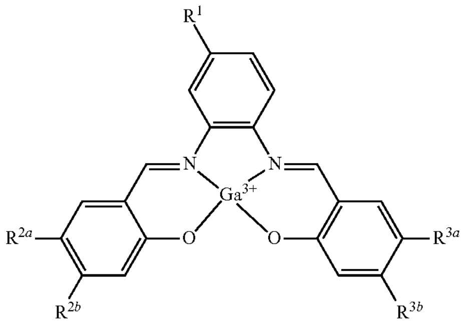
| Compound # | $R^1$ | $R^{2a}$ | $R^{2b}$ | $R^{3a}$ | $R^{3b}$ |
|---|---|---|---|---|---|
| 1177 | —OMe | 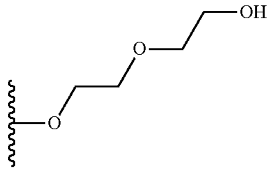 | H | 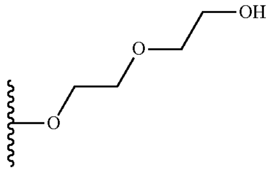 | H |
| 1178 | —OEt | 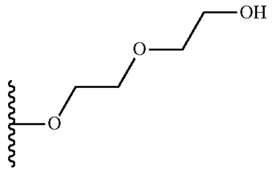 [SMILES: *OCCOCCO] | H | 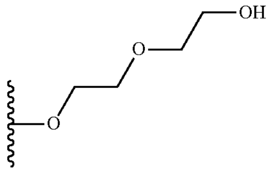 | H |
| 1179 | —OPr | 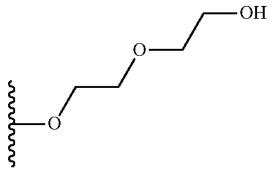 | H | 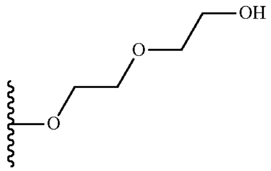 | H |
| 1180 | —OiPr | 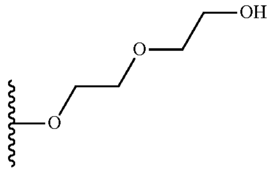 | H | 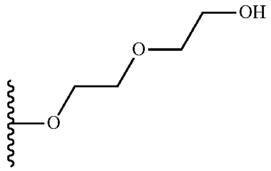 | H |

TABLE 1-continued
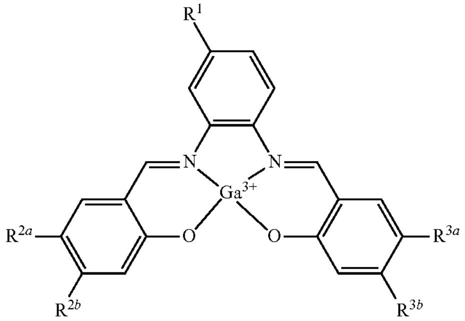
formula (II)
| Compound # | $R^1$ | $R^{2a}$ | $R^{2b}$ | $R^{3a}$ | $R^{3b}$ |
|---|---|---|---|---|---|
| 1181 | 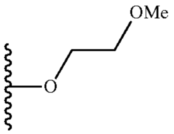 | 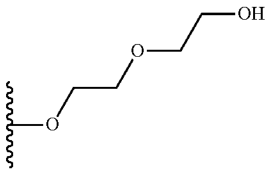 [SMILES: *OCCOCCO] | H | 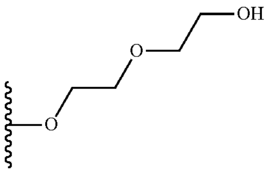 [SMILES: *OCCOCCO] | H |
| 1182 | 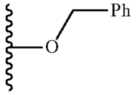 [SMILES: *OCc1ccccc1] | 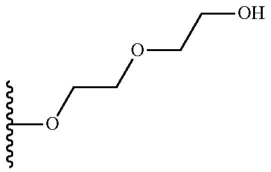 [SMILES: *OCCOCCO] | H | 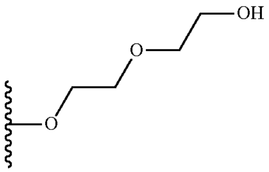 | H |
| 1183 | H | 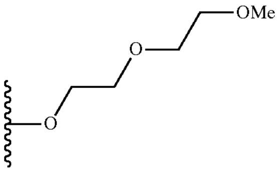 [SMILES: *OCCOCCOC] | H | 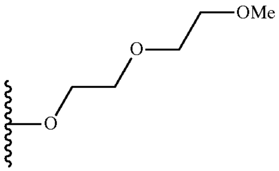 [SMILES: *OCCOCCOC] | H |

TABLE 1-continued
formula (II)
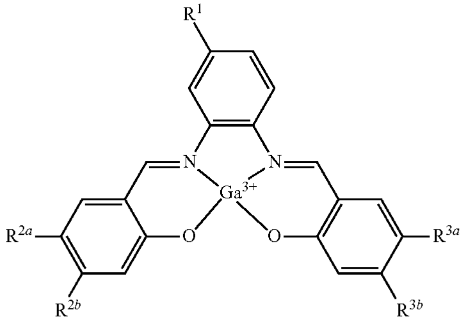
| Compound # | $R^1$ | $R^{2a}$ | $R^{2b}$ | $R^{3a}$ | $R^{3b}$ |
|---|---|---|---|---|---|
| 1184 | —OMe | 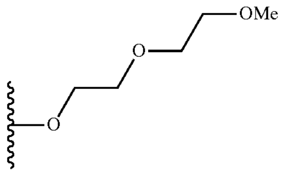 [SMILES: *OCCOCCOC] | H | 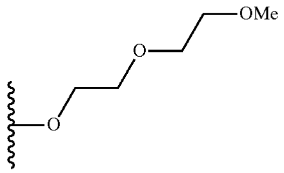 | H |
| 1185 | —OEt | 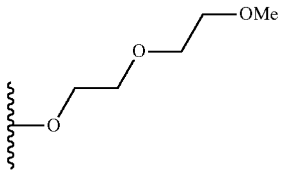 [SMILES: *OCCOCCOC] | H | 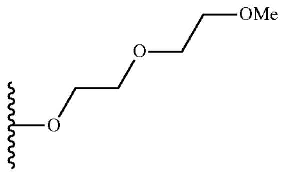 | H |
| 1186 | —OPr | 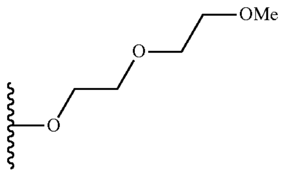 | H | 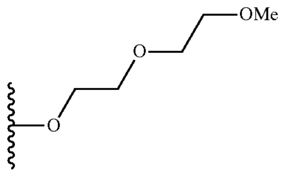 | H |
| 1187 | —OiPr | 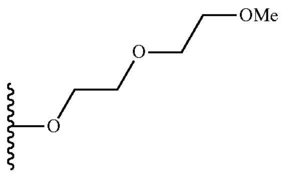 | H | 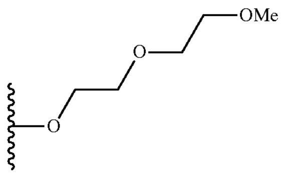 | H |

TABLE 1-continued
formula (II)
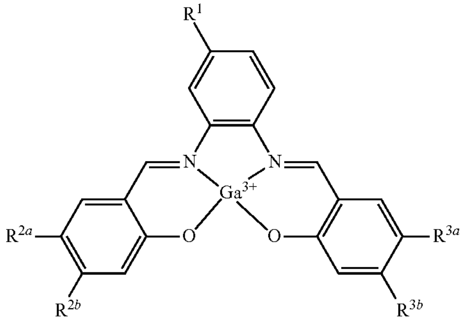
| Compound # | $R^1$ | $R^{2a}$ | $R^{2b}$ | $R^{3a}$ | $R^{3b}$ |
|---|---|---|---|---|---|
| 1188 | 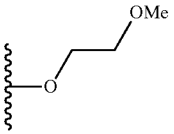 | 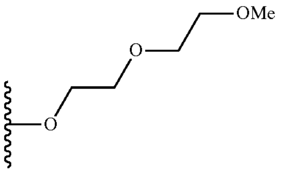 | H | 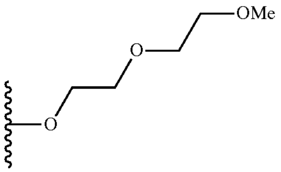 | H |
| 1189 | 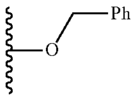 [SMILES: *OCc1ccccc1] | 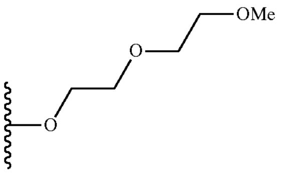 [SMILES: *OCCOCCOC] | H | 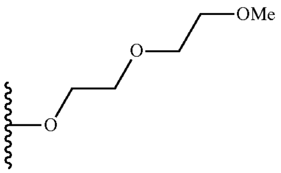 [SMILES: *OCCOCCOC] | H |
| 1190 | H | 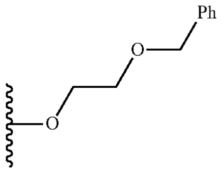 [SMILES: *OCCOCc1ccccc1] | H | 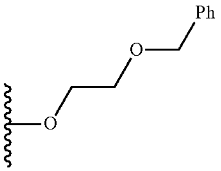 [SMILES: *OCCOCc1ccccc1] | H |

TABLE 1-continued
formula (II)
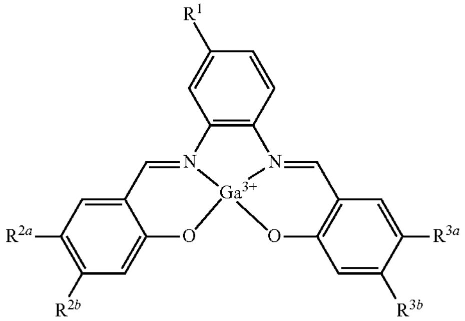
| Compound # | $R^1$ | $R^{2a}$ | $R^{2b}$ | $R^{3a}$ | $R^{3b}$ |
| --- | --- | --- | --- | --- | --- |
| 1191 | —OMe | 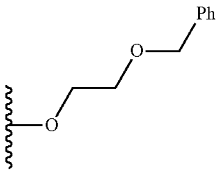 [SMILES: *OCCOCc1ccccc1] | H | 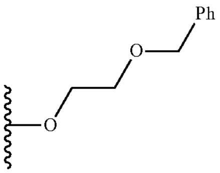 [SMILES: *OCCOCc1ccccc1] | H |
| 1192 | —OEt | 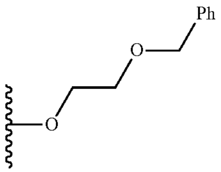 [SMILES: *OCCOCc1ccccc1] | H | 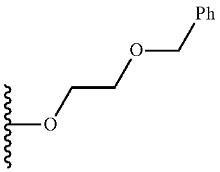 [SMILES: *OCCOCc1ccccc1] | H |
| 1193 | —OPr | 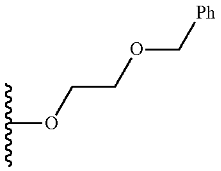 [SMILES: *OCCOCc1ccccc1] | H | 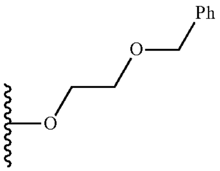 [SMILES: *OCCOCc1ccccc1] | H |
| 1194 | —OiPr | 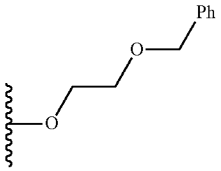 [SMILES: *OCCOCc1ccccc1] | H | 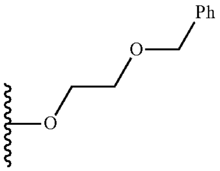 | H |

TABLE 1-continued
formula (II)
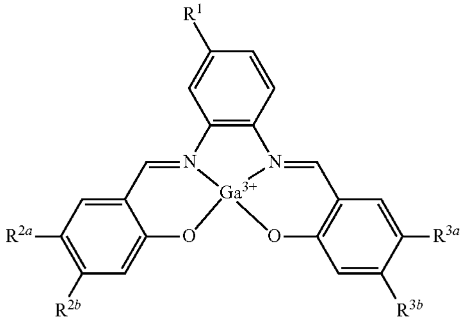
| Compound # | $R^1$ | $R^{2a}$ | $R^{2b}$ | $R^{3a}$ | $R^{3b}$ |
|---|---|---|---|---|---|
| 1195 | 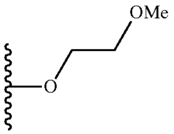 | 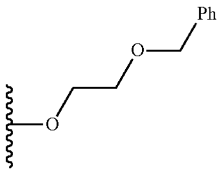 [SMILES: *OCCOCc1ccccc1] | H | 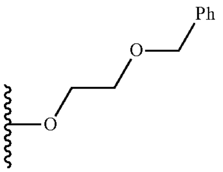 | H |
| 1196 | 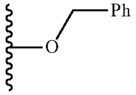 [SMILES: *OCc1ccccc1] | 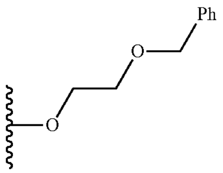 [SMILES: *OCCOCc1ccccc1] | H | 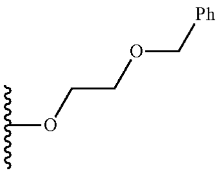 [SMILES: *OCCOCc1ccccc1] | H |
| 1197 | H | 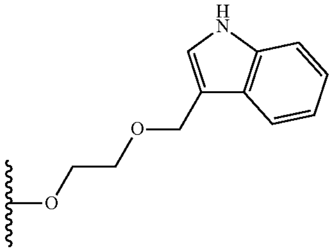 [SMILES: *OCCOCc1c[nH]c2ccccc12] | H | 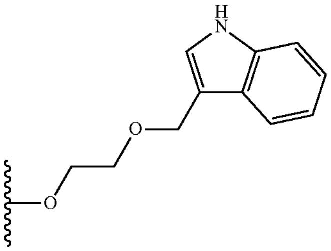 [SMILES: *OCCOCc1c[nH]c2ccccc12] | H |

TABLE 1-continued
formula (II)
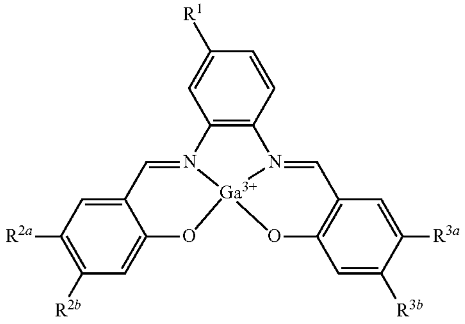
| Compound # | $R^1$ | $R^{2a}$ | $R^{2b}$ | $R^{3a}$ | $R^{3b}$ |
|---|---|---|---|---|---|
| 1198 | —OMe | 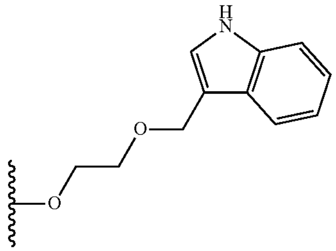 [SMILES: *OCCOCc1c[nH]c2ccccc12] | H | 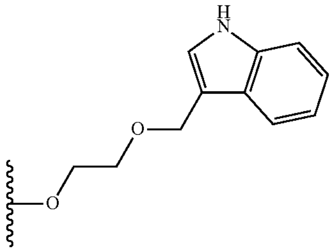 [SMILES: *OCCOCc1c[nH]c2ccccc12] | H |
| 1199 | —OEt | 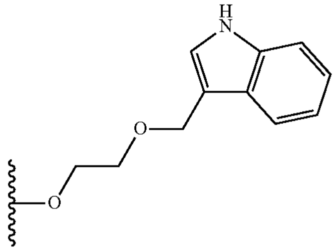 [SMILES: *OCCOCc1c[nH]c2ccccc12] | H | 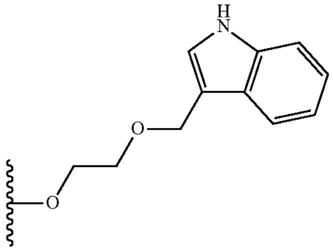 [SMILES: *OCCOCc1c[nH]c2ccccc12] | H |

TABLE 1-continued
formula (II)
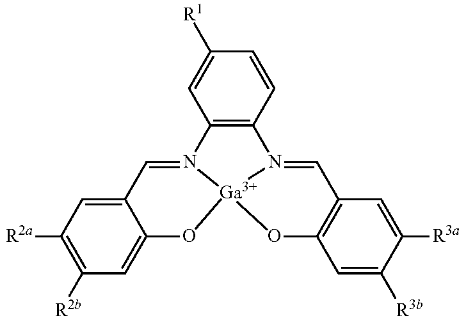
| Compound # | $R^1$ | $R^{2a}$ | $R^{2b}$ | $R^{3a}$ | $R^{3b}$ |
|---|---|---|---|---|---|
| 1200 | —OPr | 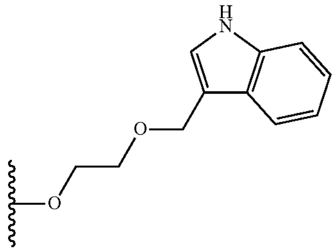 [SMILES: *OCCOCc1c[nH]c2ccccc12] | H | 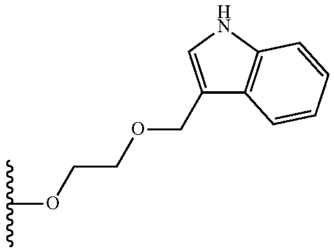 [SMILES: *OCCOCc1c[nH]c2ccccc12] | H |
| 1201 | —OiPr | 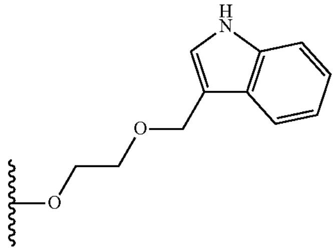 [SMILES: *OCCOCc1c[nH]c2ccccc12] | H | 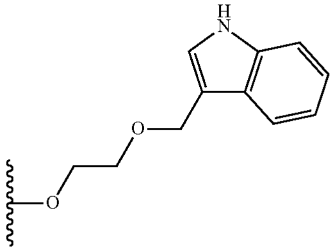 [SMILES: *OCCOCc1c[nH]c2ccccc12] | H |

TABLE 1-continued
formula (II)
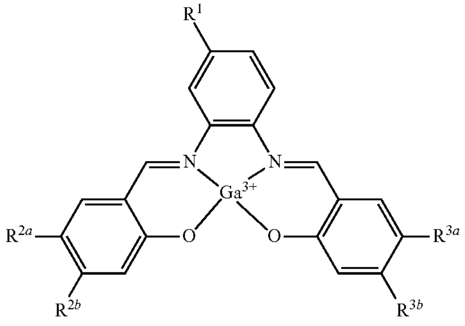
| Compound # | $R^1$ | $R^{2a}$ | $R^{2b}$ | $R^{3a}$ | $R^{3b}$ |
|---|---|---|---|---|---|
| 1202 | 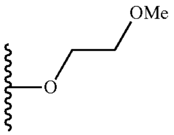 | 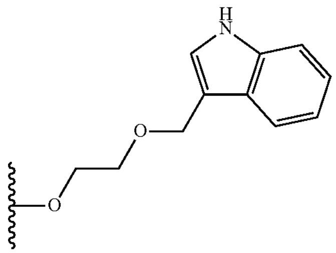 [SMILES: *OCCOCc1c[nH]c2ccccc12] | H | 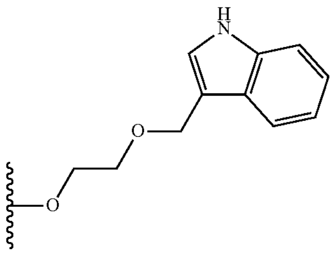 [SMILES: *OCCOCc1c[nH]c2ccccc12] | H |
| 1203 | 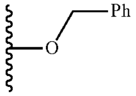 [SMILES: *OCc1ccccc1] | 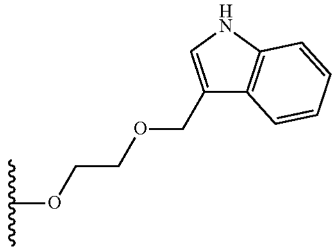 [SMILES: *OCCOCc1c[nH]c2ccccc12] | H | 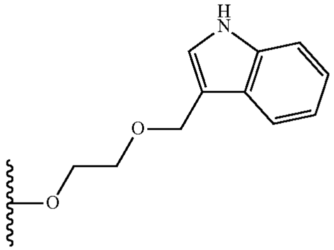 [SMILES: *OCCOCc1c[nH]c2ccccc12] | H |

TABLE 1-continued
formula (II)
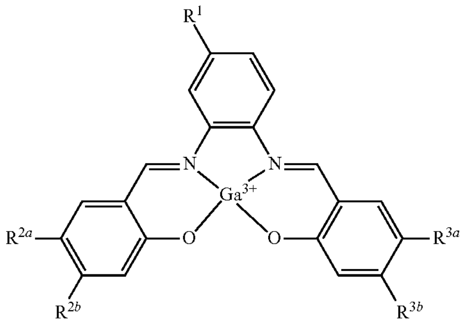
| Compound # | $R^1$ | $R^{2a}$ | $R^{2b}$ | $R^{3a}$ | $R^{3b}$ |
|---|---|---|---|---|---|
| 1204 | H | 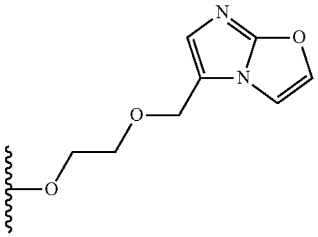 [SMILES: *OCCOCc1cnc2occn12] | H | 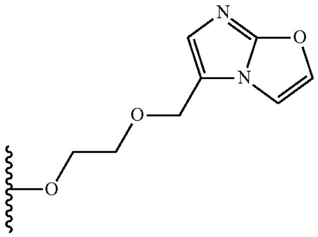 [SMILES: *OCCOCc1cnc2occn12] | H |
| 1205 | —OMe | 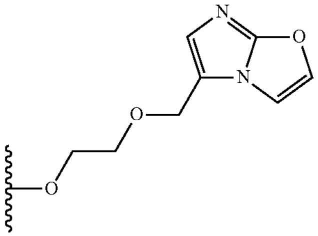 [SMILES: *OCCOCc1cnc2occn12] | H | 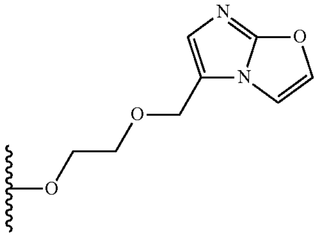 [SMILES: *OCCOCc1cnc2occn12] | H |
| 1206 | —OEt | 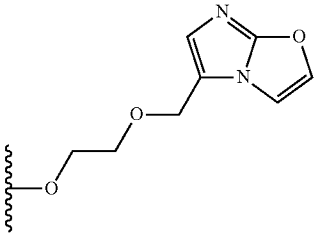 [SMILES: *OCCOCc1cnc2occn12] | H | 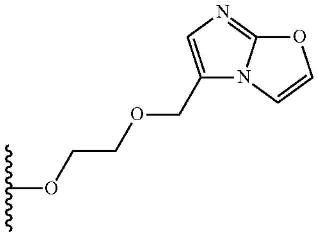 [SMILES: *OCCOCc1cnc2occn12] | H |

TABLE 1-continued
formula (II)
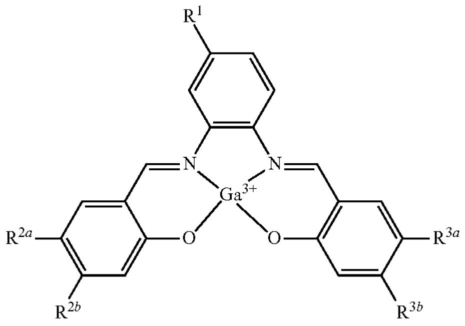
| Compound # | $R^1$ | $R^{2a}$ | $R^{2b}$ | $R^{3a}$ | $R^{3b}$ |
|---|---|---|---|---|---|
| 1207 | —OPr | 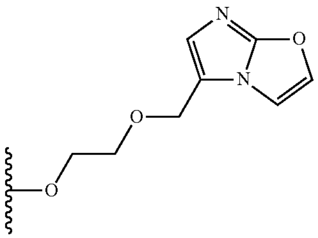 [SMILES: *OCCOCc1cnc2occn12] | H | 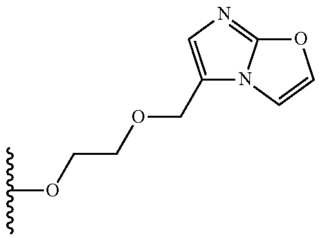 [SMILES: *OCCOCc1cnc2occn12] | H |
| 1208 | —OiPr | 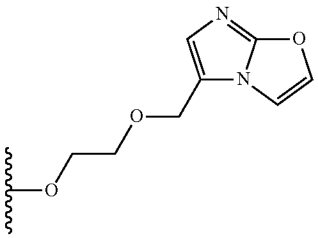 [SMILES: *OCCOCc1cnc2occn12] | H | 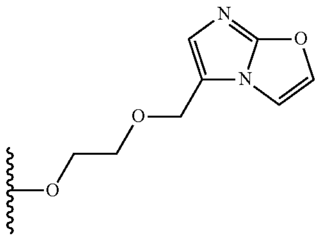 [SMILES: *OCCOCc1cnc2occn12] | H |

TABLE 1-continued
formula (II)
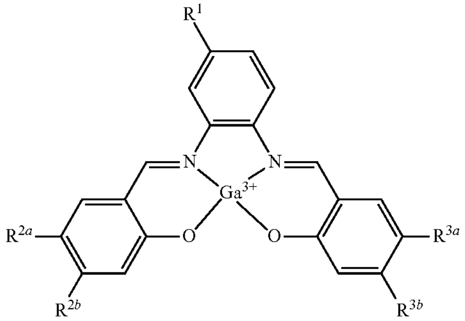
| Compound # | $R^1$ | $R^{2a}$ | $R^{2b}$ | $R^{3a}$ | $R^{3b}$ |
|---|---|---|---|---|---|
| 1209 | 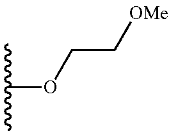 | 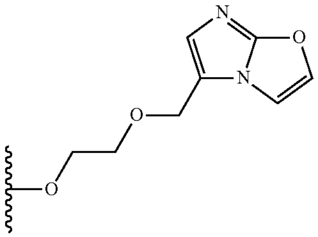 [SMILES: *OCCOCc1cnc2occn12] | H | 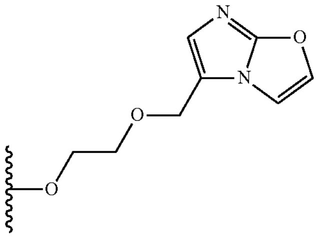 [SMILES: *OCCOCc1cnc2occn12] | H |
| 1210 | 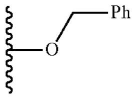 [SMILES: *OCc1ccccc1] | 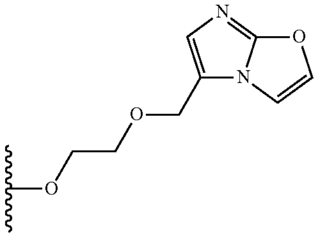 [SMILES: *OCCOCc1cnc2occn12] | H | 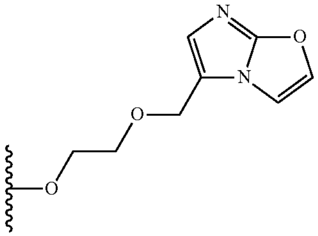 [SMILES: *OCCOCc1cnc2occn12] | H |

TABLE 1-continued
formula (II)
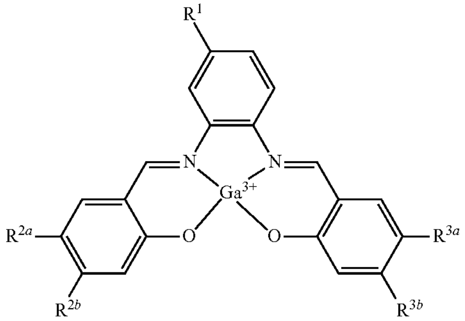
| Compound # | $R^1$ | $R^{2a}$ | $R^{2b}$ | $R^{3a}$ | $R^{3b}$ |
|---|---|---|---|---|---|
| 1211 | H | 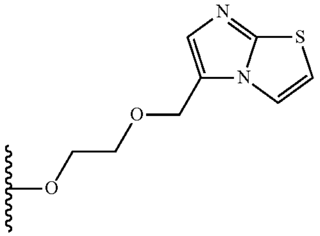 [SMILES: *OCCOCc1cnc2sccn12] | H | 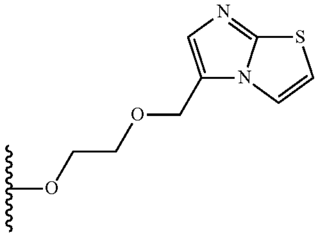 [SMILES: *OCCOCc1cnc2sccn12] | H |
| 1212 | —OMe | 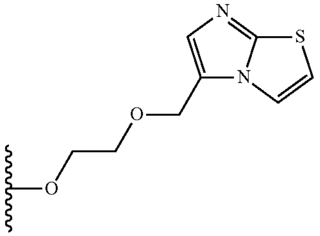 [SMILES: *OCCOCc1cnc2sccn12] | H | 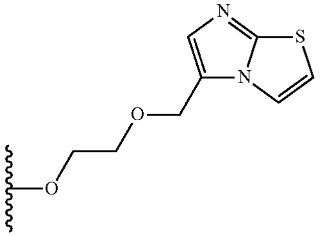 [SMILES: *OCCOCc1cnc2sccn12] | H |

TABLE 1-continued
formula (II)
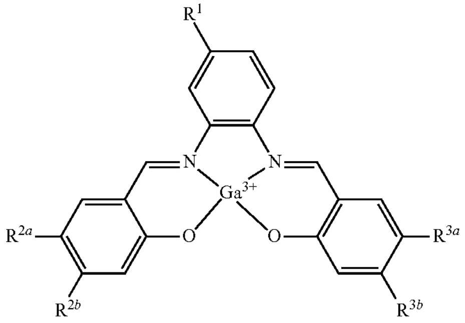
| Compound # | $R^1$ | $R^{2a}$ | $R^{2b}$ | $R^{3a}$ | $R^{3b}$ |
|---|---|---|---|---|---|
| 1213 | —OEt | 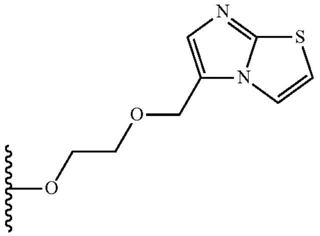 [SMILES: *OCCOCc1cnc2sccn12] | H | 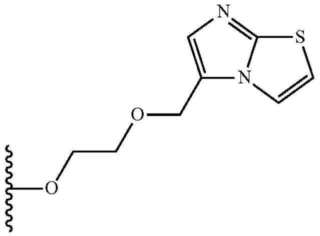 [SMILES: *OCCOCc1cnc2sccn12] | H |
| 1214 | —OPr | 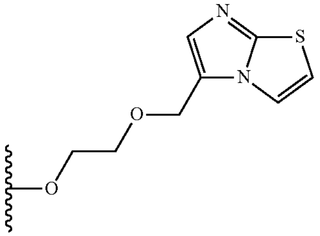 [SMILES: *OCCOCc1cnc2sccn12] | H | 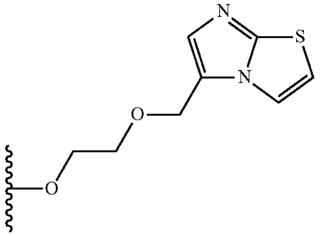 [SMILES: *OCCOCc1cnc2sccn12] | H |

TABLE 1-continued
formula (II)
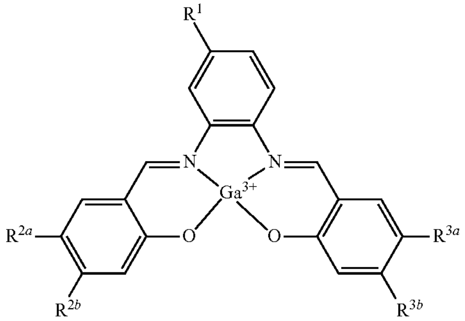
| Compound # | $R^1$ | $R^{2a}$ | $R^{2b}$ | $R^{3a}$ | $R^{3b}$ |
|---|---|---|---|---|---|
| 1215 | —OiPr | 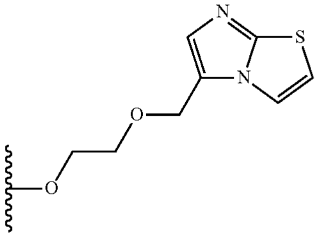 [SMILES: *OCCOCc1cnc2sccn12] | H | 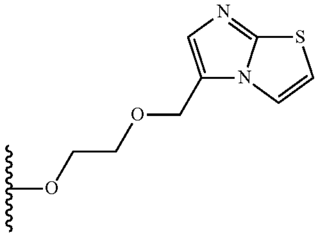 [SMILES: *OCCOCc1cnc2sccn12] | H |
| 1216 | 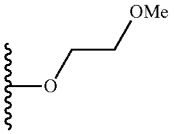 | 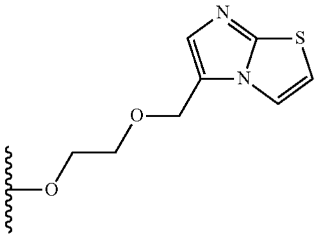 [SMILES: *OCCOCc1cnc2sccn12] | H | 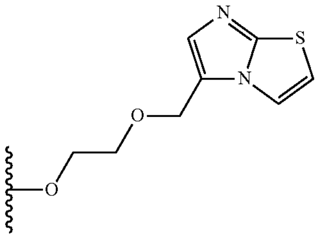 [SMILES: *OCCOCc1cnc2sccn12] | H |

TABLE 1-continued
formula (II)
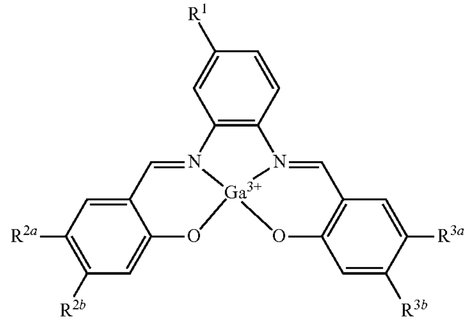
| Compound # | $R^1$ | $R^{2a}$ | $R^{2b}$ | $R^{3a}$ | $R^{3b}$ |
|---|---|---|---|---|---|
| 1217 | 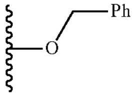 [SMILES: *OCc1ccccc1] | 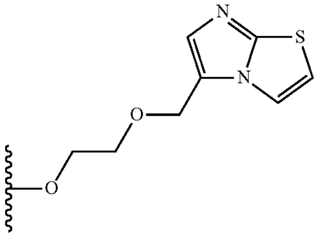 [SMILES: *OCCOCc1cnc2sccn12] | H | 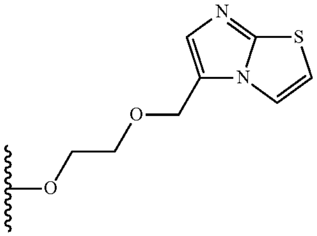 [SMILES: *OCCOCc1cnc2sccn12] | H |
| 1218 | H | 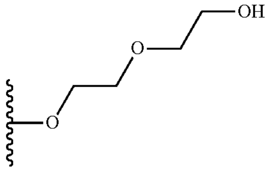 | H | H | 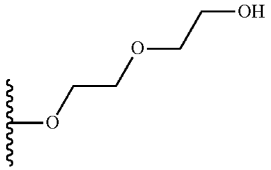 |
| 1219 | —OMe | 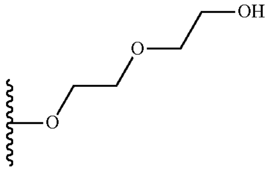 | H | H | 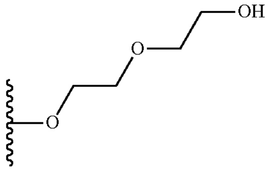 |

TABLE 1-continued
formula (II)
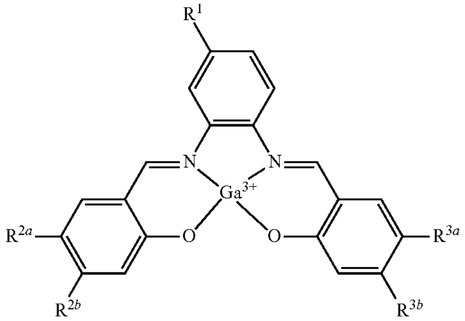
| Compound # | $R^1$ | $R^{2a}$ | $R^{2b}$ | $R^{3a}$ | $R^{3b}$ |
|---|---|---|---|---|---|
| 1220 | —OEt | 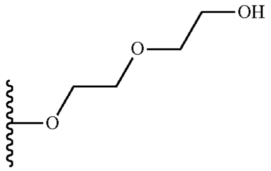 | H | H | 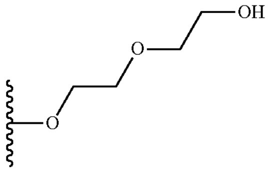 |
| 1221 | —OPr | 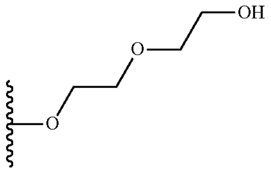 [SMILES: *OCCOCCO] | H | H | 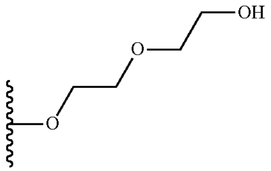 [SMILES: *OCCOCCO] |
| 1222 | —OiPr | 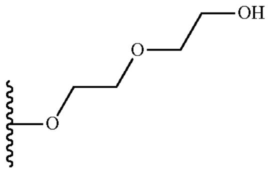 | H | H | 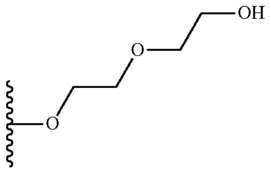 |
| 1223 | 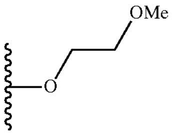 [SMILES: *OCCOC] | 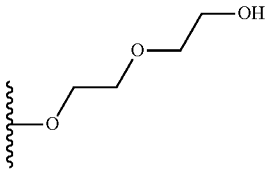 | H | H | 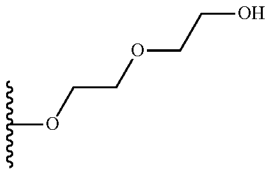 |

TABLE 1-continued
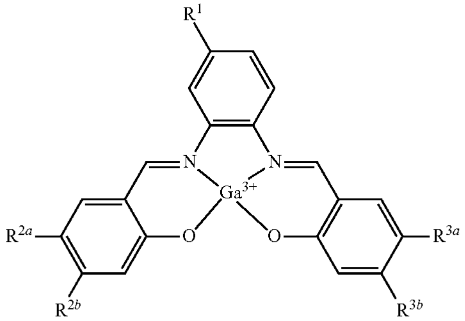
formula (II)
| Compound # | $R^1$ | $R^{2a}$ | $R^{2b}$ | $R^{3a}$ | $R^{3b}$ |
|---|---|---|---|---|---|
| 1224 | 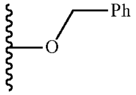 [SMILES: *OCc1ccccc1] | 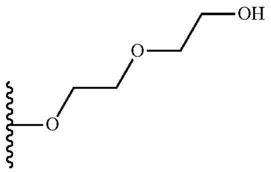 [SMILES: *OCCOCCO] | H | H | 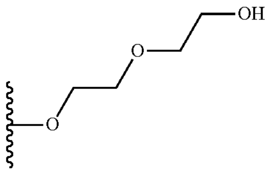 [SMILES: *OCCOCCO] |
| 1225 | H | 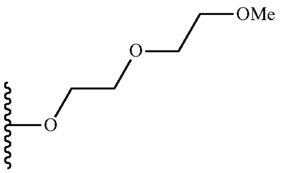 [SMILES: *OCCOCCOC] | H | H | 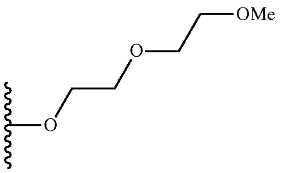 [SMILES: *OCCOCCOC] |
| 1226 | —OMe | 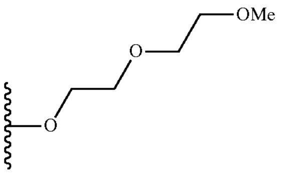 [SMILES: *OCCOCCOC] | H | H | 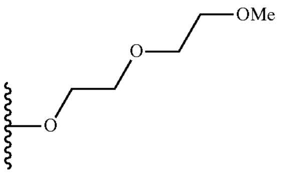 [SMILES: *OCCOCCOC] |

TABLE 1-continued
formula (II)
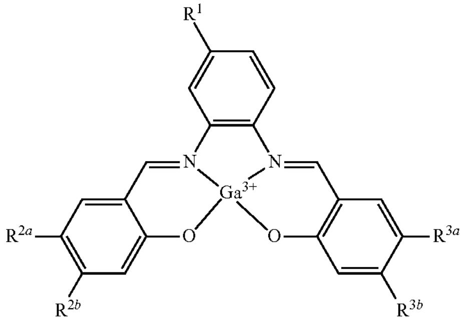
| Compound # | $R^1$ | $R^{2a}$ | $R^{2b}$ | $R^{3a}$ | $R^{3b}$ |
|---|---|---|---|---|---|
| 1227 | —OEt | 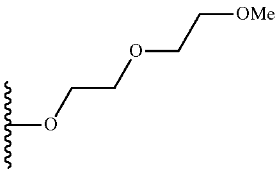 [SMILES: *OCCOCCOC] | H | H | 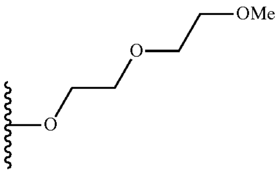 [SMILES: *OCCOCCOC] |
| 1228 | —OPr | 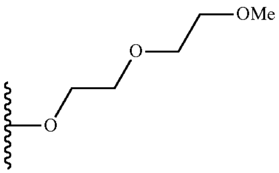 [SMILES: *OCCOCCOC] | H | H | 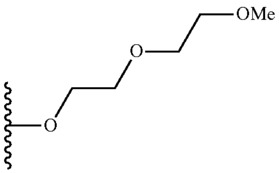 [SMILES: *OCCOCCOC] |
| 1229 | —OiPr | 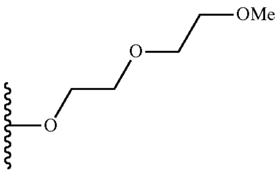 | H | H | 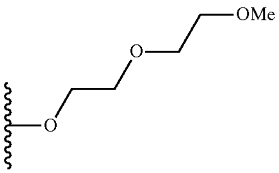 |
| 1230 | 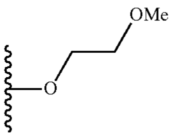 [SMILES: *OCCOC] | 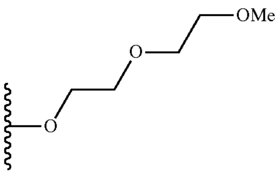 | H | H | 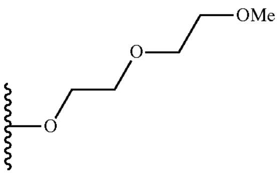 [SMILES: *OCCOCCOC] |

TABLE 1-continued
formula (II)
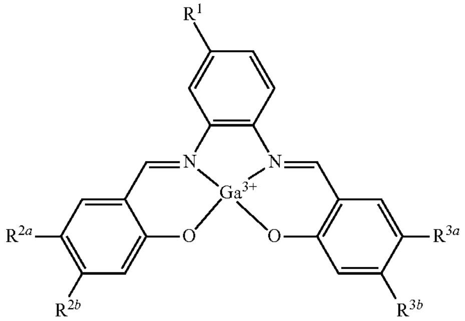
| Compound # | $R^1$ | $R^{2a}$ | $R^{2b}$ | $R^{3a}$ | $R^{3b}$ |
|---|---|---|---|---|---|
| 1231 | 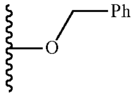 [SMILES: *OCc1ccccc1] | 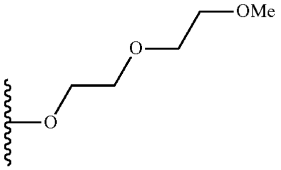 | H | H | 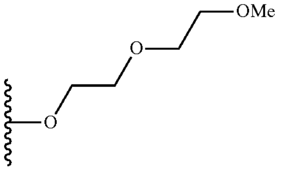 |
| 1232 | H | 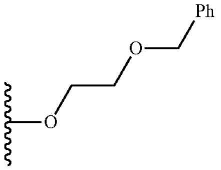 [SMILES: *OCCOCc1ccccc1] | H | H | 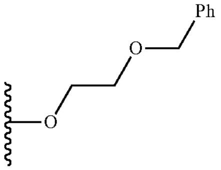 [SMILES: *OCCOCc1ccccc1] |
| 1233 | —OMe | 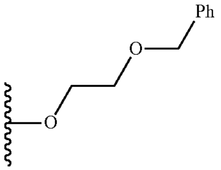 [SMILES: *OCCOCc1ccccc1] | H | H | 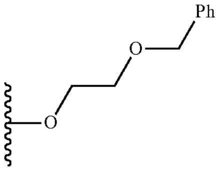 [SMILES: *OCCOCc1ccccc1] |

TABLE 1-continued
formula (II)
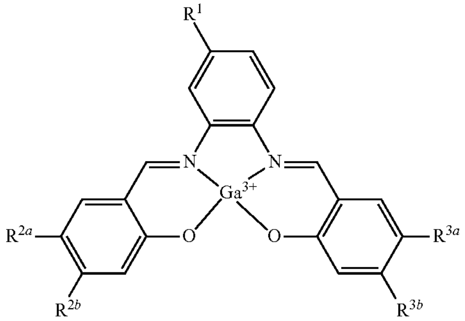
| Compound # | $R^1$ | $R^{2a}$ | $R^{2b}$ | $R^{3a}$ | $R^{3b}$ |
|---|---|---|---|---|---|
| 1234 | —OEt | 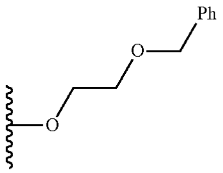 [SMILES: *OCCOCc1ccccc1] | H | H | 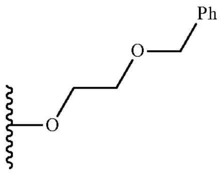 [SMILES: *OCCOCc1ccccc1] |
| 1235 | —OPr | 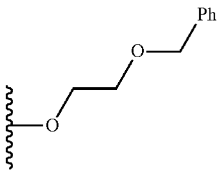 [SMILES: *OCCOCc1ccccc1] | H | H | 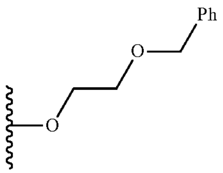 [SMILES: *OCCOCc1ccccc1] |
| 1236 | —OiPr | 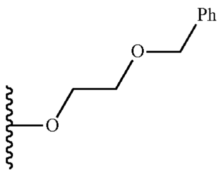 [SMILES: *OCCOCc1ccccc1] | H | H | 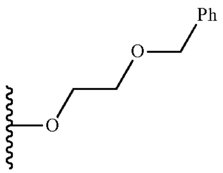 [SMILES: *OCCOCc1ccccc1] |
| 1237 | 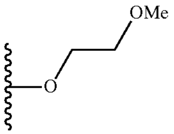 [SMILES: *OCCOC] | 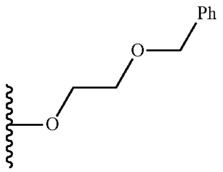 [SMILES: *OCCOCc1ccccc1] | H | H | 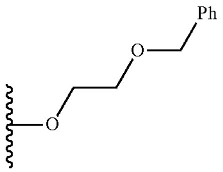 |

TABLE 1-continued
formula (II)
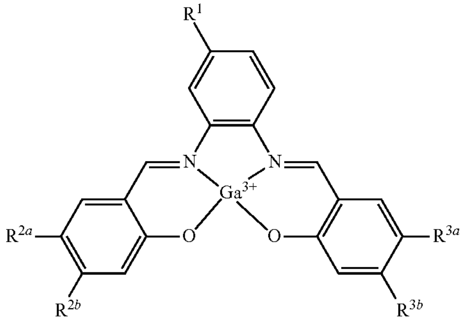
| Compound # | $R^1$ | $R^{2a}$ | $R^{2b}$ | $R^{3a}$ | $R^{3b}$ |
|---|---|---|---|---|---|
| 1238 | 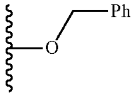 [SMILES: *OCc1ccccc1] | 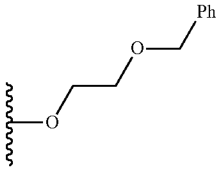 [SMILES: *OCCOCc1ccccc1] | H | H | 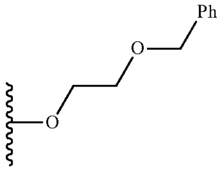 |
| 1239 | H | 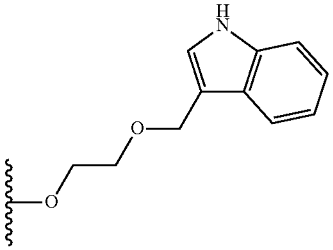 [SMILES: *OCCOCc1c[nH]c2ccccc12] | H | H | 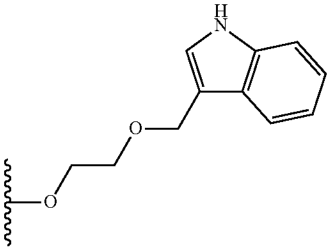 [SMILES: *OCCOCc1c[nH]c2ccccc12] |
| 1240 | —OMe | 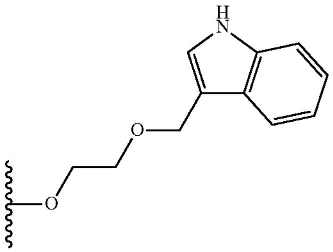 [SMILES: *OCCOCc1c[nH]c2ccccc12] | H | H | 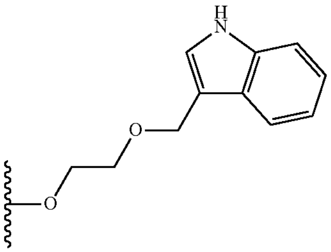 [SMILES: *OCCOCc1c[nH]c2ccccc12] |

TABLE 1-continued
formula (II)
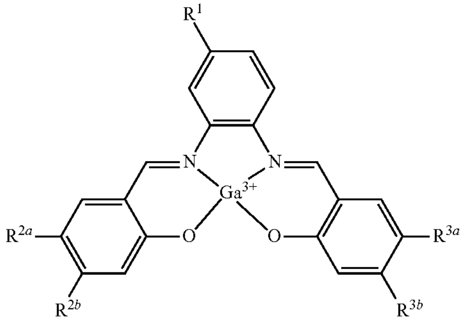
| Compound # | $R^1$ | $R^{2a}$ | $R^{2b}$ | $R^{3a}$ | $R^{3b}$ |
|---|---|---|---|---|---|
| 1241 | —OEt | 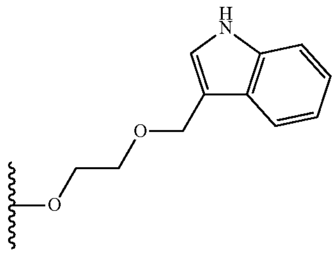 [SMILES: *OCCOCc1c[nH]c2ccccc12] | H | H | 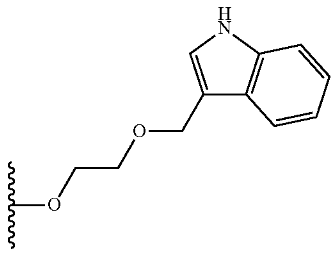 [SMILES: *OCCOCc1c[nH]c2ccccc12] |
| 1242 | —OPr | 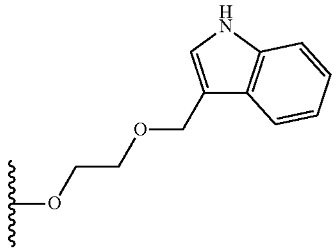 [SMILES: *OCCOCc1c[nH]c2ccccc12] | H | H | 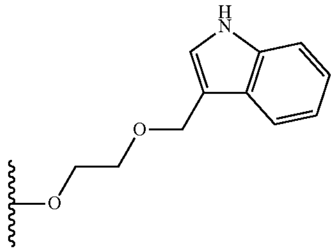 [SMILES: *OCCOCc1c[nH]c2ccccc12] |

TABLE 1-continued
formula (II)
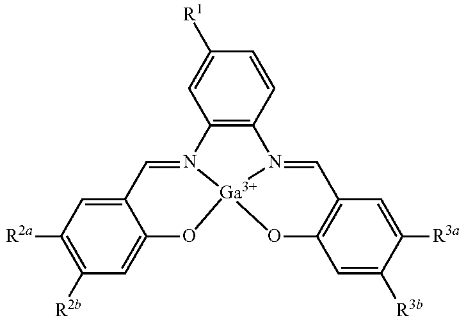
| Compound # | $R^1$ | $R^{2a}$ | $R^{2b}$ | $R^{3a}$ | $R^{3b}$ |
|---|---|---|---|---|---|
| 1243 | —OiPr | 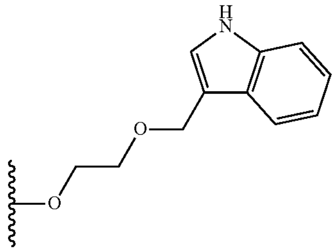 [SMILES: *OCCOCc1c[nH]c2ccccc12] | H | H | 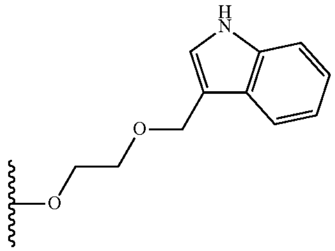 [SMILES: *OCCOCc1c[nH]c2ccccc12] |
| 1244 | 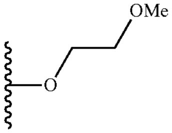 [SMILES: *OCCOC] | 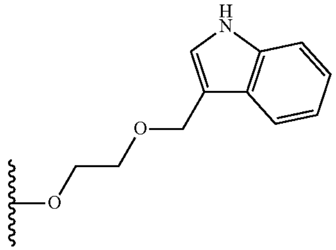 [SMILES: *OCCOCc1c[nH]c2ccccc12] | H | H | 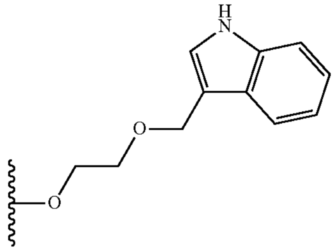 [SMILES: *OCCOCc1c[nH]c2ccccc12] |

TABLE 1-continued
formula (II)
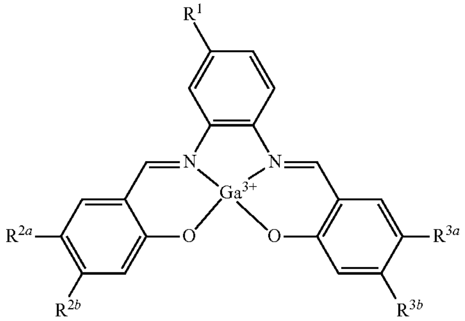
| Compound # | $R^1$ | $R^{2a}$ | $R^{2b}$ | $R^{3a}$ | $R^{3b}$ |
|---|---|---|---|---|---|
| 1245 | 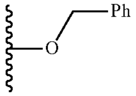 [SMILES: *OCc1ccccc1] | 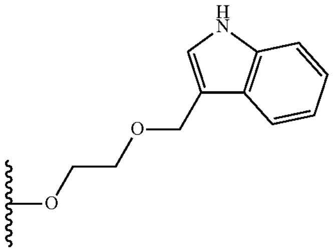 [SMILES: *OCCOCc1c[nH]c2ccccc12] | H | H | 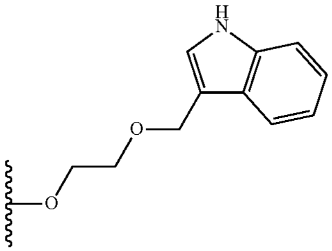 [SMILES: *OCCOCc1c[nH]c2ccccc12] |
| 1246 | H | 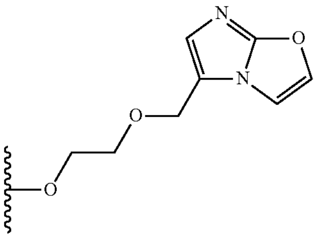 [SMILES: *OCCOCc1cnc2occn12] | H | H | 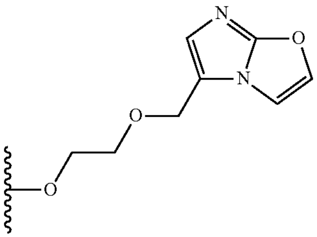 [SMILES: *OCCOCc1cnc2occn12] |

TABLE 1-continued
formula (II)
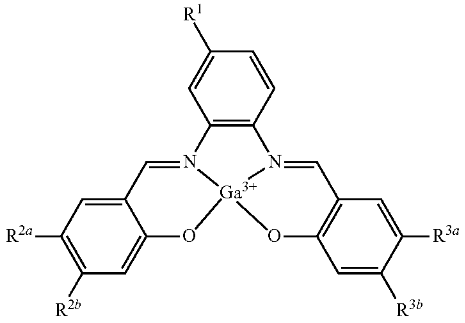
| Compound # | $R^1$ | $R^{2a}$ | $R^{2b}$ | $R^{3a}$ | $R^{3b}$ |
| --- | --- | --- | --- | --- | --- |
| 1247 | —OMe | 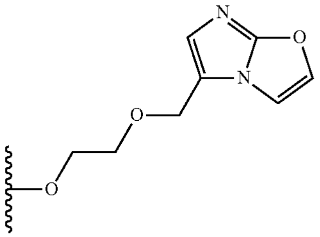 [SMILES: *OCCOCc1cnc2occn12] | H | H | 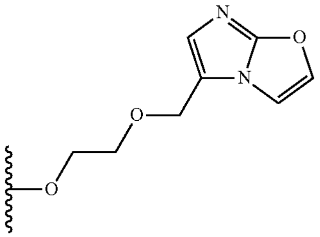 [SMILES: *OCCOCc1cnc2occn12] |
| 1248 | —OEt | 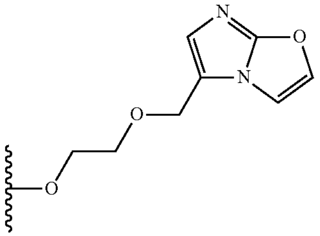 [SMILES: *OCCOCc1cnc2occn12] | H | H | 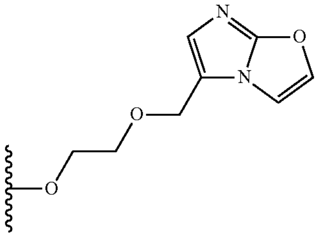 [SMILES: *OCCOCc1cnc2occn12] |
| 1249 | —OPr | 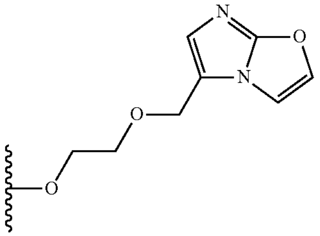 [SMILES: *OCCOCc1cnc2occn12] | H | H | 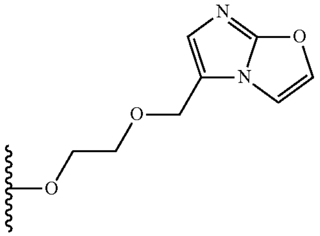 [SMILES: *OCCOCc1cnc2occn12] |

TABLE 1-continued
formula (II)
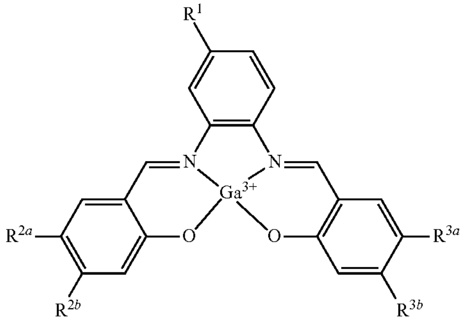
| Compound # | $R^1$ | $R^{2a}$ | $R^{2b}$ | $R^{3a}$ | $R^{3b}$ |
|---|---|---|---|---|---|
| 1250 | —OiPr | 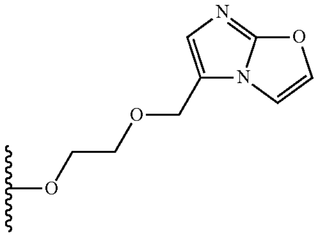 [SMILES: *OCCOCc1cnc2occn12] | H | H | 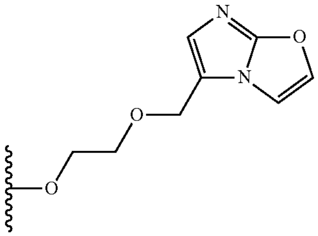 [SMILES: *OCCOCc1cnc2occn12] |
| 1251 | 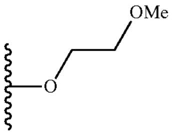 | 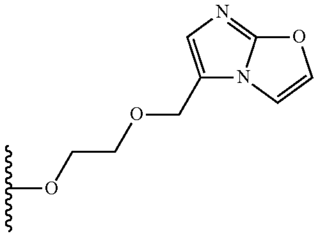 [SMILES: *OCCOCc1cnc2occn12] | H | H | 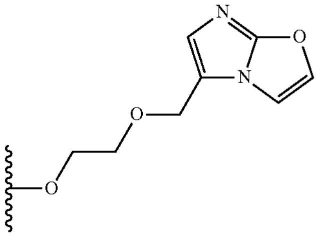 [SMILES: *OCCOCc1cnc2occn12] |

TABLE 1-continued
formula (II)
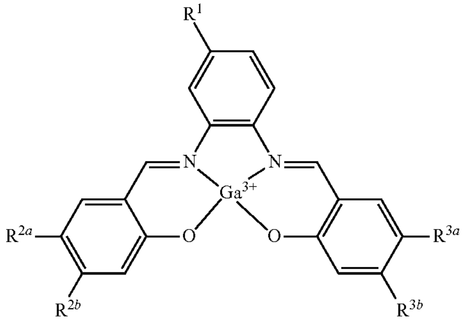
| Compound # | $R^1$ | $R^{2a}$ | $R^{2b}$ | $R^{3a}$ | $R^{3b}$ |
|---|---|---|---|---|---|
| 1252 | 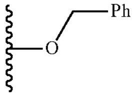 [SMILES: *OCc1ccccc1] | 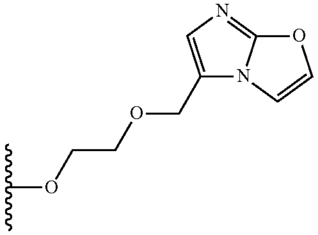 [SMILES: *OCCOCc1cnc2occn12] | H | H | 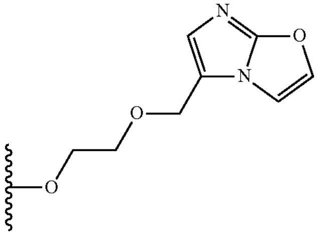 [SMILES: *OCCOCc1cnc2occn12] |
| 1253 | H | 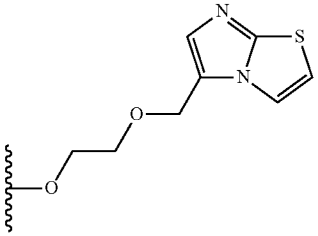 [SMILES: *OCCOCc1cnc2sccn12] | H | H | 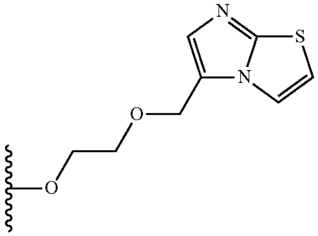 [SMILES: *OCCOCc1cnc2sccn12] |

TABLE 1-continued
formula (II)
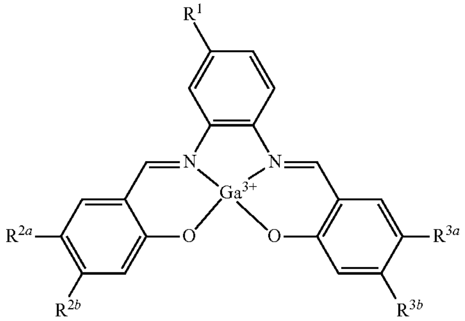
| Compound # | $R^1$ | $R^{2a}$ | $R^{2b}$ | $R^{3a}$ | $R^{3b}$ |
|---|---|---|---|---|---|
| 1254 | —OMe | 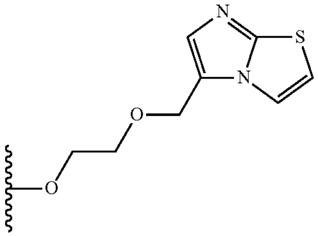 [SMILES: *OCCOCc1cnc2sccn12] | H | H | 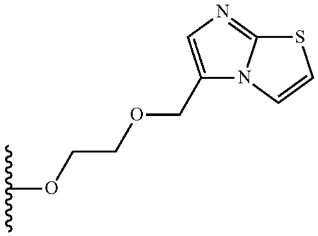 [SMILES: *OCCOCc1cnc2sccn12] |
| 1255 | —OEt | 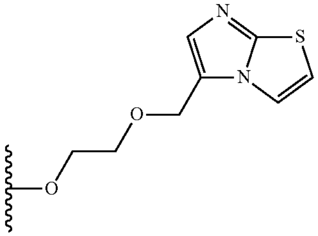 [SMILES: *OCCOCc1cnc2sccn12] | H | H | 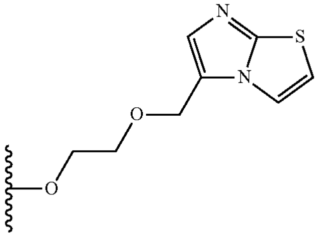 [SMILES: *OCCOCc1cnc2sccn12] |

TABLE 1-continued
formula (II)
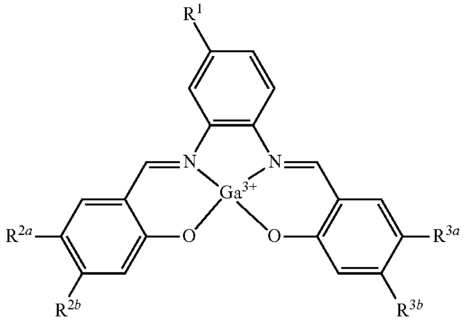
| Compound # | $R^1$ | $R^{2a}$ | $R^{2b}$ | $R^{3a}$ | $R^{3b}$ |
|---|---|---|---|---|---|
| 1256 | —OPr | 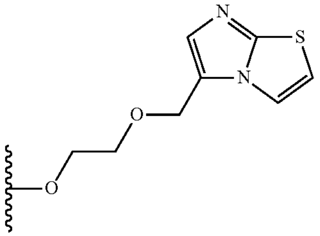 [SMILES: *OCCOCc1cnc2sccn12] | H | H | 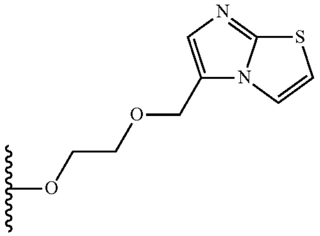 [SMILES: *OCCOCc1cnc2sccn12] |
| 1257 | —OiPr | 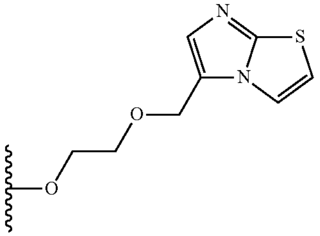 [SMILES: *OCCOCc1cnc2sccn12] | H | H | 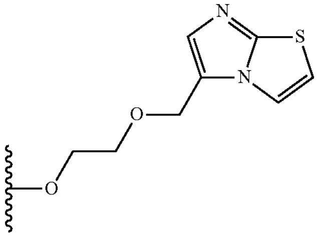 [SMILES: *OCCOCc1cnc2sccn12] |

TABLE 1-continued
formula (II)
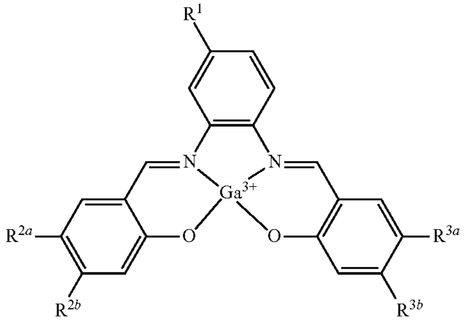
| Compound # | $R^1$ | $R^{2a}$ | $R^{2b}$ | $R^{3a}$ | $R^{3b}$ |
|---|---|---|---|---|---|
| 1258 | 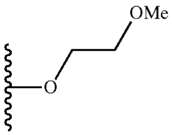 | 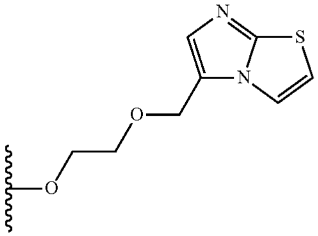 [SMILES: *OCCOCc1cnc2sccn12] | H | H | 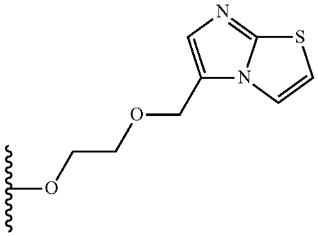 [SMILES: *OCCOCc1cnc2sccn12] |
| 1259 | 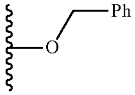 [SMILES: *OCc1ccccc1] | 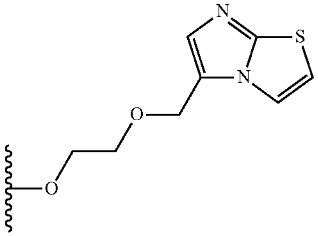 [SMILES: *OCCOCc1cnc2sccn12] | H | H | 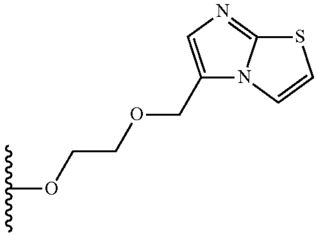 [SMILES: *OCCOCc1cnc2sccn12] |
| 1260 | H | H | 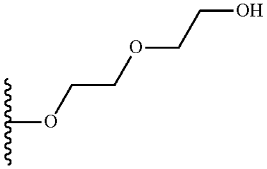 [SMILES: *OCCOCCO] | 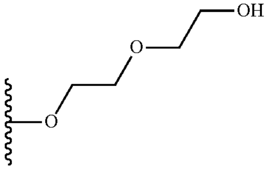 [SMILES: *OCCOCCO] | H |

TABLE 1-continued
formula (II)
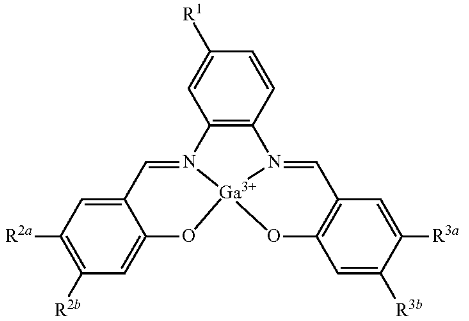
| Compound # | $R^1$ | $R^{2a}$ | $R^{2b}$ | $R^{3a}$ | $R^{3b}$ |
|---|---|---|---|---|---|
| 1261 | —OMe | H | 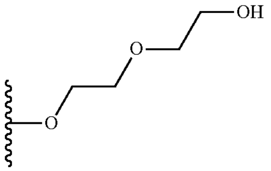 | 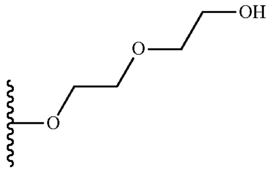 | H |
| 1262 | —OEt | H | 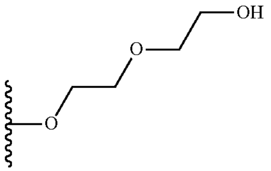 [SMILES: *OCCOCCO] | 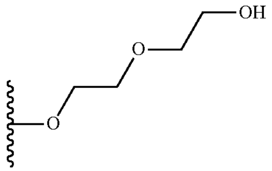 | H |
| 1263 | —OPr | H | 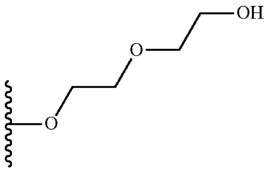 | 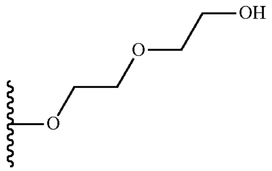 | H |
| 1264 | —OiPr | H | 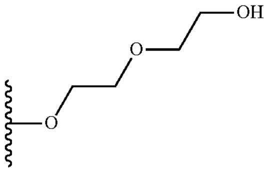 | 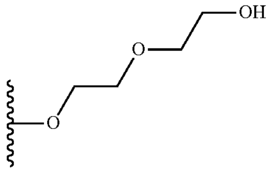 | H |

TABLE 1-continued
formula (II)
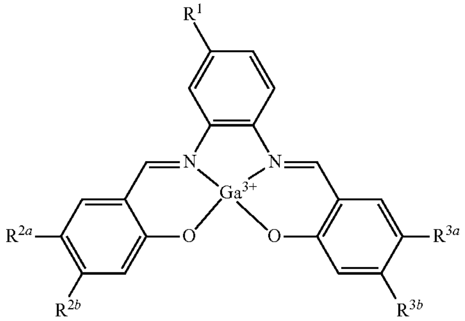
| Compound # | $R^1$ | $R^{2a}$ | $R^{2b}$ | $R^{3a}$ | $R^{3b}$ |
|---|---|---|---|---|---|
| 1265 | 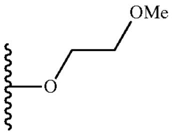 | H | 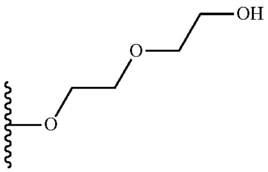 [SMILES: *OCCOCCO] | 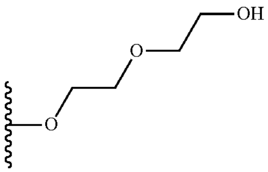 [SMILES: *OCCOCCO] | H |
| 1266 | 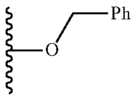 [SMILES: *OCc1ccccc1] | H | 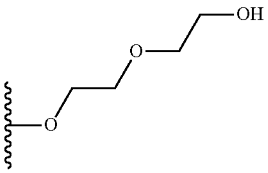 [SMILES: *OCCOCCO] | 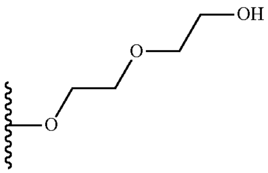 | H |
| 1267 | H | H | 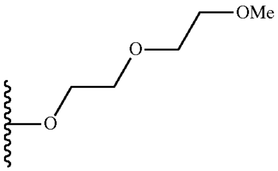 [SMILES: *OCCOCCOC] | 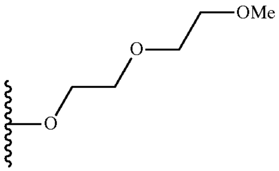 [SMILES: *OCCOCCOC] | H |

TABLE 1-continued
formula (II)
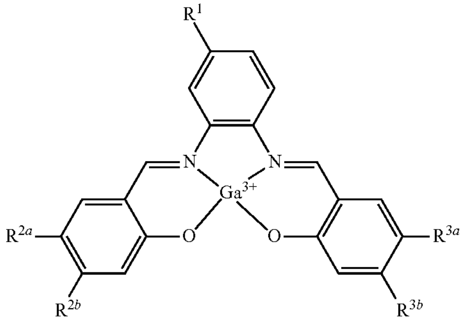
| Compound # | $R^1$ | $R^{2a}$ | $R^{2b}$ | $R^{3a}$ | $R^{3b}$ |
|---|---|---|---|---|---|
| 1268 | —OMe | H | 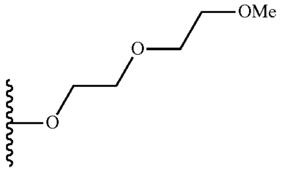 [SMILES: *OCCOCCOC] | 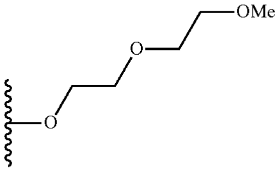 | H |
| 1269 | —OEt | H | 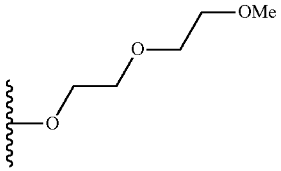 [SMILES: *OCCOCCOC] | 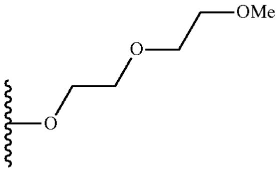 | H |
| 1270 | —OPr | H | 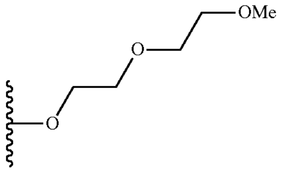 [SMILES: *OCCOCCOC] | 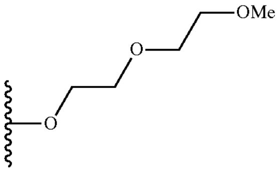 | H |
| 1271 | —OiPr | H | 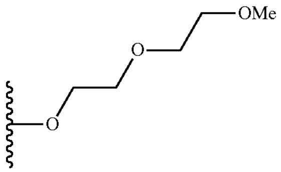 [SMILES: *OCCOCCOC] | 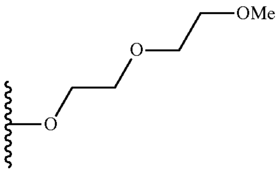 | H |

TABLE 1-continued
formula (II)
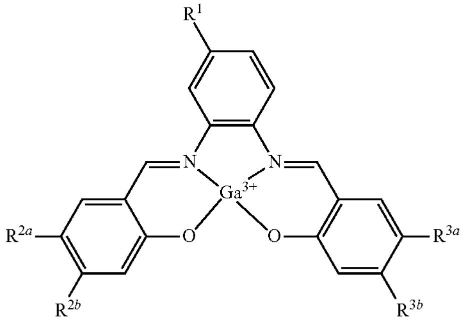
| Compound # | $R^1$ | $R^{2a}$ | $R^{2b}$ | $R^{3a}$ | $R^{3b}$ |
|---|---|---|---|---|---|
| 1272 | 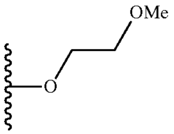 | H | 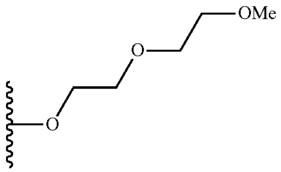 [SMILES: *OCCOCCOC] | 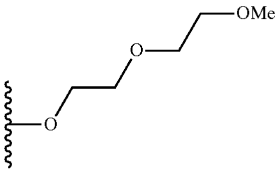 | H |
| 1273 | 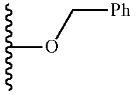 [SMILES: *OCc1ccccc1] | H | 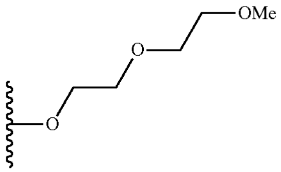 [SMILES: *OCCOCCOC] | 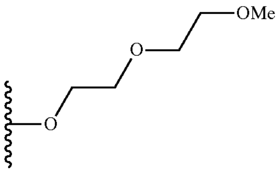 [SMILES: *OCCOCCOC] | H |
| 1274 | H | H | 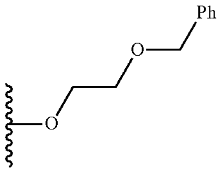 | 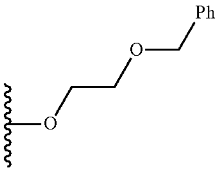 [SMILES: *OCCOCc1ccccc1] | H |

TABLE 1-continued
formula (II)
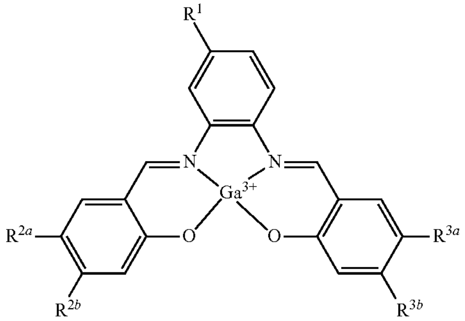
| Compound # | $R^1$ | $R^{2a}$ | $R^{2b}$ | $R^{3a}$ | $R^{3b}$ |
|---|---|---|---|---|---|
| 1275 | —OMe | H | 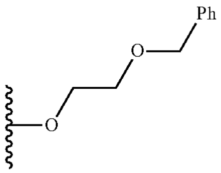 | 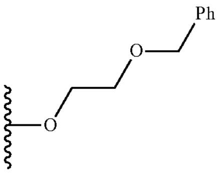 [SMILES: *OCCOCc1ccccc1] | H |
| 1276 | —OEt | H | 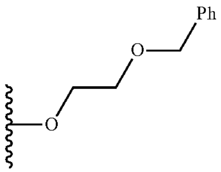 [SMILES: *OCCOCc1ccccc1] | 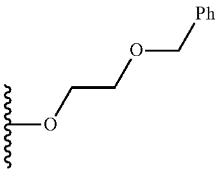 [SMILES: *OCCOCc1ccccc1] | H |
| 1277 | —OPr | H | 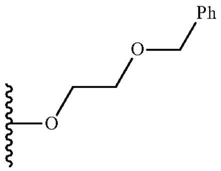 | 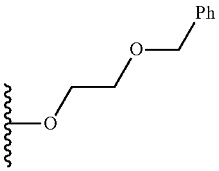 [SMILES: *OCCOCc1ccccc1] | H |
| 1278 | —OiPr | H | 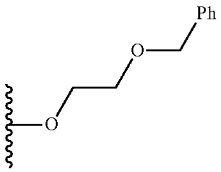 | 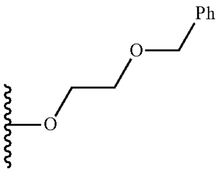 | H |

TABLE 1-continued
formula (II)
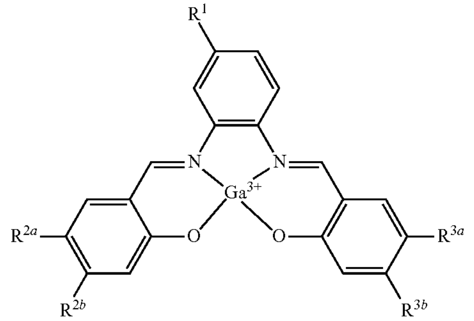
| Compound # | $R^1$ | $R^{2a}$ | $R^{2b}$ | $R^{3a}$ | $R^{3b}$ |
|---|---|---|---|---|---|
| 1279 | 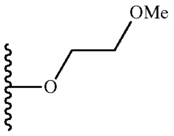 | H | 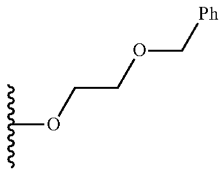 | 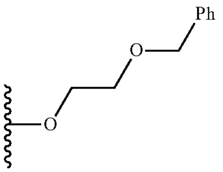 | H |
| 1280 | 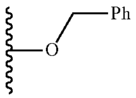 [SMILES: *OCc1ccccc1] | H | 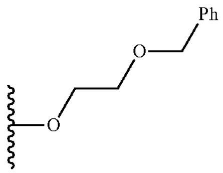 | 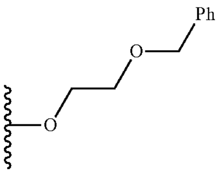 [SMILES: *OCCOCc1ccccc1] | H |
| 1281 | H | H | 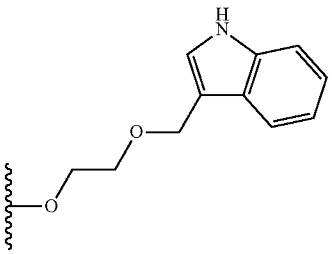 [SMILES: *OCCOCc1c[nH]c2ccccc12] | 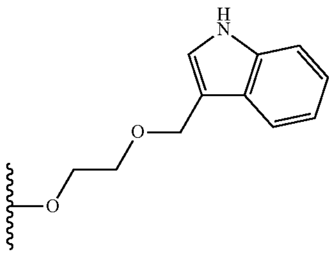 [SMILES: *OCCOCc1c[nH]c2ccccc12] | H |

TABLE 1-continued
formula (II)
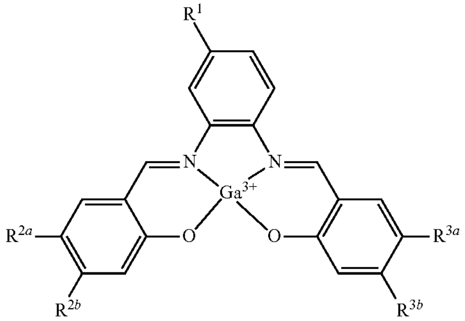
| Compound # | $R^1$ | $R^{2a}$ | $R^{2b}$ | $R^{3a}$ | $R^{3b}$ |
|---|---|---|---|---|---|
| 1282 | —OMe | H | 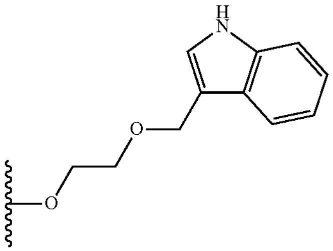 [SMILES: *OCCOCc1c[nH]c2ccccc12] | 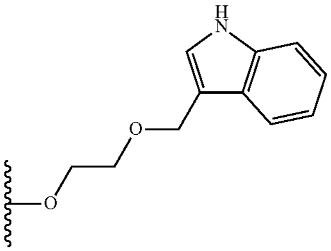 [SMILES: *OCCOCc1c[nH]c2ccccc12] | H |
| 1283 | —OEt | H | 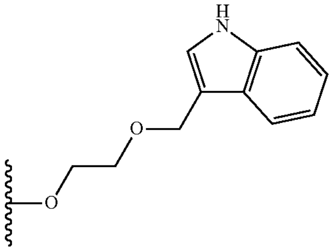 [SMILES: *OCCOCc1c[nH]c2ccccc12] | 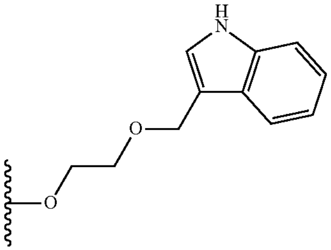 [SMILES: *OCCOCc1c[nH]c2ccccc12] | H |

TABLE 1-continued
formula (II)
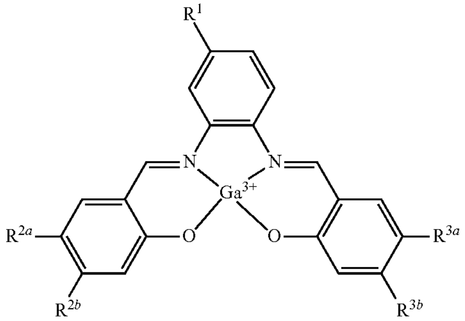
| Compound # | $R^1$ | $R^{2a}$ | $R^{2b}$ | $R^{3a}$ | $R^{3b}$ |
|---|---|---|---|---|---|
| 1284 | —OPr | H | 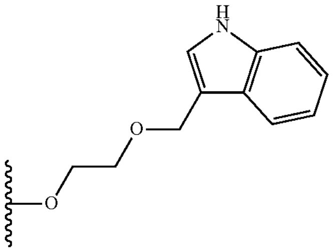 [SMILES: *OCCOCc1c[nH]c2ccccc12] | 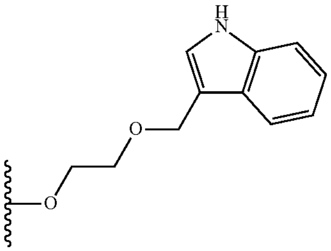 [SMILES: *OCCOCc1c[nH]c2ccccc12] | H |
| 1285 | —OiPr | H | 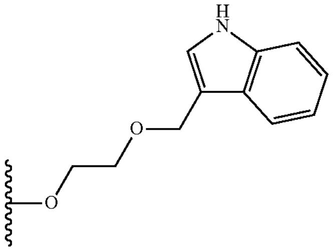 [SMILES: *OCCOCc1c[nH]c2ccccc12] | 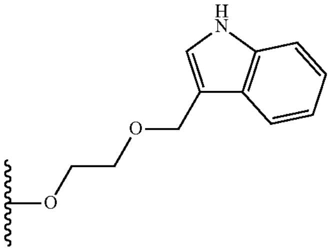 [SMILES: *OCCOCc1c[nH]c2ccccc12] | H |

TABLE 1-continued
formula (II)
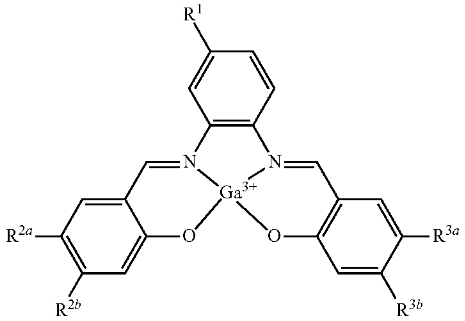
| Compound # | $R^1$ | $R^{2a}$ | $R^{2b}$ | $R^{3a}$ | $R^{3b}$ |
|---|---|---|---|---|---|
| 1286 | 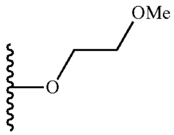 | H | 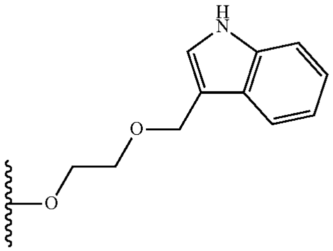 [SMILES: *OCCOCc1c[nH]c2ccccc12] | 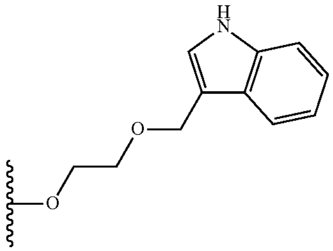 [SMILES: *OCCOCc1c[nH]c2ccccc12] | H |
| 1287 | 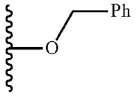 [SMILES: *OCc1ccccc1] | H | 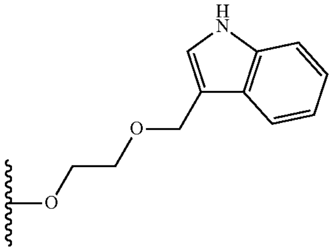 [SMILES: *OCCOCc1c[nH]c2ccccc12] | 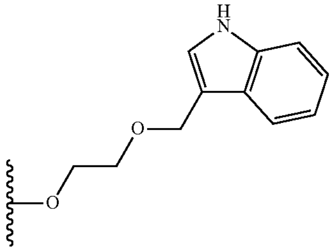 [SMILES: *OCCOCc1c[nH]c2ccccc12] | H |

TABLE 1-continued
formula (II)
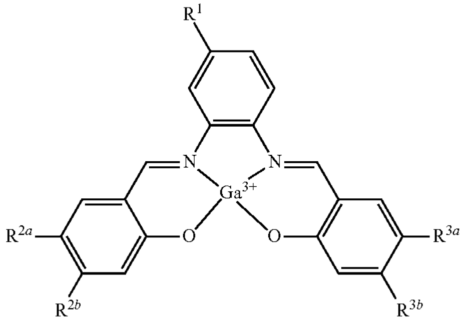
| Compound # | $R^1$ | $R^{2a}$ | $R^{2b}$ | $R^{3a}$ | $R^{3b}$ |
|---|---|---|---|---|---|
| 1288 | H | H | 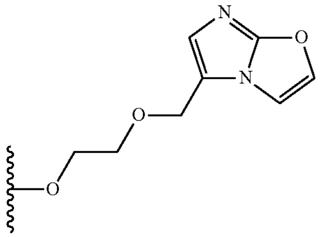 [SMILES: *OCCOCc1cnc2occn12] | 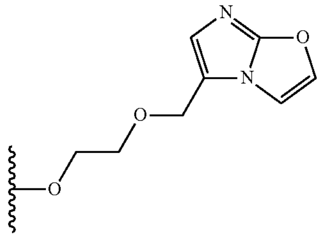 [SMILES: *OCCOCc1cnc2occn12] | H |
| 1289 | —OMe | H | 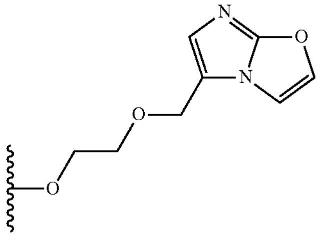 [SMILES: *OCCOCc1cnc2occn12] | 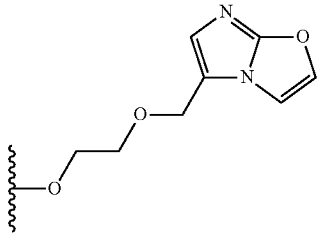 [SMILES: *OCCOCc1cnc2occn12] | H |
| 1290 | —OEt | H | 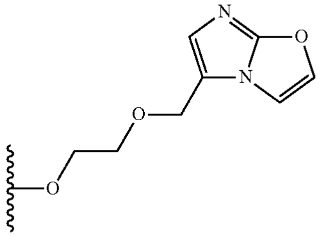 [SMILES: *OCCOCc1cnc2occn12] | 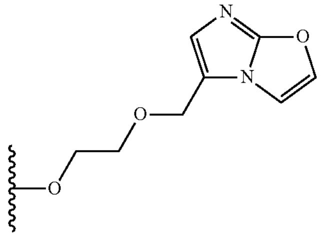 [SMILES: *OCCOCc1cnc2occn12] | H |

TABLE 1-continued
formula (II)
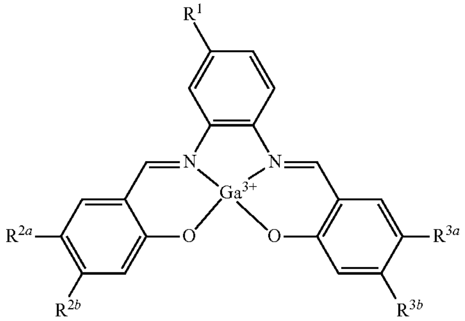
| Compound # | $R^1$ | $R^{2a}$ | $R^{2b}$ | $R^{3a}$ | $R^{3b}$ |
|---|---|---|---|---|---|
| 1291 | —OPr | H | 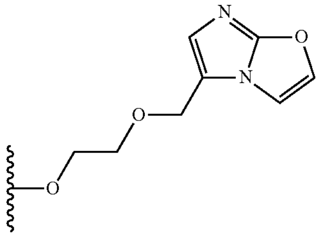 [SMILES: *OCCOCc1cnc2occn12] | 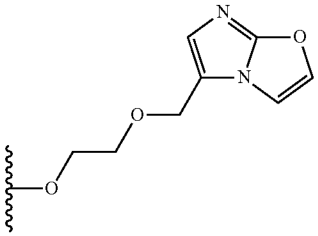 [SMILES: *OCCOCc1cnc2occn12] | H |
| 1292 | —OiPr | H | 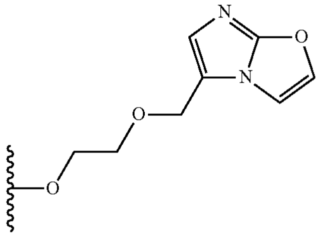 [SMILES: *OCCOCc1cnc2occn12] | 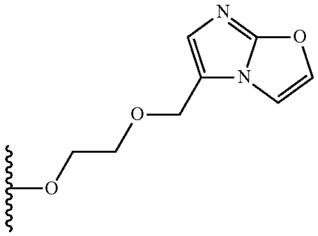 [SMILES: *OCCOCc1cnc2occn12] | H |

TABLE 1-continued
formula (II)
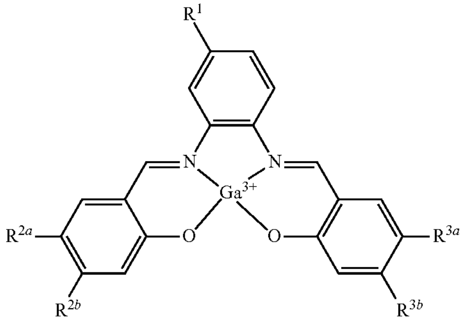
| Compound # | $R^1$ | $R^{2a}$ | $R^{2b}$ | $R^{3a}$ | $R^{3b}$ |
|---|---|---|---|---|---|
| 1293 | 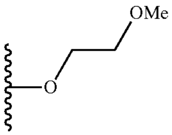 | H | 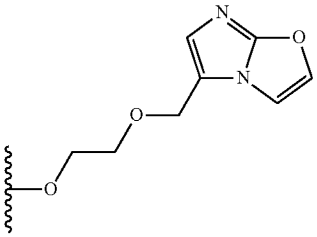 [SMILES: *OCCOCc1cnc2occn12] | 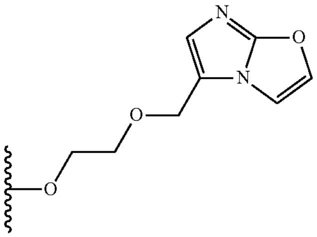 [SMILES: *OCCOCc1cnc2occn12] | H |
| 1294 | 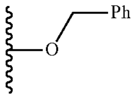 [SMILES: *OCc1ccccc1] | H | 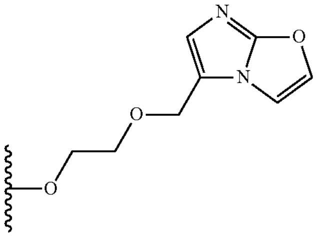 [SMILES: *OCCOCc1cnc2occn12] | 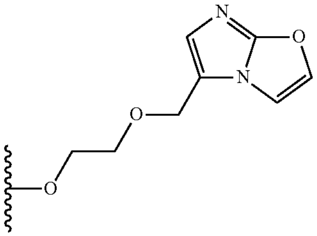 [SMILES: *OCCOCc1cnc2occn12] | H |

TABLE 1-continued
formula (II)
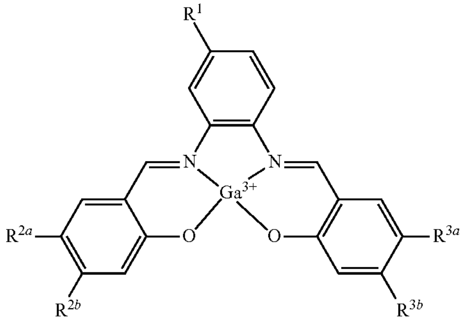
| Compound # | $R^1$ | $R^{2a}$ | $R^{2b}$ | $R^{3a}$ | $R^{3b}$ |
|---|---|---|---|---|---|
| 1295 | H | H | 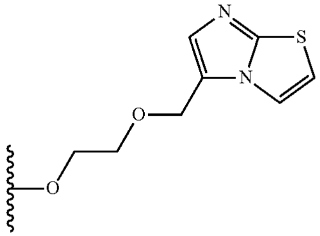 [SMILES: *OCCOCc1cnc2sccn12] | 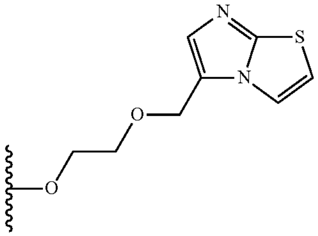 [SMILES: *OCCOCc1cnc2sccn12] | H |
| 1296 | —OMe | H | 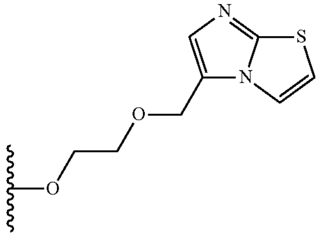 [SMILES: *OCCOCc1cnc2sccn12] | 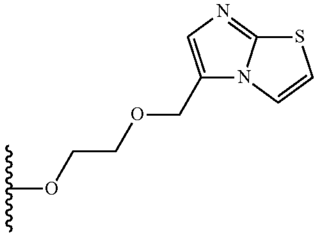 [SMILES: *OCCOCc1cnc2sccn12] | H |

TABLE 1-continued
formula (II)
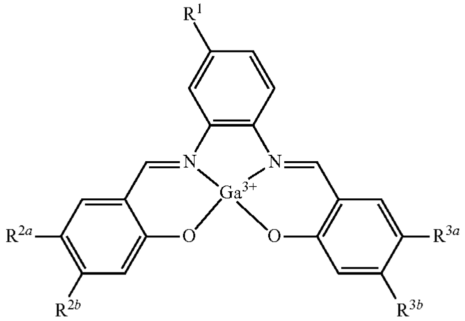
| Compound # | $R^1$ | $R^{2a}$ | $R^{2b}$ | $R^{3a}$ | $R^{3b}$ |
|---|---|---|---|---|---|
| 1297 | —OEt | H | 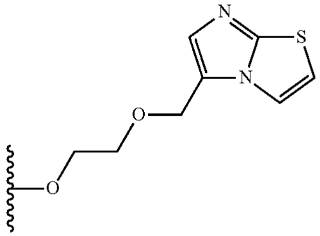 [SMILES: *OCCOCc1cnc2sccn12] | 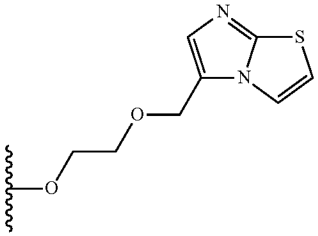 [SMILES: *OCCOCc1cnc2sccn12] | H |
| 1298 | —OPr | H | 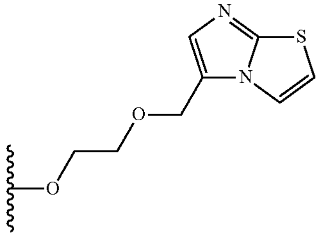 [SMILES: *OCCOCc1cnc2sccn12] | 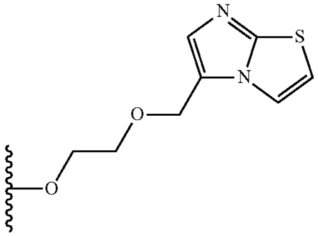 [SMILES: *OCCOCc1cnc2sccn12] | H |

TABLE 1-continued
formula (II)
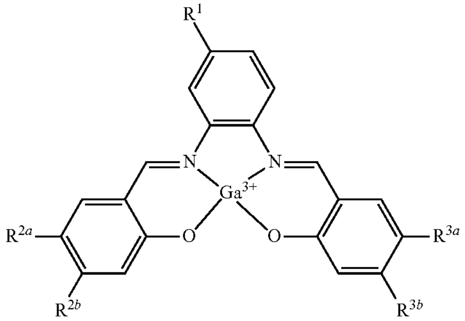
| Compound # | $R^1$ | $R^{2a}$ | $R^{2b}$ | $R^{3a}$ | $R^{3b}$ |
|---|---|---|---|---|---|
| 1299 | —OiPr | H | 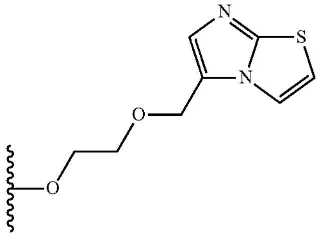 [SMILES: *OCCOCc1cnc2sccn12] | 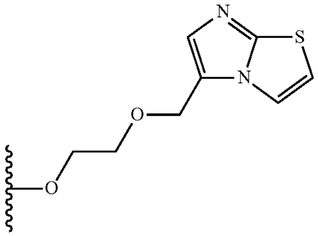 [SMILES: *OCCOCc1cnc2sccn12] | H |
| 1300 | 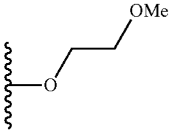 | H | 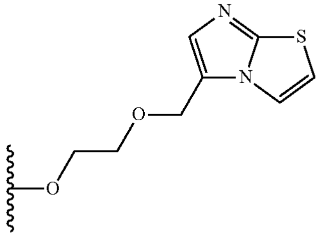 [SMILES: *OCCOCc1cnc2sccn12] | 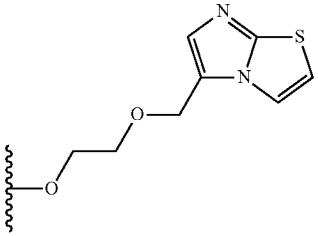 [SMILES: *OCCOCc1cnc2sccn12] | H |

TABLE 1-continued
formula (II)
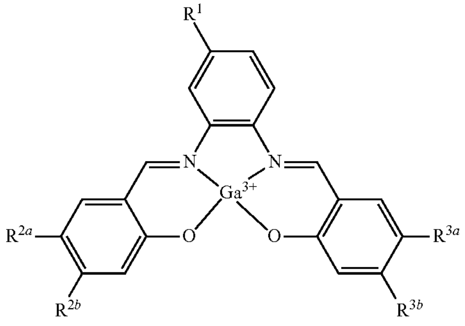
| Compound # | $R^1$ | $R^{2a}$ | $R^{2b}$ | $R^{3a}$ | $R^{3b}$ |
|---|---|---|---|---|---|
| 1301 | 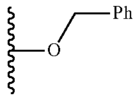 [SMILES: *OCc1ccccc1] | H | 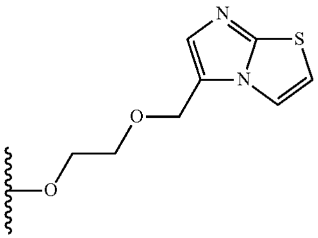 [SMILES: *OCCOCc1cnc2sccn12] | 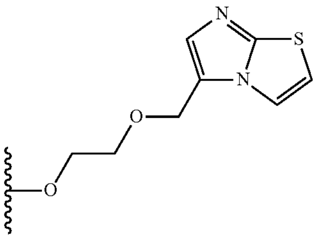 [SMILES: *OCCOCc1cnc2sccn12] | H |
| 1302 | H | H | 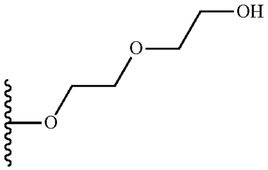 [SMILES: *OCCOCCO] | H | 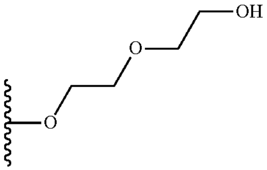 |
| 1303 | —OMe | H | 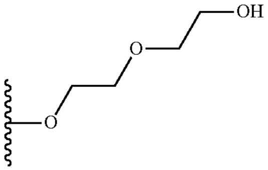 | H | 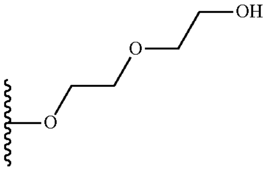 |

TABLE 1-continued
formula (II)
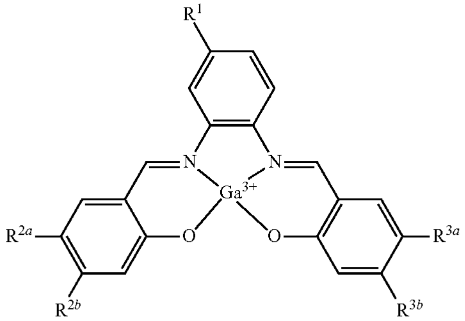
| Compound # | $R^1$ | $R^{2a}$ | $R^{2b}$ | $R^{3a}$ | $R^{3b}$ |
|---|---|---|---|---|---|
| 1304 | —OEt | H | 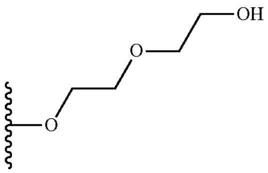 | H | 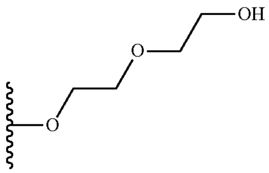 |
| 1305 | —OPr | H | 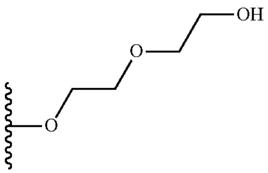 [SMILES: *OCCOCCO] | H | 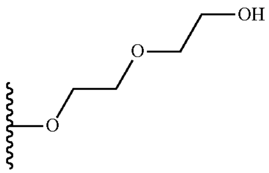 [SMILES: *OCCOCCO] |
| 1306 | —OiPr | H | 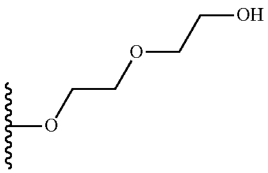 | H | 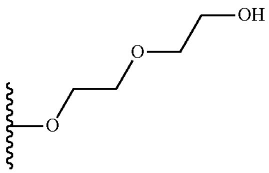 |
| 1307 | 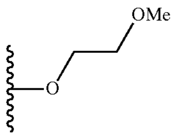 [SMILES: *OCCOC] | H | 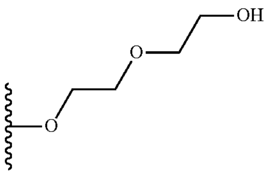 | H | 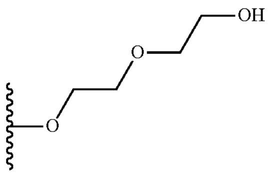 |

TABLE 1-continued
formula (II)
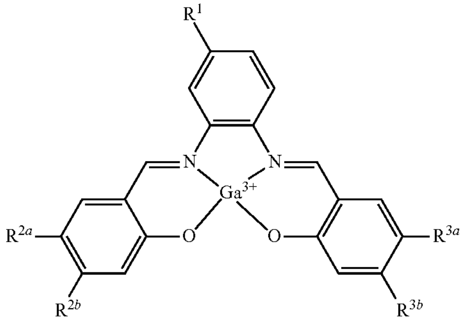
| Compound # | $R^1$ | $R^{2a}$ | $R^{2b}$ | $R^{3a}$ | $R^{3b}$ |
| --- | --- | --- | --- | --- | --- |
| 1308 | 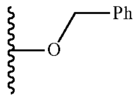 [SMILES: *OCc1ccccc1] | H | 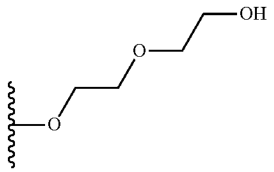 [SMILES: *OCCOCCO] | H | 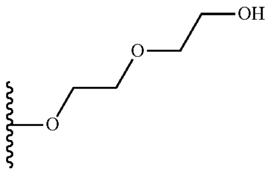 [SMILES: *OCCOCCO] |
| 1309 | H | H | 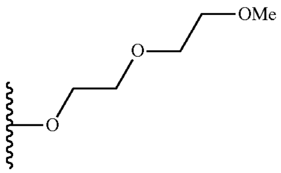 [SMILES: *OCCOCCOC] | H | 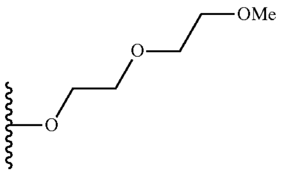 [SMILES: *OCCOCCOC] |
| 1310 | —OMe | H | 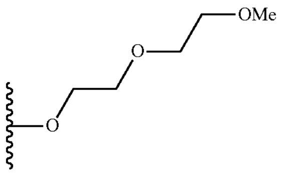 [SMILES: *OCCOCCOC] | H | 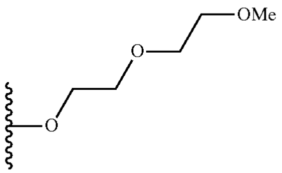 [SMILES: *OCCOCCOC] |

TABLE 1-continued
formula (II)
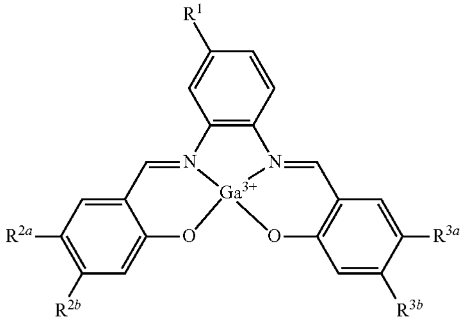
| Compound # | $R^1$ | $R^{2a}$ | $R^{2b}$ | $R^{3a}$ | $R^{3b}$ |
|---|---|---|---|---|---|
| 1311 | —OEt | H | 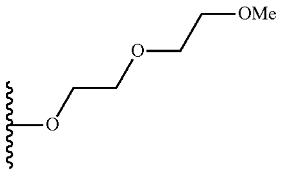 [SMILES: *OCCOCCOC] | H | 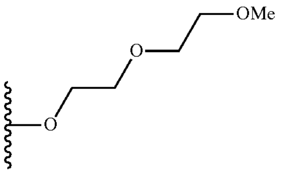 [SMILES: *OCCOCCOC] |
| 1312 | —OPr | H | 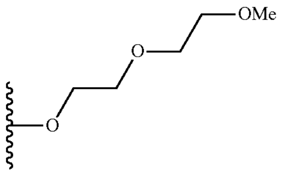 [SMILES: *OCCOCCOC] | H | 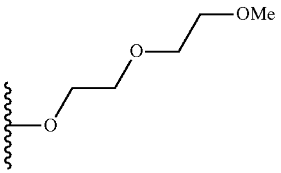 [SMILES: *OCCOCCOC] |
| 1313 | —OiPr | H | 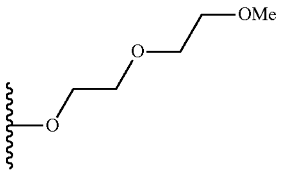 [SMILES: *OCCOCCOC] | H | 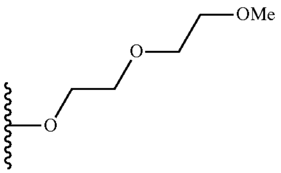 |
| 1314 | 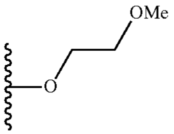 [SMILES: *OCCOC] | H | 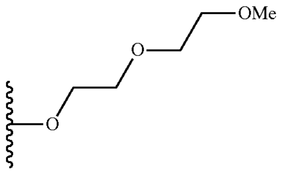 [SMILES: *OCCOCCOC] | H | 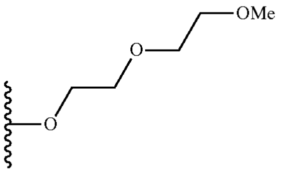 [SMILES: *OCCOCCOC] |

TABLE 1-continued
formula (II)
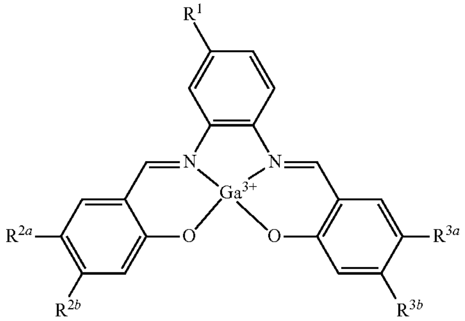
| Compound # | $R^1$ | $R^{2a}$ | $R^{2b}$ | $R^{3a}$ | $R^{3b}$ |
|---|---|---|---|---|---|
| 1315 | 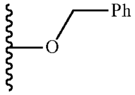 [SMILES: *OCc1ccccc1] | H | 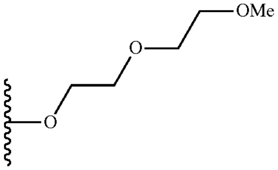 [SMILES: *OCCOCCOC] | H | 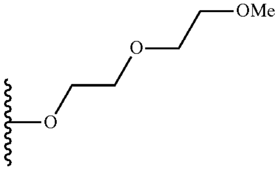 |
| 1316 | H | H | 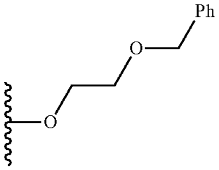 | H | 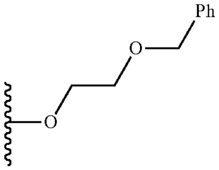 [SMILES: *OCCOCc1ccccc1] |
| 1317 | —OMe | H | 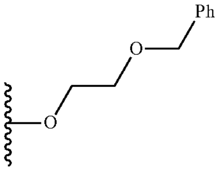 | H | 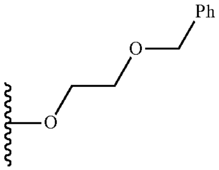 [SMILES: *OCCOCc1ccccc1] |

TABLE 1-continued
formula (II)
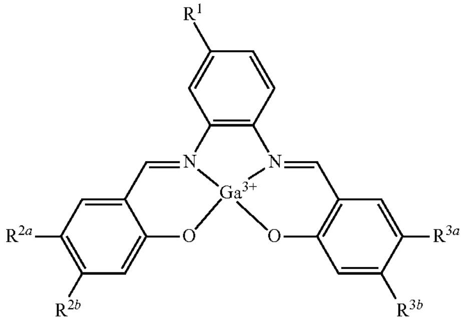
| Compound # | $R^1$ | $R^{2a}$ | $R^{2b}$ | $R^{3a}$ | $R^{3b}$ |
|---|---|---|---|---|---|
| 1318 | —OEt | H | 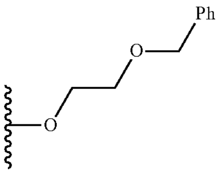 | H | 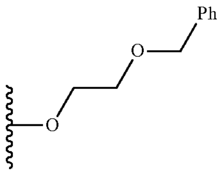 [SMILES: *OCCOCc1ccccc1] |
| 1319 | —OPr | H | 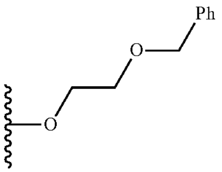 [SMILES: *OCCOCc1ccccc1] | H | 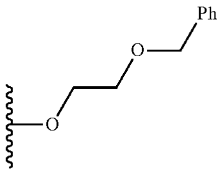 [SMILES: *OCCOCc1ccccc1] |
| 1320 | —OiPr | H | 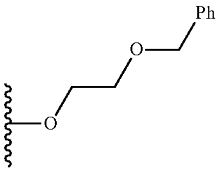 | H | 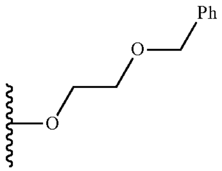 [SMILES: *OCCOCc1ccccc1] |
| 1321 | 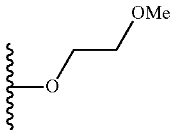 [SMILES: *OCCOC] | H | 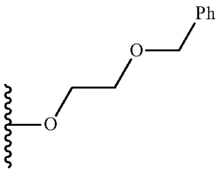 | H | 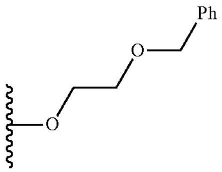 |

TABLE 1-continued
formula (II)
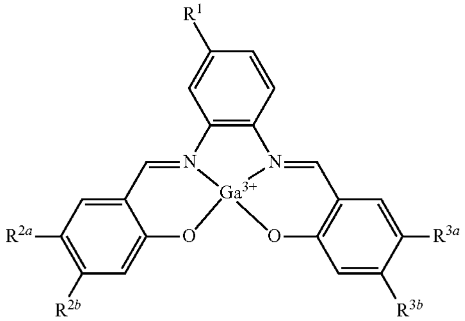
| Compound # | $R^1$ | $R^{2a}$ | $R^{2b}$ | $R^{3a}$ | $R^{3b}$ |
|---|---|---|---|---|---|
| 1322 | 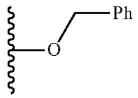 [SMILES: *OCc1ccccc1] | H | 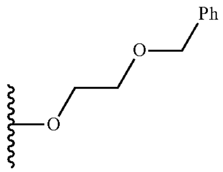 | H | 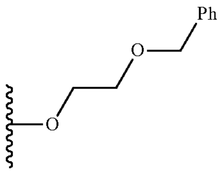 |
| 1323 | H | H | 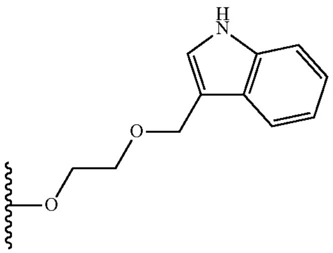 [SMILES: *OCCOCc1c[nH]c2ccccc12] | H | 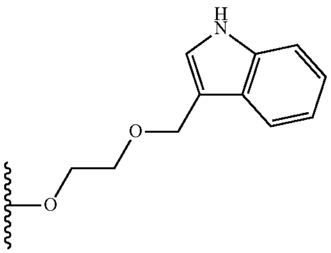 [SMILES: *OCCOCc1c[nH]c2ccccc12] |
| 1324 | —OMe | H | 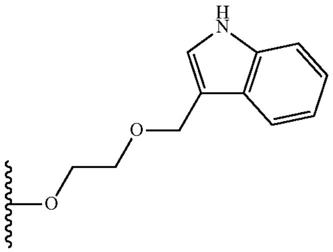 [SMILES: *OCCOCc1c[nH]c2ccccc12] | H | 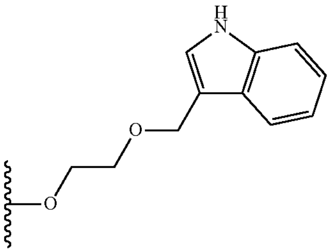 [SMILES: *OCCOCc1c[nH]c2ccccc12] |

TABLE 1-continued
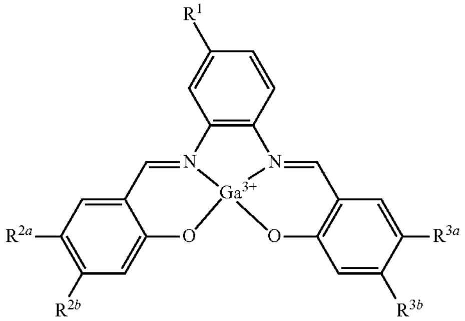
formula (II)
| Compound # | $R^1$ | $R^{2a}$ | $R^{2b}$ | $R^{3a}$ | $R^{3b}$ |
|---|---|---|---|---|---|
| 1325 | —OEt | H | 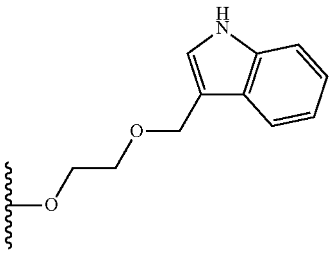 [SMILES: *OCCOCc1c[nH]c2ccccc12] | H | 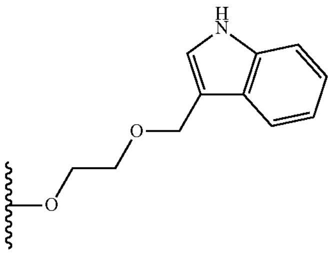 [SMILES: *OCCOCc1c[nH]c2ccccc12] |
| 1326 | —OPr | H | 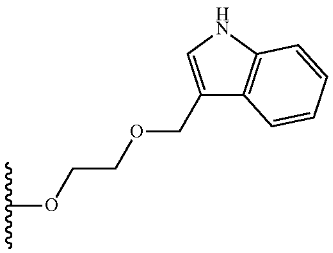 [SMILES: *OCCOCc1c[nH]c2ccccc12] | H | 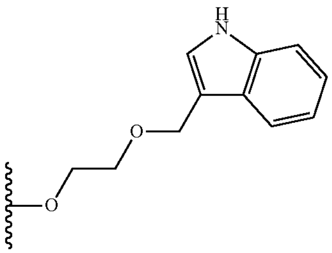 [SMILES: *OCCOCc1c[nH]c2ccccc12] |

TABLE 1-continued
formula (II)
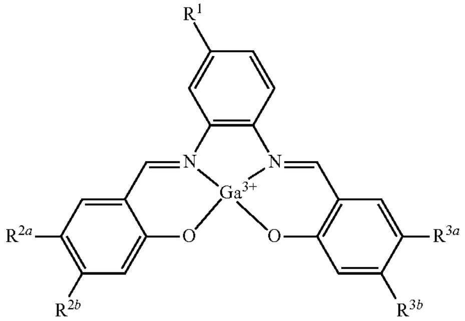
| Compound # | $R^1$ | $R^{2a}$ | $R^{2b}$ | $R^{3a}$ | $R^{3b}$ |
|---|---|---|---|---|---|
| 1327 | —OiPr | H | 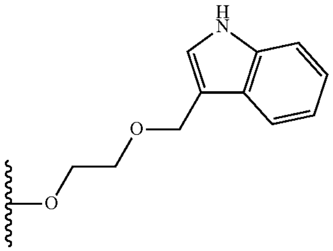 [SMILES: *OCCOCc1c[nH]c2ccccc12] | H | 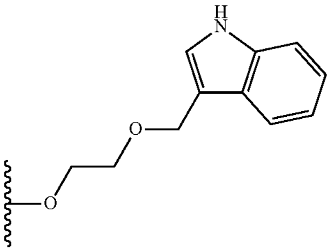 [SMILES: *OCCOCc1c[nH]c2ccccc12] |
| 1328 | 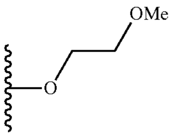 [SMILES: *OCCOC] | H | 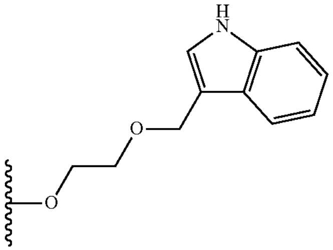 [SMILES: *OCCOCc1c[nH]c2ccccc12] | H | 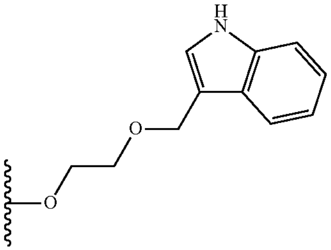 [SMILES: *OCCOCc1c[nH]c2ccccc12] |

TABLE 1-continued
formula (II)
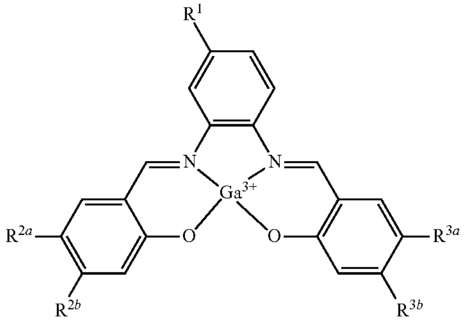
| Compound # | $R^1$ | $R^{2a}$ | $R^{2b}$ | $R^{3a}$ | $R^{3b}$ |
|---|---|---|---|---|---|
| 1329 | 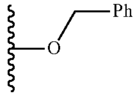 [SMILES: *OCc1ccccc1] | H | 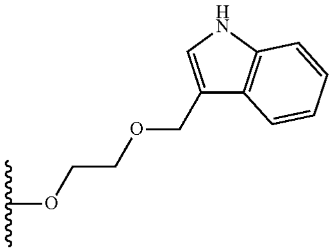 [SMILES: *OCCOCc1c[nH]c2ccccc12] | H | 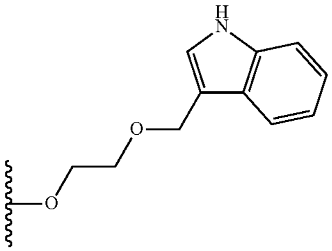 [SMILES: *OCCOCc1c[nH]c2ccccc12] |
| 1330 | H | H | 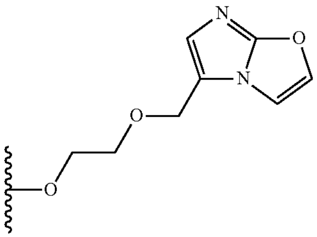 [SMILES: *OCCOCc1cnc2occn12] | H | 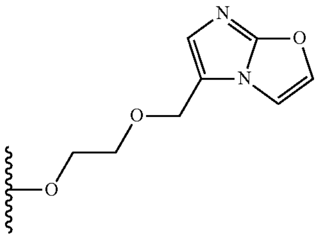 [SMILES: *OCCOCc1cnc2occn12] |

TABLE 1-continued
formula (II)
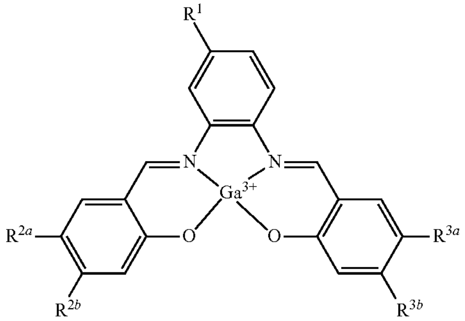
| Compound # | $R^1$ | $R^{2a}$ | $R^{2b}$ | $R^{3a}$ | $R^{3b}$ |
|---|---|---|---|---|---|
| 1331 | —OMe | H | 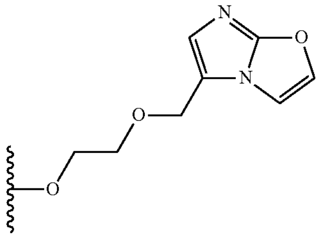 [SMILES: *OCCOCc1cnc2occn12] | H | 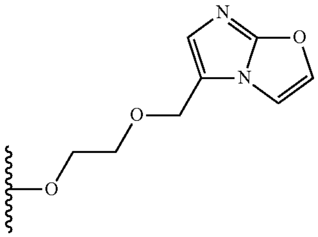 [SMILES: *OCCOCc1cnc2occn12] |
| 1332 | —OEt | H | 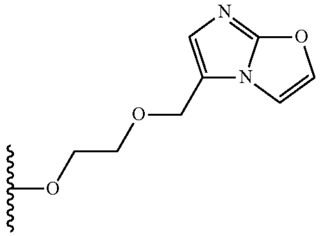 [SMILES: *OCCOCc1cnc2occn12] | H | 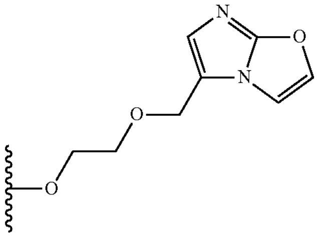 [SMILES: *OCCOCc1cnc2occn12] |
| 1333 | —OPr | H | 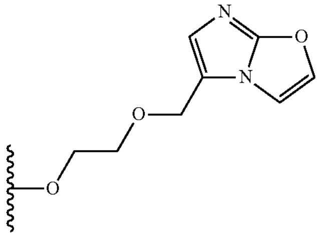 [SMILES: *OCCOCc1cnc2occn12] | H | 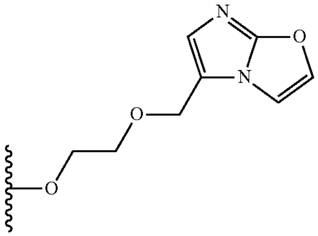 [SMILES: *OCCOCc1cnc2occn12] |

TABLE 1-continued
formula (II)
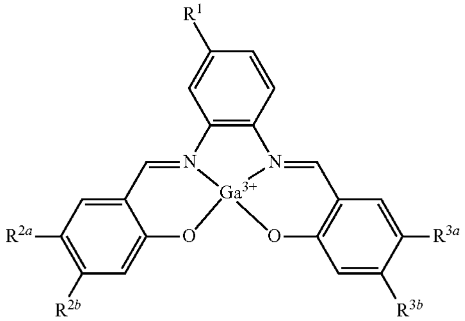
| Compound # | $R^1$ | $R^{2a}$ | $R^{2b}$ | $R^{3a}$ | $R^{3b}$ |
|---|---|---|---|---|---|
| 1334 | —OiPr | H | 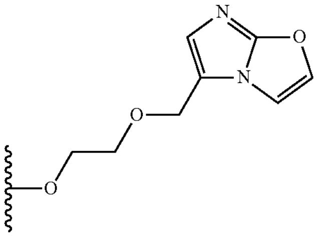 [SMILES: *OCCOCc1cnc2occn12] | H | 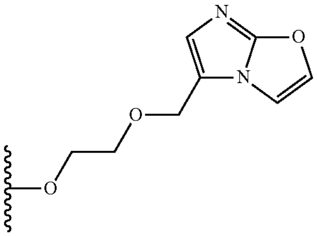 [SMILES: *OCCOCc1cnc2occn12] |
| 1335 | 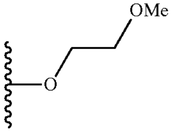 | H | 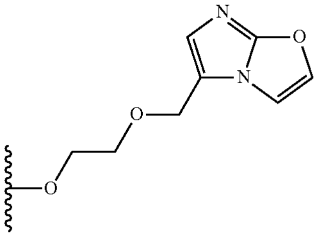 [SMILES: *OCCOCc1cnc2occn12] | H | 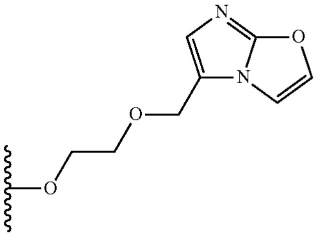 [SMILES: *OCCOCc1cnc2occn12] |

TABLE 1-continued
formula (II)
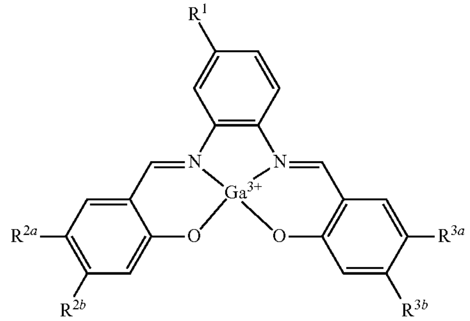
| Compound # | $R^1$ | $R^{2a}$ | $R^{2b}$ | $R^{3a}$ | $R^{3b}$ |
|---|---|---|---|---|---|
| 1336 | 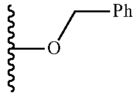 [SMILES: *OCc1ccccc1] | H | 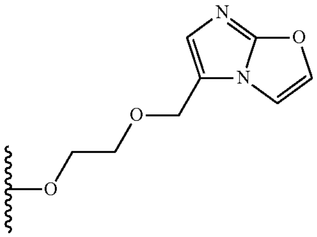 [SMILES: *OCCOCc1cnc2occn12] | H | 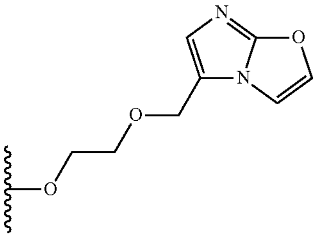 [SMILES: *OCCOCc1cnc2occn12] |
| 1337 | H | H | 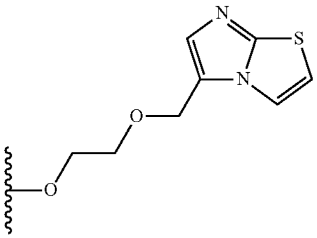 [SMILES: *OCCOCc1cnc2sccn12] | H | 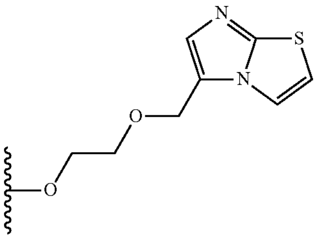 [SMILES: *OCCOCc1cnc2sccn12] |

TABLE 1-continued
formula (II)
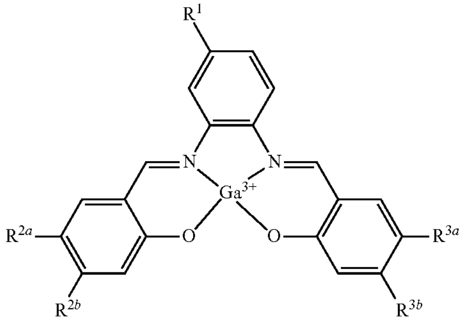
| Compound # | $R^1$ | $R^{2a}$ | $R^{2b}$ | $R^{3a}$ | $R^{3b}$ |
| --- | --- | --- | --- | --- | --- |
| 1338 | —OMe | H | 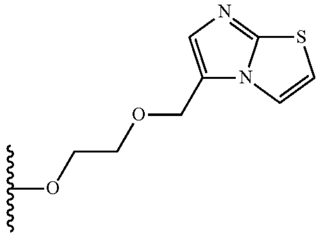 [SMILES: *OCCOCc1cnc2sccn12] | H | 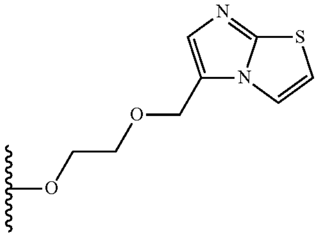 [SMILES: *OCCOCc1cnc2sccn12] |
| 1339 | —OEt | H | 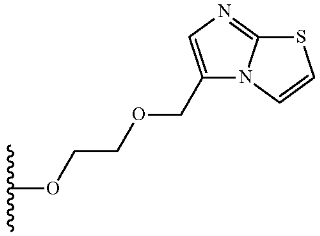 [SMILES: *OCCOCc1cnc2sccn12] | H | 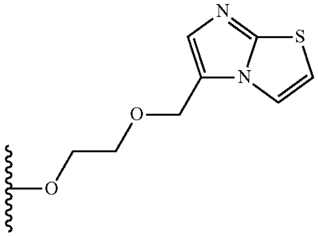 [SMILES: *OCCOCc1cnc2sccn12] |

TABLE 1-continued
formula (II)
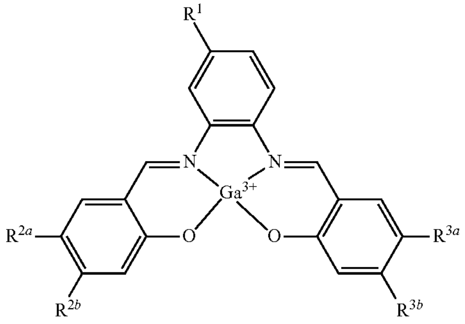
| Compound # | $R^1$ | $R^{2a}$ | $R^{2b}$ | $R^{3a}$ | $R^{3b}$ |
|---|---|---|---|---|---|
| 1340 | —OPr | H | 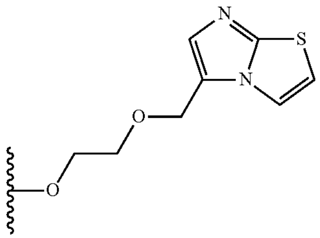 [SMILES: *OCCOCc1cnc2sccn12] | H | 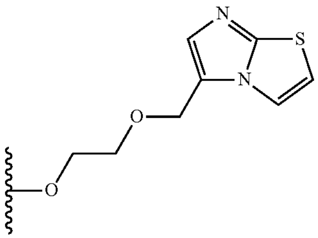 [SMILES: *OCCOCc1cnc2sccn12] |
| 1341 | —OiPr | H | 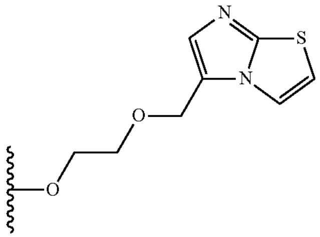 [SMILES: *OCCOCc1cnc2sccn12] | H | 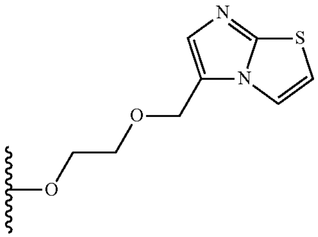 [SMILES: *OCCOCc1cnc2sccn12] |

TABLE 1-continued
formula (II)
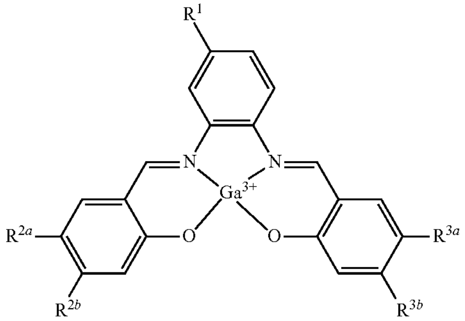
| Compound # | $R^1$ | $R^{2a}$ | $R^{2b}$ | $R^{3a}$ | $R^{3b}$ |
|---|---|---|---|---|---|
| 1342 | 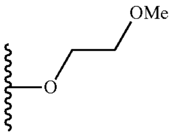 | H | 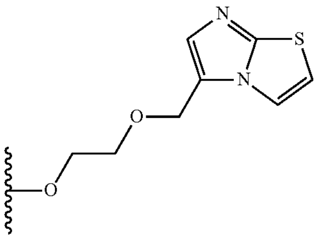 [SMILES: *OCCOCc1cnc2sccn12] | H | 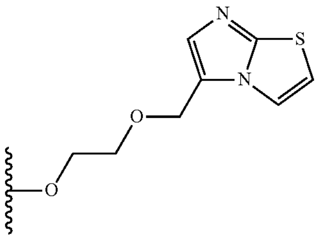 [SMILES: *OCCOCc1cnc2sccn12] |
| 1343 | 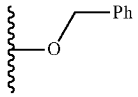 [SMILES: *OCc1ccccc1] | H | 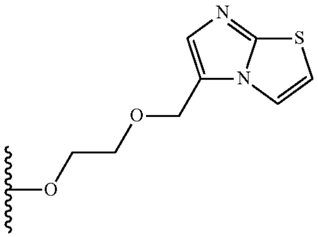 [SMILES: *OCCOCc1cnc2sccn12] | H | 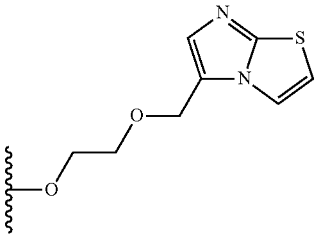 [SMILES: *OCCOCc1cnc2sccn12] |
| 1344 | H | 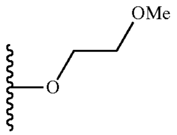 [SMILES: *OCCOC] | H | H | H |

TABLE 1-continued
formula (II)
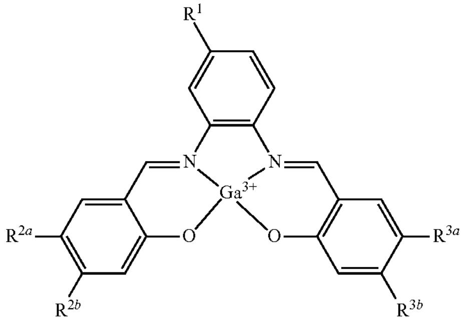
| Compound # | $R^1$ | $R^{2a}$ | $R^{2b}$ | $R^{3a}$ | $R^{3b}$ |
|---|---|---|---|---|---|
| 1345 | —OMe | 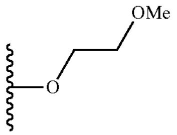 [SMILES: *OCCOC] | H | H | H |
| 1346 | —OEt | 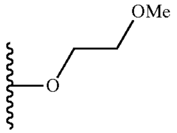 [SMILES: *OCCOC] | H | H | H |
| 1347 | —OPr | 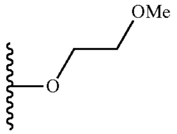 [SMILES: *OCCOC] | H | H | H |
| 1348 | —OiPr | 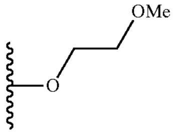 [SMILES: *OCCOC] | H | H | H |
| 1349 | 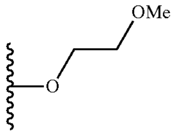 [SMILES: *OCCOC] | 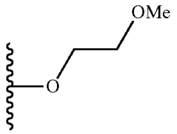 [SMILES: *OCCOC] | H | H | H |

TABLE 1-continued
formula (II)
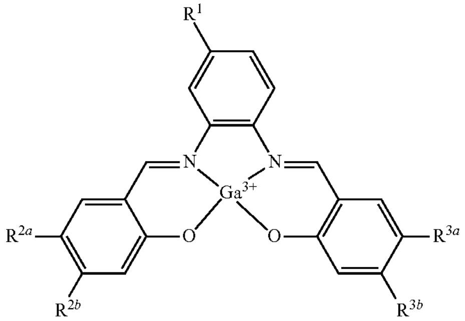
| Compound # | $R^1$ | $R^{2a}$ | $R^{2b}$ | $R^{3a}$ | $R^{3b}$ |
|---|---|---|---|---|---|
| 1350 | 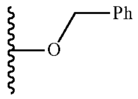 [SMILES: *OCc1ccccc1] | 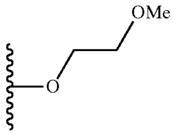 [SMILES: *OCCOC] | H | H | H |
| 1351 | H | H | 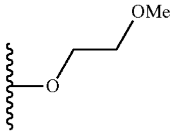 [SMILES: *OCCOC] | H | H |
| 1352 | —OMe | H | 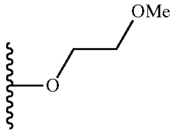 [SMILES: *OCCOC] | H | H |
| 1353 | —OEt | H | 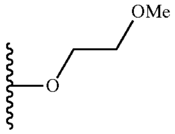 | H | H |

TABLE 1-continued
formula (II)
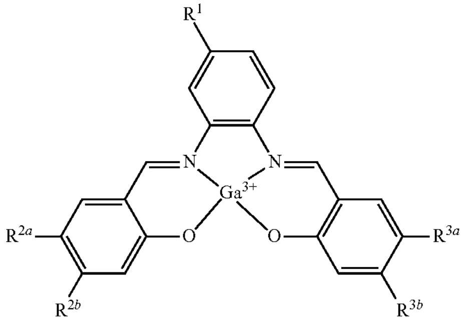
| Compound # | $R^1$ | $R^{2a}$ | $R^{2b}$ | $R^{3a}$ | $R^{3b}$ |
|---|---|---|---|---|---|
| 1354 | —OPr | H | 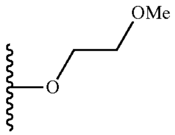 [SMILES: *OCCOC] | H | H |
| 1355 | —OiPr | H | 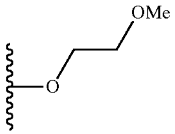 [SMILES: *OCCOC] | H | H |
| 1356 | 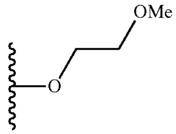 | H | 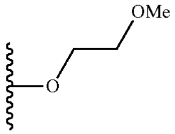 [SMILES: *OCCOC] | H | H |
| 1357 | 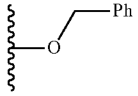 | H | 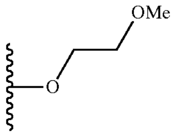 [SMILES: *OCCOC] | H | H |
| 1358 | H | H | H | 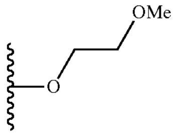 [SMILES: *OCCOC] | H |

TABLE 1-continued
formula (II)
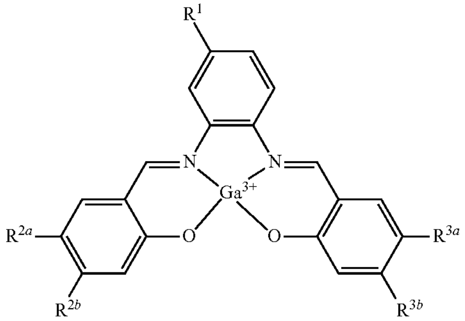
| Compound # | $R^1$ | $R^{2a}$ | $R^{2b}$ | $R^{3a}$ | $R^{3b}$ |
| --- | --- | --- | --- | --- | --- |
| 1359 | —OMe | H | H | 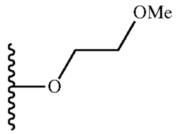 [SMILES: *OCCOC] | H |
| 1360 | —OEt | H | H | 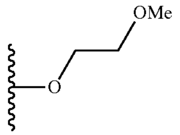 | H |
| 1361 | —OPr | H | H | 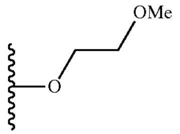 [SMILES: *OCCOC] | H |
| 1362 | —OiPr | H | H | 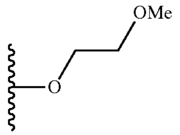 | H |

TABLE 1-continued
formula (II)
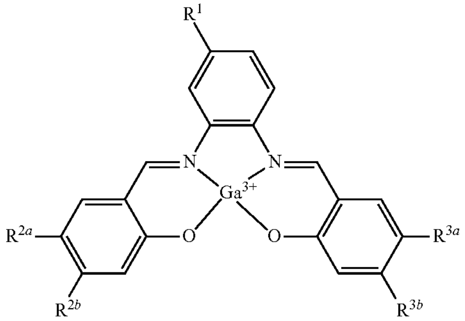
| Compound # | $R^1$ | $R^{2a}$ | $R^{2b}$ | $R^{3a}$ | $R^{3b}$ |
|---|---|---|---|---|---|
| 1363 | 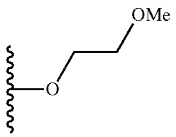 | H | H | 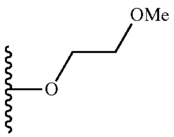 [SMILES: *OCCOC] | H |
| 1364 | 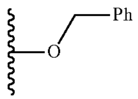 | H | H | 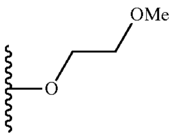 [SMILES: *OCCOC] | H |
| 1365 | H | H | H | H | 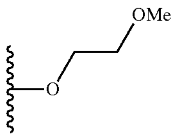 |
| 1366 | —OMe | H | H | H | 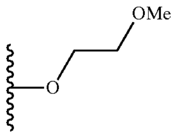 |
| 1367 | —OEt | H | H | H | 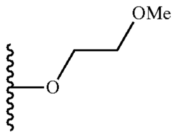 |

TABLE 1-continued
formula (II)
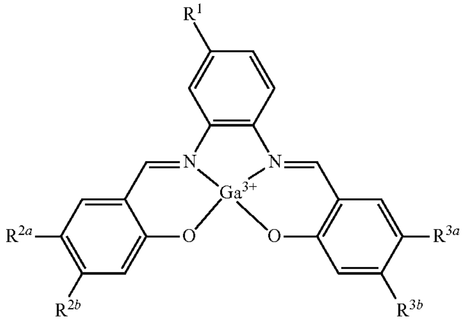
| Compound # | $R^1$ | $R^{2a}$ | $R^{2b}$ | $R^{3a}$ | $R^{3b}$ |
|---|---|---|---|---|---|
| 1368 | —OPr | H | H | H | 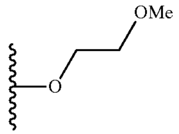 |
| 1369 | —OiPr | H | H | H | 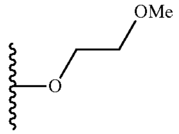 |
| 1370 | 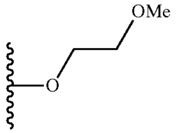 | H | H | H | 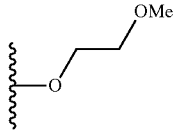 |
| 1371 | 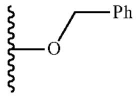 | H | H | H | 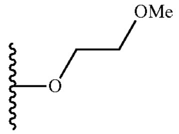 |

TABLE 1-continued
formula (II)
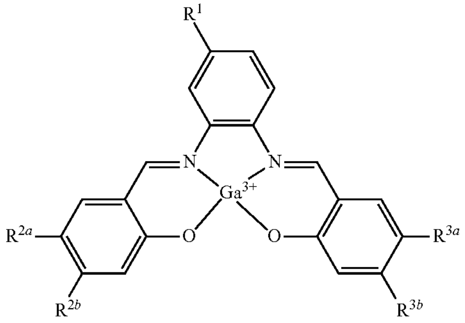
| Compound # | $R^1$ | $R^{2a}$ | $R^{2b}$ | $R^{3a}$ | $R^{3b}$ |
|---|---|---|---|---|---|
| 1372 | H | 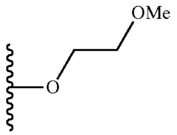 [SMILES: *OCCOC] | H | 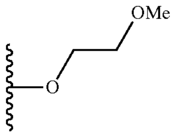 [SMILES: *OCCOC] | H |
| 1373 | —OMe | 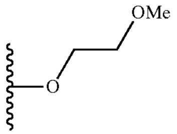 [SMILES: *OCCOC] | H | 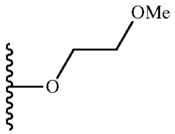 [SMILES: *OCCOC] | H |
| 1374 | —OEt | 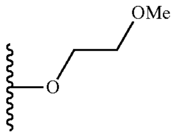 [SMILES: *OCCOC] | H | 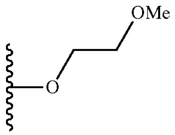 [SMILES: *OCCOC] | H |
| 1375 | —OPr | 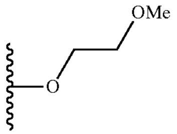 [SMILES: *OCCOC] | H | 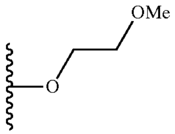 [SMILES: *OCCOC] | H |
| 1376 | —OiPr | 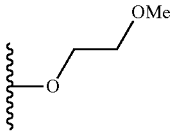 [SMILES: *OCCOC] | H | 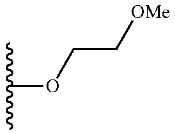 [SMILES: *OCCOC] | H |

TABLE 1-continued
formula (II)
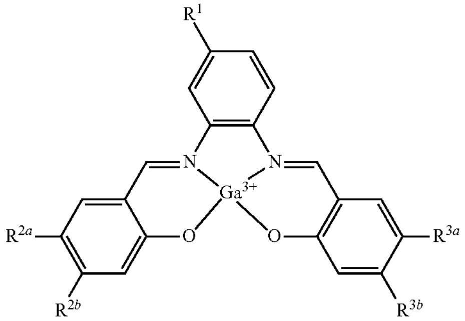
| Compound # | $R^1$ | $R^{2a}$ | $R^{2b}$ | $R^{3a}$ | $R^{3b}$ |
|---|---|---|---|---|---|
| 1377 | 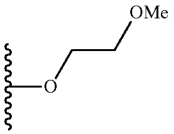 | 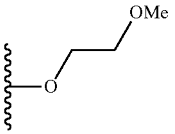 [SMILES: *OCCOC] | H | 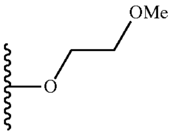 [SMILES: *OCCOC] | H |
| 1378 | 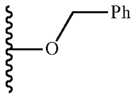 [SMILES: *OCc1ccccc1] | 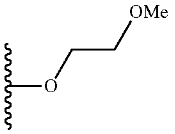 | H | 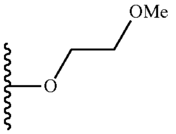 | H |
| 1379 | H | 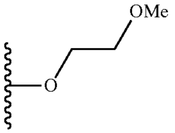 [SMILES: *OCCOC] | H | H | 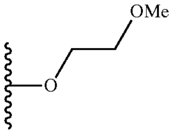 |
| 1380 | —OMe | 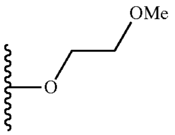 | H | H | 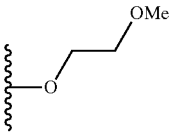 |

TABLE 1-continued
formula (II)
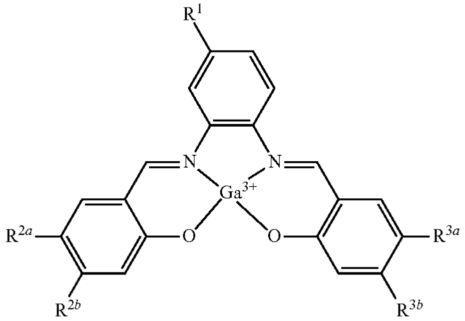
| Compound # | $R^1$ | $R^{2a}$ | $R^{2b}$ | $R^{3a}$ | $R^{3b}$ |
|---|---|---|---|---|---|
| 1381 | —OEt | 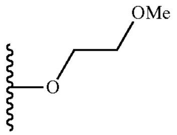 [SMILES: *OCCOC] | H | H | 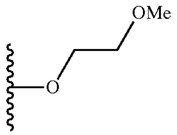 |
| 1382 | —OPr | 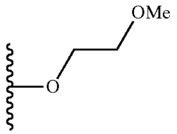 [SMILES: *OCCOC] | H | H | 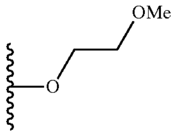 |
| 1383 | —OiPr | 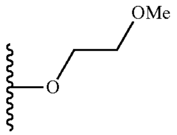 [SMILES: *OCCOC] | H | H | 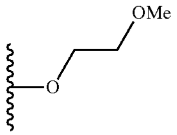 |
| 1384 | 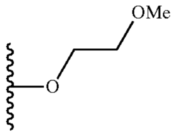 | 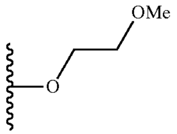 [SMILES: *OCCOC] | H | H | 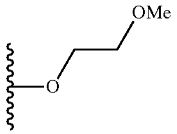 |
| 1385 | 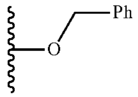 [SMILES: *OCc1ccccc1] | 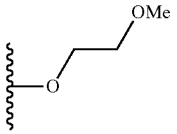 [SMILES: *OCCOC] | H | H | 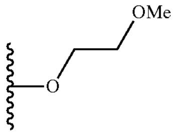 |

TABLE 1-continued
formula (II)
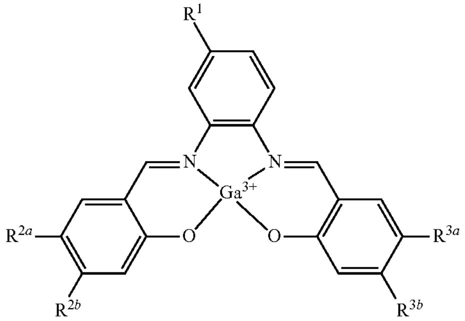
| Compound # | $R^1$ | $R^{2a}$ | $R^{2b}$ | $R^{3a}$ | $R^{3b}$ |
|---|---|---|---|---|---|
| 1386 | H | H | 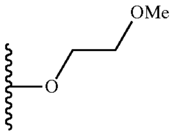 [SMILES: *OCCOC] | 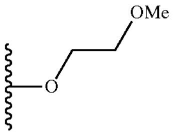 [SMILES: *OCCOC] | H |
| 1387 | —OMe | H | 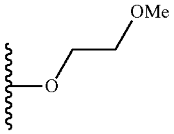 [SMILES: *OCCOC] | 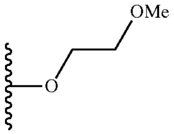 | H |
| 1388 | —OEt | H | 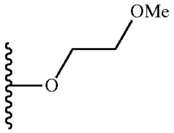 [SMILES: *OCCOC] | 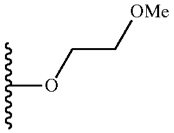 [SMILES: *OCCOC] | H |
| 1389 | —OPr | H | 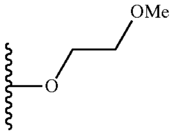 | 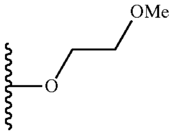 | H |

TABLE 1-continued
formula (II)
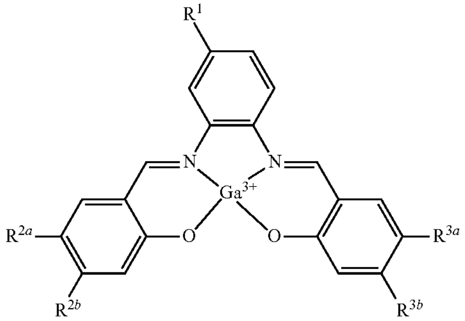
| Compound # | $R^1$ | $R^{2a}$ | $R^{2b}$ | $R^{3a}$ | $R^{3b}$ |
|---|---|---|---|---|---|
| 1390 | —OiPr | H | 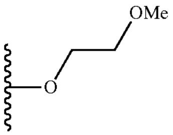 [SMILES: *OCCOC] | 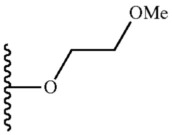 [SMILES: *OCCOC] | H |
| 1391 | 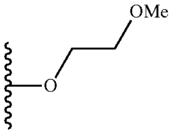 | H | 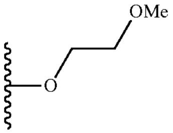 [SMILES: *OCCOC] | 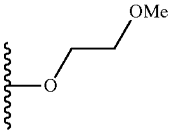 [SMILES: *OCCOC] | H |
| 1392 | 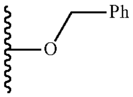 [SMILES: *OCc1ccccc1] | H | 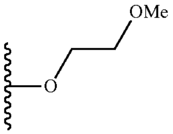 [SMILES: *OCCOC] | 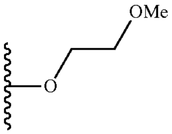 [SMILES: *OCCOC] | H |
| 1393 | H | H | 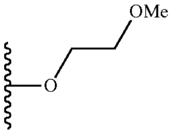 [SMILES: *OCCOC] | H | 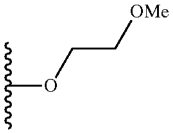 |
| 1394 | —OMe | H | 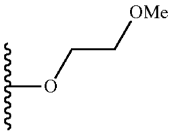 [SMILES: *OCCOC] | H | 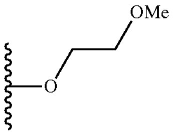 |

TABLE 1-continued
formula (II)
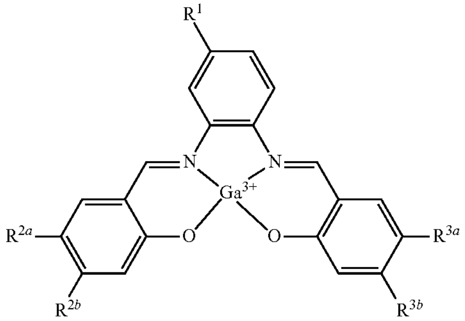
| Compound # | $R^1$ | $R^{2a}$ | $R^{2b}$ | $R^{3a}$ | $R^{3b}$ |
| --- | --- | --- | --- | --- | --- |
| 1395 | —OEt | H | 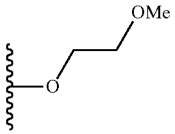 [SMILES: *OCCOC] | H | 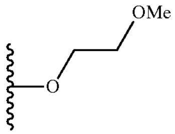 |
| 1396 | —OPr | H | 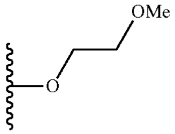 [SMILES: *OCCOC] | H | 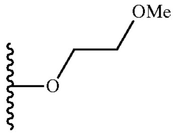 |
| 1397 | —OiPr | H | 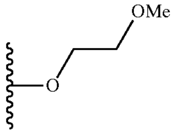 [SMILES: *OCCOC] | H | 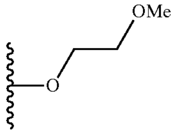 |
| 1398 | 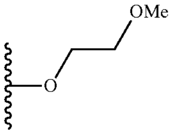 | H | 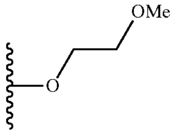 | H | 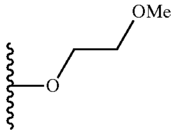 |

TABLE 1-continued
formula (II)
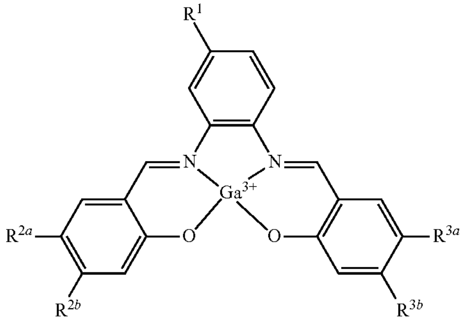
| Compound # | $R^1$ | $R^{2a}$ | $R^{2b}$ | $R^{3a}$ | $R^{3b}$ |
|---|---|---|---|---|---|
| 1399 | 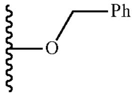 [SMILES: *OCc1ccccc1] | H | 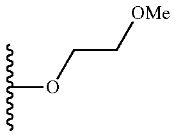 [SMILES: *OCCOC] | H | 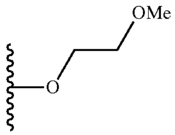 |
| 1400 | H | 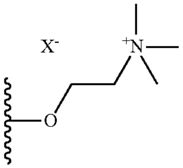 | H | H | H |
| 1401 | —OMe | 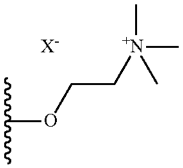 | H | H | H |
| 1402 | —OEt | 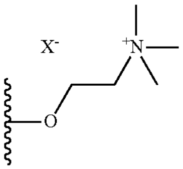 | H | H | H |

TABLE 1-continued
formula (II)
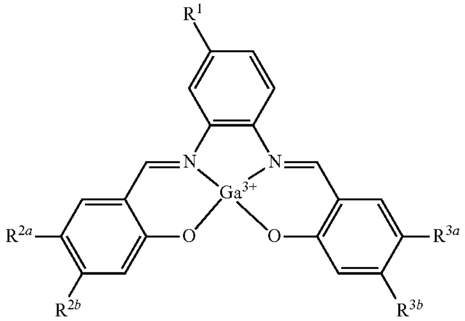
| Compound # | $R^1$ | $R^{2a}$ | $R^{2b}$ | $R^{3a}$ | $R^{3b}$ |
|---|---|---|---|---|---|
| 1403 | —OPr | 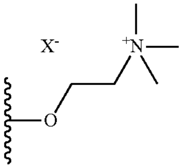 | H | H | H |
| 1404 | —OiPr | 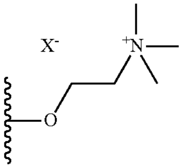 | H | H | H |
| 1405 | 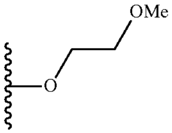 | 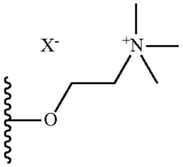 | H | H | H |
| 1406 | 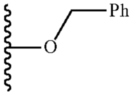 [SMILES: *OCc1ccccc1] | 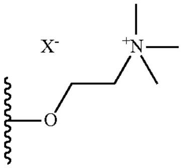 | H | H | H |

TABLE 1-continued
formula (II)
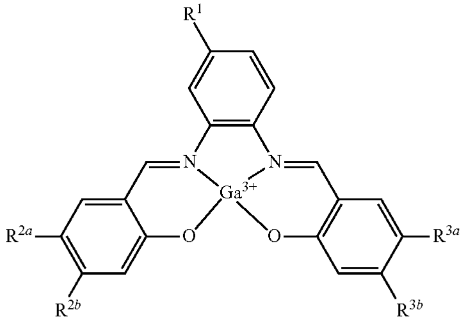
| Compound # | $R^1$ | $R^{2a}$ | $R^{2b}$ | $R^{3a}$ | $R^{3b}$ |
|---|---|---|---|---|---|
| 1407 | H | 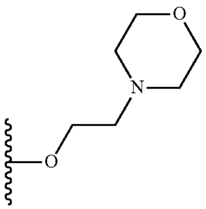 [SMILES: *OCCN1CCOCC1] | H | H | H |
| 1408 | —OMe | 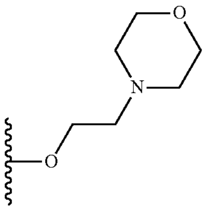 [SMILES: *OCCN1CCOCC1] | H | H | H |
| 1409 | —OEt | 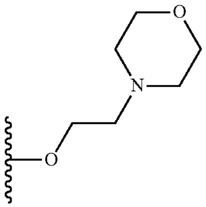 [SMILES: *OCCN1CCOCC1] | H | H | H |

TABLE 1-continued
formula (II)
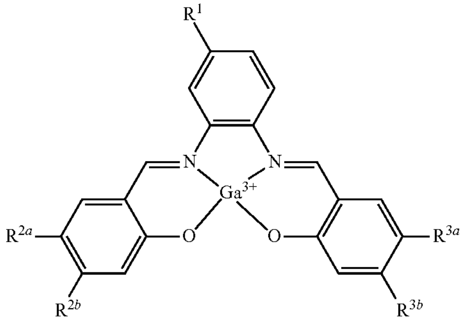
| Compound # | $R^1$ | $R^{2a}$ | $R^{2b}$ | $R^{3a}$ | $R^{3b}$ |
|---|---|---|---|---|---|
| 1410 | —OPr | 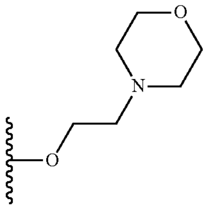 [SMILES: *OCCN1CCOCC1] | H | H | H |
| 1411 | —OiPr | 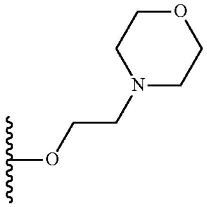 [SMILES: *OCCN1CCOCC1] | H | H | H |
| 1412 | 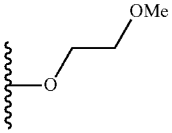 [SMILES: *OCCOC] | 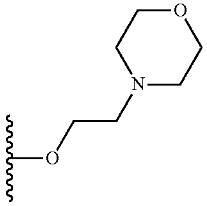 [SMILES: *OCCN1CCOCC1] | H | H | H |

TABLE 1-continued
formula (II)
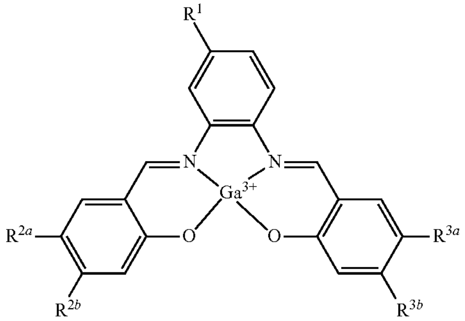
| Compound # | $R^1$ | $R^{2a}$ | $R^{2b}$ | $R^{3a}$ | $R^{3b}$ |
|---|---|---|---|---|---|
| 1413 | 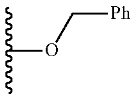 [SMILES: *OCc1ccccc1] | 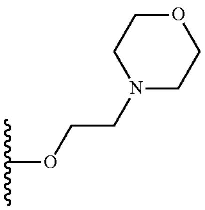 [SMILES: *OCCN1CCOCC1] | H | H | H |
| 1414 | H | 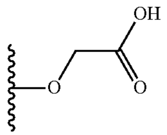 | H | H | H |
| 1415 | —OMe | 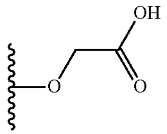 | H | H | H |
| 1416 | —OEt | 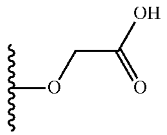 | H | H | H |

TABLE 1-continued
formula (II)
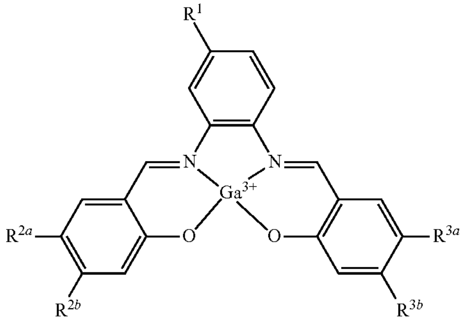
| Compound # | $R^1$ | $R^{2a}$ | $R^{2b}$ | $R^{3a}$ | $R^{3b}$ |
|---|---|---|---|---|---|
| 1417 | —OPr | 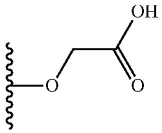 | H | H | H |
| 1418 | —OiPr | 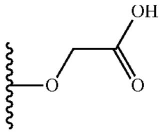 | H | H | H |
| 1419 | 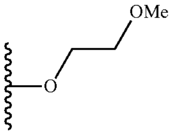 | 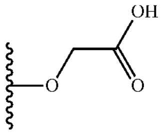 | H | H | H |
| 1420 | 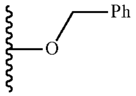 | 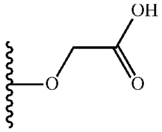 | H | H | H |

TABLE 1-continued
formula (II)
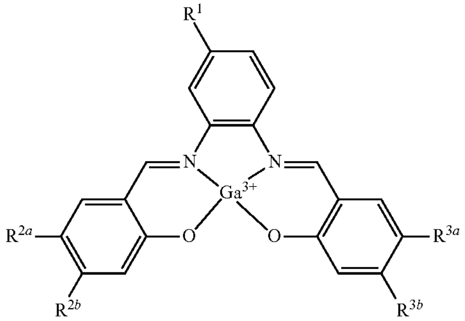
| Compound # | $R^1$ | $R^{2a}$ | $R^{2b}$ | $R^{3a}$ | $R^{3b}$ |
|---|---|---|---|---|---|
| 1421 | H | H | 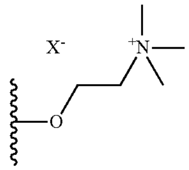 | H | H |
| 1422 | —OMe | H | 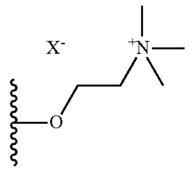 | H | H |
| 1423 | —OEt | H | 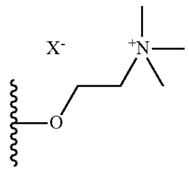 | H | H |
| 1424 | —OPr | H | 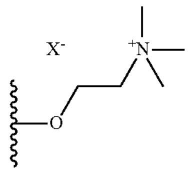 | H | H |

TABLE 1-continued
formula (II)
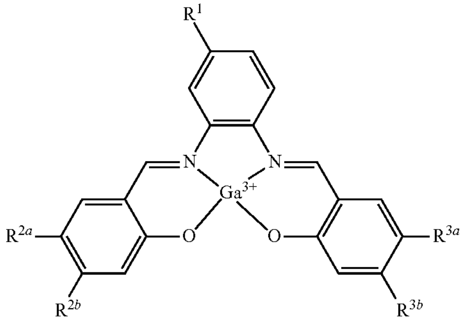
| Compound # | $R^1$ | $R^{2a}$ | $R^{2b}$ | $R^{3a}$ | $R^{3b}$ |
|---|---|---|---|---|---|
| 1425 | —OiPr | H | 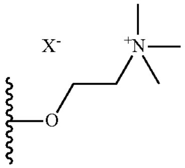 | H | H |
| 1426 | 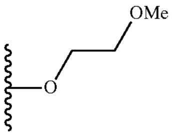 | H | 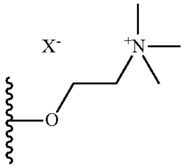 | H | H |
| 1427 | 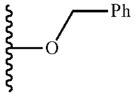 [SMILES: *OCc1ccccc1] | H | 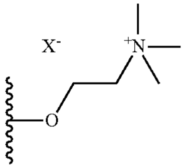 | H | H |

TABLE 1-continued
formula (II)
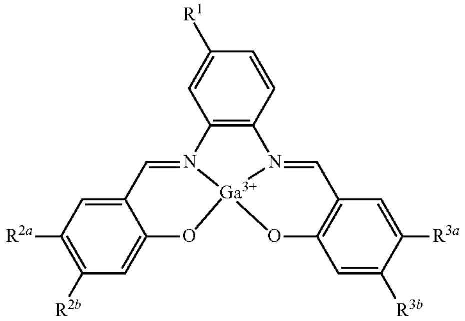
| Compound # | $R^1$ | $R^{2a}$ | $R^{2b}$ | $R^{3a}$ | $R^{3b}$ |
|---|---|---|---|---|---|
| 1428 | H | H | 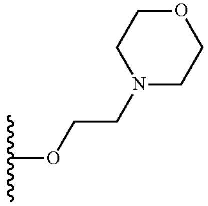 [SMILES: *OCCN1CCOCC1] | H | H |
| 1429 | —OMe | H | 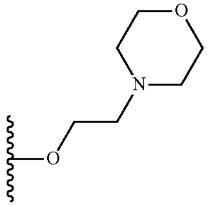 [SMILES: *OCCN1CCOCC1] | H | H |
| 1430 | —OEt | H | 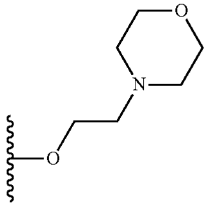 [SMILES: *OCCN1CCOCC1] | H | H |

TABLE 1-continued
formula (II)
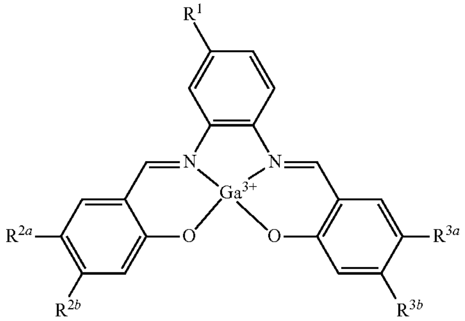
| Compound # | $R^1$ | $R^{2a}$ | $R^{2b}$ | $R^{3a}$ | $R^{3b}$ |
|---|---|---|---|---|---|
| 1431 | —OPr | H | 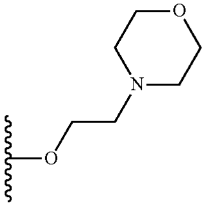 [SMILES: *OCCN1CCOCC1] | H | H |
| 1432 | —OiPr | H | 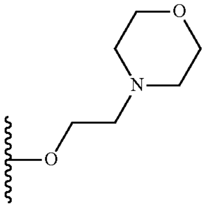 [SMILES: *OCCN1CCOCC1] | H | H |
| 1433 | 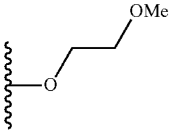 [SMILES: *OCCOC] | H | 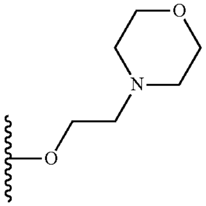 [SMILES: *OCCN1CCOCC1] | H | H |

TABLE 1-continued
formula (II)
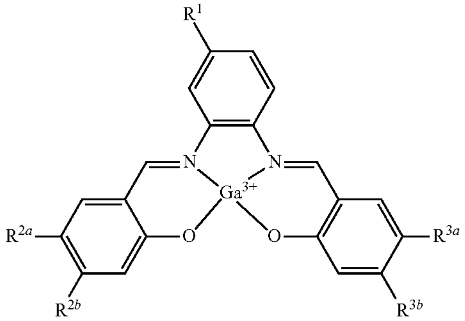
| Compound # | $R^1$ | $R^{2a}$ | $R^{2b}$ | $R^{3a}$ | $R^{3b}$ |
|---|---|---|---|---|---|
| 1434 | 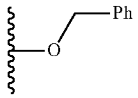 [SMILES: *OCc1ccccc1] | H | 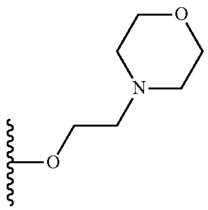 [SMILES: *OCCN1CCOCC1] | H | H |
| 1435 | H | H | 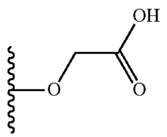 | H | H |
| 1436 | —OMe | H | 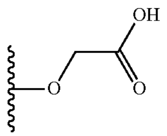 [SMILES: *OCC(=O)O] | H | H |
| 1437 | —OEt | H | 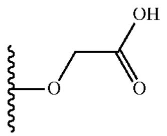 | H | H |

TABLE 1-continued
formula (II)
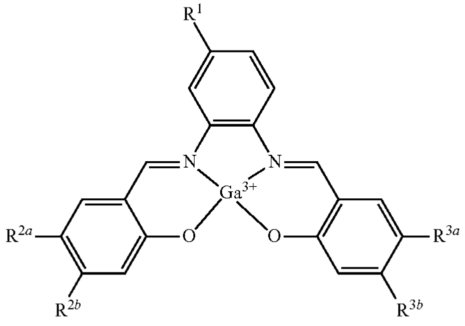
| Compound # | $R^1$ | $R^{2a}$ | $R^{2b}$ | $R^{3a}$ | $R^{3b}$ |
|---|---|---|---|---|---|
| 1438 | —OPr | H | 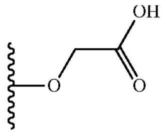 [SMILES: *OCC(=O)O] | H | H |
| 1439 | —OiPr | H | 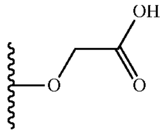 [SMILES: *OCC(=O)O] | H | H |
| 1440 | 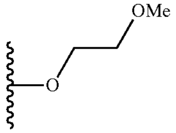 | H | 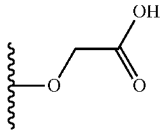 [SMILES: *OCC(=O)O] | H | H |
| 1441 | 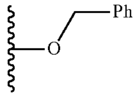 | H | 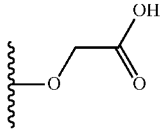 [SMILES: *OCC(=O)O] | H | H |

TABLE 1-continued
formula (II)
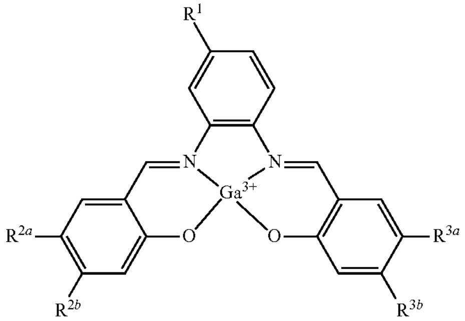
| Compound # | $R^1$ | $R^{2a}$ | $R^{2b}$ | $R^{3a}$ | $R^{3b}$ |
|---|---|---|---|---|---|
| 1442 | H | H | H | 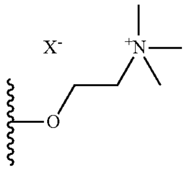 | H |
| 1443 | —OMe | H | H | 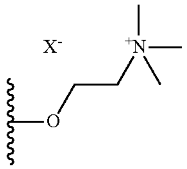 | H |
| 1444 | —OEt | H | H | 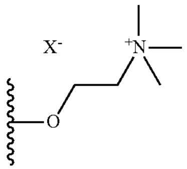 | H |
| 1445 | —OPr | H | H | 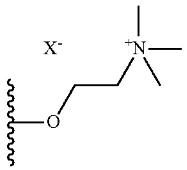 | H |

TABLE 1-continued
formula (II)
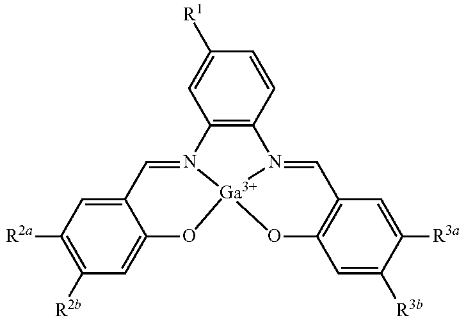
| Compound # | $R^1$ | $R^{2a}$ | $R^{2b}$ | $R^{3a}$ | $R^{3b}$ |
|---|---|---|---|---|---|
| 1446 | —OiPr | H | H | 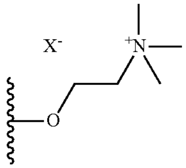 | H |
| 1447 | 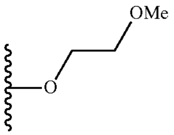 | H | H | 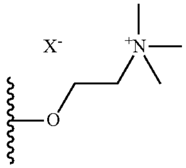 | H |
| 1448 | 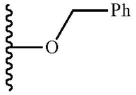 [SMILES: *OCc1ccccc1] | H | H | 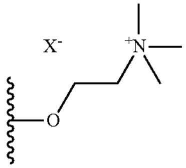 | H |

TABLE 1-continued
formula (II)
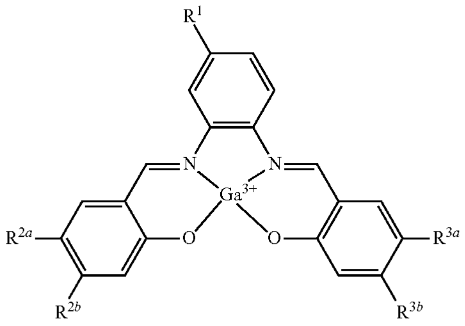
| Compound # | $R^1$ | $R^{2a}$ | $R^{2b}$ | $R^{3a}$ | $R^{3b}$ |
|---|---|---|---|---|---|
| 1449 | H | H | H | 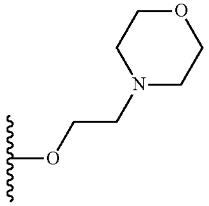 [SMILES: *OCCN1CCOCC1] | H |
| 1450 | —OMe | H | H | 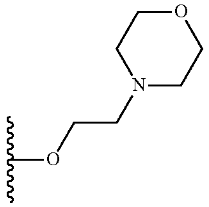 [SMILES: *OCCN1CCOCC1] | H |
| 1451 | —OEt | H | H | 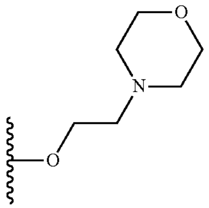 [SMILES: *OCCN1CCOCC1] | H |

TABLE 1-continued
formula (II)
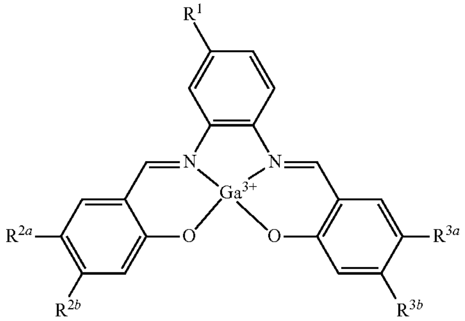
| Compound # | $R^1$ | $R^{2a}$ | $R^{2b}$ | $R^{3a}$ | $R^{3b}$ |
|---|---|---|---|---|---|
| 1452 | —OPr | H | H | 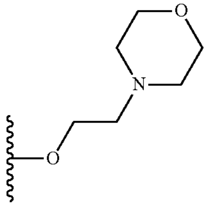 [SMILES: *OCCN1CCOCC1] | H |
| 1453 | —OiPr | H | H | 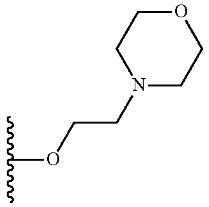 [SMILES: *OCCN1CCOCC1] | H |
| 1454 | 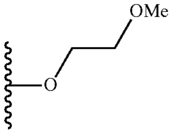 [SMILES: *OCCOC] | H | H | 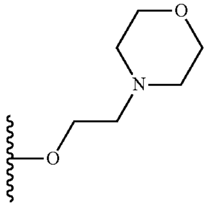 [SMILES: *OCCN1CCOCC1] | H |

TABLE 1-continued
formula (II)
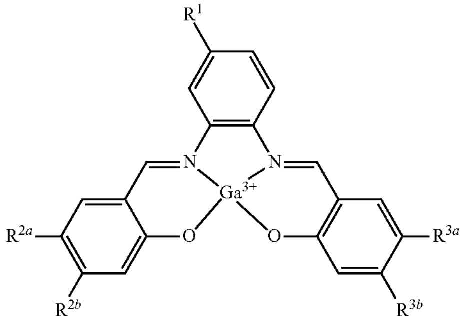
| Compound # | R1 | R2a | R2b | R3a | R3b |
|---|---|---|---|---|---|
| 1455 | 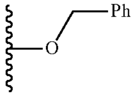 [SMILES: *OCc1ccccc1] | H | H | 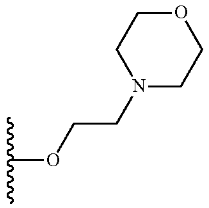 [SMILES: *OCCN1CCOCC1] | H |
| 1456 | H | H | H | 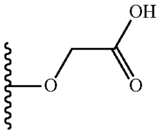 [SMILES: *OCC(=O)O] | H |
| 1457 | —OMe | H | H | 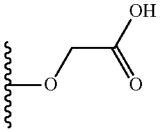 [SMILES: *OCC(=O)O] | H |
| 1458 | —OEt | H | H | 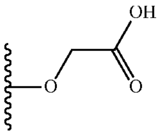 | H |

TABLE 1-continued
formula (II)
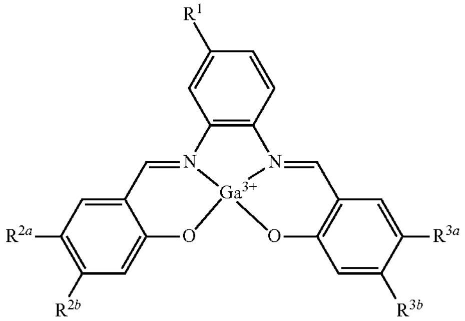
| Compound # | $R^1$ | $R^{2a}$ | $R^{2b}$ | $R^{3a}$ | $R^{3b}$ |
|---|---|---|---|---|---|
| 1459 | —OPr | H | H | 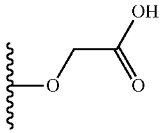 [SMILES: *OCC(=O)O] | H |
| 1460 | —OiPr | H | H | 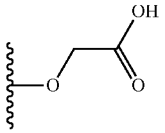 [SMILES: *OCC(=O)O] | H |
| 1461 | 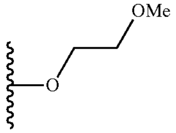 | H | H | 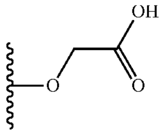 [SMILES: *OCC(=O)O] | H |
| 1462 | 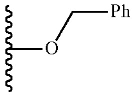 | H | H | 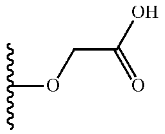 [SMILES: *OCC(=O)O] | H |

TABLE 1-continued
formula (II)
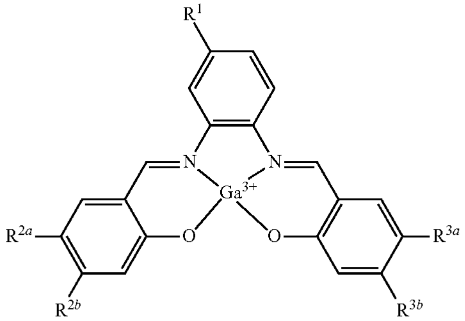
| Compound # | $R^1$ | $R^{2a}$ | $R^{2b}$ | $R^{3a}$ | $R^{3b}$ |
|---|---|---|---|---|---|
| 1463 | H | H | H | H | 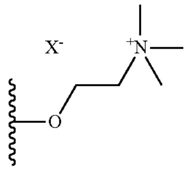 |
| 1464 | —OMe | H | H | H | 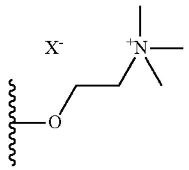 |
| 1465 | —OEt | H | H | H | 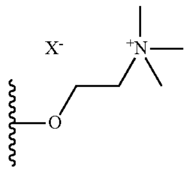 |
| 1466 | —OPr | H | H | H | 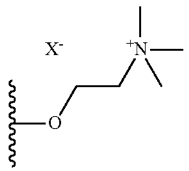 |

TABLE 1-continued
formula (II)
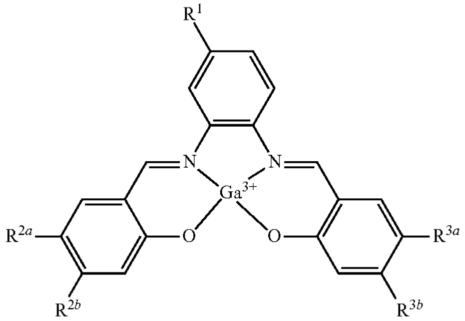
| Compound # | $R^1$ | $R^{2a}$ | $R^{2b}$ | $R^{3a}$ | $R^{3b}$ |
|---|---|---|---|---|---|
| 1467 | —OiPr | H | H | H | 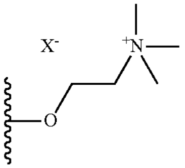 |
| 1468 | 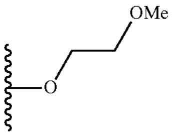 | H | H | H | 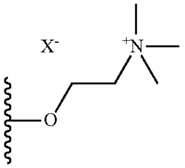 |
| 1469 | 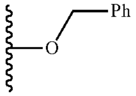 [SMILES: *OCc1ccccc1] | H | H | H | 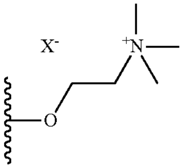 |

TABLE 1-continued
formula (II)
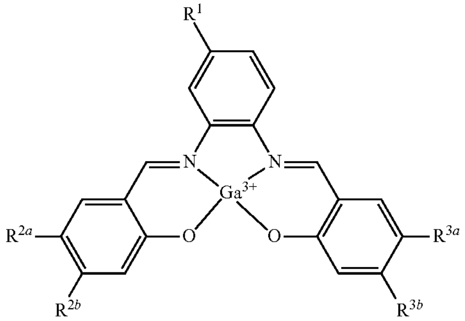
| Compound # | $R^1$ | $R^{2a}$ | $R^{2b}$ | $R^{3a}$ | $R^{3b}$ |
|---|---|---|---|---|---|
| 1470 | H | H | H | H | 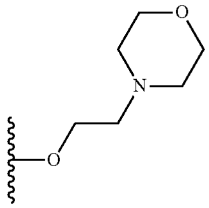 |
| 1471 | —OMe | H | H | H | 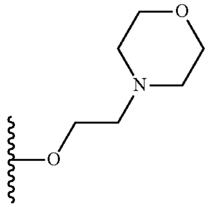 |
| 1472 | —OEt | H | H | H | 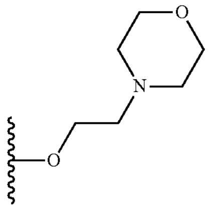 |

TABLE 1-continued
formula (II)
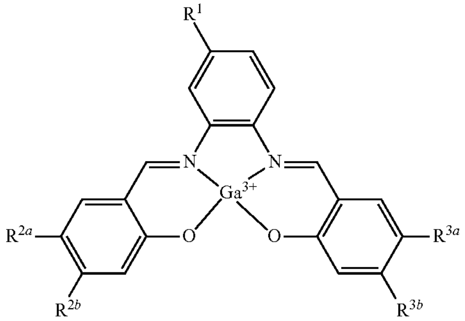
| Compound # | $R^1$ | $R^{2a}$ | $R^{2b}$ | $R^{3a}$ | $R^{3b}$ |
|---|---|---|---|---|---|
| 1473 | —OPr | H | H | H | 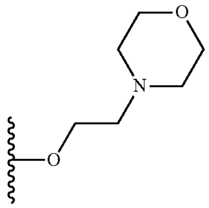 |
| 1474 | —OiPr | H | H | H | 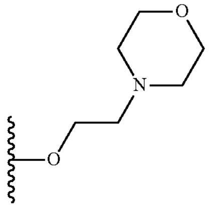 |
| 1475 | 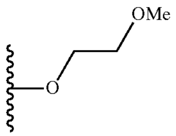 [SMILES: *OCCOC] | H | H | H | 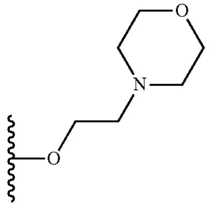 |

TABLE 1-continued
formula (II)
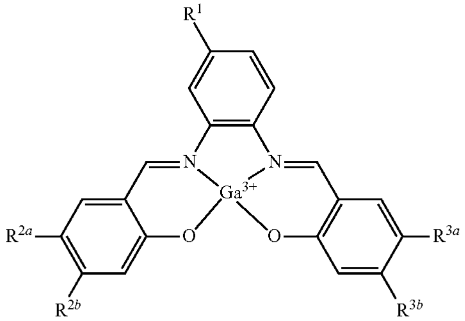
| Compound # | $R^1$ | $R^{2a}$ | $R^{2b}$ | $R^{3a}$ | $R^{3b}$ |
| --- | --- | --- | --- | --- | --- |
| 1476 | 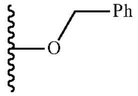 [SMILES: *OCc1ccccc1] | H | H | H | 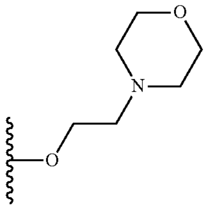 |
| 1477 | H | H | H | H | 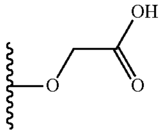 |
| 1478 | —OMe | H | H | H | 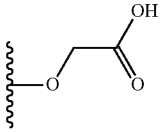 [SMILES: *OCC(=O)O] |
| 1479 | —OEt | H | H | H | 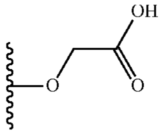 |

TABLE 1-continued
formula (II)
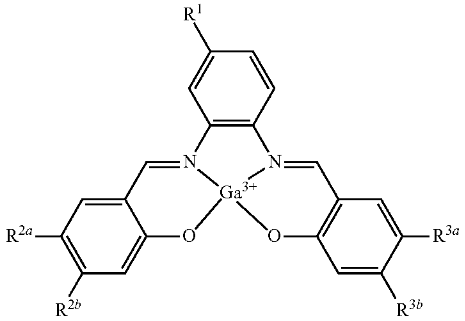
| Compound # | $R^1$ | $R^{2a}$ | $R^{2b}$ | $R^{3a}$ | $R^{3b}$ |
|---|---|---|---|---|---|
| 1480 | —OPr | H | H | H | 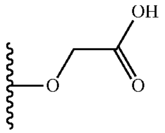 [SMILES: *OCC(=O)O] |
| 1481 | —OiPr | H | H | H | 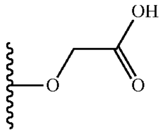 [SMILES: *OCC(=O)O] |
| 1482 | 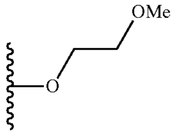 | H | H | H | 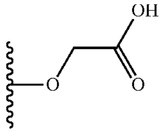 [SMILES: *OCC(=O)O] |
| 1483 | 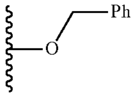 | H | H | H | 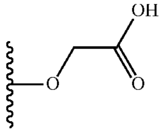 [SMILES: *OCC(=O)O] |

TABLE 1-continued
formula (II)
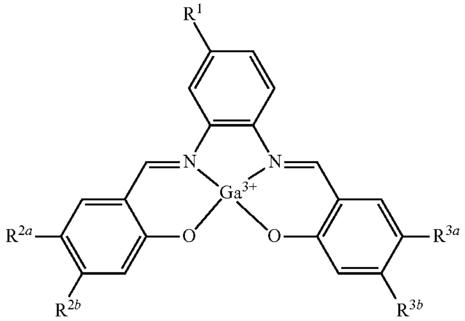
| Compound # | $R^1$ | $R^{2a}$ | $R^{2b}$ | $R^{3a}$ | $R^{3b}$ |
|---|---|---|---|---|---|
| 1484 | H | 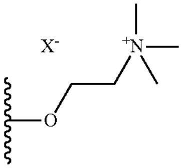 | H | 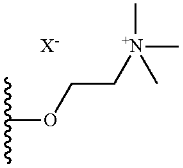 | H |
| 1485 | —OMe | 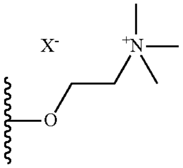 | H | 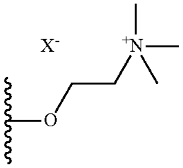 | H |
| 1486 | —OEt | 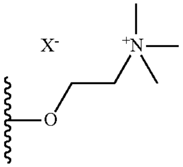 | H | 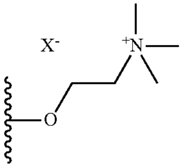 | H |
| 1487 | —OPr | 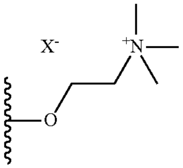 | H | 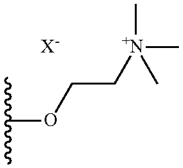 | H |

TABLE 1-continued
formula (II)
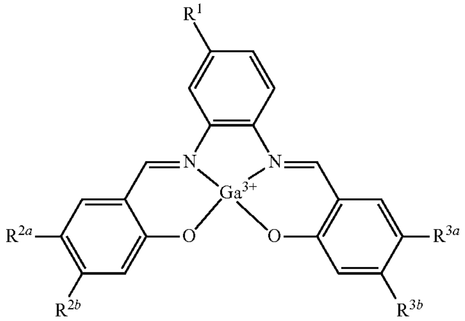
| Compound # | $R^1$ | $R^{2a}$ | $R^{2b}$ | $R^{3a}$ | $R^{3b}$ |
|---|---|---|---|---|---|
| 1488 | —OiPr | 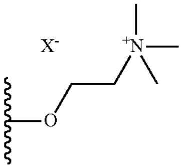 | H | 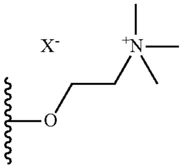 | H |
| 1489 | 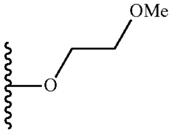 | 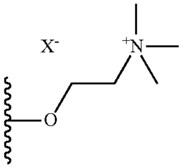 | H | 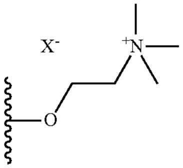 | H |
| 1490 | 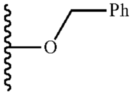 [SMILES: *OCc1ccccc1] | 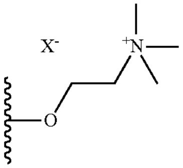 | H | 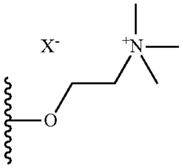 | H |

TABLE 1-continued
formula (II)
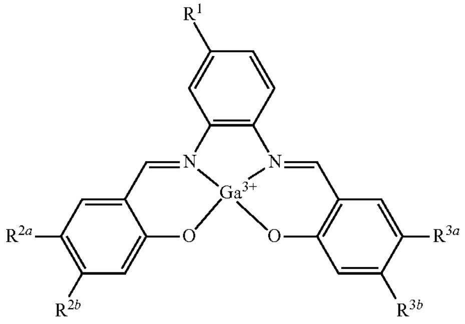
| Compound # | $R^1$ | $R^{2a}$ | $R^{2b}$ | $R^{3a}$ | $R^{3b}$ |
|---|---|---|---|---|---|
| 1491 | H | 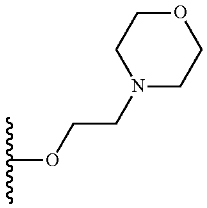 [SMILES: *OCCN1CCOCC1] | H | 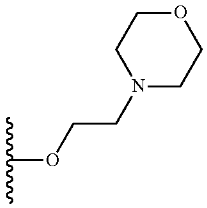 [SMILES: *OCCN1CCOCC1] | H |
| 1492 | —OMe | 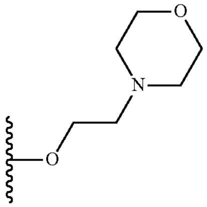 [SMILES: *OCCN1CCOCC1] | H | 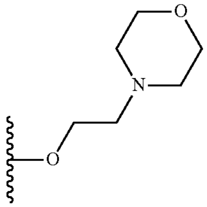 [SMILES: *OCCN1CCOCC1] | H |
| 1493 | —OEt | 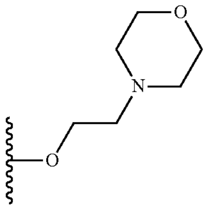 [SMILES: *OCCN1CCOCC1] | H | 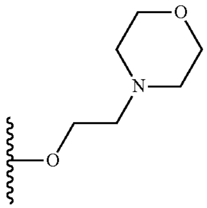 [SMILES: *OCCN1CCOCC1] | H |

TABLE 1-continued
formula (II)
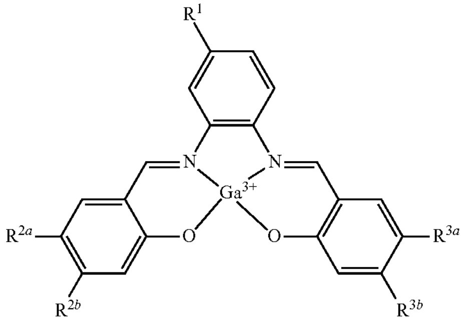
| Compound # | $R^1$ | $R^{2a}$ | $R^{2b}$ | $R^{3a}$ | $R^{3b}$ |
|---|---|---|---|---|---|
| 1494 | —OPr | 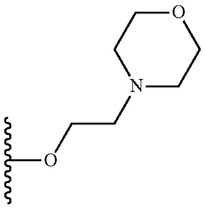 [SMILES: *OCCN1CCOCC1] | H | 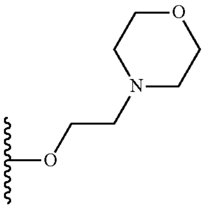 [SMILES: *OCCN1CCOCC1] | H |
| 1495 | —OiPr | 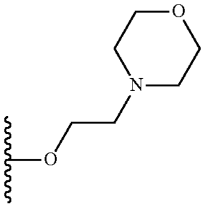 [SMILES: *OCCN1CCOCC1] | H | 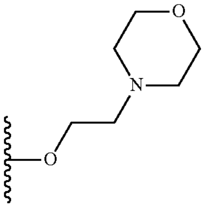 [SMILES: *OCCN1CCOCC1] | H |
| 1496 | 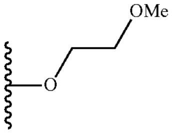 [SMILES: *OCCOC] | 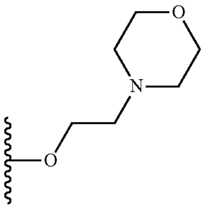 [SMILES: *OCCN1CCOCC1] | H | 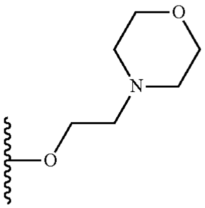 [SMILES: *OCCN1CCOCC1] | H |

TABLE 1-continued
formula (II)
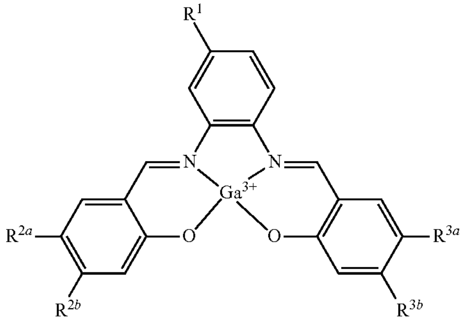
| Compound # | $R^1$ | $R^{2a}$ | $R^{2b}$ | $R^{3a}$ | $R^{3b}$ |
|---|---|---|---|---|---|
| 1497 | 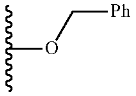 [SMILES: *OCc1ccccc1] | 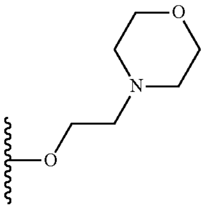 [SMILES: *OCCN1CCOCC1] | H | 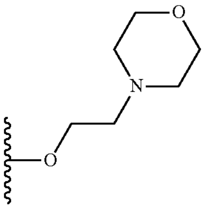 [SMILES: *OCCN1CCOCC1] | H |
| 1498 | H | 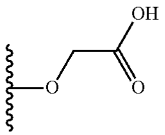 | H | 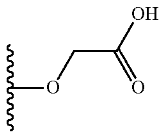 [SMILES: *OCC(=O)O] | H |
| 1499 | —OMe | 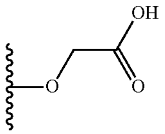 | H | 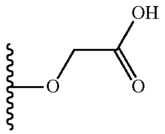 [SMILES: *OCC(=O)O] | H |
| 1500 | —OEt | 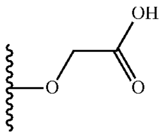 | H | 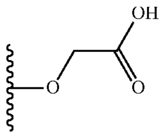 | H |

TABLE 1-continued
formula (II)
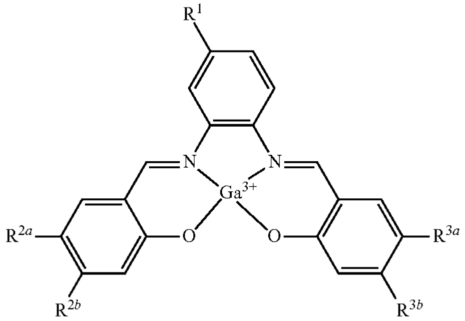
| Compound # | $R^1$ | $R^{2a}$ | $R^{2b}$ | $R^{3a}$ | $R^{3b}$ |
|---|---|---|---|---|---|
| 1501 | —OPr | 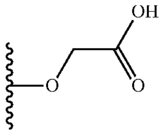 | H | 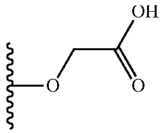 [SMILES: *OCC(=O)O] | H |
| 1502 | —OiPr | 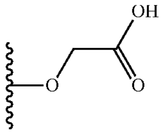 | H | 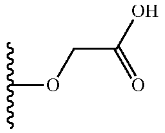 [SMILES: *OCC(=O)O] | H |
| 1503 | 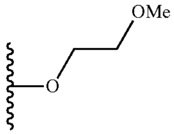 | 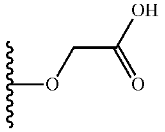 | H | 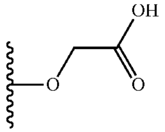 [SMILES: *OCC(=O)O] | H |
| 1504 | 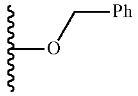 | 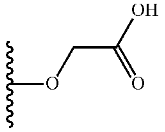 | H | 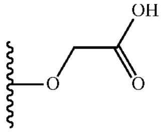 [SMILES: *OCC(=O)O] | H |

TABLE 1-continued
formula (II)
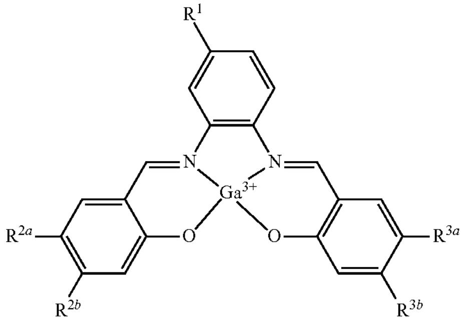
| Compound # | $R^1$ | $R^{2a}$ | $R^{2b}$ | $R^{3a}$ | $R^{3b}$ |
|---|---|---|---|---|---|
| 1505 | H | H | 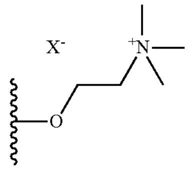 | 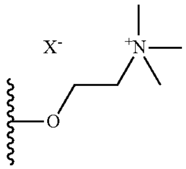 | H |
| 1506 | —OMe | H | 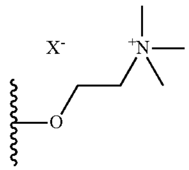 | 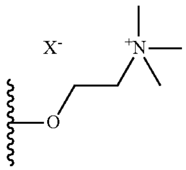 | H |
| 1507 | —OEt | H | 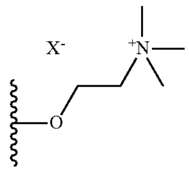 | 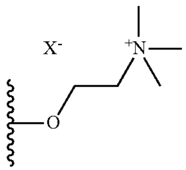 | H |
| 1508 | —OPr | H | 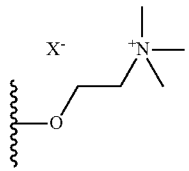 | 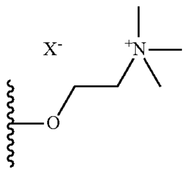 | H |

TABLE 1-continued
formula (II)
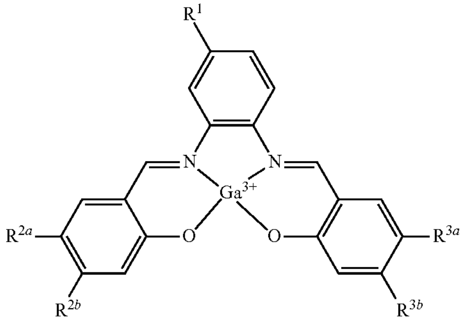
| Compound # | $R^1$ | $R^{2a}$ | $R^{2b}$ | $R^{3a}$ | $R^{3b}$ |
|---|---|---|---|---|---|
| 1509 | —OiPr | H | 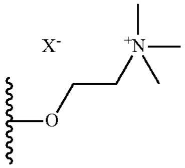 | 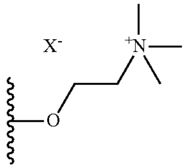 | H |
| 1510 | 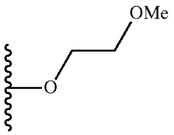 | H | 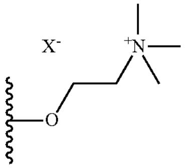 | 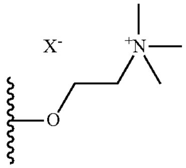 | H |
| 1511 | 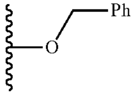 [SMILES: *OCc1ccccc1] | H | 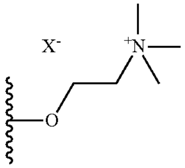 | 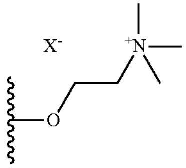 | H |

TABLE 1-continued
formula (II)
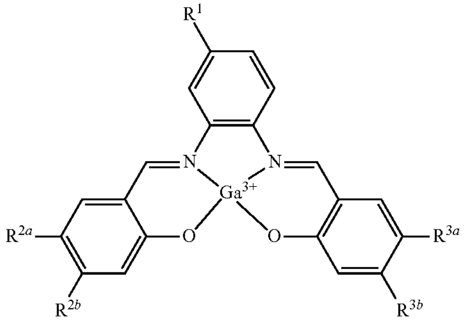
| Compound # | $R^1$ | $R^{2a}$ | $R^{2b}$ | $R^{3a}$ | $R^{3b}$ |
|---|---|---|---|---|---|
| 1512 | H | H | 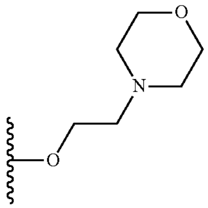 [SMILES: *OCCN1CCOCC1] | 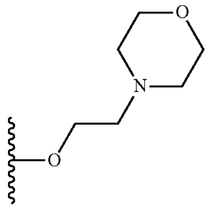 [SMILES: *OCCN1CCOCC1] | H |
| 1513 | —OMe | H | 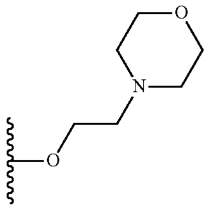 [SMILES: *OCCN1CCOCC1] | 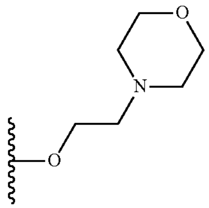 [SMILES: *OCCN1CCOCC1] | H |
| 1514 | —OEt | H | 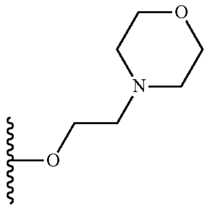 [SMILES: *OCCN1CCOCC1] | 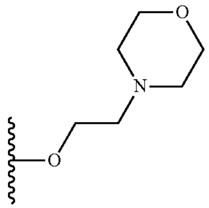 [SMILES: *OCCN1CCOCC1] | H |

TABLE 1-continued
formula (II)
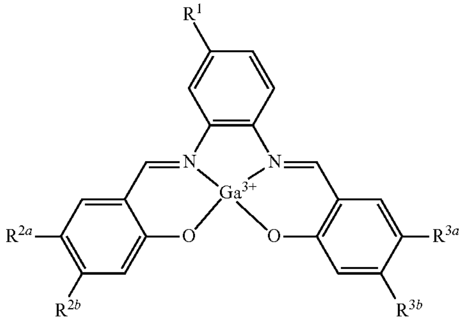
| Compound # | $R^1$ | $R^{2a}$ | $R^{2b}$ | $R^{3a}$ | $R^{3b}$ |
|---|---|---|---|---|---|
| 1515 | —OPr | H | 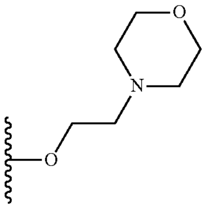 [SMILES: *OCCN1CCOCC1] | 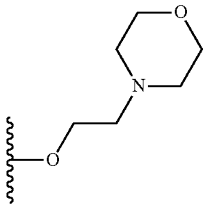 [SMILES: *OCCN1CCOCC1] | H |
| 1516 | —OiPr | H | 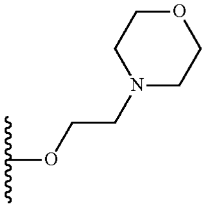 [SMILES: *OCCN1CCOCC1] | 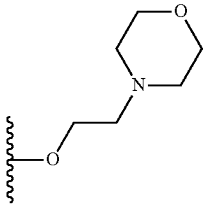 [SMILES: *OCCN1CCOCC1] | H |
| 1517 | 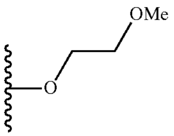 [SMILES: *OCCOC] | H | 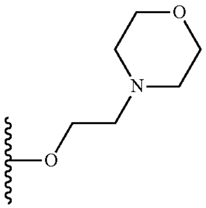 [SMILES: *OCCN1CCOCC1] | 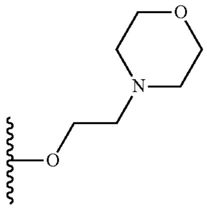 [SMILES: *OCCN1CCOCC1] | H |

TABLE 1-continued
formula (II)
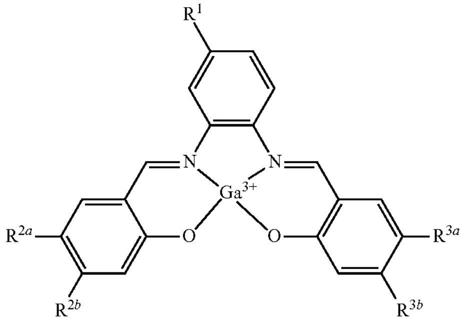
| Compound # | $R^1$ | $R^{2a}$ | $R^{2b}$ | $R^{3a}$ | $R^{3b}$ |
|---|---|---|---|---|---|
| 1518 | 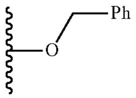 [SMILES: *OCc1ccccc1] | H | 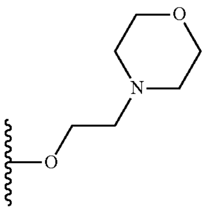 [SMILES: *OCCN1CCOCC1] | 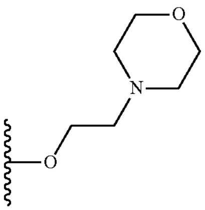 [SMILES: *OCCN1CCOCC1] | H |
| 1519 | H | H | 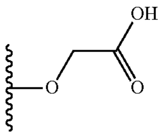 | 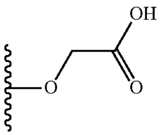 [SMILES: *OCC(=O)O] | H |
| 1520 | —OMe | H | 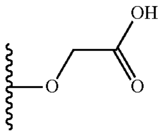 [SMILES: *OCC(=O)O] | 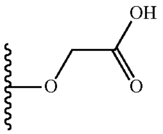 [SMILES: *OCC(=O)O] | H |
| 1521 | —OEt | H | 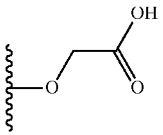 | 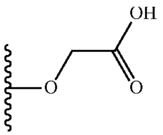 | H |

TABLE 1-continued
formula (II)
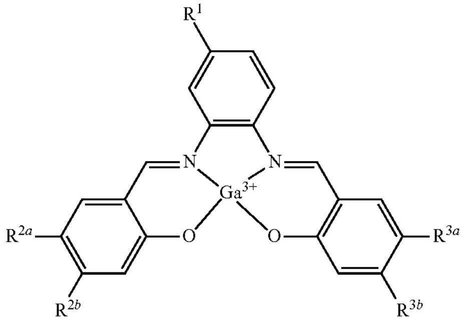
| Compound # | $R^1$ | $R^{2a}$ | $R^{2b}$ | $R^{3a}$ | $R^{3b}$ |
|---|---|---|---|---|---|
| 1522 | —OPr | H | 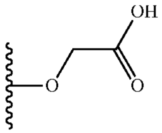 [SMILES: *OCC(=O)O] | 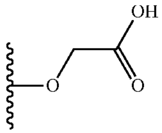 [SMILES: *OCC(=O)O] | H |
| 1523 | —OiPr | H | 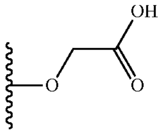 [SMILES: *OCC(=O)O] | 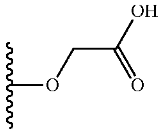 [SMILES: *OCC(=O)O] | H |
| 1524 | 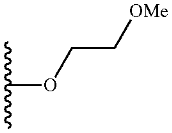 | H | 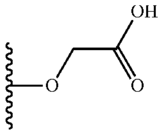 [SMILES: *OCC(=O)O] | 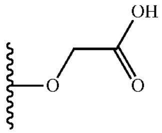 [SMILES: *OCC(=O)O] | H |
| 1525 | 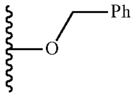 | H | 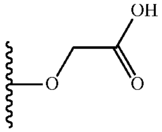 [SMILES: *OCC(=O)O] | 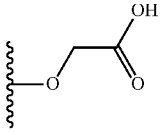 [SMILES: *OCC(=O)O] | H |

TABLE 1-continued
formula (II)
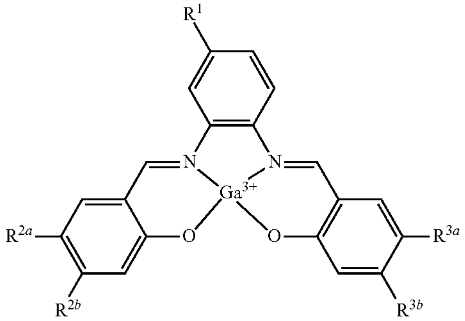
| Compound # | $R^1$ | $R^{2a}$ | $R^{2b}$ | $R^{3a}$ | $R^{3b}$ |
|---|---|---|---|---|---|
| 1526 | H | 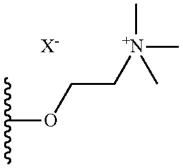 | H | H | 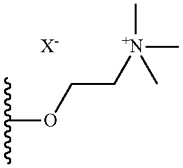 |
| 1527 | —OMe | 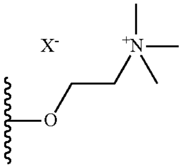 | H | H | 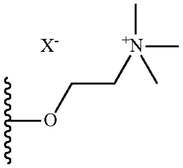 |
| 1528 | —OEt | 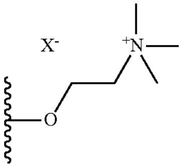 | H | H | 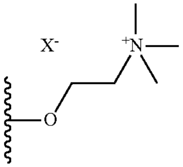 |
| 1529 | —OPr | 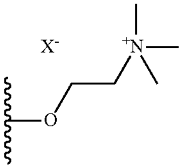 | H | H | 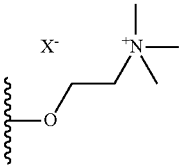 |

TABLE 1-continued
formula (II)
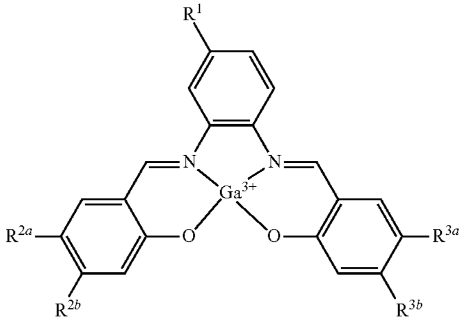
| Compound # | $R^1$ | $R^{2a}$ | $R^{2b}$ | $R^{3a}$ | $R^{3b}$ |
|---|---|---|---|---|---|
| 1530 | —OiPr | 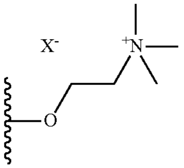 | H | H | 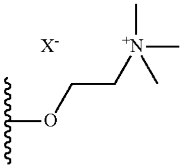 |
| 1531 | 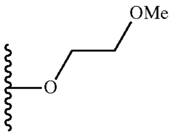 | 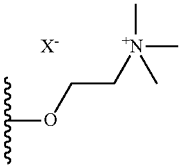 | H | H | 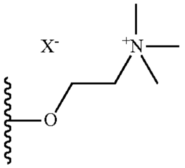 |
| 1532 | 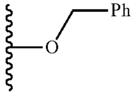 [SMILES: *OCc1ccccc1] | 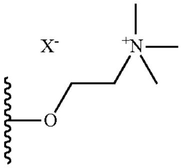 | H | H | 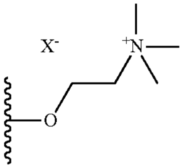 |

TABLE 1-continued
formula (II)
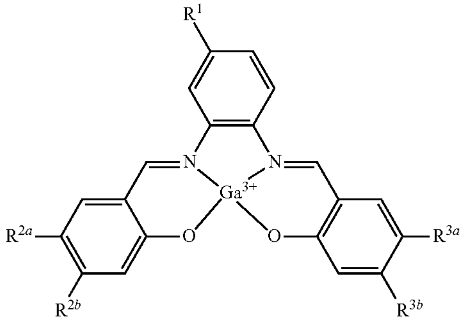
| Compound # | $R^1$ | $R^{2a}$ | $R^{2b}$ | $R^{3a}$ | $R^{3b}$ |
|---|---|---|---|---|---|
| 1533 | H | 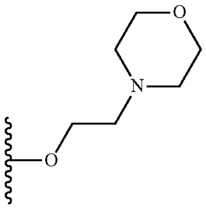 [SMILES: *OCCN1CCOCC1] | H | H | 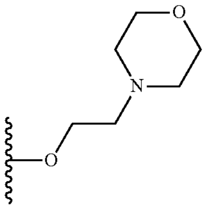 |
| 1534 | —OMe | 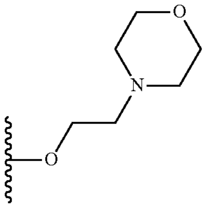 [SMILES: *OCCN1CCOCC1] | H | H | 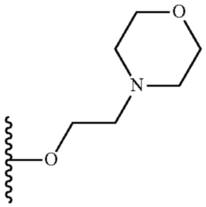 |
| 1535 | —OEt | 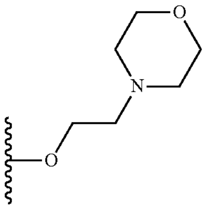 [SMILES: *OCCN1CCOCC1] | H | H | 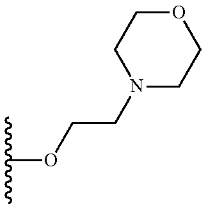 |

TABLE 1-continued
formula (II)
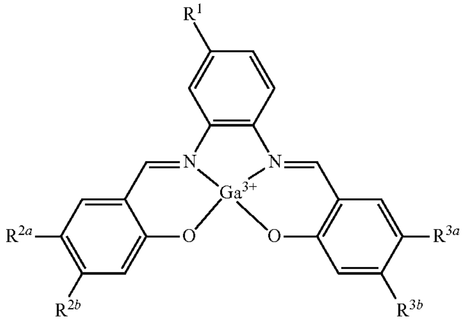
| Compound # | $R^1$ | $R^{2a}$ | $R^{2b}$ | $R^{3a}$ | $R^{3b}$ |
|---|---|---|---|---|---|
| 1536 | —OPr | 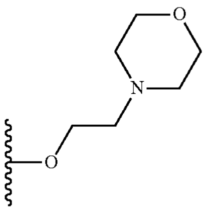 [SMILES: *OCCN1CCOCC1] | H | H | 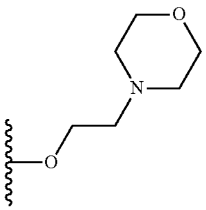 |
| 1537 | —OiPr | 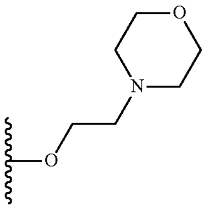 [SMILES: *OCCN1CCOCC1] | H | H | 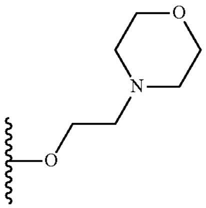 |
| 1538 | 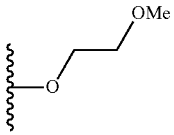 [SMILES: *OCCOC] | 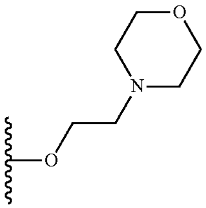 [SMILES: *OCCN1CCOCC1] | H | H | 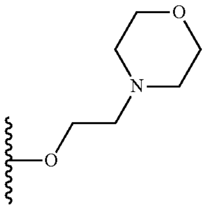 |

TABLE 1-continued
formula (II)
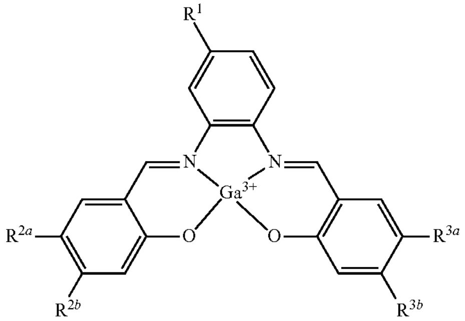
| Compound # | $R^1$ | $R^{2a}$ | $R^{2b}$ | $R^{3a}$ | $R^{3b}$ |
|---|---|---|---|---|---|
| 1539 | 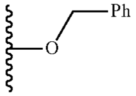 [SMILES: *OCc1ccccc1] | 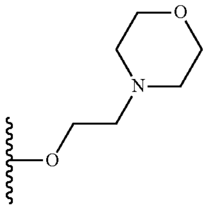 [SMILES: *OCCN1CCOCC1] | H | H | 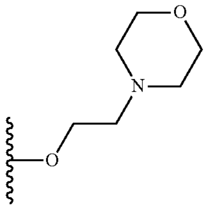 |
| 1540 | H | 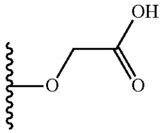 | H | H | 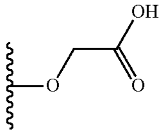 |
| 1541 | —OMe | 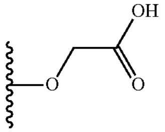 | H | H | 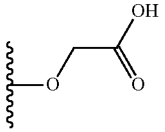 [SMILES: *OCC(=O)O] |
| 1542 | —OEt | 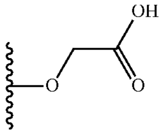 | H | H | 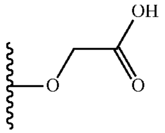 |

TABLE 1-continued
formula (II)
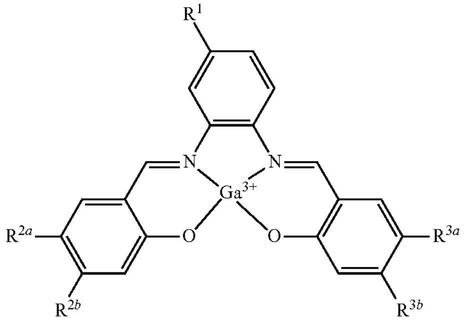
| Compound # | $R^1$ | $R^{2a}$ | $R^{2b}$ | $R^{3a}$ | $R^{3b}$ |
| --- | --- | --- | --- | --- | --- |
| 1543 | —OPr | 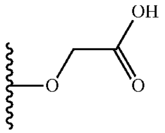 | H | H | 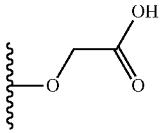 [SMILES: *OCC(=O)O] |
| 1544 | —OiPr | 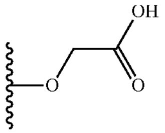 | H | H | 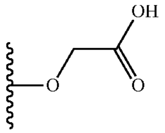 [SMILES: *OCC(=O)O] |
| 1545 | 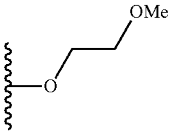 | 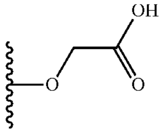 | H | H | 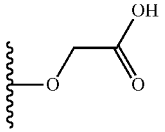 [SMILES: *OCC(=O)O] |
| 1546 | 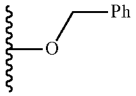 | 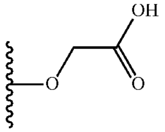 | H | H | 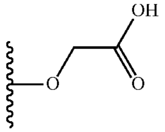 [SMILES: *OCC(=O)O] |

TABLE 1-continued
formula (II)
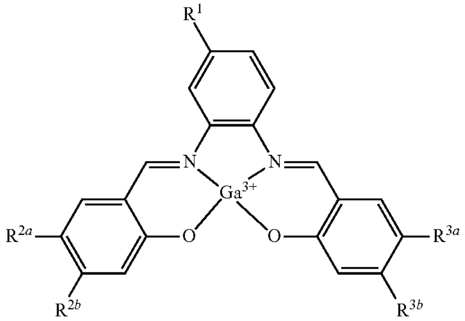
| Compound # | $R^1$ | $R^{2a}$ | $R^{2b}$ | $R^{3a}$ | $R^{3b}$ |
|---|---|---|---|---|---|
| 1547 | H | H | 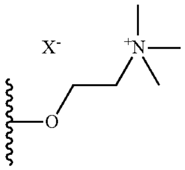 | H | 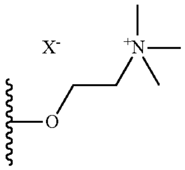 |
| 1548 | —OMe | H | 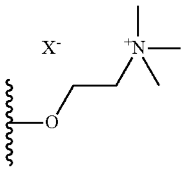 | H | 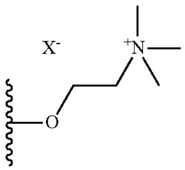 |
| 1549 | —OEt | H | 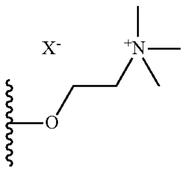 | H | 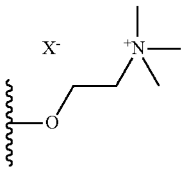 |
| 1550 | —OPr | H | 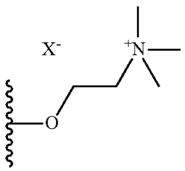 | H | 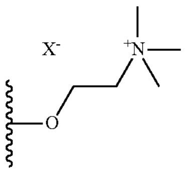 |

TABLE 1-continued
formula (II)
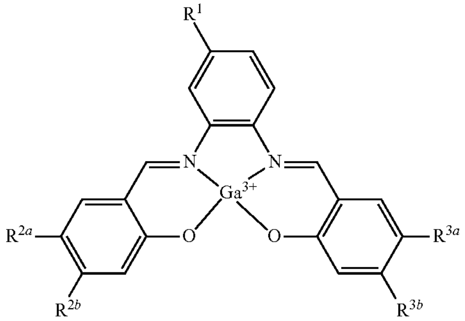
| Compound # | $R^1$ | $R^{2a}$ | $R^{2b}$ | $R^{3a}$ | $R^{3b}$ |
|---|---|---|---|---|---|
| 1551 | —OiPr | H | 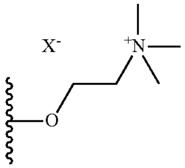 | H | 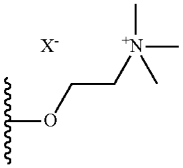 |
| 1552 | 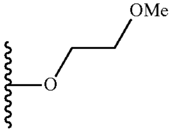 | H | 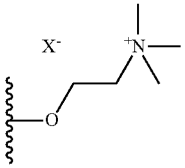 | H | 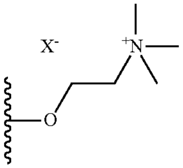 |
| 1553 | 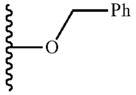 [SMILES: *OCc1ccccc1] | H | 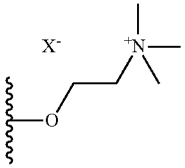 | H | 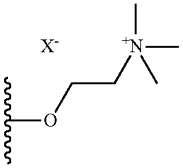 |

TABLE 1-continued
formula (II)
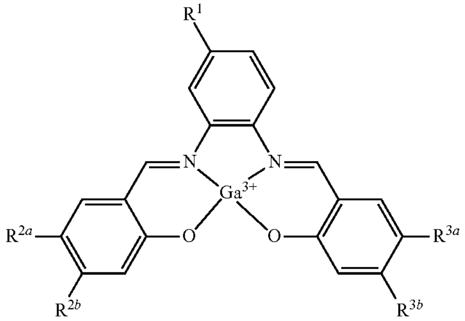
| Compound # | $R^1$ | $R^{2a}$ | $R^{2b}$ | $R^{3a}$ | $R^{3b}$ |
|---|---|---|---|---|---|
| 1554 | H | H | 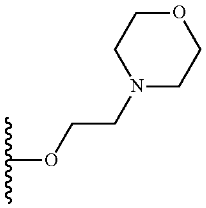 [SMILES: *OCCN1CCOCC1] | H | 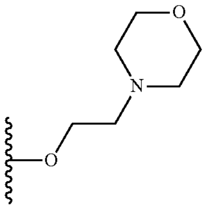 |
| 1555 | —OMe | H | 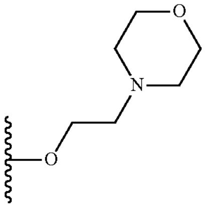 [SMILES: *OCCN1CCOCC1] | H | 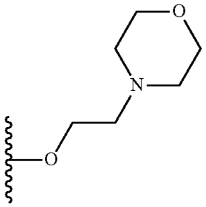 |
| 1556 | —OEt | H | 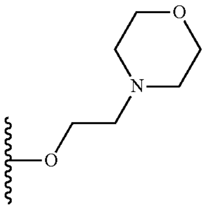 [SMILES: *OCCN1CCOCC1] | H | 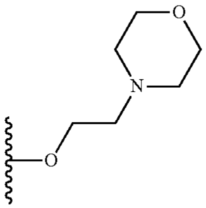 |

TABLE 1-continued
formula (II)
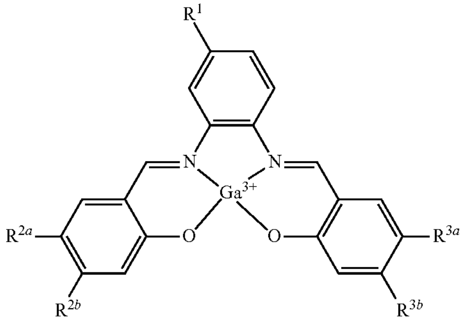
| Compound # | $R^1$ | $R^{2a}$ | $R^{2b}$ | $R^{3a}$ | $R^{3b}$ |
|---|---|---|---|---|---|
| 1557 | —OPr | H | 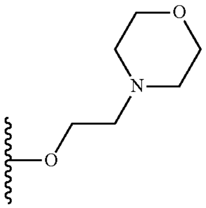 [SMILES: *OCCN1CCOCC1] | H | 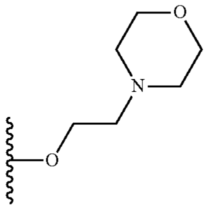 |
| 1558 | —OiPr | H | 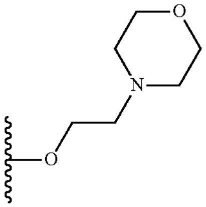 [SMILES: *OCCN1CCOCC1] | H | 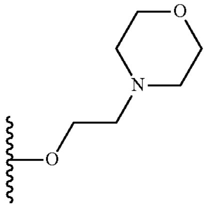 |
| 1559 | 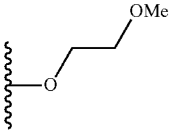 [SMILES: *OCCOC] | H | 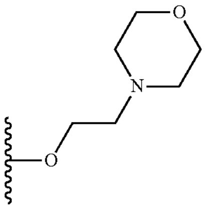 [SMILES: *OCCN1CCOCC1] | H | 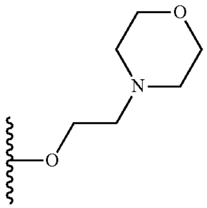 |

TABLE 1-continued
formula (II)
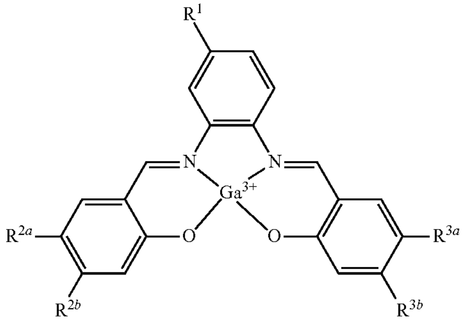
| Compound # | $R^1$ | $R^{2a}$ | $R^{2b}$ | $R^{3a}$ | $R^{3b}$ |
|---|---|---|---|---|---|
| 1560 | 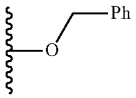 [SMILES: *OCc1ccccc1] | H | 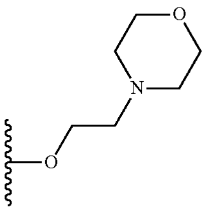 [SMILES: *OCCN1CCOCC1] | H | 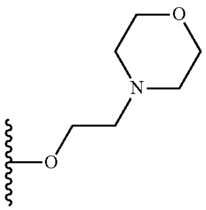 |
| 1561 | H | H | 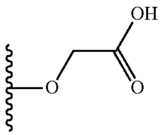 | H | 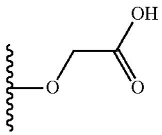 |
| 1562 | —OMe | H | 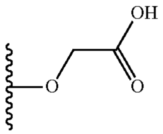 [SMILES: *OCC(=O)O] | H | 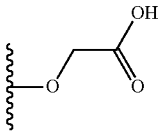 [SMILES: *OCC(=O)O] |
| 1563 | —OEt | H | 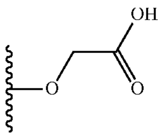 | H | 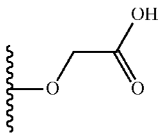 |

TABLE 1-continued
formula (II)
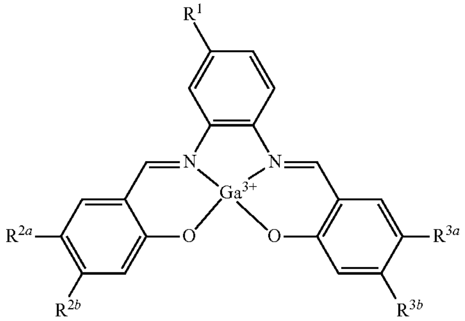
| Compound # | $R^1$ | $R^{2a}$ | $R^{2b}$ | $R^{3a}$ | $R^{3b}$ |
|---|---|---|---|---|---|
| 1564 | —OPr | H | 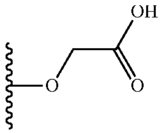 [SMILES: *OCC(=O)O] | H | 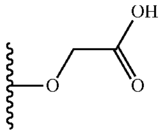 [SMILES: *OCC(=O)O] |
| 1565 | —OiPr | H | 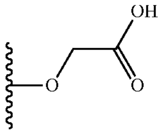 [SMILES: *OCC(=O)O] | H | 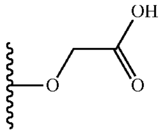 [SMILES: *OCC(=O)O] |
| 1566 | 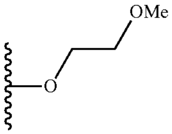 | H | 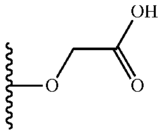 [SMILES: *OCC(=O)O] | H | 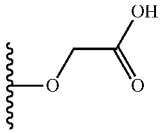 [SMILES: *OCC(=O)O] |
| 1567 | 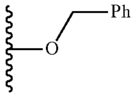 | H | 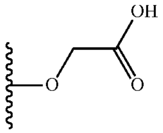 [SMILES: *OCC(=O)O] | H | 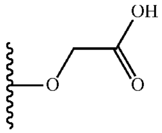 [SMILES: *OCC(=O)O] |

The disclosure provides in another aspect a compound of formula (III), formula (IV), formula (V), formula (VI), formula (VII), formula (VIII), formula (IX), or formula (X) or a pharmaceutically acceptable salt, solvate, hydrate, cocrystal, or prodrug thereof:

formula (III)

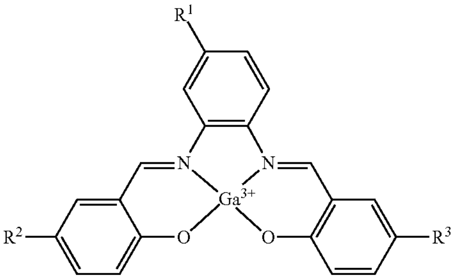

formula (IV)

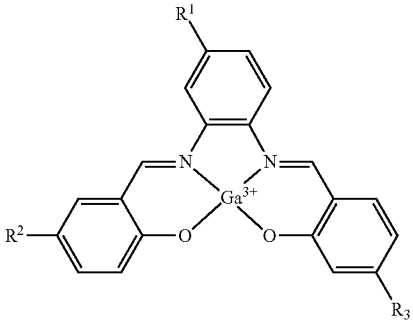

formula (V)

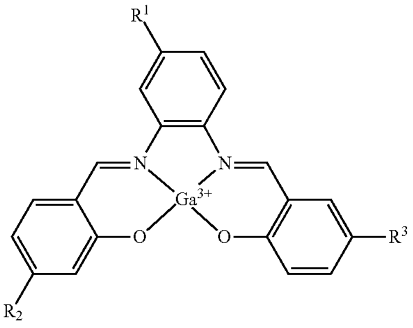

formula (VI)

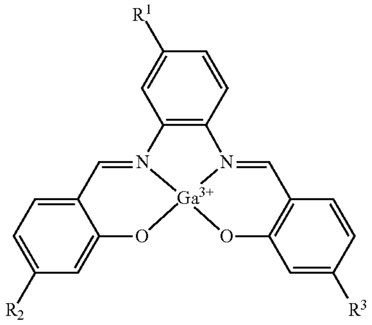

-continued formula (VII)

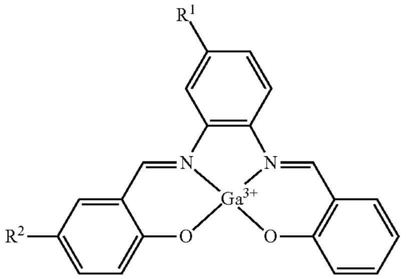

formula (VIII)

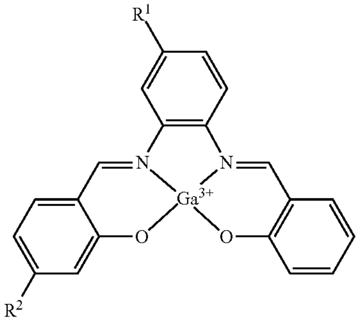

formula (IX)

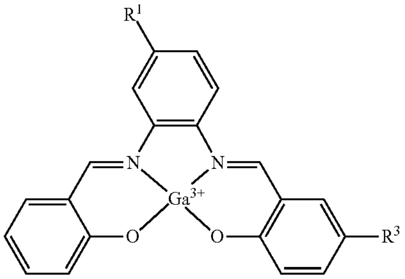

formula (X)

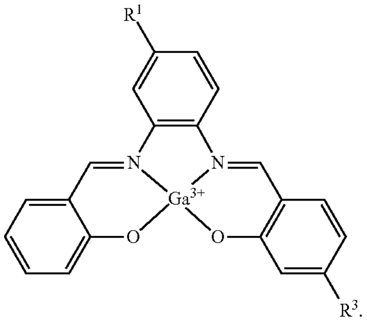

In some embodiments, $R^1$ is selected from the group consisting of —OMe, —OEt, —OPr, —OiPr,

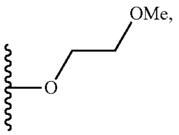

and

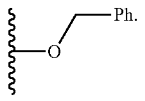

In some embodiments, $R^2$ is selected from the group consisting of
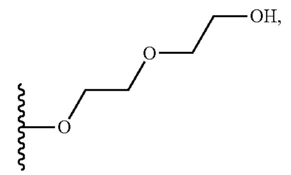
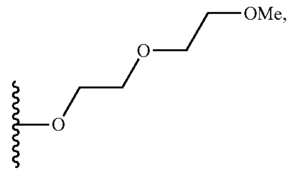
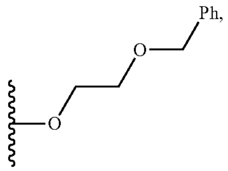
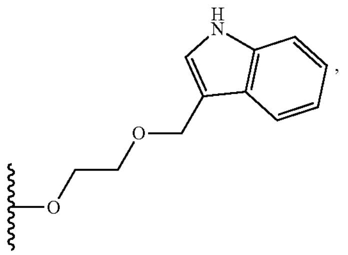
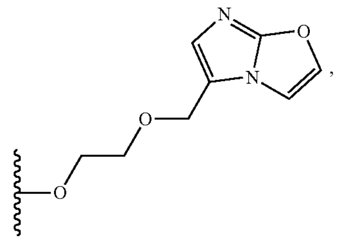
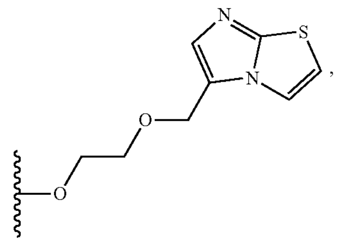
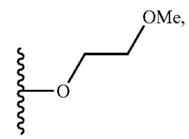
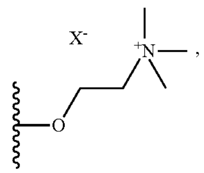
-continued
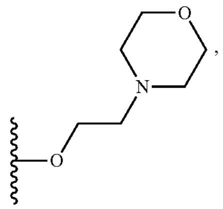
and
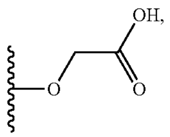
wherein $X^-$ is independently at each occurrence selected from $Br^-$, $Cl^-$, and $I^-$.
In some embodiments, $R^3$ is selected from the group consisting of
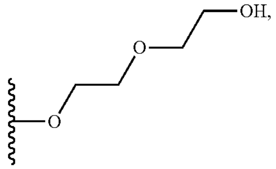
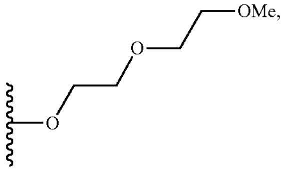
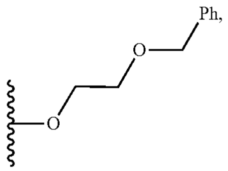
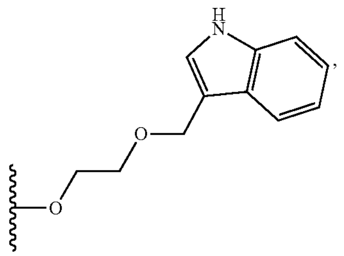
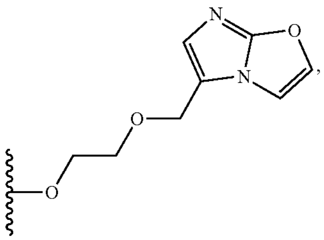
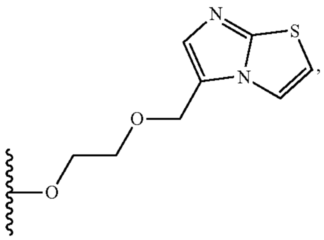

-continued

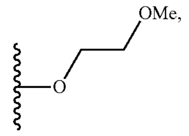

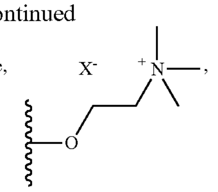

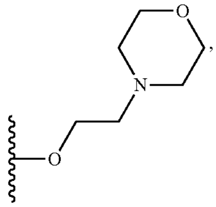

, and

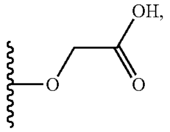

wherein $X^-$ is independently at each occurrence selected from $Br^-$, $Cl^-$, and $I^-$.

The disclosure provides in one aspect a compound of formula (XI):

formula (XI)

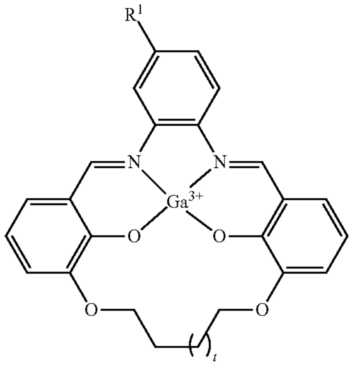

wherein in formula (XI):

$R^1$ is selected from the group consisting of H, halogen, optionally substituted alkyl, optionally substituted alkylaryl, optionally substituted alkylhetaryl, optionally substituted alkenyl, optionally substituted alkynyl, optionally substituted cycloalkyl, optionally substituted aryl, optionally substituted aralkyl, optionally substituted haloalkyl, optionally substituted alkoxy, and optionally substituted heteroaryl; and t is an integer from 1 to 4.

In some embodiments, $R^1$ is selected from the group consisting of —OMe, —OEt, —OPr, —OiPr,

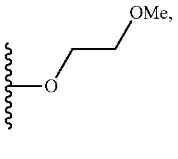

and

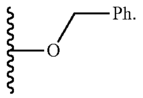

In some embodiments, the compound of formula (XI), or a pharmaceutically acceptable salt, solvate, hydrate, cocrystal, or prodrug thereof, is selected from Table 2:

TABLE 2 formula (XI)

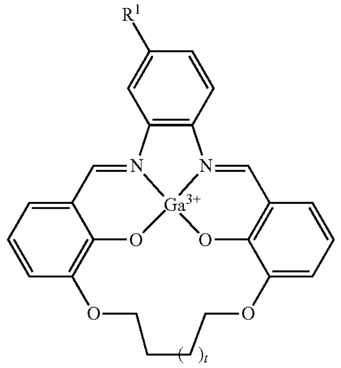

| Compound # | $R^1$ | t |
|---|---|---|
| 2001 | H | 1 |
| 2002 | —OMe | 1 |
| 2003 | —OEt | 1 |
| 2004 | —OPr | 1 |
| 2005 | —OiPr | 1 |
| 2006 | 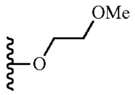 | 1 |
| 2007 | 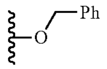 | 1 |
| 2008 | H | 2 |
| 2009 | —OMe | 2 |
| 2010 | —OEt | 2 |
| 2011 | —OPr | 2 |
| 2012 | —OiPr | 2 |
| 2013 | 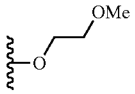 [SMILES: *OCCOC] | 2 |
| 2014 | 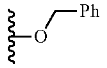 | 2 |
| 2015 | H | 3 |
| 2016 | —OMe | 3 |
| 2017 | —OEt | 3 |
| 2018 | —OPr | 3 |
| 2019 | —OiPr | 3 |
| 2020 | 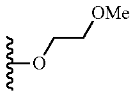 [SMILES: *OCCOC] | 3 |
| 2021 | 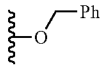 | 3 |
| 2022 | H | 4 |
| 2023 | —OMe | 4 |
| 2024 | —OEt | 4 |
| 2025 | —OPr | 4 |
| 2026 | —OiPr | 4 |
| 2027 | 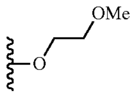 [SMILES: *OCCOC] | 4 |

TABLE 2-continued
formula (XI)
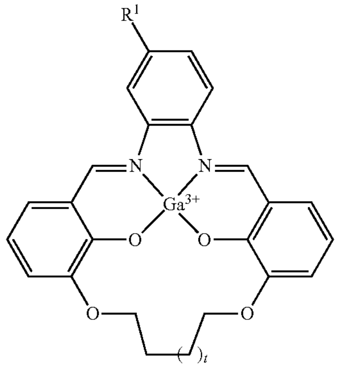
| Compound # | $R^1$ | t |
| --- | --- | --- |
| 2028 | 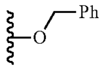 | 4 |
In some embodiments, the compound is selected from:
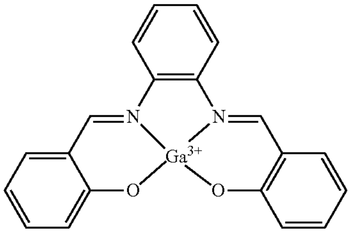
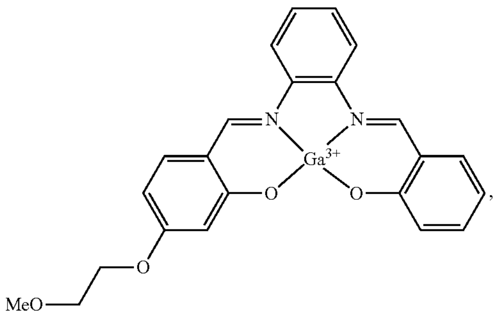
,
-continued
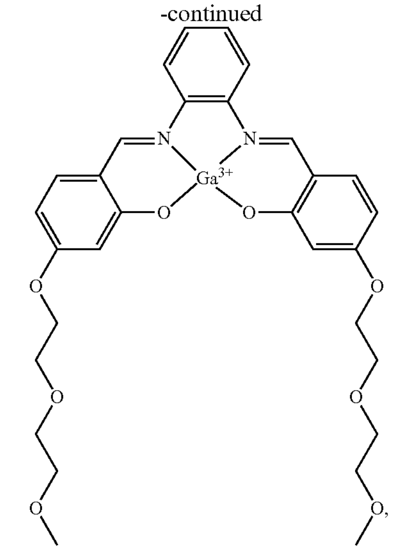
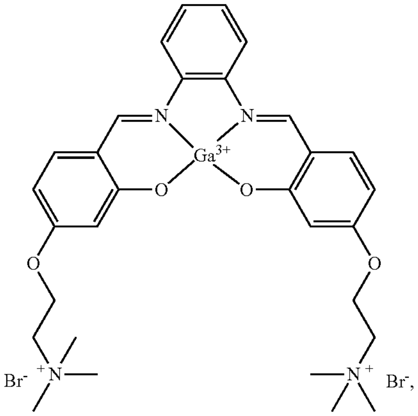
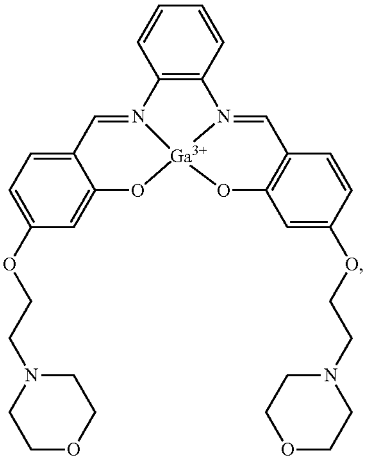
and -continued

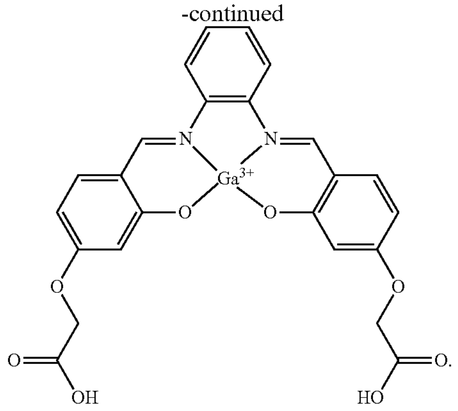

Methods of Treatment

The compounds and compositions described herein can be used in methods for treating diseases and conditions. In some embodiments, the compounds and compositions described herein can be used in methods for treating a disease or a condition associated with inhibiting HasAp protein activity and/or inhibiting the *P. aeruginosa* siderophore iron uptake system. In some embodiments, the compounds and compositions described herein are HasAp inhibitors. In some embodiments, the compounds and compositions described herein are *P. aeruginosa* siderophore iron uptake system inhibitors. In some embodiments, the compounds and compositions described herein are dual HasAp protein activity inhibitors and *P. aeruginosa* siderophore iron uptake system inhibitors. The compounds and compositions described herein may also be used in treating other diseases and conditions as described herein and in the following paragraphs.

In some embodiments, the compounds described herein are dual HasAp/*P. aeruginosa* siderophore iron uptake system inhibitors. Compounds described herein include, but are not limited to: compounds of formula (I), formula (II), formula (III), formula (IV), formula (V), formula (VI), or formula (VII), formula (VIII), formula (IX), formula (X), formula (XI), and their features and limitations as described herein; compounds of formulas 1001-1567 and 2001-2028, and their features and limitations as described herein; compounds GaSal, compound 2, compound I, compound II, complex I, complex II, macrocyclic ligand III, GaSal-1, GaSal-2, GaSal-3, and GaSal-4, and their features and limitations as described herein.

In some embodiments, the condition is selected from sepsis, meningitis, endocarditis, osteomyelitis, otitis media, sinusitis, pneumonia, chronic respiratory tract infection, catheter infection, postoperative peritonitis, postoperative biliary tract, tricuspid valve endocarditis, ecthyma gangrenosum, eyelid abscess, lacrimal cystitis, conjunctivitis, corneal ulcer, corneal abscess, panophthalmitis, orbital infection, urinary tract infection, complicated urinary tract infection, catheter infection, perianal abscess, severe burns, airway burns, pressure ulcer infections, cystic fibrosis, and a bacterial infection.

In some embodiments, the method comprises administering to the patient a therapeutically effective amount of a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, and their features and limitations as described herein.

In one aspect of the disclosure, the compounds and compositions described herein can be used for the treatment of bacterial infections. In one aspect, a method of treating or preventing a bacterial infection in a subject in need thereof is provided. In some embodiments, the method comprises administering to the patient a therapeutically effective amount of a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, and their features and limitations as described herein.

In one aspect, a method of reducing virulence of a bacteria in a subject is provided. In another aspect, a method of reducing pathogenicity and/or cytoxicity of a bacteria in a subject is provided. In one aspect, a method of reducing or preventing development of drug resistance in a bacteria is provided. In some embodiments, the subject is an animal. In some embodiments, the subject is a human.

In some embodiments, the bacteria is *P. aeruginosa*. As would be understood by one of ordinary skill in the art, any bacterial infection or condition caused by a bacterium having a similar sigma factor receptor to *P. aeruginosa* can also can also be treated or prevented using the compounds and compositions described herein. Non-limiting examples of bacteria having a similar sigma factor receptor to *P. aeruginosa* include *Serratia marcescens, Bordetella pertussis, Bordetella bronchiseptica, Bordetella avium, Yersinia pestis, Yersinia pseudotuberculosis*, and *Acinetobacter baumannii*.

In another aspect of the disclosure, the compounds and compositions described herein can be used for the treatment of cancer. In one aspect, a method of treating or preventing cancer in a subject in need thereof is provided. In some embodiments, the method comprises administering to the patient a therapeutically effective amount of a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, and their features and limitations as described herein.

In some embodiments, the cancer is selected from the group consisting of pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like.

Efficacy of the methods, compounds, and combinations of compounds described herein in treating, preventing and/or managing the indicated diseases or disorders can be tested using various animal models known in the art.

Pharmaceutical Compositions

In an embodiment, the disclosure provides a pharmaceutical composition for use in the treatment of the diseases and conditions described herein.

The pharmaceutical compositions are typically formulated to provide a therapeutically effective amount of a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, and their features and limitations as described herein, or a pharmaceutically acceptable salt, solvate, or hydrate thereof, as the active ingredient. Typically, the pharmaceutical compositions also comprise one or more pharmaceutically acceptable excipients, carriers, including inert solid diluents and fillers, diluents, including sterile aqueous solution and various organic solvents, permeation enhancers, solubilizers and adjuvants.

The pharmaceutical compositions described above are preferably for use in the treatment of sepsis, meningitis, endocarditis, osteomyelitis, otitis media, sinusitis, pneumonia, chronic respiratory tract infection, catheter infection, postoperative peritonitis, postoperative biliary tract, tricuspid valve endocarditis, ecthyma gangrenosum, eyelid abscess, lacrimal cystitis, conjunctivitis, corneal ulcer, corneal abscess, panophthalmitis, orbital infection, urinary tract infection, complicated urinary tract infection, catheter infection, perianal abscess, severe burns, airway burns, pressure ulcer infections, cystic fibrosis, a bacterial infection, and cancer.

In some embodiments, the concentration of a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or a pharmaceutically acceptable salt thereof, provided in the pharmaceutical compositions of the disclosure is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, provided in the pharmaceutical compositions of the disclosure is independently greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, $1^{2}5$, 10%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, provided in the pharmaceutical compositions of the disclosure is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, provided in the pharmaceutical compositions of the disclosure is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, provided in the pharmaceutical compositions of the disclosure is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, provided in the pharmaceutical compositions of the disclosure is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5 g, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

Each of the compounds provided according to the disclosure is effective over a wide dosage range. For example, in the treatment of adult humans, dosages independently ranging from 0.01 to 1000 mg, from 0.5 to 100 mg, from 1 to 50 mg per day, and from 5 to 40 mg per day are examples of dosages that may be used. The exact dosage will depend upon the route of administration, the form in which the compound is administered, the gender and age of the subject to be treated, the body weight of the subject to be treated, and the preference and experience of the attending physician.

Described below are non-limiting pharmaceutical compositions and methods for preparing the same.

Pharmaceutical Compositions for Oral Administration

In preferred embodiments, the disclosure provides a pharmaceutical composition for oral administration containing: a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein, and a pharmaceutical excipient suitable for administration.

In preferred embodiments, the disclosure provides a solid pharmaceutical composition for oral administration containing: (i) an effective amount of: a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, and (ii) a pharmaceutical excipient suitable for administration. In some embodiments, the composition further contains (iii) an effective amount of an additional active pharmaceutical ingredient. For example, additional active pharmaceutical ingredients, as used herein, may include one or more compounds that induce cell cycle arrest and/or apoptosis in cells containing functional Mcl-1 and/or Bcl-2 proteins. Such additional active pharmaceutical ingredients may also include those compounds used for sensitizing cells to additional agent(s), such as inducers of apoptosis and/or cell cycle arrest, and chemoprotection of normal cells through the induction of cell cycle arrest prior to treatment with chemotherapeutic agents.

In some embodiments, the pharmaceutical composition may be a liquid pharmaceutical composition suitable for oral consumption.

Pharmaceutical compositions of the disclosure suitable for oral administration can be presented as discrete dosage forms, such as capsules, sachets, or tablets, or liquids or aerosol sprays each containing a predetermined amount of an active ingredient as a powder or in granules, a solution, or a suspension in an aqueous or non-aqueous liquid, an oil-in-water emulsion, a water-in-oil liquid emulsion, powders for reconstitution, powders for oral consumptions, bottles (including powders or liquids in a bottle), orally dissolving films, lozenges, pastes, tubes, gums, and packs. Such dosage forms can be prepared by any of the methods of pharmacy, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The disclosure further encompasses anhydrous pharmaceutical compositions and dosage forms since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the disclosure can be prepared using anhydrous or low moisture containing ingredients and low moisture or low humidity conditions. Pharmaceutical compositions and dosage forms of the disclosure which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

Active pharmaceutical ingredients can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the disclosure to provide tablets that disintegrate when exposed to an aqueous environment. Too much of a disintegrant may produce tablets which disintegrate in the bottle. Too little may be insufficient for disintegration to occur, thus altering the rate and extent of release of the active ingredients from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the disclosure include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the disclosure include, but are not limited to, calcium stearate, magnesium stearate, sodium stearyl fumarate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, silicified microcrystalline cellulose, or mixtures thereof. A lubricant can optionally be added in an amount of less than about 0.5% or less than about 1% (by weight) of the pharmaceutical composition.

When aqueous suspensions and/or elixirs are desired for oral administration, the active pharmaceutical ingredient(s) may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants which can be used to form pharmaceutical compositions and dosage forms of the disclosure include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10.

However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyllactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acyllactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof, polyoxyethylated vitamins and derivatives thereof, polyoxyethylene-polyoxypropylene block copolymers; and mixtures thereof, polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In an embodiment, the composition may include a solubilizer to ensure good solubilization and/or dissolution of the compound of the present disclosure and to minimize precipitation of the compound of the present disclosure. This can be especially important for compositions for non-oral use—e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, .epsilon.-caprolactone and isomers thereof, 6-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals and alkaline earth metals. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid.

Pharmaceutical Compositions for Injection

In preferred embodiments, the disclosure provides a pharmaceutical composition for injection containing: a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein, and a pharmaceutical excipient suitable for injection. Components and amounts of compounds in the compositions are as described herein.

The forms in which the compositions of the disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, and thimerosal.

Sterile injectable solutions are prepared by incorporating: a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein, in the required amounts in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical Delivery

In preferred embodiments, the disclosure provides a pharmaceutical composition for transdermal delivery containing: a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein, and a pharmaceutical excipient suitable for transdermal delivery.

Compositions of the present disclosure can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present disclosure employs transdermal delivery devices ("patches"). Such transdermal patches may be used to provide continuous or discontinuous infusion of: a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein, in controlled amounts, either with or without another active pharmaceutical ingredient.

The construction and use of transdermal patches for the delivery of pharmaceutical agents is well known in the art. See, e.g., U.S. Pat. Nos. 5,023,252; 4,992,445 and 5,001,139. Such patches may be constructed for continuous, pulsatile, or on demand delivery of pharmaceutical agents.

Pharmaceutical Compositions for Inhalation

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner. Dry powder inhalers may also be used to provide inhaled delivery of the compositions.

Other Pharmaceutical Compositions

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, et al., eds., Handbook of Clinical Drug Data, Tenth Edition, McGraw-Hill, 2002; and Pratt and Taylor, eds., Principles of Drug Action, Third Edition, Churchill Livingston, N.Y., 1990, each of which is incorporated by reference herein in its entirety.

Administration of: a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein, or a pharmaceutical composition of these compounds can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g., transdermal application), rectal administration, via local delivery by catheter or stent or through inhalation. The compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein, can also be administered intraadiposally or intrathecally.

The compositions of the disclosure may also be delivered via an impregnated or coated device such as a stent, for example, or an artery-inserted cylindrical polymer. In some embodiments, the compounds and compositions of the disclosure can be used in conjunction with stents to treat or prevent infections and/or biofilms in the blood vessels or heart. A compound of the disclosure may be administered, for example, by local delivery from the struts of a stent, from a stent graft, from grafts, or from the cover or sheath of a stent. In some embodiments, a compound of the disclosure is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly(ether-ester) copolymers (e.g., PEO-PLLA); polydimethylsiloxane, poly(ethylene-vinylacetate), acrylate-based polymers or copolymers (e.g., polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. A compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein, may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the disclosure in a suitable solvent, followed by evaporation of the solvent. Excess drug on the surface of the stent may be removed via an additional brief solvent wash. In yet other embodiments, compounds of the disclosure may be covalently linked to a stent or graft. A covalent linker may be used which degrades in vivo, leading to the release of the compound of the disclosure. Any bio-labile linkage may be used for such a purpose, such as ester, amide or anhydride linkages. A compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein, may additionally be administered intravascularly from a balloon used during angioplasty. Extravascular administration of a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein, via the pericard or via advential application of formulations of the disclosure may also be performed.

Exemplary parenteral administration forms include solutions or suspensions of a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, in sterile aqueous solutions, for example, aqueous propylene glycol or dextrose solutions. Such dosage forms can be suitably buffered, if desired.

The disclosure also provides kits. The kits include a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein, in suitable packaging, and written material that can include instructions for use, discussion of clinical studies and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another active pharmaceutical ingredient. In some embodiments, the compound of formula (I), formula (II), formula (III), formula (IV), formula (V), formula (VI), or formula (VII), and their features and limitations as described herein; a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein, and another active pharmaceutical ingredient are provided as separate compositions in separate containers within the kit. In some embodiments, the compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

The kits described above are preferably for use in the treatment of the diseases and conditions described herein. In a preferred embodiment, the kits are for use in the treatment of conditions associated with inhibiting HasAp protein activity and/or inhibiting the *P. aeruginosa* siderophore iron uptake system.

In some embodiments, the kits described herein are for use in the treatment of sepsis, meningitis, endocarditis, osteomyelitis, otitis media, sinusitis, pneumonia, chronic respiratory tract infection, catheter infection, postoperative peritonitis, postoperative biliary tract, tricuspid valve endocarditis, ecthyma gangrenosum, eyelid abscess, lacrimal cystitis, conjunctivitis, corneal ulcer, corneal abscess, panophthalmitis, orbital infection, urinary tract infection, complicated urinary tract infection, catheter infection, perianal abscess, severe burns, airway burns, pressure ulcer infections, cystic fibrosis, a bacterial infection, and cancer.

Dosages and Dosing Regimens

The amounts of: a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein, administered will be dependent on the human or mammal being treated, the severity of the disorder or condition, the rate of administration, the disposition of the compounds and the discretion of the prescribing physician. However, an effective dosage of each is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect—e.g., by dividing such larger doses into several small doses for administration throughout the day. The dosage of a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein, may be provided in units of mg/kg of body mass or in $mg/m^2$ of body surface area.

In some embodiments, a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein is administered in multiple doses. In a preferred embodiment, a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein is administered in multiple doses. Dosing may be once, twice, three times, four times, five times, six times, or more than six times per day. Dosing may be once a month, once every two weeks, once a week, or once every other day. In other embodiments a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein, is administered about once per day to about 6 times per day. In some embodiments a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein, is administered once daily, while in other embodiments, a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein is administered twice daily, and in other embodiments a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein, is administered three times daily.

Administration of a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein, may continue as long as necessary. In some embodiments, a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein, is administered for more than 1, 2, 3, 4, 5, 6, 7, 14, or 28 days. In some embodiments a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein is administered for less than 28, 14, 7, 6, 5, 4, 3, 2, or 1 day. In some embodiments, a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein is administered chronically on an ongoing basis—e.g., for the treatment of chronic effects. In another embodiment, the administration of a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein, continues for less than about 7 days. In yet another embodiment, the administration continues for more than about 6, 10, 14, 28 days, two months, six months, or one year. In some cases, continuous dosing is achieved and maintained as long as necessary.

In some embodiments, an effective dosage of a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein, is in the range of about 1 mg to about 500 mg, about 10 mg to about 300 mg, about 20 mg to about 250 mg, about 25 mg to about 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 202 mg.

In some embodiments, an effective dosage of a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein, is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some instances, dosage levels below the lower limit of the aforesaid ranges may be more than adequate, while in other cases still larger doses may be employed without causing any harmful side effect—e.g., by dividing such larger doses into several small doses for administration throughout the day.

An effective amount of a compound of formula (I), formula (II), formula (III), formula (IV), formula (V), formula (VI), or formula (VII), formula (VIII), formula (IX), formula (X), formula (XI), and their features and limitations as described herein; a compound of formulas 1001-1567 and 2001-2028, and their features and limitations as described herein; and/or compound of compound GaSal, compound 2, compound I, compound II, complex I, complex II, macrocyclic ligand III, GaSal-1, GaSal-2, GaSal-3, GaSal-4, or pharmaceutically acceptable salt thereof, described herein, may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1: Gallium (III) Salophen as a Dual Inhibitor of *Pseudomonas aeruginosa* Heme Sensing and Iron Acquisition Example 1 describes a salophen scaffold that successfully inhibits the activation of the Has signaling system while simultaneously targeting iron uptake via xenosiderophore receptors. In this dual mechanism, free $Ga^{3+}$-salophen reduces growth through uptake and iron mimicry. A dual mechanism targeting extracellular heme signaling and uptake together with $Ga^{3+}$-induced toxicity following active $Ga^{3+}$-salophen uptake provides a significant therapeutic advantage while reducing the propensity to develop resistance.

Figure 3A:
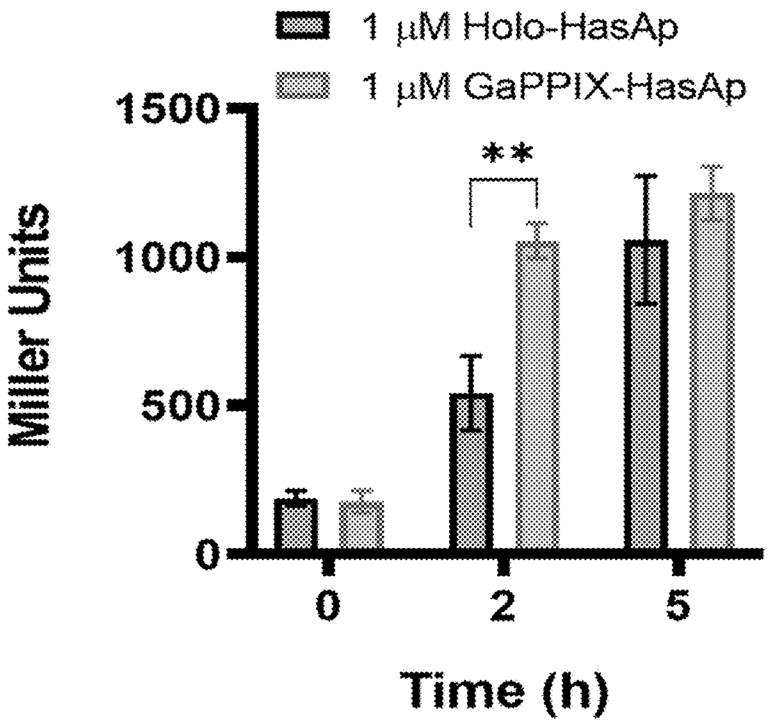
FIG. 3A illustrates the transcriptional activation of the hasR promoter with Holo- and GaPPIX-HasAp. GaPPIX shows increased (2 h) or similar transcriptional activation to heme even when accounting for differences in $OD_{600}$ due to Gallium toxicity. Cultures were supplemented with pre-formed HasAp complexes and performed in triplicate. , p<0.005.
Figure 3B:
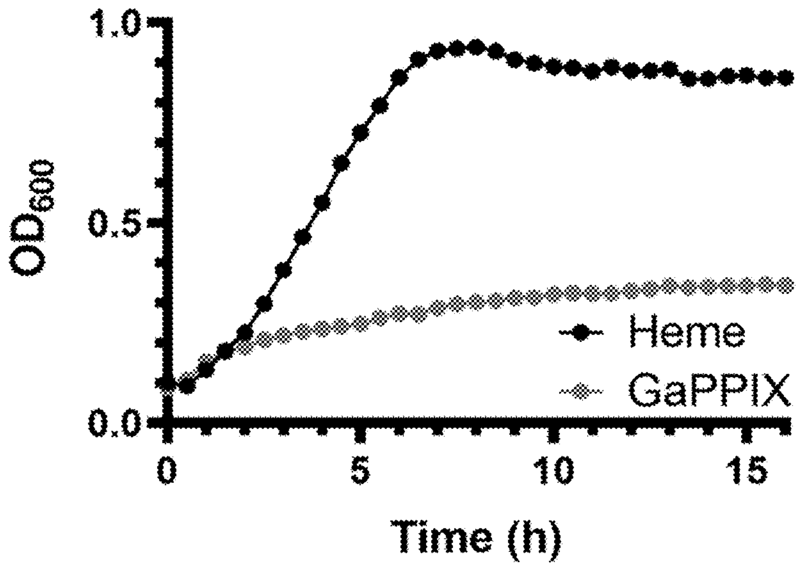
FIG. 3**B illustrates the growth of PAO1 supplemented with either 1 μM Heme or GaPPIX. Supplementation with GaPPIX inhibits growth in M9 Minimal Media. Cultures were grown in a 96-well plate.

Gallium Protoporphyrin IX (GaPPIX) Activates the has System Signaling Cascade Gallium protoporphyrin IX (GaPPIX) is a common heme mimic with antibacterial properties owing to the redox-inactive nature of $Ga^{3+}$ versus $Fe^{3+}$. Several gallium salts and nanoparticles have also found utility as antibacterial agents. To test whether GaPPIX would affect the activation of the Has signaling cascade, a p-galactosidase (p-Gal) transcriptional reporter assay previously constructed was employed. *P. aeruginosa* PAO1 was supplemented with HasAp (1 μM) bound to either heme or GaPPIX and aliquots were harvested and assayed for β-Gal activity. The results show no inhibition of transcriptional activation relative to heme (FIG. 3A), even when accounting for decreased cell density of gallium-supplemented cultures due to toxicity, as the GaPPIX is actively transported into the cell by HasR (FIG. 3B).

Salophen Complexes Bind to HasAp

Following reports that several synthetic iron complexes with heme-like features bind to HasAp in the heme-binding site and that larger macrocycles such as phthalocyanine could be transported through HasR, the o-phenylenediaminesalicylaldehyde ("salophen") scaffold for synthetic accessibility and potential for derivatization was identified. The salophen complexes were reported to bind through the same iron coordination mode and in the same site, including similar overlaps of the pyrrole rings of the porphyrin with the aromatic rings of the salophen. The FeSal and GaSal analogs were synthesized, their binding affinities characterized, and it was found that although salophen binds ~3-fold more weakly than heme, the metal substitution from $Fe^{3+}$ to $Ga^{3+}$ has minimal impact, consistent with the similarity between heme and GaPPIX (Table 1).

TABLE 1

Binding Affinities of Ligands to HasAp as determined by Fluorescence Quenching

| Compound | $K_D$ (nM) |
|---|---|
| Heme | 350 ± 50 |
| GaPPIX | 280 ± 30 |
| FeSal | 1050 ± 100 |
| GaSal | 1110 ± 220 |

Iron and Gallium Salophen Complexes Inhibit Has System Signaling

Figure 4A:
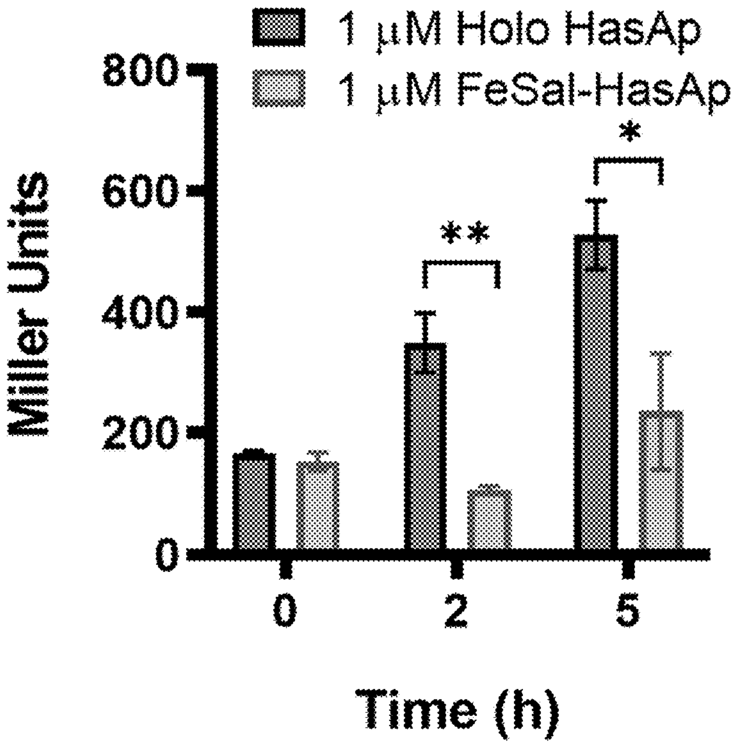
FIG. 4A illustrates the transcriptional activation of the hasR promoter with Holo- and FeSal-HasAp. FeSal shows decreased transcriptional activation relative to heme. Both cultures were supplemented with pre-formed HasAp complexes and performed in triplicate. *, p<0.05; , p<0.005.
Figure 4B:
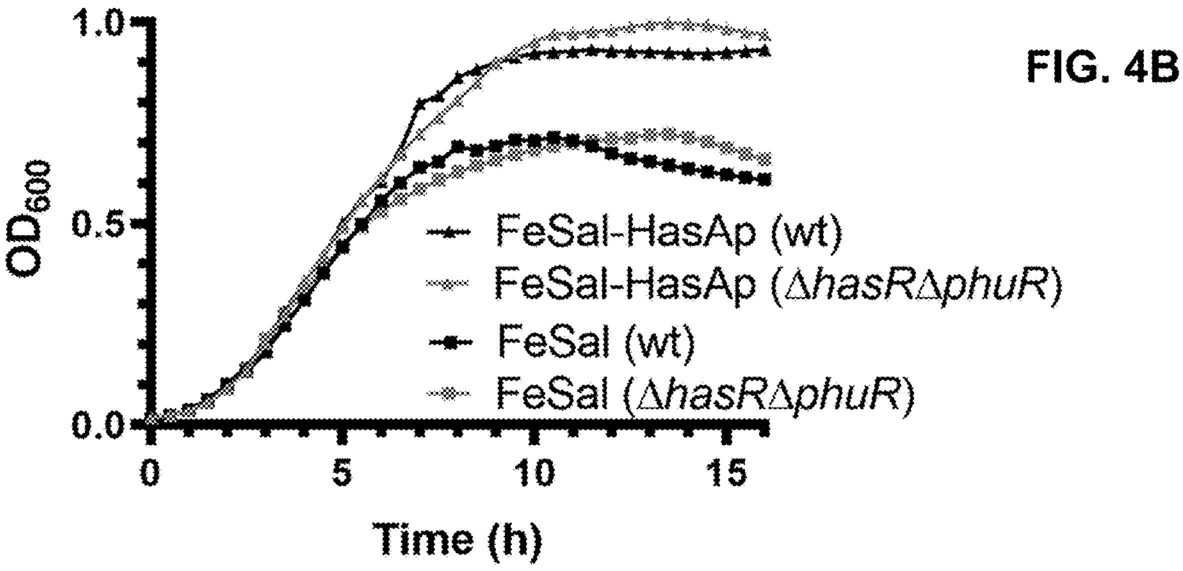
FIG. 4**B illustrates the growth of PAO1 Wild-Type and the ΔhasRΔphuR Strain with FeSal and FeSal-HasAp. Cultures were grown in a 96-well plate.
FIG. 4C illustrates the STD NMR using GaSal (1 mM) and HasAp (10 μM) in PAO1 supernatant.

PAO1 cultures supplemented with FeSal-HasAp showed decreased signaling activation (FIG. 4A), but had no effect on growth (FIG. 4B). Surprisingly, the FeSal-HasAp complex had improved growth relative to the free salophen ligand (FIG. 4B). Growth in the presence of either FeSal or FeSal-HasAp on the PAO1 ΔhasRΔphuR strain that lacks both heme receptors was next tested, and no inhibition was observed. Although not wishing to be bound by any particular theory, this result suggests that PAO1 can transport FeSal via siderophore-dependent uptake. It is not uncommon for bacteria to scavenge iron-siderophores they do not secrete, such xenosiderophore acquisition or piracy provides a viable survival and virulence trait.

Figure 5A:
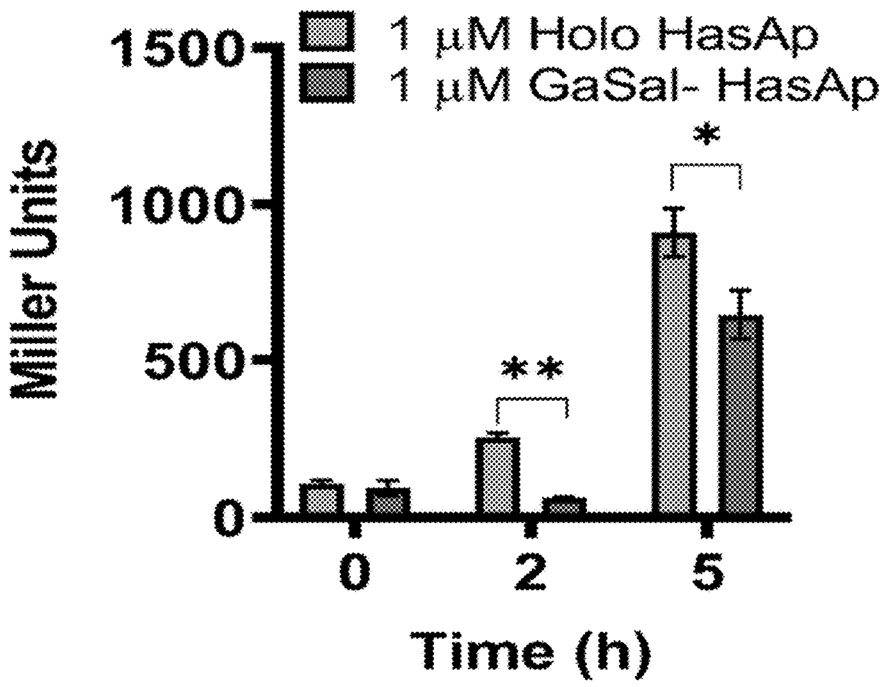
FIG. 5A illustrates the transcriptional activation of the hasR promoter with Holo- and GaSal-HasAp. GaSal shows decreased transcriptional activation relative to heme. Both cultures were supplemented with pre-formed HasAp complexes and performed in triplicate. Final values were corrected for differences in cell density. *, p<0.05; , p<0.005.
Figure 5B:
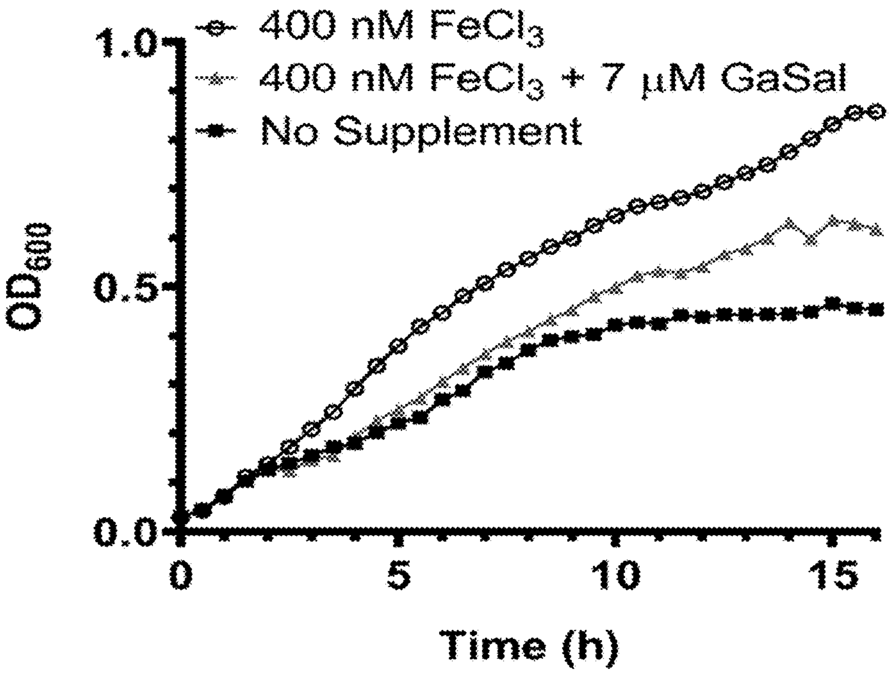
FIG. 5B illustrates the GaSal antibacterial activity in PAO1 ΔhasAp. Data represent the average of three wells in a 96-well plate with blanks (media only) subtracted. Cultures were grown in M9 minimal media with iron-limited supplements.
Figure 5C:
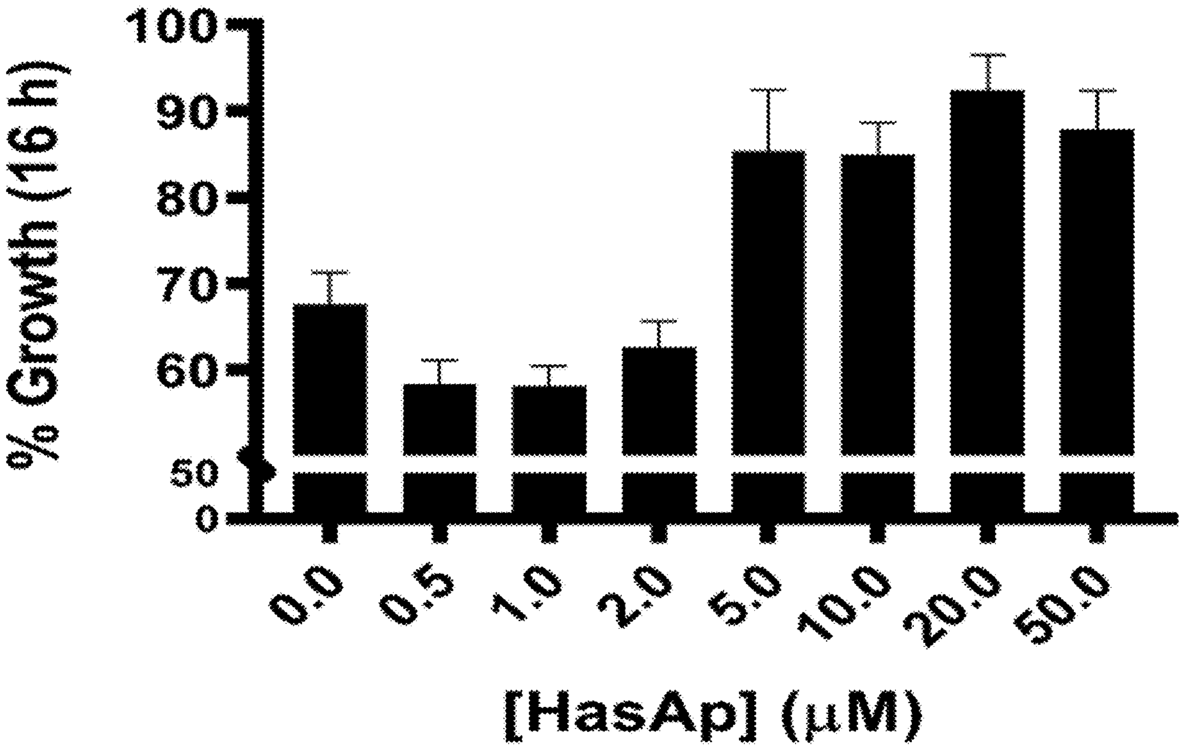
FIG. 5**C illustrates that HasAp titration alleviates GaSal toxicity in PAO1 ΔhasAp. Wells were prepared in M9 minimal media with $FeCl_3$ (400 nM) and GaSal (7 μM), with HasAp supplemented at increasing concentrations.
Figure 6A:
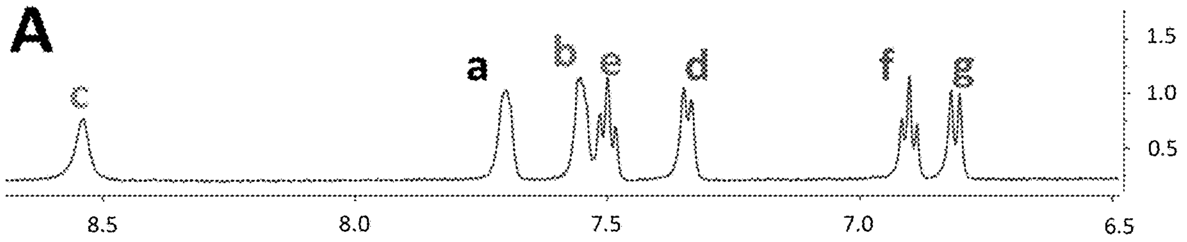
FIG. 6A illustrates the $^1H$ NMR of GaSal in M9 Minimal Media. Proton peaks were assigned and labeled as depicted for comparison in the STD spectrum.
Figure 6B:
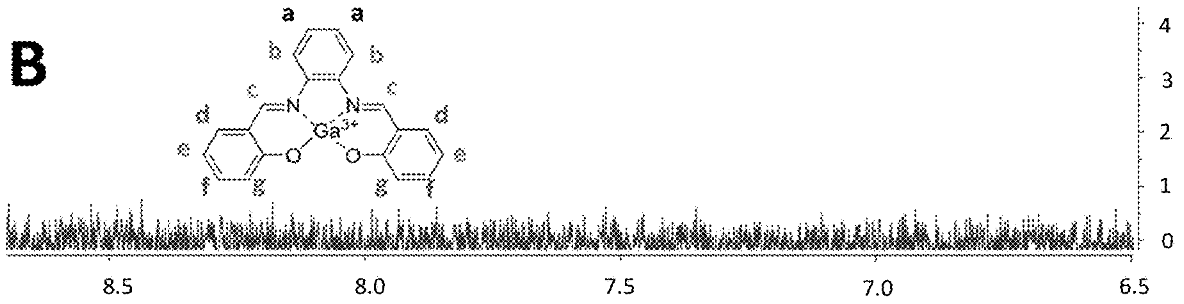
FIG. 6B illustrates the STD NMR of GaSal (1 mM) in supernatant.
Figure 6C:
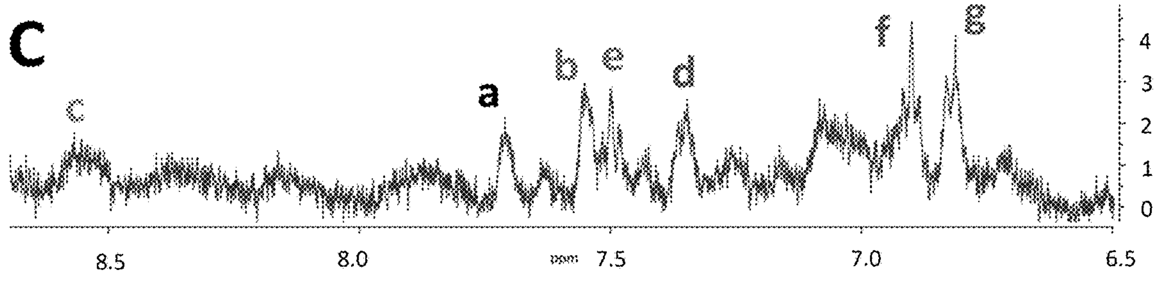

To counteract the iron-acquisition via FeSal, GaSal-HasAp was next tested and similar inhibition of has activation was observed (FIG. 5A). Considering the HasR- and PhuR-independent uptake of FeSal even with the FeSal-HasAp complex, the antipseudomonal activity of GaSal was studied. Under iron-limited conditions, GaSal showed antibacterial activity with an approximate $MIC_{50}$ of 7 μM (FIG. 5B). Titration of HasAp alleviated toxicity under the same conditions. Although not wishing to be bound by any particular theory, this result suggests that the intact salophen scaffold is neither degraded in the media nor transported through HasR (FIG. 5C). The equilibrium between uptake of GaSal and Has inhibition by GaSal-HasAp is therefore shifted by the formation of the GaSal-HasAp complex, which was confirmed by Saturation Transfer Difference (STD)-NMR (FIGS. 6A-6C).

In the STD experiment, a selective saturation pulse was delivered exclusively to HasAp and the saturation distributed throughout the protein by intramolecular spin diffusion. The saturation is transferred to any bound ligands, which were detected upon dissociation from the protein. In the resultant difference spectrum, only ligand $^1H$ peaks receiving saturation from the protein were observed and their intensities are proportional to their proximity to the protein, which is a useful observation of ligand binding epitopes. The top spectrum (FIG. 6A) is a $^1H$-NMR spectrum of GaSal in M9 minimal media to serve as a reference spectrum for the STD experiment. The middle spectrum (FIG. 6B) is an STD spectrum GaSal in PAO1 ΔhasAp supernatant with no added HasAp and shows no saturation transfer to the ligand, indicating no binding to any other secreted molecules in the supernatant. It was confirmed that despite no saturation transfer, the GaSal was still intact after 24 hr, supporting the stability and uptake of GaSal over that of free $Ga^{3+}$. The bottom spectrum (FIG. 6C) is GaSal in PAO1 ΔhasAp supernatant with added HasAp. This clearly shows saturation transfer among all protons of GaSal and confirms formation of the GaSal-HasAp complex in cellular media. Protons from the diamine ring (a and b) buried in the back of the heme binding site are clearly represented. Protons e and f are also distinguishable and can be substituted with groups that build outward from the salophen core to enhance binding affinity as they pointed away from the binding site in the crystal structure. The planarity and symmetry of GaSal also enhances the STD signals and permits binding from either face of the molecule.

To test whether the signaling inhibition was due to differences in the protein-protein interaction, the binding affinities of holo-, apo-, and GaSal-HasAp to HasR were measured by surface plasmon resonance (Table 2). All three HasAp states bind with similar affinity, indicating that the GaSal-HasAp/HasR protein-protein interaction is not significantly perturbed. The binding kinetics could not be accurately characterized due to poor fits of dissociation rates and instead steady-state binding analysis was applied to determine the dissociation constant. Physiologically, there is so saturation binding occurring as holo-HasAp binds HasR, undergoes a conformational change to release heme and then apo-HasAp is released from the receptor. The determined constants are therefore a useful metric from which to determine if the HasAp/HasR interaction is inhibited but are not reflective of a physiological complex. Instead, the lack of dissociation kinetics further supports the need for TonB-dependent heme transfer and uptake in vivo.

TABLE 2

Binding Affinities of HasAp to HasR as measured by Surface Plasmon Resonance.

| Ligand | $K_D$ (nM) |
|---|---|
| Apo-HasAp | 230 ± 80 |
| Holo-HasAp | 120 ± 20 |
| GaSal-HasAp | 140 ± 30 |

Structural Studies of the HasAp-Salophen Complex Through Hydrogen-Deuterium Exchange Mass Spectrometry and Circular Dichroism.

Figure 7A:
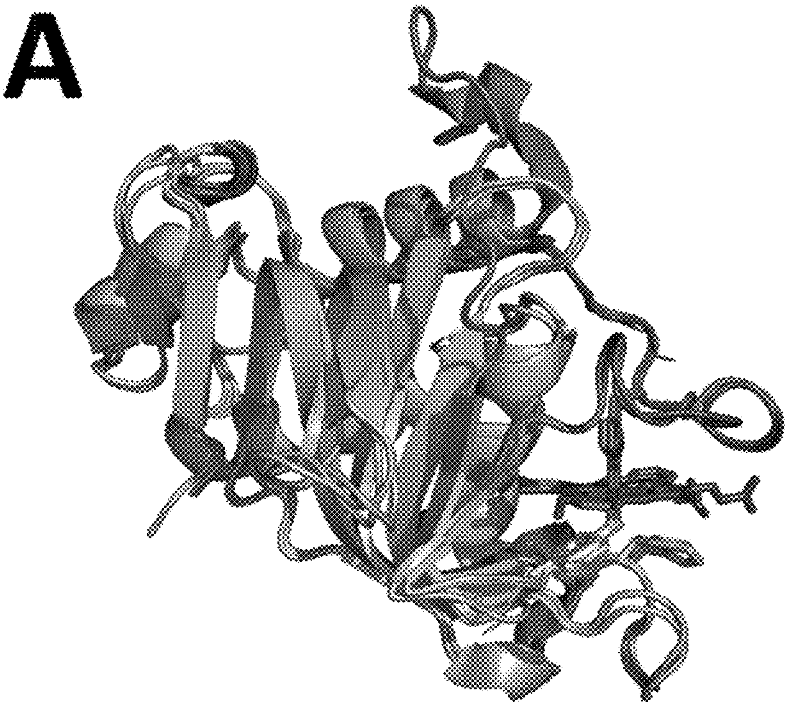
FIG. 7A illustrates alignment of apo, holo and FeSal-HasAp highlighting closure of the H32 loop from the apo (orange, PDB 3MOK) to the holo (blue, PDB 3ELL) and FeSal-HasAp (red, PDB 3W8M) forms.
Figure 7B:
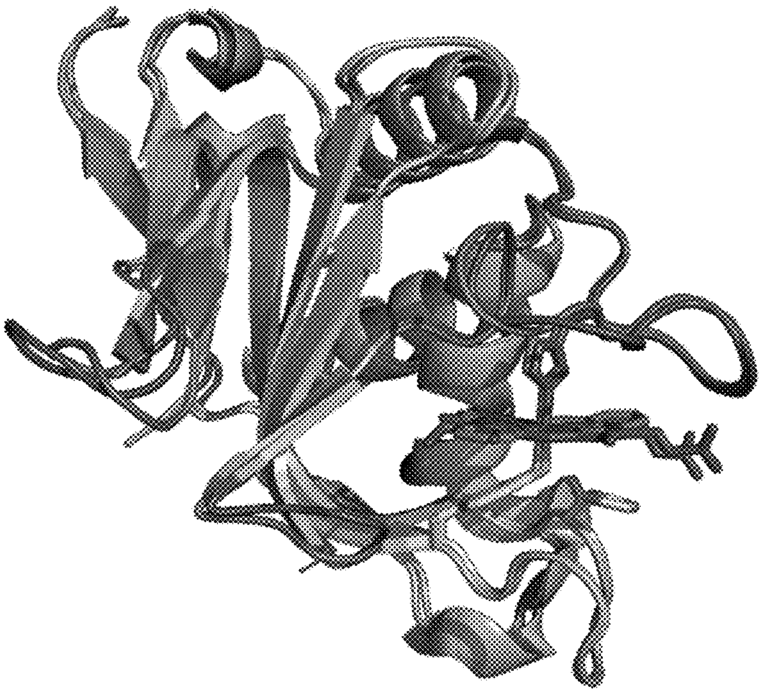
FIG. 7B illustrates alignment of holo and FeSal-HasAp highlighting the closed-loop conformation with minimal structural differences.

HasAp undergoes a large conformational rearrangement of the H32 loop upon heme binding (FIG. 7A, RMSD between apo and holo=5.7 Å, PDB 3MOK and 3ELL). In the salophen-bound crystal structures, this loop is also in the closed position and reveals less significant differences in the overall fold between holo-HasAp and the FeSal-HasAp complexes (FIG. 7B, RMSD=0.81 Å, PDB ID 3ELL and 3W8M). GaPPIX and GaSal are both toxic yet only GaSal inhibits the activation of the Has system even though the GaSal-HasAp complex still binds HasR. To determine if the differences in the activation of the heme signaling cascade are the result of differences in conformational flexibility of apo, holo and GaSal-HasAp, the solution structures of HasAp were analyzed by HDX-MS. Differences in deuterium uptake over time are reflective of how readily backbone amide hydrogens of a protein exchange with the solvent hydrogens or deuterons in a manner dependent on structure, solvent-exposure and flexibility. This technique was previously used to describe ligand induced structural and dynamic changes of the heme binding protein PhuS and HemO. Here, heme binding resulted in significant protection from deuteration throughout the heme binding site, consistent with loop closure and decreased solvent exposure (FIG. 7C). Similar protection of the heme site was observed upon GaSal binding (FIG. 7D).

Figure 8A:
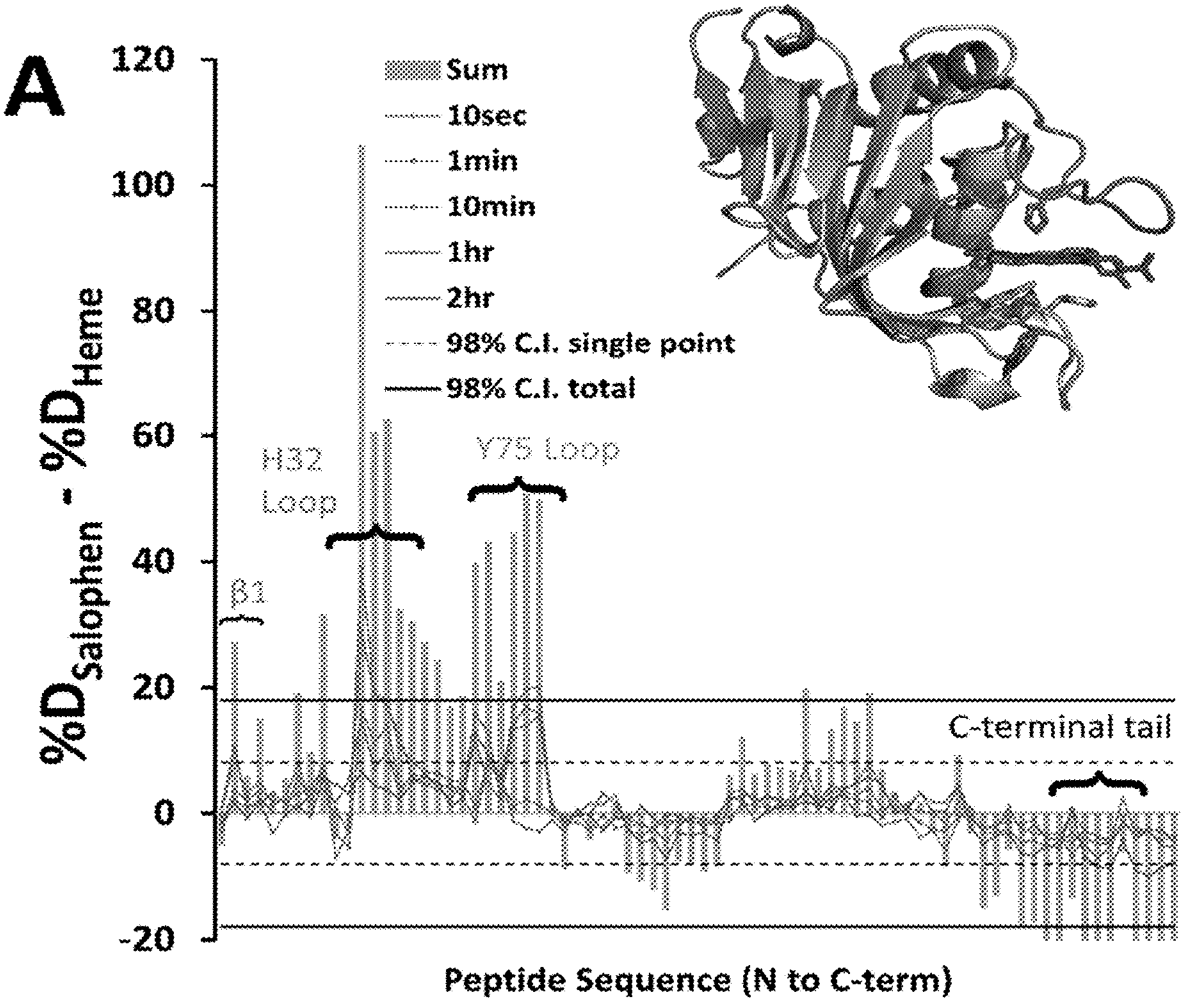
FIG. 8A illustrates the percent deuteration of GaSal-HasAp minus holo-HasAp. Positive peaks represent greater deuteration in the salophen-bound form, negative peaks indicate increased deuteration in the heme-bound form. Inset: representation of protein regions that are different between all three HasAp states.
Figure 8B:
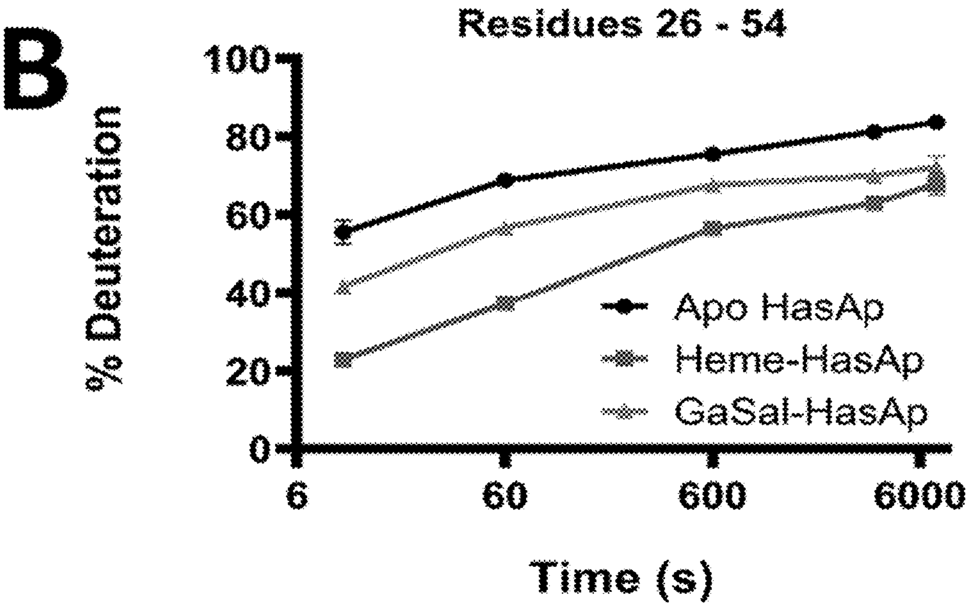
FIG. 8B illustrates the deuteration of a peptide comprising residues 26-54. FIG.
Figure 8C:
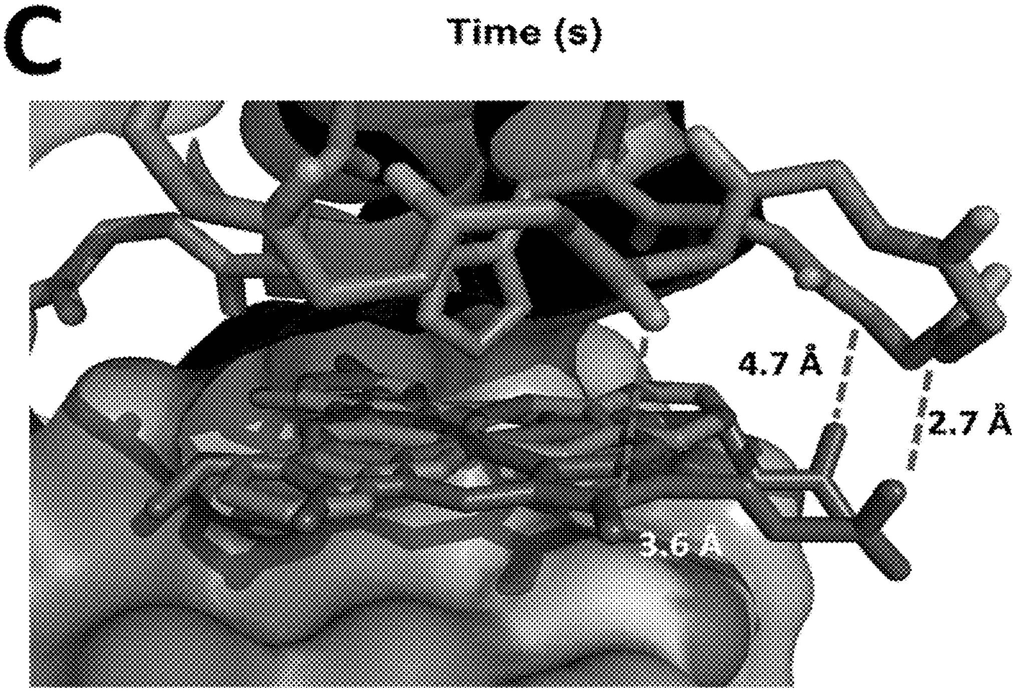
FIG. 8 illustrates the deuteration differences between ligand-bound forms.

In contrast with the crystal structure, the H32 and Y75 loops contained the greatest differences in deuterium uptake between the heme-bound and GaSal-bound states (FIG. 8A). On the H32 loop, the GaSal binding increased protection from deuteration relative to the apo form, but not at strongly as heme binding (FIG. 8B). GaSal is a smaller scaffold that does not have as extensive interactions with the protein, particularly those between the backbone of the H32 loop and heme (FIG. 8C). Notably, in the heme bound crystal structure, the His loop is observed to engage in multiple interactions with the porphyrin ring, including hydrogen bonds between the amide hydrogens of P34 and G35 with the heme propionates, or the V37 carbonyl with the heme methyl groups that are absent in the salophen-bound complex. The lack of these interactions and increased flexibility of the heme site do not prevent HasR binding, but, combined with the structural differences in the salophen ligand, likely prevent ligand release and uptake through HasR.

The lower protection afforded by GaSal suggests a greater degree of flexibility in this loop not evident from the crystal structure. To assess whether this observation carried a thermodynamic consequence, the melting temperatures of the three HasAp complexes were measured by circular dichroism. All three HasAp spectra showed similar degrees of folding at 25° C., indicating that the overall structure is not significantly impacted by ligand binding (FIG. 9A). The melting temperature of the apo form (58° C.) was significantly increased by heme binding where the protein only began to unfold at temperatures >90° C. (FIG. 9B). HasAp bound to GaSal still showed increased thermal stability (65° C.), but not nearly to the extent on heme binding. Taken together the HDX-MS and CD data indicate significant differences between the holo and GaSal-HasAp complexes not reflected in the crystal structure. These differences in solution carry physiological consequences beyond inhibiting signaling, wherein the decreased stability of the GaSal-HasAp compared to holo-HasAp may increase susceptibility to proteolytic cleavage in the host.

Conclusions

As a secreted protein, HasAp must be secreted in high amounts to counteract both diffusion from the site of infection and host defense mechanisms such as proteolysis to effectively scavenge heme. Its relative abundance and role in virulence coupled with the advantage of an extracellular target make HasAp an attractive therapeutic target that can lead to the dysregulation of heme sensing and host adaptation. GaPPIX has antibacterial effects as a redox-inactive heme mimic that enters the cell through the Has and Phu systems where it is toxic to heme proteins. However, the levels of transcriptional activation of the Has system are not decreased and will lead to a downstream increase in HasAp levels which will, over time, counteract the inhibitory effect and lead to increased heme-scavenging abilities. Additionally, the lack of iron obtained through this pathway will also lead to adaptation towards siderophore-based iron acquisition as the heme systems lead to gallium toxicity, limiting the potential of GaPPIX as a long-term therapeutic option. Structurally, GaPPIX is identical to heme, which also increases the chances for off-target effects and inhibition of human heme proteins such as heme oxygenase, highlighting a need for new scaffolds with greater selectivity towards HasAp.

Previous heme mimetic approaches reported that FeSal and FePhthalocyanine (FePc) were inhibitors of heme uptake when cultures were not supplied with holo-HasAp as an iron source, in contrast with the lack of growth inhibition observed with FeSal-HasAp. In the presence of holo-HasAp, only FePc was inhibitory. Although not wishing to be bound by any particular theory, this result suggests that the larger phthalocyanine macrocycle blocks HasR and inhibits heme uptake. More recent studies showed that GaPc inhibition is the result of active transport through HasR and not inhibition of heme uptake, as previously described. Based on these conflicting reports, the mechanism of inhibition by the salophen complexes as potential therapeutics was characterized due to their synthetic accessibility and modularity. While the salophen scaffold binds to HasAp, it is less likely that these molecules will be recognized by host heme proteins, which typically fold around heme or recognize the heme propionates for binding.

It was found that, unlike GaPPIX, both FeSal and GaSal inhibited the holo-HasAp activation of the cell surface signaling cascade. The link between signaling and transport was previously reported, and it was demonstrated that the signaling requires the release of heme from HasAp to HasR. The lack of signaling suggests that FeSal and GaSal are either not released to HasR or, if they are released, do not induce the requisite conformational change in the HasR signaling domain required to trigger the cascade or to be transported. It was also found that FeSal-HasAp promoted growth, which requires transport into the cell. Identical growth was observed with FeSal and FeSal-HasAp in both the wild type and the ΔhasRΔphuR mutant, indicating that the uptake is independent of the heme receptors. As a metal chelate, FeSal is likely a substrate for xenosiderophore receptors expressed by *P. aeruginosa* to utilize siderophores from other bacteria, a strategy that has also been used to develop siderophore-drug conjugates. Advantageously, the GaSal derivative was toxic, consistent with the use of gallium-based antibacterial therapies. It was also shown that titration with exogenous HasAp alleviated some GaSal toxicity, highlighting the distinct roles of GaSal and GaSal-HasAp in iron uptake and heme signaling, respectively. This strategy conveniently combines the use of gallium salts and porphyrins into a single compound that targets both iron and heme pathways without leading to the upregulation of the heme sensing system.

The mechanism through which GaSal is inhibitory was further characterized to better understand what features could be explored in later metallosalophen derivatives. While the salophen complexes have weaker binding affinities than the PPIX counterparts, similar binding affinities of GaSal-HasAp and holo-HasAp to HasR were found. To investigate the differences in signaling despite the lack of HasAp/HasR binding inhibition, the HasAp complexes were studied by HDX M S. These experiments showed increased conformational flexibility of the H32 loop with GaSal-HasAp relative to holo-HasAp, which is consistent with the loss of stabilizing interactions with the PPIX macrocycle. The lack of these interactions is also consistent with the decreased binding affinity of the metallosalophens relative to the PPIX counterparts. The increased flexibility of the H32 loop may therefore prevent HasR binding in a manner that triggers the conformational change and concerted ligand release even though the overall binding affinity is not significantly diminished. The increased flexibility of the loop is also reflected in the lower $T_m$ values. Since the melting temperature of GaSal-HasAp is also much closer to apo-HasAp than holo-HasAp, GaSal binding leads to a less-stable and more proteolytically susceptible HasAp complex, further diminishing the ability of *P. aeruginosa* to acquire and sense heme.

With the utility of GaSal, other GaSal derivatives are designed to include hydrophobic interactions in the heme binding site to increase HasAp affinity. Derivatives also include extending molecules anchored to the heme site into the HasAp/HasR interaction region through alternative designs or a HasR peptidomimetic approach to blocking binding to HasR entirely. Conveniently, approaches that either block the HasR interaction entirely or bind HasR without subsequent ligand release are likely to have merit. Based on these findings, the development of an inhibitor that is transported through HasR should be avoided as this will lead to the activation of the signaling cascade. Additionally, as a siderophore receptor substrate, these inhibitors should maintain affinity to iron uptake pathways to not target the heme sensing pathway exclusively, which would be overcome by adaptation to iron acquisition.

Various gallium formulations have been employed for antimicrobial applications. The use of GaSal represents a more specific approach that targets the extracellular hemophore HasAp and the heme-sensing ability of *P. aeruginosa* in addition to targeting iron uptake for antimicrobial activity. The biophysical consequences of salophen binding versus heme build on the structural characterization of the Has system previously reported. This work provides a platform for the development of new heme mimics that can target bacterial hemophore signaling as well as iron uptake. These dual mechanisms have the propensity to slow the development of resistance as the simultaneous evolution of mutations in separate pathways is likely to lead to reduced fitness and survival of the bacteria. Furthermore, that these mechanisms are critical for infection but not survival outside of the host further lowers selective pressure for the development of resistance.

The results described in Example 1 were obtained using the following materials and methods.

Experimental Procedures

Bacterial strains. *Pseudomonas aeruginosa* (PAO1 and mutants) strains were stored as glycerol stocks in LB at −80° C. and were freshly streaked on *Pseudomonas* isolation agar (BD Biosciences) before transferring to liquid culture medium. PAO1 (wild type) was used as reported. PAO1 LacZ fusions and hasAp deletion strains were constructed as described previously. The heme receptor deletion strain (PAO1 ΔhasRΔphuR) was constructed as reported.

Expression and purification of WT HasAp. HasAp was prepared from freshly transformed *E. coli* BL21(DE3) competent cells harboring the pET11a plasmid with the full-length hasAp gene as previously described with an additional purification step. Briefly, a single colony was cultured for 16 h in LB medium (50 mL) containing 100 μg/mL ampicillin. The cells were harvested by centrifugation, resuspended in M9 media, and divided evenly among 4 1-L cultures in M9 containing 100 μg/mL ampicillin and grown to an $A_{600}$ of ~1.0. The cells were once again pelleted and resuspended in 4 fresh 1-liter M9 cultures and induced with 1 mM final concentration of isopropyl-β-D-thiogalactopyranoside and grown for 16 h at 30° C. Cells were harvested by centrifugation and resuspended in 40 mL of lysis buffer (20 mM Tris-HCl (pH 7.5), 20 mM NaCl, 1 mM EDTA) containing a protease inhibitor tablet (Roche Applied Science), 1 mg/mL DNase, and 25 mg/mL lysozyme and passed through an LM-20 microfluidizer at 20,000 p.s.i. The suspension was centrifuged at 25,000 rpm for 1 h to separate the cell debris. The supernatant was applied to a Q-Sepharose column (2.6×10 cm) pre-equilibrated with 20 mM Tris-HCl (pH 7.5) and 20 mM NaCl). The column was washed (3-5 column volumes) with buffer and the protein eluted over a gradient from 20 to 600 mM NaCl in 20 mM Tris-HCl (pH 7.5). The purity of the eluted fractions was determined by SDS-PAGE, and those containing HasAp were pooled. To separate the apo-protein, the pooled fractions were concentrated to ~5 mL and exchanged into 50 mM sodium phosphate buffer with 0.7 M ammonium sulfate (pH 7.0). The concentrate was loaded onto a Butyl Sepharose Fast Flow (GE Healthcare, 2.6×10 cm) column equilibrated with the same buffer. Weakly bound contaminants and holo-HasAp were eluted with 2-3 bed volumes of 50 mM sodium phosphate containing 0.5 M ammonium sulfate. Apo-HasAp was then eluted with a linear gradient of sodium phosphate (50 to 20 mM) containing ammonium sulfate (0.5 to 0 M). Fractions were once again analyzed by SDS-PAGE and the apo-HasAp was pooled, concentrated (Spin-X UF 10 k MWCO, Corning) and exchanged into 20 mM sodium phosphate buffer.

Expression and Purification of HasR. HasR was prepared as reported with modifications to prepare the protein in lipid discs. Briefly, a single colony of freshly transformed *E. coli* BL21 (DE3) cells harboring the pHasR22b plasmid was selected to inoculate 50 mL of noninducing MDAG-135 media containing 100 μg/mL Amp and grown overnight at 37° C. and 225 rpm. This culture was used to inoculate 4 1-L flasks of autoinducing MDA-5052 media containing 100 μg/mL Amp and grown for 10 h at 25° C. Cells were harvested by centrifugation for 15 min at 7,000 rpm at 4° C.

Pellets were resuspended in 40 mL lysis buffer and passed through an LM-20 microfluidizer at 20,000 p.s.i. Cell debris was removed by centrifugation at 12,000 rpm for 15 min and the supernatant was centrifuged for an additional 1 h at 25,000 rpm to pellet the cellular membranes. Pelleted membranes were resuspended in 30 mL lysis buffer with an added EDTA-free protease inhibitor tablet and stirred overnight at 4° C. The cytoplasmic membrane proteins were solubilized by the addition of 2% (v/v) Triton X-100 (Sigma) and 0.5% (v/v)N-Lauroylsarcosine sodium salt (Sigma). The membrane fractions were stirred at room temperature for 1 h and pelleted at 25,000 rpm for 1 h at 4° C. The resulting supernatant containing only the cytoplasmic membrane proteins was discarded. The pelleted outer membrane (OM) fraction was then resuspended in 30 mL of lysis buffer containing an EDTA-free protease inhibitor cocktail tablet and stirred at 4° C. overnight.

The RC DC protein assay (Bio-Rad) was used to determine total protein concentration. The OM fragments were diluted to at least 10 mg/mL final concentration. The styrene-maleic acid copolymer (Xiran SL30010 P20) was then added to the OM suspension to a final concentration of 2.5% (v/v) and inverted continuously at r.t. for 1 h. The suspension was frozen in liquid nitrogen and thawed at 42° C. a total of 5 times followed by passage through a microfluidizer at 20,000 p.s.i. This cycle was then repeated once more. The final suspension was centrifuged at 25,000 rpm for 1 h at 4° C. and the supernatant containing the HasR in lipid nanodisc (HasR-sma1p) was collected and concentrated. The filtrate was saved as a blank to account for the UV-Vis absorption of loosely associated lipids and polymer. The HasR concentration was determined using the extinction coefficient of 126 $mM^{-1}$ $cm^{-1}$.

Chemical Synthesis. All the reagents and solvents were purchased from commercial sources and used as received, unless otherwise stated. The $^1$H and $^{13}$C NMR spectra were obtained in $(CD3)_2SO$ on a 400 MHz spectrometer with chemical shifts referenced to tetramethylsilane (TMS). Purity of FeSal and GaSal were confirmed by HPLC.

Synthesis of 2,2'-((1E,1'E)-(1,2-phenylenebis(azaneylylidene))bis(methaneylylidene))diphenol (Salophen). O-phenylenediamine (5.4 g, 50 mmol) was dissolved in dichloromethane (100 mL). To the resulting solution was added salicylaldehyde (12.2 g, 100 mmol). The mixture was stirred at room temperature for 8 h before removing solvent via rotary evaporation, to afford an orange solid (10.5 g, 99%). $^1$H NMR (400 MHz, $(CD3)_2SO$): δ 12.94 (s, 2H), 8.941 (s, 2H), 7.68-7.66 (d, 2H), 7.48-7.40 (m, 6H), 7.00-6.95 (t, 4H).

Synthesis of FeSal Chloride. To a solution of salophen (0.316 g, 1 mmol) in ethanol (3 mL) was added ferric chloride (0.16 g, 1 mmol). The reaction mixture was heated at 65° C. in a sealed pressure tube overnight. A black precipitate was washed with cold ether and collected (70 mg, 17%). NMR peaks broadened beyond detection due to paramagnetic effects of iron. IRMS (ESI) m/z: $[M-Cl]^+$ Calc'd for $C_{20}H_{14}N_2O_2Fe$ 370.0405; Found 370.0443.

Synthesis of GaSalophen Nitrate. To a solution of salophen (0.316 g, 1 mmol) in ethanol (3 mL). was added Gallium (III) nitrate hydrate (0.51 g, 2 mmol). The reaction mixture was heated at 60° C. in a sealed pressure tube for 2 h. Cold ether was added, and the resulting mixture was stirred until a yellow precipitate was formed and collected by filtration (0.3 g, 70%). $^1$H NMR (400 MHz, $(CD_3)_2SO$): δ 9.37 (s, 2H), 8.16-8.13 (m, 2H), 7.68-7.66 (dd, 2H), 7.66-7.51 (m, 4H), 7.02-6.99 (d, 2H), 6.90-6.86 (t, 2H). $^{13}$C NMR (400 MHz, $(CD_3)_2SO$): δ 167.9, 162.9, 137, 136.6, 135.4, 129, 122.3, 118.3, 117.1, 117. HIRMS (ESI) m/z: $[M-NO_3]^+$ Calc'd for $C_{20}H_{14}N_2O_2Ga$ 383.0311; Found 383.0301.

Preparation of HasAp Complexes. Heme and GaPPIX were purchased from Frontier Scientific. Heme solutions were prepared as described previously immediately before use and concentrations determined via pyridine hem chrome assay. GaPPIX solutions were prepared identically, except concentrations were determined using the extinction coefficient at 404 nm (90.6 $mM\ cm^{-1}$). Apo-HasAp was prepared at a desired concentration in 20 mM sodium phosphate buffer (pH 7.4, 25° C.). To this solution was added a 3-fold molar excess of ligand prepared in the same buffer solution. Excess unbound ligand was removed using 7K MWCO centrifugal desalting columns (Zeba™ Spin, Thermo Fisher Scientific) according to manufacturer's recommendations.

Binding Affinity Determination by Fluorescence Quenching. Binding affinities were determined on an ISS K2 multifrequency fluorometer in L-format using 1 cm quartz cuvettes. To a 1 μM solution of apo-HasAp in 20 mM sodium phosphate buffer (pH 7.4, 25° C.) was titrated ligand of interest. Emission spectra were recorded (300-500 nm) following excitation at 295 nm. The decrease in maximum emission was plotted against the ligand concentration (accounting for dilution) and fit to one-site binding using GraphPad Prism 8.

Growth Curves. *P. aeruginosa* strains were grown overnight in 50 mL LB Broth with shaking at 37° C. Cells were harvested by centrifugation and resuspended in M9 minimal medium. Strains were then inoculated at $A_{600}$=0.05 in 10 mL M9 minimal medium and grown for 3 h to deplete bacterial iron stores. Cultures were then plated in 96-well plates (Costar clear, flat-bottom with lid, Corning Inc) at $A_{600}$≈0.05 to a final volume of 200 μL in M9 medium. Supplements (2 μL) were added as 100× stock solutions. Growth curves were recorded at 600 nm with a Biotek Synergy™ HT plate reader over 16 h of growth with shaking at 37° C. To account for background absorbance, blank wells were prepared with the same supplements but only M9 medium without culture. The blank wells were subtracted from the average of three growth wells per condition.

Transcriptional Reporter Assay. The chromosomal fusions of the PhasR-lacZ and promoterless lacZ gene were previously constructed and used to report on transcriptional activation of the Has signaling cascade. For all β-gal assays, strains were grown overnight in 50 mL LB broth with shaking at 37° C. Cells were harvested by centrifugation and resuspended in M9 media. Strains were then inoculated at $A_{600}$=0.05 in triplicate in 25 mL of M9 minimal medium and cultured for 3 h to deplete bacterial iron stores. Growth cultures were then supplemented with 1 μM of either holo-HasAp, GaPPIX-HasAp, FeSal-HasAp or GaSal-HasAp. Aliquots (1 mL) at 0 (just prior to supplementation), 2 and 5 h post supplementation were harvested and assayed for p-gal activity as described previously.

Circular Dichroism. Circular dichroism experiments were performed on a Jasco J-810 spectropolarimeter using 1 mm quartz cuvettes. All samples were recorded with 10 μM HasAp in 10 mM potassium phosphate (pH 7.4) at 25° C.

from 190 to 260 nm at a scan rate of 50 nm/min, with each spectrum representing 5 accumulations. Data were acquired at 0.2-mm resolution and 10 nm bandwidth. The mean residue ellipticity (degrees $cm^2$ $dmol^{-1}$) was calculated using CDPRO software as recommended by Jasco. Thermal denaturation studies were performed over a temperature range of 20-90° C. at 222 nm. Melting temperatures were determined by fitting denaturation data to a Boltzmann-Sigmoidal distribution in GraphPad Prism 8.

Saturation Transfer Difference NMR. PAO1 ΔhasAp was cultured overnight from a single colony in LB Broth. The cells were harvested by centrifugation and resuspended in M9 Minimal Media. 10 mL of M9 were inoculated at $A_{600}$~0.05 and grown for 3 h. Cell-free supernatant was obtained by centrifugation and subsequent filter-sterilization by a 22 μM syringe filter. Supernatant was then used as the solvent for subsequent STD experiments. Final sample volume contained 600 μL of supernatant with or without 10 μM HasAp (as a negative control) and 5% $D_2O$ for solvent locking.

The STD experiments were performed at 25° C. on an Agilent DD2 500 MHz spectrometer. The vendor supplied pulse sequences, dpfgse_satxfer.c was used, the on- and off-resonance fids are subtracted in-place through phase-cycling, to yield only the difference fid. Selective saturation was performed for 2.5 s and consisted of 50 ms Gaussian pulses separated by a 1-ms delay at a field strength of 50 Hz. A spectral width of 6,000 Hz (12 ppm), a 90-degree pulse of 9.6 μs, and 16,384 points were used to collect the data with a 0.5 s delay between transients. Transmitter offset was on the water signal. Solvent suppression was achieved via excitation sculpting. The selective irradiation on-resonance with the protein was at 1.5 ppm and the off-resonance irradiation was at 25 ppm.

Surface Plasmon Resonance. Apo-HasAp, GaSal-HasAp and holo-HasAp were covalently bound to the surface of flow cells 2, 3 and 4 of a CM5 chip to a final level of 50 RU using the NHS-EDC kit (GE Life Sciences, Piscataway, N.J.). Flow cell 1 was treated as blank. HasR-his (0-1000 nM) in 120 μl of HBS-EP buffer (GE Life Sciences) was injected into flow cells 1-4 at 25° C. The surface was then washed with buffer for 3 min and the dissociation of analyte-ligand complexes was followed over time. The flow cells were regenerated by injecting 15 μl aliquots of 10 mM glycine, pH 1.5 followed by 15 μl aliquots of 10 mM NaOH and the process was repeated. Sensorgrams were analyzed with BIAeval 4.1 software (Biacore). Values from the reference flow cell were subtracted to obtain the values for specific binding. Data were fitted to a Steady-State Affinity model.

Hydrogen-Deuterium Exchange Mass Spectrometry. The coverage maps for all proteins were obtained from undeuterated controls as follows: 3 μL of 20 μM sample in 20 mM sodium phosphate buffer (pH 7.4, 25° C.) was diluted with 27 μL of ice-cold quench (100 mM Glycine, 5.5 M Guanidine-HCl, pH 2.4). After 5 min, 120 μL of 50 mM Glycine buffer, pH 2.4 was added prior to the injection. 50 μL of quenched samples were injected into a Waters HDX nano-Acquity UPLC (Waters, Milford, Mass.) with in-line digestion (NovaBioAssays Immobulized protease type XVIII/pepsin column). Peptic fragments were trapped on an Acquity UPLC BEH C18 peptide trap and separated on an Acquity UPLC BEH C18 column. A 7 min, 5% to 35% acetonitrile (0.1% formic acid) gradient was used to elute peptides directly into a Waters Synapt G2-Si mass spectrometer (Waters, Milford, Mass.). MSE data were acquired with a 20 to 30 V ramp trap CE for high energy acquisition of product ions as well as continuous lock mass (Leu-Enk) for mass accuracy correction. Peptides were identified using the ProteinLynx Global Server 3.0.3 (PLGS) from Waters. Further filtering of 0.3 fragments per residues was applied in DynamX 3.0.

For each state (i.e. apo and ligand bound), the HD exchange reactions and controls were acquired using a LEAP autosampler controlled by Chronos software. The reactions were performed as follows: 2 μL of 20 μM of apo HasAp or in complex with ligand in 20 mM sodium phosphate buffer (pH 7.4, 25° C.) was incubated in 18 μL of 20 mM sodium phosphate buffer containing 30 μM ligand (99.99% $D_2O$, pD 7.4). All reactions were performed at 25° C. Prior to injection, deuteration reactions were quenched at various times (10 s, 1 min, 10 min, 1 h and 2 h) with 60 μL of 100 mM Glycine buffer, 5.5 M Guanidine-HCl, pH 2.4, followed 1 min later by a post quench dilution of 170 μL of 50 mM Glycine buffer, pH 2.4. The resulting sample volume was injected. Back exchange correction was performed against fully deuterated controls acquired by incubating 2 μL of 20 μM HasAp containing 6.0 M guanidine HCl in 18 μL 20 mM sodium phosphate buffer (99.99% $D_2O$, pD 7.4) for 2 h at 25° C. prior to data collection. All deuteration time points and controls were acquired in triplicates.

The deuterium uptake for all identified peptides with increasing deuteration time and for the fully deuterated control was determined using Water's DynamX 3.0 software. The normalized percentage of deuterium uptake (% $D_t$) at an incubation time t for a given peptide was calculated as follows:

$$\% D_t = \frac{100(m_t - m_0)}{m_f - m_0},$$

with $m_t$ the centroid mass at incubation time t, $m_0$ the centroid mass of the undeuterated control, and mf the centroid mass of the fully deuterated control. Percent deuteration difference plots, Δ% $D_t$(Apo–Liganded), displaying the difference in percent deuteration between the apo and ligand bound HasAp for all identified peptides, at all deuterium incubation time probed were generated. Confidence intervals for the Δ% D plots were determined using the method outlined by Houde et al, adjusted to percent deuteration using the fully deuterated controls. Confidence intervals (98%) were plotted on the Δ% D plots as horizontal dashed lines and used to determined peptides with statistically significant differences in deuterium uptake between the apo and complexed state.

Example 2: Synthesis and Testing of Small Molecule HasAp Inhibitors

Iron is critical for *P. aeruginosa* survival and virulence but extremely scarce within the host. *P. aeruginosa* overcomes host iron limitation through a variety of mechanisms, including the secretion of ferric ($Fe^{3+}$) siderophores (pyoverdine and pyochelin), ferrous ($Fe^{2+}$) uptake (Feo) system, and two heme uptake systems, the heme assimilation (has) and *Pseudomonas* heme uptake (phu) systems. It has been previously shown that *P. aeruginosa* longitudinal clinical isolates from CF patients over time decrease pyoverdine biosynthesis, while increasing their ability to utilize heme. Genetic and biochemical analysis characterized the Phu system as the high capacity transport system, whereas the Has system is primarily required for heme sensing and signaling. Transcriptomics showed mRNA levels of the extracellular hemophore hasAp and its outer membrane receptor hasR are the most significantly upregulated genes in an acute murine lung infection model. Moreover, in the same animal model a *P. aeruginosa* ΔhasR strain showed significantly reduced growth and virulence. Recently, the Wilks Lab identified that the terminal heme metabolite of *P. aeruginosa* biliverdin (BV) IXP, functions as a feedback regulator of HasAp and several virulence-associated traits including pyochelin, Zn/Ni-pseudopaline uptake, Type III secretion systems, and extracellular proteases. Therefore, the cells ability to sense and utilize heme, as well as regulate effectors of colonization and virulence, is in part dependent on the transcriptional activation of the Has system.

Formulations of the redox inactive metal gallium (e.g., Ganite) have been clinically used as antimicrobials based on being an excellent mimic of iron due to its similar size. Studies described herein have shown that the stable gallium-salophen complex, GaSal, binds to the extracellular hemophore HasAp and blocks the heme-signaling cascade, decreasing the ability of *P. aeruginosa* to sense and utilize heme. Simultaneously, GaSal functions as a xenosiderophore for one or more of the siderophore uptake systems of *P. aeruginosa*, leading to intracellular dysregulation of iron homeostasis. Using the HasAp crystal structure, the surface of the protein was characterized using a novel computer-aided drug design method SILCS (site identification of ligand competitive saturation). The SILCS results revealed the presence of a "sweet spot" that maps to HasAp-HasR interface near the heme-binding site. Coupling compound activity at both sites, combined with in-depth structure-activity relationship (SAR), leads to potent inhibitors of the HasAp-HasR signaling system. In addition, targeting the extracellular HasAp has the significant advantage of not having to cross the bacterial cell membrane or be subjected to potential drug efflux. It is hypothesized that simultaneous inhibition of *P. aeruginosa* heme sensing by targeting the extracellular hemophore HasAp while optimizing xenosiderophore receptor uptake is a novel antivirulence strategy for the treatment of *P. aeruginosa* infection. A series of Ga-salophen complexes are synthesized and tested using established assays, to identify, validate, and characterize potent inhibitors of heme signaling and iron homeostasis.

To this end, a series of test compounds that inhibit heme signaling and function as xenosiderophores are synthesized. The compounds represent a new class of HasAp inhibitors designed by CADD method SILCS based on GaSal. Binding affinities of new compounds are assayed with a high throughput fluorescence quenching (FQ) assay. Selected compounds are studied for their ability to inhibit heme signaling and uptake with established reporter and $^{13}C$-heme isotopic labeling assays. Siderophore-dependent uptake of GaSal complexes uptake by ICP-MS is established.

The pharmacological consequences of simultaneously targeting HasAp and xenosiderophore receptor uptake are determined by determining minimum inhibitory concentrations (MICs) of selected GaSal complexes in iron/heme defined and synthetic cystic fibrosis sputum media (SSM), assaying inhibition of biofilm formation using the MBEC plate assay, assessing the efficacy of selected compounds in the *C. elegans* infection model, and investigating the binding mode/pharmacophore of the top compounds using saturation transfer difference (STD)-NMR, $^{1}H$,$^{15}N$-HSQC NMR, and hydrogen deuterium exchange mass spectrometry (HDX-MS).

A critical innovation is the development of a first in class small molecule with the dual activity of inhibiting the heme dependent CSS cascade while acting as a substrate for siderophore receptor uptake. Targeting HasAp with GaSal blocks the ability of *P. aeruginosa* to sense its environment while also limiting iron availability. Moreover, as it can be actively taken up as a xenosiderophore, the ability of *P. aeruginosa* to switch from heme to iron-uptake will increase the potential for Ga-associated toxicity and dysregulation of iron homeostasis.

The heme sensing and uptake systems represent virulence mechanisms that can be targeted within the host but are not essential for survival outside of the host, thus face less selective pressure to develop resistance. GaSal and its analogs described herein represent a novel formulation strategy for gallium.

Figure 2B:
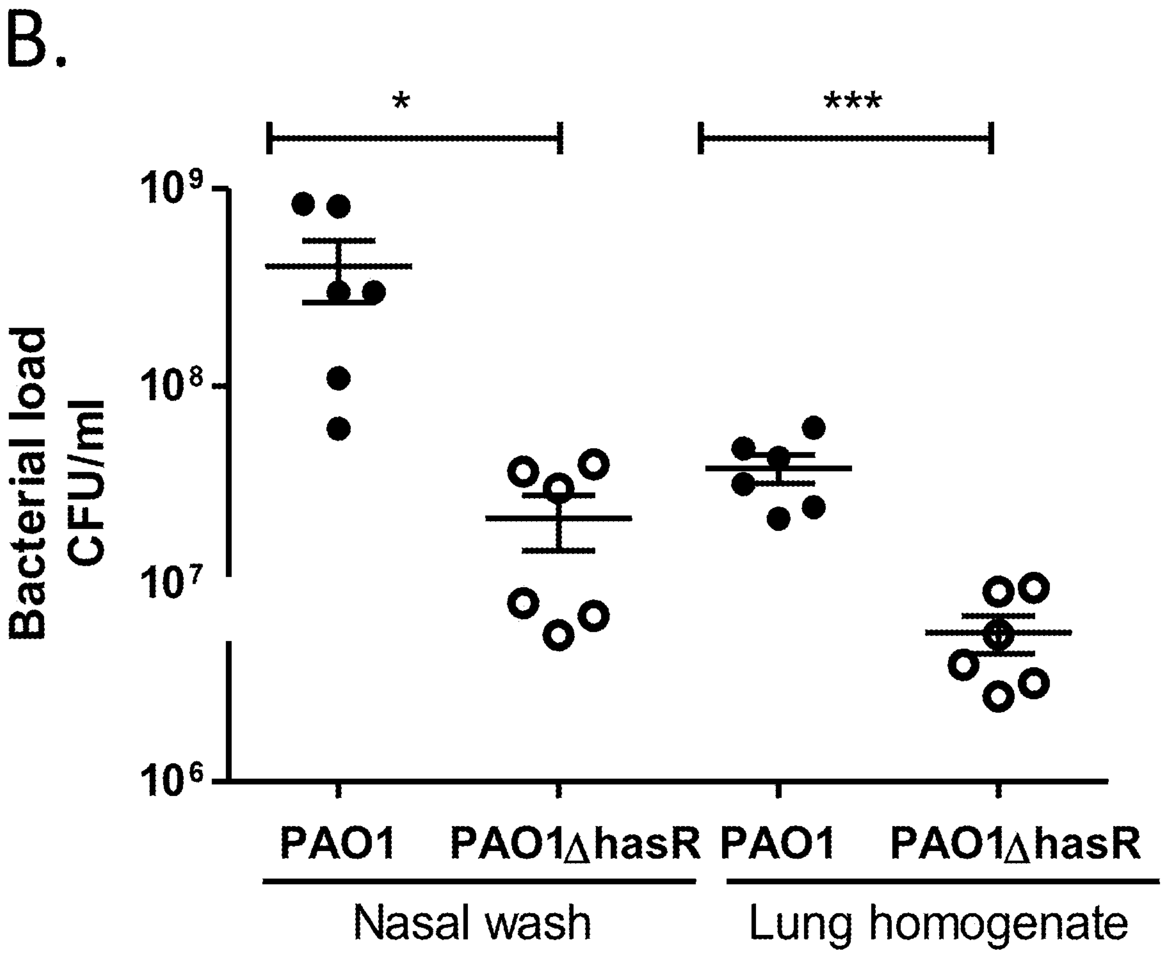
FIG. 2B illustrates bacterial load PAO1 (●) versus ΔhasR (○) in CD1 infected mice.

The Has heme uptake system is required for colonization and infection in the murine lung model. Transcriptomic studies showed the has system is the most upregulated operon in a murine infection model (FIG. 2A) and is required for adaptation within the host (FIG. 2B). The product of heme degradation, BVIXβ, has also been shown to positively regulate HasAp protein levels. Proteomics and thermal protein profiling (TPP) studies further identified a BVIXβ-dependent transcriptional repressor that regulates several operons including the pch biosynthesis genes (data not shown), consistent with the upregulation of the pyochelin (pch) system over that of pyoverdine (pvd) in a murine lung infection (FIG. 2B). Overall, heme metabolism plays a central role in iron acquisition, homeostasis and virulence. Thus, the ability to manipulate heme signaling and uptake has the potential to induce a system-wide disruption of intracellular iron homeostasis and virulence.

Inhibition of heme transfer from HasAp to HasR disrupts heme signaling. It has been shown that HasAp mutants that disrupt heme release to HasR lead to a down regulation of the 6-factor HasI and the ability of the bacterial cell to sense and utilize heme. Transcriptional reporter assays with the HasAp Y75H mutant which does not release heme to HasR showed no transcriptional activation of the has operon when compared to WT HasAp. The combined effect of dampening down the CSS cascade and reduction of intracellular accumulation of BVIX metabolites resulted in a further decrease in HasAp protein and secreted pyochelin levels. Thus disruption of the CSS cascade leads to a global disruption in iron uptake and intracellular iron homeostasis.

GaSal simultaneous inhibits heme sensing/transport and iron uptake. FeSal and GaSal bind to HasAp ~3-fold weaker than heme, although metal substitution from $Fe^{3+}$ to $Ga^{3+}$ had minimal impact (FIG. 10A). Using a β-galactosidase (β-Gal) hasR transcriptional reporter assay, the ability of the salophen complexes to induce the heme dependent CSS cascade was assessed. Both FeSal and GaSal showed inhibition of transcriptional activation relative to heme or GaPPIX. Although not wishing to be bound by any particular theory, this result suggests that the scaffold is critical for triggering the CSS cascade (FIG. 10B). However, while FeSal-HasAp supported growth, the GaSal-HasAp showed antibacterial activity with an $MIC_{50}$ of ~2.8 μg/mL (FIG. 10C). Subsequent growth studies with the ΔhasRΔphuR strain and FeSal demonstrated that growth was independent of uptake by the heme receptors, suggesting FeSal is actively taken up, probably via a siderophore receptor and is acting as a xenosiderophore (FIG. 10D). *P. aeruginosa* encodes several iron-regulated xenosiderophore receptors including PfuA and PiuA. Therefore, in contrast to FeSal, GaSal upon active uptake is toxic to the cell. Although not wishing to be bound by any particular theory, this results suggests that in addition to binding to HasAp and disrupting heme signaling and uptake, GaSal as a xenosiderophore causes disruption of intracellular iron homeostasis. This was further confirmed by growth studies with a ΔhasAp strain in the presence of a fixed concentration of GaSal and increasing amounts of exogenously added HasAp (FIG. 10E). Increasing concentrations of HasAp on sequestering GaSal alleviated the toxicity associated with active siderophore uptake. However, cultures were grown in the presence of high iron (0.4 μM $FeCl_3$) to ensure measurable growth and are not representative of physiological conditions where the combined effect of inhibiting heme signaling and GaSal active uptake would disrupt both the ability to sense and adapt to the extracellular environment, as well as dysregualtion of iron homeostasis on active uptake of Ga.

GaSal-HasAp binds to HasR with similar affinity as holo-HasAp. Formation of the GaSal-HasAp complex on addition of GaSal to the extracellular *P. aeruginosa* media containing secreted HasAp was confirmed by STD NMR (FIG. 11A). It was shown that the decreased activation of the CSS cascade was not due to the inability of the GaSal-HasAp to interact with the HasR receptor by surface plasmon resonance (SPR) (FIG. 11B). Holo-HasAp and the GaSal-HasAp bind to HasR with similar affinities. Attempts to measure binding kinetics were hampered by the lack of a measurable off rate ($k_{off}$) for HasAp, which relies on the energy dependent TonB-driven release of heme from HasAp to HasR. To determine if the decreased transcriptional activation and uptake of GaSal by the HasR receptor is the result of conformational differences between the GaSal- and holo-HasAp, the apo-, holo- and GaSal-HasAp complexes were analyzed by HDX-MS (FIGS. 12A-12C). Both heme and GaSal binding to HasAp resulted in significant protection from deuteration in the H32 and Y75 loops, as well as the heme binding site (β-sheets 1, 2, 3, and 5), consistent with loop closure and decreased solvent exposure on ligand binding (FIG. 12A). However, the H32 and Y75 loops showed significant differences between the two ligand-bound complexes. GaSal binding increased protection from deuteration on the H32 loop relative to the apo form, but not as strongly as heme binding (FIG. 12B). To assess if this observation carried a thermodynamic consequence, the melting temperatures of the three HasAp complexes were measured by circular dichroism (FIG. 12C). All three HasAp spectra showed similar degrees of folding at 25° C., indicating that the overall secondary structure is not significantly different upon ligand binding. However, the melting temperature of apo-HasAp (58° C.) was significantly increased by heme binding (>90° C.). The GaSal-HasAp also indicated increased thermal stability (65° C.), but not nearly to the extent of heme binding. Taken together the HDX-MS and CD data show significant differences between the holo- and GaSal-HasAp complexes not reflected in the crystal structure. These differences in conformational flexibility result in physiological consequences beyond the inability to trigger heme signaling and uptake, wherein the decreased stability of GaSal-HasAp compared to holo-HasAp may increase susceptibility to proteolysis within the host.

CADD SILCS characterization of HasAp. The SILCS methodology has been applied to map the functional group requirement to aid in directing ligand design (FIG. 13). Using SILCS, the 3D functional group probability distribution maps (termed FragMaps) are obtained that identify surface regions where different functional groups have favorable interactions. SILCS allows for 1) qualitative analysis of the protein-binding pocket to drive the design of accessible modifications and 2) quantitative predictions of changes in binding affinity for designed modifications. Shown in FIG. 13 are the resulting SILCS FragMaps overlaid on the GaSal-HasAp complex. Evident is the overlap of apolar FragMaps with the middle ring of salophen and Hbond acceptor FragMaps with the bridge nitrogen atoms. These results emphasize the importance of these groups for the activity of GaSal. Notably, the apolar FragMaps are extended to encompass the left ring of salophen, indicating that the 1, 2-positions are the most likely position for a substituent. FIG. 13 shows the spacious HasR docking site that is targeted for designing new compounds. These CADD tools have been effectively employed to design new ligands in efforts targeting transcriptional factor BCL6, GPCR mGluR5 and HemO.

Example 4: Synthesis and Testing of Small Molecule HasAp Inhibitors

CADD, chemistry, and validated assays are used to develop GaSal analogs with dual activities (FIG. 14). In Aim 1, 40 new GaSal analogs are initially synthesized. After determining the binding affinity, those with $K_D$<1 μM are further tested for inhibition of heme signaling and uptake using transcriptional reporter assays and $^{13}C$-heme LC-MS/MS assay, respectively. GaSal uptake by the siderophore receptors is quantified by measuring the intracellular Ga levels using ICP-MS. These efforts yield 2-4 candidates prioritized for further evaluation. In Aim 2, the $MIC_{50}$ and biofilm inhibition of the 2-4 selected compounds is determined on a panel of *P. aeruginosa* strains. For 1-2 top compounds, in vivo efficacy is tested in *C. elegans*. The HasAp binding epitope for the top compounds is then determined by STD-, HSQC-NMR, and HDX-MS. Completion of the studies provides tractable leads that simultaneously inhibit Pa heme signaling while inducing xenosiderophore uptake.

Synthesizing new HasAp inhibitors based on GaSal. It has been shown in this Example that GaSal binds to HasAp and inhibits the heme signaling while simultaneous acting as a xenosiderophore (FIGS. 11A-11B). SILCS CADD has also been used to design compounds that bind to the heme site and the HasR docking site of HasAp (FIG. 13). A new compound 2 has been synthesized by including a hydrophobic tail designed to fit into the HasR docking site of HasAp (FIG. 15A). An exemplary synthesis of compound 2 is shown in FIG. 28. 2,4-dihydroxybenzaldehyde is treated with 1-iodobutane and potassium carbonate in acetone, and stirred for 6 hours to produce aldehyde 2a, which was then treated with o-phenylenediamine in ethanol and heated to reflux overnight to produce imine 2b. Imine 2b was reacted with 2-hydroxybenzaldehyde in ethanol and heated to reflux for 2 hours to produce salophen complex 2c. Treatment of ligand 2c with $Ga(NO_3)_3$ and water in ethanol stirred overnight at reflux produced compound 2.

Compared to GaSal, the ether fragment of compound 2 can occupy the HasR interface (FIG. 13). To further enhance the potency of inhibitors, specific modifications are undertaken (FIG. 15A), and evaluated for their biological efficacy. Synthesis of compounds I-II begins with compound 3. Regioselective alkylation of 3 using iodoalkane (4) in the presence of $K_2CO_3$ provides ether 5. Condensation of 5 with amino precursor 6 yields the ligand 9. Treatment of ligand 9 with $Ga(NO_3)_3$ yields the final compounds I-II. Presented in FIG. 15B are the SILCS LGFE (ligand grid free energy) differences (kcal/mol) for the new compounds compared to compound 2 (LGFE −6.08 kcal/mol). Red are modifications that lead to most favorable LGFE values while yellow indicates those within 1.0 kcal/mol to 2. Priority is given to the ones shown in red followed by those in yellow.

Determine binding affinities ($K_D$) by FQ. $K_D$ values of all synthesized compounds are calculated by FQ using previously described methods. Binding affinities are determined in a final volume of 200 µL in black flat-bottom 96-well plates using microplate reader. HasAp concentration is kept at 1.0 µM in Tris-HCl buffer (20 mM, pH 8.0). Inhibitors solvated in DMSO are added across a concentration range of 0.01 to 100 µM. The HasAp excitation (295 nm) emission spectrum is recorded from 300-500 nm. The $K_D$ values are calculated from plots of total binding vs. ligand concentration, where total binding corresponds to the fraction of binding sites represented by the decrease in fluorescence at the maximum emission (332 nm). All experiments are performed in triplicate.

Testing new GaSal analogs ($K_D$<1 µM) for inhibition of heme sensing by transcriptional reporter assays. Transcriptional reporter assays to determine inhibition of the dependent CSS cascade are performed. It was previously shown that GaSal-HasAp inhibits transcriptional activation of the has operon (FIG. 10B). Furthermore, as the deletion of hasR attenuates virulence, inhibition of the signaling pathway combined with decreased heme uptake is a viable therapeutic strategy. PAO1 hasR-lacZ cultures are grown under iron limiting conditions in defined media (M9 or SSM) pelleted and washed to remove exogenous HasAp. Cells are resuspended to a final $OD_{600}$ of 0.05 and supplemented with 1.0 µM HasAp reconstituted with heme or selected GaSal derivatives. Samples are removed at various times (0.5-5 h) and assayed for β-Gal activity and corrected for differences in $OD_{600}$. Competition assays are also performed in the presence of varying heme and salophen concentrations.

Testing the inhibitory effects of selected GaSal analogs on heme uptake by $^{13}$C-heme isotopic labeling experiments. A quantitative isotopic $^{13}$C-heme labeling LC-MS/MS method was developed to distinguish BVIX metabolites derived from extracellular uptake ($^{13}$C-heme) versus those derived from intracellular biosynthesis ($^{12}$C-heme). Compounds that inhibit heme signaling are further tested for their ability to inhibit heme transport into the cell. Briefly, BVIX extracted from cultures at 2, 5 and 7 h (spiked with internal standard) are re-suspended in DMSO (10 µL) and diluted to 40 µL with the mobile phase (acetone: 20 mM formic acid 50:50, v/v) and filtered through a 0.45 µm PTFE syringe. The BVIX isomers are separated and analyzed by LC-MS/MS on a Waters TQD triple quadrupole mass spectrometer with an AQUITY H-Class UPLC over a reverse phase analytical column (4.6×250 mm) with a flow rate of 0.6 mL/min.

Testing the uptake of GaSal analogs by ICP-MS. Aliquots (2 mL) are removed from cultures grown as described for the heme uptake studies, pelleted, and washed in M9 media. Pellets are dissolved in trace-metal-free ultrapure 20% $HNO_3$ and boiled overnight at 100° C. Samples are diluted with ultrapure $H_2O$ to a final concentration of 2% $HNO_3$ and subjected to ICP-MS (Agilent 7700 ICP-MS). ICP-MS runs are calibrated with high purity iron standard solution, and raw ICP-MS data (ppb) are corrected for drift using values for scandium and germanium added as internal standards. Corrected values are normalized to culture density as determined by the $OD_{600}$. Experimentally determined values re the average of six biological replicates.

The characterization of GaSal as a dual mechanism inhibitor targeting both heme signaling and iron uptake provides a platform for the development of more potent antivirulents. Although the FQ assay can generate false positives, the robust suite of assays including MIC/biofilm screening, transcriptional reporter, heme- and Ga-uptake assays further validates compounds with $K_D$ values (<1 µM) (FIG. 14). The screening efforts provide several (4-6) inhibitors with varying degrees of potency in vitro. Selection of lead candidates (2-4) is based on those that further disrupt the heme signaling, while not significantly decreasing active siderophore uptake. Although ICP-MS measures Ga uptake and not necessarily the salophen scaffold, the stability of the GaSal-HasAp in the secreted media (FIG. 11A) supports transport via a siderophore receptor. GaSal uptake can also be confirmed by performing $^{13}$C-salophen uptake studies similar to those described for heme. Other analogues include macrocyclic ligand (III) (FIG. 9), wherein the linker "n" is varied in length. The top 5-10% of compounds are then subjected to mechanistic studies and in vivo efficacy in *C. elegans* as described below.

Determine MICs of selected GaSal and analogs in defined media. *P. aeruginosa* growth inhibition is performed on a Bioscreen C automated growth curve (100×100 sample well) system. Briefly, the high throughput liquid handling system is used to seed the plates with *P. aeruginosa* (PAO1 strain) at an $OD_{600}$ of 0.05, following which the inhibitor or the solvent (0.1% DMSO or MeOH) is added to a final volume of 200 µL. Growth at 600 nm is recorded every 30 min over 12 h. Growth inhibition studies are performed in minimal media (M9) supplemented with or without heme, and in SSM which mimics the growth environment of the CF lung. Using a similar protocol, the killing effects of GaSal and new analogs in are also screened in 15 clinical isolates that are obtained from CF lung, eye infections, and skin wounds.

Assaying biofilm inhibition by GaSal and selected derivatives. Minimal biofilm eradication concentrations (MBEC) are determined in 96-well MBEC plates. Plates containing M9 are inoculated with *P. aeruginosa* (1×$10^8$ CFU/mL), covered, and incubated at 37° C. for 48 h, allowing biofilms to form on the pegs. After incubation the peg lid is washed with 0.9% saline to remove non-adherent bacteria, then transferred to a fresh 96-well challenge plate containing M9 supplemented with selected inhibitors (9-300 µg/mL) and either 10 µM heme (pH 7.5) or 10 µM $FeCl_3$. Biofilms are incubated at 37° C. for 24 h, at which point the pegs are washed with 0.9% saline, stained with 0.1% crystal violet solution for 10 min and rinsed with water. After drying, the peg lid is destained in 200 µL of acetic acid (30%), diluted 1 in 10 and the dye measured at $OD_{595}$. MBEC values represent the lowest concentration of compound to which 99.9% of cells will be dispersed from the biofilm. MBEC values are calculated by subtracting the $OD_{595}$ of wells containing M9 and all supplements minus *P. aeruginosa* and averaged from at least 5 biological replicates.

Testing efficacy of GaSal and top derivatives in a *C. elegans* infection model. The *C. elegans* infection model is valuable for screening potential antimicrobials as it retains innate immune responses tractable to mammalian systems. The model has been used to screen *P. aeruginosa* HemO inhibitors and is adapted to a HTS 96-well microplate format. *C. elegans* glp-4(bn2)1 worms are synchronized and L1-stage worms plated on NGM agar for 8 to 12 h at 25° C. Following washing in M9 media, 15 worms are used to seed 96-microtiter plates containing *P. aeruginosa* ($OD_{600}$ 0.04) in 70% M9 buffer, 10% TSB, and 1% DMSO or compounds dissolved in DMSO. Following 1-4 days incubation cell debris and bacteria are removed by aspiration and live worms counted by staining with Sytox Orange and measuring fluorescence em at 610 nm (ex 535 nm). The bacterial load (CFUs) recovered from the worm intestines following infection are determined using previously described methods. The uninfected *C. elegans* on treatment with compound alone provide a first pass toxicity assay.

Determine the binding mode of GaSal and top derivatives by STD-, $^{1}H$-$^{15}N$ HSQC-NMR, and HDX-MS. STD-, $^{1}H$-$^{15}N$ HSQC-NMR, and HDX-MS techniques have previously been used to determine the binding epitope of Pa HemO inhibitors. STD-NMR is performed on HasAp (5-10 μM) in potassium phosphate (50 mM, pH 7.4, $D_2O$) to which is added 50 μL saturated compound in DMSO$d_6$. Following incubation (4 h) 4,4-dimethyl-4-silapentane-1-sulfonic acid (DSS, 3 μL in D20) is added as internal standard and spectra recorded as reported. HSQC-NMR is performed using 512 (t1)×4096 (t2) complex points with a width of 1800 and 9000 Hz, respectively. Data is collected using an interscan delay of 1 s and 16 transients per fid, and processed with NMR-Pipe. Combined chemical shift differences between the apo and each of the titration points are calculated using the following equation:

$$\Delta ppm=(\Delta\delta HN)^2+(\Delta\delta N\times 0.2)^2$$

The nitrogen shift changes are multiplied by 0.2 to compensate for the difference in chemical shift range between proton and nitrogen. Samples contain HasAp (125 μM), compound (250 μM) phosphate (50 mM), KCl (100 mM) in $H_2O$/DMSO$d_6$ (95:5).

HDX-MS is performed with HasAp (100 μM) in HEPES (20 mM, pH 7.4) diluted 50-fold with 20 mM HEPES buffer in $D_2O$. Aliquots (100 pmol) are removed at 0, 10 and 30 min, and the deuteration reaction quenched by lowering the pH to 2.5 with HCl. For reactions of inhibitor bound HasAp, the inhibitor required for 95% binding is estimated from the $K_D$, and a 10 to 20-fold excess is incubated with HasAp. A 2-fold excess of inhibitor is added to the deuteration buffer to account for exchange during incubation. Quenched samples are analyzed on a Waters nanoACQUITY UPLC system with HDX manager. The protein is digested online at 10° C. by rapid passage over an Enzymate BEH Pepsin Column. The digest is trapped and desalted online on an ACQUITY Vanguard BEH C18 pre-column at 0° C. for 4 min at a flow rate of 125 μL/min in 0.1% formic acid. Peptides are separated on an ACQUITY UPLC BEH C18 column at 0° C. over a 15 min acetonitrile gradient (5-50%) with 0.1% formic acid at a flow rate of 40 μL/min. The eluent is directed into the ion source of a coupled SYNAPT G2 HDMS mass spectrometer. Mass spectra are acquired in MSE mode (m/z range 50-2000). Non-deuterated peptides generated on digestion of HasAp and identified using Waters ProteinLynx Global Server software are used to generate a peptide list for import into Waters DynamX software for identification of deuterated peptides, and to calculate their relative deuterium incorporation using the 0 s sample as reference.

All chromosomal or plasmid borne assays are checked by PCR following the assay. *E. coli* expression plasmids for protein generation are routinely checked by sequencing. Purified proteins are analyzed by SDS-PAGE and by MALDI-TOF mass spectrometry. Reporter, $^{13}C$-heme uptake, and ICP-MS assays are performed on a minimum of 5 biological and 3 technical replicates per sample. Metabolite extraction efficiency are determined by addition of internal standard and concentrations from calibration curves for each metabolite. MS instrumentation sensitivity is determined by running internal standards to assess day to day variation of instrumentation. Peptide assignments are set at 1% false detection rate (FDR) and relative abundance will be considered significant >1.5 fold and $p<0.05$. All SMPs and are verified by NMR and high accuracy mass spectrometry prior to use.

Example 3: Gallium-Salophen Complex for *P. aeruginosa* Infections

*P. aeruginosa* is a gram-negative bacteria which have multiple mechanisms for protection from immune cells and antibiotics, such as efflux pumps, β-lactamases, aminoglycoside-modifying enxymes, and biofilms (FIG. 16).

*P. aeruginosa* causes opportunistic but life-threatening infections in immunocompromised patients, such as in patients with cystic fibrosis, Type 2 diabetes, IV drug abuses, and patients with burns or deep wounds (FIG. 17). These subjects are at risk for pneumonia, osteomyeleitis, tricuspid valve endocarditis, and ecthyma gangrenosum, respectively, resulting from *P. aeruginosa* infection. Although there are treatments available for *P. aeruginosa* infections (FIG. 18), overall the only effective family is highly toxic, causing kidney failure. At the same time, *P. aeruginosa* has developed strong resistance to all other classes. Recent efforts have focused on the development of novel anti-pseudomonal agents by targeting the virulence factors that is important for bacterial cells to communicate with each other, especially for the essential metal iron.

*P. aeruginosa* has developed two systems for iron acquisition—the heme aquisition system and the siderophore iron uptake system (FIG. 19). The siderophore iron uptake system operates in an aerobic environment, while the heme uptake system results in the formation of biofilms. FIG. 20 shows a more detailed description of the heme acquisition system of *P. aeruginosa.*

In some embodiments, the antibiotic itself can be the siderophore (FIG. 21). For example, Cefiderocol is a catechol-mimic siderophore, which was approved in IV form in November 2019 for use against complicated UTI infections (kidney disease) (FIG. 21). For cephalosporin, resistance is due to decreased permeability of the OM (lower porin expression) active drug efflux. Some compounds are transported by xenosiderophore receptors, such as in *E. coli* (CirA and GiuA) and *P. aeruginosa* (PiuA), while mutations with a deficiency in PiuA led to increase in MIC (~20-fold). Resistance rates are lower than ceftazidime alone but do appear ($<7\times10^{-9}$ at 10×MIC). The mechanism of resistance is similar to the conjugates but not as rapid.

Accordingly, there is a need to design and synthesize compounds that simultaneously target both the heme signaling and utilization and the iron acquisition system as a therapeutic strategy. In some embodiments, the compound design strategy described herein includes compounds that bind to HasAp while simultaneously targeting the iron update system to enter the cell (FIG. 22). The binding affinity ($K_D$, nM) of GaSal to HasAp was found to be 1000 220, which is lower than the binding affinity of FeSal for Has Ap (1100±100) (FIG. 23). GalSal was also found to inhibit heme signaling and utilization (FIG. 24). Inhibition of heme signaling results in the production of β-galactosidase (FIG. 24). β-galactosidase was quantitatively examined, and it was found that at 5 hours, treatment with GaSal resulted in increased β-galactosidase when compared to FeSal. GaSal was also found to kill *P. aeruginosa* by way of gallium toxicity (FIGS. 25A-25B). While FeSal-HasAp was found to support growth (FIG. 25A), GaSal-HasAp exhibited antibacterial activity with an $MIC_{50}$ of ~2.8 μg/mL (FIG. 25B).

As described in this Example, the small molecule compounds disclosed herein exhibit the dual activity of inhibiting the heme dependent CSS cascade while acting as a substrate for siderophore receptor uptake. Further, targeting HasAp with GaSal was found to blocks the ability of *P. aeruginosa* to sense its environment while also limiting iron availability. Moreover, as GaSal can be actively taken up as a xenosiderophore, the ability of *P. aeruginosa* to switch from heme to iron-uptake will increase the potential for Ga-associated toxicity and dysregulation of iron homeostasis. The heme sensing and uptake systems represent virulence mechanisms that can be targeted within the host but are not essential for survival outside of the host, and therefore the bacteria face less selective pressure to develop resistance. Thus, GaSal and analogues as described herein represent a novel formulation strategy for gallium, which was found to be an effective an iron-mimicking element.

Example 4: Synthesis and Examples of Gallium Salophen Complexes

This Example describes an example of a synthesis of gallium salophen compounds. In one embodiment, compounds of I are prepared by reacting a dianiline with an aldehyde to form an imine, which is then further reacted with a different aldehyde to arrive at the salophen ligand. This ligand is treated with $Ga(NO_3)_3$ in a solvent such as ethanol and then heated to reflux in order to arrive at the general gallium salophen complex I (FIG. 26). In one embodiment, compounds of II are prepared by reacting a dianiline with at least two equivalents of aldehyde to form a salophen ligand. This ligand is treated with $Ga(NO_3)_3$ in a solvent such as ethanol and then heated to reflux in order to arrive at the general gallium salophen complex II (FIG. 26). Examples of analogs of complexes I and II are also illustrated in FIG. 26.

In one embodiment, gallium salophen complexes of formula (I) are prepared by reacting a dianiline with an aldehyde that comprises $(R^2)_p$ to form an imine, which is then further reacted with an aldehyde comprising $(R^3)_q$, to arrive at the salophen ligand. This ligand is treated with $Ga(NO_3)_3$ in a solvent such as ethanol and then heated to reflux in order to arrive at the general gallium salophen complex of formula (I) (FIG. 27). In some embodiments, $R^2$ is not equivalent to $R^3$. In some embodiments, $R^2$ and $R^3$ are equivalent.

Example 5: Synthesis and Examples of Gallium Salophen Complexes

The structures of GaSal-1, GaSal-2, GaSal-3, and GaSal-4 are shown in FIG. 29.

Synthesis of GaSal-1

The synthesis of GaSal-1 began with 2,4-dihydroxybenzaldehyde (FIG. 30). Regioselective alkylation of the 4-hydroxy group using 1-bromo-2-(2-methoxyethoxy)ethane provided 2-hydroxy-4-(2-(2-methoxyethoxy)ethoxy)benzaldehyde, which was allowed to react with $Ga(NO_3)_3$ in refluxing EtOH to yield the complex GaSal-1.

Synthesis of GaSal-2

The synthesis of GaSal-2 started with 2,4-dihydroxybenzaldehyde (FIG. 31). Regioselective alkylation of the 4-hydroxy group using 1,2-dibromoethane provided 4-(2-bromoethoxy)-2-hydroxybenzaldehyde. Nucleophilic substitution of the bromide using trimethylamine (4.2 M) in EtOH generated 2-(4-formyl-3-hydroxyphenoxy)-N,N,N-trimethylethan-1-aminium bromide, which was allowed to react with $Ga(NO_3)_3$ in refluxing EtOH to yield the complex GaSal-2.

Synthesis of GaSal-3

The synthesis of GaSal-3 is detailed in FIG. 32. Regioselective alkylation of the 4-hydroxy group of 2,4-dihydroxybenzaldehyde using 1,2-dibromoethane provided 4-(2-bromoethoxy)-2-hydroxybenzaldehyde. Nucleophilic substitution of the bromide using morpholine in the presence of KHCO3 and KI generated 2-hydroxy-4-(2-morpholinoethoxy)benzaldehyde, which was allowed to react with $Ga(NO_3)_3$ in refluxing EtOH to yield the complex GaSal-3.

Synthesis of GaSal-4

The synthesis of GaSal-4 is detailed in FIG. 33. Regioselective alkylation of the 4-hydroxy group of 2,4-dihydroxybenzaldehyde using ethyl 2-bromoacetate in the presence of $K_2CO_3$ provided ethyl 2-(4-formyl-3-hydroxyphenoxy)acetate. Saponification of the ethylester in NaOH generated 2-(4-formyl-3-hydroxyphenoxy)acetic acid, which was allowed to react with $Ga(NO_3)_3$ in Refluxing EtOH to Yield the Complex GaSal-4.

REFERENCES

1. CDC. Antibiotic Resistance Threats in the United States, 2019; Atlanta, Ga., 2019.
2. Kerr, K. G., Snelling, A. M. (2009) *Pseudomonas aeruginosa*: A Formidable and Ever-Present Adversary. J. Hosp. Infect. 73 (4), 338-344. DOI: 10.1016/j.jhin.2009.04.020.
3. Costerton, J. W. (2001) Cystic Fibrosis Pathogenesis and the Role of Biofilms in Persistent Infection. Trends Microbiol. 9 (2), 50-52.
4. Brussow, H. (2012) *Pseudomonas* Biofilms, Cystic Fibrosis, and Phage: A Silver Lining?MBio 3 (2), e00061-12. DOI: 10.1128/mBio.00061-12.
5. Burrows, L. L. (2018) The Therapeutic Pipeline for *Pseudomonas aeruginosa* Infections. ACS Infect. Dis. 4 (7), 1041-1047. DOI: 10.1021/acsinfecdis.8b00112.
6. Lee, H. H., Collins, J. J. (2012) Microbial Environments Confound Antibiotic Efficacy. Nat. Chem. Biol. 8 (1), 6-9. DOI: 10.1038/nchembio.740.
7. Dickey, S. W., Cheung, G. Y. C., Otto, M. (2017) Different Drugs for Bad Bugs: Antivirulence Strategies in the Age of Antibiotic Resistance. Nat. Rev. Drug Discov. 16 (7), 457-471. DOI: 10.1038/nrd.2017.23.
8. Runyen-Janecky, L. J. (2013) Role and Regulation of Heme Iron Acquisition in Gram-Negative Pathogens. Front. Cell. Infect. Microbiol. 3, 55. DOI: 10.3389/fcimb.2013.00055.
9. Fetherston, J. D., Bertolino, V. J., Perry, R. D. (1999) YbtP and YbtQ: Two ABC Transporters Required for Iron Uptake in *Yersinia pestis*. Mol. Microbiol. 32 (2), 289-299. DOI: 10.1046/j.1365-2958.1999.01348.x.
10. Schryvers, A. B., Stojiljkovic, I. (1999) Iron Acquisition Systems in the Pathogenic *Neisseria*. Mol. Microbiol. 32 (6), 1117-1123. DOI: 10.1046/j.1365-2958.1999.01411.x.
11. Wandersman, C., Stojiljkovic, I. (2000) Bacterial Heme Sources: The Role of Heme, Hemoprotein Receptors and Hemophores. Curr. Opin. Microbiol. 3 (2), 215-220. DOI: 10.1016/S1369-5274(00)00078-3.
12. Skaar, E. P. (2010) The Battle for Iron between Bacterial Pathogens and Their Vertebrate Hosts. PLoS Pathog. 6 (8), e1000949. DOI: 10.1371/journal.ppat.1000949.
13. Takase, H., Nitanai, H., Hoshino, K., Otani, T. (2000) Impact of Siderophore Production on *Pseudomonas aeruginosa* Infections in Immunosuppressed Mice. Infect. Immun. 68 (4), 1834-1839. DOI: 10.1128/IAI.68.4.1834-1839.2000.
14. Skaar, E. P., Humayun, M., Bae, T., DeBord, K. L., Schneewind, O. (2004) Iron-Source Preference of *Staphy-*

*lococcus aureus* Infections. Science. 305 (5690), 1626-1628. DOI: 10.1126/science.1099930.

15. Konings, A. F., Martin, L. W., Sharples, K. J., Roddam, L. F., Latham, R., Reid, D. W., Lamont, I. L. (2013) *Pseudomonas aeruginosa* Uses Multiple Pathways To Acquire Iron during Chronic Infection in Cystic Fibrosis Lungs. Infect. Immun. 81 (8), 2697-2704. DOI: 10.1128/IAI.00418-13.
16. Marvig, R. L., Sommer, L. M., Molin, S., Johansen, H. K. (2015) Convergent Evolution and Adaptation of *Pseudomonas aeruginosa* within Patients with Cystic Fibrosis. Nat. Genet. 47 (1), 57-64. DOI: 10.1038/ng.3148.
17. Nguyen, A. T., O'Neill, M. J., Watts, A. M., Robson, C. L., Lamont, I. L., Wilks, A., Oglesby-Sherrouse, A. G. (2014) Adaptation of Iron Homeostasis Pathways by a *Pseudomonas aeruginosa* Pyoverdine Mutant in the Cystic Fibrosis Lung. J. Bacteriol. 196 (12). DOI: 10.1128/JB.01491-14.
18. Smith, A. D., Wilks, A. (2015) Differential Contributions of the Outer Membrane Receptors PhuR and HasR to Heme Acquisition in *Pseudomonas aeruginosa*. J. Biol. Chem. 290 (12), 7756-7766. DOI: 10.1074/jbc.M114.633495.
19. Mouriño, S., Giardina, B. J., Reyes-Caballero, H., Wilks, A. (2016) Metabolite-Driven Regulation of Heme Uptake by the Biliverdin IXP/S-Selective Heme Oxygenase (HemO) of *Pseudomonas aeruginosa*. J. Biol. Chem. 291 (39), 20503-20515. DOI: 10.1074/jbc.M116.728527.
20. Dent, A. T., Mouriño, S., Huang, W., Wilks, A. (2019) Post-Transcriptional Regulation of the *Pseudomonas aeruginosa* Heme Assimilation System (Has) Fine-Tunes Extracellular Heme Sensing. J. Biol. Chem. 294 (8), 2771-2785. DOI: 10.1074/jbc.RA118.006185.
21. Damron, F. H., Oglesby-Sherrouse, A. G., Wilks, A., Barbier, M. (2016) Dual-Seq Transcriptomics Reveals the Battle for Iron during *Pseudomonas aeruginosa* Acute Murine Pneumonia. Sci. Rep. 6 (1), 39172. DOI: 10.1038/srep39172.
22. Winkler, M. L., Papp-Wallace, K. M., Hujer, A. M., Domitrovic, T. N., Hujer, K. M., Hurless, K. N., Tuohy, M., Hall, G., Bonomo, R. A. (2015) Unexpected Challenges in Treating Multidrug-Resistant Gram-Negative Bacteria: Resistance to Ceftazidime-Avibactam in Archived Isolates of *Pseudomonas aeruginosa*. Antimicrob. Agents Chemother. 59 (2), 1020-1029. DOI: 10.1128/AAC.04238-14.
23. Braz, V. S., Furlan, J. P. R., Fernandes, A. F. T., Stehling, E. G. (2016) Mutations in NalC Induce MexAB-OprM Overexpression Resulting in High Level of Aztreonam Resistance in Environmental Isolates of *Pseudomonas aeruginosa*. FEMS Microbiol. Lett. 363 (16). DOI: 10.1093/femsle/fnw166.
24. Létoffé, S., Redeker, V., Wandersman, C. (1998) Isolation and Characterization of an Extracellular Haem-Binding Protein from *Pseudomonas aeruginosa* That Shares Function and Sequence Similarities with the *Serratia Marcescens* HasA Haemophore. Mol. Microbiol. 28 (6), 1223-1234. DOI: 10.1046/j.1365-2958.1998.00885.x.
25. Jepkorir, G., Rodriguez, J. C., Rui, H., Im, W., Lovell, S., Battaile, K. P., Alontaga, A. Y., Yukl, E. T., Moënne-Loccoz, P., Rivera, M. (2010) Structural, NMR Spectroscopic, and Computational Investigation of Hemin Loading in the Hemophore HasAp from *Pseudomonas aeruginosa*. J. Am. Chem. Soc. 132 (28), 9857-9872. DOI: 10.1021/ja103498z.
26. Kumar, R., Qi, Y., Matsumura, H., Lovell, S., Yao, H., Battaile, K. P., Im, W., Moënne-Loccoz, P., Rivera, M. (2016) Replacing Arginine 33 for Alanine in the Hemophore HasA from *Pseudomonas aeruginosa* Causes Closure of the H32 Loop in the Apo-Protein. Biochemistry 55 (18), 2622-2631. DOI: 10.1021/acs.biochem.6b00239.
27. Kumar, R., Matsumura, H., Lovell, S., Yao, H., Rodriguez, J. C., Battaile, K. P., Moënne-Loccoz, P., Rivera, M. (2014) Replacing the Axial Ligand Tyrosine 75 or Its Hydrogen Bond Partner Histidine 83 Minimally Affects Hemin Acquisition by the Hemophore HasAp from *Pseudomonas aeruginosa*. Biochemistry 53 (13), 2112-2125. DOI: 10.1021/bi500030p.
28. Caillet-Saguy, C., Piccioli, M., Turano, P., Izadi-Pruneyre, N., Delepierre, M., Bertini, I., Lecroisey, A. (2009) Mapping the Interaction between the Hemophore HasA and Its Outer Membrane Receptor HasR Using CRINEPT-TROSY NMR Spectroscopy. J. Am. Chem. Soc. 131 (5), 1736-1744. DOI: 10.1021/ja804783x.
29. Wojtowicz, H., Prochnicka-Chalufour, A., de Amorim, G. C., Roudenko, O., Simenel, C., Malki, I., Pehau-Arnaudet, G., Gubellini, F., Koutsioubas, A., Perez, J., Delepelaire, P., Delepierre, M., Fronzes, R., Izadi-Pruneyre, N. (2016) Structural Basis of the Signalling through a Bacterial Membrane Receptor HasR Deciphered by an Integrative Approach. Biochem. J. 473 (14). DOI: 10.1042/BCJ20160131.
30. Shirataki, C., Shoji, O., Terada, M., Ozaki, S., Sugimoto, H., Shiro, Y., Watanabe, Y. (2014) Inhibition of Heme Uptake in *Pseudomonas aeruginosa* by Its Hemophore (HasA p) Bound to Synthetic Metal Complexes. Angew. Chemie Int. Ed. 53 (11), 2862-2866. DOI: 10.1002/anie.201307889.
31. Shisaka, Y., Iwai, Y., Yamada, S., Uehara, H., Tosha, T., Sugimoto, H., Shiro, Y., Stanfield, J. K., Ogawa, K., Watanabe, Y., Shoji, O. (2019) Hijacking the Heme Acquisition System of *Pseudomonas aeruginosa* for the Delivery of Phthalocyanine as an Antimicrobial. ACS Chem. Biol. 14 (7), 1637-1642. DOI: 10.1021/acschembio.9b00373.
32. Mandal, S. S. (2011) Metallo-Salen Complexes Show Promise towards Treatment of Leukemia. Leuk. Res. 35 (5), 571-572. DOI: 10.1016/j.leukres.2010.12.027.
33. Vanco, J., Sindelár, Z., Dvorár, Z., Trávnícek, Z. (2015) Iron-Salophen Complexes Involving Azole-Derived Ligands: A New Group of Compounds with High-Level and Broad-Spectrum in Vitro Antitumor Activity. J. Inorg. Biochem. 142, 92-100. DOI: 10.1016/J.J-INORGBIO.2014.10.002.
34. Sagasser, J., Ma, B. N., Baecker, D., Salcher, S., Hermann, M., Lamprecht, J., Angerer, S., Obexer, P., Kircher, B., Gust, R. (2019) A New Approach in Cancer Treatment: Discovery of Chlorido[N, N'-Disalicylidene-1,2-Phenylenediamine]Iron(III) Complexes as Ferroptosis Inducers. J. Med. Chem. 62 (17), 8053-8061. DOI: 10.1021/acs.jmedchem.9b00814.
35. Kaneko, Y., Thoendel, M., Olakanmi, O., Britigan, B. E., Singh, P. K. (2007) The Transition Metal Gallium Disrupts *Pseudomonas aeruginosa* Iron Metabolism and Has Antimicrobial and Antibiofilm Activity. J. Clin. Invest. 117 (4), 877-888. DOI: 10.1172/JCI30783.
36. Apseloff, G. (1999) Therapeutic Uses of Gallium Nitrate: Past, Present, and Future. Am. J. Ther. 6 (6), 327-339. DOI: 10.1097/00045391-199911000-00008.
37. Chang, D., Garcia, R. A., Akers, K. S., Mende, K., Murray, C. K., Wenke, J. C., Sanchez, C. J., Jr. (2016) Activity of Gallium Meso- and Protoporphyrin IX against Biofilms of Multidrug-Resistant *Acinetobacter baumannii* Isolates. Pharmaceuticals (Basel). 9 (1). DOI: 10.3390/ph9010016.

38. Hijazi, S., Visca, P., Frangipani, E. (2017) Gallium-Protoporphyrin IX Inhibits *Pseudomonas aeruginosa* Growth by Targeting Cytochromes. Front. Cell. Infect. Microbiol. 7, 12. DOI: 10.3389/fcimb.2017.00012.
39. Banin, E., Lozinski, A., Brady, K. M., Berenshtein, E., Butterfield, P. W., Moshe, M., Chevion, M., Greenberg, E. P., Banin, E. (2008) The Potential of Desferrioxamine-Gallium as an Anti-*Pseudomonas* Therapeutic Agent. Proc. Natl. Acad. Sci. 105 (43), 16761-16766. DOI: 10.1073/pnas.0808608105.
40. Pandey, A., Savino, C., Ahn, S. H., Yang, Z., Van Lanen, S. G., Boros, E. (2019) Theranostic Gallium Siderophore Ciprofloxacin Conjugate with Broad Spectrum Antibiotic Potency. J. Med. Chem. 62 (21), 9947-9960. DOI: 10.1021/acs.jmedchem.9b01388.
41. Goss, C. H., Kaneko, Y., Khuu, L., Anderson, G. D., Ravishankar, S., Aitken, M. L., Lechtzin, N., Zhou, G., Czyz, D. M., McLean, K., Olakanmi, O., Shuman, H. A., Teresi, M., Wilhelm, E., Caldwell, E., Salipante, S. J., Hornick, D. B., Siehnel, R. J., Becker, L., Britigan, B. E., Singh, P. K. (2018) Gallium Disrupts Bacterial Iron Metabolism and Has Therapeutic Effects in Mice and Humans with Lung Infections. Sci. Transl. Med. 10 (460). DOI: 10.1126/scitranslmed.aat7520.
42. Silva, P. CF Foundation Grant to Support Testing of Bacterial Lung Infection Treatment. Cystic Fibrosis News Today. Jan. 12, 2017.
43. García-Contreras, R., Pérez-Eretza, B., Lira-Silva, E., Jasso-Chávez, R., Coria-Jiménez, R., Rangel-Vega, A., Maeda, T., Wood, T. K. (2014) Gallium Induces the Production of Virulence Factors in *Pseudomonas aeruginosa*. Pathog. Dis. 70 (1), 95-98. DOI: 10.1111/2049-632X.12105.
44. Stojiljkovic, I., Kumar, V., Srinivasan, N. (1999) Non-Iron Metalloporphyrins: Potent Antibacterial Compounds That Exploit Haem/Hb Uptake Systems of Pathogenic Bacteria. Mol. Microbiol. 31 (2), 429-442. DOI: 10.1046/j.1365-2958.1999.01175.x.
45. Bonchi, C., Imperi, F., Minandri, F., Visca, P., Frangipani, E. (2014) Repurposing of Gallium-Based Drugs for Antibacterial Therapy. BioFactors 40 (3), 303-312. DOI: 10.1002/biof.1159.
46. Rangel-Vega, A., Bernstein, L. R., Mandujano-Tinoco, E. A., Garci-a-Contreras, S. J., Garcia-Contreras, R. (2015) Drug Repurposing as an Alternative for the Treatment of Recalcitrant Bacterial Infections. Front. Microbiol. 6, 282. DOI: 10.3389/fmicb.2015.00282.
47. Luscher, A., Moynie, L., Auguste, P. Saint, Bumann, D., Mazza, L., Pletzer, D., Naismith, J. H., Köhler, T. (2018) TonB-Dependent Receptor Repertoire of *Pseudomonas aeruginosa* for Uptake of Siderophore-Drug Conjugates. Antimicrob. Agents Chemother. 62 (6). DOI: 10.1128/AAC.00097-18.
48. Mayer, M., Meyer, B. (2001) Group Epitope Mapping by Saturation Transfer Difference NMR To Identify Segments of a Ligand in Direct Contact with a Protein Receptor. J. Am. Chem. Soc. 123 (25), 6108-6117. DOI: 10.1021/JA0100120.
49. Wolff, N., Izadi-Pruneyre, N., Couprie, J., Habeck, M., Linge, J., Rieping, W., Wandersman, C., Nilges, M., Delepierre, M., Lecroisey, A. (2008) Comparative Analysis of Structural and Dynamic Properties of the Loaded and Unloaded Hemophore HasA: Functional Implications. J. Mol. Biol. 376 (2), 517-525. DOI: 10.1016/J.JMB.2007.11.072.
50. (50) Deredge, D. J., Huang, W., Hui, C., Matsumura, H., Yue, Z., Moënne-Loccoz, P., Shen, J., Wintrode, P. L., Wilks, A. (2017) Ligand-Induced Allostery in the Interaction of the *Pseudomonas aeruginosa* Heme Binding Protein with Heme Oxygenase. Proc. Natl. Acad. Sci. U.S.A 114 (13), 3421-3426. DOI: 10.1073/pnas.1606931114.
51. Heinzl, G. A., Huang, W., Robinson, E., Xue, F., Moenne-Loccoz, P., Wilks, A. (2018) The Asp99-Arg188 Salt Bridge of the *Pseudomonas aeruginosa* HemO Is Critical in Allowing Conformational Flexibility during Catalysis. JBIC J. Biol. Inorg. Chem. 23 (7), 1057-1070. DOI: 10.1007/s00775-018-1609-x.
52. Wong, R. J., Vreman, H. J., Schulz, S., Kalish, F. S., Pierce, N. W., Stevenson, D. K. (2011) In Vitro Inhibition of Heme Oxygenase Isoenzymes by Metalloporphyrins. J. Perinatol. 31 (1), S35-S41. DOI: 10.1038/jp.2010.173.
53. Thöny-Meyer, L. Heme Transport and Incorporation into Proteins. In Tetrapyrroles; Warren, M. J., Smith, A. G., Eds.; Springer New York: New York, N.Y., 2009; pp 149-159. DOI: 10.1007/978-0-387-78518-9_9.
54. Sudhamsu, J., Kabir, M., Airola, M. V., Patel, B. A., Yeh, S.-R., Rousseau, D. L., Crane, B. R. (2010) Co-Expression of Ferrochelatase Allows for Complete Heme Incorporation into Recombinant Proteins Produced in *E. coli*. Protein Expr. Purif. 73 (1), 78-82. DOI: 10.1016/J.PEP.2010.03.010.
55. Cornelis, P., Dingemans, J. (2013) *Pseudomonas aeruginosa* Adapts Its Iron Uptake Strategies in Function of the Type of Infections. Front. Cell. Infect. Microbiol. 3, 75. DOI: 10.3389/fcimb.2013.00075.
56. Moynié, L., Milenkovic, S., Mislin, G. L. A., Gasser, V., Malloci, G., Baco, E., McCaughan, R. P., Page, M. G. P., Schalk, I. J., Ceccarelli, M., Naismith, J. H. (2019) The Complex of Ferric-Enterobactin with Its Transporter from *Pseudomonas aeruginosa* Suggests a Two-Site Model. Nat. Commun. 10 (1), 3673. DOI: 10.1038/s41467-019-11508-y.
57. Choi, S.-R., Britigan, B. E., Narayanasamy, P. (2019) Iron/Heme Metabolism-Targeted Gallium(III) Nanoparticles Are Active against Extracellular and Intracellular *Pseudomonas aeruginosa* and *Acinetobacter baumannii*. Antimicrob. Agents Chemother. 63 (4), e02643-18. DOI: 10.1128/AAC.02643-18.
58. Holloway, B. W. (1955) Genetic Recombination in *Pseudomonas aeruginosa*. J. Gen. Microbiol. 13, 572-581. DOI: 10.1099/00221287-13-3-572.
59. Samuelsen, S. V., Santilli, C., Ahlquist, M. S. G., Madsen, R. (2019) Development and Mechanistic Investigation of the Manganese(Iii) Salen-Catalyzed Dehydrogenation of Alcohols. Chem. Sci. 10 (4), 1150-1157. DOI: 10.1039/C8SC03969K.
60. Porphyrins and Metalloporphyrins; Fuhrop, J. H., Smith, K. M., Eds.; Elsevier: Amsterdam, 1975.
61. Miller, J. H. (1992) A Short Course in Bacterial Genetics: A Laboratory Manual and Handbook for *Escherichia coli* and Related Bacteria. Cold Spring Harb. Lab. Press. DOI: 10.1002/jobm.3620330412.
62. Houde, D., Berkowitz, S. A., Engen, J. R. (2011) The Utility of Hydrogen/Deuterium Exchange Mass Spectrometry in Biopharmaceutical Comparability Studies. J. Pharm. Sci. 100 (6), 2071-2086. DOI: 10.1002/jps.22432.

63. Hampton T. Report reveals scope of US antibiotic resistance threat. JAMA. 2013; 310(16):1661-3. doi: 10.1001/jama.2013.280695. PubMed PMID: 24150445.
64. Cox C D. Effect of pyochelin on the virulence of *Pseudomonas aeruginosa*. Infect Immun. 1982; 36(1):17-23. Epub 1982/04/01. PubMed PMID: 6804387; PMCID: 351178.
65. Meyer J M, Neely A, Stintzi A, Georges C, Holder I A. Pyoverdin is essential for virulence of *Pseudomonas aeruginosa*. Infect Immun. 1996; 64(2):518-23. Epub 1996/02/01. PubMed PMID: 8550201; PMCID: 173795.
66. Takase H, Nitanai H, Hoshino K, Otani T. Impact of siderophore production on *Pseudomonas aeruginosa* infections in immunosuppressed mice. Infect Immun. 2000; 68(4):1834-9. Epub 2000/03/18. PubMed PMID: 10722571; PMCID: 97355.
67. Otto B R, Verweij-van Vught A M, MacLaren DM. Transferrins and heme-compounds as iron sources for pathogenic bacteria. Crit Rev Microbiol. 1992; 18(3):217-33. PubMed PMID: 1532495.
68. Hood M I, Skaar E P. Nutritional immunity: transition metals at the pathogen-host interface. Nat Rev Microbiol. 2012; 10(8):525-37. Epub 2012/07/17. doi: 10.1038/nrmicro2836. PubMed PMID: 22796883; PMCID: PMC3875331.
69. Heinrichs D E, Young L, Poole K. Pyochelin-mediated iron transport in *Pseudomonas aeruginosa*: involvement of a high-molecular-mass outer membrane protein. Infect Immun. 1991; 59(10):3680-4. PubMed PMID: 1910015; PMCID: 258938.
70. Royt P W. Pyoverdine-mediated iron transport. Fate of iron and ligand in *Pseudomonas aeruginosa*. Biol Met. 1990; 3(1):28-33. PubMed PMID: 2119198.
71. Marlovits T C, Haase W, Herrmann C, Aller S G, Unger V M. The membrane protein FeoB contains an intramolecular G protein essential for Fe(II) uptake in bacteria. Proc Natl Acad Sci USA. 2002; 99(25):16243-8. doi: 10.1073/pnas.242338299. PubMed PMID: 12446835; PMCID: 138596.
72. Ochsner U A, Johnson Z, Vasil M L. Genetics and regulation of two distinct haem-uptake systems, phu and has, in *Pseudomonas aeruginosa*. Microbiology. 2000; 146 (Pt 1):185-98. doi: 10.1099/00221287-146-1-185. PubMed PMID: 10658665.
73. Binet R, Letoffe S, Ghigo J M, Delepelaire P, Wandersman C. Protein secretion by Gram-negative bacterial ABC exporters—a review. Gene. 1997; 192(1):7-11. Epub 1997/06/11. doi: S0378-1119(96)00829-3 [pii]. PubMed PMID: 9224868.
74. Dent A T, Mourino S, Huang W, Wilks A. Post-transcriptional regulation of the *Pseudomonas aeruginosa* heme assimilation system (Has) fine-tunes extracellular heme sensing. J Biol Chem. 2019; 294(8):2771-85. Epub 2018/12/30. doi: 10.1074/jbc.RA118.006185. PubMed PMID: 30593511; PMCID: PMC 6393591.
75. Bhakta M N, Wilks A. The mechanism of heme transfer from the cytoplasmic heme binding protein PhuS to the delta-regioselective heme oxygenase of *Pseudomonas aeruginosa*. Biochemistry-Us. 2006; 45(38):11642-9. doi: Doi 10.1021/Bi0609801. PubMed PMID: ISI: 000240575900039.
76. Block D R, Lukat-Rodgers G S, Rodgers K R, Wilks A, Bhakta M N, Lansky I B. Identification of two heme-binding sites in the cytoplasmic heme-trafficking protein PhuS from *Pseudomonas aeruginosa* and their relevance to function. Biochemistry-Us. 2007; 46(50):14391-402. doi: Doi 10.1021/Bi701509n. PubMed PMID: ISI: 000251547700007.
77. Lansky I B, Lukat-Rodgers G S, Block D, Rodgers K R, Ratliff M, Wilks A. The Cytoplasmic Heme-binding Protein (PhuS) from the Heme Uptake System of *Pseudomonas aeruginosa* Is an Intracellular Heme-trafficking Protein to the □-Regioselective Heme Oxygenase. J Biol Chem. 2006; 281(19):13652-62. PubMed PMID: 16533806.
78. O'Neill M J, Bhakta M N, Fleming K G, Wilks A. Induced fit on heme binding to the *Pseudomonas aeruginosa* cytoplasmic protein (PhuS) drives interaction with heme oxygenase (HemO). Proc Natl Acad Sci USA. 2012; 109(15):5639-44. Epub 2012/03/28. doi: 10.1073/pnas.1121549109. PubMed PMID: 22451925; PMCID: 3326490.
79. Hunter R C, Asfour F, Dingemans J, Osuna B L, Samad T, Malfroot A, Cornelis P, Newman D K. Ferrous iron is a significant component of bioavailable iron in cystic fibrosis airways. mBio. 2013; 4(4). Epub 2013/08/22. doi: 10.1128/mBio.00557-13. PubMed PMID: 23963183; PMCID: 3753050.
80. Jiricny N, Molin S, Foster K, Diggle S P, Scanlan P D, Ghoul M, Johansen H K, Santorelli L A, Popat R, West S A, Griffin A S. Loss of Social Behaviours in Populations of *Pseudomonas aeruginosa* Infecting Lungs of Patients with Cystic Fibrosis. PLoS One. 2014; 9(1):e83124. Epub 2014/01/24. doi: 10.1371/journal.pone.0083124. PubMed PMID: 24454693; PMCID: 3891558.
81. Marvig R L, Damkiaer S, Khademi S M, Markussen T M, Molin S, Jelsbak L. Within-host evolution of *Pseudomonas aeruginosa* reveals adaptation toward iron acquisition from hemoglobin. MBio. 2014; 5(3):e00966-14. doi: 10.1128/mBio.00966-14. PubMed PMID: 24803516; PMCID: PMC4010824.
82. Deffebach M E, Charan N B, Lakshminarayan S, Butler J. The bronchial circulation. Small, but a vital attribute of the lung. Am Rev Respir Dis. 1987; 135(2):463-81. PubMed PMID: 3544986.
83. Moreau-Marquis S, Bomberger J M, Anderson G G, Swiatecka-Urban A, Ye S, O'Toole G A, Stanton B A. The DeltaF508-CFTR mutation results in increased biofilm formation by *Pseudomonas aeruginosa* by increasing iron availability. American journal of physiology Lung cellular and molecular physiology. 2008; 295(1):L25-37. doi: 10.1152/ajplung.00391.2007. PubMed PMID: 18359885; PMCID: 2494796.
84. Stenbit A, Flume P A. Pulmonary complications in adult patients with cystic fibrosis. Am J Med Sci. 2008; 335 (1):55-9. doi: 10.1097/MAJ.0b013e31815d2611. PubMed PMID: 18195585.
85. Ghio A J, Roggli V L, Soukup J M, Richards J H, Randell S H, Muhlebach M S. Iron accumulates in the lavage and explanted lungs of cystic fibrosis patients. Journal of cystic fibrosis: official journal of the European Cystic Fibrosis Society. 2013; 12(4):390-8. doi: 10.1016/j.jcf.2012.10.010. PubMed PMID: 23176785.
86. Guvench O, MacKerell Jr A D. Computational Fragment-Based Binding Site Identification by Ligand Competitive Saturation. PLoS Comp Biol. 2009; 5:e1000435.
87. Raman E P, Yu W, Guvench O, Mackerell A D. Reproducing crystal binding modes of ligand functional groups using Site-Identification by Ligand Competitive Saturation (SILCS) simulations. J Chem Inf Model. 2011; 51(4):877-96. Epub 2011/04/05. doi: 10.1021/ci100462t. PubMed PMID: 21456594; PMCID: 3090225.

88. Foster T J, MacKerell A D, Jr., Guvench O. Balancing target flexibility and target denaturation in computational fragment-based inhibitor discovery. J Comput Chem. 2012; 33(23):1880-91. Epub 2012/05/30. doi: 10.1002/jcc.23026. PubMed PMID: 22641475; PMCID: 3438888.

89. Lakkaraju S K, Yu W B, Raman E P, Hershfeld A V, Fang L, Deshpande D A, MacKerell AD. Mapping Functional Group Free Energy Patterns at Protein Occluded Sites: Nuclear Receptors and G-Protein Coupled Receptors. J Chem Inf Model. 2015; 55(3):700-8. doi: 10.1021/ci500729k. PubMed PMID: ISI:000351652900021.

90. Lakkaraju S K, Raman E P, Yu W, MacKerell A D, Jr. Sampling of Organic Solutes in Aqueous and Heterogeneous Environments Using Oscillating Excess Chemical Potentials in Grand Canonical-like Monte Carlo-Molecular Dynamics Simulations. Journal of chemical theory and computation. 2014; 10(6):2281-90. Epub 2014/06/17. doi: 10.1021/ct500201y. PubMed PMID: 24932136; PMCID: 4053307.

91. Cheng H, Linhares B M, Yu W, Cardenas M G, Ai Y, Jiang W, Winkler A, Cohen S, Melnick A, MacKerell A, Jr., Cierpicki T, Xue F. Identification of Thiourea-Based Inhibitors of the B-Cell Lymphoma 6 BTB Domain via NMR-Based Fragment Screening and Computer-Aided Drug Design. J Med Chem. 2018; 61(17):7573-88. Epub 2018/07/04. doi: 10.1021/acs.jmedchem.8b00040. PubMed PMID: 29969259; PMCID: 6334293.

92. He X H, Lakkaraju S K, Hanscom M, Zhao Z R, Wu J F, Stoica B, MacKerell A D, Faden A I, Xue F T. Acyl-2-aminobenzimidazoles: A novel class of neuroprotective agents targeting mGluR5. Bioorgan Med Chem. 2015; 23(9):2211-20. doi: 10.1016/j.bmc.2015.02.054. PubMed PMID: ISI:000352698700031.

93. Lakkaraju S K, Mbatia H, Hanscom M, Zhao Z R, Wu J F, Stoica B, MacKerell A D, Faden A I, Xue F T. Cyclopropyl-containing positive allosteric modulators of metabotropic glutamate receptor subtype 5. Bioorg Med Chem Lett. 2015; 25(11):2275-9. doi: 10.1016/j.bmcl.2015.04.042. PubMed PMID: ISI:000354115400003.

94. Heinzl G A, Huang W, Yu W, Giardina B J, Zhou Y, MacKerell A D, Jr., Wilks A, Xue F. Iminoguanidines as Allosteric Inhibitors of the Iron-Regulated Heme Oxygenase (HemO) of *Pseudomonas aeruginosa*. J Med Chem. 2016; 59(14):6929-42. doi: 10.1021/acs.jmedchem.6b00757. PubMed PMID: 27353344.

95. Mourino S, Giardina B J, Reyes-Caballero H, Wilks A. Metabolite-driven Regulation of Heme Uptake by the Biliverdin I Xbeta/delta-Selective Heme Oxygenase (HemO) of *Pseudomonas aeruginosa*. J Biol Chem. 2016; 291(39):20503-15. doi: 10.1074/jbc.M116.728527. PubMed PMID: 27493207.

96. Hom K, Heinzl G A, Eakanunkul S, Lopes P E, Xue F, Mackerell A D, Jr., Wilks A. Small Molecule Antivirulents Targeting the Iron-Regulated Heme Oxygenase (HemO) of *P. aeruginosa*. J Med Chem. 2013; 56(5):2097-he. Epub 2013/02/06. doi: 10.1021/jm301819k. PubMed PMID: 23379514.

97. Oglesby-Sherrouse A G, Djapgne L, Nguyen A T, Vasil A I, Vasil M L. The complex interplay of iron, biofilm formation, and mucoidy affecting antimicrobial resistance of *Pseudomonas aeruginosa*. Pathog Dis. 2014; 70(3): 307-20. Epub 2014/01/18. doi: 10.1111/2049-632X.12132. PubMed PMID: 24436170; PMCID: 4084922.

98. Aballay A, Ausubel F M. *Caenorhabditis elegans* as a host for the study of host-pathogen interactions. Curr Opin Microbiol. 2002; 5(1):97-101. PubMed PMID: 11834377.

99. Alegado R A, Campbell M C, Chen W C, Slutz S S, Tan M W. Characterization of mediators of microbial virulence and innate immunity using the *Caenorhabditis elegans* host-pathogen model. Cell Microbiol. 2003; 5(7): 435-44. PubMed PMID: 12814434.

100. Kurz C L, Ewbank J J. *Caenorhabditis elegans* for the study of host-pathogen interactions. Trends Microbiol. 2000; 8(3):142-4. PubMed PMID: 10707068.

101. Mahajan-Miklos S, Tan M W, Rahme L G, Ausubel F M. Molecular mechanisms of bacterial virulence elucidated using a *Pseudomonas aeruginosa-Caenorhabditis elegans* pathogenesis model. Cell. 1999; 96(1):47-56. PubMed PMID: 9989496.

102. Tan M W, Mahajan-Miklos S, Ausubel F M. Killing of *Caenorhabditis elegans* by *Pseudomonas aeruginosa* used to model mammalian bacterial pathogenesis. Proc Natl Acad Sci USA. 1999; 96(2):715-20. PubMed PMID: 9892699.

103. Moy T I, Ball A R, Anklesaria Z, Casadei G, Lewis K, Ausubel F M. Identification of novel antimicrobials using a live-animal infection model. Proc Natl Acad Sci USA. 2006; 103(27):10414-9. PubMedPMID: 16801562.

104. Johnson C D, Liu L X. Novel antimicrobial targets from combined pathogen and host genetics. Proc Natl Acad Sci USA. 2000; 97(3):958-9. PubMed PMID: 10655466.

105. Liang D D, Robinson E, Hom K, Yu W B, Nguyen N, Li Y, Zong Q S, Wilks A, Xue F T. Structure-based design and biological evaluation of inhibitors of the *Pseudomonas aeruginosa* heme oxygenase (pa-HemO). Bioorg Med Chem Lett. 2018; 28(6):1024-9. doi: 10.1016/j.bmcl.2018.02.027. PubMed PMID: ISI:000427531500008.

A number of patent and non-patent publications are cited herein in order to describe the state of the art to which this disclosure pertains. The entire disclosure of each of these publications is incorporated by reference herein.

While certain embodiments of the present disclosure have been described and/or exemplified above, various other embodiments will be apparent to those skilled in the art from the foregoing disclosure. The present disclosure is, therefore, not limited to the particular embodiments described and/or exemplified, but is capable of considerable variation and modification without departure from the scope and spirit of the appended claims.

The invention claimed is:

1. A compound of formula (I), or a pharmaceutically acceptable salt, solvate, hydrate, cocrystal, or prodrug thereof:

formula (I)

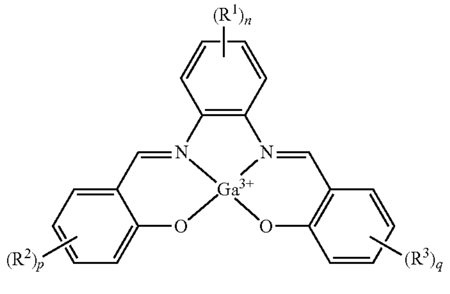

wherein in formula (I):

each $R^1$ is a substituent independently selected at each occurrence from halogen, optionally substituted alkyl, optionally substituted alkylaryl, optionally substituted alkylheteroaryl, optionally substituted alkenyl, optionally substituted alkynyl, optionally substituted cycloalkyl, optionally substituted aryl, optionally substituted aralkyl, optionally substituted haloalkyl, optionally substituted alkoxy, and optionally substituted heteroaryl;

each $R^2$ and $R^3$ is a substituent independently selected at each occurrence from halogen, optionally substituted alkyl, optionally substituted alkylaryl, optionally substituted alkylheteroaryl, optionally substituted alkenyl, optionally substituted alkynyl, optionally substituted cycloalkyl, optionally substituted aryl, optionally substituted aralkyl, optionally substituted haloalkyl, optionally substituted alkoxy, and optionally substituted heteroaryl;

wherein one $R^1$ and one $R^2$, one $R^1$ and one $R^3$, or one $R^2$ and one $R^3$ may optionally be joined together;

n is an integer from 0 to 4;

p is an integer from 0 to 4;

q is an integer from 0 to 4; and wherein the compound of formula (I) is limited by at least one of i), ii), or iii);

i) each $R^1$ is independently —$OR^a$, wherein each $R^a$ is independently selected at each occurrence from the group consisting of optionally substituted alkyl, optionally substituted alkylaryl, optionally substituted alkylcycloalkyl, and optionally substituted alkylheteroaryl;

ii) each $R^2$ and $R^3$ is independently —$OR^b$ or —$(CH_2)OR^b$, wherein each $R^b$ is independently selected at each occurrence from the group consisting of optionally substituted alkyl, optionally substituted alkylaryl, optionally substituted alkylcycloalkyl, and optionally substituted alkylheteroaryl; and iii) one $R^2$ and one $R^3$ join together to form —$O(CH_2)_r$-O—, wherein r is an integer from 4 to 7.

2. The compound of claim 1, wherein the compound of formula (I) is limited by at least one of i), ii), or iii):

i) each $R^1$ is independently selected at each occurrence from the group consisting of OMe, —Oet, —Opr, —OiPr,

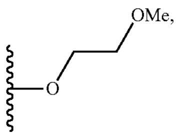

and

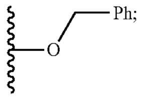

ii) each $R^2$ is independently selected at each occurrence from the group consisting of

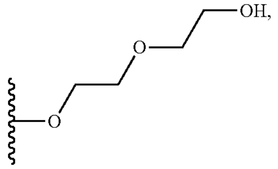

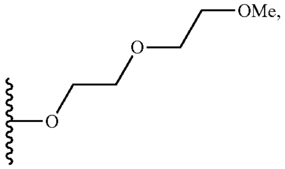

-continued

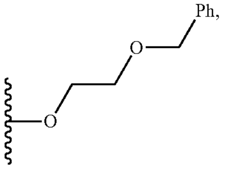

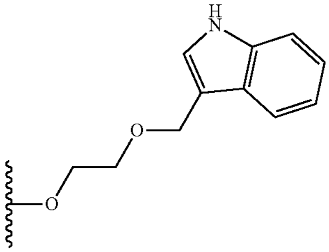

,

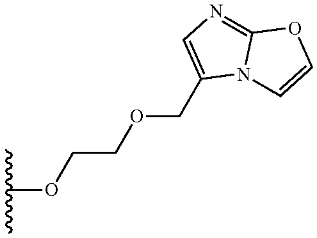

,

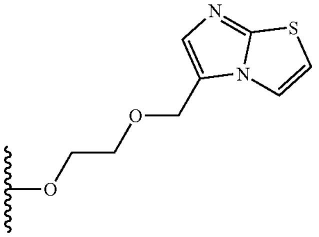

,

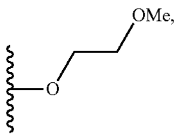

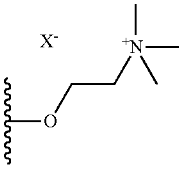

,

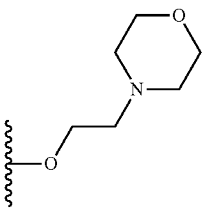

, and

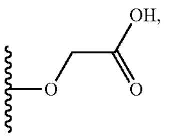

wherein $X^-$ is independently at each occurrence selected from $Br^-$, $Cl^-$, and $I^-$; or iii) each $R^3$ is selected at each occurrence from the group consisting of

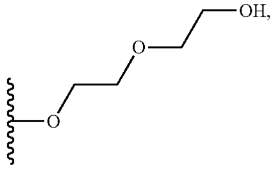

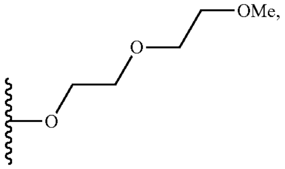

-continued

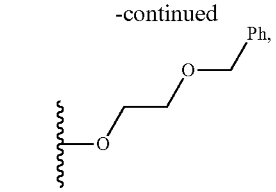

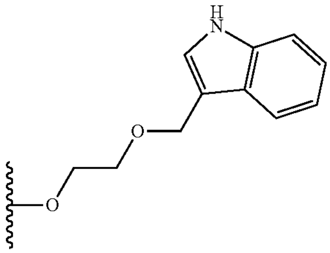

,

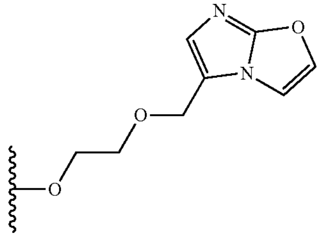

,

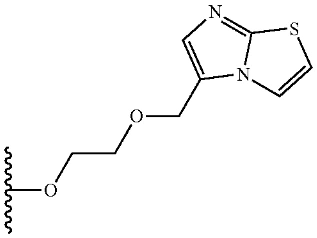

,

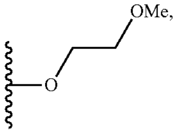

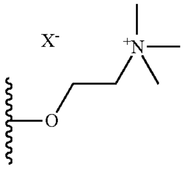

,

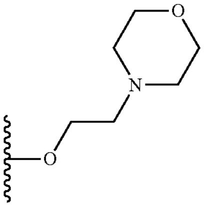

, and

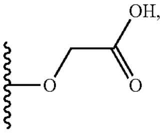

wherein X-is independently at each occurrence selected from $Br^-$, $Cl^-$, and $I^-$.

3. The compound of claim 1, wherein the compound of formula (I) is limited by at least one of i), ii), or iii):

i) n is 1 or 2;

ii) p is 1 or 2; or iii) q is 1 or 2.

4. A compound of formula (II), or a pharmaceutically acceptable salt, solvate, hydrate, cocrystal, or prodrug thereof:

formula (II)

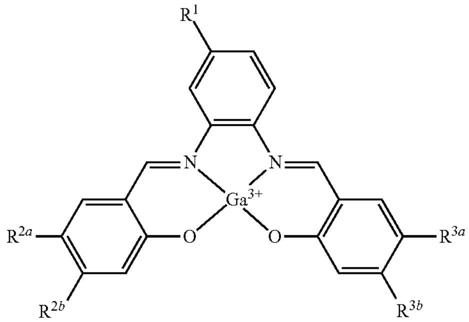

wherein in formula (II):

$R^1$ is selected from the group consisting of H, halogen, optionally substituted alkyl, optionally substituted alkylaryl, optionally substituted alkylhetaryl, optionally substituted alkenyl, optionally substituted alkynyl, optionally substituted cycloalkyl, optionally substituted aryl, optionally substituted aralkyl, optionally substituted haloalkyl, optionally substituted alkoxy, and optionally substituted heteroaryl; and $R^{2a}$, $R^{2b}$, $R^{3a}$ and $R^{3b}$ is each independently selected from the group consisting of H, halogen, optionally substituted alkyl, optionally substituted alkylaryl, optionally substituted alkylhetaryl, optionally substituted alkenyl, optionally substituted alkynyl, optionally substituted cycloalkyl, optionally substituted aryl, optionally substituted aralkyl, optionally substituted haloalkyl, optionally substituted alkoxy, and optionally substituted heteroaryl; and wherein the compound of formula (II) is limited by at least one of i), ii), or iii);

i) $R^1$ is selected from the group consisting of —OMe, —OEt, —OPr, —OiPr,

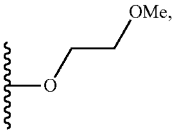

and

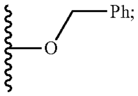

ii) $R^{2a}$ and $R^{2b}$ are each independently selected from the group consisting of H,

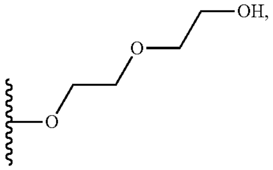

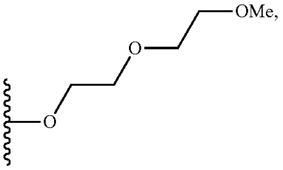

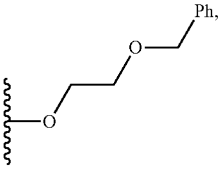

-continued

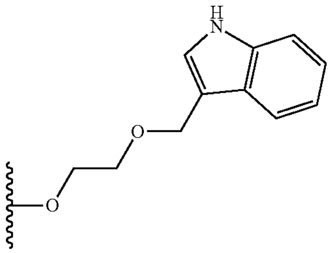

,

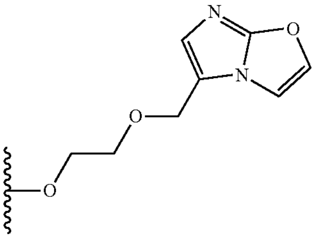

,

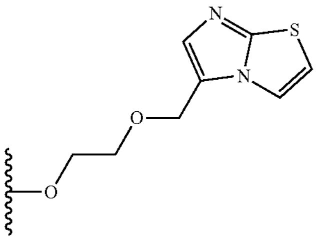

,

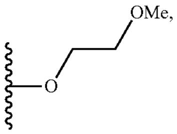

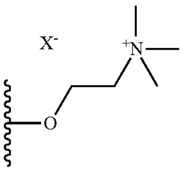

,

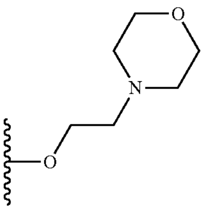

, and

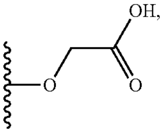

wherein $X^-$ is independently at each occurrence selected from $Br^-$, $Cl^-$, and $I^-$; or iii) $R^{3a}$ and $R^{3b}$ are each independently selected from the group consisting of H

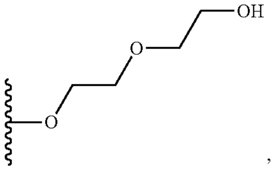

,

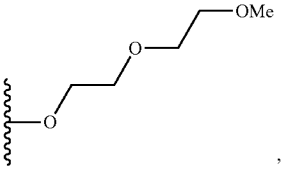

,

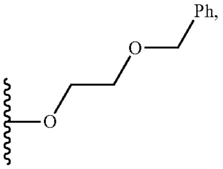

-continued

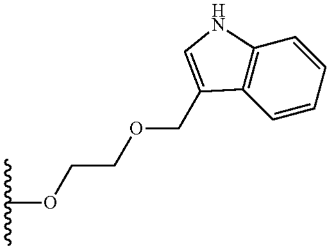

,

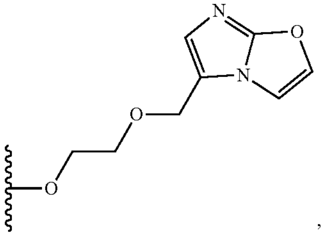

,

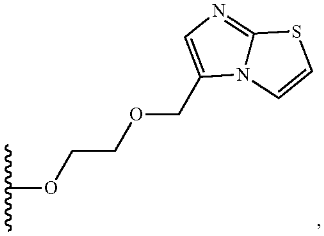

,

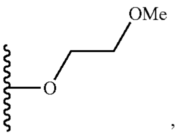

,

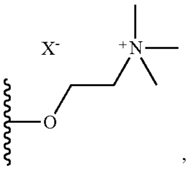

,

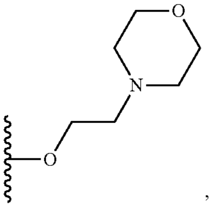

, and

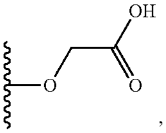

, wherein $X^-$ is independently at each occurrence selected from $Br^-$, $Cl^-$, and $I^-$.

5. The compound of claim 1, wherein the compound of formula (I) is a compound of formula (III), formula (IV), formula (V), formula (VI), formula (VII), formula (VIII), formula (IX), or formula (X), or a pharmaceutically acceptable salt, solvate, hydrate, cocrystal, or prodrug thereof:

formula (III)

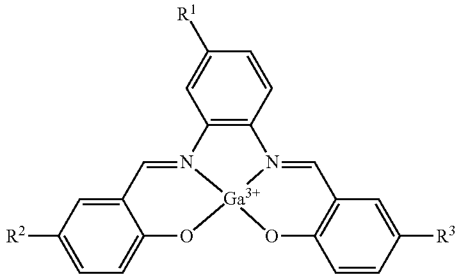

-continued
formula (IV)
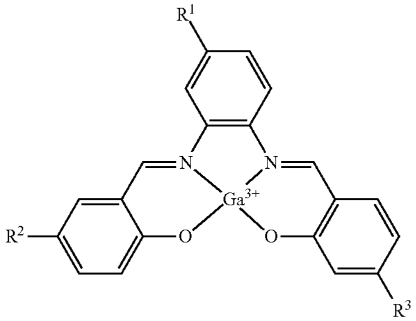
formula (V)
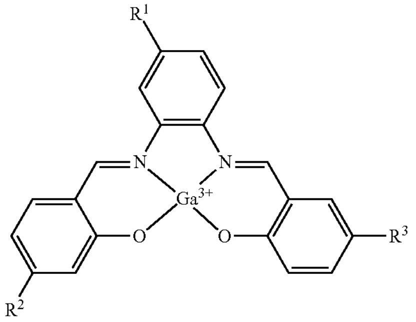
formula (VI)
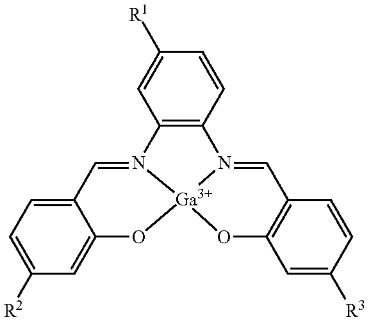
formula (VII)
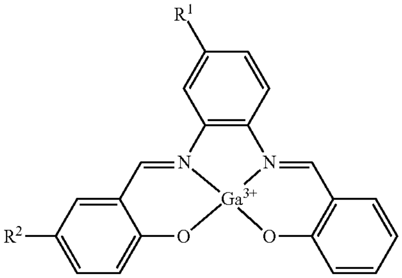
formula (VIII)
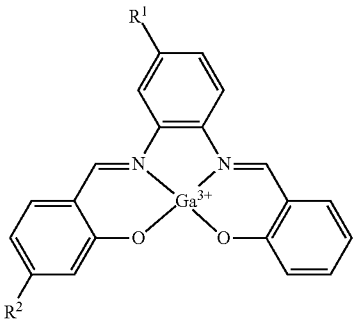
-continued
formula (IX)
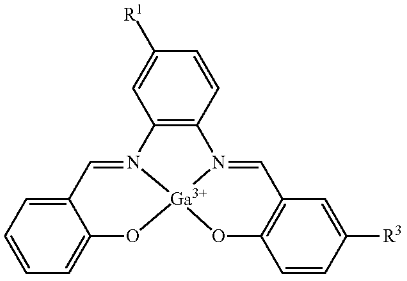
formula (X)
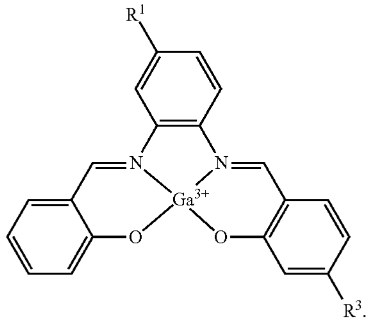
6. The compound of claim 5, wherein the compound of formula (I) is limited by at least one of i), ii), or iii):
i) $R^1$ is selected from the group consisting of —OMe, —Oet, —Opr, —OiPr,
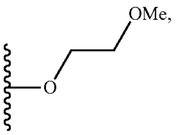
and
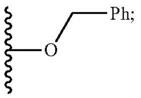
ii) $R^2$ is selected from the group consisting of H
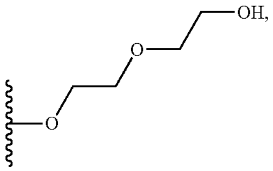
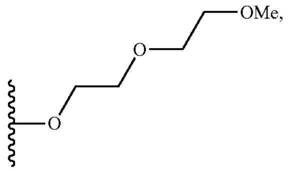
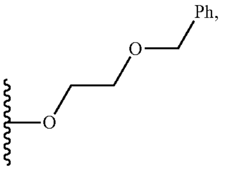
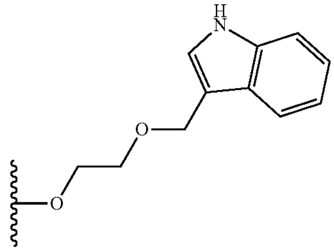
, -continued

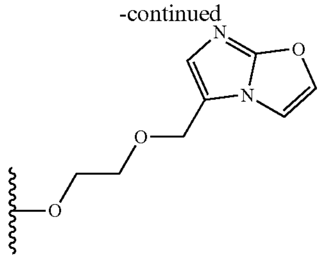
,

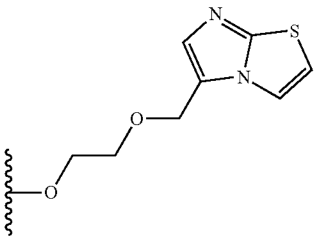
,
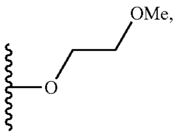

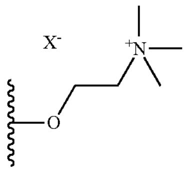
,
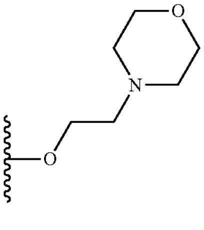
, and

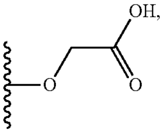

wherein $X^-$ is independently at each occurrence selected from $Br^-$, $Cl^-$, and $I^-$; or iii) $R^3$ is selected from the group consisting of H,

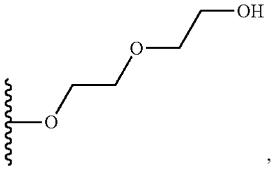
,
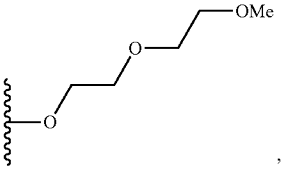
,

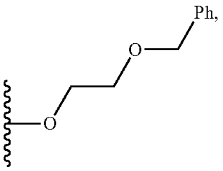

-continued

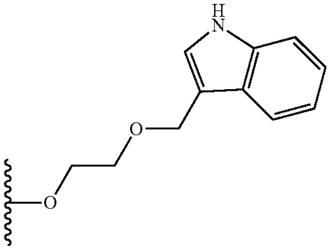
,

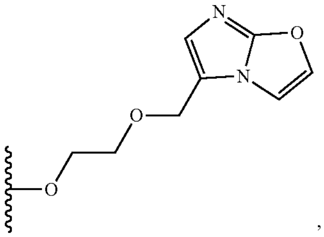
,

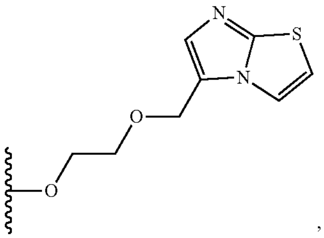
,

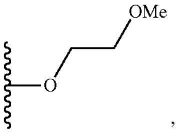
,
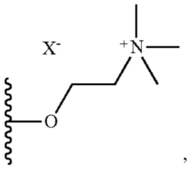
,

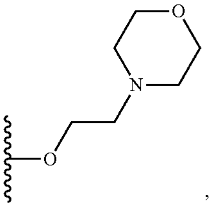
, and
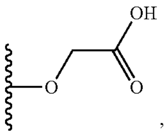
, wherein $X^-$ is independently at each occurrence selected from $Br^-$, $Cl^-$, and $I^-$.

7. The compound of claim 4, wherein the compound is of any one of formulas 1001 to 1567, or a pharmaceutically acceptable salt, solvate, hydrate, cocrystal, or prodrug thereof wherein $X^-$ is independently at each occurrence selected from $Br^-$, $Cl^-$, or $I^-$:

formula (II)
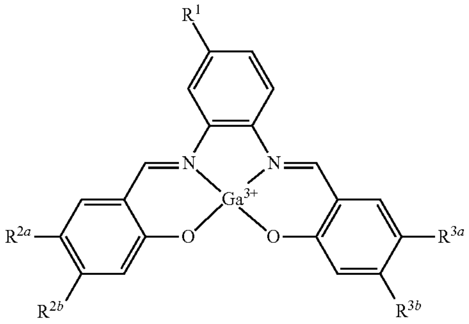
| Compound # | $R^1$ | $R^{2a}$ | $R^{2b}$ | $R^{3a}$ | $R^{3b}$ |
|---|---|---|---|---|---|
| 1001 | H | H | H | H | H |
| 1002 | —OMe | H | H | H | H |
| 1003 | —OEt | H | H | H | H |
| 1004 | —OPr | H | H | H | H |
| 1005 | —OiPr | H | H | H | H |
| 1006 | 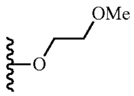 | H | H | H | H |
| 1007 | 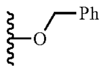 | H | H | H | H |
| 1008 | H | 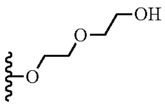 [SMILES: *OCCOCCO] | H | H | H |
| 1009 | —OMe | 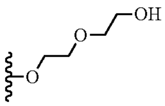 [SMILES: *OCCOCCO] | H | H | H |
| 1010 | —OEt | 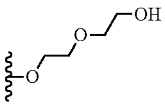 [SMILES: *OCCOCCO] | H | H | H |
| 1011 | —OPr | 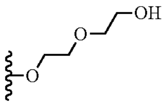 [SMILES: *OCCOCCO] | H | H | H |
| 1012 | —OiPr | 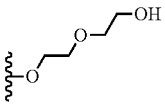 [SMILES: *OCCOCCO] | H | H | H |
| 1013 | 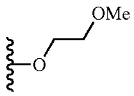 | 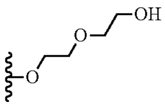 [SMILES: *OCCOCCO] | H | H | H |
| 1014 | 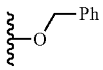 | 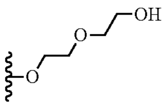 [SMILES: *OCCOCCO] | H | H | H |

-continued
formula (II)
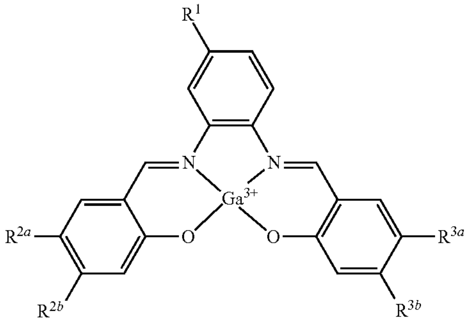
| Compound # | $R^1$ | $R^{2a}$ | $R^{2b}$ | $R^{3a}$ | $R^{3b}$ |
|---|---|---|---|---|---|
| 1015 | H | 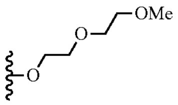 [SMILES: *OCCOCCOC] | H | H | H |
| 1016 | —OMe | 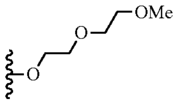 [SMILES: *OCCOCCOC] | H | H | H |
| 1017 | —OEt | 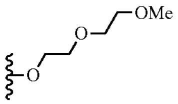 [SMILES: *OCCOCCOC] | H | H | H |
| 1018 | —OPr | 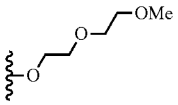 [SMILES: *OCCOCCOC] | H | H | H |
| 1019 | —OiPr | 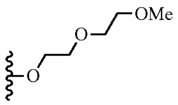 [SMILES: *OCCOCCOC] | H | H | H |
| 1020 | 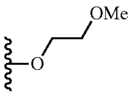 | 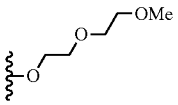 [SMILES: *OCCOCCOC] | H | H | H |
| 1021 | 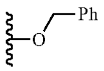 | 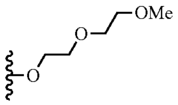 [SMILES: *OCCOCCOC] | H | H | H |
| 1022 | H | 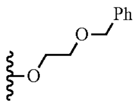 [SMILES: *OCCOCc1ccccc1] | H | H | H |
| 1023 | —OMe | 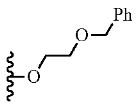 [SMILES: *OCCOCc1ccccc1] | H | H | H |
| 1024 | —OEt | 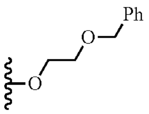 | H | H | H |

-continued
formula (II)
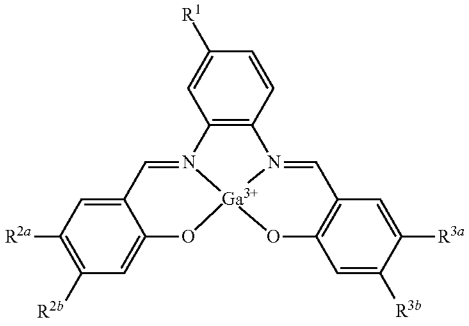
| Compound # | $R^1$ | $R^{2a}$ | $R^{2b}$ | $R^{3a}$ | $R^{3b}$ |
|---|---|---|---|---|---|
| 1025 | —OPr | 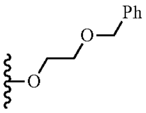 [SMILES: *OCCOCc1ccccc1] | H | H | H |
| 1026 | —OiPr | 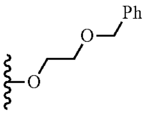 [SMILES: *OCCOCc1ccccc1] | H | H | H |
| 1027 | 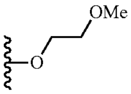 | 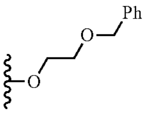 [SMILES: *OCCOCc1ccccc1] | H | H | H |
| 1028 | 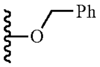 | 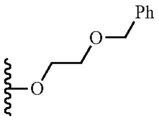 [SMILES: *OCCOCc1ccccc1] | H | H | H |
| 1029 | H | 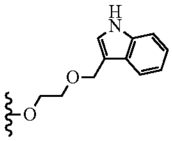 [SMILES: *OCCOCc1c[nH]c2ccccc12] | H | H | H |
| 1030 | —OMe | 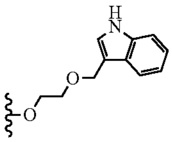 | H | H | H |
| 1031 | —OEt | 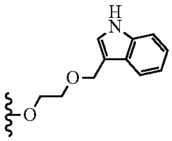 | H | H | H |
| 1032 | —OPr | 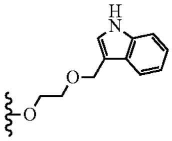 [SMILES: *OCCOCc1c[nH]c2ccccc12] | H | H | H |

-continued
formula (II)
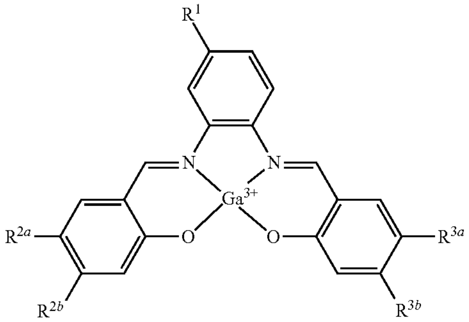
| Compound # | $R^1$ | $R^{2a}$ | $R^{2b}$ | $R^{3a}$ | $R^{3b}$ |
|---|---|---|---|---|---|
| 1033 | —OiPr | 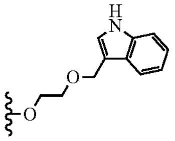 [SMILES: *OCCOCc1c[nH]c2ccccc12] | H | H | H |
| 1034 | 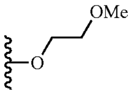 | 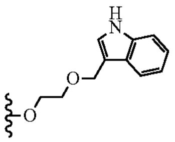 [SMILES: *OCCOCc1c[nH]c2ccccc12] | H | H | H |
| 1035 | 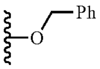 | 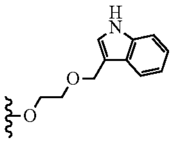 | H | H | H |
| 1036 | H | 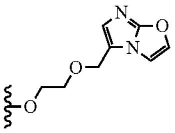 [SMILES: *OCCOCc1cnc2occn12] | H | H | H |
| 1037 | —OMe | 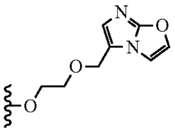 | H | H | H |
| 1038 | —OEt | 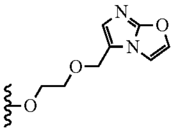 | H | H | H |
| 1039 | —OPr | 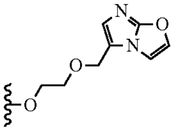 | H | H | H |
| 1040 | —OiPr | 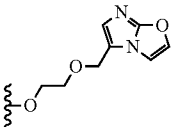 [SMILES: *OCCOCc1cnc2occn12] | H | H | H |

-continued
formula (II)
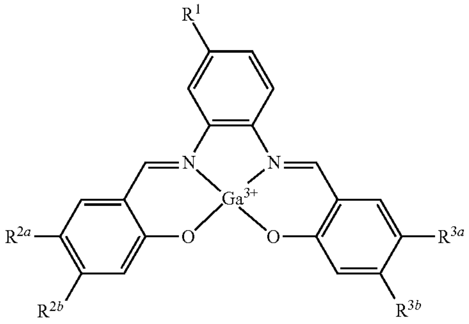
| Compound # | $R^1$ | $R^{2a}$ | $R^{2b}$ | $R^{3a}$ | $R^{3b}$ |
|---|---|---|---|---|---|
| 1041 | 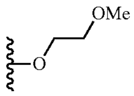 | 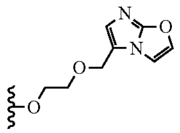 [SMILES: *OCCOCc1cnc2occn12] | H | H | H |
| 1042 | 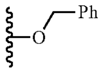 | 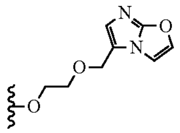 | H | H | H |
| 1043 | H | 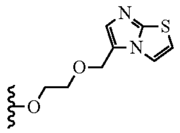 [SMILES: *OCCOCc1cnc2sccn12] | H | H | H |
| 1044 | —OMe | 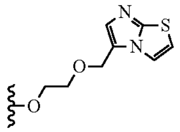 | H | H | H |
| 1045 | —OEt | 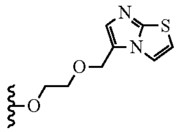 [SMILES: *OCCOCc1cnc2sccn12] | H | H | H |
| 1046 | —OPr | 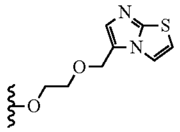 [SMILES: *OCCOCc1cnc2sccn12] | H | H | H |
| 1047 | —OiPr | 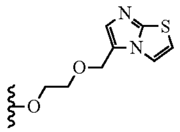 [SMILES: *OCCOCc1cnc2sccn12] | H | H | H |
| 1048 | 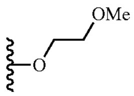 | 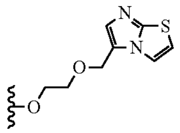 [SMILES: *OCCOCc1cnc2sccn12] | H | H | H |

-continued
formula (II)
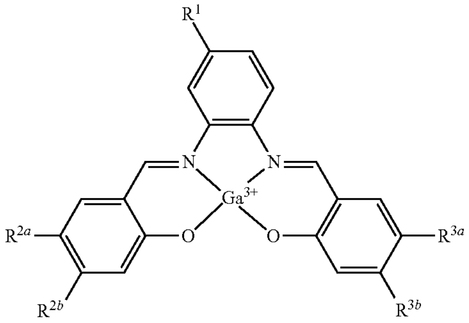
| Compound # | $R^1$ | $R^{2a}$ | $R^{2b}$ | $R^{3a}$ | $R^{3b}$ |
|---|---|---|---|---|---|
| 1049 | 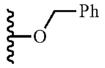 | 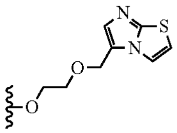 [SMILES: *OCCOCc1cnc2sccn12] | H | H | H |
| 1050 | H | H | 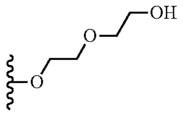 [SMILES: *OCCOCCO] | H | H |
| 1051 | —OMe | H | 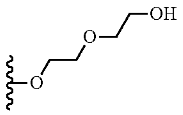 [SMILES: *OCCOCCO] | H | H |
| 1052 | —OEt | H | 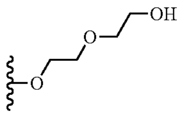 [SMILES: *OCCOCCO] | H | H |
| 1053 | —OPr | H | 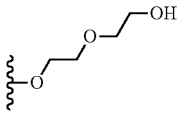 [SMILES: *OCCOCCO] | H | H |
| 1054 | —OiPr | H | 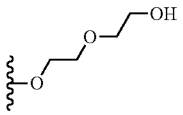 [SMILES: *OCCOCCO] | H | H |
| 1055 | 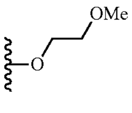 | H | 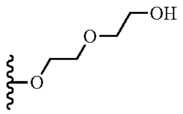 [SMILES: *OCCOCCO] | H | H |
| 1056 | 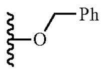 | H | 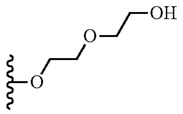 [SMILES: *OCCOCCO] | H | H |
| 1057 | H | H | 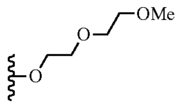 [SMILES: *OCCOCCOC] | H | H |

-continued
formula (II)
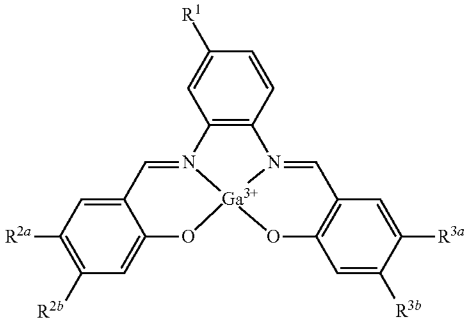
| Compound # | $R^1$ | $R^{2a}$ | $R^{2b}$ | $R^{3a}$ | $R^{3b}$ |
|---|---|---|---|---|---|
| 1058 | —OMe | H | 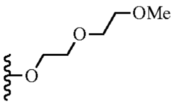 | H | H |
| 1059 | —OEt | H | 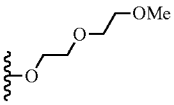 [SMILES: *OCCOCCOC] | H | H |
| 1060 | —OPr | H | 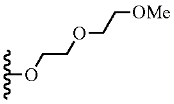 [SMILES: *OCCOCCOC] | H | H |
| 1061 | —OiPr | H | 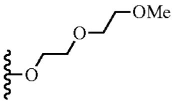 | H | H |
| 1062 | 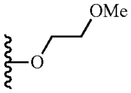 | H | 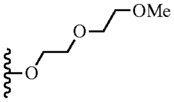 [SMILES: *OCCOCCOC] | H | H |
| 1063 | 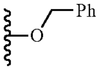 | H | 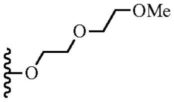 [SMILES: *OCCOCCOC] | H | H |
| 1064 | H | H | 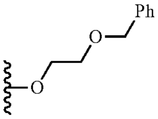 | H | H |
| 1065 | —OMe | H | 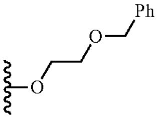 | H | H |
| 1066 | —OEt | H | 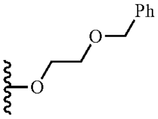 | H | H |

-continued
formula (II)
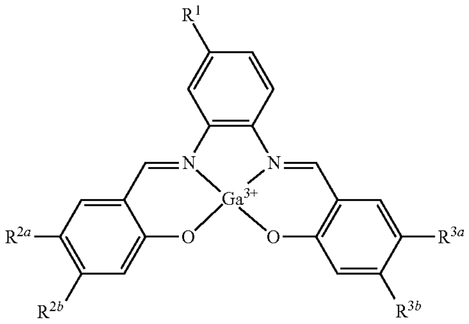
| Compound # | $R^1$ | $R^{2a}$ | $R^{2b}$ | $R^{3a}$ | $R^{3b}$ |
|---|---|---|---|---|---|
| 1067 | —OPr | H | 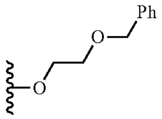 | H | H |
| 1068 | —OiPr | H | 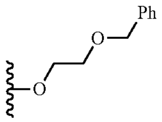 | H | H |
| 1069 | 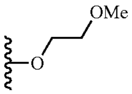 | H | 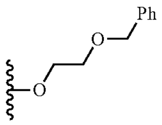 | H | H |
| 1070 | 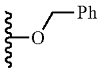 | H | 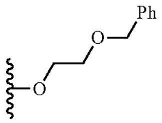 | H | H |
| 1071 | H | H | 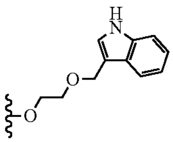 [SMILES: *OCCOCc1c[nH]c2ccccc12] | H | H |
| 1072 | —OMe | H | 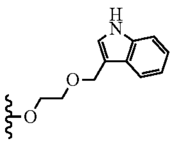 [SMILES: *OCCOCc1c[nH]c2ccccc12] | H | H |
| 1073 | —OEt | H | 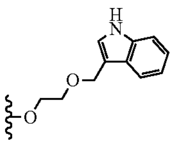 [SMILES: *OCCOCc1c[nH]c2ccccc12] | H | H |
| 1074 | —OPr | H | 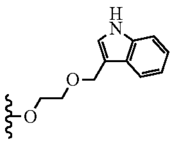 [SMILES: *OCCOCc1c[nH]c2ccccc12] | H | H |

-continued
formula (II)
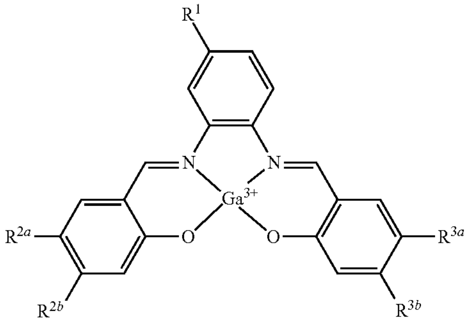
| Compound # | $R^1$ | $R^{2a}$ | $R^{2b}$ | $R^{3a}$ | $R^{3b}$ |
|---|---|---|---|---|---|
| 1075 | —OiPr | H | 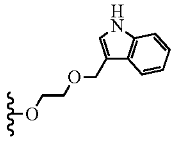 [SMILES: *OCCOCc1c[nH]c2ccccc12] | H | H |
| 1076 | 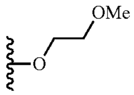 | H | 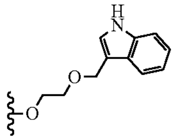 [SMILES: *OCCOCc1c[nH]c2ccccc12] | H | H |
| 1077 | 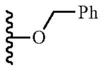 | H | 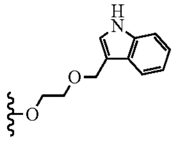 [SMILES: *OCCOCc1c[nH]c2ccccc12] | H | H |
| 1078 | H | H | 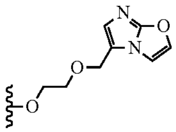 [SMILES: *OCCOCc1cnc2occn12] | H | H |
| 1079 | —OMe | H | 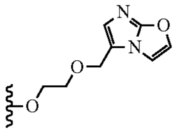 [SMILES: *OCCOCc1cnc2occn12] | H | H |
| 1080 | —OEt | H | 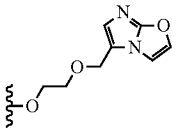 [SMILES: *OCCOCc1cnc2occn12] | H | H |
| 1081 | —OPr | H | 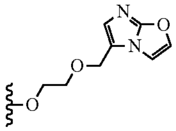 | H | H |
| 1082 | —OiPr | H | 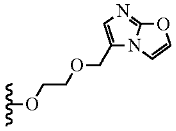 | H | H |

-continued
formula (II)
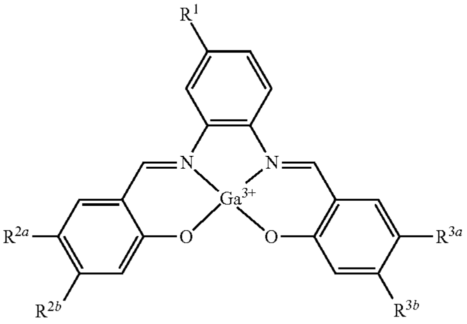
| Compound # | $R^1$ | $R^{2a}$ | $R^{2b}$ | $R^{3a}$ | $R^{3b}$ |
|---|---|---|---|---|---|
| 1083 | 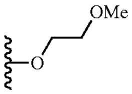 | H | 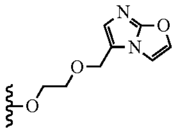 [SMILES: *OCCOCc1cnc2occn12] | H | H |
| 1084 | 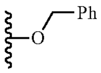 | H | 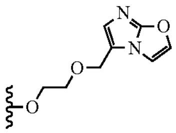 [SMILES: *OCCOCc1cnc2occn12] | H | H |
| 1085 | H | H | 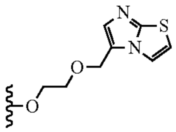 [SMILES: *OCCOCc1cnc2sccn12] | H | H |
| 1086 | —OMe | H | 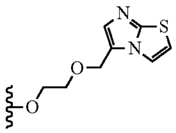 [SMILES: *OCCOCc1cnc2sccn12] | H | H |
| 1087 | —OEt | H | 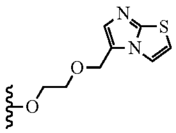 [SMILES: *OCCOCc1cnc2sccn12] | H | H |
| 1088 | —OPr | H | 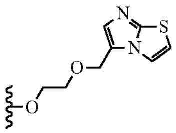 [SMILES: *OCCOCc1cnc2sccn12] | H | H |
| 1089 | —OiPr | H | 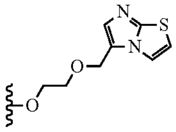 | H | H |
| 1090 | 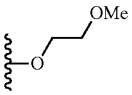 | H | 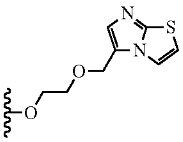 [SMILES: *OCCOCc1cnc2sccn12] | H | H |

-continued
formula (II)
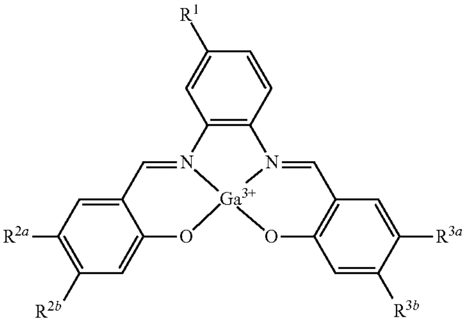
| Compound # | $R^1$ | $R^{2a}$ | $R^{2b}$ | $R^{3a}$ | $R^{3b}$ |
|---|---|---|---|---|---|
| 1091 | 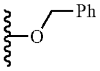 | H | 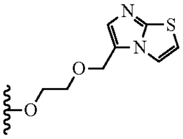 | H | H |
| 1092 | H | H | H | 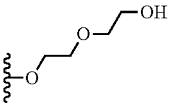 [SMILES: *OCCOCCO] | H |
| 1093 | —OMe | H | H | 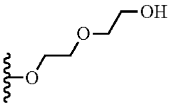 [SMILES: *OCCOCCO] | H |
| 1094 | —OEt | H | H | 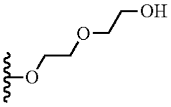 | H |
| 1095 | —OPr | H | H | 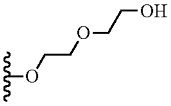 [SMILES: *OCCOCCO] | H |
| 1096 | —OiPr | H | H | 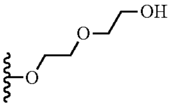 [SMILES: *OCCOCCO] | H |
| 1097 | 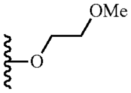 | H | H | 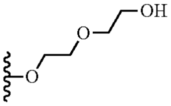 | H |
| 1098 | 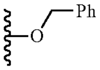 | H | H | 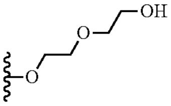 [SMILES: *OCCOCCO] | H |
| 1099 | H | H | H | 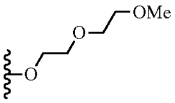 [SMILES: *OCCOCCOC] | H |

-continued
formula (II)
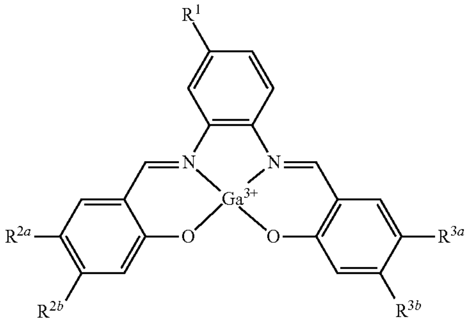
| Compound # | $R^1$ | $R^{2a}$ | $R^{2b}$ | $R^{3a}$ | $R^{3b}$ |
|---|---|---|---|---|---|
| 1100 | —OMe | H | H | 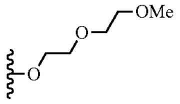 [SMILES: *OCCOCCOC] | H |
| 1101 | —OEt | H | H | 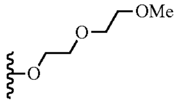 [SMILES: *OCCOCCOC] | H |
| 1102 | —OPr | H | H | 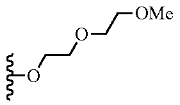 [SMILES: *OCCOCCOC] | H |
| 1103 | —OiPr | H | H | 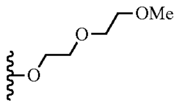 [SMILES: *OCCOCCOC] | H |
| 1104 | 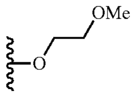 | H | H | 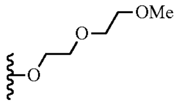 [SMILES: *OCCOCCOC] | H |
| 1105 | 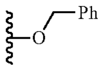 | H | H | 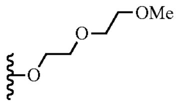 [SMILES: *OCCOCCOC] | H |
| 1106 | H | H | H | 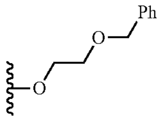 [SMILES: *OCCOCc1ccccc1] | H |
| 1107 | —OMe | H | H | 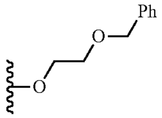 [SMILES: *OCCOCc1ccccc1] | H |
| 1108 | —OEt | H | H | 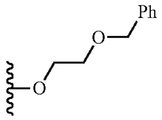 [SMILES: *OCCOCc1ccccc1] | H |

-continued
formula (II)
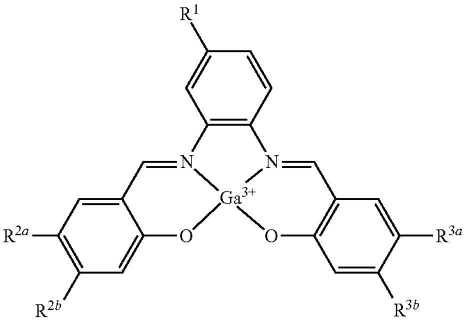
| Compound # | $R^1$ | $R^{2a}$ | $R^{2b}$ | $R^{3a}$ | $R^{3b}$ |
|---|---|---|---|---|---|
| 1109 | —OPr | H | H | 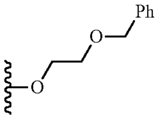 [SMILES: *OCCOCc1ccccc1] | H |
| 1110 | —OiPr | H | H | 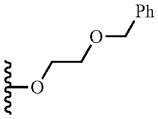 [SMILES: *OCCOCc1ccccc1] | H |
| 1111 | 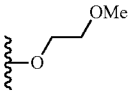 | H | H | 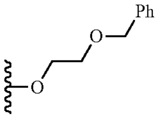 [SMILES: *OCCOCc1ccccc1] | H |
| 1112 | 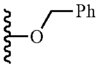 | H | H | 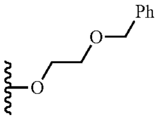 | H |
| 1113 | H | H | H | 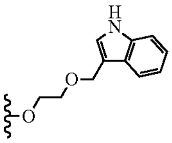 [SMILES: *OCCOCc1c[nH]c2ccccc12] | H |
| 1114 | —OMe | H | H | 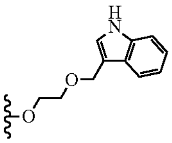 [SMILES: *OCCOCc1c[nH]c2ccccc12] | H |
| 1115 | —OEt | H | H | 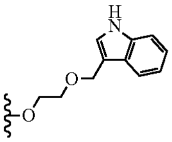 [SMILES: *OCCOCc1c[nH]c2ccccc12] | H |
| 1116 | —OPr | H | H | 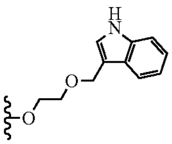 [SMILES: *OCCOCc1c[nH]c2ccccc12] | H |

-continued
formula (II)
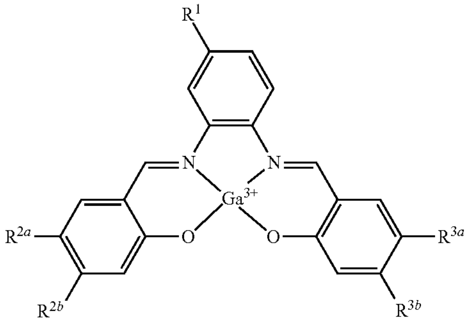
| Compound # | $R^1$ | $R^{2a}$ | $R^{2b}$ | $R^{3a}$ | $R^{3b}$ |
|---|---|---|---|---|---|
| 1117 | —OiPr | H | H | 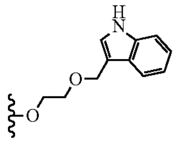 [SMILES: *OCCOCc1c[nH]c2ccccc12] | H |
| 1118 | 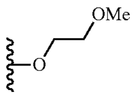 | H | H | 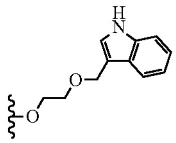 [SMILES: *OCCOCc1c[nH]c2ccccc12] | H |
| 1119 | 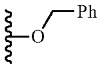 | H | H | 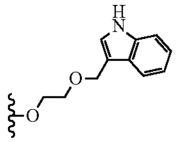 [SMILES: *OCCOCc1c[nH]c2ccccc12] | H |
| 1120 | H | H | H | 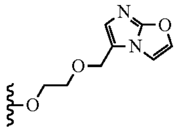 [SMILES: *OCCOCc1cnc2occn12] | H |
| 1121 | —OMe | H | H | 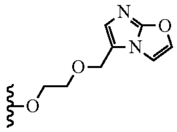 | H |
| 1122 | —OEt | H | H | 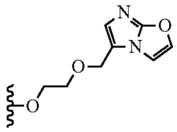 [SMILES: *OCCOCc1cnc2occn12] | H |
| 1123 | —OPr | H | H | 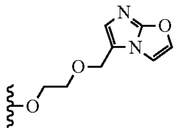 [SMILES: *OCCOCc1cnc2occn12] | H |
| 1124 | —OiPr | H | H | 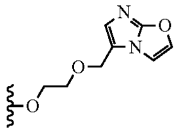 [SMILES: *OCCOCc1cnc2occn12] | H |

-continued
formula (II)
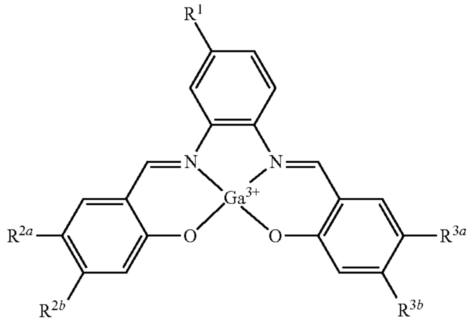
| Compound # | $R^1$ | $R^{2a}$ | $R^{2b}$ | $R^{3a}$ | $R^{3b}$ |
|---|---|---|---|---|---|
| 1125 | 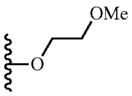 | H | H | 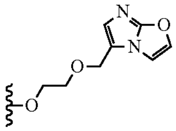 | H |
| 1126 | 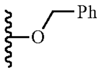 | H | H | 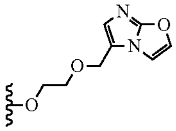 | H |
| 1127 | H | H | H | 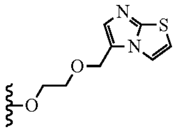 [SMILES: *OCCOCc1cnc2sccn12] | H |
| 1128 | —OMe | H | H | 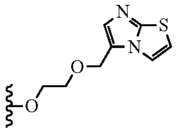 [SMILES: *OCCOCc1cnc2sccn12] | H |
| 1129 | —OEt | H | H | 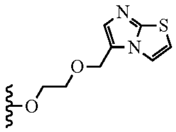 | H |
| 1130 | —OPr | H | H | 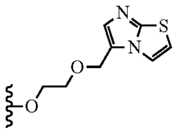 [SMILES: *OCCOCc1cnc2sccn12] | H |
| 1131 | —OiPr | H | H | 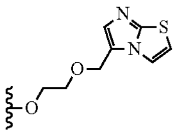 | H |
| 1132 | 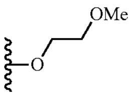 | H | H | 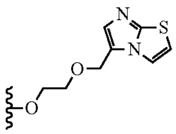 | H |

-continued
formula (II)
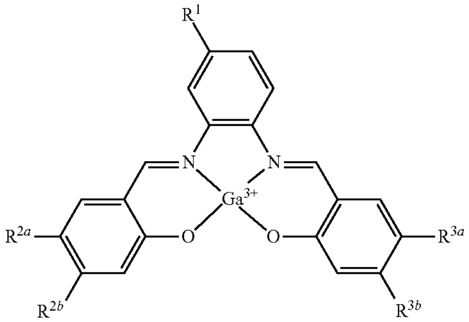
| Compound # | $R^1$ | $R^{2a}$ | $R^{2b}$ | $R^{3a}$ | $R^{3b}$ |
|---|---|---|---|---|---|
| 1133 | 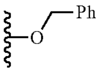 | H | H | 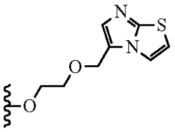 | H |
| 1134 | H | H | H | H | 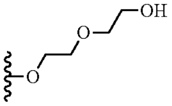 [SMILES: *OCCOCCO] |
| 1135 | —OMe | H | H | H | 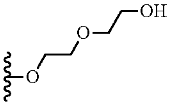 [SMILES: *OCCOCCO] |
| 1136 | —OEt | H | H | H | 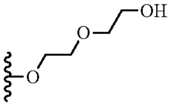 [SMILES: *OCCOCCO] |
| 1137 | —OPr | H | H | H | 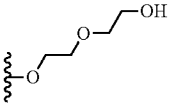 |
| 1138 | —OiPr | H | H | H | 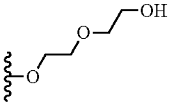 [SMILES: *OCCOCCO] |
| 1139 | 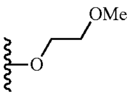 | H | H | H | 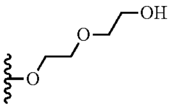 [SMILES: *OCCOCCO] |
| 1140 | 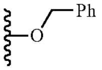 | H | H | H | 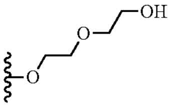 [SMILES: *OCCOCCO] |
| 1141 | H | H | H | H | 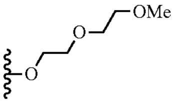 [SMILES: *OCCOCCOC] |

-continued
formula (II)
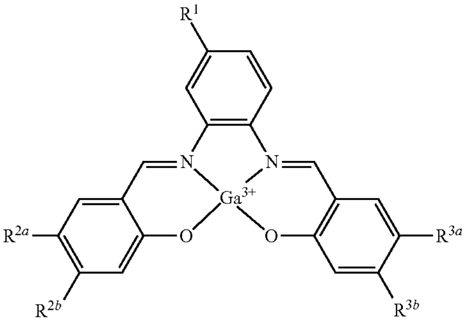
| Compound # | $R^1$ | $R^{2a}$ | $R^{2b}$ | $R^{3a}$ | $R^{3b}$ |
|---|---|---|---|---|---|
| 1142 | —OMe | H | H | H | 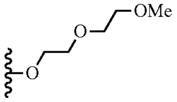 [SMILES: *OCCOCCOC] |
| 1143 | —OEt | H | H | H | 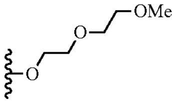 [SMILES: *OCCOCCOC] |
| 1144 | —OPr | H | H | H | 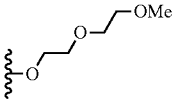 |
| 1145 | —OiPr | H | H | H | 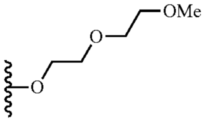 |
| 1146 | 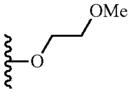 | H | H | H | 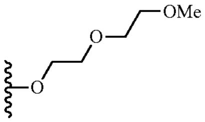 |
| 1147 | 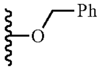 | H | H | H | 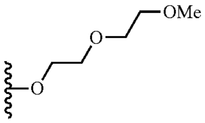 |
| 1148 | H | H | H | H | 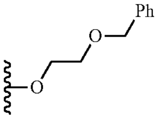 [SMILES: *OCCOCc1ccccc1] |
| 1149 | —OMe | H | H | H | 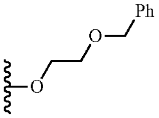 [SMILES: *OCCOCc1ccccc1] |
| 1150 | —OEt | H | H | H | 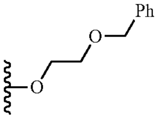 [SMILES: *OCCOCc1ccccc1] |

-continued
formula (II)
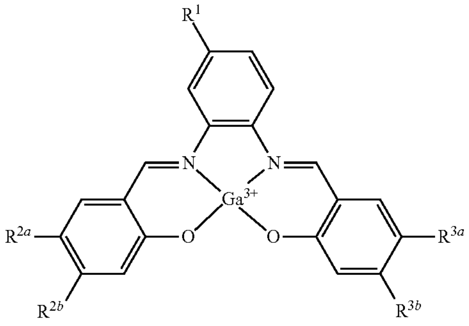
| Compound # | $R^1$ | $R^{2a}$ | $R^{2b}$ | $R^{3a}$ | $R^{3b}$ |
|---|---|---|---|---|---|
| 1151 | —OPr | H | H | H | 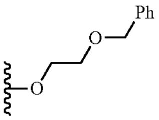 [SMILES: *OCCOCc1ccccc1] |
| 1152 | —OiPr | H | H | H | 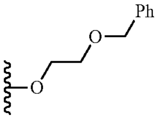 [SMILES: *OCCOCc1ccccc1] |
| 1153 | 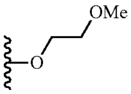 | H | H | H | 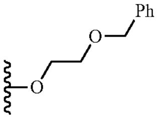 [SMILES: *OCCOCc1ccccc1] |
| 1154 | 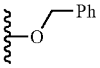 | H | H | H | 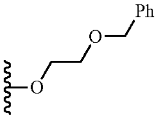 [SMILES: *OCCOCc1ccccc1] |
| 1155 | H | H | H | H | 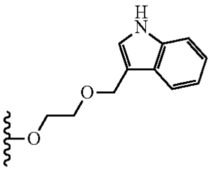 [SMILES: *OCCOCc1c[nH]c2ccccc12] |
| 1156 | —OMe | H | H | H | 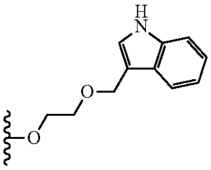 [SMILES: *OCCOCc1c[nH]c2ccccc12] |
| 1157 | —OEt | H | H | H | 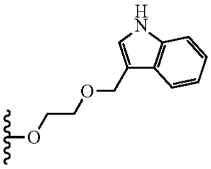 [SMILES: *OCCOCc1c[nH]c2ccccc12] |

-continued
formula (II)
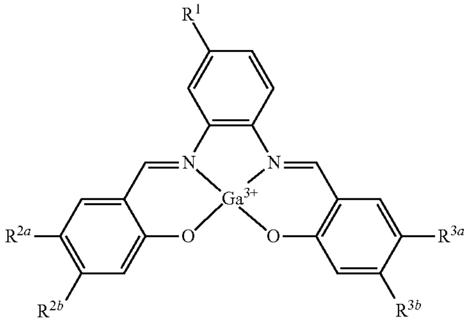
| Compound # | $R^1$ | $R^{2a}$ | $R^{2b}$ | $R^{3a}$ | $R^{3b}$ |
|---|---|---|---|---|---|
| 1158 | —OPr | H | H | H | 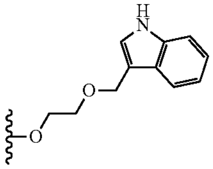 [SMILES: *OCCOCc1c[nH]c2ccccc12] |
| 1159 | —OiPr | H | H | H | 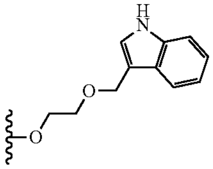 [SMILES: *OCCOCc1c[nH]c2ccccc12] |
| 1160 | 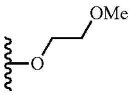 | H | H | H | 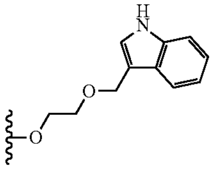 [SMILES: *OCCOCc1c[nH]c2ccccc12] |
| 1161 | 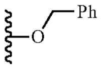 | H | H | H | 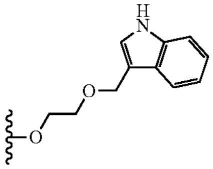 [SMILES: *OCCOCc1c[nH]c2ccccc12] |
| 1162 | H | H | H | H | 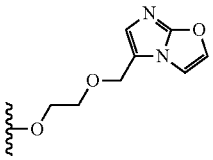 |
| 1163 | —OMe | H | H | H | 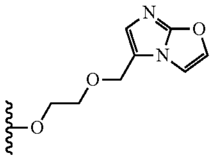 [SMILES: *OCCOCc1cnc2occn12] |

-continued
formula (II)
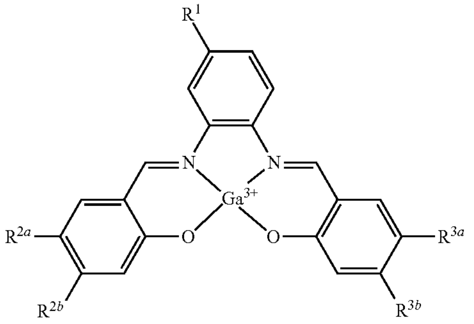
| Compound # | $R^1$ | $R^{2a}$ | $R^{2b}$ | $R^{3a}$ | $R^{3b}$ |
|---|---|---|---|---|---|
| 1164 | —OEt | H | H | H | 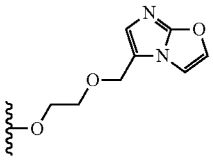 [SMILES: *OCCOCc1cnc2occn12] |
| 1165 | —OPr | H | H | H | 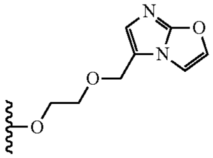 [SMILES: *OCCOCc1cnc2occn12] |
| 1166 | —OiPr | H | H | H | 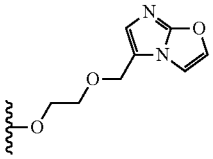 [SMILES: *OCCOCc1cnc2occn12] |
| 1167 | 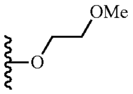 | H | H | H | 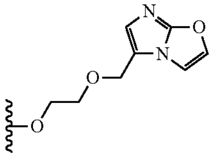 [SMILES: *OCCOCc1cnc2occn12] |
| 1168 | 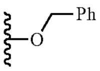 | H | H | H | 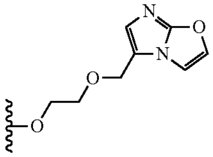 [SMILES: *OCCOCc1cnc2occn12] |
| 1169 | H | H | H | H | 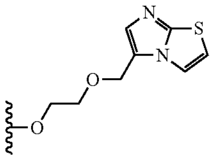 [SMILES: *OCCOCc1cnc2sccn12] |
| 1170 | —OMe | H | H | H | 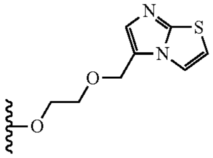 [SMILES: *OCCOCc1cnc2sccn12] |

-continued
formula (II)
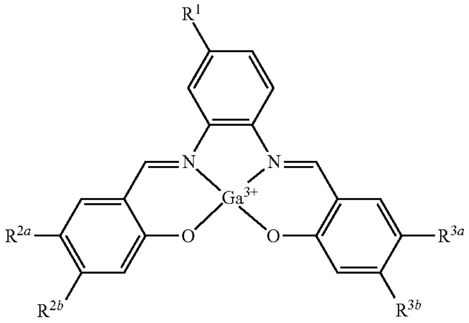
| Compound # | $R^1$ | $R^{2a}$ | $R^{2b}$ | $R^{3a}$ | $R^{3b}$ |
|---|---|---|---|---|---|
| 1171 | —OEt | H | H | H | 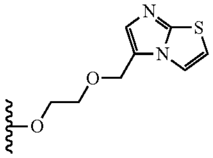 [SMILES: *OCCOCc1cnc2sccn12] |
| 1172 | —OPr | H | H | H | 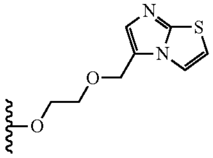 |
| 1173 | —OiPr | H | H | H | 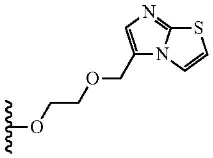 [SMILES: *OCCOCc1cnc2sccn12] |
| 1174 | 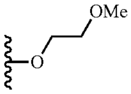 | H | H | H | 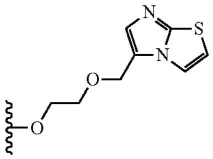 |
| 1175 | 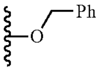 | H | H | H | 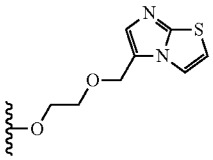 [SMILES: *OCCOCc1cnc2sccn12] |
| 1176 | H | 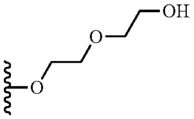 [SMILES: *OCCOCCO] | H | 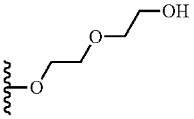 [SMILES: *OCCOCCO] | H |
| 1177 | —OMe | 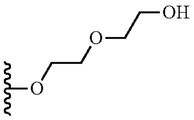 [SMILES: *OCCOCCO] | H | 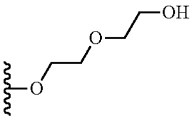 [SMILES: *OCCOCCO] | H |

-continued
formula (II)
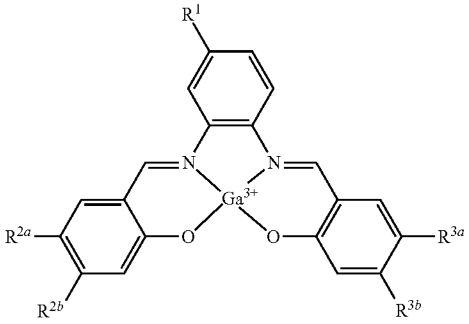
| Compound # | $R^1$ | $R^{2a}$ | $R^{2b}$ | $R^{3a}$ | $R^{3b}$ |
|---|---|---|---|---|---|
| 1178 | —OEt | 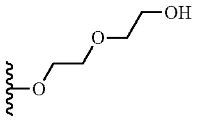 [SMILES: *OCCOCCO] | H | 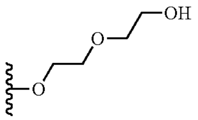 [SMILES: *OCCOCCO] | H |
| 1179 | —OPr | 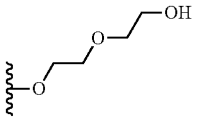 [SMILES: *OCCOCCO] | H | 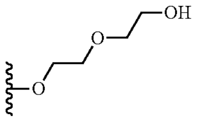 [SMILES: *OCCOCCO] | H |
| 1180 | —OiPr | 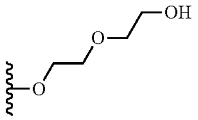 [SMILES: *OCCOCCO] | H | 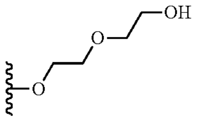 [SMILES: *OCCOCCO] | H |
| 1181 | 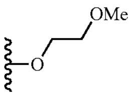 | 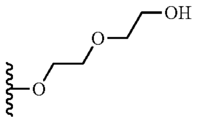 [SMILES: *OCCOCCO] | H | 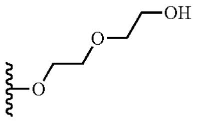 [SMILES: *OCCOCCO] | H |
| 1182 | 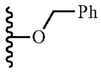 | 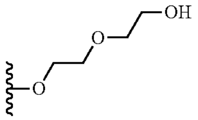 [SMILES: *OCCOCCO] | H | 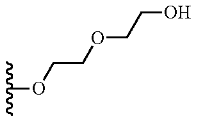 [SMILES: *OCCOCCO] | H |
| 1183 | H | 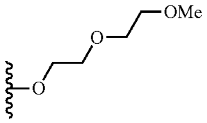 | H | 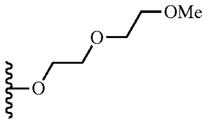 [SMILES: *OCCOCCOC] | H |
| 1184 | —OMe | 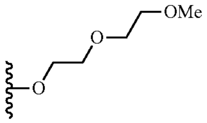 | H | 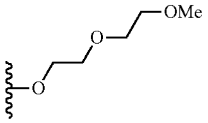 | H |
| 1185 | —OEt | 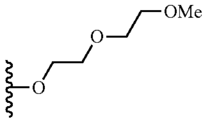 | H | 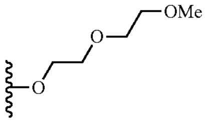 [SMILES: *OCCOCCOC] | H |
| 1186 | —OPr | 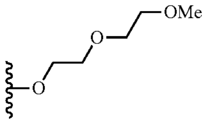 | H | 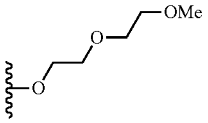 [SMILES: *OCCOCCOC] | H |

-continued
formula (II)
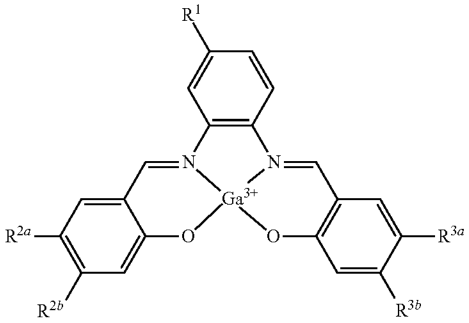
| Compound # | $R^1$ | $R^{2a}$ | $R^{2b}$ | $R^{3a}$ | $R^{3b}$ |
|---|---|---|---|---|---|
| 1187 | —OiPr | 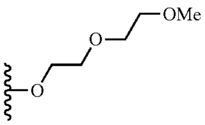 | H | 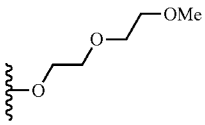 [SMILES: *OCCOCCOC] | H |
| 1188 | 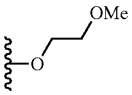 | 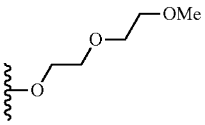 | H | 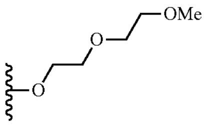 | H |
| 1189 | 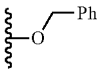 | 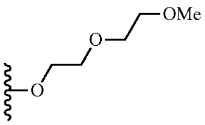 | H | 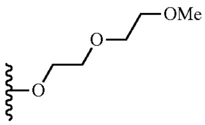 | H |
| 1190 | H | 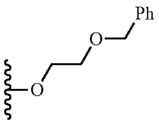 [SMILES: *OCCOCc1ccccc1] | H | 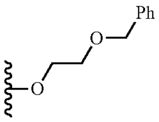 [SMILES: *OCCOCc1ccccc1] | H |
| 1191 | —OMe | 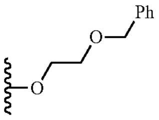 [SMILES: *OCCOCc1ccccc1] | H | 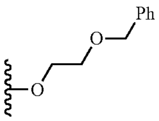 [SMILES: *OCCOCc1ccccc1] | H |
| 1192 | —OEt | 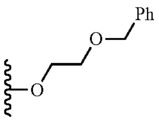 [SMILES: *OCCOCc1ccccc1] | H | 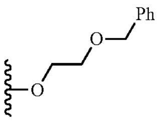 [SMILES: *OCCOCc1ccccc1] | H |
| 1193 | —OPr | 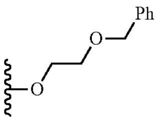 [SMILES: *OCCOCc1ccccc1] | H | 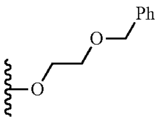 [SMILES: *OCCOCc1ccccc1] | H |
| 1194 | —OiPr | 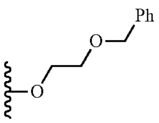 [SMILES: *OCCOCc1ccccc1] | H | 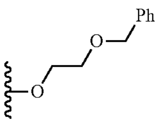 [SMILES: *OCCOCc1ccccc1] | H |

-continued
formula (II)
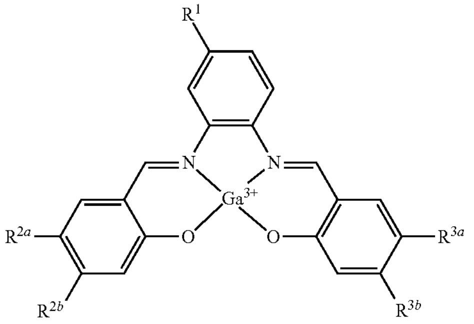
| Compound # | $R^1$ | $R^{2a}$ | $R^{2b}$ | $R^{3a}$ | $R^{3b}$ |
|---|---|---|---|---|---|
| 1195 | 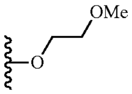 | 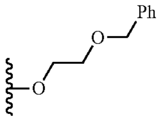 [SMILES: *OCCOCc1ccccc1] | H | 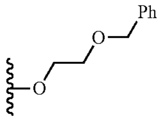 [SMILES: *OCCOCc1ccccc1] | H |
| 1196 | 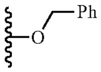 | 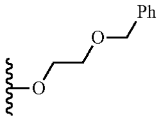 [SMILES: *OCCOCc1ccccc1] | H | 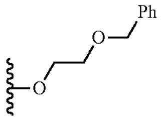 [SMILES: *OCCOCc1ccccc1] | H |
| 1197 | H | 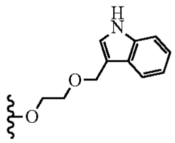 | H | 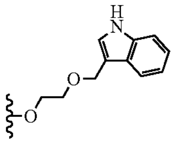 [SMILES: *OCCOCc1c[nH]c2ccccc12] | H |
| 1198 | —OMe | 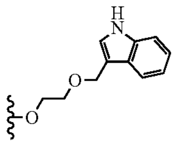 | H | 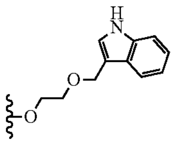 [SMILES: *OCCOCc1c[nH]c2ccccc12] | H |
| 1199 | —OEt | 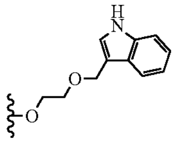 [SMILES: *OCCOCc1c[nH]c2ccccc12] | H | 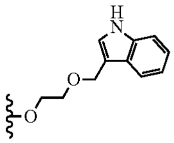 [SMILES: *OCCOCc1c[nH]c2ccccc12] | H |
| 1200 | —OPr | 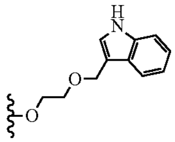 | H | 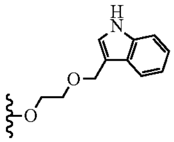 [SMILES: *OCCOCc1c[nH]c2ccccc12] | H |
| 1201 | —OiPr | 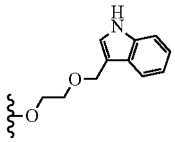 | H | 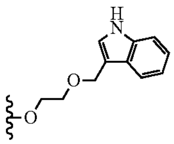 [SMILES: *OCCOCc1c[nH]c2ccccc12] | H |
| 1202 | 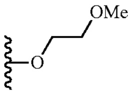 | 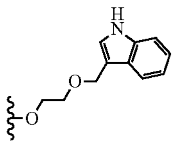 | H | 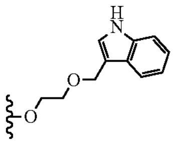 [SMILES: *OCCOCc1c[nH]c2ccccc12] | H |

-continued
formula (II)
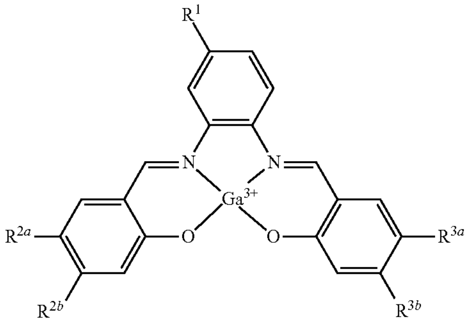
| Compound # | $R^1$ | $R^{2a}$ | $R^{2b}$ | $R^{3a}$ | $R^{3b}$ |
|---|---|---|---|---|---|
| 1203 | 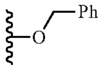 | 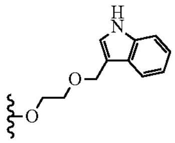 | H | 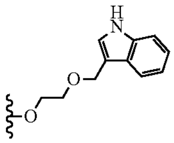 [SMILES: *OCCOCc1c[nH]c2ccccc12] | H |
| 1204 | H | 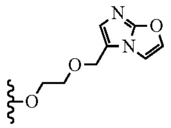 | H | 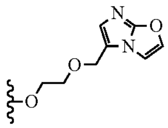 | H |
| 1205 | —OMe | 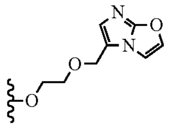 | H | 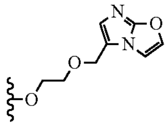 [SMILES: *OCCOCc1cnc2occn12] | H |
| 1206 | —OEt | 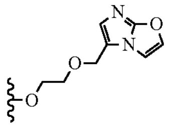 [SMILES: *OCCOCc1cnc2occn12] | H | 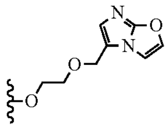 [SMILES: *OCCOCc1cnc2occn12] | H |
| 1207 | —OPr | 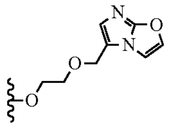 [SMILES: *OCCOCc1cnc2occn12] | H | 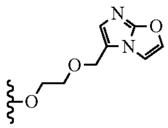 | H |
| 1208 | —OiPr | 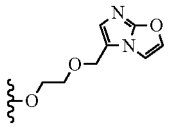 | H | 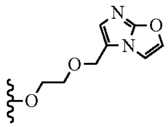 | H |
| 1209 | 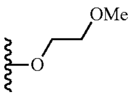 | 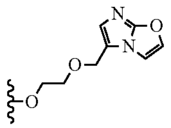 [SMILES: *OCCOCc1cnc2occn12] | H | 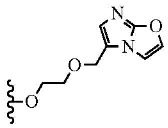 | H |
| 1210 | 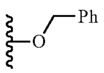 | 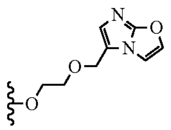 [SMILES: *OCCOCc1cnc2occn12] | H | 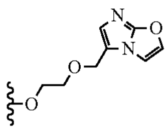 [SMILES: *OCCOCc1cnc2occn12] | H |

-continued
formula (II)
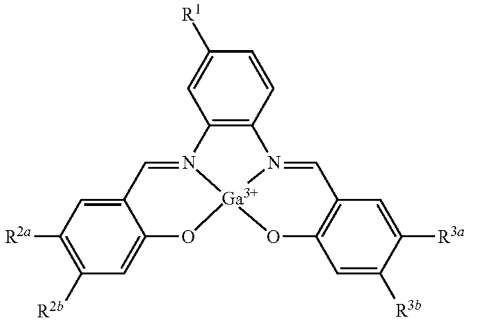
| Compound # | $R^1$ | $R^{2a}$ | $R^{2b}$ | $R^{3a}$ | $R^{3b}$ |
|---|---|---|---|---|---|
| 1211 | H | 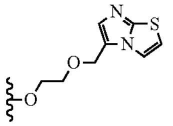 [SMILES: *OCCOCc1cnc2sccn12] | H | 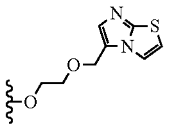 [SMILES: *OCCOCc1cnc2sccn12] | H |
| 1212 | —OMe | 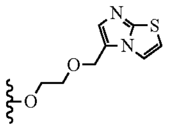 [SMILES: *OCCOCc1cnc2sccn12] | H | 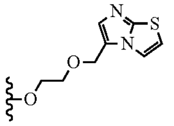 | H |
| 1213 | —OEt | 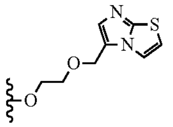 [SMILES: *OCCOCc1cnc2sccn12] | H | 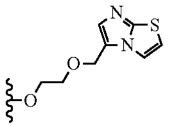 | H |
| 1214 | —OPr | 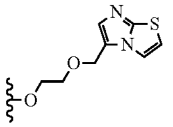 [SMILES: *OCCOCc1cnc2sccn12] | H | 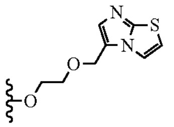 [SMILES: *OCCOCc1cnc2sccn12] | H |
| 1215 | —OiPr | 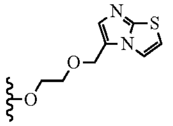 [SMILES: *OCCOCc1cnc2sccn12] | H | 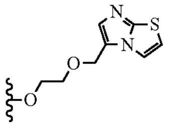 | H |
| 1216 | 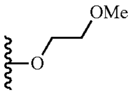 | 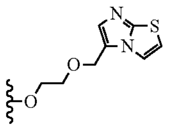 [SMILES: *OCCOCc1cnc2sccn12] | H | 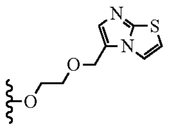 | H |
| 1217 | 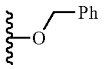 | 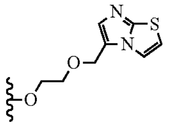 [SMILES: *OCCOCc1cnc2sccn12] | H | 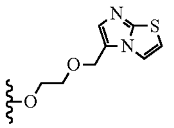 | H |
| 1218 | H | 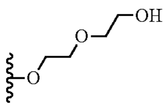 [SMILES: *OCCOCCO] | H | H | 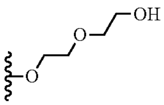 |
| 1219 | —OMe | 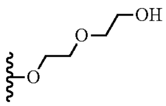 [SMILES: *OCCOCCO] | H | H | 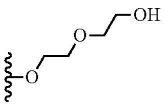 |

-continued
formula (II)
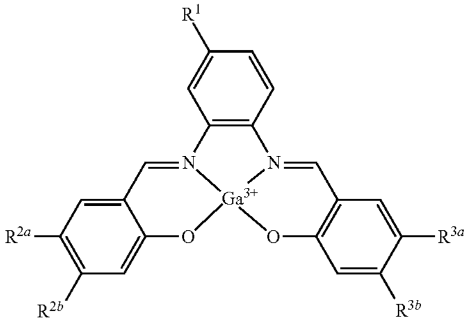
| Compound # | $R^1$ | $R^{2a}$ | $R^{2b}$ | $R^{3a}$ | $R^{3b}$ |
|---|---|---|---|---|---|
| 1220 | —OEt | 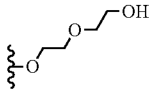 | H | H | 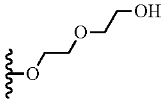 |
| 1221 | —OPr | 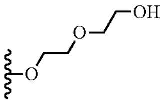 [SMILES: *OCCOCCO] | H | H | 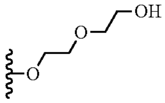 |
| 1222 | —OiPr | 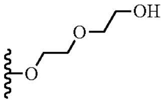 [SMILES: *OCCOCCO] | H | H | 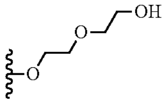 |
| 1223 | 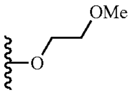 | 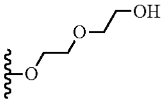 [SMILES: *OCCOCCO] | H | H | 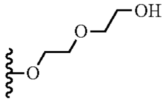 |
| 1224 | 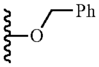 | 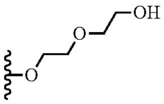 [SMILES: *OCCOCCO] | H | H | 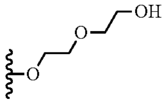 |
| 1225 | H | 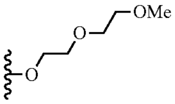 | H | H | 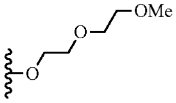 |
| 1226 | —OMe | 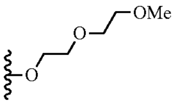 [SMILES: *OCCOCCOC] | H | H | 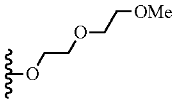 [SMILES: *OCCOCCOC] |
| 1227 | —OEt | 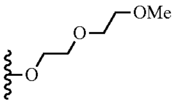 [SMILES: *OCCOCCOC] | H | H | 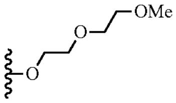 [SMILES: *OCCOCCOC] |
| 1228 | —OPr | 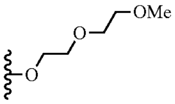 [SMILES: *OCCOCCOC] | H | H | 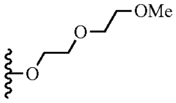 [SMILES: *OCCOCCOC] |
| 1229 | —OiPr | 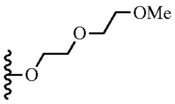 [SMILES: *OCCOCCOC] | H | H | 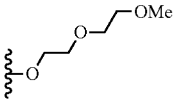 [SMILES: *OCCOCCOC] |

-continued
formula (II)
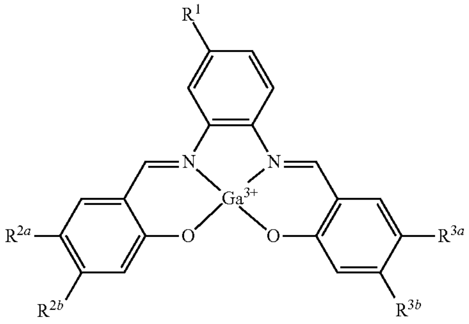
| Compound # | $R^1$ | $R^{2a}$ | $R^{2b}$ | $R^{3a}$ | $R^{3b}$ |
|---|---|---|---|---|---|
| 1230 | 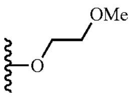 | 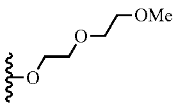 [SMILES: *OCCOCCOC] | H | H | 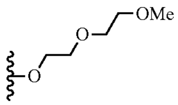 [SMILES: *OCCOCCOC] |
| 1231 | 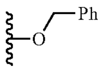 | 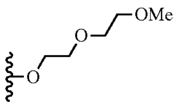 | H | H | 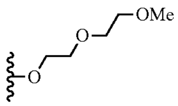 |
| 1232 | H | 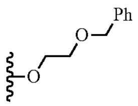 | H | H | 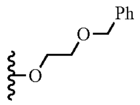 |
| 1233 | —OMe | 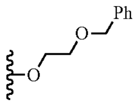 | H | H | 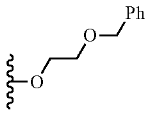 [SMILES: *OCCOCc1ccccc1] |
| 1234 | —OEt | 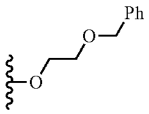 | H | H | 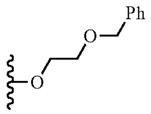 |
| 1235 | —OPr | 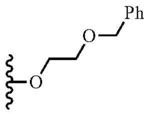 | H | H | 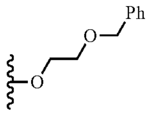 |
| 1236 | —OiPr | 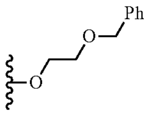 [SMILES: *OCCOCc1ccccc1] | H | H | 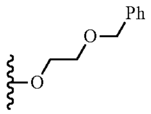 [SMILES: *OCCOCc1ccccc1] |
| 1237 | 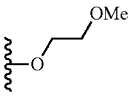 | 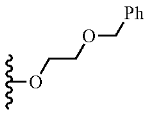 [SMILES: *OCCOCc1ccccc1] | H | H | 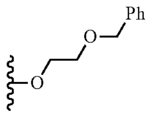 [SMILES: *OCCOCc1ccccc1] |
| 1238 | 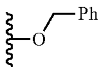 | 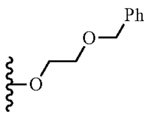 [SMILES: *OCCOCc1ccccc1] | H | H | 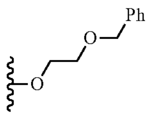 [SMILES: *OCCOCc1ccccc1] |

-continued
formula (II)
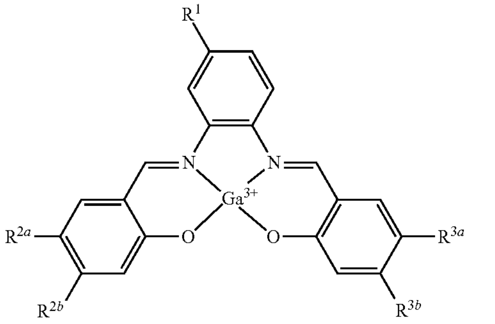
| Compound # | $R^1$ | $R^{2a}$ | $R^{2b}$ | $R^{3a}$ | $R^{3b}$ |
|---|---|---|---|---|---|
| 1239 | H | 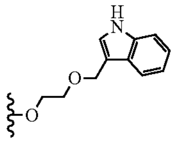 | H | H | 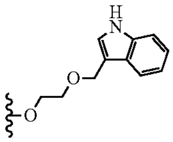 [SMILES: *OCCOCc1c[nH]c2ccccc12] |
| 1240 | —OMe | 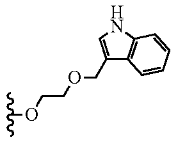 [SMILES: *OCCOCc1c[nH]c2ccccc12] | H | H | 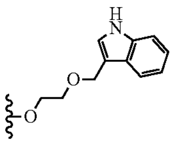 [SMILES: *OCCOCc1c[nH]c2ccccc12] |
| 1241 | —OEt | 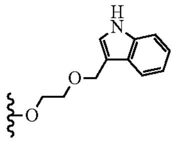 | H | H | 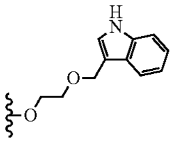 [SMILES: *OCCOCc1c[nH]c2ccccc12] |
| 1242 | —OPr | 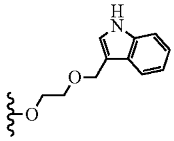 [SMILES: *OCCOCc1c[nH]c2ccccc12] | H | H | 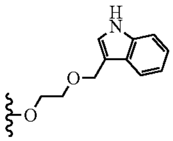 [SMILES: *OCCOCc1c[nH]c2ccccc12] |
| 1243 | —OiPr | 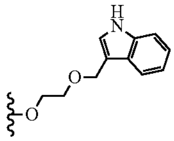 [SMILES: *OCCOCc1c[nH]c2ccccc12] | H | H | 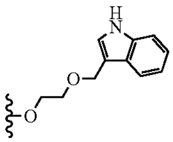 [SMILES: *OCCOCc1c[nH]c2ccccc12] |
| 1244 | 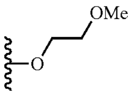 | 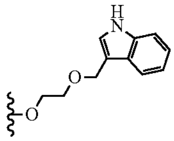 [SMILES: *OCCOCc1c[nH]c2ccccc12] | H | H | 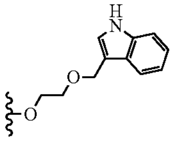 [SMILES: *OCCOCc1c[nH]c2ccccc12] |
| 1245 | 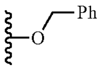 | 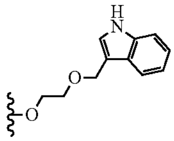 [SMILES: *OCCOCc1c[nH]c2ccccc12] | H | H | 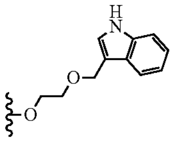 [SMILES: *OCCOCc1c[nH]c2ccccc12] |
| 1246 | H | 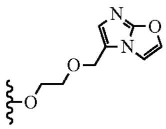 [SMILES: *OCCOCc1cnc2occn12] | H | H | 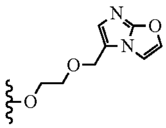 |

-continued
formula (II)
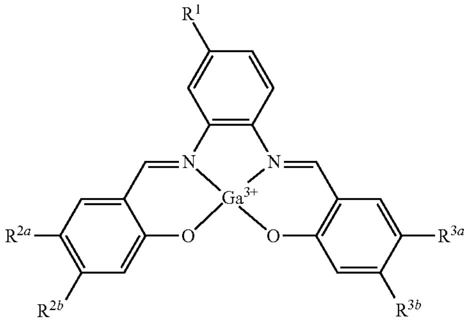
| Compound # | $R^1$ | $R^{2a}$ | $R^{2b}$ | $R^{3a}$ | $R^{3b}$ |
|---|---|---|---|---|---|
| 1247 | —OMe | 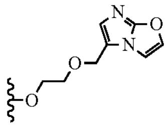 | H | H | 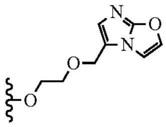 |
| 1248 | —OEt | 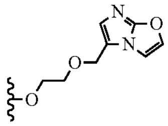 | H | H | 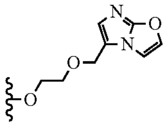 |
| 1249 | —OPr | 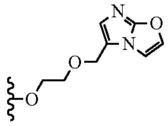 [SMILES: *OCCOCc1cnc2occn12] | H | H | 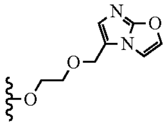 |
| 1250 | —OiPr | 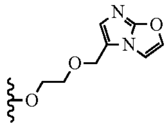 [SMILES: *OCCOCc1cnc2occn12] | H | H | 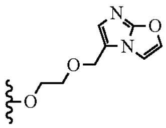 |
| 1251 | 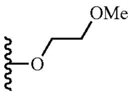 | 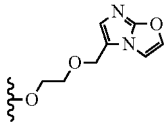 [SMILES: *OCCOCc1cnc2occn12] | H | H | 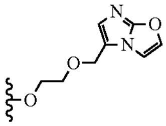 |
| 1252 | 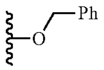 | 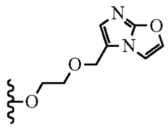 [SMILES: *OCCOCc1cnc2occn12] | H | H | 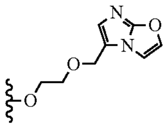 |
| 1253 | H | 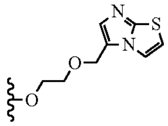 [SMILES: *OCCOCc1cnc2sccn12] | H | H | 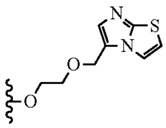 [SMILES: *OCCOCc1cnc2sccn12] |
| 1254 | —OMe | 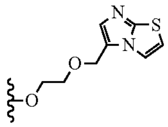 [SMILES: *OCCOCc1cnc2sccn12] | H | H | 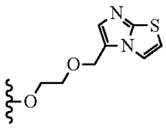 |

-continued
formula (II)
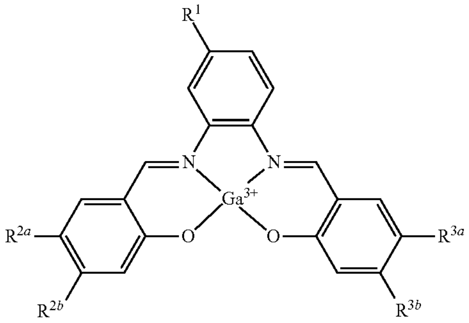
| Compound # | $R^1$ | $R^{2a}$ | $R^{2b}$ | $R^{3a}$ | $R^{3b}$ |
|---|---|---|---|---|---|
| 1255 | —OEt | 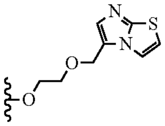 [SMILES: *OCCOCc1cnc2sccn12] | H | H | 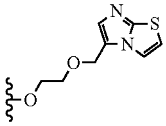 |
| 1256 | —OPr | 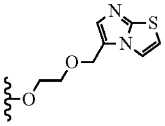 [SMILES: *OCCOCc1cnc2sccn12] | H | H | 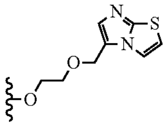 |
| 1257 | —OiPr | 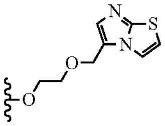 [SMILES: *OCCOCc1cnc2sccn12] | H | H | 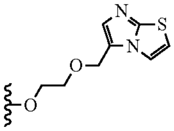 [SMILES: *OCCOCc1cnc2sccn12] |
| 1258 | 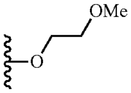 | 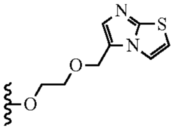 [SMILES: *OCCOCc1cnc2sccn12] | H | H | 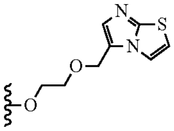 [SMILES: *OCCOCc1cnc2sccn12] |
| 1259 | 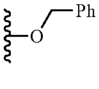 | 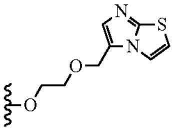 | H | H | 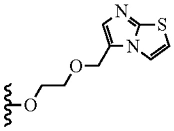 [SMILES: *OCCOCc1cnc2sccn12] |
| 1260 | H | H | 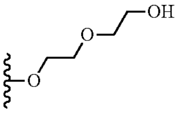 [SMILES: *OCCOCCO] | 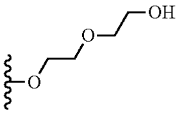 | H |
| 1261 | —OMe | H | 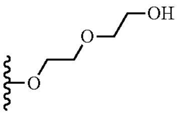 [SMILES: *OCCOCCO] | 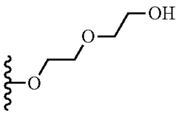 | H |
| 1262 | —OEt | H | 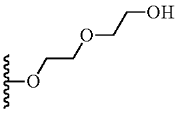 [SMILES: *OCCOCCO] | 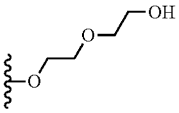 | H |

-continued
formula (II)
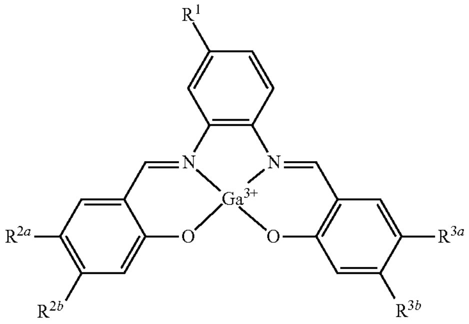
| Compound # | $R^1$ | $R^{2a}$ | $R^{2b}$ | $R^{3a}$ | $R^{3b}$ |
|---|---|---|---|---|---|
| 1263 | —OPr | H | 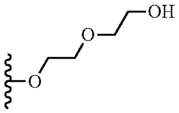 [SMILES: *OCCOCCO] | 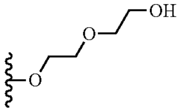 | H |
| 1264 | —OiPr | H | 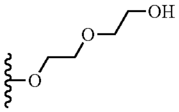 [SMILES: *OCCOCCO] | 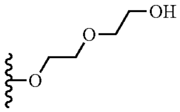 | H |
| 1265 | 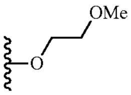 | H | 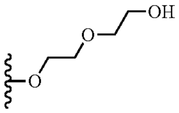 [SMILES: *OCCOCCO] | 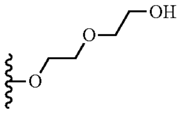 | H |
| 1266 | 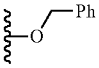 | H | 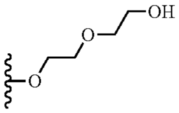 [SMILES: *OCCOCCO] | 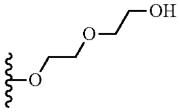 | H |
| 1267 | H | H | 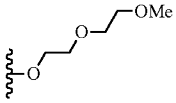 [SMILES: *OCCOCCOC] | 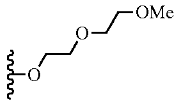 [SMILES: *OCCOCCOC] | H |
| 1268 | —OMe | H | 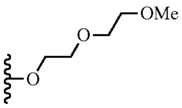 [SMILES: *OCCOCCOC] | 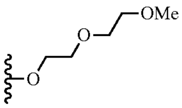 [SMILES: *OCCOCCOC] | H |
| 1269 | —OEt | H | 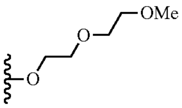 [SMILES: *OCCOCCOC] | 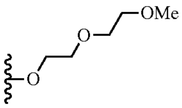 [SMILES: *OCCOCCOC] | H |
| 1270 | —OPr | H | 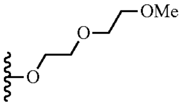 [SMILES: *OCCOCCOC] | 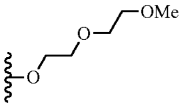 | H |
| 1271 | —OiPr | H | 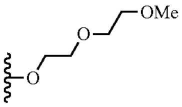 [SMILES: *OCCOCCOC] | 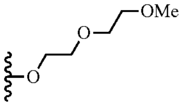 [SMILES: *OCCOCCOC] | H |

-continued
formula (II)
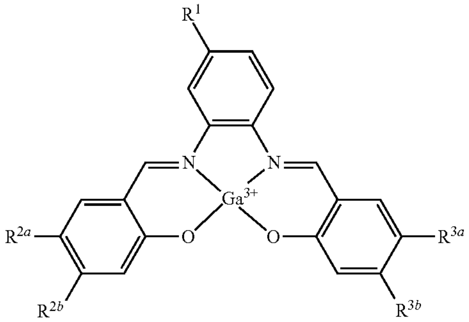
| Compound # | $R^1$ | $R^{2a}$ | $R^{2b}$ | $R^{3a}$ | $R^{3b}$ |
|---|---|---|---|---|---|
| 1272 | 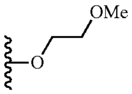 | H | 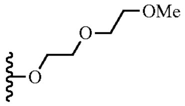 [SMILES: *OCCOCCOC] | 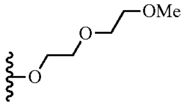 [SMILES: *OCCOCCOC] | H |
| 1273 | 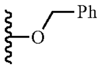 | H | 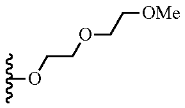 [SMILES: *OCCOCCOC] | 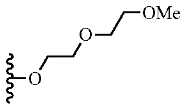 | H |
| 1274 | H | H | 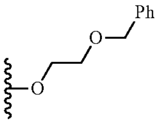 | 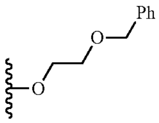 [SMILES: *OCCOCc1ccccc1] | H |
| 1275 | —OMe | H | 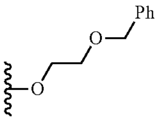 | 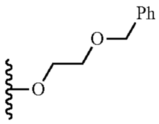 [SMILES: *OCCOCc1ccccc1] | H |
| 1276 | —OEt | H | 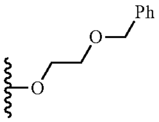 | 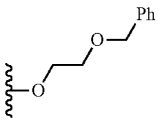 [SMILES: *OCCOCc1ccccc1] | H |
| 1277 | —OPr | H | 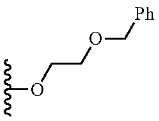 | 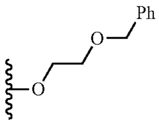 [SMILES: *OCCOCc1ccccc1] | H |
| 1278 | —OiPr | H | 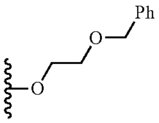 | 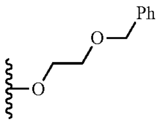 | H |
| 1279 | 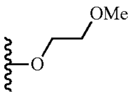 | H | 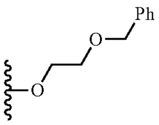 | 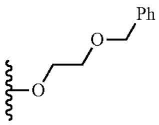 [SMILES: *OCCOCc1ccccc1] | H |
| 1280 | 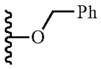 | H | 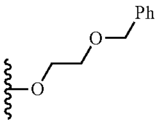 | 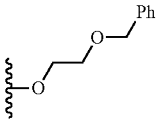 [SMILES: *OCCOCc1ccccc1] | H |

-continued
formula (II)
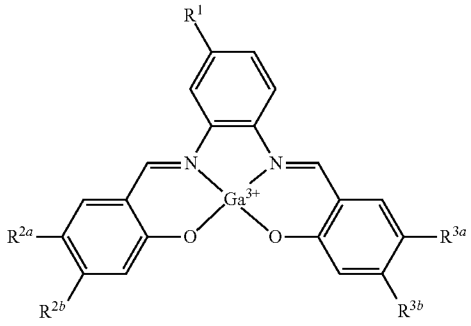
| Compound # | $R^1$ | $R^{2a}$ | $R^{2b}$ | $R^{3a}$ | $R^{3b}$ |
|---|---|---|---|---|---|
| 1281 | H | H | 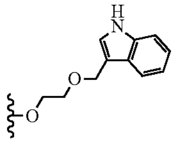 [SMILES: *OCCOCc1c[nH]c2ccccc12] | 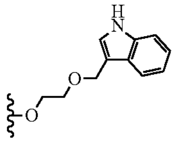 [SMILES: *OCCOCc1c[nH]c2ccccc12] | H |
| 1282 | —OMe | H | 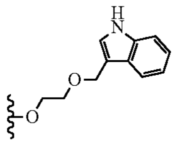 [SMILES: *OCCOCc1c[nH]c2ccccc12] | 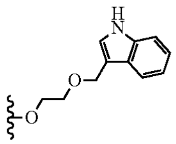 [SMILES: *OCCOCc1c[nH]c2ccccc12] | H |
| 1283 | —OEt | H | 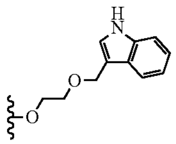 [SMILES: *OCCOCc1c[nH]c2ccccc12] | 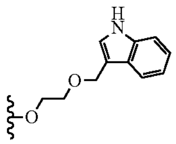 [SMILES: *OCCOCc1c[nH]c2ccccc12] | H |
| 1284 | —OPr | H | 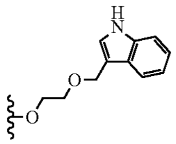 [SMILES: *OCCOCc1c[nH]c2ccccc12] | 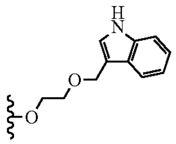 [SMILES: *OCCOCc1c[nH]c2ccccc12] | H |
| 1285 | —OiPr | H | 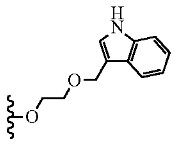 [SMILES: *OCCOCc1c[nH]c2ccccc12] | 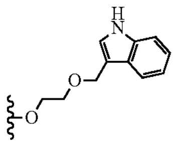 [SMILES: *OCCOCc1c[nH]c2ccccc12] | H |
| 1286 | 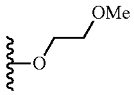 | H | 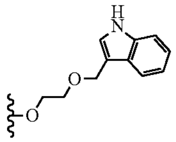 [SMILES: *OCCOCc1c[nH]c2ccccc12] | 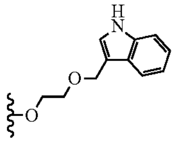 [SMILES: *OCCOCc1c[nH]c2ccccc12] | H |
| 1287 | 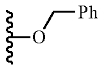 | H | 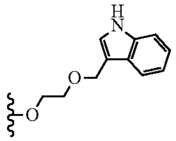 [SMILES: *OCCOCc1c[nH]c2ccccc12] | 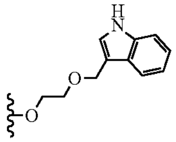 [SMILES: *OCCOCc1c[nH]c2ccccc12] | H |

-continued
formula (II)
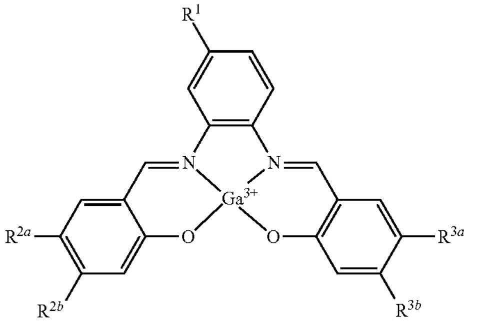
| Compound # | $R^1$ | $R^{2a}$ | $R^{2b}$ | $R^{3a}$ | $R^{3b}$ |
|---|---|---|---|---|---|
| 1288 | H | H | 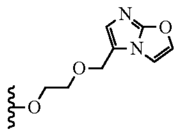 [SMILES: *OCCOCc1cnc2occn12] | 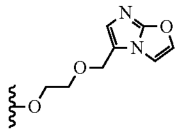 [SMILES: *OCCOCc1cnc2occn12] | H |
| 1289 | —OMe | H | 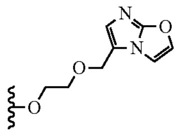 | 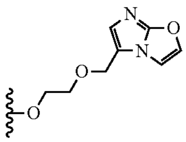 [SMILES: *OCCOCc1cnc2occn12] | H |
| 1290 | —OEt | H | 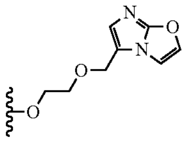 [SMILES: *OCCOCc1cnc2occn12] | 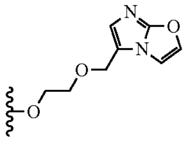 | H |
| 1291 | —OPr | H | 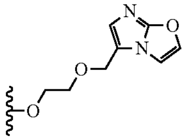 | 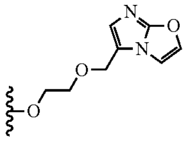 [SMILES: *OCCOCc1cnc2occn12] | H |
| 1292 | —OiPr | H | 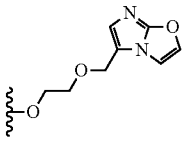 | 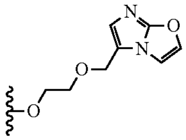 [SMILES: *OCCOCc1cnc2occn12] | H |
| 1293 | 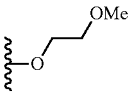 | H | 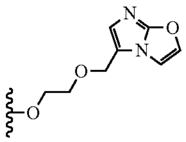 | 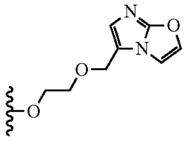 | H |
| 1294 | 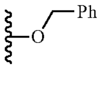 | H | 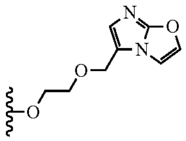 | 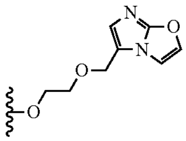 [SMILES: *OCCOCc1cnc2occn12] | H |
| 1295 | H | H | 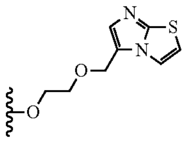 [SMILES: *OCCOCc1cnc2sccn12] | 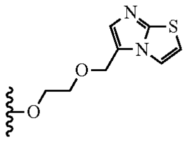 | H |

-continued
formula (II)
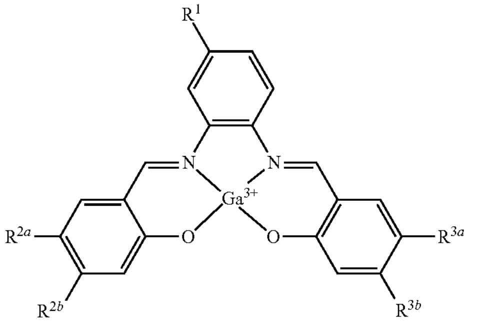
| Compound # | $R^1$ | $R^{2a}$ | $R^{2b}$ | $R^{3a}$ | $R^{3b}$ |
|---|---|---|---|---|---|
| 1296 | —OMe | H | 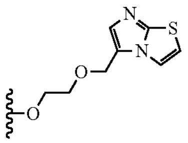 | 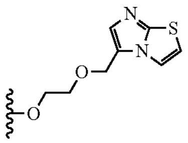 | H |
| 1297 | —OEt | H | 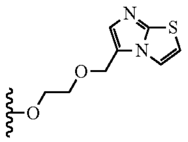 | 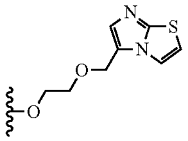 | H |
| 1298 | —OPr | H | 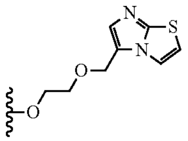 [SMILES: *OCCOCc1cnc2sccn12] | 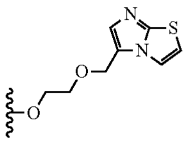 | H |
| 1299 | —OiPr | H | 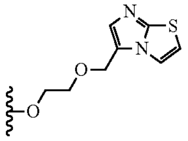 [SMILES: *OCCOCc1cnc2sccn12] | 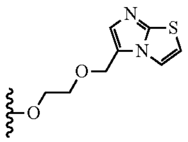 [SMILES: *OCCOCc1cnc2sccn12] | H |
| 1300 | 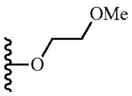 | H | 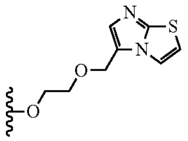 | 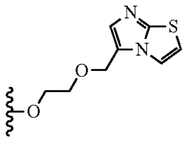 | H |
| 1301 | 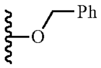 | H | 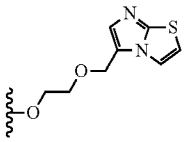 [SMILES: *OCCOCc1cnc2sccn12] | 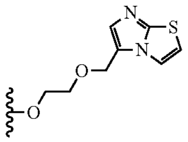 | H |
| 1302 | H | H | 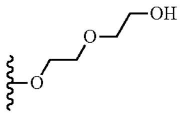 [SMILES: *OCCOCCO] | H | 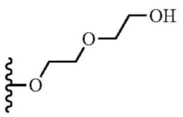 [SMILES: *OCCOCCO] |
| 1303 | —OMe | H | 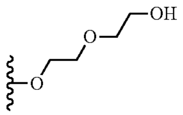 [SMILES: *OCCOCCO] | H | 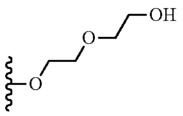 |

-continued
formula (II)
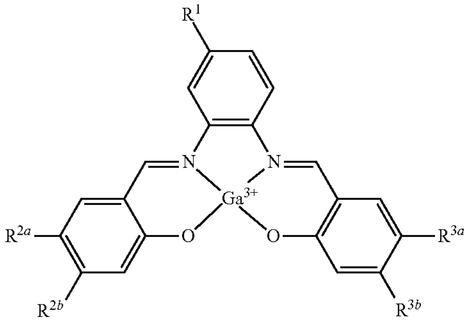
| Compound # | $R^1$ | $R^{2a}$ | $R^{2b}$ | $R^{3a}$ | $R^{3b}$ |
|---|---|---|---|---|---|
| 1304 | —OEt | H | 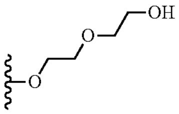 [SMILES: *OCCOCCO] | H | 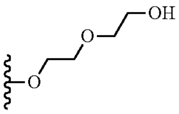 [SMILES: *OCCOCCO] |
| 1305 | —OPr | H | 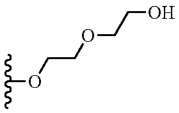 [SMILES: *OCCOCCO] | H | 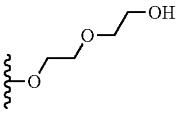 [SMILES: *OCCOCCO] |
| 1306 | —OiPr | H | 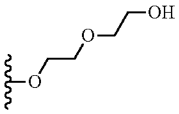 [SMILES: *OCCOCCO] | H | 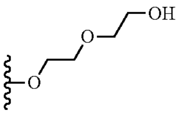 [SMILES: *OCCOCCO] |
| 1307 | 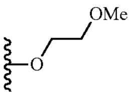 | H | 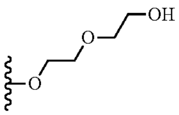 [SMILES: *OCCOCCO] | H | 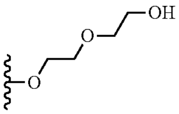 [SMILES: *OCCOCCO] |
| 1308 | 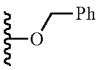 [SMILES: *OCc1ccccc1] | H | 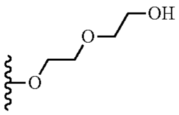 [SMILES: *OCCOCCO] | H | 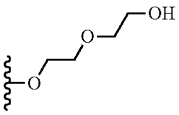 |
| 1309 | H | H | 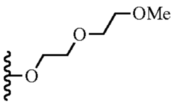 | H | 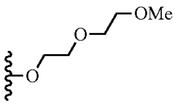 [SMILES: *OCCOCCOC] |
| 1310 | —OMe | H | 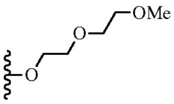 [SMILES: *OCCOCCOC] | H | 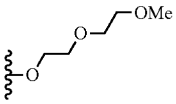 [SMILES: *OCCOCCOC] |
| 1311 | —OEt | H | 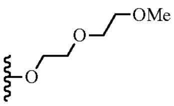 [SMILES: *OCCOCCOC] | H | 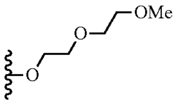 [SMILES: *OCCOCCOC] |
| 1312 | —OPr | H | 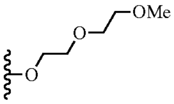 | H | 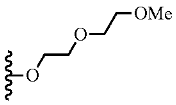 |

-continued
formula (II)
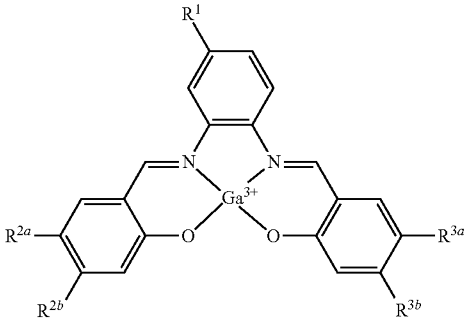
| Compound # | $R^1$ | $R^{2a}$ | $R^{2b}$ | $R^{3a}$ | $R^{3b}$ |
|---|---|---|---|---|---|
| 1313 | —OiPr | H | 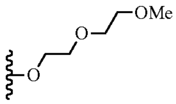 [SMILES: *OCCOCCOC] | H | 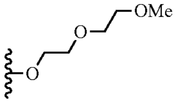 |
| 1314 | 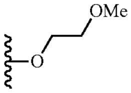 | H | 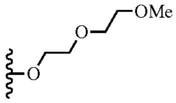 [SMILES: *OCCOCCOC] | H | 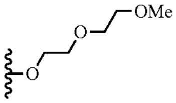 |
| 1315 | 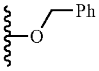 | H | 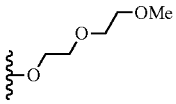 [SMILES: *OCCOCCOC] | H | 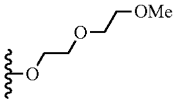 [SMILES: *OCCOCCOC] |
| 1316 | H | H | 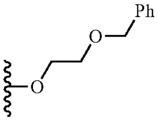 [SMILES: *OCCOCc1ccccc1] | H | 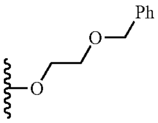 [SMILES: *OCCOCc1ccccc1] |
| 1317 | —OMe | H | 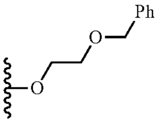 | H | 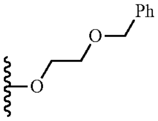 [SMILES: *OCCOCc1ccccc1] |
| 1318 | —OEt | H | 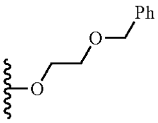 | H | 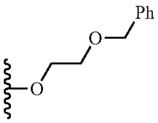 [SMILES: *OCCOCc1ccccc1] |
| 1319 | —OPr | H | 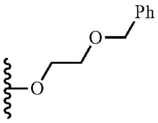 | H | 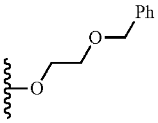 [SMILES: *OCCOCc1ccccc1] |
| 1320 | —OiPr | H | 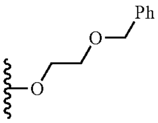 | H | 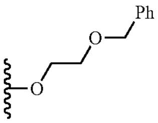 [SMILES: *OCCOCc1ccccc1] |
| 1321 | 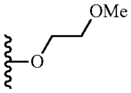 | H | 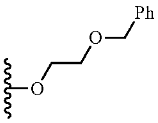 | H | 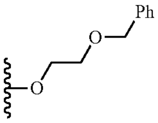 [SMILES: *OCCOCc1ccccc1] |

-continued
formula (II)
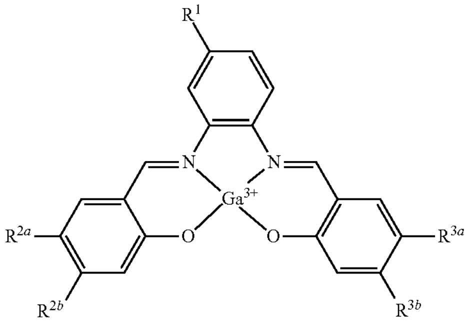
| Compound # | $R^1$ | $R^{2a}$ | $R^{2b}$ | $R^{3a}$ | $R^{3b}$ |
|---|---|---|---|---|---|
| 1322 | 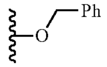 | H | 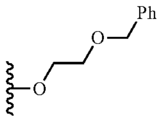 | H | 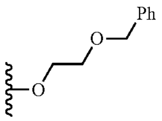 [SMILES: *OCCOCc1ccccc1] |
| 1323 | H | H | 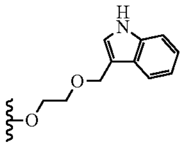 [SMILES: *OCCOCc1c[nH]c2ccccc12] | H | 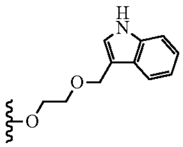 [SMILES: *OCCOCc1c[nH]c2ccccc12] |
| 1324 | —OMe | H | 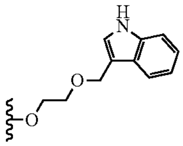 [SMILES: *OCCOCc1c[nH]c2ccccc12] | H | 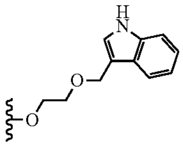 [SMILES: *OCCOCc1c[nH]c2ccccc12] |
| 1325 | —OEt | H | 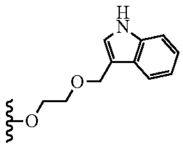 [SMILES: *OCCOCc1c[nH]c2ccccc12] | H | 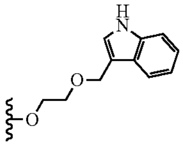 [SMILES: *OCCOCc1c[nH]c2ccccc12] |
| 1326 | —OPr | H | 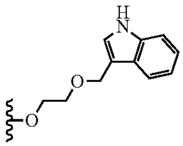 [SMILES: *OCCOCc1c[nH]c2ccccc12] | H | 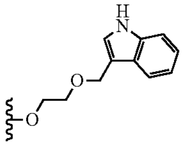 [SMILES: *OCCOCc1c[nH]c2ccccc12] |
| 1327 | —OiPr | H | 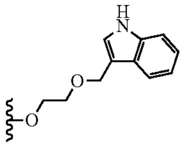 [SMILES: *OCCOCc1c[nH]c2ccccc12] | H | 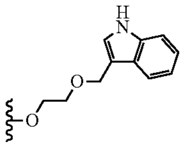 [SMILES: *OCCOCc1c[nH]c2ccccc12] |
| 1328 | 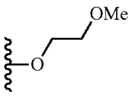 | H | 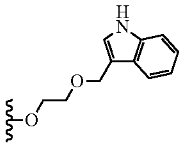 [SMILES: *OCCOCc1c[nH]c2ccccc12] | H | 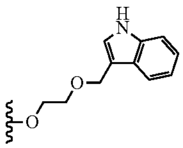 [SMILES: *OCCOCc1c[nH]c2ccccc12] |

-continued
formula (II)
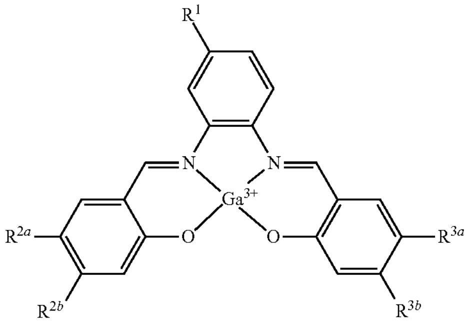
| Compound # | $R^1$ | $R^{2a}$ | $R^{2b}$ | $R^{3a}$ | $R^{3b}$ |
|---|---|---|---|---|---|
| 1329 | 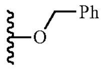 | H | 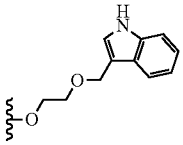 [SMILES: *OCCOCc1c[nH]c2ccccc12] | H | 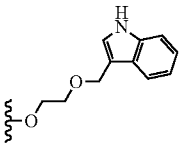 [SMILES: *OCCOCc1c[nH]c2ccccc12] |
| 1330 | H | H | 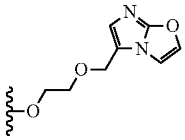 [SMILES: *OCCOCc1cnc2occn12] | H | 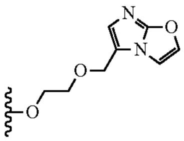 [SMILES: *OCCOCc1cnc2occn12] |
| 1331 | —OMe | H | 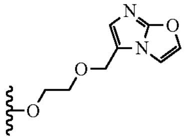 [SMILES: *OCCOCc1cnc2occn12] | H | 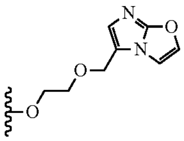 [SMILES: *OCCOCc1cnc2occn12] |
| 1332 | —OEt | H | 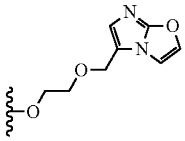 | H | 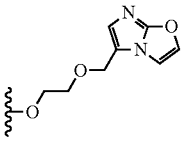 |
| 1333 | —OPr | H | 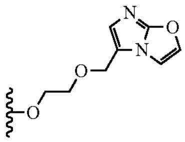 [SMILES: *OCCOCc1cnc2occn12] | H | 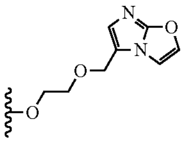 [SMILES: *OCCOCc1cnc2occn12] |
| 1334 | —OiPr | H | 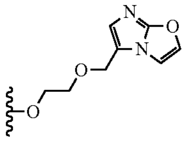 | H | 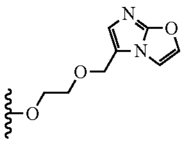 [SMILES: *OCCOCc1cnc2occn12] |
| 1335 | 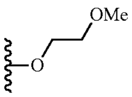 | H | 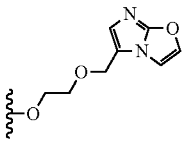 | H | 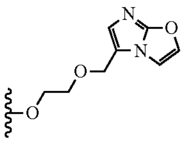 [SMILES: *OCCOCc1cnc2occn12] |

-continued
formula (II)
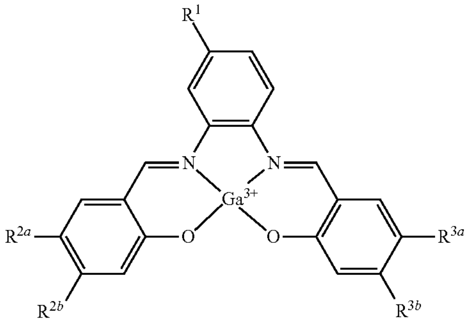
| Compound # | $R^1$ | $R^{2a}$ | $R^{2b}$ | $R^{3a}$ | $R^{3b}$ |
|---|---|---|---|---|---|
| 1336 | 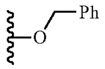 | H | 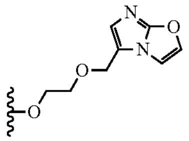 | H | 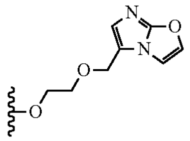 [SMILES: *OCCOCc1cnc2occn12] |
| 1337 | H | H | 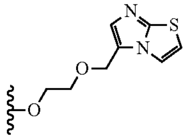 [SMILES: *OCCOCc1cnc2sccn12] | H | 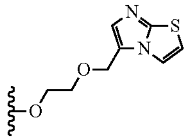 [SMILES: *OCCOCc1cnc2sccn12] |
| 1338 | —OMe | H | 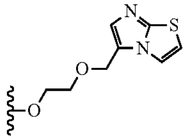 | H | 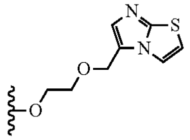 |
| 1339 | —OEt | H | 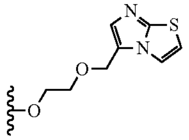 | H | 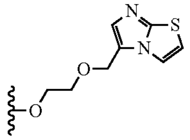 |
| 1340 | —OPr | H | 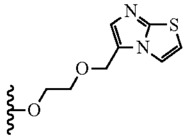 [SMILES: *OCCOCc1cnc2sccn12] | H | 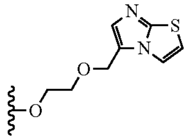 |
| 1341 | —OiPr | H | 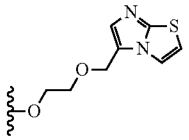 [SMILES: *OCCOCc1cnc2sccn12] | H | 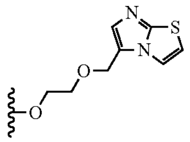 [SMILES: *OCCOCc1cnc2sccn12] |
| 1342 | 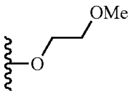 | H | 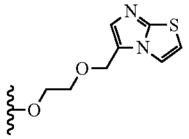 [SMILES: *OCCOCc1cnc2sccn12] | H | 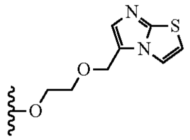 [SMILES: *OCCOCc1cnc2sccn12] |

-continued
formula (II)
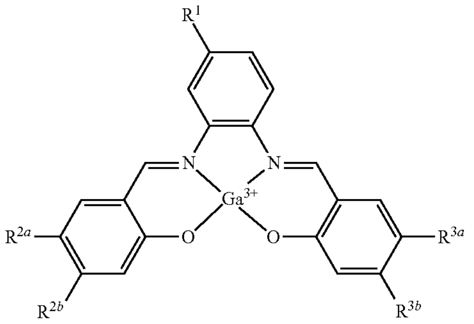
| Compound # | $R^1$ | $R^{2a}$ | $R^{2b}$ | $R^{3a}$ | $R^{3b}$ |
|---|---|---|---|---|---|
| 1343 | 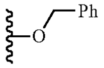 | H | 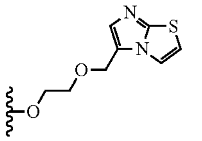 [SMILES: *OCCOCc1cnc2sccn12] | H | 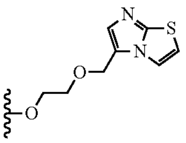 [SMILES: *OCCOCc1cnc2sccn12] |
| 1344 | H | 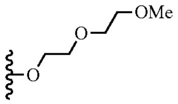 [SMILES: *OCCOCCOC] | H | H | H |
| 1345 | —OMe | 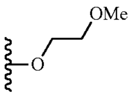 [SMILES: *OCCOC] | H | H | H |
| 1346 | —OEt | 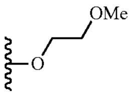 [SMILES: *OCCOC] | H | H | H |
| 1347 | —OPr | 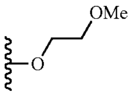 [SMILES: *OCCOC] | H | H | H |
| 1348 | —OiPr | 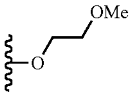 | H | H | H |
| 1349 | 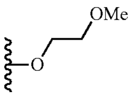 | 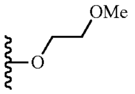 [SMILES: *OCCOC] | H | H | H |
| 1350 | 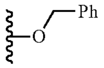 | 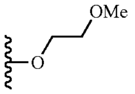 [SMILES: *OCCOC] | H | H | H |
| 1351 | H | H | 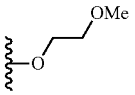 [SMILES: *OCCOC] | H | H |
| 1352 | —OMe | H | 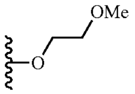 | H | H |

-continued
formula (II)
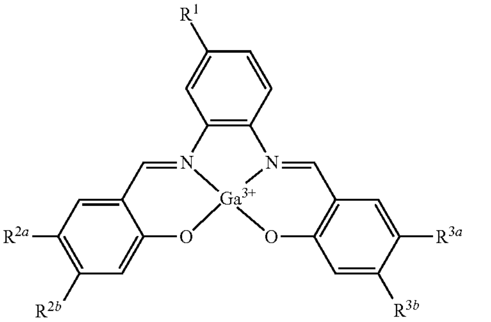
| Compound # | $R^1$ | $R^{2a}$ | $R^{2b}$ | $R^{3a}$ | $R^{3b}$ |
|---|---|---|---|---|---|
| 1353 | —OEt | H | 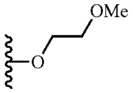 [SMILES: *OCCOC] | H | H |
| 1354 | —OPr | H | 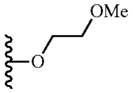 [SMILES: *OCCOC] | H | H |
| 1355 | —OiPr | H | 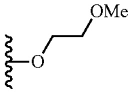 [SMILES: *OCCOC] | H | H |
| 1356 | 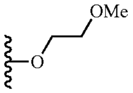 | H | 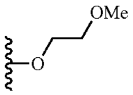 | H | H |
| 1357 | 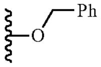 | H | 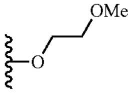 | H | H |
| 1358 | H | H | H | 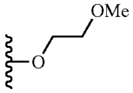 | H |
| 1359 | —OMe | H | H | 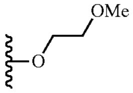 [SMILES: *OCCOC] | H |
| 1360 | —OEt | H | H | 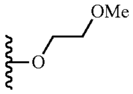 [SMILES: *OCCOC] | H |
| 1361 | —OPr | H | H | 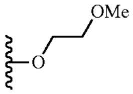 [SMILES: *OCCOC] | H |
| 1362 | —OiPr | H | H | 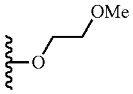 | H |
| 1363 | 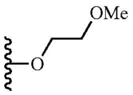 | H | H | 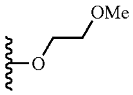 [SMILES: *OCCOC] | H |

-continued
formula (II)
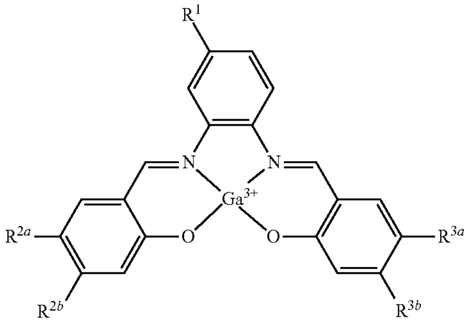
| Compound # | $R^1$ | $R^{2a}$ | $R^{2b}$ | $R^{3a}$ | $R^{3b}$ |
|---|---|---|---|---|---|
| 1364 | 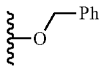 | H | H | 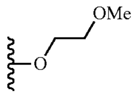 [SMILES: *OCCOC] | H |
| 1365 | H | H | H | H | 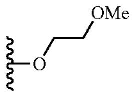 |
| 1366 | —OMe | H | H | H | 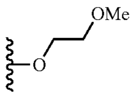 |
| 1367 | —OEt | H | H | H | 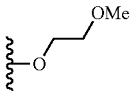 |
| 1368 | —OPr | H | H | H | 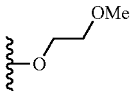 |
| 1369 | —OiPr | H | H | H | 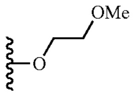 |
| 1370 | 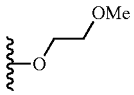 | H | H | H | 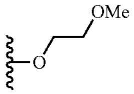 |
| 1371 | 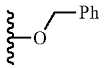 | H | H | H | 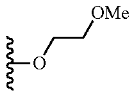 |
| 1372 | H | 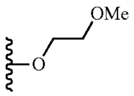 [SMILES: *OCCOC] | H | 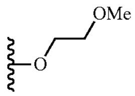 [SMILES: *OCCOC] | H |
| 1373 | —OMe | 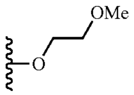 [SMILES: *OCCOC] | H | 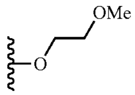 [SMILES: *OCCOC] | H |

-continued
formula (II)
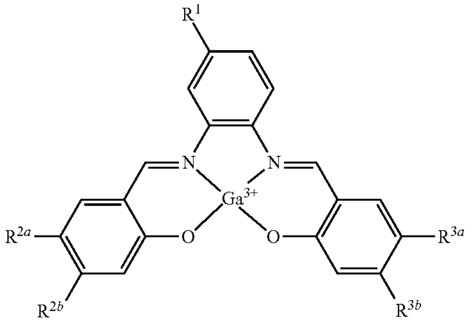
| Compound # | $R^1$ | $R^{2a}$ | $R^{2b}$ | $R^{3a}$ | $R^{3b}$ |
|---|---|---|---|---|---|
| 1374 | —OEt | 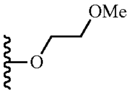 [SMILES: *OCCOC] | H | 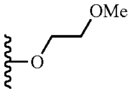 [SMILES: *OCCOC] | H |
| 1375 | —OPr | 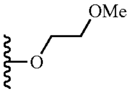 [SMILES: *OCCOC] | H | 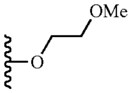 [SMILES: *OCCOC] | H |
| 1376 | —OiPr | 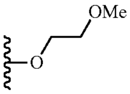 [SMILES: *OCCOC] | H | 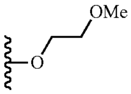 [SMILES: *OCCOC] | H |
| 1377 | 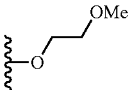 | 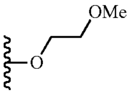 [SMILES: *OCCOC] | H | 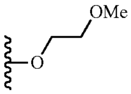 [SMILES: *OCCOC] | H |
| 1378 | 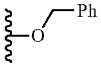 | 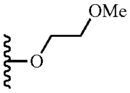 [SMILES: *OCCOC] | H | 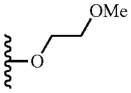 [SMILES: *OCCOC] | H |
| 1379 | H | 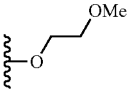 | H | H | 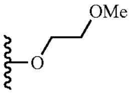 |
| 1380 | —OMe | 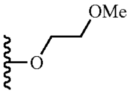 [SMILES: *OCCOC] | H | H | 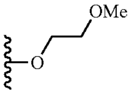 |
| 1381 | —OEt | 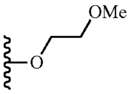 [SMILES: *OCCOC] | H | H | 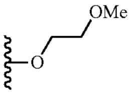 |
| 1382 | —OPr | 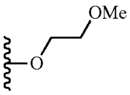 [SMILES: *OCCOC] | H | H | 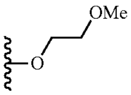 |
| 1383 | —OiPr | 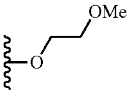 [SMILES: *OCCOC] | H | H | 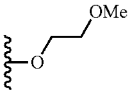 |
| 1384 | 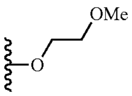 | 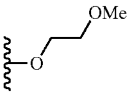 | H | H | 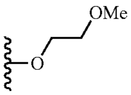 |

-continued
formula (II)
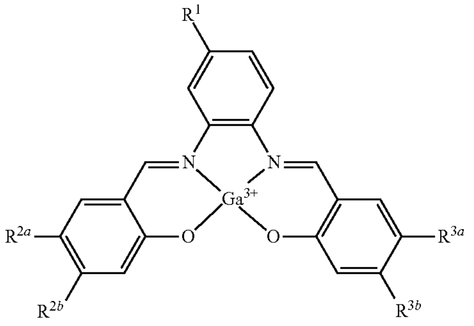
| Compound # | $R^1$ | $R^{2a}$ | $R^{2b}$ | $R^{3a}$ | $R^{3b}$ |
|---|---|---|---|---|---|
| 1385 | 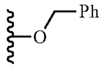 [SMILES: *OCc1ccccc1] | 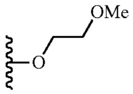 [SMILES: *OCCOC] | H | H | 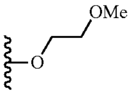 |
| 1386 | H | H | 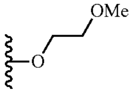 [SMILES: *OCCOC] | 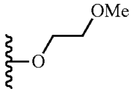 [SMILES: *OCCOC] | H |
| 1387 | —OMe | H | 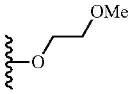 [SMILES: *OCCOC] | 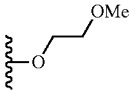 [SMILES: *OCCOC] | H |
| 1388 | —OEt | H | 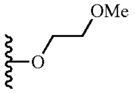 [SMILES: *OCCOC] | 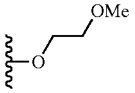 [SMILES: *OCCOC] | H |
| 1389 | —OPr | H | 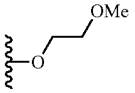 | 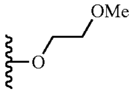 | H |
| 1390 | —OiPr | H | 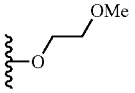 | 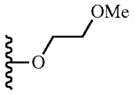 [SMILES: *OCCOC] | H |
| 1391 | 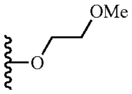 | H | 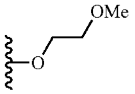 [SMILES: *OCCOC] | 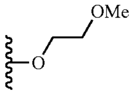 [SMILES: *OCCOC] | H |
| 1392 | 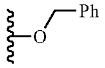 | H | 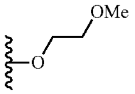 [SMILES: *OCCOC] | 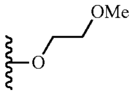 [SMILES: *OCCOC] | H |
| 1393 | H | H | 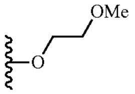 [SMILES: *OCCOC] | H | 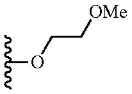 |
| 1394 | —OMe | H | 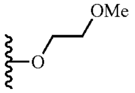 [SMILES: *OCCOC] | H | 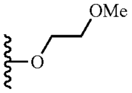 |

-continued
formula (II)
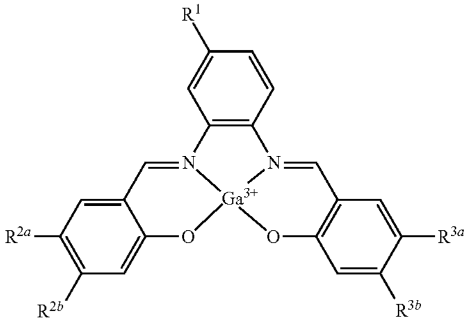
| Compound # | $R^1$ | $R^{2a}$ | $R^{2b}$ | $R^{3a}$ | $R^{3b}$ |
|---|---|---|---|---|---|
| 1395 | —OEt | H | 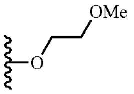 [SMILES: *OCCOC] | H | 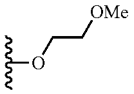 |
| 1396 | —OPr | H | 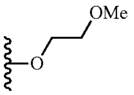 [SMILES: *OCCOC] | H | 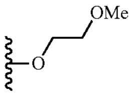 |
| 1397 | —OiPr | H | 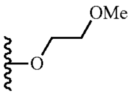 [SMILES: *OCCOC] | H | 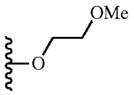 |
| 1398 | 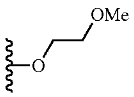 | H | 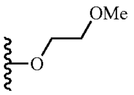 [SMILES: *OCCOC] | H | 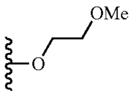 |
| 1399 | 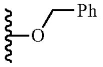 | H | 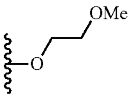 [SMILES: *OCCOC] | H | 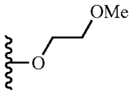 |
| 1400 | H | 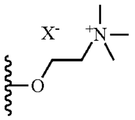 | H | H | H |
| 1401 | —OMe | 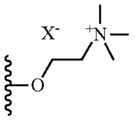 | H | H | H |
| 1402 | —OEt | 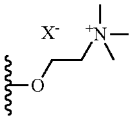 | H | H | H |
| 1403 | —OPr | 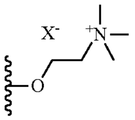 | H | H | H |
| 1404 | —OiPr | 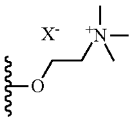 | H | H | H |

-continued
formula (II)
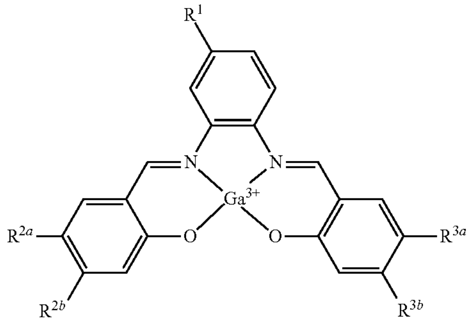
| Compound # | $R^1$ | $R^{2a}$ | $R^{2b}$ | $R^{3a}$ | $R^{3b}$ |
|---|---|---|---|---|---|
| 1405 | 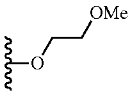 | 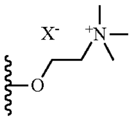 | H | H | H |
| 1406 | 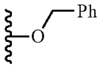 | 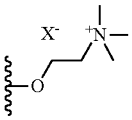 | H | H | H |
| 1407 | H | 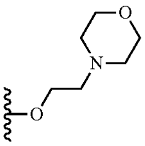 [SMILES: *OCCN1CCOCC1] | H | H | H |
| 1408 | —OMe | 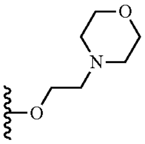 [SMILES: *OCCN1CCOCC1] | H | H | H |
| 1409 | —OEt | 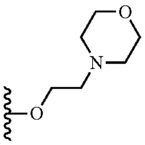 [SMILES: *OCCN1CCOCC1] | H | H | H |
| 1410 | —OPr | 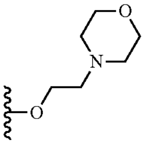 | H | H | H |
| 1411 | —OiPr | 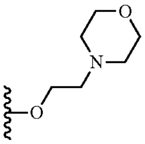 [SMILES: *OCCN1CCOCC1] | H | H | H |

-continued
formula (II)
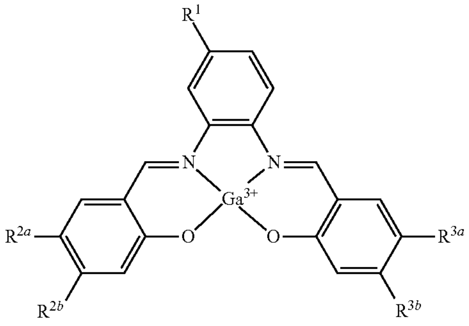
| Compound # | $R^1$ | $R^{2a}$ | $R^{2b}$ | $R^{3a}$ | $R^{3b}$ |
|---|---|---|---|---|---|
| 1412 | 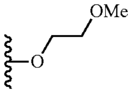 | 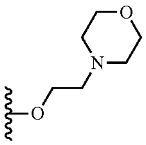 [SMILES: *OCCN1CCOCC1] | H | H | H |
| 1413 | 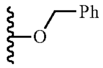 | 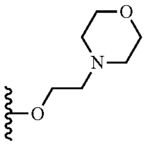 | H | H | H |
| 1414 | H | 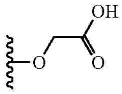 | H | H | H |
| 1415 | —OMe | 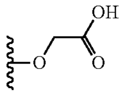 [SMILES: *OCC(=O)O] | H | H | H |
| 1416 | —OEt | 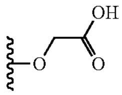 [SMILES: *OCC(=O)O] | H | H | H |
| 1417 | —OPr | 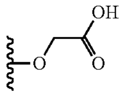 [SMILES: *OCC(=O)O] | H | H | H |
| 1418 | —OiPr | 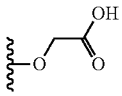 [SMILES: *OCC(=O)O] | H | H | H |
| 1419 | 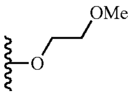 | 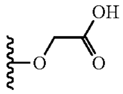 [SMILES: *OCC(=O)O] | H | H | H |
| 1420 | 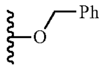 | 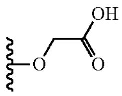 [SMILES: *OCC(=O)O] | H | H | H |

-continued
formula (II)
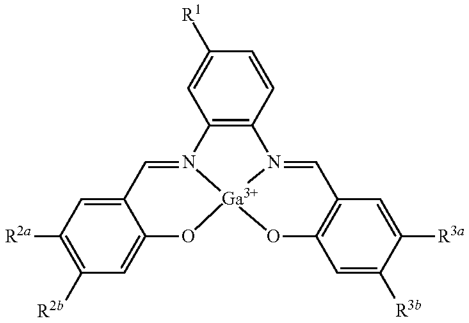
| Compound # | $R^1$ | $R^{2a}$ | $R^{2b}$ | $R^{3a}$ | $R^{3b}$ |
|---|---|---|---|---|---|
| 1421 | H | H | 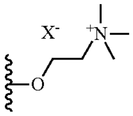 | H | H |
| 1422 | —OMe | H | 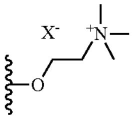 | H | H |
| 1423 | —OEt | H | 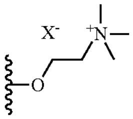 | H | H |
| 1424 | —OPr | H | 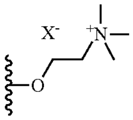 | H | H |
| 1425 | —OiPr | H | 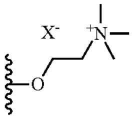 | H | H |
| 1426 | 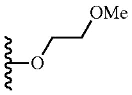 | H | 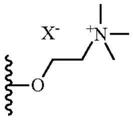 | H | H |
| 1427 | 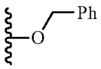 | H | 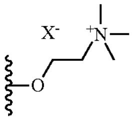 | H | H |
| 1428 | H | H | 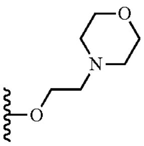 [SMILES: *OCCN1CCOCC1] | H | H |

-continued
formula (II)
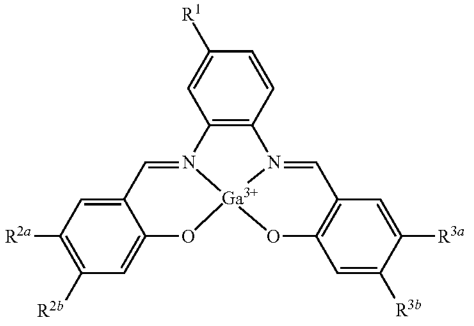
| Compound # | $R^1$ | $R^{2a}$ | $R^{2b}$ | $R^{3a}$ | $R^{3b}$ |
|---|---|---|---|---|---|
| 1429 | —OMe | H | 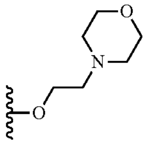 [SMILES: *OCCN1CCOCC1] | H | H |
| 1430 | —OEt | H | 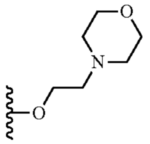 [SMILES: *OCCN1CCOCC1] | H | H |
| 1431 | —OPr | H | 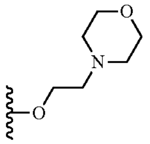 [SMILES: *OCCN1CCOCC1] | H | H |
| 1432 | —OiPr | H | 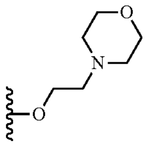 [SMILES: *OCCN1CCOCC1] | H | H |
| 1433 | 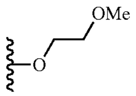 | H | 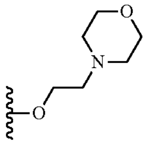 [SMILES: *OCCN1CCOCC1] | H | H |
| 1434 | 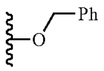 | H | 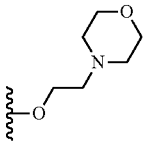 [SMILES: *OCCN1CCOCC1] | H | H |
| 1435 | H | H | 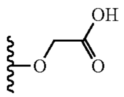 | H | H |
| 1436 | —OMe | H | 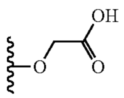 | H | H |

-continued
formula (II)
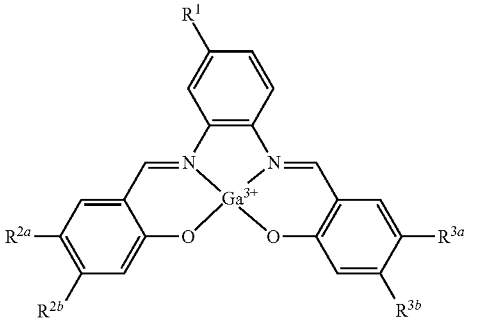
| Compound # | $R^1$ | $R^{2a}$ | $R^{2b}$ | $R^{3a}$ | $R^{3b}$ |
|---|---|---|---|---|---|
| 1437 | —OEt | H | 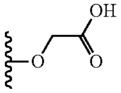 [SMILES: *OCC(=O)O] | H | H |
| 1438 | —OPr | H | 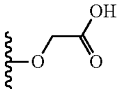 [SMILES: *OCC(=O)O] | H | H |
| 1439 | —OiPr | H | 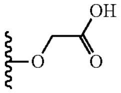 [SMILES: *OCC(=O)O] | H | H |
| 1440 | 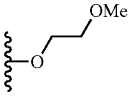 | H | 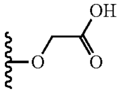 | H | H |
| 1441 | 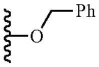 | H | 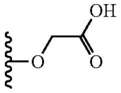 | H | H |
| 1442 | H | H | H | 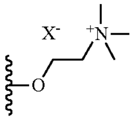 | H |
| 1443 | —OMe | H | H | 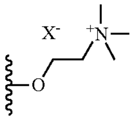 | H |
| 1444 | —OEt | H | H | 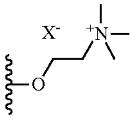 | H |
| 1445 | —OPr | H | H | 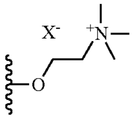 | H |
| 1446 | —OiPr | H | H | 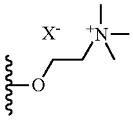 | H |

-continued
formula (II)
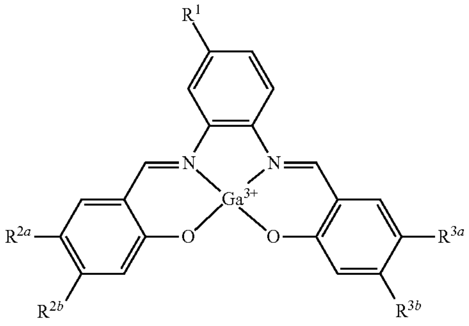
| Compound # | $R^1$ | $R^{2a}$ | $R^{2b}$ | $R^{3a}$ | $R^{3b}$ |
|---|---|---|---|---|---|
| 1447 | 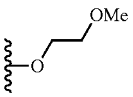 | H | H | 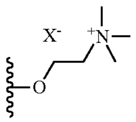 | H |
| 1448 | 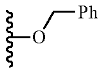 | H | H | 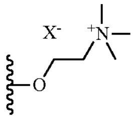 | H |
| 1449 | H | H | H | 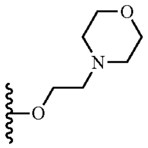 [SMILES: *OCCN1CCOCC1] | H |
| 1450 | —OMe | H | H | 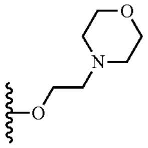 | H |
| 1451 | —OEt | H | H | 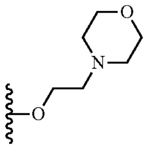 | H |
| 1452 | —OPr | H | H | 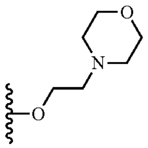 | H |
| 1453 | —OiPr | H | H | 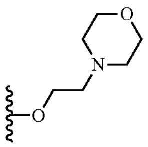 | H |

-continued
formula (II)
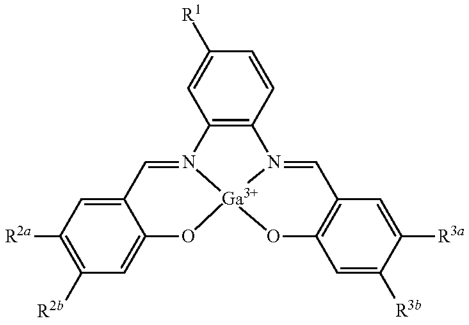
| Compound # | $R^1$ | $R^{2a}$ | $R^{2b}$ | $R^{3a}$ | $R^{3b}$ |
|---|---|---|---|---|---|
| 1454 | 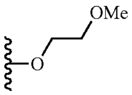 | H | H | 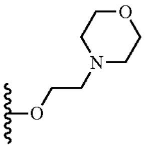 | H |
| 1455 | 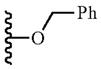 | H | H | 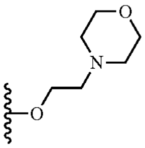 | H |
| 1456 | H | H | H | 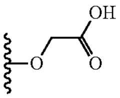 | H |
| 1457 | —OMe | H | H | 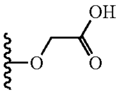 | H |
| 1458 | —OEt | H | H | 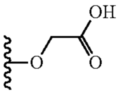 | H |
| 1459 | —OPr | H | H | 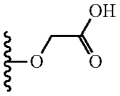 | H |
| 1460 | —OiPr | H | H | 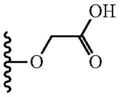 | H |
| 1461 | 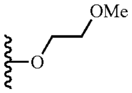 | H | H | 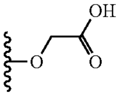 | H |
| 1462 | 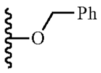 | H | H | 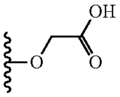 | H |

-continued
formula (II)
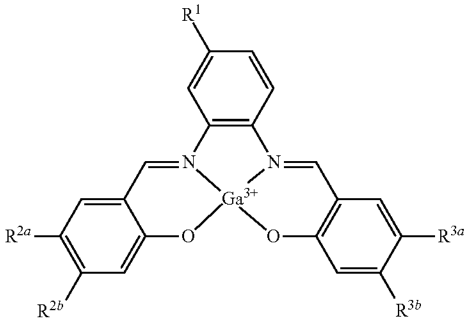
| Compound # | $R^1$ | $R^{2a}$ | $R^{2b}$ | $R^{3a}$ | $R^{3b}$ |
|---|---|---|---|---|---|
| 1463 | H | H | H | H | 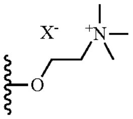 |
| 1464 | —OMe | H | H | H | 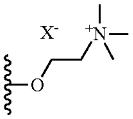 |
| 1465 | —OEt | H | H | H | 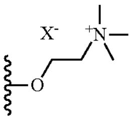 |
| 1466 | —OPr | H | H | H | 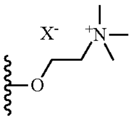 |
| 1467 | —OiPr | H | H | H | 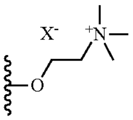 |
| 1468 | 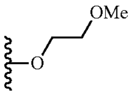 | H | H | H | 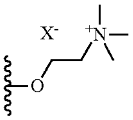 |
| 1469 | 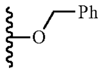 | H | H | H | 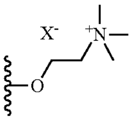 |
| 1470 | H | H | H | H | 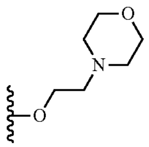 |

-continued
formula (II)
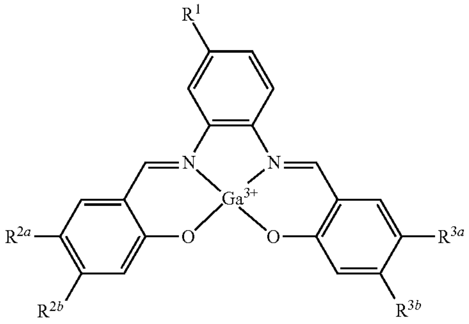
| Compound # | $R^1$ | $R^{2a}$ | $R^{2b}$ | $R^{3a}$ | $R^{3b}$ |
|---|---|---|---|---|---|
| 1471 | —OMe | H | H | H | 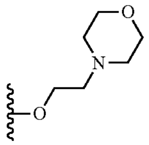 |
| 1472 | —OEt | H | H | H | 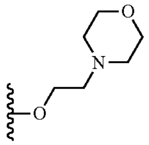 |
| 1473 | —OPr | H | H | H | 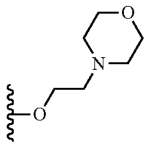 |
| 1474 | —OiPr | H | H | H | 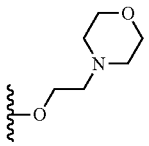 |
| 1475 | 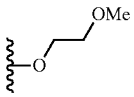 | H | H | H | 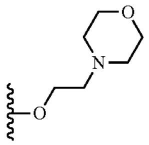 |
| 1476 | 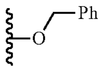 | H | H | H | 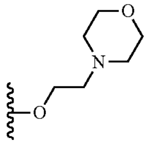 |
| 1477 | H | H | H | H | 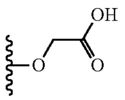 [SMILES: *OCC(=O)O] |
| 1478 | —OMe | H | H | H | 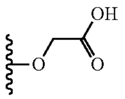 |

-continued
formula (II)
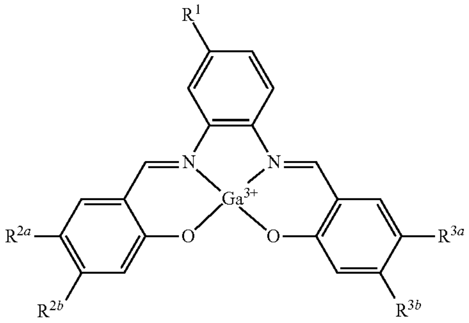
| Compound # | $R^1$ | $R^{2a}$ | $R^{2b}$ | $R^{3a}$ | $R^{3b}$ |
|---|---|---|---|---|---|
| 1479 | —OEt | H | H | H | 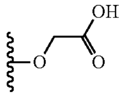 |
| 1480 | —OPr | H | H | H | 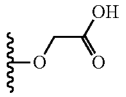 |
| 1481 | —OiPr | H | H | H | 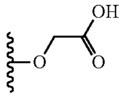 |
| 1482 | 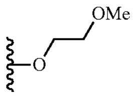 | H | H | H | 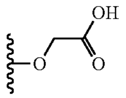 |
| 1483 | 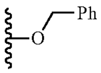 | H | H | H | 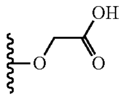 [SMILES: *OCC(=O)O] |
| 1484 | H | 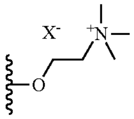 | H | 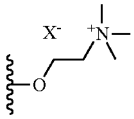 | H |
| 1485 | —OMe | 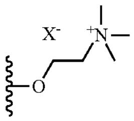 | H | 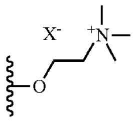 | H |
| 1486 | —OEt | 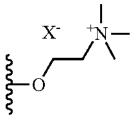 | H | 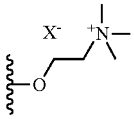 | H |
| 1487 | —OPr | 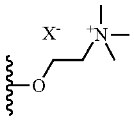 | H | 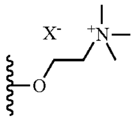 | H |

-continued
formula (II)
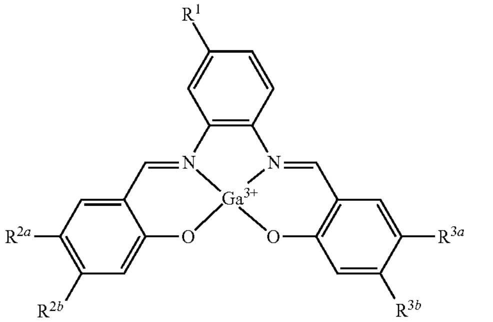
| Compound # | $R^1$ | $R^{2a}$ | $R^{2b}$ | $R^{3a}$ | $R^{3b}$ |
|---|---|---|---|---|---|
| 1488 | —OiPr | 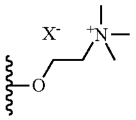 | H | 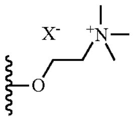 | H |
| 1489 | 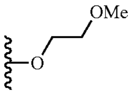 | 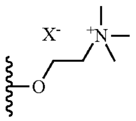 | H | 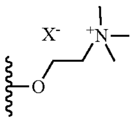 | H |
| 1490 | 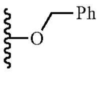 | 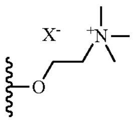 | H | 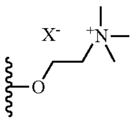 | H |
| 1491 | H | 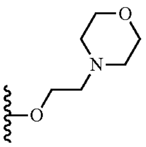 [SMILES: *OCCN1CCOCC1] | H | 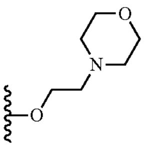 | H |
| 1492 | —OMe | 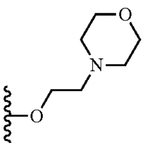 [SMILES: *OCCN1CCOCC1] | H | 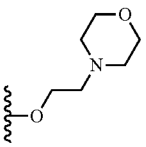 | H |
| 1493 | —OEt | 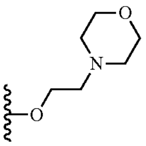 | H | 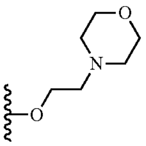 | H |
| 1494 | —OPr | 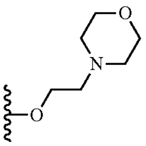 | H | 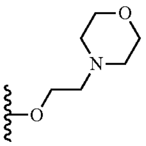 | H |
| 1495 | —OiPr | 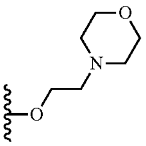 | H | 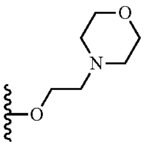 | H |

-continued
formula (II)
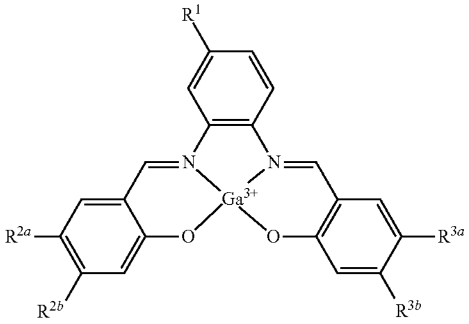
| Compound # | $R^1$ | $R^{2a}$ | $R^{2b}$ | $R^{3a}$ | $R^{3b}$ |
|---|---|---|---|---|---|
| 1496 | 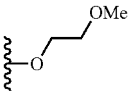 | 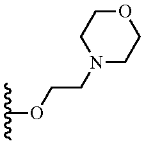 [SMILES: *OCCN1CCOCC1] | H | 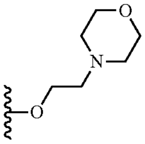 | H |
| 1497 | 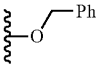 | 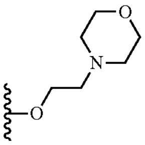 [SMILES: *OCCN1CCOCC1] | H | 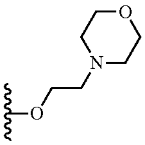 | H |
| 1498 | H | 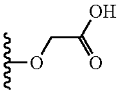 [SMILES: *OCC(=O)O] | H | 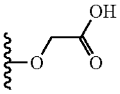 | H |
| 1499 | —OMe | 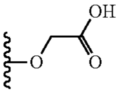 [SMILES: *OCC(=O)O] | H | 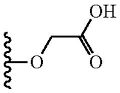 | H |
| 1500 | —OEt | 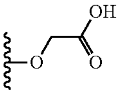 [SMILES: *OCC(=O)O] | H | 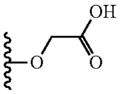 | H |
| 1501 | —OPr | 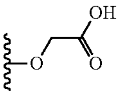 [SMILES: *OCC(=O)O] | H | 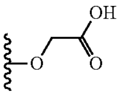 | H |
| 1502 | —OiPr | 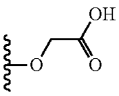 [SMILES: *OCC(=O)O] | H | 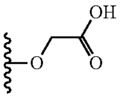 | H |
| 1503 | 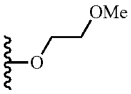 | 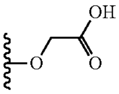 [SMILES: *OCC(=O)O] | H | 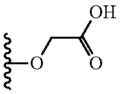 | H |
| 1504 | 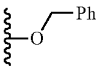 | 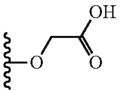 [SMILES: *OCC(=O)O] | H | 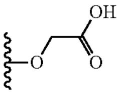 | H |

-continued
formula (II)
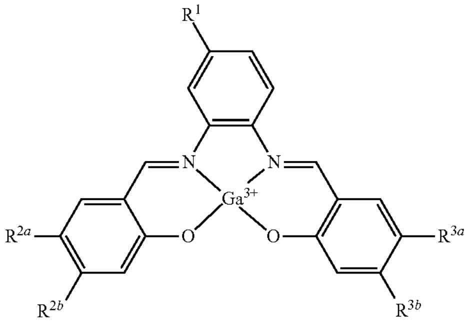
| Compound # | $R^1$ | $R^{2a}$ | $R^{2b}$ | $R^{3a}$ | $R^{3b}$ |
|---|---|---|---|---|---|
| 1505 | H | H | 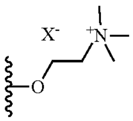 | 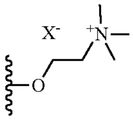 | H |
| 1506 | —OMe | H | 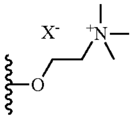 | 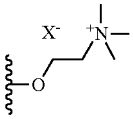 | H |
| 1507 | —OEt | H | 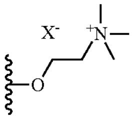 | 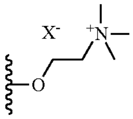 | H |
| 1508 | —OPr | H | 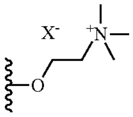 | 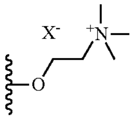 | H |
| 1509 | —OiPr | H | 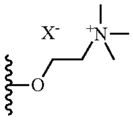 | 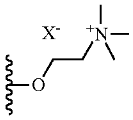 | H |
| 1510 | 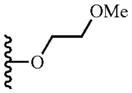 | H | 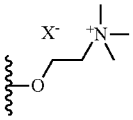 | 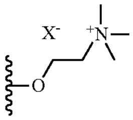 | H |
| 1511 | 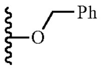 | H | 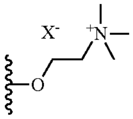 | 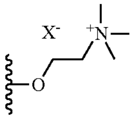 | H |
| 1512 | H | H | 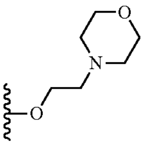 [SMILES: *OCCN1CCOCC1] | 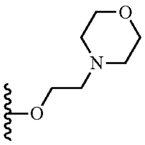 | H |

-continued
formula (II)
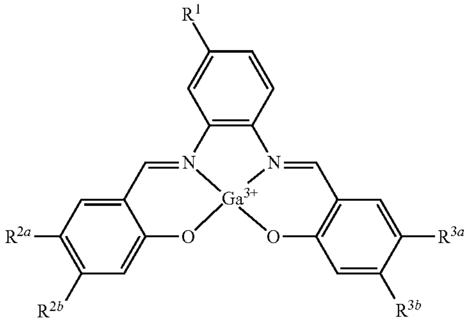
| Compound # | $R^1$ | $R^{2a}$ | $R^{2b}$ | $R^{3a}$ | $R^{3b}$ |
|---|---|---|---|---|---|
| 1513 | —OMe | H | 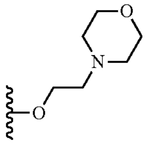 [SMILES: *OCCN1CCOCC1] | 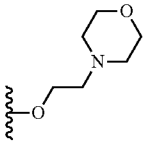 | H |
| 1514 | —OEt | H | 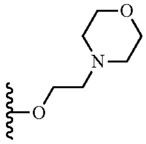 [SMILES: *OCCN1CCOCC1] | 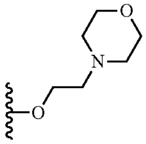 | H |
| 1515 | —OPr | H | 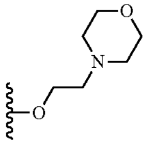 [SMILES: *OCCN1CCOCC1] | 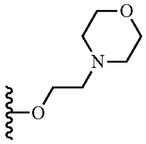 | H |
| 1516 | —OiPr | H | 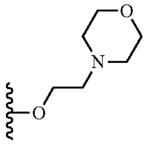 [SMILES: *OCCN1CCOCC1] | 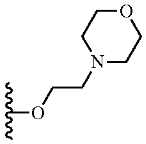 | H |
| 1517 | 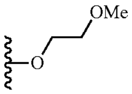 | H | 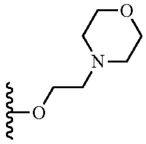 [SMILES: *OCCN1CCOCC1] | 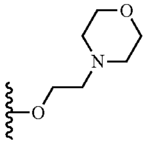 | H |
| 1518 | 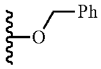 | H | 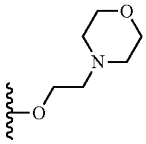 [SMILES: *OCCN1CCOCC1] | 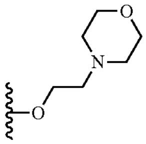 | H |
| 1519 | H | H | 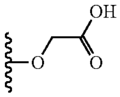 [SMILES: *OCC(=O)O] | 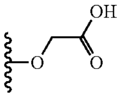 | H |
| 1520 | —OMe | H | 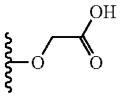 [SMILES: *OCC(=O)O] | 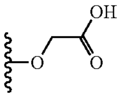 | H |

-continued
formula (II)
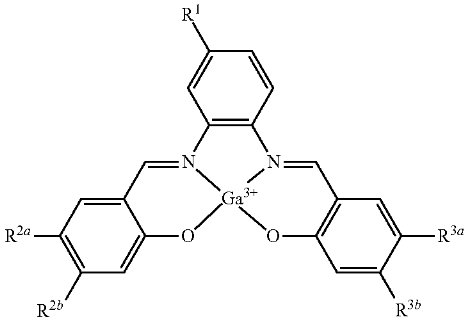
| Compound # | $R^1$ | $R^{2a}$ | $R^{2b}$ | $R^{3a}$ | $R^{3b}$ |
|---|---|---|---|---|---|
| 1521 | —OEt | H | 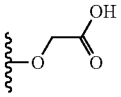 [SMILES: *OCC(=O)O] | 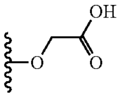 | H |
| 1522 | —OPr | H | 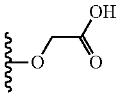 [SMILES: *OCC(=O)O] | 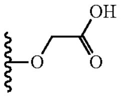 | H |
| 1523 | —OiPr | H | 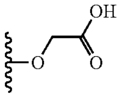 [SMILES: *OCC(=O)O] | 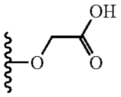 | H |
| 1524 | 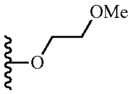 | H | 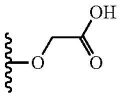 [SMILES: *OCC(=O)O] | 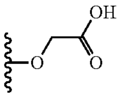 | H |
| 1525 | 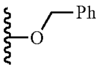 | H | 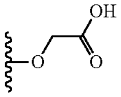 [SMILES: *OCC(=O)O] | 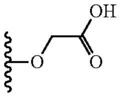 | H |
| 1526 | H | 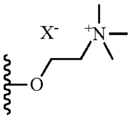 | H | H | 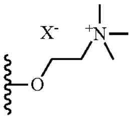 |
| 1527 | —OMe | 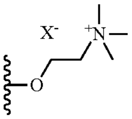 | H | H | 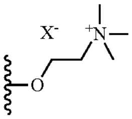 |
| 1528 | —OEt | 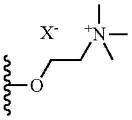 | H | H | 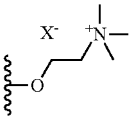 |
| 1529 | —OPr | 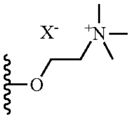 | H | H | 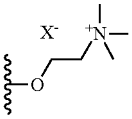 |

-continued
formula (II)
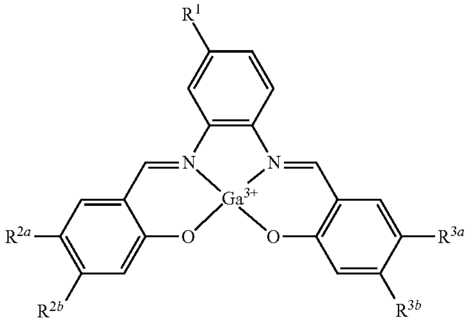
| Compound # | $R^1$ | $R^{2a}$ | $R^{2b}$ | $R^{3a}$ | $R^{3b}$ |
|---|---|---|---|---|---|
| 1530 | —OiPr | 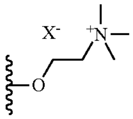 | H | H | 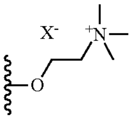 |
| 1531 | 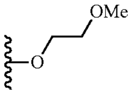 | 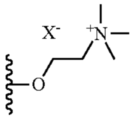 | H | H | 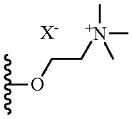 |
| 1532 | 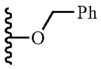 | 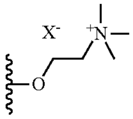 | H | H | 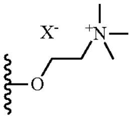 |
| 1533 | H | 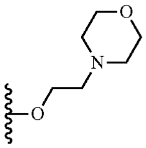 [SMILES: *OCCN1CCOCC1] | H | H | 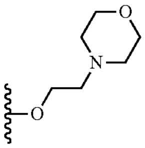 |
| 1534 | —OMe | 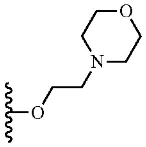 [SMILES: *OCCN1CCOCC1] | H | H | 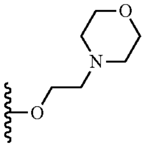 |
| 1535 | —OEt | 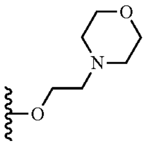 [SMILES: *OCCN1CCOCC1] | H | H | 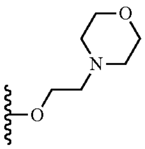 |
| 1536 | —OPr | 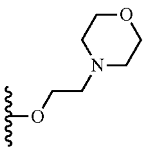 [SMILES: *OCCN1CCOCC1] | H | H | 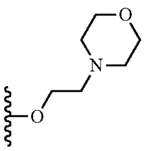 [SMILES: *OCCN1CCOCC1] |
| 1537 | —OiPr | 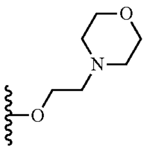 [SMILES: *OCCN1CCOCC1] | H | H | 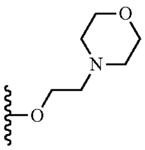 |

-continued
formula (II)
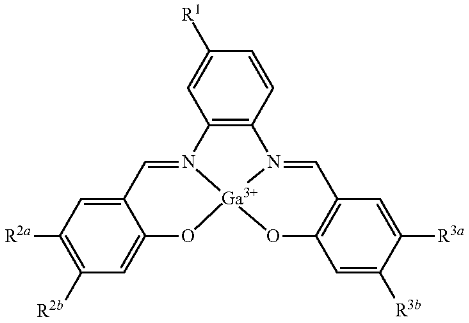
| Compound # | $R^1$ | $R^{2a}$ | $R^{2b}$ | $R^{3a}$ | $R^{3b}$ |
|---|---|---|---|---|---|
| 1538 | 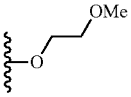 | 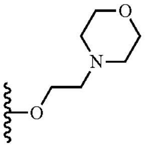 [SMILES: *OCCN1CCOCC1] | H | H | 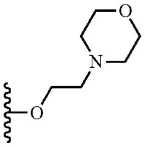 [SMILES: *OCCN1CCOCC1] |
| 1539 | 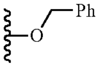 | 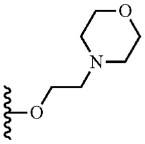 | H | H | 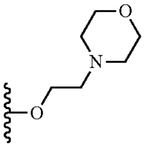 |
| 1540 | H | 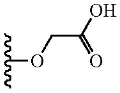 [SMILES: *OCC(=O)O] | H | H | 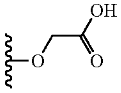 |
| 1541 | —OMe | 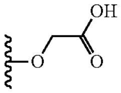 [SMILES: *OCC(=O)O] | H | H | 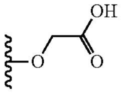 |
| 1542 | —OEt | 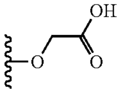 [SMILES: *OCC(=O)O] | H | H | 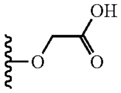 |
| 1543 | —OPr | 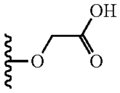 [SMILES: *OCC(=O)O] | H | H | 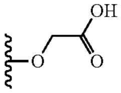 [SMILES: *OCC(=O)O] |
| 1544 | —OiPr | 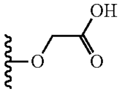 [SMILES: *OCC(=O)O] | H | H | 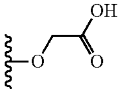 |
| 1545 | 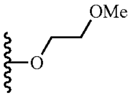 | 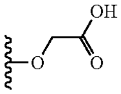 | H | H | 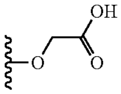 |
| 1546 | 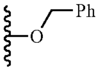 | 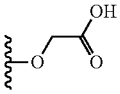 [SMILES: *OCC(=O)O] | H | H | 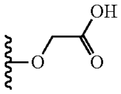 |

-continued
formula (II)
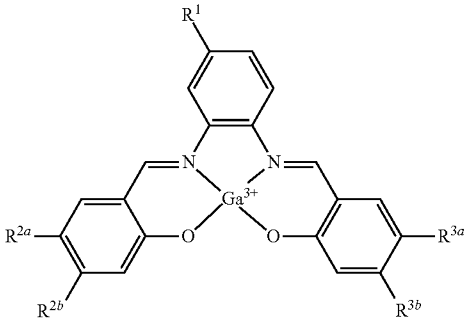
| Compound # | $R^1$ | $R^{2a}$ | $R^{2b}$ | $R^{3a}$ | $R^{3b}$ |
|---|---|---|---|---|---|
| 1547 | H | H | 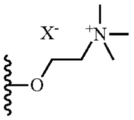 | H | 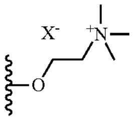 |
| 1548 | —OMe | H | 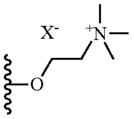 | H | 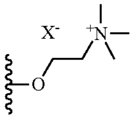 |
| 1549 | —OEt | H | 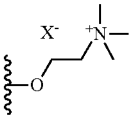 | H | 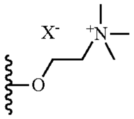 |
| 1550 | —OPr | H | 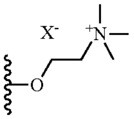 | H | 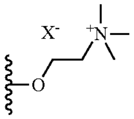 |
| 1551 | —OiPr | H | 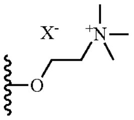 | H | 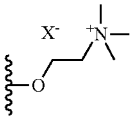 |
| 1552 | 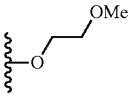 | H | 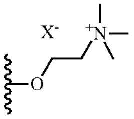 | H | 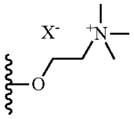 |
| 1553 | 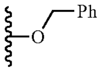 | H | 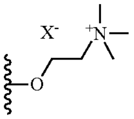 | H | 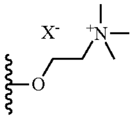 |
| 1554 | H | H | 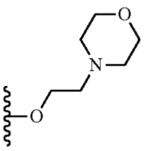 [SMILES: *OCCN1CCOCC1] | H | 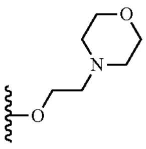 |

-continued
formula (II)
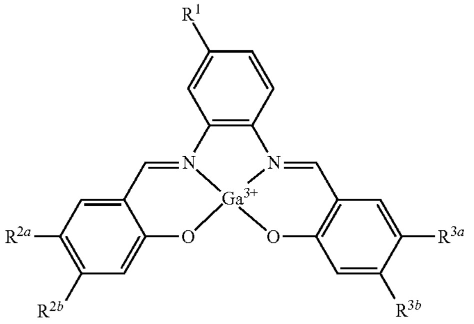
| Compound # | $R^1$ | $R^{2a}$ | $R^{2b}$ | $R^{3a}$ | $R^{3b}$ |
|---|---|---|---|---|---|
| 1555 | —OMe | H | 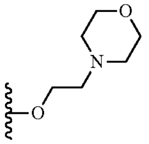 [SMILES: *OCCN1CCOCC1] | H | 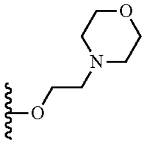 |
| 1556 | —OEt | H | 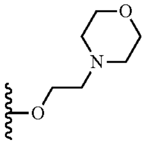 [SMILES: *OCCN1CCOCC1] | H | 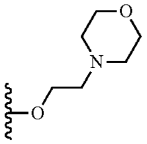 |
| 1557 | —OPr | H | 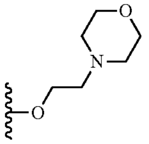 [SMILES: *OCCN1CCOCC1] | H | 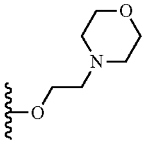 |
| 1558 | —OiPr | H | 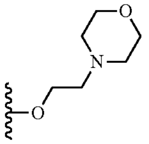 [SMILES: *OCCN1CCOCC1] | H | 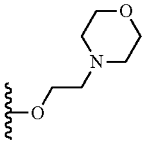 |
| 1559 | 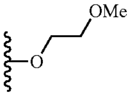 | H | 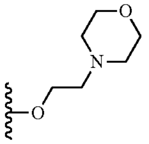 [SMILES: *OCCN1CCOCC1] | H | 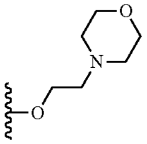 |
| 1560 | 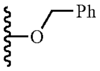 | H | 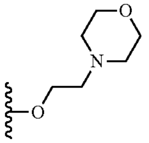 [SMILES: *OCCN1CCOCC1] | H | 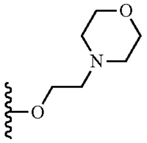 |
| 1561 | H | H | 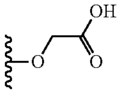 [SMILES: *OCC(=O)O] | H | 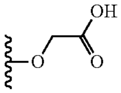 [SMILES: *OCC(=O)O] |
| 1562 | —OMe | H | 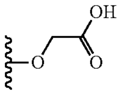 [SMILES: *OCC(=O)O] | H | 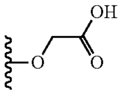 |

-continued formula (II)

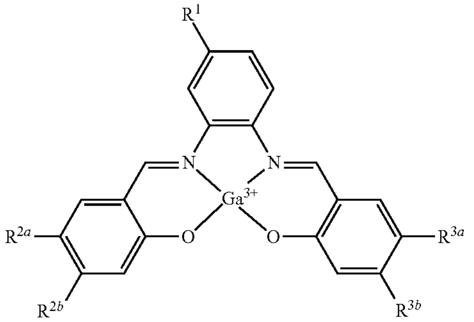

| Compound # | $R^1$ | $R^{2a}$ | $R^{2b}$ | $R^{3a}$ | $R^{3b}$ |
|---|---|---|---|---|---|
| 1563 | —OEt | H | 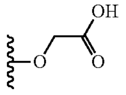 [SMILES: *OCC(=O)O] | H | 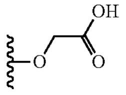 [SMILES: *OCC(=O)O] |
| 1564 | —OPr | H | 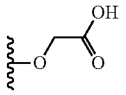 [SMILES: *OCC(=O)O] | H | 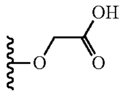 |
| 1565 | —OiPr | H | 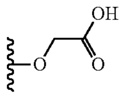 [SMILES: *OCC(=O)O] | H | 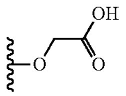 |
| 1566 | 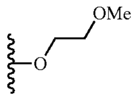 | H | 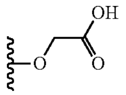 [SMILES: *OCC(=O)O] | H | 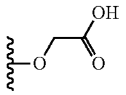 |
| 1567 | 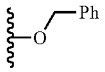 | H | 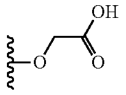 [SMILES: *OCC(=O)O] | H | 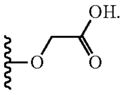 [SMILES: *OCC(=O)O] |

8. The compound of claim 1, wherein the compound of formula (I) is a compound of formula (XI), or a pharmaceutically acceptable salt, solvate, hydrate, cocrystal, or prodrug thereof:

formula (XI)

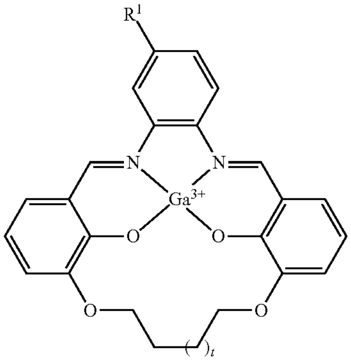

wherein in formula (XI):

$R^1$ is selected from the group consisting of H, halogen, optionally substituted alkyl, optionally substituted alkylaryl, optionally substituted alkylhetaryl, optionally substituted alkenyl, optionally substituted alkynyl, optionally substituted cycloalkyl, optionally substituted aryl, optionally substituted aralkyl, optionally substituted haloalkyl, optionally substituted alkoxy, and optionally substituted heteroaryl; and t is an integer from 1 to 4.

9. The compound of claim 8, wherein $R^1$ is selected from the group consisting of —OMe, —OEt, —OPr, —OiPr,

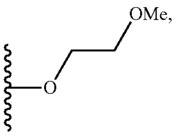 and 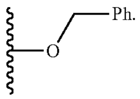

10. The compound of claim 8, wherein the compound is of any one of formulas 2001 to 2028:

formula (XI)
formula (XI)
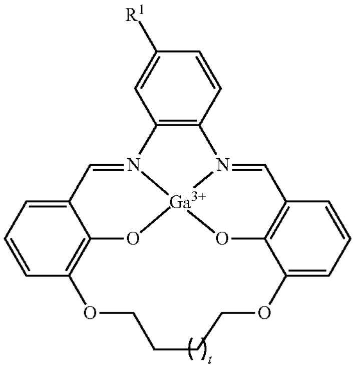
| Compound # | $R^1$ | t |
|---|---|---|
| 2001 | H | 1 |
| 2002 | —OMe | 1 |
| 2003 | —OEt | 1 |
| 2004 | —OPr | 1 |
| 2005 | —OiPr | 1 |
| 2006 | 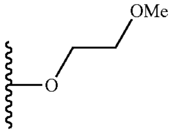 [SMILES: *OCCOC] | 1 |
| 2007 | 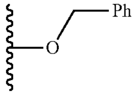 | 1 |
| 2008 | H | 2 |
| 2009 | —OMe | 2 |
| 2010 | —OEt | 2 |
| 2011 | —OPr | 2 |
| 2012 | —OiPr | 2 |
| 2013 | 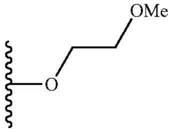 [SMILES: *OCCOC] | 2 |
| 2014 | 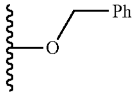 [SMILES: *OCc1ccccc1] | 2 |
| 2015 | H | 3 |
| 2016 | —OMe | 3 |
| 2017 | —OEt | 3 |
| 2018 | —OPr | 3 |
| 2019 | —OiPr | 3 |
| 2020 | 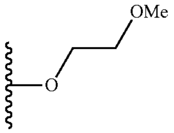 [SMILES: *OCCOC] | 3 |
| 2021 | 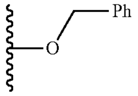 [SMILES: *OCc1ccccc1] | 3 |
| 2022 | H | 4 |
| 2023 | —OMe | 4 |
| 2024 | —OEt | 4 |
-continued
formula (XI)
formula (XI)
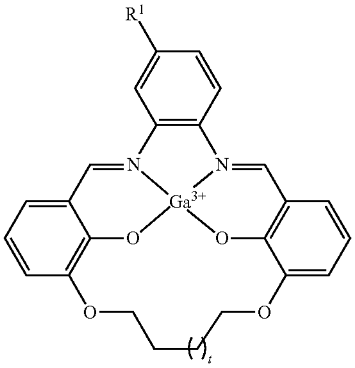
| Compound # | $R^1$ | t |
|---|---|---|
| 2025 | —OPr | 4 |
| 2026 | —OiPr | 4 |
| 2027 | 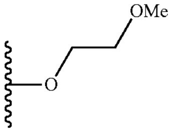 [SMILES: *OCCOC] | 4 |
| 2028 | 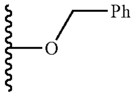 [SMILES: *OCc1ccccc1] | 4. |
11. A compound is selected from:
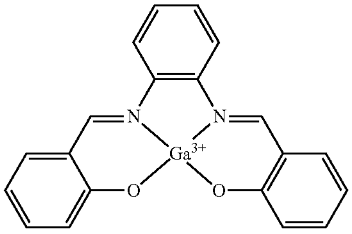
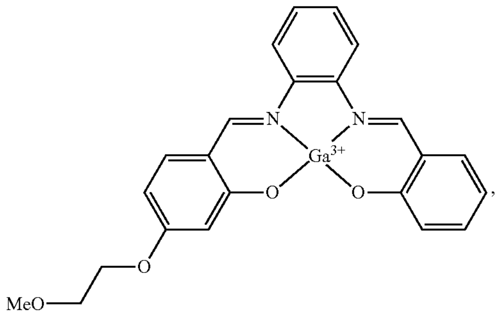
, -continued

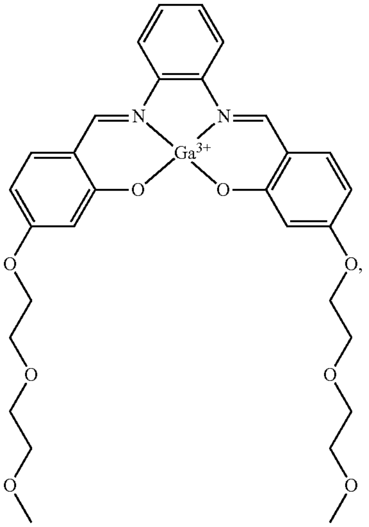

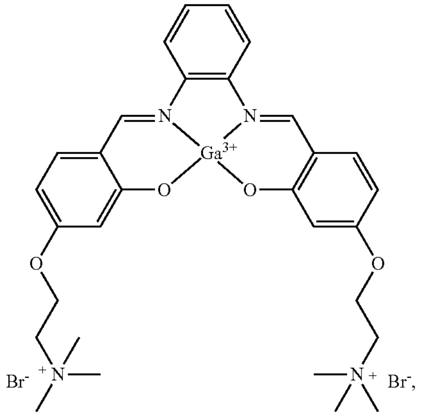

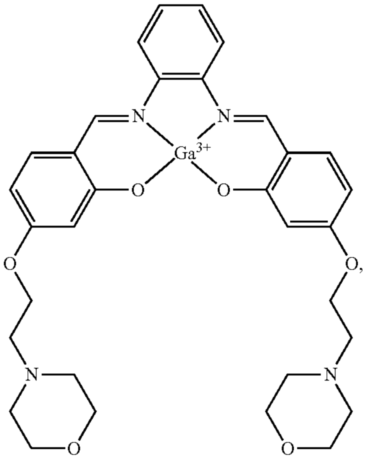

and

-continued

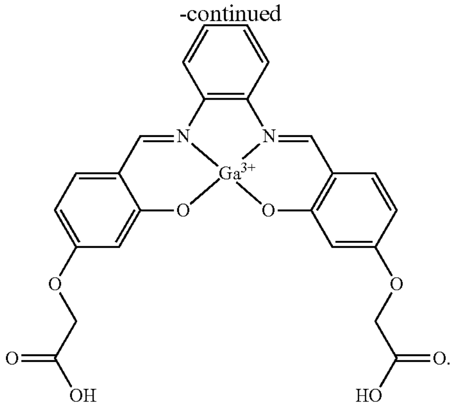

12. A pharmaceutical composition for treating a condition alleviated by inhibiting HasAp protein activity, or by inhibiting the *P. aeruginosa* siderophore iron uptake system, or by dual inhibition of HasAp protein activity and the *P. aeruginosa* siderophore iron uptake system, the pharmaceutical composition comprising one or more compounds according to claim 1, or a pharmaceutically acceptable salt, solvate, hydrate, cocrystal, or prodrug thereof, and a pharmaceutically acceptable carrier.

13. The pharmaceutical composition of claim 12, wherein the condition is selected from sepsis, meningitis, endocarditis, osteomyelitis, otitis media, sinusitis, pneumonia, chronic respiratory tract infection, catheter infection, postoperative peritonitis, postoperative biliary tract, tricuspid valve endocarditis, ecthyma gangrenosum, eyelid abscess, lacrimal cystitis, conjunctivitis, corneal ulcer, corneal abscess, panophthalmitis, orbital infection, urinary tract infection, complicated urinary tract infection, catheter infection, perianal abscess, severe burns, airway burns, pressure ulcer infections, cystic fibrosis, and a bacterial infection.

14. A pharmaceutical composition for treating or preventing a bacterial infection, the pharmaceutical composition comprising one or more compounds according to claim 1, or a pharmaceutically acceptable salt, solvate, hydrate, cocrystal, or prodrug thereof, and a pharmaceutically acceptable carrier.

15. The pharmaceutical composition of claim 14, wherein the bacterial infection is caused by a bacterium selected from *P. aeruginosa, Serratia marcescens, Bordetella pertussis, Bordetella bronchiseptica, Bordetella avium, Yersinia pestis, Yersinia pseudotuberculosis*, and *Acinetobacter baumannii.*

16. A method of treating a condition by inhibiting HasAp protein activity, or by inhibiting the *P. aeruginosa* siderophore iron uptake system, or by dual inhibition of the HasAp protein activity and the *P. aeruginosa* siderophore iron uptake system in a patient in need of said treatment, the method comprising administering to the patient a therapeutically effective amount of a compound of claim 1, or a pharmaceutically acceptable salt, solvate, hydrate, cocrystal, or prodrug thereof.

17. The method of claim 16, wherein the condition is selected from sepsis, meningitis, endocarditis, osteomyelitis, otitis media, sinusitis, pneumonia, chronic respiratory tract infection, catheter infection, postoperative peritonitis, postoperative biliary tract, tricuspid valve endocarditis, ecthyma gangrenosum, eyelid abscess, lacrimal cystitis, conjunctivitis, corneal ulcer, corneal abscess, panophthalmitis, orbital infection, urinary tract infection, complicated urinary tract infection, catheter infection, perianal abscess, severe burns, airway burns, pressure ulcer infections, cystic fibrosis, and a bacterial infection.

18. A method for treating or preventing a bacterial infection in a patient in need of said treatment, the method comprising administering to the patient a therapeutically effective amount of a compound of claim 1, or a pharmaceutically acceptable salt, solvate, hydrate, cocrystal, or prodrug thereof.

19. The method of claim 18, wherein the bacterial infection is caused by a bacterium selected from *P. aeruginosa, Serratia marcescens, Bordetella pertussis, Bordetella bronchiseptica, Bordetella avium, Yersinia pestis, Yersinia pseudotuberculosis*, and *Acinetobacter baumannii.*

* * * * *